(12) United States Patent
Sun et al.

(10) Patent No.: US 8,536,177 B2
(45) Date of Patent: Sep. 17, 2013

(54) THERAPEUTIC AGENTS USEFUL FOR TREATING PAIN

(75) Inventors: Qun Sun, Princeton, NJ (US); Laykea Tafesse, Robbinsville, NJ (US); Sam Victory, Oak Ridge, NC (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 13/205,323

(22) Filed: Aug. 8, 2011

(65) Prior Publication Data
US 2012/0004217 A1    Jan. 5, 2012

Related U.S. Application Data

(60) Continuation of application No. 12/499,480, filed on Jul. 8, 2009, now Pat. No. 8,008,300, which is a division of application No. 10/739,190, filed on Dec. 19, 2003, now Pat. No. 7,582,635.

(60) Provisional application No. 60/435,917, filed on Dec. 24, 2002, provisional application No. 60/459,626, filed on Apr. 3, 2003, provisional application No. 60/473,856, filed on May 29, 2003.

(51) Int. Cl.
*A61K 31/497* (2006.01)
*A61K 31/435* (2006.01)
*C07D 279/10* (2006.01)
*C07D 401/14* (2006.01)

(52) U.S. Cl.
USPC .................. 514/252.03; 514/253.1; 514/277; 544/58.6; 544/238; 544/364

(58) Field of Classification Search
USPC ..... 514/253.1, 252.03, 277.8, 277; 544/58.6, 544/238, 364
See application file for complete search history.

(56) References Cited

U.S. PATENT DOCUMENTS 3,536,809 A   10/1970   Applezweig
3,598,123 A    8/1971   Zaffaroni
(Continued)

FOREIGN PATENT DOCUMENTS

| JP | 11-199573 | 7/1999 |
|---|---|---|
| JP | 2003-192673 | 7/2003 |
| WO | WO 99/26927 | 6/1999 |
| WO | WO 99/37304 | 7/1999 |
| WO | WO 00/59510 | 10/2000 |
| WO | WO 01/10846 | 2/2001 |
| WO | WO 01/57008 | 8/2001 |
| WO | WO 02/08221 | 1/2002 |

OTHER PUBLICATIONS

Bartho et al., "Involvement of Capsaicin-sensitive Neurones in Hyperalgesia and Enhanced Opioid Antinociception in Inflammation," Naunyn-Schmiedeberg's Archives of Pharmacology 342:666-670 (1990).
Berkow et al., (eds), "Seizure Disorder", The Merck Manual of Medical Information 345-350 (1997).
Berkow et al., (eds), "Crohn's Disease", The Merck Manual of Medical Information 528-530 (1997).
Berkow et al., (eds), "Irritable Bowel Syndrome", The Merck Manual of Medical Information 525-526 (1997).
Berkow et al., (eds), "Peptic Ulcer", The Merck Manual of Medical Information 496-500 (1997).
Berkow et al., (eds), "Stroke", The Merck Manual of Medical Information 352-355 (1997).
Berkow et al., (eds), "Ulcerative Colitis", The Merck Manual of Medical Information 530-532 (1997).
Berkow et al., (eds), "Urinary Incontinence", The Merck Manual of Medical Information 631-634 (1997).
Brunton, "Agents for control of gastric acidity and treatment of peptic ulcers", Goodman and Gilman's The Pharmacological Basis of Therapeutics 901-915 (J. Hardman and L. Limbird eds., $9^{th}$ ed. 1996).
Buchwald et al., "Long-term, continuous intravenous heparin administration by an implantable infusion pump in ambulatory patients with recurrent venous thrombosis", Surgery 88 (4):507-16 (1980).
Chiamulera et al., "Reinforcing and locomotor stimulant effects of cocaine are absent in mGluR5 null mutant mice", Nat Neurosci. 4(9):873-4 (2001).
Chu-Moyer et al., "Orally-effective, log-acting sorbitol dehydrogenase inhibitors: synthesis, structure-activity relationships, and in vivo evaluations of novel heterocycle-substituted piperazinopyrimidines", J. Med. Chem. 45:511-528 (2002).
Cooke et al., "Glycopyrrolate in bladder dysfunction", S. Afr. Med. J. 63(1):3 (1983). D'Amour et al., "A Method for Determining Loss of Pain Sensation," J. Pharmacol. Exp. Ther. 72:74-79 (1941).

(Continued)

Primary Examiner — James O Wilson
Assistant Examiner — Ebenezer O Sackey
(74) Attorney, Agent, or Firm — Dechert LLP

(57) ABSTRACT

A compound of formula:

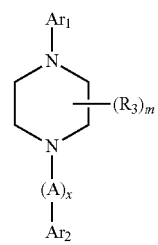

wherein $Ar_1$, A, $R_3$, x, and m are as disclosed herein and $Ar_2$ is a benzothiazolyl, benzooxazolyl, or benzoimidazolyl group or a pharmaceutically acceptable salt thereof (a "Benzoazolylpiperazine Compound"), compositions comprising a Benzoazolylpiperazine Compound, and methods for treating or preventing pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, amyotrophic lateral sclerosis, dementia, retinopathy, a muscle spasm, a migraine, vomiting, dyskinesia, or depression in an animal comprising administering to an animal in need thereof an effective amount of a Benzoazolylpiperazine Compound are disclosed.

57 Claims, No Drawings

(56) References Cited

U.S. PATENT DOCUMENTS

| | | | |
|---|---|---|---|
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 5,039,680 A | 8/1991 | Imperato et al. | |
| 5,059,595 A | 10/1991 | Le Grazie | |
| 5,073,543 A | 12/1991 | Marshall et al. | |
| 5,075,341 A | 12/1991 | Mendelson et al. | |
| 5,120,548 A | 6/1992 | McClelland et al. | |
| 5,198,459 A | 3/1993 | Imperato et al. | |
| 5,232,934 A | 8/1993 | Downs | |
| 5,354,556 A | 10/1994 | Sparks et al. | |
| 5,529,998 A | 6/1996 | Habich et al. | |
| 5,536,721 A | 7/1996 | Jakobsen et al. | |
| 5,556,837 A | 9/1996 | Nestler et al. | |
| 5,556,838 A | 9/1996 | Mayer et al. | |
| 5,574,052 A | 11/1996 | Rose et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,698,155 A | 12/1997 | Grosswald et al. | |
| 5,733,566 A | 3/1998 | Lewis | |
| 5,762,925 A | 6/1998 | Sagen | |
| 6,109,269 A | 8/2000 | Rise et al. | |
| 6,136,839 A | 10/2000 | Isakson et al. | |
| 6,150,129 A | 11/2000 | Cook et al. | |
| 6,204,284 B1 | 3/2001 | Beer et al. | |
| 6,239,267 B1 | 5/2001 | Duckworth et al. | |
| 6,335,180 B1 | 1/2002 | Julius et al. | |
| 6,406,908 B1 | 6/2002 | McIntyre et al. | |
| 6,482,479 B1 | 11/2002 | Dubal et al. | |
| 7,071,335 B2 | 7/2006 | Kyle et al. | |
| 7,256,193 B2 | 8/2007 | Kyle et al. | |
| 7,262,194 B2 * | 8/2007 | Kyle et al. | 514/252.02 |
| 7,696,207 B2 | 4/2010 | Kyle et al. | |
| 7,754,723 B2 | 7/2010 | Sun et al. | |
| 7,799,786 B2 | 9/2010 | Kyle et al. | |
| 8,129,388 B2 | 3/2012 | Sun | |
| 2004/0152690 A1 | 8/2004 | Balan et al. | |
| 2011/0082152 A1 | 4/2011 | Sun et al. | |
| 2011/0288100 A1 | 11/2011 | Sun | |

OTHER PUBLICATIONS

Dogrul et al., "Peripheral and spinal antihyperalgesic activity of SIB-1757, a metabotropic glutamate receptor (mGLUR(5)) antagonist, in experimental neuropathic pain in rats", Neurosci Lett. 292(2):115-8 (2000).

During et al., "Controlled release of dopamine from a polymeric brain implant: in vivo characterization", Ann. Neurol. 25(4):351-6 (1989).

Foley, Pain, in Cecil Textbook of Medicine 100-107 (J.C. Bennett and F. Plum eds., 20th ed. 1996).

Goodson, "Dental applications", in Medical Applications of Controlled Release, supra, vol. 2, pp. 115-138 (1984).

Grupp et al., "Protection against hypoxia-reoxygenation in the absence of poly (ADP-ribose) synthetase in isolated working hearts", J. Mol. Cell. Cardiol. 31(1):297-303 (1999).

Hanson, Analgesic, Antipyretic and Anti-Inflammatory Drugs in Remington: The Science and Practice of Pharmacy vol. II 1196-1221 (A.R. Gennaro ed. 19th ed. 1995).

Hargreaves et al., "A New and Sensitive Method for Measuring Thermal Nociception in Cutaneous Hyperalgesia," Pain 32(1):77-88 (1988).

Herzog et al., "Urinary incontinence: medical and psychosocial aspects", Annu. Rev. Gerontol. Geriatr. 9:74-119 (1989).

Howard et al., "Intracerebral drug delivery in rats with lesion-induced memory deficits", J. Neurosurg. 71(1):105-12 (1989).

Insel, Analgesic-Antipyretic and Anti-inflammatory Agents and Drugs Employed in the Treatment of Gout, in Goodman & Gilman's The Pharmaceutical Basis of Therapeutics 617-57 (Perry B. Molinhoff and Raymond W. Ruddon eds., $9^{th}$ ed 1996).

Khadse et al., "Synthesis and Study of 2-($N^4$-substituted-$N^1$-piperazinyl) pyrido (3,2-d) thiazoles, 5-nitro-2-($N^4$-substituted-$N^1$-piperazinyl) Benzthiazoles and allied compounds as possible anthelmintic agents", Bull. Haff. Instt. 1(3):27-32 (1975).

Kim, "An Experimental Model for Peripheral Neuropathy Produced by Segmental Spinal Nerve Ligation in the Rat," Pain 50(3):355-363 (1992).

Langer, "New methods of drug delivery", Science. 249(4976):1527-33 (1990).

Levin et al., "Direct measurement of the anticholinergic activity of a series of pharmacological compounds on the canine and rabbit urinary bladder", J. Urol. 128(2):396-8 (1982).

Levy et al., "Inhibition of calcification of bioprosthetic heart valves by local controlled-release diphosphonate", Science, 228 (4696):190-2 (1985).

Masu et al., "Sequence and expression of a metabotropic glutamate receptor", Nature 349(6312):760-5 (1991).

Miller et al., "Growth Factor Upregulation of a Phosphoinositide-Coupled Metabotropic Glutamate Receptor in Cortical Astrocytes", J. Neurosci. 15(9):6103-6109 (1995).

Mirakhur et al., "Glycopyrrolate: pharmacology and clinical use", Anaesthesia 38(12):1195-204 (1983).

Wein et al., "Pharmacology of incontinence", Urol. Clin. North Am. 22(3):557-77 (1995).

Orjales et al., "New 2-Pieperazinylbenzimidazole Derivatives as 5-$HT_3$ Antagonists. Synthesis and Pharmacological Evaluation", J. Med. Chem. 40:586-593 (1997).

Ossowska et al., "Blockade of the metabotropic glutamate receptor subtype 5 (mGluR5) produces antiparkinsonian-like effects in rats", Neuropharmacology 41(4):413-20 (2001).

Langer et al., "Chemical and physical structure of polymers as carriers for controlled release of bioactive agents: a review", J. Macromol. Sci. Rev. Macromol. Chem. 23:61 (1983).

Spooren et al., "Novel allosteric antagonists shed light on $mglu_5$ receptors and CNS disorders", Trends in Pharmacological Sciences 22(7):331-37 (2001).

Resnick, "Urinary incontinence", Lancet 346:94-9 (1995).

Saudek et al., "A preliminary trial of the programmable implantable medication system for insulin delivery", N. Engl. J. Med. 321:574 (1989).

Sefton, "Implantable pumps", .CRC Crit. Ref. Biomed. Eng. 14(3):201-40 (1987).

Seltzer et al., "A Novel Behavioral Model of Neuropathic Pain Disorders Produced in Rats by Partial Sciatic Nerve Injury," Pain 43:205-218 (1990).

Standaert et al., "Parkinson's Disease", Goodman and Gillman's The Pharmaceutical Basis of Therapeutics 506 ($9^{th}$ ed. 1996) (J. Hardman and L. Limbird eds., $9^{th}$ ed. 1996).

Stein, "Unilateral Inflammation of the Hindpaw in Rats as a Model of Prolonged Noxious Stimulation: Alterations in Behavior and Nociceptive Thresholds," Pharmacology Biochemistry and Behavior 31:451-455 (1988).

Tatarczynska et al., "Potential anxiolytic- and antidepressant-like effects of MPEP, a potent, selective and systemically active mGlu5 receptor antagonist", Br. J. Pharmacol.

Lopez-Berestein., Liposomes in the Therapy of Infectious Disease and Cancer 317-327 and 353-365 (1989).

Treit, "Animal Models for the Study of Anti-anxiety Agents: A Review," Neuroscience & Biobehavioral Reviews 9(2):203-222 (1985).

Walker et al., Neuropharmacology 40:1-9 (2000).

Bevan et al., "Vanilloid receptors: pivotal molecules in nocciception," *Current Opinions in CPNS Investigational Drugs*, 2(2):178-185 (2000).

Lopez-Rodriguez et al., "VR1 Receptor modulators as potential drugs for neuropathic pain," *Mini-Revs. in Medicinal Chem.* 3(7):729-748 (2003).

Pomonis et al., "N-(4-Tertiarybutylphenyl)-4-(3-chloropyridin-2-yl)tetrahydropyrazine-1(2H)-carboxamide (BCTC), a novel, orally effective vanilloid receptor 1 antagonist with analgesic properties: II. In vivo characterization in rat models of inflammatory and neuropathic pain," *J. Pharmacol. Exper. Therapeutics*, 306(1):387-393 (2003).

Rami et al., "The therapeutic potential of TRPV1 (VR1) antagonists: Clinical answers await," *Drug Discovery Today: Therapeutic Strategies* 1(1):97-104 (Sep. 2004).

Szallasi et al., "Vanilloid (Capsaicin) receptors and mechanisma," *Pharmacol. Revs.* 51(2):159-211 (1999).

Szallasi et al., "The cloned rat vanilloid receptor VR1 mediates both R-type binding and C-type calcium response in dorsal root ganglion neurons," *Mol. Pharmacol* 56:581-587 (1999).

Wang et al., "High affinity antagonists of the vanilloid receptor," *Mol. Pharmacol.* 62(4):947-956 (2002).

Wrigglesworth et al., "Capsaicin-like agonists," *Drugs of the Future* 23(5):531-538 (1998).

* cited by examiner

SEQUENCE LISTING

<160> NUMBER OF SEQ ID NOS: 2

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
aagatcttcg ctggttgcac actgggccac a        31

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
gaagatcttc ggggacagtg acggttggat gt        32

THERAPEUTIC AGENTS USEFUL FOR TREATING PAIN

This application is a continuation of U.S. application Ser. No. 12/499,480, filed Jul. 8, 2009, now U.S. Pat. No. 8,008,300 B2; which is a divisional of U.S. application Ser. No. 10/739,190, filed Dec. 19, 2003, now U.S. Pat. No. 7,582,635 B2; which claims the benefit under 35 U.S.C. §119(e) of U.S. Provisional Application No. 60/435,917, filed Dec. 24, 2002; U.S. Provisional Application No. 60/459,626, filed Apr. 3, 2003; and U.S. Provisional Application No. 60/473,856, filed May 29, 2003, the contents of all of which are incorporated herein by reference.

1. FIELD OF THE INVENTION

The present invention relates to Benzoazolylpiperazine Compounds, compositions comprising a Benzoazolylpiperazine Compound and methods for treating or preventing pain, urinary incontinence (UI), an ulcer, inflammatory-bowel disease (IBD), irritable-bowel syndrome (IBS), an addictive disorder, Parkinson's disease, parkinsonism, anxiety, epilepsy, stroke, a seizure, a pruritic condition, psychosis, a cognitive disorder, a memory deficit, restricted brain function, Huntington's chorea, amyotrophic lateral sclerosis (ALS), dementia, retinopathy, a muscle spasm, a migraine, vomiting, dyskinesia or depression, comprising administering to an animal in need thereof an effective amount of a Benzoazolylpiperazine Compound.

2. BACKGROUND OF THE INVENTION

Pain is the most common symptom for which patients seek medical advice and treatment. Pain can be acute or chronic. While acute pain is usually self-limited, chronic pain persists for 3 months or longer and can lead to significant changes in a patient's personality, lifestyle, functional ability and overall quality of life (K. M. Foley, Pain, in Cecil Textbook of Medicine 100-107 (IC. Bennett and F. Plum eds., 20th ed. 1996)).

Pain has been traditionally managed by administering non-opioid analgesics, such as acetylsalkylic acid, choline magnesium trisalkylate, acetaminophen, ibuprofen, fenoprofen, diflusinal, and naproxen; or opioid analgesics, including morphine, hydromorphone, methadone, levorphanol, fentanyl, oxycodone, and oxymorphone. Id.

UI is uncontrollable urination, generally caused by bladder-detrusor-muscle instability. UI affects people of all ages and levels of physical health, both in health care settings and in the community at large. At present, UI afflicts 15-30% of elderly people living at home, one-third of those living in acute-care settings, and at least one-half of those living in long-term care institutions (R. M. Resnick, Lancet 346:94 (1995)). Persons having UI are predisposed to also having urinary-tract infections, pressure ulcers, perineal rashes and urosepsis. Psychosocially, UI is associated with embarrassment, social stigmatization, depression and a risk of institutionalization (Herzo et al., Annu. Rev. Gerontol. Geriatr. 9:74 (1989)). Economically, the costs of UI are great; in the United States alone, health-care costs associated with UI are over $15 billion per annum.

Physiologic bladder contraction results in large part from acetylcholine-induced stimulation of post-ganglionic muscarinic-receptor sites on bladder smooth muscle. Treatments for UI include the administration of drugs having bladder-relaxant properties, which help to control bladder-detrusor-muscle overactivity. For example, anticholinergics such as propantheline bromide and glycopyrrolate, and combinations of smooth-muscle relaxants such as a combination of racemic oxybutynin and dicyclomine or an anticholinergic, have been used to treat UI (See, e.g., A. J. Wein, Urol. Clin. N. Am. 22:557-577 (1995); Levin et al., J. Urol. 128:396-398 (1982); Cooke et al., S. Afr. Med. J. 63:3 (1983); R. K. Mirakhur et al., Anaesthesia 38:1195-1204 (1983)). These drugs are not effective, however, in all patients having uninhibited bladder contractions. Administration of anticholinergic medications represent the mainstay of this type of treatment.

None of the existing commercial drug treatments for UI, however, has achieved complete success in all classes of UI patients, nor has treatment occurred without significant adverse side effects. For example, drowsiness, dry mouth, constipation, blurred vision, headaches, tachycardia, and cardiac arrhythmia, which are related to the anticholinergic activity of traditional anti-UI drugs, can occur frequently and adversely affect patient compliance. Yet despite the prevalence of unwanted anticholinergic effects in many patients, anticholinergic drugs are currently prescribed for patients having UI. The Merck Manual of Medical Information 631-634 (R. Berkow ed., 1997).

Ulcers are sores occurring where the lining of the digestive tract has been eroded by stomach acids or digestive juices. The sores are typically well-defined round or oval lesions primarily occurring in the stomach and duodenum. About 1 in 10 people develop an ulcer. Ulcers develop as a result of an imbalance between acid-secretory factors, also known as "aggressive factors," such as stomach acid, pepsin, and Helicobacter pylori infection, and local mucosal-protective factors, such as secretion of bicarbonate, mucus, and prostaglandins.

Treatment of ulcers typically involves reducing or inhibiting the aggressive factors. For example, antacids such as aluminum hydroxide, magnesium hydroxide, sodium bicarbonate, and calcium bicarbonate can be used to neutralize stomach acids. Antacids, however, can cause alkalosis, leading to nausea, headache, and weakness. Antacids can also interfere with the absorption of other drugs into the blood stream and cause diarrhea.

$H_2$ antagonists, such as cimetidine, ranitidine, famotidine, and nizatidine, are also used to treat ulcers. $H_2$ antagonists promote ulcer healing by reducing gastric acid and digestive-enzyme secretion elicited by histamine and other $H_2$ agonists in the stomach and duodenum. $H_2$ antagonists, however, can cause breast enlargement and impotence in men, mental changes (especially in the elderly), headache, dizziness, nausea, myalgia, diarrhea, rash, and fever.

$H^+$, $K^+$-ATPase inhibitors such as omeprazole and lansoprazole are also used to treat ulcers. $H^+$, $K^+$-ATPase inhibitors inhibit the production of enzymes used by the stomach to secrete acid. Side effects associated with $H^+$, $K^+$-ATPase inhibitors include nausea, diarrhea, abdominal colic, headache, dizziness, somnolence, skin rashes, and transient elevations of plasma activities of aminotransferases.

Sucraflate is also used to treat ulcers. Sucraflate adheres to epithelial cells and is believed to form a protective coating at the base of an ulcer to promote healing. Sucraflate, however, can cause constipation, dry mouth, and interfere with the absorption of other drugs.

Antibiotics are used when Helicobacter pylori is the underlying cause of the ulcer. Often antibiotic therapy is coupled with the administration of bismuth compounds such as bismuth subsalkylate and colloidal bismuth citrate. The bismuth compounds are believed to enhance secretion of mucous and $HCO_3^-$, inhibit pepsin activity, and act as an antibacterial against H. pylori. Ingestion of bismuth compounds, however, can lead to elevated plasma concentrations of $Bi^{+3}$ and can interfere with the absorption of other drugs.

Prostaglandin analogues, such as misoprostal, inhibit secretion of acid and stimulate the secretion of mucous and bicarbonate and are also used to treat ulcers, especially ulcers in patients who require nonsteroidal anti-inflammatory drugs. Effective oral doses of prostaglandin analogues, however, can cause diarrhea and abdominal cramping. In addition, some prostaglandin analogues are abortifacients.

Carbenoxolone, a mineral corticoid, can also be used to treat ulcers. Carbenoxolone appears to alter the composition and quantity of mucous, thereby enhancing the mucosal barrier. Carbenoxolone, however, can lead to $Na^+$ and fluid retention, hypertension, hypokalemia, and impaired glucose tolerance.

Muscarinic cholinergic antagonists such as pirenzapine and telenzapine can also be used to reduce acid secretion and treat ulcers. Side effects of muscarinic cholinergic antagonists include dry mouth, blurred vision, and constipation. *The Merck Manual of Medical Information* 496-500 (R. Berkow ed., 1997) and *Goodman and Gilman's The Pharmacological Basis of Therapeutics* 901-915 (J. Hardman and L. Limbird eds., $9^{th}$ ed. 1996).

IBD is a chronic disorder in which the bowel becomes inflamed, often causing recurring abdominal cramps and diarrhea. The two types of IBD are Crohn's disease and ulcerative colitis.

Crohn's disease, which can include regional enteritis, granulomatous ileitis, and ileocolitis, is a chronic inflammation of the intestinal wall. Crohn's disease occurs equally in both sexes and is more common in Jews of eastern-European ancestry. Most cases of Crohn's disease begin before age 30 and the majority start between the ages of 14 and 24. The disease typically affects the full thickness of the intestinal wall. Generally the disease affects the lowest portion of the small intestine (ileum) and the large intestine, but can occur in any part of the digestive tract.

Early symptoms of Crohn's disease are chronic diarrhea, crampy abdominal pain, fever, loss of appetite, and weight loss. Complications associated with Crohn's disease include the development of intestinal obstructions, abnormal connecting channels (fistulas), and abscesses. The risk of cancer of the large intestine is increased in people who have Crohn's disease. Often Crohn's disease is associated with other disorders such as gallstones, inadequate absorption of nutrients, amyloidosis, arthritis, episcleritis, aphthous stomatitis, erythema nodosum, pyoderma gangrenosum, ankylosing spondylitis, sacroilitis, uveitis, and primary sclerosing cholangitis. There is no known cure for Crohn's disease.

Cramps and diarrhea, side effects associated with Crohn's disease, can be relieved by anticholinergic drugs, diphenoxylate, loperamide, deodorized opium tincture, or codeine. Generally, the drug is taken orally before a meal.

Broad-spectrum antibiotics are often administered to treat the symptoms of Crohn's disease. The antibiotic metronidazole is often administered when the disease affects the large intestine or causes abscesses and fistulas around the anus. Long-term use of metronidazole, however, can damage nerves, resulting in pins-and-needles sensations in the arms and legs. Sulfasalazine and chemically related drugs can suppress mild inflammation, especially in the large intestine. These drugs, however, are less effective in sudden, severe flare-ups. Corticosteroids, such as prednisone, reduce fever and diarrhea and relieve abdominal pain and tenderness. Long-term corticosteroid therapy, however, invariably results in serious side effects such as high blood-sugar levels, increased risk of infection, osteoporosis, water retention, and fragility of the skin. Drugs such as azathioprine and mercaptourine can compromise the immune system and are often effective for Crohn's disease in patients that do not respond to other drugs. These drugs, however, usually need 3 to 6 months before they produce benefits and can cause serious side effects such as allergy, pancreatitis, and low white-blood-cell count.

When Crohn's disease causes the intestine to be obstructed or when abscesses or fistulas do not heal, surgery can be necessary to remove diseased sections of the intestine. Surgery, however, does not cure the disease, and inflammation tends to recur where the intestine is rejoined. In almost half of the cases a second operation is needed. *The Merck Manual of Medical Information* 528-530 (R. Berkow ed., 1997).

Ulcerative colitis is a chronic disease in which the large intestine becomes inflamed and ulcerated, leading to episodes of bloody diarrhea, abdominal cramps, and fever. Ulcerative colitis usually begins between ages 15 and 30; however, a small group of people have their first attack between ages 50 and 70. Unlike Crohn's disease, ulcerative colitis never affects the small intestine and does not affect the full thickness of the intestine. The disease usually begins in the rectum and the sigmoid colon and eventually spreads partially or completely through out the large intestine. The cause of ulcerative colitis is unknown.

Treatment of ulcerative colitis is directed to controlling inflammation, reducing symptoms, and replacing lost fluids and nutrients. Anticholinergic drugs and low doses of diphenoxylate or loperamide are administered for treating mild diarrhea. For more intense diarrhea higher doses of diphenoxylate or loperamide, or deodorized opium tincture or codeine are administered. Sulfasalazine, olsalazie, prednisone, or mesalamine can be used to reduce inflammation. Azathioprine and mercaptopurine have been used to maintain remissions in ulcerative-colitis patients who would otherwise need long-term corticosteroid treatment. In severe cases of ulcerative colitis the patient is hospitalized and given corticosteroids intravenously. People with severe rectal bleeding can require transfusions and intravenous fluids. If toxic colitis develops and treatments fail, surgery to remove the large intestine can be necessary. Non-emergency surgery can be performed if cancer is diagnosed, precancerous legions are detected, or unremitting chronic disease would otherwise make the person an invalid or dependent on high doses of corticosteroids. Complete removal of the large intestine and rectum permanently cures ulcerative colitis. *The Merck Manual of Medical Information* 530-532 (R. Berkow ed., 1997) and *Goodman and Gilman's The Pharmacological Basis of Therapeutics* (J. Hardman and L. Limbird eds., $9^{th}$ ed. 1996).

IBS is a disorder of motility of the entire gastrointestinal tract, causing abdominal pain, constipation, and/or diarrhea. IBS affects three-times more women than men. In IBS stimuli such as stress, diet, drugs, hormones, or irritants can cause the gastrointestinal tract to contract abnormally. During an episode of IBS contractions of the gastrointestinal tract become stronger and more frequent, resulting in the rapid transit of food and feces through the small intestine, often leading to diarrhea. Cramps result from the strong contractions of the large intestine and increased sensitivity of pain receptors in the large intestine.

There are two major types of res. The first type, spastic-colon type, is commonly triggered by eating, and usually produces periodic constipation and diarrhea with pain. Mucous often appears in the stool. The pain can come in bouts of continuous dull aching pain or cramps, usually in the lower abdomen. The person suffering from spastic-colon type IBS can also experience bloating, gas, nausea, headache, fatigue, depression, anxiety, and difficulty concentrating. The second type of IBS usually produces painless diarrhea or constipation. The diarrhea can begin suddenly and with extreme urgency. Often the diarrhea occurs soon after a meal and can sometimes occur immediately upon awakening.

Treatment of IBS typically involves modification of an IBS-patient's diet. Often it is recommended that an IBS patient avoid beans, cabbage, sorbitol, and fructose. A low-fat, high-fiber diet can also help some IBS patients. Regular physical activity can also help keep the gastrointestinal tract functioning properly. Drugs such as propantheline that slow the function of the gastrointestinal tract are generally not effective for treating IBS. Antidiarrheal drugs, such as diphenoxylate and loperamide, help with diarrhea. *The Merck Manual of Medical Information* 525-526 (R. Berkow ed., 1997).

Many drugs can cause physical and/or psychological addiction. Those most well known types of these drugs include opiates, such as heroin, opium, and morphine; sympathomimetics, including cocaine and amphetamines; sedative-hypnotics, including alcohol, benzodiazepines and barbiturates; and nicotine, which has effects similar to opioids and sympathomimetics. Drug addiction is characterized by a craving or compulsion for taking the drug and an inability to limit its intake. Additionally, drug dependence is associated with drug tolerance, the loss of effect of the drug following repeated administration, and withdrawal, the appearance of physical and behavioral symptoms when the drug is not consumed. Sensitization occurs if repeated administration of a drug leads to an increased response to each dose. Tolerance, sensitization, and withdrawal are phenomena evidencing a change in the central nervous system resulting from continued use of the drug. This change can motivate the addicted individual to continue consuming the drug despite serious social, legal, physical and/or professional consequences. (See, e.g., U.S. Pat. No. 6,109,269 to Rise et al.).

Certain pharmaceutical agents have been administered for treating addiction. U.S. Pat. No. 5,556,838 to Mayer et al. discloses the use of nontoxic NMDA-blocking agents co-administered with an addictive substance to prevent the development of tolerance or withdrawal symptoms. U.S. Pat. No. 5,574,052 to Rose et al. discloses co-administration of an addictive substance with an antagonist to partially block the pharmacological effects of the substance. U.S. Pat. No. 5,075, 341 to Mendelson et al. discloses the use of a mixed opiate agonist/antagonist to treat cocaine and opiate addiction. U.S. Pat. No. 5,232,934 to Downs discloses administration of 3-phenoxypyridine to treat addiction. U.S. Pat. Nos. 5,039, 680 and 5,198,459 to Imperato et al. disclose using a serotonin antagonist to treat chemical addiction. U.S. Pat. No. 5,556,837 to Nestler et. al. discloses infusing BDNF or NT-4 growth factors to inhibit or reverse neurological adaptive changes that correlate with behavioral changes in an addicted individual. U.S. Pat. No. 5,762,925 to Sagan discloses implanting encapsulated adrenal medullary cells into an animal's central nervous system to inhibit the development of opioid intolerance. U.S. Pat. No. 6,204,284 to Beer et al. discloses racemic (±)-1-(3,4-dichlorophenyl)-3-azabicyclo [3.1.0]hexane for use in the prevention or relief of a withdrawal syndrome resulting from addiction to drugs and for the treatment of chemical dependencies.

Parkinson's disease is a clinical syndrome comprising bradykinesia (slowness and poverty of movement), muscular rigidity, resting tremor (which usually abates during voluntary movement), and an impairment of postural balance leading to disturbance of gait and falling. The features of Parkinson's disease are a loss of pigmented, dopaminergic neurons of the substantia nigra pars compacta and the appearance of intracellular inclusions known as Lewy bodies (*Goodman and Gillman's The Pharmaceutical Basis of Therapeutics* 506 (9$^{th}$ ed. 1996)). Without treatment, Parkinson's disease progresses to a rigid akinetic state in which patients are incapable of caring for themselves. Death frequently results from complications of immobility, including aspiration pneumonia or pulmonary embolism. Drugs commonly used for the treatment of Parkinson's disease include carbidopa/levodopa, pergolide, bromocriptine, selegiline, amantadine, and trihexyphenidyl hydrochloride. There remains, however, a need for drugs useful for the treatment of Parkinson's disease and having an improved therapeutic profile.

Anxiety is a fear, apprehension, or dread of impending danger often accompanied by restlessness, tension, tachycardia, and dyspnea. Other symptoms commonly associated with anxiety include depression, especially accompanied with dysthymic disorder (chronic "neurotic" depression); panic disorder; agoraphobia and other specific phobias; eating disorders; and many personality disorders. Often anxiety is unattached to a clearly identified treatable primary illness. If a primary illness is found, however, it can be desirable to deal with the anxiety at the same time as the primary illness.

Currently, benzodiazepines are the most commonly used anti-anxiety agents for generalized anxiety disorder. Benzodiazepines, however, carry the risk of producing impairment of cognition and skilled motor functions, particularly in the elderly, which can result in confusion, delerium, and falls with fractures. Sedatives are also commonly prescribed for treating anxiety. The azapirones, such as buspirone, are also used to treat moderate anxiety. The azapirones, however, are less useful for treating severe anxiety accompanied with panic attacks.

Epilepsy is a disorder characterized by the tendency to have recurring seizures. The etiology commonly consists of lesions in some part of the cortex, such as a tumor; developmental malformation; or damage due to trauma or stroke. In some cases the etiology is genetic. An epileptic seizure can be triggered by repetitive sounds, flashing lights, video games, or touching certain parts of the body. Epilepsy is typically treated with anti-seizure drugs. In epilepsy cases, where anti-seizure drugs are ineffective, and the defect in the brain is isolated to a small area of the brain, surgical removal of that part of the brain can be helpful in alleviating the seizures. In patients who have several sources for the seizures or who have seizures that spread quickly to all parts of the brain, surgical removal of the nerve fibers that connect the two sides of the brain can be helpful.

Examples of drugs for treating a seizure and epilepsy include carbamazepine, ethosuximide, gabapentin, lamotrignine, phenobarbital, phenyloin, primidone, valproic acid, trimethadione, bemzodiaepines, γ-vinyl GABA, acetazolamide, and felbamate. Anti-seizure drugs, however, can have side effects such as drowsiness; hyperactivity; hallucinations; inability to concentrate; central and peripheral nervous system toxicity, such as nystagmus, ataxia, diplopia, and vertigo; gingival hyperplasia; gastrointestinal disturbances such as nausea, vomiting, epigastric pain, and anorexia; endocrine effects such as inhibition of antidiuretic hormone, hyperglycemia, glycosuria, osteomalacia; and hypersensitivity such as scarlatiniform rash, morbilliform rash, Stevens-Johnson syndrome, systemic lupus erythematosus, and hepatic necrosis; and hematological reactions such as red-cell aplasia, agranulocytosis, thrombocytopenia, aplastic anemia, and megaloblastic anemia. *The Merck Manual of Medical Information* 345-350 (R. Berkow ed., 1997).

A seizure is the result of abnormal electrical discharge in the brain. The discharge can involve a small area of the brain and lead to the person only noticing an odd taste or smell or it can involve a large area of the brain and lead to convulsions, i.e., a seizure that causes jerking and spasms of the muscles throughout the body. Convulsions can also result in brief attacks of altered consciousness and loss of consciousness, muscle control, or bladder control. A seizures is often preceded by auras, i.e., unusual sensations of smell, taste, or vision or an intense feeling that a seizure is about to begin. A seizure typically lasts for about 2 to 5 minutes. When the seizure ends the person can have headache, sore muscles, unusual sensations, confusion, and profound fatigue (postictal state). Usually the person cannot remember what happened during the seizure.

A stroke or cerebrovascular accident, is the death of brain tissue (cerebral infarction) resulting from the lack of blood flow and insufficient oxygen to the brain. A stroke can be either ischemic or hemorrhagic. In an ischemic stroke, blood supply to the brain is cut off because of athersclerosis or a blood clot that has blocked a blood vessel. In a hemorrhagic stroke, a blood vessel bursts preventing normal blood flow and allowing blood to leak into an area of the brain and destroying it. Most strokes develop rapidly and cause brain damage within minutes. In some cases, however, strokes can continue to worsen for several hours or days. Symptoms of strokes vary depending on what part of the brain is effected. Symptoms include loss or abnormal sensations in an arm or leg or one side of the body, weakness or paralysis of an arm or leg or one side of the body, partial loss of vision or hearing, double vision, dizziness, slurred speech, difficulty in thinking of the appropriate word or saying it, inability to recognize parts of the body, unusual movements, loss of bladder control, imbalance, and falling, and fainting. The symptoms can be permanent and can be associated with coma or stupor. Strokes can cause edema or swelling of the brain which can further damage brain tissue. For persons suffering from a stroke, intensive rehabilitation can help overcome the disability caused by impairment of brain tissue. Rehabilitation trains other parts of the brain to assume the tasks previously performed by the damaged part.

Examples of drugs for treating strokes include anticoagulants such as heparin, drugs that break up clots such as streptokinase or tissue plasminogen activator, and drugs that reduce swelling such as mannitol or corticosteroids. *The Merck Manual of Medical Information* 352-355 (R. Berkow ed., 1997).

Pruritus is an unpleasant sensation that prompts scratching. Pruritus can be attributed to dry skin, scabies, dermatitis, herpetiformis, atopic dermatitis, pruritus vulvae et ani, miliaria, insect bites, pediculosis, contact dermatitis, drug reactions, urticaria, urticarial eruptions of pregnancy, psoriasis, lichen planus, lichen simplex chronicus, exfoliative dermatitis, folliculitis, bullous pemphigoid, and fiberglass dermatitis. Conventionally, pruritus is treated by phototherapy with ultraviolet B or PUVA or with therapeutic agents such as naltrexone, nalmefene, danazol, tricyclics, and antidepressants.

Selective antagonists of the metabotropic glutamate receptor 5 ("mGluR5") have been shown to exert analgesic activity in in vivo animal models (K. Walker et al., *Neuropharmacology* 40:1-9 (2000) and A. Dogrul et al., *Neuroscience Letters*, 292(2):115-118 (2000)).

Selective antagonists of the mGluR5 receptor have also been shown to exert anxiolytic and anti-depressant activity in in vivo animal models (E. Tatarczynska et al., *Br. J. Pharmacol.* 132(7):1423-1430 (2001) and P. J. M. Will et al., *Trends in Pharmacological Sciences* 22(7):331-37 (2001)).

Selective antagonists of the mGluR5 receptor have also been shown to exert anti-Parkinson activity in vivo (K. J. Ossowska et al., *Neuropharmacology* 41(4):413-20 (2001) and P. J. M. Will et al., *Trends in Pharmacological Sciences* 22(7):331-37 (2001)).

Selective antagonists of the mGluR5 receptor have also been shown to exert anti-dependence activity in vivo (C. Chiamulera et al., *Nature Neuroscience* 4(9):873-74 (2001)).

U.S. Pat. No. 6,150,129 to Cook et al. describes a class of dinitrogen heterocycles useful as antibiotics.

U.S. Pat. No. 5,529,998 to Habich et al. describes a class of benzooxazolyl- and benzothiazolyloxazolidones useful as antibacterials.

International publication no. WO 01/57008 describes a class of 2-benzothiazolyl urea derivatives useful as inhibitors of serine/threonine and tyrosine kinases.

International publication no. WO 02/08221 describes aryl piperazine compounds useful for treating chronic and acute pain conditions, itch, and urinary incontinence.

International publication no. WO 99/37304 describes substituted oxoazaheterocycly compounds useful for inhibiting factor Xa.

International publication no. WO 00/59510 describes aminopyrimidines useful as sorbitol dehydrogenase inhibitors.

Japanese patent application no. 11-199573 to Kiyoshi et al. describes benzothiazole derivatives that are neuronal 5HT3 receptor agonists in the intestinal canal nervous system and useful for treating digestive disorders and pancreatic insufficiency.

German patent application no 199 34 799 to Rainer et al. describes a chiral-smectic liquid crystal mixture containing compounds with 2 linked (hetero)aromatic rings or compounds with 3 linked (hetero)aromatic rings.

M. Chu-Moyer et al., *J. Med. Chem.* 45:511-528 (2002) describes heterocycle-substituted piperazino-pyrimidines useful as sorbitol dehydrogenase inhibitors.

B. G. Khadse et al., *Bull. Haff. Instt.* 1(3):27-32 (1975) describes 2-($N^4$-substituted-$N^1$-piperazinyl)pyrido(3,2-d) thiazoles and 5-nitro-2-($N^4$-substituted-$N^1$-piperazinyl)benzthiazoles useful as anthelmintic agents.

There remains, however, a clear need in the art for new drugs useful for treating or preventing pain, UI, an ulcer, IBD, MS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression.

Citation of any reference in Section 2 of this application is not to be construed as an admission that such reference is prior art to the present application.

3. SUMMARY OF THE INVENTION

The present invention encompasses compounds having the formula (Ia):

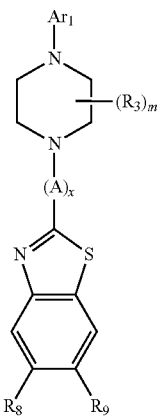

and pharmaceutically acceptable salts thereof, wherein $Ar_1$ is

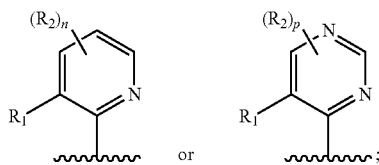

A is

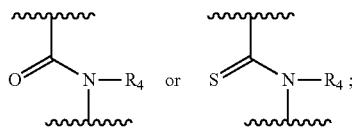

$R_1$ is —Cl, —Br, —I, —$(C_1-C_6)$alkyl, —$NO_2$, —CN, —OH, —$OCH_3$, —$NH_2$, —C(halo)$_3$, —CH(halo)$_2$, or —$CH_2$(halo);

each $R^2$ is independently:
(a) -halo, —CN, —OH, —O$(C_1-C_6)$alkyl, —$NO_2$, or —$NH_2$;
(b) —$(C_1-C_{10})$alkyl, —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, —$(C_8-C_{14})$bicycloalkenyl, —$(C_8-C_{14})$tricycloalkenyl, -(3- to 7-membered)heterocycle, or -(7- to 10-membered)bicycloheterocycle, each of which is unsubstituted or substituted with one or more $R_5$ groups; or
(c) -phenyl, -naphthyl, —$(C_{14})$aryl, or -(5- to 10-membered)heteroaryl, each of which is unsubstituted or substituted with one or more $R_6$ groups;

each $R_3$ is independently:
(a) -halo, —CN, —OH, —O$(C_1-C_6)$alkyl, —$NO_2$, or —$NH_2$;
(b) —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, —$(C_8-C_{14})$bicycloalkenyl, —$(C_8-C_{14})$tricycloalkenyl, -(3- to 7-membered)heterocycle, or -(7- to 10-membered)bicycloheterocycle, each of which is unsubstituted or substituted with one or more $R_5$ groups; or
(c) -phenyl, -naphthyl, —$(C_{14})$aryl or -(5- to 10-membered)heteroaryl, each of which is unsubstituted or substituted with one or more $R_6$ groups;

$R_4$ is —H or —$(C_1-C_6)$alkyl;

each $R_5$ is independently —CN, —OH, -halo, —$N_3$, —$NO_2$, —$N(R_7)_2$, —CH=$NR_7$, —$NR_7OH$, —$OR_7$, —$COR_7$, —C(O)$OR_7$, —OC(O)$R_7$, —OC(O)$OR_7$, —$SR_7$, —S(O)$R_7$, or —S(O)$_2R_7$;

each $R_6$ is independently —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, —$(C_3-C_5)$heterocycle, —C(halo)$_3$, —CH(halo)$_2$, —$CH_2$(halo), —CN, —OH, -halo, —$N_3$, —$NO_2$, —$N(R_7)_2$, —CH=$NR_7$, —$NR_7OH$, —$OR_7$, —$COR_7$, —C(O)$OR_7$, —OC(O)$R_7$, —OC(O)$OR_7$, —$SR_7$, —S(O)$R_7$, or —S(O)$_2R_7$;

each $R_7$ is independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, —$(C_3-C_5)$heterocycle, —C(halo)$_3$, —$CH_2$(halo), or —CH(halo)$_2$;

$R_8$ and $R_9$ are each independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, —C(halo)$_3$, —CH(halo)$_2$, —$CH_2$(halo), —OC(halo)$_3$, —OCH(halo)$_2$, —$OCH_2$(halo), —CN, —OH, -halo, —$N_3$, —$N(R_7)_2$, —CH=$NR_7$, —$NR_7OH$, —$OR_7$, —$COR_7$, —C(O)$OR_7$, —OC(O)$R_7$, —OC(O)$OR_7$, —$SR_7$, —S(O)$R_7$, or —S(O)$_2R_7$;

each -halo is —F, —Cl, —Br—, or —I;

n is an integer ranging from 0 to 3;

p is an integer ranging from 0 to 2;

m is 0 or 1; and x is 0 or 1.

The present invention encompasses compounds having the formula (Ib):

(Ib)

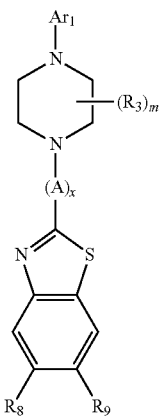

and pharmaceutically acceptable salts thereof, wherein $Ar_1$ is

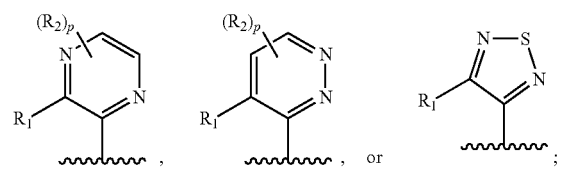

A is

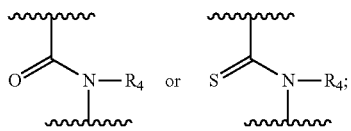

$R_1$ is —H, -halo, —$(C_1-C_6)$alkyl, —$NO_2$, —CN, —OH, —$OCH_3$, —$NH_2$, —$C(halo)_3$, —$CH(halo)_2$, or —$CH_2(halo)$;

each $R^2$ is independently:
(a) -halo, —CN, —OH, —$O(C_1-C_6)$alkyl, —$NO_2$, or —$NH_2$;
(b) —$(C_1-C_{10})$alkyl, —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, —$(C_8-C_{14})$bicycloalkenyl, —$(C_8-C_{14})$tricycloalkenyl, -(3- to 7-membered)heterocycle, or -(7- to 10-membered)bicycloheterocycle, each of which is unsubstituted or substituted with one or more $R_5$ groups; or
(c) -phenyl, -naphthyl, —$(C_{14})$aryl, or -(5- to 10-membered)heteroaryl, each of which is unsubstituted or substituted with one or more $R_6$ groups;

each $R_3$ is independently:
(a) -halo, —CN, —OH, —$O(C_1-C_6)$alkyl, —$NO_2$, or —$NH_2$;
(b) —$(C_1-C_{10})$alkyl, —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, —$(C_8-C_{14})$bicycloalkenyl, —$(C_8-C_{14})$tricycloalkenyl, -(3- to 7-membered)heterocycle, or -(7- to 10-membered)bicycloheterocycle, each of which is unsubstituted or substituted with one or more $R_5$ groups; or
(c) -phenyl, -naphthyl, —$(C_{14})$aryl or -(5- to 10-membered)heteroaryl, each of which is unsubstituted or substituted with one or more $R_6$ groups;

$R_4$ is —H or —$(C_1-C_6)$alkyl;

each $R_5$ is independently —CN, —OH, -halo, —$N_3$, —$NO_2$, —$N(R_7)_2$, —CH=$NR_7$, —$NR_7$OH, —$OR_7$, —$COR_7$, —$C(O)OR_7$, —$OC(O)R_7$, —$OC(O)OR_7$, —$SR_7$, —$S(O)R_7$, or —$S(O)_2R_7$;

each $R_6$ is independently —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, —$(C_3-C_5)$heterocycle, —$C(halo)_3$, —$CH(halo)_2$, —$CH_2(halo)$, —CN, —OH, -halo, —$N_3$, —$NO_2$, —$N(R_7)_2$, —CH=$NR_7$, —$NR_7$OH, —$OR_7$, —$COR_7$, —$C(O)OR_7$, —$OC(O)R_7$, —$OC(O)OR_7$, —$SR_7$, —$S(O)R_7$, or —$S(O)_2R_7$;

each $R_7$ is independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, —$(C_3-C_5)$heterocycle, —$C(halo)_3$, —$CH_2(halo)$, or —$CH(halo)_2$;

$R_8$ and $R_9$ are each independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, —$C(halo)_3$, —$CH(halo)_2$, —$CH_2(halo)$, —$OC(halo)_3$, —$OCH(halo)_2$, —$OCH_2(halo)$, —CN, —OH, -halo, —$N_3$, —$N(R_7)_2$, —CH=$NR_7$, —$NR_7$OH, —$OR_7$, —$COR_7$, —$C(O)OR_7$, —$OC(O)R_7$, —$OC(O)OR_7$, —$SR_7$, —$S(O)R_7$, or —$S(O)_2R_7$;

each -halo is —F, —Cl, —Br, — or —I;
p is an integer ranging from 0 to 2;
m is 0 or 1; and
x is 0 or 1.

The present invention encompasses compounds having the formula (IIa):

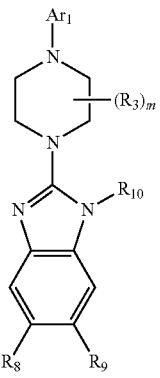

(IIa)

and pharmaceutically acceptable salts thereof, wherein
$Ar_1$ is

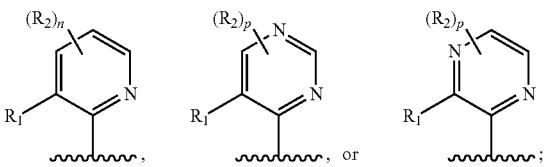

$R_1$ is —Cl, —Br, —I, —$(C_1-C_6)$alkyl, —$NO_2$, —CN, —OH, —$OCH_3$, —$NH_2$, —$C(halo)_3$, —$CH(halo)_2$, or —$CH_2(halo)$;

each $R^2$ is independently:
(a) -halo, —CN, —OH, —$O(C_1-C_6)$alkyl, —$NO_2$, or —$NH_2$;
(b) —$(C_1-C_{10})$alkyl, —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, —$(C_8-C_{14})$bicycloalkenyl, —$(C_8-C_{14})$tricycloalkenyl, -(3- to 7-membered)heterocycle, or -(7- to 10-membered)bicycloheterocycle, each of which is =substituted or substituted with one or more $R_5$ groups; or
(c) -phenyl, -naphthyl, —$(C_{14})$aryl, or -(5- to 10-membered)heteroaryl, each of which is unsubstituted or substituted with one or more $R_6$ groups;

each $R_3$ is independently:
(a) -halo, —CN, —OH, —$O(C_1-C_6)$alkyl, —$NO_2$, or —$NH_2$;
(b) —$(C_1-C_{10})$alkyl, —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, —$(C_8-C_{14})$bicycloalkenyl, —$(C_8-C_{14})$tricycloalkenyl, -(3- to 7-membered)heterocycle, or -(7- to 10-membered)bicycloheterocycle, each of which is unsubstituted or substituted with one or more $R_5$ groups; or
(c) -phenyl, -naphthyl, —$(C_{14})$aryl or -(5- to 10-membered)heteroaryl, each of which is unsubstituted or substituted with one or more $R_6$ groups;

each $R_5$ is independently —CN, —OH, -halo, —$N_3$, —$NO_2$, —$N(R_7)_2$, —CH=$NR_7$, —$NR_7$OH, —$OR_7$, —$COR_7$, —$C(O)OR_7$, —$OC(O)R_7$, —$OC(O)OR_7$, —$SR_7$, —$S(O)R_7$, or —$S(O)_2R_7$;

each $R_6$ is independently —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, —$(C_3-C_5)$heterocycle, —$C(halo)_3$, —$CH(halo)_2$, —$CH_2(halo)$, —CN, —OH, -halo, —$N_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$;

each R$_7$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —(C$_3$-C$_5$)heterocycle, —C(halo)$_3$, —CH$_2$(halo), or —CH(halo)$_2$;

R$_8$ and R$_9$ are each independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —C(halo)$_3$, —CH(halo)$_2$, —CH$_2$(halo), —OC(halo)$_3$, —OCH(halo)$_2$, —OCH$_2$(halo), —CN, —OH, -halo, —N$_3$, —N(R$_7$)$_2$, —CH=NR$_7$, —NR$_7$OH, —OR$_7$, OR$_7$, —C(O)OR$_7$, —OC(O)R$_7$, —OC(O)OR$_7$, —SR$_7$, —S(O)R$_7$, or —S(O)$_2$R$_7$;

R$_{10}$ is —H or —(C$_1$-C$_4$)alkyl;
each -halo is —F, —Cl, —Br—, or —I;
n is an integer ranging from 0 to 3;
p is an integer ranging from 0 to 2; and
m is 0 or 1.

The present invention encompasses compounds having the formula (IIb):

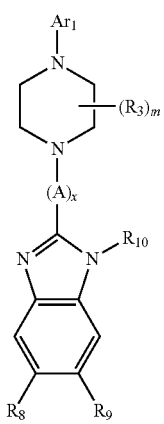

(IIb)

and pharmaceutically acceptable salts thereof, wherein Ar$_1$ is

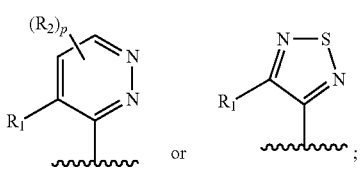

A is

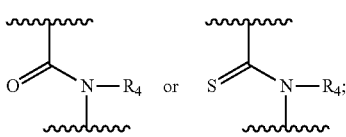

R$_1$ is —H, -halo, —(C$_1$-C$_6$)alkyl, —NO$_2$, —CN, —OH, —OCH$_3$, —NH$_2$, —C(halo)$_3$, —CH(halo)$_2$, or —CH$_2$(halo);

each R$^2$ is independently:
(a) -halo, —CN, —OH, —O(C$_1$-C$_6$)alkyl, —NO$_2$, or —NH$_2$;
(b) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more R$_5$ groups; or
(c) -phenyl, -naphthyl, —(C$_{14}$)aryl, or -(5- to 10-membered)heteroaryl, each of which is unsubstituted or substituted with one or more R$_6$ groups;

each R$_3$ is independently:
(a) -halo, —CN, —OH, —O(C$_1$-C$_6$)alkyl, —NO$_2$, or —NH$_2$;
(b) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more R$_5$ groups; or
(c) -phenyl, -naphthyl, —(C$_{14}$)aryl or -(5- to 10-membered)heteroaryl, each of which is unsubstituted or substituted with one or more R$_6$ groups;

R$_4$ is —H or —(C$_1$-C$_6$)alkyl;
each R$_5$ is independently —CN, —OH, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$;

each R$_6$ is independently —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —(C$_3$-C$_5$)heterocycle, —C(halo)$_3$, —CH(halo)$_2$, —CH$_2$(halo), —CN, —OH, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$;

each R$_7$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —(C$_3$-C$_5$)heterocycle, —C(halo)$_3$, —CH$_2$(halo), or —CH(halo)$_2$;

R$_8$ and R$_9$ are each independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —C(halo)$_3$, —CH(halo)$_2$, —CH$_2$(halo), —OC(halo)$_3$, —OCH(halo)$_2$, —OCH$_2$(halo), —CN, —OH, -halo, —N$_3$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$;

R$_{10}$ is —H or —(C$_1$-C$_4$)alkyl;
each -halo is —F, —Cl, —Br—, or —I;
p is an integer ranging from 0 to 2;
m is 0 or 1; and
x is 0 or 1.

The present invention encompasses compounds having the formula (IIIa):

(IIIa)

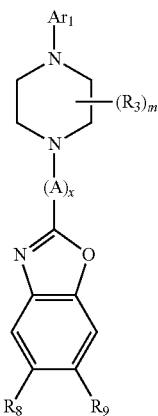

and pharmaceutically acceptable salts thereof, wherein
Ar$_1$ is

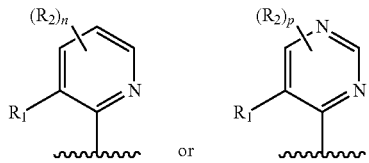

or

A is

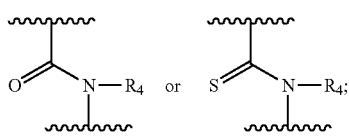

R$_1$ is —Cl, —Br, —I, —(C$_1$-C$_6$)alkyl, —NO$_2$, —CN, —OH, —OCH$_3$, —NH$_2$, —C(halo)$_3$, —CH(halo)$_2$, or —CH$_2$(halo);

each R$^2$ is independently:
(a) -halo, —CN, —OH, —O(C$_1$-C$_6$)alkyl, —NO$_2$, or —NH$_2$;
(b) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more R$_5$ groups; or
(c) -phenyl, -naphthyl, —(C$_{14}$)aryl, or -(5- to 10-membered)heteroaryl, each of which is unsubstituted or substituted with one or more R$_6$ groups;

each R$_3$ is independently:
(a) -halo, —CN, —OH, —O(C$_1$-C$_6$)alkyl, —NO$_2$, or —NH$_2$;
(b) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more R$_5$ groups; or
(c) -phenyl, -naphthyl, —(C$_{14}$)aryl or -(5- to 10-membered)heteroaryl, each of which is unsubstituted or substituted with one or more R$_6$ groups;

R$_4$ is —H or —(C$_1$-C$_6$)alkyl;

each R$_5$ is independently —CN, —OH, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$;

each R$_6$ is independently —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —(C$_3$-C$_5$)heterocycle, —C(halo)$_3$, —CH(halo)$_2$, —CH$_2$(halo), —CN, —OH, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$;

each R$_7$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —(C$_3$-C$_5$)heterocycle, —C(halo)$_3$, —CH$_2$(halo), or —CH(halo)$_2$;

R$_8$ and R$_9$ are each independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —C(halo)$_3$, —CH(halo)$_2$, —CH$_2$(halo), —OC(halo)$_3$, —OCH(halo)$_2$, —OCH$_2$(halo), —CN, —OH, -halo, —N$_3$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$;

each -halo is —F, —Cl, —Br—, or —I;

n is an integer ranging from 0 to 3;

p is an integer ranging from 0 to 2;

m is 0 or 1; and x is 0 or 1.

The present invention encompasses compounds having the formula (IIIb):

(IIIb)

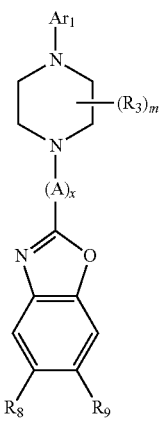

and pharmaceutically acceptable salts thereof, wherein
Ar$_1$ is

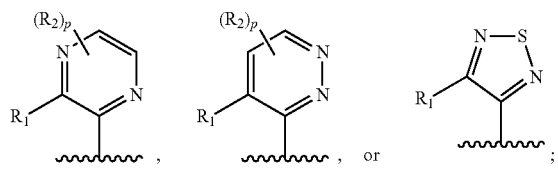

A is

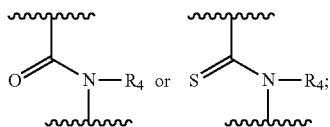 or ;

$R_1$ is —H, -halo, —$(C_1-C_6)$alkyl, —$NO_2$, —CN, —OH, —$OCH_3$, —$NH_2$, —$C(halo)_3$, —$CH(halo)_2$, or —$CH_2(halo)$;

each $R^2$ is independently:
 (a) -halo, —CN, —OH, —$O(C_1-C_6)$alkyl, —$NO_2$, or —$NH_2$;
 (b) —$(C_1-C_{10})$alkyl, —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, —$(C_8-C_{14})$bicycloalkenyl, —$(C_8-C_{14})$tricycloalkenyl, or -(7- to 10-membered)bicycloheterocycle, each of which is unsubstituted or substituted with one or more $R_5$ groups; or
 (c) -phenyl, -naphthyl, or —$(C_{14})$aryl each of which is unsubstituted or substituted with one or more $R_6$ groups;

each $R_3$ is independently:
 (a) -halo, —CN, —OH, —$O(C_1-C_6)$alkyl, —$NO_2$, or —$NH_2$;
 (b) —$(C_1-C_{10})$alkyl, —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, —$(C_8-C_{14})$bicycloalkenyl, —$(C_8-C_{14})$tricycloalkenyl, -(3- to 7-membered)heterocycle, or -(7- to 10-membered)bicycloheterocycle, each of which is unsubstituted or substituted with one or more $R_5$ groups; or
 (c) -phenyl, -naphthyl, —$(C_{14})$aryl or -(5- to 10-membered)heteroaryl, each of which is unsubstituted or substituted with one or more $R_6$ groups;

$R_4$ is —H or —$(C_1-C_6)$alkyl;

each $R_5$ is independently —CN, —OH, -halo, —$N_3$, —$NO_2$, —$N(R_7)_2$, —CH=$NR_7$, —$NR_7OH$, —$OR_7$, —$COR_7$, —$C(O)OR_7$, —$OC(O)R_7$, —$OC(O)OR_7$, —$SR_7$, —$S(O)R_7$, or —$S(O)_2R_7$;

each $R_6$ is independently —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, —$(C_3-C_5)$heterocycle, —$C(halo)_3$, —$CH(halo)_2$, —$CH_2(halo)$, —CN, —OH, -halo, —$N_3$, —$NO_2$, —$N(R_7)_2$, —CH=$NR_7$, —$NR_7OH$, —$OR_7$, —$COR_7$, —$C(O)OR_7$, —$OC(O)R_7$, —$OC(O)OR_7$, —$SR_7$, —$S(O)R_7$, or —$S(O)_2R_7$;

each $R_7$ is independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, —$(C_3-C_5)$heterocycle, —$C(halo)_3$, —$CH_2(halo)$, or —$CH(halo)_2$;

$R_8$ and $R_9$ are each independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, —$C(halo)_3$, —$CH(halo)_2$, —$CH_2(halo)$, —$OC(halo)_3$, —$OCH(halo)_2$, —$OCH_2(halo)$, —CN, —OH, -halo, —$N_3$, —$N(R_7)_2$, —CH=$NR_7$, —$NR_7OH$, —$OR_7$, —$COR_7$, —$C(O)OR_7$, —$OC(O)R_7$, —$OC(O)OR_7$, —$SR_7$, —$S(O)R_7$, or —$S(O)_2R_7$;

each -halo is —F, —Cl, —Br—, or —I;

p is an integer ranging from 0 to 2;

m is 0 or 1; and x is 0 or 1.

The present invention also encompasses compounds having the formula (IVa):

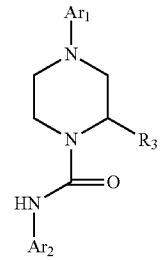

(IVa)

and pharmaceutically acceptable salts thereof, wherein $Ar_1$ is

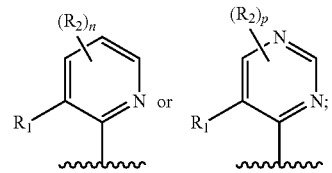

$Ar_2$ is

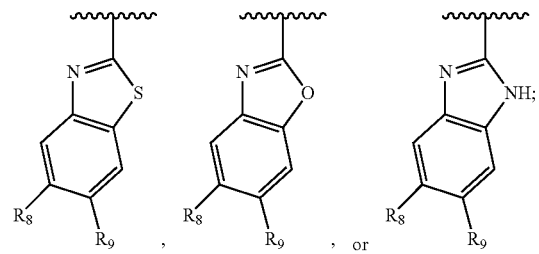

$R_1$ is -halo, —$(C_1-C_6)$alkyl, —$NO_2$, —CN, —OH, —$OCH_3$, —$NH_2$, —$C(halo)_3$, —$CH(halo)_2$, or —$CH_2(halo)$;

each $R^2$ is independently:
 (a) -halo, —CN, —OH, —$O(C_1-C_6)$alkyl, —$NO_2$, or —$NH_2$;
 (b) —$(C_1-C_{10})$alkyl, —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, —$(C_8-C_{14})$bicycloalkenyl, —$(C_8-C_{14})$tricycloalkenyl, -(3- to 7-membered) heterocycle, or -(7- to 10-membered)bicycloheterocycle, each of which is unsubstituted or substituted with one or more $R_5$ groups; or
 (c) -phenyl, -naphthyl, —$(C_{14})$aryl, or -(5- to 10-membered)heteroaryl, each of which is unsubstituted or substituted with one or more $R_6$ groups;

$R_3$ is —H or —$CH_3$:

each $R_5$ is independently —CN, —OH, -halo, —$N_3$, —$NO_2$, —$N(R_7)_2$, —CH=$NR_7$, —$NR_7OH$, —$OR_7$, —$COR_7$, —$C(O)OR_7$, —$OC(O)R_7$, —$OC(O)OR_7$, —$SR_7$, —$S(O)R_7$, or —$S(O)_2R_7$;

each $R_6$ is independently —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, —$(C_3-C_5)$heterocycle, —$C(halo)_3$, —$CH(halo)_2$, —$CH_2(halo)$, —CN, —OH, -halo, —$N_3$, —$NO_2$, —$N(R_7)_2$, —CH=$NR_7$, —$NR_7OH$, —$OR_7$, —$COR_7$, —$C(O)OR_7$, —$OC(O)R_7$, —$OC(O)OR_7$, —$SR_7$, —$S(O)R_7$, or —$S(O)_2R_7$;

each $R_7$ is independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$ cycloalkenyl, -phenyl, —(C$_3$-C$_5$)heterocycle, —C(halo)$_3$, —CH$_2$(halo), or —CH(halo)$_2$;

R$_8$ and R$_9$ are each independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —C(halo)$_3$, —CH(halo)$_2$, —CH$_2$(halo), —OC(halo)$_3$, —OCH(halo)$_2$, —OCH$_2$(halo), —CN, —OH, -halo, —N$_3$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$;

each -halo is —F, —Cl, —Br—, or —I;

n is an integer ranging from 0 to 3; and p is an integer ranging from 0 to 2.

The present invention also encompasses compounds having the formula (IVb):

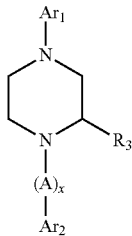

(IVb)

and pharmaceutically acceptable salts thereof, wherein
Ar$_1$ is

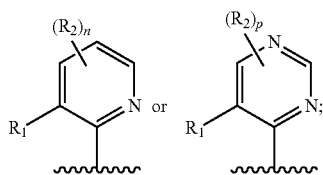

Ar$_2$ is

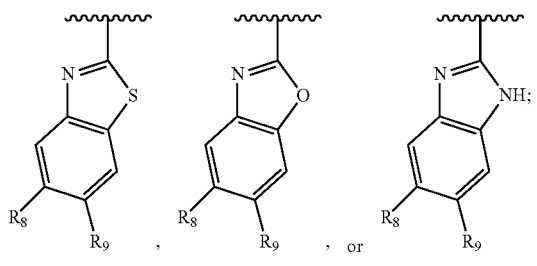

A is

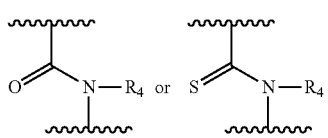

R$_1$ is -halo, —(C$_1$-C$_6$)alkyl, —NO$_2$, —CN, —OH, —OCH$_3$, —NH$_2$, —C(halo)$_3$, —CH(halo)$_2$, or —CH$_2$(halo);

each R$^2$ is independently:

(a) -halo, —CN, —OH, —O(C$_1$-C$_6$)alkyl, —NO$_2$, or —NH$_2$;

(b) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more R$_5$ groups; or (c) -phenyl, -naphthyl, —(C$_{14}$)aryl, or -(5- to 10-membered)heteroaryl, each of which is unsubstituted or substituted with one or more R$_6$ groups;

R$_3$ is —CH$_3$;

R$_4$ is —H or —(C$_1$-C$_6$)alkyl;

each R$_5$ is independently —CN, —OH, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$;

each R$_6$ is independently —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —(C$_3$-C$_5$)heterocycle, —C(halo)$_3$, —CH(halo)$_2$, —CH$_2$(halo), —CN, —OH, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$;

each R$_7$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —(C$_3$-C$_5$)heterocycle, —C(halo)$_3$, —CH$_2$(halo), or —CH(halo)$_2$;

R$_8$ and R$_9$ are each independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —C(halo)$_3$, —CH(halo)$_2$, —CH$_2$(halo), —OC(halo)$_3$, —OCH(halo)$_2$, —OCH$_2$(halo), —CN, —OH, -halo, —N$_3$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$;

each -halo is —F, —Cl, —Br—, or —I;

n is an integer ranging from 0 to 3;

p is an integer ranging from 0 to 2; and x is 0 or 1.

The present invention also encompasses compounds having the formula (V):

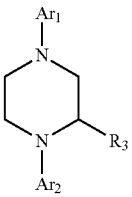

(V)

and pharmaceutically acceptable salts thereof, wherein
Ar$_1$ is

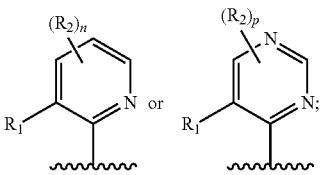

Ar$_2$ is

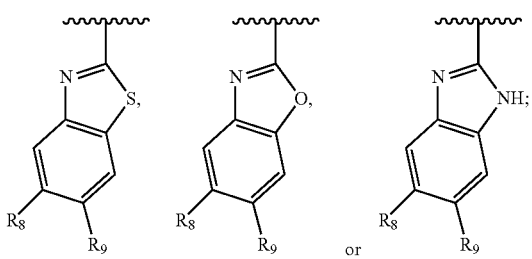

R$_1$ is —halo, —(C$_1$-C$_6$)alkyl, —NO$_2$, —CN, —OH, —OCH$_3$, —NH$_2$, —C(halo)$_3$, —CH(halo)$_2$, or —CH$_2$(halo);
each R$^2$ is independently:
(a) -halo, —CN, —OH, —O(C$_1$-C$_6$)alkyl, —NO$_2$, or —NH$_2$;
(b) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more R$_5$ groups; or
(c) -phenyl, -naphthyl, —(C$_{14}$)aryl, or -(5- to 10-membered)heteroaryl, each of which is unsubstituted or substituted with one or more R$_6$ groups;
R$_3$ is —H or —CH$_3$;
each R$_5$ is independently —CN, —OH, -halo, —N$_3$, —NO$_2$, —N(R$_7$)$_2$, —CH═NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$;
each R$_6$ is independently —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —(C$_3$-C$_5$)heterocycle, —C(halo)$_3$, —CH(halo)$_2$, —CH$_2$(halo), —CN, —OH, -halo, —N$_3$, —NO$_2$, —N(R$_7$)$_2$, —CH═NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$;
each R$_7$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —(C$_3$-C$_5$)heterocycle, —C(halo)$_3$, —CH$_2$(halo), or —CH(halo)$_2$;
R$_8$ and R$_9$ are each independently —H, —(C$_1$-C$_6$)alkyl; —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —C(halo)$_3$, —CH(halo)$_2$, —CH$_2$(halo), —OC(halo)$_3$, —OCH(halo)$_2$, —OCH$_2$(halo), —CN, —OH, -halo, —N$_3$, —N(R$_7$)$_2$, —CH═NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$;
each -halo is —F, —Cl, —Br—, or —I;
n is an integer ranging from 0 to 3; and
p is an integer ranging from 0 to 2.
A compound of formula (Ia), (Ib), (IIa), (IIb), (IIIa), (IIIb), (IVa), (IVb), and (V) or a pharmaceutically acceptable salt thereof (a "Benzoazolylpiperazine Compound") is useful for treating or preventing pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression in an animal.

The invention also relates to compositions comprising an effective amount of a Benzoazolylpiperazine Compound and a pharmaceutically acceptable carrier or excipient. The compositions are useful for treating or preventing pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression in an animal.

The invention further relates to methods for treating pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression comprising administering to an animal in need thereof an effective amount of a Benzoazolylpiperazine Compound.

The invention further relates to methods for preventing pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression comprising administering to an animal in need thereof an effective amount of a Benzoazolylpiperazine Compound.

The invention still further relates to methods for inhibiting Vanilloid Receptor 1 ("VR1") function in a cell, comprising contacting a cell capable of expressing VR1 with an effective amount of a Benzoazolylpiperazine Compound.

The invention still further relates to methods for inhibiting mGluR5 function in a cell, comprising contacting a cell capable of expressing mGluR5 with an effective amount of a Benzoazolylpiperazine Compound.

The invention still further relates to methods for inhibiting metabotropic glutamate receptor 1 ("mGluR1") function in a cell, comprising contacting a cell capable of expressing mGluR1 with an effective amount of a Benzoazolylpiperazine Compound.

The invention still further relates to a method for preparing a composition comprising the step of admixing a Benzoazolylpiperazine Compound and a pharmaceutically acceptable carrier or excipient.

The invention still further relates to a kit comprising a container containing an effective amount of a Benzoazolylpiperazine Compound.

The present invention still further relates to a compound selected from the group consisting of

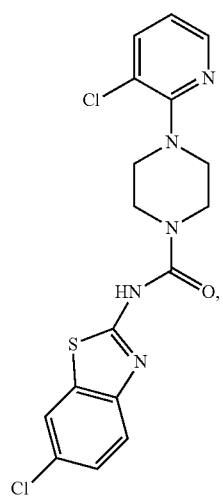

-continued
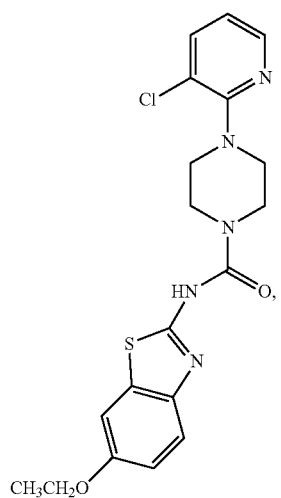
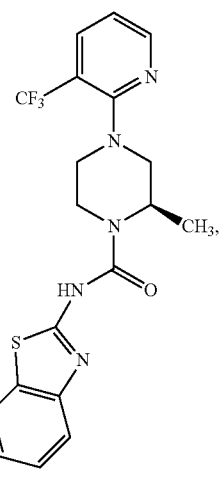
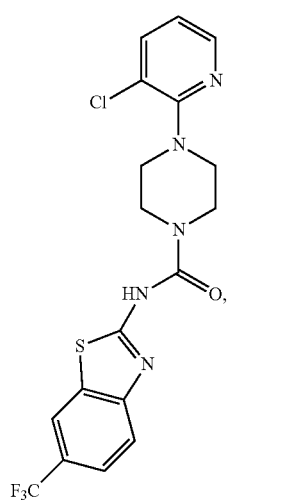
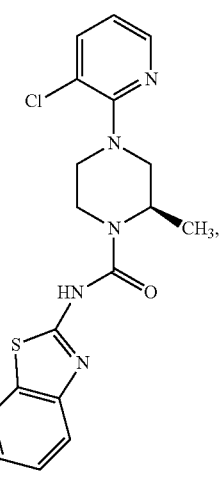
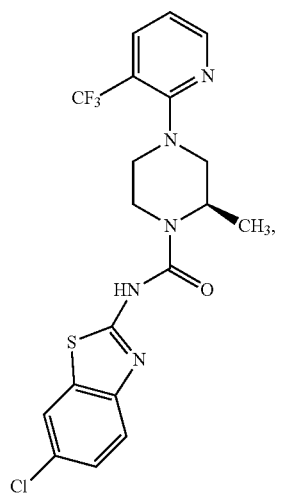

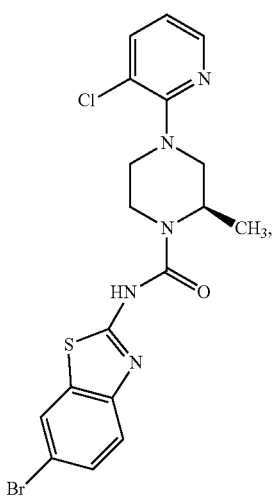
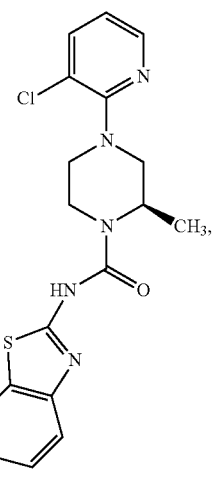
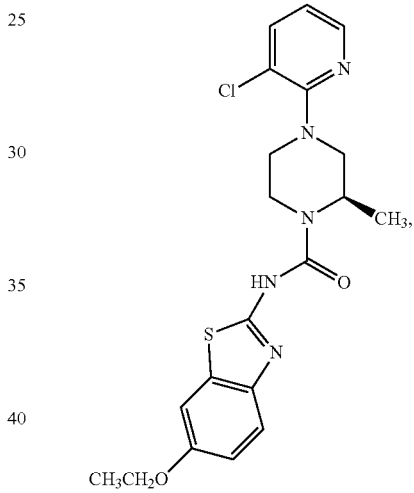
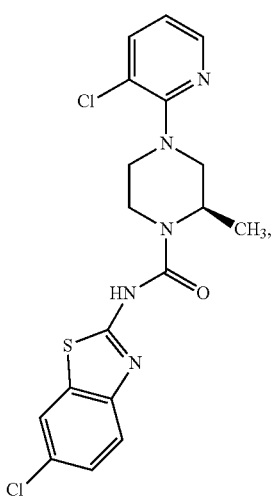
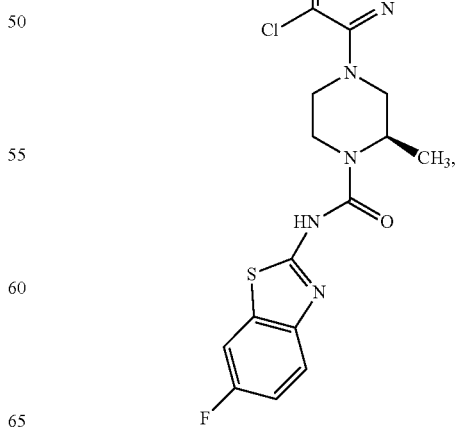

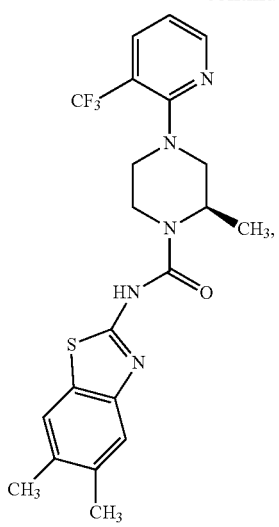
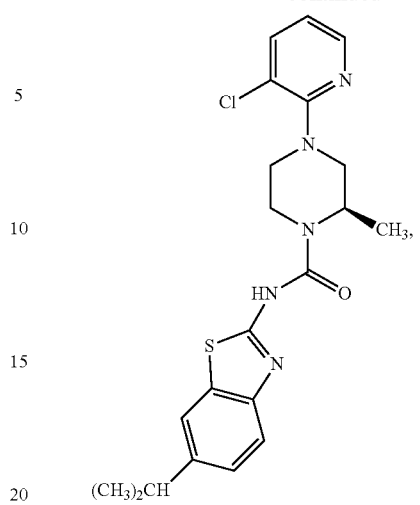
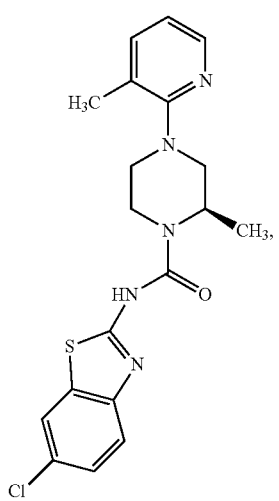
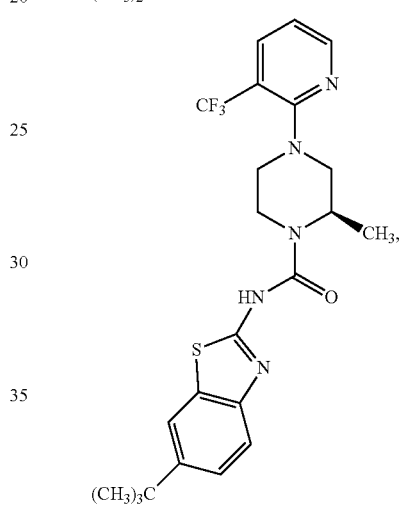
and pharmaceutically acceptable salts thereof.
The present invention still further relates to a compound selected from the group consisting of
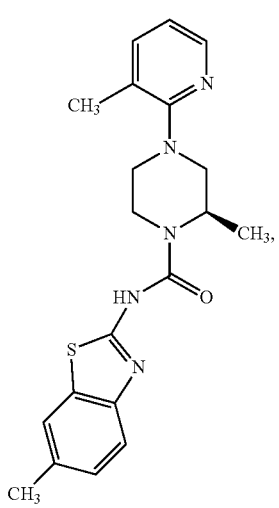
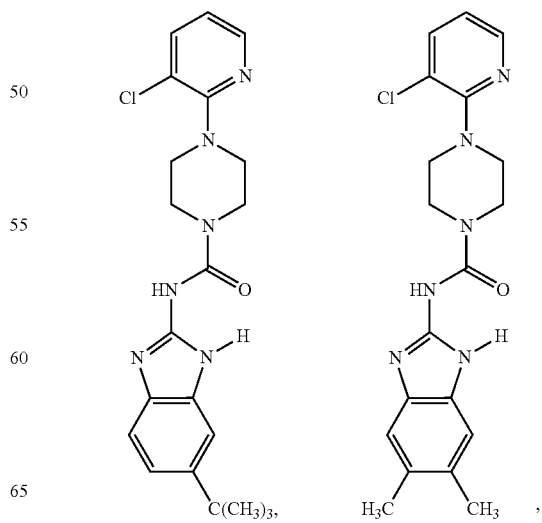

-continued
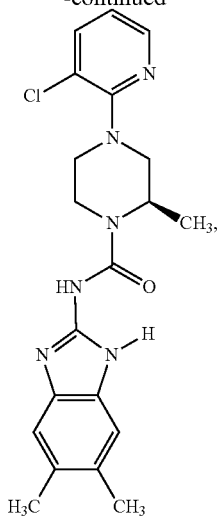
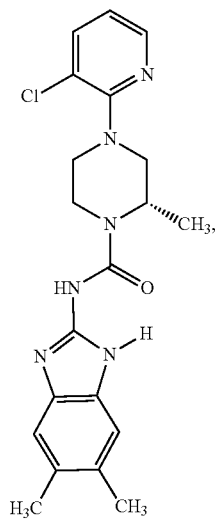
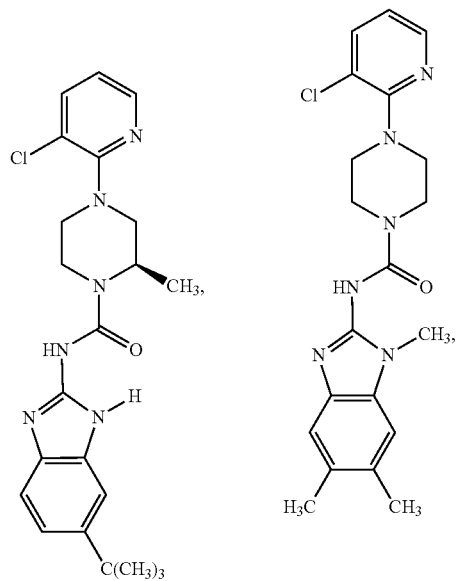
-continued
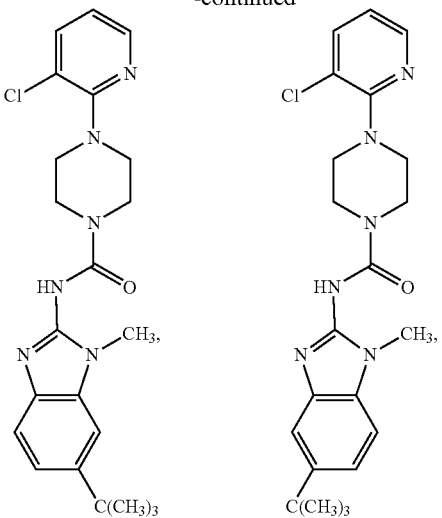
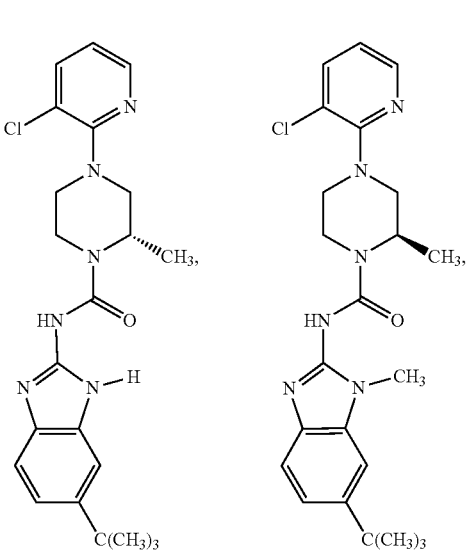
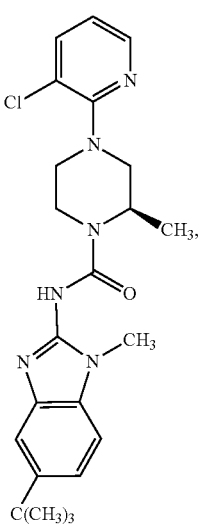

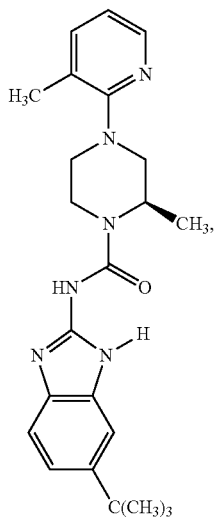
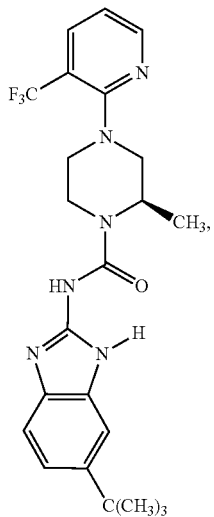
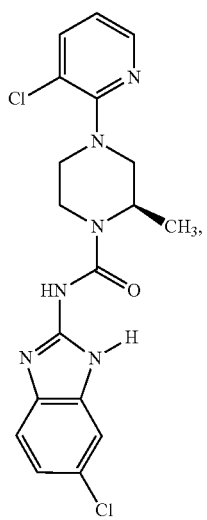
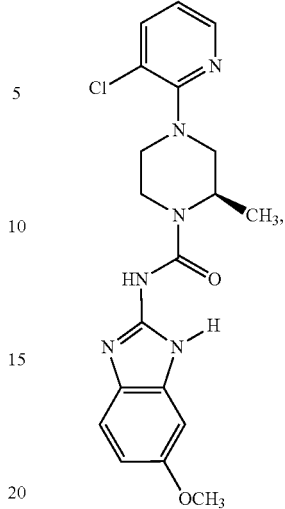
and pharmaceutically acceptable salts thereof.
The present invention still further relates to a compound selected from the group consisting of
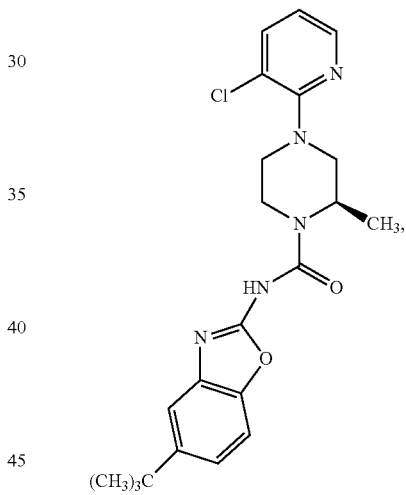
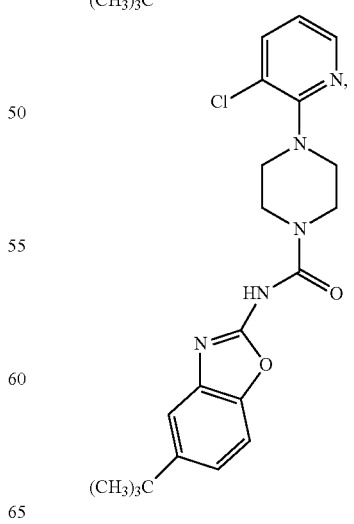
and pharmaceutically acceptable salts thereof.

4. DETAILED DESCRIPTION OF THE INVENTION

4.1 The Compounds of Formula (Ia)

As stated above, the present invention encompasses compounds of Formula (Ia)

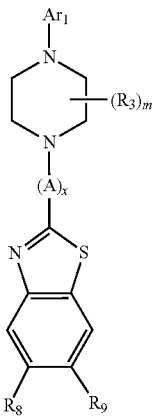

(Ia)

and pharmaceutically acceptable salts thereof, where $Ar_1$, $R_3$, $R_8$, $R_9$, A, x, and m, are defined above for the Benzoazolylpiperazine Compounds of formula (Ia).

In one embodiment, $Ar_1$ is a pyridyl group.
In another embodiment, $Ar_1$ is a pyrimidinyl group.
In another embodiment, x is 1 and A is —C(O)—N($R_4$)—.
In another embodiment, x is 1 and A is —C(S)—N($R_4$)—.
In another embodiment x is 0.
In another embodiment, n or p is 0.
In another embodiment, n or p is 1.
In another embodiment, m is 0.
In another embodiment, m is 1.
In another embodiment, $R_4$ is —H.
In another embodiment, $R_4$ is —($C_1$-$C_6$)alkyl.
In another embodiment, $Ar_1$ is a pyridyl group, x is 1, and A is —C(O)N($R_4$)—.
In another embodiment, $Ar_1$ is a pyridyl group, x is 1, and A is —C(S)N($R_4$)—.
In another embodiment, $Ar_1$ is a pyrimidinyl group, x is 1, and A is —C(O)N($R_4$)—.
In another embodiment, $Ar_1$ is a pyrimidinyl group, x is 1, and A is —C(S)N($R_4$)—.
In another embodiment, $R_1$ is —Cl.
In another embodiment, $R_1$ is —Br.
In another embodiment, $R_1$ is —I.
In another embodiment, $R_1$ is —($C_1$-$C_6$)alkyl.
In another embodiment, $R_1$ is —$CH_3$.
In another embodiment, $R_1$ is —$NO_2$.
In another embodiment, $R_1$ is —CN.
In another embodiment, $R_1$ is —OH.
In another embodiment, $R_1$ is —$OCH_3$.
In another embodiment, $R_1$ is —$NH_2$.
In another embodiment, $R_1$ is —C(halo)$_3$.
In another embodiment, $R_1$ is —CH(halo)$_2$.
In another embodiment, $R_1$ is —$CH_2$(halo).

In another embodiment, n and p are 1 and $R_2$ is -halo, —CN, —OH, —O($C_1$-$C_6$)alkyl, —$NO_2$, or —$NH_2$.
In another embodiment, n and p are 1 and $R_2$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups.
In another embodiment, n and p are 1 and $R_2$ is -phenyl, -naphthyl, —($C_{14}$)aryl, or -(5- to 10-membered)heteroaryl, each of which is unsubstituted or substituted with one or more $R_6$ groups;
In another embodiment, m is 1 and $R_3$ is -halo, —CN, —OH, —O($C_1$-$C_6$)alkyl, —$NO_2$, or —$NH_2$.
In another embodiment, m is 1 and $R_3$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups.
In another embodiment, m is 1 and $R_3$ is -phenyl, -naphthyl, —($C_{14}$)aryl or -(5- to 10-membered)heteroaryl, each of which is unsubstituted or substituted with one or more $R_6$ groups.
In another embodiment, $R_8$ and $R_9$ are each independently —H, -halo, —($C_1$-$C_6$)alkyl, —O($C_1$-$C_6$)alkyl, —C(halo)$_3$, —CH(halo)$_2$, or —$CH_2$(halo).
In another embodiment, at least one of $R_8$ and $R_9$ is —H.
In another embodiment, n, p, and m are 0; $R_1$ is —Cl, —Br, or, —I; x is 1; A is —C(O)—N($R_4$)—; $R_4$ is —H; and $R_8$ and $R_9$ are —H.
In another embodiment, n, p, and m are 0; $R_1$ is —Cl, x is 1, A is —C(O)—N($R_4$)—, $R_4$ is —H, and $R_8$ and $R_9$ are —H.
In another embodiment, n, p, and m are 0; $R_1$ is —Cl, —Br, or —I; x is 1; A is —C(O)—N($R_4$)—; $R_4$ is —H; $R_8$ is —H; and $R_9$ is -halo. In another embodiment, $R_1$ is —Cl. In another embodiment, $R_9$ is —Cl. In another embodiment, $R_9$ is —Br. In another embodiment, $R_9$ is —F.
In another embodiment, n, p, and m are 0; $R_1$ is —Cl, x is 1, A is —C(O)—N($R_4$)—, $R_4$ is —H, $R_8$ is —H, and $R_9$ is -halo. In another embodiment, $R_1$ is —Cl. In another embodiment, $R_9$ is —Cl. In another embodiment, $R_9$ is —Br. In another embodiment, $R_9$ is —F.
In another embodiment, n, p, and m are 0; $R_1$ is —Cl, —Br, or —I; x is 1; A is —C(O)—N($R_4$)—; $R_4$ is —H; $R_8$ is -halo; and $R_9$ is —H. In another embodiment, $R_1$ is —Cl. In another embodiment, $R_8$ is —Cl. In another embodiment, $R_8$ is —Br. In another embodiment, $R_8$ is —F.
In another embodiment, n, p, and m are 0; $R_1$ is —Cl, x is 1, A is —C(O)—N($R_4$)—, $R_4$ is —H, $R_8$ is -halo, and $R_9$ is —H. In another embodiment, $R_1$ is —Cl. In another embodiment, $R_8$ is —Cl. In another embodiment, $R_8$ is —Br. In another embodiment, $R_8$ is —F.
In another embodiment, n, p, and m are 0; $R_1$ is —Cl, —Br, or —I; x is 1; A is —C(O)—N($R_4$)—; $R_4$ is —H; $R_8$ is —H; and $R_9$ is —$CH_3$.
In another embodiment, n, p, and m are 0; $R_1$ is —Cl, x is 1, A is —C(O)—N($R_4$)—, $R_4$ is —H, $R_8$ is —H, and $R_9$ is —$CH_3$.
In another embodiment, n, p, and m are 0; $R_1$ is —Cl, —Br, or —I; x is 1; A is —C(O)—N($R_4$)—; $R_4$ is —H; $R_8$ is —$CH_3$; and $R_9$ is —H.
In another embodiment, n, p, and m are 0; $R_1$ is —Cl, x is 1, A is —C(O)—N($R_4$)—, $R_4$ is —H, $R_8$ is —$CH_3$, and $R_9$ is —H.

In another embodiment, n, p, and m are 0; $R_1$ is —Cl, —Br, or —I; x is 1; A is —C(O)—N($R_4$)—; $R_4$ is —H; $R_8$ is —H; and $R_9$ is —$CF_3$.

In another embodiment, n, p, and m are 0; $R_1$ is —Cl; x is 1; A is —C(O)—N($R_4$)—; $R_4$ is —H; $R_8$ is —H; and $R_9$ is —$CF_3$.

In another embodiment, n, p, and m are 0; $R_1$ is —Cl, —Br, or —I; x is 1; A is —C(O)—N($R_4$)—; $R_4$ is —H; $R_8$ is —$CF_3$; and $R_9$ is —H.

In another embodiment, n, p, and m are 0; $R_1$ is —Cl; x is 1; A is —C(O)—N($R_4$)—; $R_4$ is —H; $R_8$ is —$CF_3$; and $R_9$ is —H.

In another embodiment, n, p, and m are 0; $R_1$ is —Cl, —Br, or —I; x is 1; A is —C(O)—N($R_4$)—; $R_4$ is —H; $R_8$ is —H; and $R_9$ is —$OCH_2CH_3$.

In another embodiment, n, p, and m are 0; $R_1$ is —Cl, x is 1; A is —C(O)—N($R_4$)—; $R_4$ is —H; $R_8$ is —H; and $R_9$ is —$OCH_2CH_3$.

In another embodiment, n, p, and m are 0; $R_1$ is —Cl, —Br, or —I; x is 1; A is —C(O)—N($R_4$)—; $R_4$ is —H; $R_8$ is —$OCH_2CH_3$; and $R_9$ is —H.

In another embodiment, n, p, and m are 0; $R_1$ is —Cl, x is 1; A is —C(O)—N($R_4$)—; $R_4$ is —H; $R_8$ is —$OCH_2CH_3$; and $R_9$ is —H.

In another embodiment, n, p, and m are 0; $R_1$ is —$CH_3$, x is 1; A is —C(O)—N($R_4$)—; $R_4$ is —H; and $R_8$ and $R_9$ are —H.

In another embodiment, n, p, and m are 0; $R_1$ is —$CH_3$, x is 1; A is —C(O)—N($R_4$)—; $R_4$ is —H; $R_8$ is —H; and $R_9$ is -halo. In another embodiment, $R_9$ is —Cl. In another embodiment, $R_9$ is —Br. In another embodiment, $R_9$ is —F.

In another embodiment, n, p, and m are 0; $R_1$ is —$CH_3$, x is 1; A is —C(O)—N($R_4$)—; $R_4$ is —H; $R_8$ is -halo; and $R_9$ is —H. In another embodiment, $R_8$ is —Cl. In another embodiment, $R_8$ is —Br. In another embodiment, $R_8$ is —F.

In another embodiment, n, p, and m are 0; $R_1$ is —$CH_3$, x is 1; A is —C(O)—N($R_4$)—; $R_4$ is —H; $R_8$ is —H; and $R_9$ is —$CH_3$.

In another embodiment, n, p, and m are 0; $R_1$ is —$CH_3$, x is 1; A is —C(O)—N($R_4$)—; $R_4$ is —H; $R_8$ is —$CH_3$; and $R_9$ is —H.

In another embodiment, n, p, and m are 0; $R_1$ is —$CH_3$; x is 1; A is —C(O)—N($R_4$)—; $R_4$ is —H; $R_8$ is —H; and $R_9$ is —$CF_3$.

In another embodiment, n, p, and m are 0; $R_1$ is —$CH_3$; x is 1; A is —C(O)—N($R_4$)—; $R_4$ is —H; $R_8$ is —$CF_3$; and $R_9$ is —H.

In another embodiment, n, p, and m are 0; $R_1$ is —$CH_3$; x is 1; A is —C(O)—N($R_4$)—; $R_4$ is —H; $R_8$ is —H; and $R_9$ is —$OCH_2CH_3$.

In another embodiment, n, p, and m are 0; $R_1$ is —$CH_3$; x is 1; A is —C(O)—N($R_4$)—; $R_4$ is —H; $R_8$ is —$OCH_2CH_3$; and $R_9$ is —H.

In another embodiment, n, p, and m are 0; $R_1$ is —$CF_3$; x is 1; A is —C(O)—N($R_4$)—; $R_4$ is —H; and $R_8$ and $R_9$ are —H.

In another embodiment, n, p, and m are 0; $R_1$ is —$CF_3$; x is 1; A is —C(O)—N($R_4$)—; $R_4$ is —H; $R_8$ is —H; and $R_9$ is -halo. In another embodiment, $R_9$ is —Cl. In another embodiment, $R_9$ is —Br. In another embodiment, $R_9$ is —F.

In another embodiment, n, p, and m are 0; $R_1$ is —$CF_3$; x is 1; A is —C(O)—N($R_4$)—; $R_4$ is —H; $R_8$ is -halo; and $R_9$ is —H. In another embodiment, $R_8$ is —Cl. In another embodiment, $R_8$ is —Br. In another embodiment, $R_8$ is —F.

In another embodiment, n, p, and m are 0; $R_1$ is —$CF_3$; x is 1; A is —C(O)—N($R_4$)—; $R_4$ is —H; $R_8$ is —H; and $R_9$ is —$CH_3$.

In another embodiment, n, p, and m are 0; $R_1$ is —$CF_3$; x is 1; A is —C(O)—N($R_4$)—; $R_4$ is —H; $R_8$ is —$CH_3$; and $R_9$ is —H.

In another embodiment, n, p, and m are 0; $R_1$ is —$CF_3$; x is 1; A is —C(O)—N($R_4$)—; $R_4$ is —H; $R_8$ is —H; and $R_9$ is —$CF_3$.

In another embodiment, n, p, and m are 0; $R_1$ is —$CF_3$; x is 1; A is —C(O)—N($R_4$)—; $R_4$ is —H; $R_8$ is —$CF_3$; and $R_9$ is —H.

In another embodiment, n, p, and m are 0; $R_1$ is —$CF_3$; x is 1; A is —C(O)—N($R_4$)—; $R_4$ is —H; $R_8$ is —H; and $R_9$ is —$OCH_2CH_3$.

In another embodiment, n, p, and m are 0; $R_1$ is —$CF_3$; x is 1; A is —C(O)—N($R_4$)—; $R_4$ is —H; $R_8$ is —$OCH_2CH_3$; and $R_9$ is —H.

In another embodiment, n, p, and m are 0; $R_1$ is —Cl, —Br, or —I; x is 1; A is —C(O)—N($R_4$)—; $R_4$ is —H; $R_8$ is -tert-butyl; and $R_9$ is —H.

In another embodiment, n, p, and m are 0; $R_1$ is —Cl; x is 1; A is —C(O)—N($R_4$)—; $R_4$ is —H; $R_8$ is -tert-butyl; and $R_9$ is —H.

In another embodiment, n, p, and m are 0; $R_1$ is $R_1$ is —Cl, —Br, or —I; x is 1; A is —C(O)—N($R_4$)—; $R_4$ is —H; $R_8$ is —H; and $R_9$ is -tert-butyl.

In another embodiment, n, p, and m are 0; $R_1$ is $R_1$ is —Cl; x is 1; A is —C(O)—N($R_4$)—; $R_4$ is —H; $R_8$ is —H; and $R_9$ is -tert-butyl.

In another embodiment, n, p, and m are 0; $R_1$ is —$CH_3$; x is 1; A is —C(O)—N($R_4$)—; $R_4$ is —H; $R_8$ is -tert-butyl; and $R_9$ is —H.

In another embodiment, n, p, and m are 0; $R_1$ is —$CH_3$; x is 1; A is —C(O)—N($R_4$)—; $R_4$ is —H; $R_8$ is —H; and $R_9$ is -tert-butyl.

In another embodiment, n, p, and m are 0; $R_1$ is —$CH_3$; x is 1; A is —C(O)—N($R_4$)—; $R_4$ is —H; $R_8$ is —$CH_3$; and $R_9$ is —$CH_3$.

In another embodiment, n is 0, $Ar_1$ is -2-(3-nitropyridyl)-, m is 0, x is 0, and $R_8$ and $R_9$ are —H.

In another embodiment, n is 0, $Ar_1$ is -2-(3-chloropyridyl)-, x is 1, A is —C(S)—N($R_4$)—, m is 1, $R_3$ is —$CH_3$, $R_3$ is attached to the carbon atom adjacent to the nitrogen attached to the —C(SO)—N($R_4$)— group, the carbon atom to which the $R_3$ group is attached has the R configuration, $R_8$ is —H, and $R_9$ is —$CH_3$.

In another embodiment, n and p are 0; m is 1; $R_1$ is —Cl, —Br, or —I; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —Cl; x is 1, A is —C(O)—N($R_4$)—, $R_4$ is —H, $R_3$ is —$CH_3$ and is attached to the carbon atom adjacent to the nitrogen attached to the —C(O)—N($R_4$)— group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; $R_8$ is —H; and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; $R_8$ is -halo; and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is -halo, and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; $R_3$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is -halo, and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is -halo, and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CF_3$. In another embodiment, the carbon atom to which the $R_3$ group is attached has the R configuration.

In another embodiment, n and p are 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 1; A is —C(O)—N($R_4$)—; $R_3$ is —$CH_3$ and is attached to the carbon atom adjacent to the nitrogen attached to the —C(O)—N($R_4$)— group; $R_4$ is —H; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —Cl, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 1; A is —C(O)—N($R_4$)—; $R_3$ is —$CH_3$ and is attached to the carbon atom adjacent to the nitrogen attached to the —C(O)—N($R_4$)— group; $R_4$ is —H; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —Cl, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —$CH_3$, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, n, p, and m are 0; $R_1$ is —Cl, —Br, or, —I; x is 0; $R_4$ is —H; and $R_8$ and $R_9$ are —H.

In another embodiment, n, p, and m are 0; $R_1$ is —Cl; x is 0; $R_4$ is —H; and $R_8$ and $R_9$ are —H.

In another embodiment, n, p, and m are 0; $R_1$ is —Cl, —Br, or, —I; x is 0; $R_4$ is —H; $R_8$ is —H; and $R_9$ is -halo. In another embodiment, $R_9$ is —Cl. In another embodiment, $R_9$ is —Br. In another embodiment, $R_9$ is —F.

In another embodiment, n, p, and m are 0; $R_1$ is —Cl; x is 0; $R_4$ is —H; $R_8$ is —H; and $R_9$ is -halo. In another embodiment, $R_9$ is —Cl. In another embodiment, $R_9$ is —Br. In another embodiment, $R_9$ is —F.

In another embodiment, n, p, and m are 0; $R_1$ is —Cl, —Br, or, —I; x is 0; $R_4$ is —H; $R_8$ is -halo; and $R_9$ is —H. In another embodiment, $R_8$ is —Cl. In another embodiment, $R_8$ is —Br. In another embodiment, $R_8$ is —F.

In another embodiment, n, p, and m are 0; $R_1$ is —Cl; x is 0; $R_4$ is —H; $R_8$ is -halo; and $R_9$ is —H. In another embodiment, $R_8$ is —Cl. In another embodiment, $R_8$ is —Br. In another embodiment, $R_8$ is —F.

In another embodiment, n, p, and m are 0; $R_1$ is —Cl, —Br, or, —I; x is 0; $R_4$ is —H; $R_8$ is —H; and $R_9$ is —$CH_3$.

In another embodiment, n, p, and m are 0; $R_1$ is —Cl; x is 0; $R_4$ is —H; $R_8$ is —H; and $R_9$ is —$CH_3$.

In another embodiment, n, p, and m are 0; $R_1$ is —Cl, —Br, or, —I; x is 0; $R_4$ is —H; $R_8$ is —$CH_3$; and $R_9$ is —H.

In another embodiment, n, p, and m are 0; $R_1$ is —Cl; x is 0; $R_4$ is —H; $R_8$ is —$CH_3$; and $R_9$ is —H.

In another embodiment, n, p, and m are 0; $R_1$ is —Cl, —Br, or, —I; x is 0; $R_4$ is —H; $R_8$ is —H; and $R_9$ is —$CF_3$.

In another embodiment, n, p, and m are 0; $R_1$ is —Cl; x is 0; $R_4$ is —H; $R_8$ is —H; and $R_9$ is —$CF_3$.

In another embodiment, n, p, and m are 0; $R_1$ is —Cl, —Br, or, —I; x is 0; $R_4$ is —H; $R_8$ is —$CF_3$; and $R_9$ is —H.

In another embodiment, n, p, and m are 0; $R_1$ is —Cl; x is 0; $R_4$ is —H; $R_8$ is —$CF_3$; and $R_9$ is —H.

In another embodiment, n, p, and m are 0; $R_1$ is —Cl, —Br, or, —I; x is 0; $R_4$ is —H; $R_8$ is —H; and $R_9$ is —$OCH_2CH_3$.

In another embodiment, n, p, and m are 0; $R_1$ is —Cl; x is 0; $R_4$ is —H; $R_8$ is —H; and $R_9$ is —$OCH_2CH_3$.

In another embodiment, n, p, and m are 0; $R_1$ is —Cl, —Br, or, —I; x is 0; $R_4$ is —H; $R_8$ is —$OCH_2CH_3$; and $R_9$ is —H.

In another embodiment, n, p, and m are 0; $R_1$ is —Cl; x is 0; $R_4$ is —H; $R_8$ is —$OCH_2CH_3$; and $R_9$ is —H.

In another embodiment, n, p, and m are 0; $R_1$ is —$CH_3$; x is 0; $R_4$ is —H; and $R_8$ and $R_9$ are —H.

In another embodiment, n, p, and m are 0; $R_1$ is —$CH_3$; x is 0; $R_4$ is —H; $R_8$ is —H; and $R_9$ is -halo. In another embodiment, $R_9$ is —Cl. In another embodiment, $R_9$ is —Br. In another embodiment, $R_8$ is —F.

In another embodiment, n, p, and m are 0; $R_1$ is —$CH_3$; x is 0; $R_4$ is —H; $R_8$ is -halo; and $R_9$ is —H. In another embodiment, $R_8$ is —Cl. In another embodiment, $R_8$ is —Br. In another embodiment, $R_8$ is —F.

In another embodiment, n, p, and m are 0; $R_1$ is —$CH_3$; x is 0; $R_4$ is —H; $R_8$ is —H; and $R_9$ is —$CH_3$.

In another embodiment, n, p, and m are 0; $R_1$ is —$CH_3$; x is 0; $R_4$ is —H; $R_8$ is —$CH_3$; and $R_9$ is —H.

In another embodiment, n, p, and m are 0; $R_1$ is —$CH_3$; x is 0; $R_4$ is —H; $R_8$ is —H; and $R_9$ is —$CF_3$.

In another embodiment, n, p, and m are 0; $R_1$ is —$CH_3$; x is 0; $R_4$ is —H; $R_8$ is —$CF_3$; and $R_9$ is —H.

In another embodiment, n, p, and m are 0; $R_1$ is —$CH_3$; x is 0; $R_4$ is —H; $R_8$ is —H; and $R_9$ is —$OCH_2CH_3$.

In another embodiment, n, p, and m are 0, $R_1$ is —$CH_3$; x is 0; $R_4$ is —H; $R_8$ is —$OCH_2CH_3$; and $R_9$ is —H.

In another embodiment, n, p, and m are 0; $R_1$ is —$CF_3$; x is 0; $R_4$ is —H; and $R_8$ and $R_9$ are —H.

In another embodiment, n, p, and m are 0; $R_1$ is —$CF_3$; x is 0; $R_4$ is —H; $R_8$ is —H; and $R_9$ is -halo. In another embodiment, $R_9$ is —Cl. In another embodiment, $R_9$ is —Br. In another embodiment, $R_9$ is —F.

In another embodiment, n, p, and m are 0; $R_1$ is —$CF_3$; x is 0; $R_4$ is —H; $R_8$ is -halo; and $R_9$ is —H. In another embodiment, $R_8$ is —Cl. In another embodiment, $R_8$ is —Br. In another embodiment, $R_8$ is —F.

In another embodiment, n, p, and m are 0, $R_1$ is —$CF_3$; x is 0; $R_4$ is —H; $R_8$ is —H; and $R_9$ is —$CH_3$.

In another embodiment, n, p, and m are 0; $R_1$ is —$CF_3$; x is 0; $R_4$ is —H; $R_8$ is —$CH_3$; and $R_9$ is —H.

In another embodiment, n, p, and m are 0; $R_1$ is —$CF_3$; x is 0; $R_4$ is —H; $R_8$ is —H; and $R_9$ is —$CF_3$.

In another embodiment, n, p, and m are 0; $R_1$ is —$CF_3$; x is 0; $R_4$ is —H; $R_8$ is —$CF_3$; and $R_9$ is —H.

In another embodiment, n, p, and m are 0; $R_1$ is —$CF_3$; x is 0; $R_4$ is —H; $R_8$ is —H; and $R_9$ is —$OCH_2CH_3$.

In another embodiment, n, p, and m are 0; $R_1$ is —$CF_3$; x is 0; $R_4$ is —H; $R_8$ is —$OCH_2CH_3$; and $R_9$ is —H.

In another embodiment, n, p, and m are 0; $R_1$ is —Cl, —Br, or, —I; x is 0; $R_4$ is —H; $R_8$ is -tert-butyl; and $R_9$ is —H.

In another embodiment, n, p, and m are 0; $R_1$ is —Cl; x is 0; $R_4$ is —H; $R_8$ is -tert-butyl; and $R_9$ is —H.

In another embodiment, n, p, and m are 0; $R_1$ is —Cl, —Br, or, —I; x is 0; $R_4$ is —H; $R_8$ is —H; and $R_9$ is -tert-butyl.

In another embodiment, n, p, and m are 0; $R_1$ is —Cl; x is 0; $R_4$ is —H; $R_8$ is —H; and $R_9$ is -tert-butyl.

In another embodiment, n, p, and m are 0; $R_1$ is —$CH_3$; x is 0; $R_4$ is —H; $R_8$ is -tert-butyl; and $R_9$ is —H.

In another embodiment, n, p, and m are 0; $R_1$ is —$CH_3$; x is 0; $R_4$ is —H; $R_8$ is —H; and $R_9$ is -tert-butyl.

In another embodiment, n, p, and m are 0; $R_1$ is —$CH_3$; x is 0; $R_4$ is —H; $R_8$ is —$CH_3$; and $R_9$ is —$CH_3$.

In another embodiment, n and p are 0; m is 1; $R_1$ is —Cl, —Br, or —I; x is 0; $R_4$ is —H; $R_3$ is —$CH_3$ and is attached to the carbon atom adjacent to the nitrogen attached to the benzothiazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; x is 0; $R_4$ is —H; $R_3$ is —$CH_3$ and is attached to the carbon atom adjacent to the nitrogen attached to the benzothiazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 0; $R_4$ is —H; $R_3$ is —$CH_3$ and is attached to the carbon atom adjacent to the nitrogen attached to the benzothiazolyl group; $R_8$ is —H; and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —Cl, x is 0, $R_4$ is —H, $R_3$ is —$CH_3$ and is attached to the carbon atom adjacent to the nitrogen attached to the benzothiazolyl group, $R_8$ is —H, and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 0; $R_4$ is —H; $R_3$ is —$CH_3$ and is attached to the carbon atom adjacent to the nitrogen attached to the benzothiazolyl group; $R_8$ is -halo; and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —Cl, x is 0, $R_4$ is —H, $R_3$ is —$CH_3$ and is attached to the carbon atom adjacent to the nitrogen attached to the benzothiazolyl group, $R_8$ is -halo, and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 0; $R_4$ is —H; $R_3$ is —$CH_3$ and is attached to the carbon atom adjacent to the nitrogen attached to the benzothiazolyl group; $R_8$ is —H; and $R_9$ is —$CH_3$. In another embodiment, the carbon atom to which the $R_3$ group is attached has the R configuration.

In another embodiment, n and p are 0, m is 1, $R_1$ is —Cl, x is 0, $R_4$ is —H, $R_3$ is —$CH_3$ and is attached to the carbon atom adjacent to the nitrogen attached to the benzothiazolyl group, $R_8$ is —H, and $R_9$ is —$CH_3$. In another embodiment, the carbon atom to which the $R_3$ group is attached has the R configuration.

In another embodiment, n and p are 0; m is 1; $R_1$ is —Cl, —Br, or —I; x is 0; $R_4$ is —H; $R_3$ is —$CH_3$ and is attached to the carbon atom adjacent to the nitrogen attached to the benzothiazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —Cl, x is 0, $R_4$ is —H, $R_3$ is —$CH_3$ and is attached to the carbon atom adjacent to the nitrogen attached to the benzothiazolyl group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 0; $R_4$ is —H; $R_3$ is —$CH_3$ and is attached to the carbon atom adjacent to the nitrogen attached to the benzothiazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —Cl, x is 0, $R_4$ is —H, $R_3$ is —$CH_3$ and is attached to the carbon atom adjacent to the nitrogen attached to the benzothiazolyl group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 0; $R_4$ is —H; $R_3$ is —$CH_3$ and is attached to the carbon atom adjacent to the nitrogen attached to the benzothiazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —Cl, x is 0, $R_4$ is —H, $R_3$ is —$CH_3$ and is attached to the carbon atom adjacent to the nitrogen attached to the benzothiazolyl group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 0; $R_4$ is —H; $R_3$ is —$CH_3$ and is attached to the carbon atom adjacent to the nitrogen attached to the benzothiazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —Cl, x is 0, $R_4$ is —H, $R_3$ is —$CH_3$ and is attached to the carbon atom adjacent to the nitrogen attached to the benzothiazolyl group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 0; $R_4$ is —H; $R_3$ is —$CH_3$ and is attached to the carbon atom adjacent to the nitrogen attached to the benzothiazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —Cl, x is 0, $R_4$ is —H, $R_3$ is —$CH_3$ and is attached to the carbon atom adjacent to the nitrogen attached to the benzothiazolyl group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 0, $R_4$ is —H, $R_3$ is —$CH_3$ and is attached to the carbon atom adjacent to the nitrogen attached to the benzothiazolyl group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 0, $R_4$ is —H, $R_3$ is —$CH_3$ and is attached to the carbon atom adjacent to the nitrogen attached to the benzothiazolyl group, $R_8$ is —H, and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 0, $R_4$ is —H, $R_3$ is —$CH_3$ and is attached to the carbon atom adjacent to the nitrogen attached to the benzothiazolyl group, $R_8$ is -halo, and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 0, $R_4$ is —H, $R_3$ is —$CH_3$ and is attached to the carbon atom adjacent to the nitrogen attached to the benzothiazolyl group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 0, $R_4$ is —H, $R_3$ is —$CH_3$ and is attached to the carbon atom adjacent to the nitrogen attached to the benzothiazolyl group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 0, $R_4$ is —H, $R_3$ is —$CH_3$ and is attached to the carbon atom adjacent to the nitrogen attached to the benzothiazolyl group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 0, $R_4$ is —H, $R_3$ is —$CH_3$ and is attached to the carbon atom adjacent to the nitrogen attached to the benzothiazolyl group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 0, $R_4$ is —H, $R_3$ is —$CH_3$ and is attached to the carbon atom adjacent to the nitrogen attached to the benzothiazolyl group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 0, $R_4$ is —H, $R_3$ is —$CH_3$ and is attached to the carbon atom adjacent to the nitrogen attached to the benzothiazolyl group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 0, $R_4$ is —H, $R_3$ is —$CH_3$ and is attached to the carbon atom adjacent to the nitrogen attached to the benzothiazolyl group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 0, $R_4$ is —H, $R_3$ is —$CH_3$ and is attached to the carbon atom adjacent to the nitrogen attached to the benzothiazolyl group, $R_8$ is —H, and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 0, $R_4$ is —H, $R_3$ is —$CH_3$ and is attached to the carbon atom adjacent to the nitrogen attached to the benzothiazolyl group, $R_8$ is -halo, and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 0, $R_4$ is —H, $R_3$ is —$CH_3$ and is attached to the carbon atom adjacent to the nitrogen attached to the benzothiazolyl group, $R_8$ is —H, and $R_9$ is —CH$_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —CF$_3$, x is 0, $R_4$ is —H, $R_3$ is —CH$_3$ and is attached to the carbon atom adjacent to the nitrogen attached to the benzothiazolyl group, $R_8$ is —CH$_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —CF$_3$, x is 0, $R_4$ is —H, $R_3$ is —CH$_3$ and is attached to the carbon atom adjacent to the nitrogen attached to the benzothiazolyl group, $R_8$ is —H, and $R_9$ is —CF$_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —CF$_3$, x is 0, $R_4$ is —H, $R_3$ is —CH$_3$ and is attached to the carbon atom adjacent to the nitrogen attached to the benzothiazolyl group, $R_8$ is —CF$_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —CF$_3$, x is 0, $R_4$ is —H, $R_3$ is —CH$_3$ and is attached to the carbon atom adjacent to the nitrogen attached to the benzothiazolyl group, $R_8$ is —H, and $R_9$ is —OCH$_2$CH$_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —CF$_3$, x is 0, $R_4$ is —H, $R_3$ is —CH$_3$ and is attached to the carbon atom adjacent to the nitrogen attached to the benzothiazolyl group, $R_8$ is —OCH$_2$CH$_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 0; $R_3$ is —CH$_3$ and is attached to the carbon atom adjacent to the nitrogen attached to the benzothiazolyl group; $R_4$ is —H; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —Cl, x is 0, $R_3$ is —CH$_3$ and is attached to the carbon atom adjacent to the nitrogen attached to the benzothiazolyl group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or, —I; x is 0; $R_3$ is —CH$_3$ and is attached to the carbon atom adjacent to the nitrogen attached to the benzothiazolyl group; $R_4$ is —H; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —Cl, x is 0, $R_3$ is —CH$_3$ and is attached to the carbon atom adjacent to the nitrogen attached to the benzothiazolyl group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —CH$_3$, x is 0, $R_3$ is —CH$_3$ and is attached to the carbon atom adjacent to the nitrogen attached to the benzothiazolyl group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —CH$_3$, x is 0, $R_3$ is —CH$_3$ and is attached to the carbon atom adjacent to the nitrogen attached to the benzothiazolyl group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —CH$_3$, x is 0, $R_3$ is —CH$_3$ and is attached to the carbon atom adjacent to the nitrogen attached to the benzothiazolyl group, $R_4$ is —H, $R_8$ is —CH$_3$, and $R_9$ is —CH$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; m is 1; $R_1$ is —CH$_3$, —Cl, —Br, or —I; x is 1; A is —C(O)—N($R_4$)—; $R_3$ is —CH$_3$ and is attached to the carbon atom adjacent to the nitrogen attached to the —C(O)—N($R_4$)— group; $R_4$ is —H; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0, m is 1, $R_1$ is —CH$_3$, x is 1, A is —C(O)—N($R_4$)—, $R_3$ is —CH$_3$ and is attached to the carbon atom adjacent to the nitrogen attached to the —C(O)—N($R_4$)— group, $R_4$ is —H, $R_8$ is —H, and $R_9$ is —Cl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group; n is 0; m is 1; $R_1$ is —Cl, —Br, or —I; x is 1; A is —C(O)—N($R_4$)—; $R_3$ is —CH$_3$ and is attached to the carbon atom adjacent to the nitrogen attached to the —C(O)—N($R_4$)— group; $R_4$ is —H; $R_8$ is —H; and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0, m is 1, $R_1$ is —Cl, x is 1, A is —C(O)—N($R_4$)—, $R_3$ is —CH$_3$ and is attached to the carbon atom adjacent to the nitrogen attached to the —C(O)—N($R_4$)— group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0, m is 1, $R_1$ is —CH$_3$, x is 1, A is —C(O)—N($R_4$)—, $R_3$ is —CH$_3$ and is attached to the carbon atom adjacent to the nitrogen attached to the —C(O)—N($R_4$)— group, $R_4$ is —H, $R_8$ is —H, and $R_9$ is —F. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group; p is 0; m is 1; $R_1$ is —CH$_3$, —Cl, —Br, or —I; x is 1; A is —C(O)—N($R_4$)—; $R_3$ is —CH$_3$ and is attached to the carbon atom adjacent to the nitrogen attached to the —C(O)—N($R_4$)— group; $R_4$ is —H; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Cl. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group; p is 0; m is 1; $R_1$ is —Cl, —Br, or —I; x is 1; A is —C(O)—N($R_4$)—; $R_3$ is —$CH_3$ and is attached to the carbon atom adjacent to the nitrogen attached to the —C(O)—N($R_4$)— group; $R_4$ is —H; $R_8$ is —H; and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0, m is 1, $R_1$ is —Cl, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —F. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group; n is 0; m is 1; $R_1$ is —$CH_3$, —Cl, —Br, or —I; x is 0; $R_3$ is —$CH_3$ and is attached to the carbon atom adjacent to the nitrogen attached to the benzothiazolyl group; $R_4$ is —H; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0, m is 1, $R_1$ is —$CH_3$, x is 0, $R_3$ is —$CH_3$ and is attached to the carbon atom adjacent to the nitrogen attached to the benzothiazolyl group, $R_4$ is —H, $R_8$ is —H, and $R_9$ is —Cl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group; n is 0; m is 1; $R_1$ is —Cl, —Br, or —I; x is 0; $R_3$ is —$CH_3$ and is attached to the carbon atom adjacent to the nitrogen attached to the benzothiazolyl group; $R_4$ is —H; $R_8$ is —H; and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0, m is 1, $R_1$ is —Cl, x is 0, $R_3$ is —$CH_3$ and is attached to the carbon atom adjacent to the nitrogen attached to the benzothiazolyl group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0, m is 1, $R_1$ is —$CH_3$, x is 0, $R_3$ is —$CH_3$ and is attached to the carbon atom adjacent to the nitrogen attached to the benzothiazolyl group, $R_4$ is —H, $R_8$ is —H, and $R_9$ is —F. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group; p is 0; m is 1; $R_1$ is —$CH_3$, —Cl, —Br, or —I; x is 0; $R_3$ is —$CH_3$ and is attached to the carbon atom adjacent to the nitrogen attached to the benzothiazolyl group; $R_4$ is —H; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0, m is 1, $R_1$ is —$CH_3$, x is 0, $R_3$ is —$CH_3$ and is attached to the carbon atom adjacent to the nitrogen attached to the benzothiazolyl group, $R_4$ is —H, $R_8$ is —H, and $R_9$ is —Cl. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group; p is 0; m is 1; $R_1$ is —Cl, —Br, or —I; x is 0; $R_3$ is —$CH_3$ and is attached to the carbon atom adjacent to the nitrogen attached to the benzothiazolyl group; $R_4$ is —H; $R_8$ is —H; and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0, m is 1, $R_1$ is —Cl, x is 0, $R_3$ is —$CH_3$ and is attached to the carbon atom adjacent to the nitrogen attached to the benzothiazolyl group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0, m is 1, $R_1$ is —$CH_3$, x is 0, $R_3$ is —$CH_3$ and is attached to the carbon atom adjacent to the nitrogen attached to the benzothiazolyl group, $R_4$ is —H, $R_8$ is —H, and $R_9$ is —F. In another embodiment, the carbon atom to which the $R_3$ group is attached has the R configuration. In another embodiment, the carbon atom to which the $R_3$ group is attached has the S configuration.

In another embodiment, m is 1 and $R_3$ is —($C_1$-$C_4$)alkyl and is attached to the carbon atom adjacent to the nitrogen attached to the —C(O)—N($R_4$)— when x is 1 or the benzothiazolyl group when x is 0. In another embodiment, m is 1 and $R_3$ is —($C_1$-$C_4$)alkyl and is attached to the carbon atom adjacent to the nitrogen attached to the —C(O)—N($R_4$)— when x is 1 or the benzothiazolyl group when x is 0 and the carbon to which the $R_3$ group is attached is in the R configuration.

In another embodiment, m is 1 and $R_3$ is —$CH_3$ and is attached to the carbon atom adjacent to the nitrogen attached to the —C(O)—N($R_4$)— when x is 1 or the benzothiazolyl group when x is 0. In another embodiment, m is 1 and $R_3$ is —$CH_3$ and is attached to the carbon atom adjacent to the nitrogen attached to the —C(O)—N($R_4$)— when x is 1 or the benzothiazolyl group when x is 0 and the carbon to which the $R_3$ group is attached is in the R configuration.

In another embodiment, m is 1 and $R_3$ is —($C_1$-$C_4$)alkyl and is attached to the carbon atom adjacent to the nitrogen attached to the —C(O)—N($R_4$)— when x is 1 or the benzothiazolyl group when x is 0. In another embodiment, m is 1 and $R_3$ is —($C_1$-$C_4$)alkyl and is attached to the carbon atom adjacent to the nitrogen attached to the —C(O)—N(R$_4$)— when x is 1 or the benzothiazolyl group when x is 0 and the carbon to which the R$_3$ group is attached is in the S configuration.

In another embodiment, m is 1 and R$_3$ is —CH$_3$ and is attached to the carbon atom adjacent to the nitrogen attached to the —C(O)—N(R$_4$)— when x is 1 or the benzothiazolyl group when x is 0. In another embodiment, m is 1 and R$_3$ is —CH$_3$ and is attached to the carbon atom adjacent to the nitrogen attached to the —C(O)—N(R$_4$)— when x is 1 or the benzothiazolyl group when x is 0 and the carbon to which the R$_3$ group is attached is in the S configuration.

In another embodiment, m is 1 and R$_3$ is —(C$_1$-C$_4$)alkyl and is attached to the carbon atom adjacent to the nitrogen attached to the pyridyl group or pyrimidinyl group. In another embodiment, m is 1 and R$_3$ is —(C$_1$-C$_4$)alkyl and is attached to the carbon atom adjacent to the nitrogen attached to the pyridyl group or pyrimidinyl group and the carbon to which the R$_3$ group is attached is in the R configuration.

In another embodiment, m is 1 and R$_3$ is —CH$_3$ and is attached to the carbon atom adjacent to the nitrogen attached to the pyridyl group or pyrimidinyl group. In another embodiment, m is 1 and R$_3$ is —CH$_3$ and is attached to the carbon atom adjacent to the nitrogen attached to the pyridyl group or pyrimidinyl group and the carbon to which the R$_3$ group is attached is in the R configuration.

In another embodiment, m is 1 and R$_3$ is —(C$_1$-C$_4$)alkyl and is attached to the carbon atom adjacent to the nitrogen attached to the pyridyl group or pyrimidinyl group. In another embodiment, m is 1 and R$_3$ is —(C$_1$-C$_4$)alkyl and is attached to the carbon atom adjacent to the nitrogen attached to the pyridyl group or pyrimidinyl group and the carbon to which the R$_3$ group is attached is in the S configuration.

In another embodiment, m is 1 and R$_3$ is —CH$_3$ and is attached to the carbon atom adjacent to the nitrogen attached to the pyridyl group or pyrimidinyl group. In another embodiment, m is 1 and R$_3$ is —CH$_3$ and is attached to the carbon atom adjacent to the nitrogen attached to the pyridyl group or pyrimidinyl group and the carbon to which the R$_3$ group is attached is in the S configuration.

4.2 The Compounds of Formula (Ib)

The present invention also encompasses compounds of formula (Ib):

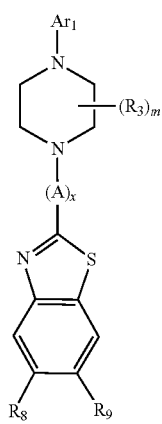

(Ib)

and pharmaceutically acceptable salts thereof, where Ar$_1$, R$_3$, R$_8$, R$_9$, A, x, and m, are defined above for the Benzoazolylpiperazine Compounds of formula (Ib).

In one embodiment, Ar$_1$ is a pyrazinyl group.
In another embodiment, Ar$_1$ is a pyridazinyl group.
In another embodiment, Ar$_1$ is a thiazanyl group.
In another embodiment, x is 1 and A is —C(O)—N(R$_4$)—.
In another embodiment, x is 1 and A is —C(S)—N(R$_4$)—.
In another embodiment x is 0.
In another embodiment, p is 0.
In another embodiment, p is 1.
In another embodiment, m is 0.
In another embodiment, m is 1.
In another embodiment, R$_4$ is —H.
In another embodiment, R$_4$ is —(C$_1$-C$_6$)alkyl.
In another embodiment, Ar$_1$ is a pyrazinyl group, x is 1, and A is —C(O)N(R$_4$)—.
In another embodiment, Ar$_1$ is a pyrazinyl group, x is 1, and A is —C(S)N(R$_4$)—.
In another embodiment, Ar$_1$ is a pyridazinyl group, x is 1, and A is —C(O)N(R$_4$)—.
In another embodiment, Ar$_1$ is a pyridazinyl group, x is 1, and A is —C(S)N(R$_4$)—.
In another embodiment, Ar$_1$ is a thiazanyl group, x is 1, and A is —C(O)N(R$_4$)—.
In another embodiment, Ar$_1$ is a thiazanyl group, x is 1, and A is —C(S)N(R$_4$)—.
In another embodiment, R$_1$ is —H.
In another embodiment, R$_1$ is —Cl.
In another embodiment, R$_1$ is —Br.
In another embodiment, R$_1$ is —I.
In another embodiment, R$_1$ is —F.
In another embodiment, R$_1$ is —(C$_1$-C$_6$)alkyl.
In another embodiment, R$_1$ is —CH$_3$.
In another embodiment, R$_1$ is —NO$_2$.
In another embodiment, R$_1$ is —CN.
In another embodiment, R$_1$ is —OH.
In another embodiment, R$_1$ is —OCH$_3$.
In another embodiment, R$_1$ is —NH$_2$.
In another embodiment, R$_1$ is —C(halo)$_3$.
In another embodiment, R$_1$ is —CH(halo)$_2$.
In another embodiment, R$_1$ is —CH$_2$(halo).

In another embodiment, p is 1 and R$_2$ is -halo, —CN, —OH, —O(C$_1$-C$_6$)alkyl, —NO$_2$, or —NH$_2$.

In another embodiment, p is 1 and R$_2$ is —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more R$_5$ groups.

In another embodiment, p is 1 and R$_2$ is -phenyl, -naphthyl, —(C$_{14}$)aryl, or -(5- to 10-membered)heteroaryl, each of which is unsubstituted or substituted with one or more R$_6$ groups.

In another embodiment, m is 1 and R$_3$ is -halo, —CN, —OH, —O(C$_1$-C$_6$)alkyl, —NO$_2$, or —NH$_2$.

In another embodiment, m is 1 and R$_3$ is —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more R$_5$ groups.

In another embodiment, m is 1 and $R_3$ is -phenyl, -naphthyl, —($C_{14}$)aryl or -(5- to 10-membered)heteroaryl, each of which is unsubstituted or substituted with one or more $R_6$ groups.

In another embodiment, $R_8$ and $R_9$ are each independently —H, halo, —($C_1$-$C_6$)alkyl, —O($C_1$-$C_6$)alkyl, —C(halo)$_3$, —CH(halo)$_2$, or —CH$_2$(halo).

In another embodiment, at least one of $R_8$ or $R_9$ is —H.

In another embodiment, p and m are 0, $R_1$ is -halo, x is 1, A is —C(O)—N($R_4$)—, $R_4$ is —H, and $R_8$ and $R_9$ are —H.

In another embodiment, p and m are 0, $R_1$ is —Cl, x is 1, A is —C(O)—N($R_4$)—, $R_4$ is —H, and $R_8$ and $R_9$ are —H.

In another embodiment, p and m are 0, $R_1$ is -halo, x is 1, A is —C(O)—N($R_4$)—, $R_4$ is —H, $R_8$ is —H, and $R_9$ is -halo. In another embodiment, $R_9$ is —Cl. In another embodiment, $R_9$ is —Br. In another embodiment, $R_9$ is —F.

In another embodiment, p and m are 0, $R_1$ is —Cl, x is 1, A is —C(O)—N($R_4$)—, $R_4$ is —H, $R_8$ is —H, and $R_9$ is -halo. In another embodiment, $R_9$ is —Cl. In another embodiment, $R_9$ is —Br. In another embodiment, $R_9$ is —F.

In another embodiment, p and m are 0, $R_1$ is -halo, x is 1, A is —C(O)—N($R_4$)—, $R_4$ is —H, $R_8$ is -halo, and $R_9$ is —H. In another embodiment, $R_8$ is —Cl. In another embodiment, $R_8$ is —Br. In another embodiment, $R_8$ is —F.

In another embodiment, p and m are 0, $R_1$ is —Cl, x is 1, A is —C(O)—N($R_4$)—, $R_4$ is —H, $R_8$ is -halo, and $R_9$ is —H. In another embodiment, $R_8$ is —Cl. In another embodiment, $R_8$ is —Br. In another embodiment, $R_8$ is —F.

In another embodiment, p and m are 0, $R_1$ is -halo, x is 1, A is —C(O)—N($R_4$)—, $R_4$ is —H, $R_8$ is —H, and $R_9$ is —CH$_3$.

In another embodiment, p and m are 0, $R_1$ is —Cl, x is 1, A is —C(O)—N($R_4$)—, $R_4$ is —H, $R_8$ is —H, and $R_9$ is —CH$_3$.

In another embodiment, p and m are 0, $R_1$ is -halo, x is 1, A is —C(O)—N($R_4$)—, $R_4$ is —H, $R_8$ is —CH$_3$, and $R_9$ is —H.

In another embodiment, p and m are 0, $R_1$ is —Cl, x is 1, A is —C(O)—N($R_4$)—, $R_4$ is —H, $R_8$ is —CH$_3$, and $R_9$ is —H.

In another embodiment, p and m are 0, $R_1$ is -halo, x is 1, A is —C(O)—N($R_4$)—, $R_4$ is —H, $R_8$ is —H, and $R_9$ is —CF$_3$.

In another embodiment, p and m are 0, $R_1$ is —Cl, x is 1, A is —C(O)—N($R_4$)—, $R_4$ is —H, $R_8$ is —H, and $R_9$ is —CF$_3$.

In another embodiment, p and m are 0, $R_1$ is -halo, x is 1, A is —C(O)—N($R_4$)—, $R_4$ is —H, $R_8$ is —CF$_3$, and $R_9$ is —H.

In another embodiment, p and m are 0, $R_1$ is —Cl, x is 1, A is —C(O)—N($R_4$)—, $R_4$ is —H, $R_8$ is —CF$_3$, and $R_9$ is —H.

In another embodiment, p and m are 0, $R_1$ is -halo, x is 1, A is —C(O)—N($R_4$)—, $R_4$ is —H, $R_8$ is —H, and $R_9$ is —OCH$_2$CH$_3$.

In another embodiment, p and m are 0, $R_1$ is —Cl, x is 1, A is —C(O)—N($R_4$)—, $R_4$ is —H, $R_8$ is —H, and $R_9$ is —OCH$_2$CH$_3$.

In another embodiment, p and m are 0, $R_1$ is -halo, x is 1, A is —C(O)—N($R_4$)—, $R_4$ is —H, $R_8$ is —OCH$_2$CH$_3$, and $R_9$ is —H.

In another embodiment, p and m are 0, $R_1$ is —Cl, x is 1, A is —C(O)—N($R_4$)—, $R_4$ is —H, $R_8$ is —OCH$_2$CH$_3$, and $R_9$ is —H.

In another embodiment, p and m are 0, $R_1$ is —CH$_3$, x is 1, A is —C(O)—N($R_4$)—, $R_4$ is —H, and $R_8$ and $R_9$ are —H.

In another embodiment, p and m are 0, $R_1$ is —CH$_3$, x is 1, A is —C(O)—N($R_4$)—, $R_4$ is —H, $R_8$ is —H, and $R_9$ is -halo. In another embodiment, $R_9$ is —Cl. In another embodiment, $R_9$ is —Br. In another embodiment, $R_9$ is —F.

In another embodiment, p and m are 0, $R_1$ is —CH$_3$, x is 1, A is —C(O)—N($R_4$)—, $R_4$ is —H, $R_8$ is -halo, and $R_9$ is —H. In another embodiment, $R_8$ is —Cl. In another embodiment, $R_8$ is —Br. In another embodiment, $R_8$ is —F.

In another embodiment, p and m are 0, $R_1$ is —CH$_3$, x is 1, A is —C(O)—N($R_4$)—, $R_4$ is —H, $R_8$ is —H, and $R_9$ is —CH$_3$.

In another embodiment, p and m are 0, $R_1$ is —CH$_3$, x is 1, A is —C(O)—N($R_4$)—, $R_4$ is —H, $R_8$ is —CH$_3$, and $R_9$ is —H.

In another embodiment, p and m are 0, $R_1$ is —CH$_3$, x is 1, A is —C(O)—N($R_4$)—, $R_4$ is —H, $R_8$ is —H, and $R_9$ is —CF$_3$.

In another embodiment, p and m are 0, $R_1$ is —CH$_3$, x is 1, A is —C(O)—N($R_4$)—, $R_4$ is —H, $R_8$ is —CF$_3$, and $R_9$ is —H.

In another embodiment, p and m are 0, $R_1$ is —CH$_3$, x is 1, A is —C(O)—N($R_4$)—, $R_4$ is —H, $R_8$ is —H, and $R_9$ is —OCH$_2$CH$_3$.

In another embodiment, p and m are 0, $R_1$ is —CH$_3$, x is 1, A is —C(O)—N($R_4$)—, $R_4$ is —H, $R_8$ is —OCH$_2$CH$_3$, and $R_9$ is —H.

In another embodiment, p and m are 0, $R_1$ is —CF$_3$, x is 1, A is —C(O)—N($R_4$)—, $R_4$ is —H, and $R_8$ and $R_9$ are —H.

In another embodiment, p and m are 0, $R_1$ is —CF$_3$, x is 1, A is —C(O)—N($R_4$)—, $R_4$ is —H, $R_8$ is —H, and $R_9$ is -halo. In another embodiment, $R_9$ is —Cl. In another embodiment, $R_9$ is —Br. In another embodiment, $R_9$ is —F.

In another embodiment, p and m are 0, $R_1$ is —CF$_3$, x is 1, A is —C(O)—N($R_4$)—, $R_4$ is —H, $R_8$ is -halo, and $R_9$ is —H. In another embodiment, $R_8$ is —Cl. In another embodiment, $R_8$ is —Br. In another embodiment, $R_8$ is —F.

In another embodiment, p and m are 0, $R_1$ is —CF$_3$, x is 1, A is —C(O)—N($R_4$)—, $R_4$ is —H, $R_8$ is —H, and $R_9$ is —CH$_3$.

In another embodiment, p and m are 0, $R_1$ is —CF$_3$, x is 1, A is —C(O)—N($R_4$)—, $R_4$ is —H, $R_8$ is —CH$_3$, and $R_9$ is —H.

In another embodiment, p and m are 0, $R_1$ is —CF$_3$, x is 1, A is —C(O)—N($R_4$)—, $R_4$ is —H, $R_8$ is —H, and $R_9$ is —CF$_3$.

In another embodiment, p and m are 0, $R_1$ is —CF$_3$, x is 1, A is —C(O)—N($R_4$)—, $R_4$ is —H, $R_8$ is —CF$_3$, and $R_9$ is —H.

In another embodiment, p and m are 0, $R_1$ is —CF$_3$, x is 1, A is —C(O)—N($R_4$)—, $R_4$ is —H, $R_8$ is —H, and $R_9$ is —OCH$_2$CH$_3$.

In another embodiment, p and m are 0, $R_1$ is —CF$_3$, x is 1, A is —C(O)—N($R_4$)—, $R_4$ is —H, $R_8$ is —OCH$_2$CH$_3$, and $R_9$ is —H.

In another embodiment, p and m are 0, $R_1$ is -halo, x is 1, A is —C(O)—N($R_4$)—, $R_4$ is —H, $R_8$ is -tert-butyl, and $R_9$ is —H.

In another embodiment, p and m are 0, $R_1$ is —Cl, x is 1, A is —C(O)—N($R_4$)—, $R_4$ is —H, $R_8$ is -tert-butyl, and $R_9$ is —H.

In another embodiment, p and m are 0, $R_1$ is -halo, x is 1, A is —C(O)—N($R_4$)—, $R_4$ is —H, $R_8$ is —H, and $R_9$ is -tert-butyl.

In another embodiment, p and m are 0, $R_1$ is —Cl, x is 1, A is —C(O)—N($R_4$)—, $R_4$ is —H, $R_8$ is —H, and $R_9$ is -tert-butyl.

In another embodiment, p and m are 0, $R_1$ is —CH$_3$, x is 1, A is —C(O)—N($R_4$)—, $R_4$ is —H, $R_8$ is -tert-butyl, and $R_9$ is —H.

In another embodiment, p and m are 0, $R_1$ is —CH$_3$, x is 1, A is —C(O)—N($R_4$)—, $R_4$ is —H, $R_8$ is —H, and $R_9$ is -tert-butyl.

In another embodiment, p and m are 0, $R_1$ is —CH$_3$, x is 1, A is —C(O)—N($R_4$)—, $R_4$ is —H, $R_8$ is —CH$_3$, and $R_9$ is —CH$_3$.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is -halo. In another embodiment, $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is -halo. In another embodiment, $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is -halo, and $R_9$ is —H. In another embodiment, $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is -halo, and $R_9$ is —H. In another embodiment, $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is -halo, and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is -halo, and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —$CH_3$, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, p and m are 0, $R_1$ is -halo, x is 0, $R_4$ is —H, and $R_8$ and $R_9$ are —H.

In another embodiment, p and m are 0, $R_1$ is —Cl, x is 0, $R_4$ is —H, and $R_8$ and $R_9$ are —H.

In another embodiment, p and m are 0, $R_1$ is -halo, x is 0, $R_4$ is —H, $R_8$ is —H, and $R_9$ is -halo. In another embodiment, $R_9$ is —Cl. In another embodiment, $R_9$ is —Br. In another embodiment, $R_9$ is —F.

In another embodiment, p and m are 0, $R_1$ is —Cl, x is 0, $R_4$ is —H, $R_8$ is —H, and $R_9$ is -halo. In another embodiment, $R_9$ is —Cl. In another embodiment, $R_9$ is —Br. In another embodiment, $R_9$ is —F.

In another embodiment, p and m are 0, $R_1$ is -halo, x is 0, $R_4$ is —H, $R_8$ is -halo, and $R_9$ is —H. In another embodiment, $R_8$ is —Cl. In another embodiment, $R_8$ is —Br. In another embodiment, $R_8$ is —F.

In another embodiment, p and m are 0, $R_1$ is —Cl, x is 0, $R_4$ is —H, $R_8$ is -halo, and $R_9$ is —H. In another embodiment, $R_8$ is —Cl. In another embodiment, $R_8$ is —Br. In another embodiment, $R_8$ is —F.

In another embodiment, p and m are 0, $R_1$ is -halo, x is 0, $R_4$ is —H, $R_8$ is —H, and $R_9$ is —$CH_3$.

In another embodiment, p and m are 0, $R_1$ is —Cl, x is 0, $R_4$ is —H, $R_8$ is —H, and $R_9$ is —$CH_3$.

In another embodiment, p and m are 0, $R_1$ is -halo, x is 0, $R_4$ is —H, $R_8$ is —$CH_3$, and $R_9$ is —H.

In another embodiment, p and m are 0, $R_1$ is —Cl, x is 0, $R_4$ is —H, $R_8$ is —$CH_3$, and $R_9$ is —H.

In another embodiment, p and m are 0, $R_1$ is -halo, x is 0, $R_4$ is —H, $R_8$ is —H, and $R_9$ is —$CF_3$.

In another embodiment, p and m are 0, $R_1$ is —Cl, x is 0, $R_4$ is —H, $R_8$ is —H, and $R_9$ is —$CF_3$.

In another embodiment, p and m are 0, $R_1$ is -halo, x is 0, $R_4$ is —H, $R_8$ is —$CF_3$, and $R_9$ is —H.

In another embodiment, p and m are 0, $R_1$ is —Cl, x is 0, $R_4$ is —H, $R_8$ is —$CF_3$, and $R_9$ is —H.

In another embodiment, p and m are 0, $R_1$ is -halo, x is 0, $R_4$ is —H, $R_8$ is —H, and $R_9$ is —$OCH_2CH_3$.

In another embodiment, p and m are 0, $R_1$ is —Cl, x is 0, $R_4$ is —H, $R_8$ is —H, and $R_9$ is —$OCH_2CH_3$.

In another embodiment, p and m are 0, $R_1$ is -halo, x is 0, $R_4$ is —H, $R_8$ is —$OCH_2CH_3$, and $R_9$ is —H.

In another embodiment, p and m are 0, $R_1$ is —Cl, x is 0, $R_4$ is —H, $R_8$ is —OCH$_2$CH$_3$, and $R_9$ is —H.

In another embodiment, p and m are 0, $R_1$ is —CH$_3$, x is 0, $R_4$ is —H, and $R_8$ and $R_9$ are —H.

In another embodiment, p and m are 0, $R_1$ is —CH$_3$, x is 0, $R_4$ is —H, $R_8$ is —H, and $R_9$ is -halo. In another embodiment, $R_9$ is —Cl. In another embodiment, $R_9$ is —Br. In another embodiment, $R_9$ is —F.

In another embodiment, p and m are 0, $R_1$ is —CH$_3$, x is 0, $R_4$ is —H, $R_8$ is -halo, and $R_9$ is —H. In another embodiment, $R_8$ is —Cl. In another embodiment, $R_8$ is —Br. In another embodiment, $R_8$ is —F.

In another embodiment, p and m are 0, $R_1$ is —CH$_3$, x is 0, $R_4$ is —H, $R_8$ is —H, and $R_9$ is —CH$_3$.

In another embodiment, p and m are 0, $R_1$ is —CH$_3$, x is 0, $R_4$ is —H, $R_8$ is —CH$_3$, and $R_9$ is —H.

In another embodiment, p and m are 0, $R_1$ is —CH$_3$, x is 0, $R_4$ is —H, $R_8$ is —H, and $R_9$ is —CF$_3$.

In another embodiment, p and m are 0, $R_1$ is —CH$_3$, x is 0, $R_4$ is —H, $R_8$ is —CF$_3$, and $R_9$ is —H.

In another embodiment, p and m are 0, $R_1$ is —CH$_3$, x is 0, $R_4$ is —H, $R_8$ is —H, and $R_9$ is —OCH$_2$CH$_3$.

In another embodiment, p and m are 0, $R_1$ is —CH$_3$, x is 0, $R_4$ is —H, $R_8$ is —OCH$_2$CH$_3$, and $R_9$ is —H.

In another embodiment, p and m are 0, $R_1$ is —CF$_3$, x is 0, $R_4$ is —H, and $R_8$ and $R_9$ are —H.

In another embodiment, p and m are 0, $R_1$ is —CF$_3$, x is 0, $R_4$ is —H, $R_8$ is —H, and $R_9$ is -halo. In another embodiment, $R_9$ is —Cl. In another embodiment, $R_9$ is —Br. In another embodiment, $R_9$ is —F.

In another embodiment, p and m are 0, $R_1$ is —CF$_3$, x is 0, $R_4$ is —H, $R_8$ is -halo, and $R_9$ is —H. In another embodiment, $R_8$ is —Cl. In another embodiment, $R_8$ is —Br. In another embodiment, $R_8$ is —F.

In another embodiment, p and m are 0, $R_1$ is —CF$_3$, x is 0, $R_4$ is —H, $R_8$ is —H, and $R_9$ is —CH$_3$.

In another embodiment, p and m are 0, $R_1$ is —CF$_3$, x is 0, $R_4$ is —H, $R_8$ is —CH$_3$, and $R_9$ is —H.

In another embodiment, p and m are 0, $R_1$ is —CF$_3$, x is 0, $R_4$ is —H, $R_8$ is —H, and $R_9$ is —CF$_3$.

In another embodiment, p and m are 0, $R_1$ is —CF$_3$, x is 0, $R_4$ is —H, $R_8$ is —CF$_3$, and $R_9$ is —H.

In another embodiment, p and m are 0, $R_1$ is —CF$_3$, x is 0, $R_4$ is —H, $R_8$ is —H, and $R_9$ is —OCH$_2$CH$_3$.

In another embodiment, p and m are 0, $R_1$ is —CF$_3$, x is 0, $R_4$ is —H, $R_8$ is —OCH$_2$CH$_3$, and $R_9$ is —H.

In another embodiment, p and m are 0, $R_1$ is -halo, x is 0, $R_4$ is —H, $R_8$ is -tert-butyl, and $R_9$ is —H.

In another embodiment, p and m are 0, $R_1$ is —Cl, x is 0, $R_4$ is —H, $R_8$ is -tert-butyl, and $R_9$ is —H.

In another embodiment, p and m are 0, $R_1$ is -halo, x is 0, $R_4$ is —H, $R_8$ is —H, and $R_9$ is -tert-butyl.

In another embodiment, p and m are 0, $R_1$ is —Cl, x is 0, $R_4$ is —H, $R_8$ is —H, and $R_9$ is -tert-butyl.

In another embodiment, p and m are 0, $R_1$ is —CH$_3$, x is 0, $R_4$ is —H, $R_8$ is -tert-butyl, and $R_9$ is —H.

In another embodiment, p and m are 0, $R_1$ is —CH$_3$, x is 0, $R_4$ is —H, $R_8$ is —H, and $R_9$ is -tert-butyl.

In another embodiment, p and m are 0, $R_1$ is —CH$_3$, x is 0, $R_4$ is —H, $R_8$ is —CH$_3$, and $R_9$ is —CH$_3$.

In another embodiment, p is 0, m is 1, $R_1$ is -halo, x is 0, $R_4$ is —H, $R_3$ is —CH$_3$ and is attached to the carbon atom adjacent to the nitrogen attached to the benzothiazolyl group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —CH$_3$ and is attached to the carbon atom adjacent to the nitrogen attached to the benzothiazolyl group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_4$ is —H, $R_3$ is —CH$_3$ and is attached to the carbon atom adjacent to the nitrogen attached to the benzothiazolyl group, $R_8$ is —H, and $R_9$ is -halo. In another embodiment, $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —CH$_3$ and is attached to the carbon atom adjacent to the nitrogen attached to the benzothiazolyl group, $R_8$ is —H, and $R_9$ is -halo. In another embodiment, $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_4$ is —H, $R_3$ is —CH$_3$ and is attached to the carbon atom adjacent to the nitrogen attached to the benzothiazolyl group, $R_8$ is -halo, and $R_9$ is —H. In another embodiment, $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —CH$_3$ and is attached to the carbon atom adjacent to the nitrogen attached to the benzothiazolyl group, $R_8$ is -halo, and $R_9$ is —H. In another embodiment, $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_4$ is —H, $R_3$ is —CH$_3$ and is attached to the carbon atom adjacent to the nitrogen attached to the benzothiazolyl group, $R_8$ is —H, and $R_9$ is —CH$_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —CH$_3$ and is attached to the carbon atom adjacent to the nitrogen attached to the benzothiazolyl group, $R_8$ is —H, and $R_9$ is —CH$_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_4$ is —H, $R_3$ is —CH$_3$ and is attached to the carbon atom adjacent to the nitrogen attached to the benzothiazolyl group, $R_8$ is —CH$_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —CH$_3$ and is attached to the carbon atom adjacent to the nitrogen attached to the benzothiazolyl group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_4$ is —H, $R_3$ is —$CH_3$ and is attached to the carbon atom adjacent to the nitrogen attached to the benzothiazolyl group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —$CH_3$ and is attached to the carbon atom adjacent to the nitrogen attached to the benzothiazolyl group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_4$ is —H, $R_3$ is —$CH_3$ and is attached to the carbon atom adjacent to the nitrogen attached to the benzothiazolyl group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —$CH_3$ and is attached to the carbon atom adjacent to the nitrogen attached to the benzothiazolyl group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_4$ is —H, $R_3$ is —$CH_3$ and is attached to the carbon atom adjacent to the nitrogen attached to the benzothiazolyl group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —$CH_3$ and is attached to the carbon atom adjacent to the nitrogen attached to the benzothiazolyl group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_4$ is —H, $R_3$ is —$CH_3$ and is attached to the carbon atom adjacent to the nitrogen attached to the benzothiazolyl group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —$CH_3$ and is attached to the carbon atom adjacent to the nitrogen attached to the benzothiazolyl group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_4$ is —H, $R_3$ is —$CH_3$ and is attached to the carbon atom adjacent to the nitrogen attached to the benzothiazolyl group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_4$ is —H, $R_3$ is —$CH_3$ and is attached to the carbon atom adjacent to the nitrogen attached to the benzothiazolyl group, $R_8$ is —H, and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_4$ is —H, $R_3$ is —$CH_3$ and is attached to the carbon atom adjacent to the nitrogen attached to the benzothiazolyl group, $R_8$ is -halo, and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_4$ is —H, $R_3$ is —$CH_3$ and is attached to the carbon atom adjacent to the nitrogen attached to the benzothiazolyl group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_4$ is —H, $R_3$ is —$CH_3$ and is attached to the carbon atom adjacent to the nitrogen attached to the benzothiazolyl group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_4$ is —H, $R_3$ is —$CH_3$ and is attached to the carbon atom adjacent to the nitrogen attached to the benzothiazolyl group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_4$ is —H, $R_3$ is —$CH_3$ and is attached to the carbon atom adjacent to the nitrogen attached to the benzothiazolyl group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_4$ is —H, $R_3$ is —$CH_3$ and is attached to the carbon atom adjacent to the nitrogen attached to the benzothiazolyl group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_4$ is —H, $R_3$ is —$CH_3$ and is attached to the carbon atom adjacent to the nitrogen attached to the benzothiazolyl group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 0, $R_4$ is —H, $R_3$ is —$CH_3$ and is attached to the carbon atom adjacent to the nitrogen attached to the benzothiazolyl group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 0, $R_4$ is —H, $R_3$ is —$CH_3$ and is attached to the carbon atom adjacent to the nitrogen attached to the benzothiazolyl group, $R_8$ is —H, and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 0, $R_4$ is —H, $R_3$ is —$CH_3$ and is attached to the carbon atom adjacent to the nitrogen attached to the benzothiazolyl group, $R_8$ is -halo, and $R_9$ is —H. In another embodiment $R_8$ is —Cl. In another embodiment, $R_8$ is —Br. In one embodiment, $R_8$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 0, $R_4$ is —H, $R_3$ is —$CH_3$ and is attached to the carbon atom adjacent to the nitrogen attached to the benzothiazolyl group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 0, $R_4$ is —H, $R_3$ is —$CH_3$ and is attached to the carbon atom adjacent to the nitrogen attached to the benzothiazolyl group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 0, $R_4$ is —H, $R_3$ is —$CH_3$ and is attached to the carbon atom adjacent to the nitrogen attached to the benzothiazolyl group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 0, $R_4$ is —H, $R_3$ is —$CH_3$ and is attached to the carbon atom adjacent to the nitrogen attached to the benzothiazolyl group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 0, $R_4$ is —H, $R_3$ is —$CH_3$ and is attached to the carbon atom adjacent to the nitrogen attached to the benzothiazolyl group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 0, $R_4$ is —H, $R_3$ is —$CH_3$ and is attached to the carbon atom adjacent to the nitrogen attached to the benzothiazolyl group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_3$ is —$CH_3$ and is attached to the carbon atom adjacent to the nitrogen attached to the benzothiazolyl group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_3$ is —$CH_3$ and is attached to the carbon atom adjacent to the nitrogen attached to the benzothiazolyl group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_3$ is —$CH_3$ and is attached to the carbon atom adjacent to the nitrogen attached to the benzothiazolyl group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_3$ is —$CH_3$ and is attached to the carbon atom adjacent to the nitrogen attached to the benzothiazolyl group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_3$ is —$CH_3$ and is attached to the carbon atom adjacent to the nitrogen attached to the benzothiazolyl group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_3$ is —$CH_3$ and is attached to the carbon atom adjacent to the nitrogen attached to the benzothiazolyl group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_3$ is —$CH_3$ and is attached to the carbon atom adjacent to the nitrogen attached to the benzothiazolyl group, $R_4$ is —H, $R_8$ is —$CH_3$, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group, p is 0, m is 1, $R_1$ is —$CH_3$ or -halo, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Cl. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group, p is 0, m is 1, $R_1$ is -halo, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group, p is 0, m is 1, $R_1$ is —Cl, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —F. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is —$CH_3$ or -halo, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Cl. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is -halo, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is —Cl, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —F. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is —$CH_3$ or -halo, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Cl. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is -halo, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is —Cl, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —F. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group, p is 0, m is 1, $R_1$ is —$CH_3$ or -halo, x is 0, $R_3$ is —$CH_3$ and is attached to the carbon atom adjacent to the nitrogen attached to the benzothiazolyl group, $R_4$ is —H, $R_8$ is —H, and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group, p is 0, m is 1, $R_1$ is —$CH_3$, x is 0, $R_3$ is —$CH_3$ and is attached to the carbon atom adjacent to the nitrogen attached to the benzothiazolyl group, $R_4$ is —H, $R_8$ is —H, and $R_9$ is —Cl. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group, p is 0, m is 1, $R_1$ is -halo, x is 0, $R_3$ is —$CH_3$ and is attached to the carbon atom adjacent to the nitrogen attached to the benzothiazolyl group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group, p is 0, m is 1, $R_1$ is —Cl, x is 0, $R_3$ is —$CH_3$ and is attached to the carbon atom adjacent to the nitrogen attached to the benzothiazolyl group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group, p is 0, m is 1, $R_1$ is —$CH_3$, x is 0, $R_3$ is —$CH_3$ and is attached to the carbon atom adjacent to the nitrogen attached to the benzothiazolyl group, $R_4$ is —H, $R_8$ is —H, and $R_9$ is —F. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is —$CH_3$ or -halo, x is 0, $R_3$ is —$CH_3$ and is attached to the carbon atom adjacent to the nitrogen attached to the benzothiazolyl group, $R_4$ is —H, $R_8$ is —H, and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is —$CH_3$, x is 0, $R_3$ is —$CH_3$ and is attached to the carbon atom adjacent to the nitrogen attached to the benzothiazolyl group, $R_4$ is —H, $R_8$ is —H, and $R_9$ is —Cl. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is -halo, x is 0, $R_3$ is —$CH_3$ and is attached to the carbon atom adjacent to the nitrogen attached to the benzothiazolyl group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is —Cl, x is 0, $R_3$ is —$CH_3$ and is attached to the carbon atom adjacent to the nitrogen attached to the benzothiazolyl group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is —$CH_3$, x is 0, $R_3$ is —$CH_3$ and is attached to the carbon atom adjacent to the nitrogen attached to the benzothiazolyl group, $R_4$ is —H, $R_8$ is —H, and $R_9$ is —F. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is —$CH_3$ or -halo, x is 0, $R_3$ is —$CH_3$ and is attached to the carbon atom adjacent to the nitrogen attached to the benzothiazolyl group, $R_4$ is —H, $R_8$ is —H, and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is —$CH_3$, x is 0, $R_3$ is —$CH_3$ and is attached to the carbon atom adjacent to the nitrogen attached to the benzothiazolyl group, $R_4$ is —H, $R_8$ is —H, and $R_9$ is —Cl. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is -halo, x is 0, $R_3$ is —$CH_3$ and is attached to the carbon atom adjacent to the nitrogen attached to the benzothiazolyl group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is —Cl, x is 0, $R_3$ is —$CH_3$ and is attached to the carbon atom adjacent to the nitrogen attached to the benzothiazolyl group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is —$CH_3$, x is 0, $R_3$ is —$CH_3$ and is attached to the carbon atom adjacent to the nitrogen attached to the benzothiazolyl group, $R_4$ is —H, $R_8$ is —H, and $R_9$ is —F. In another embodiment, the carbon atom to which the $R_3$ group is attached has the R configuration. In another embodiment, the carbon atom to which the $R_3$ group is attached has the S configuration.

In another embodiment, m is 1 and $R_3$ is —$(C_1$-$C_4)$alkyl and is attached to the carbon atom adjacent to the nitrogen attached to the —C(O)—N($R_4$)— when x is 1 or the benzothiazolyl group when x is 0. In another embodiment, m is 1 and $R_3$ is —$(C_1$-$C_4)$alkyl and is attached to the carbon atom adjacent to the nitrogen attached to the —C(O)—N($R_4$)— when x is 1 or the benzothiazolyl group when x is 0 and the carbon to which the $R_3$ group is attached is in the R configuration.

In another embodiment, m is 1 and $R_3$ is —$CH_3$ and is attached to the carbon atom adjacent to the nitrogen attached to the —C(O)—N($R_4$)— when x is 1 or the benzothiazolyl group when x is 0. In another embodiment, m is 1 and $R_3$ is —$CH_3$ and is attached to the carbon atom adjacent to the nitrogen attached to the —C(O)—N($R_4$)— when x is 1 or the benzothiazolyl group when x is 0 and the carbon to which the $R_3$ group is attached is in the R configuration.

In another embodiment, m is 1 and $R_3$ is —$(C_1$-$C_4)$alkyl and is attached to the carbon atom adjacent to the nitrogen attached to the —C(O)—N($R_4$)— when x is 1 or the benzothiazolyl group when x is 0. In another embodiment, m is 1 and $R_3$ is —$(C_1$-$C_4)$alkyl and is attached to the carbon atom adjacent to the nitrogen attached to the —C(O)—N($R_4$)— when x is 1 or the benzothiazolyl group when x is 0 and the carbon to which the $R_3$ group is attached is in the S configuration.

In another embodiment, m is 1 and $R_3$ is —$CH_3$ and is attached to the carbon atom adjacent to the nitrogen attached to the —C(O)—N($R_4$)— when x is 1 or the benzothiazolyl group when x is 0. In another embodiment, m is 1 and $R_3$ is —$CH_3$ and is attached to the carbon atom adjacent to the nitrogen attached to the —C(O)—N($R_4$)— when x is 1 or the benzothiazolyl group when x is 0 and the carbon to which the $R_3$ group is attached is in the S configuration.

In another embodiment, m is 1 and $R_3$ is —$(C_1$-$C_4)$alkyl and is attached to the carbon atom adjacent to the nitrogen attached to the pyrazinyl group, pyridazinyl group, or a thiazanyl group. In another embodiment, m is 1 and $R_3$ is —$(C_1$-$C_4)$alkyl and is attached to the carbon atom adjacent to the nitrogen attached to the pyrazinyl group, pyridazinyl group, or a thiazanyl group and the carbon to which the $R_3$ group is attached is in the R configuration.

In another embodiment, m is 1 and $R_3$ is —$CH_3$ and is attached to the carbon atom adjacent to the nitrogen attached to the pyrazinyl group, pyridazinyl group, or thiazanyl group. In another embodiment, m is 1 and $R_3$ is —$CH_3$ and is attached to the carbon atom adjacent to the nitrogen attached to the pyrazinyl group, pyridazinyl group, or thiazanyl group and the carbon to which the $R_3$ group is attached is in the R configuration.

In another embodiment, m is 1 and $R_3$ is —($C_1$-$C_4$)alkyl and is attached to the carbon atom adjacent to the nitrogen attached to the pyrazinyl group, pyridazinyl group, or thiazanyl group. In another embodiment, m is 1 and $R_3$ is —($C_1$-$C_4$)alkyl and is attached to the carbon atom adjacent to the nitrogen attached to the pyrazinyl group, pyridazinyl group, or thiazanyl group and the carbon to which the $R_3$ group is attached is in the S configuration.

In another embodiment, m is 1 and $R_3$ is —$CH_3$ and is attached to the carbon atom adjacent to the nitrogen attached to the pyrazinyl group, pyridazinyl group, or thiazanyl group. In another embodiment, m is 1 and $R_3$ is —$CH_3$ and is attached to the carbon atom adjacent to the nitrogen attached to the pyrazinyl group, pyridazinyl group, or thiazanyl group and the carbon to which the $R_3$ group is attached is in the S configuration.

The present invention also encompasses compounds of formula (IIa):

4.3 The Compounds of Formula (IIa)

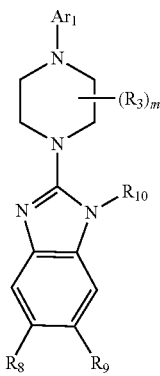

(IIa)

and pharmaceutically acceptable salts thereof, where $Ar_1$, $R_3$, $R_8$, $R_9$, $R_{10}$ and m, are defined above for the Benzoazolylpiperazine Compounds of formula (IIa).

In one embodiment, $Ar_1$ is a pyridyl group.
In another embodiment, $Ar_1$ is a pyrimidinyl group.
In another embodiment, $Ar_1$ is a pyrazinyl group.
In another embodiment, n or p is 0.
In another embodiment, n or p is 1.
In another embodiment, m is 0.
In another embodiment, m is 1.
In another embodiment, $R_{10}$ is —H.
In another embodiment, $R_{10}$ is —($C_1$-$C_4$)alkyl.
In another embodiment, $R_{10}$ is —$CH_3$.
In another embodiment, $R_1$ is —Cl.
In another embodiment, $R_1$ is —Br.
In another embodiment, $R_1$ is —I.
In another embodiment, $R_1$ is —($C_1$-$C_6$)alkyl.
In another embodiment, $R_1$ is —$CH_3$.
In another embodiment, $R_1$ is —$NO_2$.
In another embodiment, $R_1$ is —CN.
In another embodiment, $R_1$ is —OH.
In another embodiment, $R_1$ is —$OCH_3$.
In another embodiment, $R_1$ is —$NH_2$.
In another embodiment, $R_1$ is —C(halo)$_3$.
In another embodiment, $R_1$ is —CH(halo)$_2$.
In another embodiment, $R_1$ is —$CH_2$(halo).

In another embodiment, n and p are 1 and $R_2$ is -halo, —CN, —OH, —O($C_1$-$C_6$)alkyl, —$NO_2$, or —$NH_2$.

In another embodiment, n and p are 1 and $R_2$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups.

In another embodiment, n and p are 1 and $R_2$ is -phenyl, -naphthyl, —($C_{14}$)aryl, or -(5- to 10-membered)heteroaryl, each of which is unsubstituted or substituted with one or more $R_6$ groups;

In another embodiment, m is 1 and $R_3$ is -halo, —CN, —OH, —O($C_1$-$C_6$)alkyl, —$NO_2$, or —$NH_2$.

In another embodiment, m is 1 and $R_3$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups.

In another embodiment, m is 1 and $R_3$ is -phenyl, -naphthyl, —($C_{14}$)aryl or -(5- to 10-membered)heteroaryl, each of which is unsubstituted or substituted with one or more $R_6$ groups.

In another embodiment, $R_8$ and $R_9$ are each independently —H, halo, —($C_1$-$C_6$)alkyl, —O($C_1$-$C_6$)alkyl, —C(halo)$_3$, —CH(halo)$_2$, or —$CH_2$(halo).

In another embodiment, at least one of $R_8$ or $R_9$ is —H.

In another embodiment, n, p, and m are 0; $R_1$ is —Cl, —Br, or —I; $R_4$ is —H; and $R_8$ and $R_9$ are —H.

In another embodiment, n, p, and m are 0; $R_1$ is —Cl; $R_4$ is —H; and $R_8$ and $R_9$ are —H.

In another embodiment, n, p, and m are 0; $R_1$ is —Cl, —Br, or —I; $R_4$ is —H; $R_8$ is -halo H; and $R_9$ is —H. In another embodiment, $R_9$ is —Cl. In another embodiment, $R_9$ is —Br. In another embodiment, $R_9$ is —F.

In another embodiment, n, p, and m are 0; $R_1$ is —Cl; $R_4$ is —H; $R_8$ is -halo; and $R_9$ is —H. In another embodiment, $R_9$ is —Cl. In another embodiment, $R_9$ is —Br. In another embodiment, $R_9$ is —F.

In another embodiment, n, p, and m are 0; $R_1$ is —Cl, —Br, or —I; $R_4$ is —H; $R_8$ is —H; and $R_9$ is —$CH_3$. In another embodiment, $R_9$ is —Cl. In another embodiment, $R_9$ is —Br. In another embodiment, $R_9$ is —F.

In another embodiment, n, p, and m are 0; $R_1$ is —Cl; $R_8$ is —H; $R_8$ is —H; and $R_9$ —$CH_3$. In another embodiment, $R_9$ is —Cl. In another embodiment, $R_9$ is —Br. In another embodiment, $R_9$ is —F.

In another embodiment, n, p, and m are 0; $R_1$ is —Cl, —Br, or —I; $R_4$ is —H; $R_8$ is —$CH_3$; and $R_9$ is —H. In another embodiment, $R_9$ is —Cl. In another embodiment, $R_9$ is —Br. In another embodiment, $R_9$ is —F.

In another embodiment, n, p, and m are 0; $R_1$ is —Cl; $R_4$ is —H; $R_8$ is —$CH_3$; and $R_9$ is —H. In another embodiment, $R_9$ is —Cl. In another embodiment, $R_9$ is —Br. In another embodiment, $R_9$ is —F.

In another embodiment, n, p, and m are 0; $R_1$ is —Cl, —Br, or —I; $R_4$ is —H; $R_8$ is —H; and $R_9$ is —$CF_3$. In another embodiment, $R_9$ is —Cl. In another embodiment, $R_9$ is —Br. In another embodiment, $R_9$ is —F.

In another embodiment, n, p, and m are 0; $R_1$ is —Cl; $R_4$ is —H; $R_8$ is —H; and $R_9$ is —$CF_3$. In another embodiment, $R_9$ is —Cl. In another embodiment, $R_9$ is —Br. In another embodiment, $R_9$ is —F.

In another embodiment, n, p, and m are 0; $R_1$ is —Cl, —Br, or —I; $R_4$ is —H; $R_8$ is —CF$_3$; and $R_9$ is —H. In another embodiment, $R_9$ is —Cl. In another embodiment, $R_9$ is —Br. In another embodiment, $R_9$ is —F.

In another embodiment, n, p, and m are 0; $R_1$ is —Cl; $R_4$ is —H; $R_8$ is —CF$_3$; and $R_9$ is —H. In another embodiment, $R_9$ is —Cl. In another embodiment, $R_9$ is —Br. In another embodiment, $R_9$ is —F.

In another embodiment, n, p, and m are 0; $R_1$ is —Cl, —Br, or —I; $R_4$ is —H; $R_8$ is —H; and $R_9$ is —OCH$_2$CH$_3$. In another embodiment, $R_9$ is —Cl. In another embodiment, $R_9$ is —Br. In another embodiment, $R_9$ is —F.

In another embodiment, n, p, and m are 0; $R_1$ is —Cl; $R_4$ is —H; $R_8$ is —H; and $R_9$ is —OCH$_2$CH$_3$. In another embodiment, $R_9$ is —Cl. In another embodiment, $R_9$ is —Br. In another embodiment, $R_9$ is —F.

In another embodiment, n, p, and m are 0; $R_1$ is —Cl, —Br, or —I; $R_4$ is —H; $R_8$ is —OCH$_2$CH$_3$; and $R_9$ is —H. In another embodiment, $R_9$ is —Cl. In another embodiment, $R_9$ is —Br. In another embodiment, $R_9$ is —F.

In another embodiment, n, p, and m are 0; $R_1$ is —Cl; $R_4$ is —H; $R_8$ is —OCH$_2$CH$_3$; and $R_9$ is —H. In another embodiment, $R_9$ is —Cl. In another embodiment, $R_9$ is —Br. In another embodiment, $R_9$ is —F.

In another embodiment, n, p, and m are 0; $R_1$ is —Cl, Br, or —I; $R_4$ is —H; $R_8$ is —H; and $R_9$ is —CH$_3$.

In another embodiment, n, p, and m are 0; $R_1$ is —Cl; $R_4$ is —H; $R_8$ is —H; and $R_9$ is —CH$_3$.

In another embodiment, n, p, and m are 0; $R_1$ is —Cl, Br, or —I; $R_4$ is —H; $R_8$ is —CH$_3$; and $R_9$ is —H.

In another embodiment, n, p, and m are 0; $R_1$ is —Cl; $R_4$ is —H; $R_8$ is —CH$_3$; and $R_9$ is —H.

In another embodiment, n, p, and m are 0; $R_1$ is —Cl, Br, or —I; $R_4$ is —H; $R_8$ is —H; and $R_9$ is —CF$_3$.

In another embodiment, n, p, and m are 0; $R_1$ is —Cl; $R_4$ is —H; $R_8$ is —H; and $R_9$ is —CF$_3$.

In another embodiment, n, p, and m are 0; $R_1$ is —Cl, Br, or —I; $R_4$ is —H; $R_8$ is —CF$_3$; and $R_9$ is —H.

In another embodiment, n, p, and m are 0; $R_1$ is —Cl; $R_4$ is —H; $R_8$ is —CF$_3$; and $R_9$ is —H.

In another embodiment, n, p, and m are 0; $R_1$ is —Cl, Br, or —I; $R_4$ is —H; $R_8$ is —H; and $R_9$ is —OCH$_2$CH$_3$.

In another embodiment, n, p, and m are 0; $R_1$ is —Cl; $R_4$ is —H; $R_8$ is —H; and $R_9$ is —OCH$_2$CH$_3$.

In another embodiment, n, p, and m are 0; $R_1$ is —Cl, Br, or —I; $R_4$ is —H; $R_8$ is —OCH$_2$CH$_3$; and $R_9$ is —H.

In another embodiment, n, p, and m are 0; $R_1$ is —Cl; $R_4$ is —H; $R_8$ is —OCH$_2$CH$_3$; and $R_9$ is —H.

In another embodiment, n, p, and m are 0, $R_1$ is —CH$_3$, $R_4$ is —H, and $R_8$ and $R_9$ are —H.

In another embodiment, n, p, and m are 0; $R_1$ is —CH$_3$; $R_4$ is —H; $R_8$ is —H; and $R_9$ is -halo. In another embodiment, $R_9$ is —Cl. In another embodiment, $R_9$ is —Br. In another embodiment, $R_9$ is —F.

In another embodiment, n, p, and m are 0; $R_1$ is —CH$_3$; $R_4$ is —H; $R_8$ is -halo; and $R_9$ is —H. In another embodiment, $R_8$ is —Cl. In another embodiment, $R_8$ is —Br. In another embodiment, $R_8$ is —F.

In another embodiment, n, p, and m are 0; $R_1$ is —CH$_3$; $R_4$ is —H; $R_8$ is —H; and $R_9$ is —CH$_3$.

In another embodiment, n, p, and m are 0; $R_1$ is —CH$_3$; $R_4$ is —H; $R_8$ is —CH$_3$; and $R_9$ is —H.

In another embodiment, n, p, and m are 0; $R_1$ is —CH$_3$; $R_4$ is —H; $R_8$ is —H; and $R_9$ is —CF$_3$.

In another embodiment, n, p, and m are 0; $R_1$ is —CH$_3$; $R_4$ is —H; $R_8$ is —CF$_3$; and $R_9$ is —H.

In another embodiment, n, p, and m are 0; $R_1$ is —CH$_3$; $R_4$ is —H; $R_8$ is —H; and $R_9$ is —OCH$_2$CH$_3$.

In another embodiment, n, p, and m are 0; $R_1$ is —CH$_3$; $R_4$ is —H; $R_8$ is —OCH$_2$CH$_3$; and $R_9$ is —H.

In another embodiment, n, p, and m are 0; $R_1$ is —CF$_3$; $R_4$ is —H; $R_8$ is —H; and $R_9$ are —H.

In another embodiment, n, p, and m are 0; $R_1$ is —CF$_3$; $R_4$ is —H; $R_8$ is —H; and $R_9$ is -halo. In another embodiment, $R_9$ is —Cl. In another embodiment, $R_9$ is —Br. In another embodiment, $R_9$ is —F.

In another embodiment, n, p, and m are 0; $R_1$ is —CF$_3$; $R_4$ is —H; $R_8$ is -halo; and $R_9$ is —H. In another embodiment, $R_8$ is —Cl. In another embodiment, $R_8$ is —Br. In another embodiment, $R_8$ is —F.

In another embodiment, n, p, and m are 0; $R_1$ is —CF$_3$; $R_4$ is —H; $R_8$ is —H; and $R_9$ is —CH$_3$.

In another embodiment, n, p, and m are 0; $R_1$ is —CF$_3$; $R_4$ is —H; $R_8$ is —CH$_3$; and $R_9$ is —H.

In another embodiment, n, p, and m are 0; $R_1$ is —CF$_3$; $R_4$ is —H; $R_8$ is —H; and $R_9$ is —CF$_3$.

In another embodiment, n, p, and m are 0; $R_1$ is —CF$_3$; $R_4$ is —H; $R_8$ is —CF$_3$; and $R_9$ is —H.

In another embodiment, n, p, and m are 0; $R_1$ is —CF$_3$; $R_4$ is —H; $R_8$ is —H; and $R_9$ is —OCH$_2$CH$_3$.

In another embodiment, n, p, and m are 0; $R_1$ is —CF$_3$; $R_4$ is —H; $R_8$ is —OCH$_2$CH$_3$; and $R_9$ is —H.

In another embodiment, n, p, and m are 0; $R_1$ is —Cl, —Br, or —I; $R_4$ is —H; $R_8$ is -tert-butyl; and $R_9$ is —H.

In another embodiment, n, p, and m are 0; $R_1$ is —Cl; $R_4$ is —H; $R_8$ is -tert-butyl; and $R_9$ is —H.

In another embodiment, n, p, and m are 0; $R_1$ is —Cl, —Br, or —I; $R_4$ is —H; $R_8$ is —H; and $R_9$ is -tert-butyl.

In another embodiment, n, p, and m are 0; $R_1$ is —Cl; $R_4$ is —H; $R_8$ is —H; and $R_9$ is -tert-butyl.

In another embodiment, n, p, and m are 0; $R_1$ is —CH$_3$; $R_4$ is —H; $R_8$ is -tert-butyl; and $R_9$ is —H.

In another embodiment, n, p, and m are 0; $R_1$ is —CH$_3$; $R_4$ is —H; $R_8$ is —H; and $R_9$ is -tert-butyl.

In another embodiment, n, p, and m are 0; $R_1$ is —CH$_3$; $R_4$ is —H; $R_8$ is —CH$_3$; and $R_9$ is —CH$_3$.

In another embodiment, n is 0, $Ar_1$ is -2-(3-chloropyridyl)-, m is 1, $R_3$ is —CH$_3$ and is attached to the carbon atom adjacent to the nitrogen attached to the benzoimidazole group, the carbon atom to which the $R_3$ group is attached has the R configuration, $R_{10}$ is —H, $R_8$ is methyl, and $R_9$ is iso-propyl.

In another embodiment, n is 0, $Ar_1$ is -2-(3-chloropyridyl)-, m is 1, $R_3$ is —CH$_3$ and is attached to the carbon atom adjacent to the nitrogen attached to the benzoimidazole group, the carbon atom to which the $R_3$ group is attached has the R configuration, $R_{10}$ is —H, $R_8$ is iso-propyl, and $R_9$ is methyl.

In another embodiment, n and p are 0; m is 1; $R_1$ is —Cl, —Br, or —I; $R_4$ is —H; $R_3$ is —CH$_3$ and is attached to the carbon atom adjacent to the nitrogen attached to the benzoimidazole group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; $R_4$ is —H; $R_3$ is —CH$_3$ and is attached to the carbon atom adjacent to the nitrogen attached to the benzoimidazole group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; $R_4$ is —H; $R_3$ is —CH$_3$ and is attached to the carbon atom adjacent to the nitrogen attached to the benzoimidazole group; $R_8$ is —H; and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; $R_4$ is —H; $R_3$ is —CH$_3$ and is attached to the carbon atom adjacent to the nitrogen attached to the benzoimidazole group; $R_8$ is —H; and $R_9$ is -halo. In another embodiment $R_9$ is —Cl. In another embodiment, $R_9$ is —Br. In another embodiment, $R_1$ is —F. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; $R_4$ is —H; $R_3$ is —CH$_3$ and is attached to the carbon atom adjacent to the nitrogen attached to the benzoimidazole group; $R_8$ is -halo; and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; $R_4$ is —H; $R_3$ is —CH$_3$ and is attached to the carbon atom adjacent to the nitrogen attached to the benzoimidazole group; $R_8$ is -halo; and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; $R_4$ is —H; $R_3$ is —CH$_3$ and is attached to the carbon atom adjacent to the nitrogen attached to the benzoimidazole group; $R_8$ is —H; and $R_9$ is —CH$_3$. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; $R_4$ is —H; $R_3$ is —CH$_3$ and is attached to the carbon atom adjacent to the nitrogen attached to the benzoimidazole group; $R_8$ is —H; and $R_9$ is —CH$_3$. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; $R_4$ is —H; $R_3$ is —CH$_3$ and is attached to the carbon atom adjacent to the nitrogen attached to the benzoimidazole group; $R_8$ is —CH$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; $R_4$ is —H; $R_3$ is —CH$_3$ and is attached to the carbon atom adjacent to the nitrogen attached to the benzoimidazole group; $R_8$ is —CH$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; $R_4$ is —H; $R_3$ is —CH$_3$ and is attached to the carbon atom adjacent to the nitrogen attached to the benzoimidazole group; $R_8$ is —H; and $R_9$ is —CF$_3$. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; $R_4$ is —H; $R_3$ is —CH$_3$ and is attached to the carbon atom adjacent to the nitrogen attached to the benzoimidazole group; $R_8$ is —H; and $R_9$ is —CF$_3$. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; $R_4$ is —H; $R_3$ is —CH$_3$ and is attached to the carbon atom adjacent to the nitrogen attached to the benzoimidazole group; $R_8$ is —CF$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; $R_4$ is —H; $R_3$ is —CH$_3$ and is attached to the carbon atom adjacent to the nitrogen attached to the benzoimidazole group; $R_8$ is —CF$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; $R_4$ is —H; $R_3$ is —CH$_3$ and is attached to the carbon atom adjacent to the nitrogen attached to the -benzoimidazole group; $R_8$ is —H; and $R_9$ is —OCH$_2$CH$_3$. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; $R_4$ is —H; $R_3$ is —CH$_3$ and is attached to the carbon atom adjacent to the nitrogen attached to the -benzoimidazole group; $R_8$ is —H; and $R_9$ is —OCH$_2$CH$_3$. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; $R_4$ is —H; $R_3$ is —CH$_3$ and is attached to the carbon atom adjacent to the nitrogen attached to the benzoimidazole group; $R_8$ is —OCH$_2$CH$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; $R_4$ is —H; $R_3$ is —CH$_3$ and is attached to the carbon atom adjacent to the nitrogen attached to the benzoimidazole group; $R_8$ is —OCH$_2$CH$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —CH$_3$, $R_4$ is —H, $R_3$ is —CH$_3$ and is attached to the carbon atom adjacent to the nitrogen attached to the benzoimidazole group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, $R_4$ is —H, $R_3$ is —$CH_3$ and is attached to the carbon atom adjacent to the nitrogen attached to the benzoimidazole group, $R_8$ is —H, and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, $R_4$ is —H, $R_3$ is —$CH_3$ and is attached to the carbon atom adjacent to the nitrogen attached to the benzoimidazole group, $R_8$ is -halo, and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, $R_4$ is —H, $R_3$ is —$CH_3$ and is attached to the carbon atom adjacent to the nitrogen attached to the benzoimidazole group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, $R_4$ is —H, $R_3$ is —$CH_3$ and is attached to the carbon atom adjacent to the nitrogen attached to the benzoimidazole group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, $R_4$ is —H, $R_3$ is —$CH_3$ and is attached to the carbon atom adjacent to the nitrogen attached to the benzoimidazole group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, $R_4$ is —H, $R_3$ is —$CH_3$ and is attached to the carbon atom adjacent to the nitrogen attached to the benzoimidazole group, $R_8$ is —$CF_3$, and $R_9$ is —H. In another embodiment, the carbon atom to which the $R_3$ group is attached has the R configuration.

In another embodiment, n and p are 0, m is 1, $R_1$ is —$CH_3$, $R_4$ is —H, $R_3$ is —$CH_3$ and is attached to the carbon atom adjacent to the nitrogen attached to the benzoimidazole group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, $R_4$ is —H, $R_3$ is —$CH_3$ and is attached to the carbon atom adjacent to the nitrogen attached to the benzoimidazole group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, $R_4$ is —H, $R_3$ is —$CH_3$ and is attached to the carbon atom adjacent to the nitrogen attached to the benzoimidazole group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, $R_4$ is —H, $R_3$ is —$CH_3$ and is attached to the carbon atom adjacent to the nitrogen attached to the benzoimidazole group, $R_8$ is —H, and $R_9$ is -halo. In another embodiment, $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, $R_4$ is —H, $R_3$ is —$CH_3$ and is attached to the carbon atom adjacent to the nitrogen attached to the benzoimidazole group, $R_8$ is -halo, and $R_9$ is —H. In another embodiment, $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, $R_4$ is —H, $R_3$ is —$CH_3$ and is attached to the carbon atom adjacent to the nitrogen attached to the benzoimidazole group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, $R_4$ is —H, $R_3$ is —$CH_3$ and is attached to the carbon atom adjacent to the nitrogen attached to the benzoimidazole group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, $R_4$ is —H, $R_3$ is —$CH_3$ and is attached to the carbon atom adjacent to the nitrogen attached to the benzoimidazole group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, $R_4$ is —H, $R_3$ is —$CH_3$ and is attached to the carbon atom adjacent to the nitrogen attached to the benzoimidazole group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, $R_4$ is —H, $R_3$ is —$CH_3$ and is attached to the carbon atom adjacent to the nitrogen attached to the benzoimidazole group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, $R_4$ is —H, $R_3$ is —$CH_3$ and is attached to the carbon atom adjacent to the nitrogen attached to the benzoimidazole group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; $R_3$ is —$CH_3$ and is attached to the carbon atom adjacent to the nitrogen attached to the benzoimidazole group; $R_4$ is —H; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —Cl, $R_3$ is —$CH_3$ and is attached to the carbon atom adjacent to the nitrogen attached to the benzoimidazole group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; $R_3$ is —$CH_3$ and is attached to the carbon atom adjacent to the nitrogen attached to the benzoimidazole group; $R_4$ is —H; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —Cl, $R_3$ is —$CH_3$ and is attached to the carbon atom adjacent to the nitrogen attached to the benzoimidazole group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, $R_3$ is —$CH_3$ and is attached to the carbon atom adjacent to the nitrogen attached to the benzoimidazole group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, $R_3$ is —$CH_3$ and is attached to the carbon atom adjacent to the nitrogen attached to the benzoimidazole group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, $R_3$ is —$CH_3$ and is attached to the carbon atom adjacent to the nitrogen attached to the benzoimidazole group, $R_4$ is —H, $R_8$ is —$CH_3$, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group; n is 0; m is 1; $R_1$ is —$CH_3$, —Cl, —Br, or —I; $R_3$ is —$CH_3$ and is attached to the carbon atom adjacent to the nitrogen attached to the benzoimidazolyl group; $R_4$ is —H; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group n is 0, m is 1, $R_1$ is —$CH_3$, $R_3$ is —$CH_3$ and is attached to the carbon atom adjacent to the nitrogen attached to the benzoimidazolyl group, $R_4$ is —H, $R_8$ is —H, and $R_9$ is —Cl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group; n is 0; m is 1; $R_1$ is —Cl, —Br, or —I; $R_3$ is —$CH_3$ and is attached to the carbon atom adjacent to the nitrogen attached to the benzoimidazolyl group; $R_4$ is —H; $R_8$ is —H; and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0, m is 1, $R_1$ is —Cl, $R_3$ is —$CH_3$ and is attached to the carbon atom adjacent to the nitrogen attached to the benzoimidazolyl group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0, m is 1, $R_1$ is —$CH_3$, $R_3$ is —$CH_3$ and is attached to the carbon atom adjacent to the nitrogen attached to the benzoimidazolyl group, $R_4$ is —H, $R_8$ is —H, and $R_9$ is —F. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group; p is 0; m is 1; $R_1$ is —$CH_3$, —Cl, —Br, or —I; $R_3$ is —$CH_3$ and is attached to the carbon atom adjacent to the nitrogen attached to the benzimidazolyl group; $R_4$ is —H; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0, m is 1, $R_1$ is —$CH_3$, $R_3$ is —$CH_3$ and is attached to the carbon atom adjacent to the nitrogen attached to the benzimidazolyl group, $R_4$ is —H, $R_8$ is —H, and $R_9$ is —Cl. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group; p is 0; m is 1; $R_1$ is —Cl, —Br, or —I; $R_3$ is —$CH_3$ and is attached to the carbon atom adjacent to the nitrogen attached to the benzimidazolyl group; $R_4$ is —H; $R_8$ is —H; and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0, m is 1, $R_1$ is —Cl, $R_3$ is —$CH_3$ and is attached to the carbon atom adjacent to the nitrogen attached to the benzimidazolyl group, $R_4$ is —H, $R_3$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0, m is 1, $R_1$ is —$CH_3$, $R_3$ is —$CH_3$ and is attached to the carbon atom adjacent to the nitrogen attached to the benzimidazolyl group, $R_4$ is —H, $R_8$ is —H, and $R_9$ is —F. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group; p is 0; m is 1; $R_1$ is —$CH_3$, —Cl, —Br, or —I; $R_3$ is —$CH_3$ and is attached to the carbon atom adjacent to the nitrogen attached to the benzimidazolyl group; $R_4$ is —H; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group, p is 0, m is 1, $R_1$ is —$CH_3$, $R_3$ is —$CH_3$ and is attached to the carbon atom adjacent to the nitrogen attached to the benzimidazolyl group, $R_4$ is —H, $R_8$ is —H, and $R_9$ is —Cl. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group; p is 0; m is 1; $R_1$ is —Cl, —Br, or —I; $R_3$ is —$CH_3$ and is attached to the carbon atom adjacent to the nitrogen attached to the benzimidazolyl group; $R_4$ is —H; $R_8$ is —H; and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group, p is 0, m is 1, $R_1$ is —Cl, $R_3$ is —$CH_3$ and is attached to the carbon atom adjacent to the nitrogen attached to the benzimidazolyl group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group, p is 0, m is 1, $R_1$ is —$CH_3$, $R_3$ is —$CH_3$ and is attached to the carbon atom adjacent to the nitrogen attached to the benzimidazolyl group, $R_4$ is —H, $R_8$ is —H, and $R_9$ is —F. In another embodiment, the carbon atom to which the $R_3$ group is attached has the R configuration. In another embodiment, the carbon atom to which the $R_3$ group is attached has the S configuration.

In another embodiment, m is 1 and $R_3$ is —$(C_1$-$C_4)$alkyl and is attached to the carbon atom adjacent to the nitrogen attached to the benzoimidazolyl group. In another embodiment, m is 1 and $R_3$ is —$(C_1$-$C_4)$alkyl and is attached to the carbon atom adjacent to the nitrogen attached to the benzoimidazolyl group and the carbon to which the $R_3$ group is attached is in the R configuration.

In another embodiment, m is 1 and $R_3$ is —$CH_3$ and is attached to the carbon atom adjacent to the nitrogen attached to the benzoimidazolyl group. In another embodiment, m is 1 and $R_3$ is —$CH_3$ and is attached to the carbon atom adjacent to the nitrogen attached to the benzoimidazolyl group and the carbon to which the $R_3$ group is attached is in the R configuration.

In another embodiment, m is 1 and $R_3$ is —$(C_1$-$C_4)$alkyl and is attached to the carbon atom adjacent to the nitrogen attached to the benzoimidazolyl group. In another embodiment, m is 1 and $R_3$ is —$(C_1$-$C_4)$alkyl and is attached to the carbon atom adjacent to the nitrogen attached to the benzoimidazolyl group and the carbon to which the $R_3$ group is attached is in the S configuration.

In another embodiment, m is 1 and $R_3$ is —$CH_3$ and is attached to the carbon atom adjacent to the nitrogen attached to the benzoimidazolyl group. In another embodiment, m is 1 and $R_3$ is —$CH_3$ and is attached to the carbon atom adjacent to the nitrogen attached to the —C(O)—N($R_4$)— or the benzothiazolyl group and the carbon to which the $R_3$ group is attached is in the S configuration.

In another embodiment, m is 1 and $R_3$ is —$(C_1$-$C_4)$alkyl and is attached to the carbon atom adjacent to the nitrogen attached to the pyridyl group, pyrimidinyl group, or pyrazinyl group. In another embodiment, m is 1 and $R_3$ is —$(C_1$-$C_4)$alkyl and is attached to the carbon atom adjacent to the nitrogen attached to the pyridyl group, pyrimidinyl group, or pyrazinyl group and the carbon to which the $R_3$ group is attached is in the R configuration.

In another embodiment, m is 1 and $R_3$ is —$CH_3$ and is attached to the carbon atom adjacent to the nitrogen attached to the pyridyl group, pyrimidinyl group, or pyrazinyl group. In another embodiment, m is 1 and $R_3$ is —$CH_3$ and is attached to the carbon atom adjacent to the nitrogen attached to the pyridyl group, pyrimidinyl group, or pyrazinyl group and the carbon to which the $R_3$ group is attached is in the R configuration.

In another embodiment, m is 1 and $R_3$ is —$(C_1$-$C_4)$alkyl and is attached to the carbon atom adjacent to the nitrogen attached to the pyridyl group, pyrimidinyl group, or pyrazinyl group. In another embodiment, m is 1 and $R_3$ is —$(C_1$-$C_4)$ alkyl and is attached to the carbon atom adjacent to the nitrogen attached to the pyridyl group, pyrimidinyl group, or pyrazinyl group and the carbon to which the $R_3$ group is attached is in the S configuration.

In another embodiment, m is 1 and $R_3$ is —$CH_3$ and is attached to the carbon atom adjacent to the nitrogen attached to the pyridyl group, pyrimidinyl group, or pyrazinyl group. In another embodiment, m is 1 and $R_3$ is —$CH_3$ and is attached to the carbon atom adjacent to the nitrogen attached to the pyridyl group, pyrimidinyl group, or pyrazinyl group and the carbon to which the $R_3$ group is attached is in the S configuration.

4.4 The Compounds of Formula (IIb)

The present invention also encompasses compounds of formula (IIb):

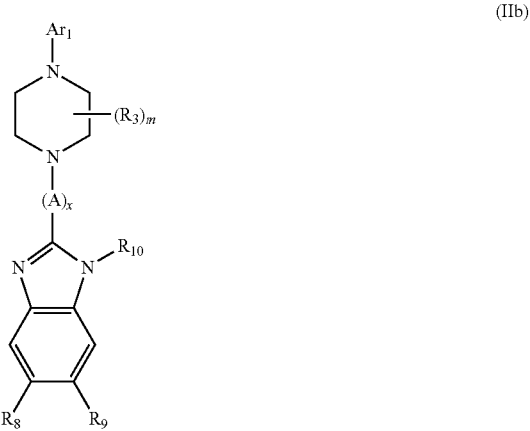

and pharmaceutically acceptable salts thereof, where $Ar_1$, $R_3$, $R_8$, $R_9$, A, x, and m, are defined above for the Benzoazolylpiperazine Compounds of formula (IIb).

In one embodiment, $Ar_1$ is a pyridazinyl group.
In another embodiment, $Ar_1$ is a thiazanyl group.
In another embodiment, x is 1 and A is —C(O)—N($R_4$)—.
In another embodiment, x is 1 and A is —C(S)—N($R_4$)—.
In another embodiment x is 0.
In another embodiment, x is 1.
In another embodiment p is 0.
In another embodiment, p is 1.
In another embodiment m is 0.
In another embodiment, m is 1.
In another embodiment, $R_4$ is —H.
In another embodiment, $R_4$ is —$(C_1$-$C_6)$alkyl.
In another embodiment, $R_{10}$ is —H.
In another embodiment, $R_{10}$ is —$(C_1$-$C_4)$alkyl.
In another embodiment, $R_{10}$ is —$CH_3$.
In another embodiment, $Ar_1$ is a pyrazinyl group, x is 1, and A is —C(O)N($R_4$)—.

In another embodiment, $Ar_1$ is a pyrazinyl group, x is 1, and A is —C(S)N($R_4$)—.

In another embodiment, $Ar_1$ is a thiazanyl group, x is 1, and A is —C(O)N($R_4$)—.

In another embodiment, $Ar_1$ is a thiazanyl group, x is 1, and A is —C(S)N($R_4$)—.

In another embodiment, $R_1$ is —H.
In another embodiment, $R_1$ is —Cl.
In another embodiment, $R_1$ is —Br.
In another embodiment, $R_1$ is —I.
In another embodiment, $R_1$ is —F.
In another embodiment, $R_1$ is —($C_1$-$C_6$)alkyl.
In another embodiment, $R_1$ is —$CH_3$.
In another embodiment, $R_1$ is —$NO_2$.
In another embodiment, $R_1$ is —CN.
In another embodiment, $R_1$ is —OH.
In another embodiment, $R_1$ is —$OCH_3$.
In another embodiment, $R_1$ is —$NH_2$.
In another embodiment, $R_1$ is —C(halo)$_3$.
In another embodiment, $R_1$ is —CH(halo)$_2$.
In another embodiment, $R_1$ is —$CH_2$(halo).

In another embodiment, p is 1 and $R_2$ is -halo, —CN, —OH, —O($C_1$-$C_6$)alkyl, —$NO_2$, or —$NH_2$.

In another embodiment, p is 1 and $R_2$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups.

In another embodiment, p is 1 and $R_2$ is -phenyl, -naphthyl, —($C_{14}$)aryl, or -(5- to 10-membered)heteroaryl, each of which is unsubstituted or substituted with one or more $R_6$ groups;

In another embodiment, m is 1 and $R_3$ is -halo, —CN, —OH, —O($C_1$-$C_6$)alkyl, —$NO_2$, or —$NH_2$.

In another embodiment, m is 1 and $R_3$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups.

In another embodiment, m is 1 and $R_3$ is -phenyl, -naphthyl, —($C_{14}$)aryl or -(5- to 10-membered)heteroaryl, each of which is unsubstituted or substituted with one or more $R_6$ groups.

In another embodiment, $R_8$ and $R_9$ are each independently —H, halo, —($C_1$-$C_6$)alkyl, —O($C_1$-$C_6$)alkyl, —C(halo)$_3$, —CH(halo)$_2$, or —$CH_2$(halo).

In another embodiment, at least one of $R_8$ or $R_9$ is —H.

In another embodiment, p and m are 0, $R_1$ is -halo, x is 1, A is —C(O)—N($R_4$)—, $R_4$ is —H, and $R_8$ and $R_9$ are —H.

In another embodiment, p and m are 0, $R_1$ is —Cl, x is 1, A is —C(O)—N($R_4$)—, $R_4$ is —H, and $R_8$ and $R_9$ are —H.

In another embodiment, p and m are 0, $R_1$ is -halo, x is 1, A is —C(O)—N($R_4$)—, $R_4$ is —H, $R_8$ is —H, and $R_9$ is -halo. In another embodiment, $R_9$ is —Cl. In another embodiment, $R_9$ is —Br. In another embodiment, $R_9$ is —F.

In another embodiment, p and m are 0, $R_1$ is —Cl, x is 1, A is —C(O)—N($R_4$)—, $R_4$ is —H, $R_8$ is —H, and $R_9$ is -halo. In another embodiment, $R_9$ is —Cl. In another embodiment, $R_9$ is —Br. In another embodiment, $R_9$ is —F.

In another embodiment, p and m are 0, $R_1$ is -halo, x is 1, A is —C(O)—N($R_4$)—, $R_4$ is —H, $R_8$ is -halo, and $R_9$ is —H. In another embodiment, $R_8$ is —Cl. In another embodiment, $R_8$ is —Br. In another embodiment, $R_8$ is —F.

In another embodiment, p and m are 0, $R_1$ is —Cl, x is 1, A is —C(O)—N($R_4$)—, $R_4$ is —H, $R_8$ is -halo, and $R_9$ is —H. In another embodiment, $R_8$ is —Cl. In another embodiment, $R_8$ is —Br. In another embodiment, $R_8$ is —F.

In another embodiment, p and m are 0, $R_1$ is -halo, x is 1, A is —C(O)—N($R_4$)—, $R_4$ is —H, $R_8$ is —H, and $R_9$ is —$CH_3$.

In another embodiment, p and m are 0, $R_1$ is —Cl, x is 1, A is —C(O)—N($R_4$)—, $R_4$ is —H, $R_8$ is —H, and $R_9$ is —$CH_3$.

In another embodiment, p and m are 0, $R_1$ is -halo, x is 1, A is —C(O)—N($R_4$)—, $R_4$ is —H, $R_8$ is —$CH_3$, and $R_9$ is —H.

In another embodiment, p and m are 0, $R_1$ is —Cl, x is 1, A is —C(O)—N($R_4$)—, $R_4$ is —H, $R_8$ is —$CH_3$, and $R_9$ is —H.

In another embodiment, p and m are 0, $R_1$ is -halo, x is 1, A is —C(O)—N($R_4$)—, $R_4$ is —H, $R_8$ is —H, and $R_9$ is —$CF_3$.

In another embodiment, p and m are 0, $R_1$ is —Cl, x is 1, A is —C(O)—N($R_4$)—, $R_4$ is —H, $R_8$ is —H, and $R_9$ is —$CF_3$.

In another embodiment, p and m are 0, $R_1$ is -halo, x is 1, A is —C(O)—N($R_4$)—, $R_4$ is —H, $R_8$ is —$CF_3$, and $R_9$ is —H.

In another embodiment, p and m are 0, $R_1$ is —Cl, x is 1, A is —C(O)—N($R_4$)—, $R_4$ is —H, $R_8$ is —$CF_3$, and $R_9$ is —H.

In another embodiment, p and m are 0, $R_1$ is -halo, x is 1, A is —C(O)—N($R_4$)—, $R_4$ is —H, $R_8$ is —H, and $R_9$ is —$OCH_2CH_3$.

In another embodiment, p and m are 0, $R_1$ is —Cl, x is 1, A is —C(O)—N($R_4$)—, $R_4$ is —H, $R_8$ is —H, and $R_9$ is —$OCH_2CH_3$.

In another embodiment, p and m are 0, $R_1$ is -halo, x is 1, A is —C(O)—N($R_4$)—, $R_4$ is —H, $R_8$ is —$OCH_2CH_3$, and $R_9$ is —H.

In another embodiment, p and m are 0, $R_1$ is —Cl, x is 1, A is —C(O)—N($R_4$)—, $R_4$ is —H, $R_8$ is —$OCH_2CH_3$, and $R_9$ is —H.

In another embodiment, p and m are 0, $R_1$ is —$CH_3$, x is 1, A is —C(O)—N($R_4$)—, $R_4$ is —H, and $R_8$ and $R_9$ are —H.

In another embodiment, p and m are 0, $R_1$ is —$CH_3$, x is 1, A is —C(O)—N($R_4$)—, $R_4$ is —H, $R_8$ is —H, and $R_9$ is -halo. In another embodiment, $R_9$ is —Cl. In another embodiment, $R_9$ is —Br. In another embodiment, $R_9$ is —F.

In another embodiment, p and m are 0, $R_1$ is —$CH_3$, x is 1, A is —C(O)—N($R_4$)—, $R_4$ is —H, $R_8$ is -halo, and $R_9$ is —H. In another embodiment, $R_8$ is —Cl. In another embodiment, $R_8$ is —Br. In another embodiment, $R_8$ is —F.

In another embodiment, p and m are 0, $R_1$ is —$CH_3$, x is 1, A is —C(O)—N($R_4$)—, $R_4$ is —H, $R_8$ is —H, and $R_9$ is —$CH_3$.

hi another embodiment, p and m are 0, $R_1$ is —$CH_3$, x is 1, A is —C(O)—N($R_4$)—, $R_4$ is —H, $R_8$ is —$CH_3$, and $R_9$ is —H.

In another embodiment, p and m are 0, $R_1$ is —$CH_3$, x is 1, A is —C(O)—N($R_4$)—, $R_4$ is —H, $R_8$ is —H, and $R_9$ is —$CF_3$.

In another embodiment, p and m are 0, $R_1$ is —$CH_3$, x is 1, A is —C(O)—N($R_4$)—, $R_4$ is —H, $R_8$ is —$CF_3$, and $R_9$ is —H.

In another embodiment, p and m are 0, $R_1$ is —$CH_3$, x is 1, A is —C(O)—N($R_4$)—, $R_4$ is —H, $R_8$ is —H, and $R_9$ is —$OCH_2CH_3$.

In another embodiment, p and m are 0, $R_1$ is —$CH_3$, x is 1, A is —C(O)—N($R_4$)—, $R_4$ is —H, $R_8$ is —$OCH_2CH_3$, and $R_9$ is —H.

In another embodiment, p and m are 0, $R_1$ is —$CF_3$, x is 1, A is —C(O)—N($R_4$)—, $R_4$ is —H, and $R_8$ and $R_9$ are —H.

In another embodiment, p and m are 0, $R_1$ is —$CF_3$, x is 1, A is —C(O)—N($R_4$)—, $R_4$ is —H, $R_8$ is —H, and $R_9$ is -halo. In another embodiment, $R_9$ is —Cl. In another embodiment, $R_9$ is —Br. In another embodiment, $R_9$ is —F.

In another embodiment, p and m are 0, $R_1$ is —$CF_3$, x is 1, A is —C(O)—N($R_4$)—, $R_4$ is —H, $R_8$ is -halo, and $R_9$ is —H. In another embodiment, $R_8$ is —Cl. In another embodiment, $R_8$ is —Br. In another embodiment, $R_8$ is —F.

In another embodiment, p and m are 0, $R_1$ is —$CF_3$, x is 1, A is —C(O)—N($R_4$)—, $R_4$ is —H, $R_8$ is —H, and $R_9$ is —$CH_3$.

In another embodiment, p and m are 0, $R_1$ is —$CF_3$, x is 1, A is —C(O)—N($R_4$)—, $R_4$ is —H, $R_8$ is —$CH_3$, and $R_9$ is —H.

In another embodiment, p and m are 0, $R_1$ is —$CF_3$, x is 1, A is —C(O)—N($R_4$)—, $R_4$ is —H, $R_8$ is —H, and $R_9$ is —$CF_3$.

In another embodiment, p and m are 0, $R_1$ is —$CF_3$, x is 1, A is —C(O)—N($R_4$)—, $R_4$ is —H, $R_8$ is —$CF_3$, and $R_9$ is —H.

In another embodiment, p and m are 0, $R_1$ is —$CF_3$, x is 1, A is —C(O)—N($R_4$)—, $R_4$ is —H, $R_8$ is —H, and $R_9$ is —$OCH_2CH_3$.

In another embodiment, p and m are 0, $R_1$ is —$CF_3$, x is 1, A is —C(O)—N($R_4$)—, $R_4$ is —H, $R_8$ is —$OCH_2CH_3$, and $R_9$ is —H.

In another embodiment, p and m are 0, $R_1$ is -halo, x is 1, A is —C(O)—N($R_4$)—, $R_4$ is —H, $R_8$ is -tert-butyl, and $R_9$ is —H.

In another embodiment, p and m are 0, $R_1$ is —Cl, x is 1, A is —C(O)—N($R_4$)—, $R_4$ is —H, $R_8$ is -tert-butyl, and $R_9$ is —H.

In another embodiment, p and m are 0, $R_1$ is -halo, x is 1, A is —C(O)—N($R_4$)—, $R_4$ is —H, $R_8$ is —H, and $R_9$ is -tert-butyl.

In another embodiment, p and m are 0, $R_1$ is —Cl, x is 1, A is —C(O)—N($R_4$)—, $R_4$ is —H, $R_8$ is —H, and $R_9$ is -tert-butyl.

In another embodiment, p and m are 0, $R_1$ is —$CH_3$, x is 1, A is —C(O)—N($R_4$)—, $R_4$ is —H, $R_8$ is -tert-butyl, and $R_9$ is —H.

In another embodiment, p and m are 0, $R_1$ is —$CH_3$, x is 1, A is —C(O)—N($R_4$)—, $R_4$ is —H, $R_8$ is —H, and $R_9$ is -tert-butyl.

In another embodiment, p and m are 0, $R_1$ is —$CH_3$, x is 1, A is —C(O)—N($R_4$)—, $R_4$ is —H, $R_8$ is —$CH_3$, and $R_9$ is —$CH_3$.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is -halo. In another embodiment, $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is -halo. In another embodiment, $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is -halo, and $R_9$ is —H. In another embodiment, $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is -halo, and $R_9$ is —H. In another embodiment, $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is -halo. In another embodiment, $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is -halo, and $R_9$ is —H. In another embodiment, $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is -halo. In another embodiment, $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is -halo, and $R_9$ is —H. In another embodiment, $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)-M$R_4$)—, $R_4$ is —H, $R_3$ is —$CH_3$ and is attached to the carbon atom adjacent to the nitrogen attached to the —C(O)—N($R_4$)— group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —OCH$_2$CH$_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —OCH$_2$CH$_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —$CH_3$, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, p and m are 0, $R_1$ is -halo, x is 0, $R_4$ is —H, and $R_8$ and $R_9$ are —H.

In another embodiment, p and m are 0, $R_1$ is —Cl, x is 0, $R_4$ is —H, and $R_8$ and $R_9$ are —H.

In another embodiment, p and m are 0, $R_1$ is -halo, x is 0, $R_4$ is —H, $R_8$ is —H, and $R_9$ is -halo. In another embodiment, $R_9$ is —Cl. In another embodiment, $R_9$ is —Br. In another embodiment, $R_9$ is —F.

In another embodiment, p and m are 0, $R_1$ is —Cl, x is 0, $R_4$ is —H, $R_8$ is —H, and $R_9$ is -halo. In another embodiment, $R_9$ is —Cl. In another embodiment, $R_9$ is —Br. In another embodiment, $R_9$ is —F.

In another embodiment, p and m are 0, $R_1$ is -halo, x is 0, $R_4$ is —H, $R_8$ is -halo, and $R_9$ is —H. In another embodiment, $R_8$ is —Cl. In another embodiment, $R_8$ is —Br. In another embodiment, $R_8$ is —F.

In another embodiment, p and m are 0, $R_1$ is —Cl, x is 0, $R_4$ is —H, $R_8$ is -halo, and $R_9$ is —H. In another embodiment, $R_8$ is —Cl. In another embodiment, $R_8$ is —Br. In another embodiment, $R_8$ is —F.

In another embodiment, p and m are 0, $R_1$ is -halo, x is 0, $R_4$ is —H, $R_8$ is —H, and $R_9$ is —CH$_3$.

In another embodiment, p and m are 0, $R_1$ is —Cl, x is 0, $R_4$ is —H, $R_8$ is —H, and $R_9$ is —CH$_3$.

In another embodiment, p and m are 0, $R_1$ is -halo, x is 0, $R_4$ is —H, $R_8$ is —CH$_3$, and $R_9$ is —H.

In another embodiment, p and m are 0, $R_1$ is —Cl, x is 0, $R_4$ is —H, $R_8$ is —CH$_3$, and $R_9$ is —H.

In another embodiment, p and m are 0, $R_1$ is -halo, x is 0, $R_4$ is —H, $R_8$ is —H, and $R_9$ is —CF$_3$.

In another embodiment, p and m are 0, $R_1$ is —Cl, x is 0, $R_4$ is —H, $R_8$ is —H, and $R_9$ is —CF$_3$.

In another embodiment, p and m are 0, $R_1$ is -halo, x is 0, $R_4$ is —H, $R_8$ is —CF$_3$, and $R_9$ is —H.

In another embodiment, p and m are 0, $R_1$ is —Cl, x is 0, $R_4$ is —H, $R_8$ is —CF$_3$, and $R_9$ is —H.

In another embodiment, p and m are 0, $R_1$ is -halo, x is 0, $R_4$ is —H, $R_8$ is —H, and $R_9$ is —OCH$_2$CH$_3$.

In another embodiment, p and m are 0, $R_1$ is —Cl, x is 0, $R_4$ is —H, $R_8$ is —H, and $R_9$ is —OCH$_2$CH$_3$.

In another embodiment, p and m are 0, $R_1$ is -halo, x is 0, $R_4$ is —H, $R_8$ is —OCH$_2$CH$_3$, and $R_9$ is —H.

In another embodiment, p and m are 0, $R_1$ is —Cl, x is 0, $R_4$ is —H, $R_8$ is —OCH$_2$CH$_3$, and $R_9$ is —H.

In another embodiment, p and m are 0, $R_1$ is —CH$_3$, x is 0, $R_4$ is —H, and $R_8$ and $R_9$ are —H.

In another embodiment, p and m are 0, $R_1$ is —CH$_3$, x is 0, $R_4$ is —H, $R_8$ is —H, and $R_9$ is -halo. In another embodiment, $R_9$ is —Cl. In another embodiment, $R_9$ is —Br. In another embodiment, $R_9$ is —F.

In another embodiment, p and m are 0, $R_1$ is —CH$_3$, x is 0, $R_4$ is —H, $R_8$ is -halo, and $R_9$ is —H. In another embodiment, $R_8$ is —Cl. In another embodiment, $R_8$ is —Br. In another embodiment, $R_8$ is —F.

In another embodiment, p and m are 0, $R_1$ is —CH$_3$, x is 0, $R_4$ is —H, $R_8$ is —H, and $R_9$ is —CH$_3$.

In another embodiment, p and m are 0, $R_1$ is —CH$_3$, x is 0, $R_4$ is —H, $R_8$ is —CH$_3$, and $R_9$ is —H.

In another embodiment, p and m are 0, $R_1$ is —CH$_3$, x is 0, $R_4$ is —H, $R_8$ is —H, and $R_9$ is —CF$_3$.

In another embodiment, p and m are 0, $R_1$ is —CH$_3$, x is 0, $R_4$ is —H, $R_8$ is —CF$_3$, and $R_9$ is —H.

In another embodiment, p and m are 0, $R_1$ is —CH$_3$, x is 0, $R_4$ is —H, $R_8$ is —H, and $R_9$ is —OCH$_2$CH$_3$.

In another embodiment, p and m are 0, $R_1$ is —CH$_3$, x is 0, $R_4$ is —H, $R_8$ is —OCH$_2$CH$_3$, and $R_9$ is —H.

In another embodiment, p and m are 0, $R_1$ is —CF$_3$, x is 0, $R_4$ is —H, and $R_8$ and $R_9$ are —H.

In another embodiment, p and m are 0, $R_1$ is —CF$_3$, x is 0, $R_4$ is —H, $R_8$ is —H, and $R_9$ is -halo. In another embodiment, $R_9$ is —Cl. In another embodiment, $R_9$ is —Br. In another embodiment, $R_9$ is —F.

In another embodiment, p and m are 0, $R_1$ is —CF$_3$, x is 0, $R_4$ is —H, $R_8$ is -halo, and $R_9$ is —H. In another embodiment, $R_8$ is —Cl. In another embodiment, $R_8$ is —Br. In another embodiment, $R_8$ is —F.

In another embodiment, p and m are 0, $R_1$ is —CF$_3$, x is 0, $R_4$ is —H, $R_8$ is —H, and $R_9$ is —CH$_3$.

In another embodiment, p and m are 0, $R_1$ is —CF$_3$, x is 0, $R_4$ is —H, $R_8$ is —CH$_3$, and $R_9$ is —H.

In another embodiment, p and m are 0, $R_1$ is —CF$_3$, x is 0, $R_4$ is —H, $R_8$ is —H, and $R_9$ is —CF$_3$.

In another embodiment, p and m are 0, $R_1$ is —CF$_3$, x is 0, $R_4$ is —H, $R_8$ is —CF$_3$, and $R_9$ is —H.

In another embodiment, p and m are 0, $R_1$ is —CF$_3$, x is 0, $R_4$ is —H, $R_8$ is —H, and $R_9$ is —OCH$_2$CH$_3$.

In another embodiment, p and m are 0, $R_1$ is —CF$_3$, x is 0, $R_4$ is —H, $R_8$ is —OCH$_2$CH$_3$, and $R_9$ is —H.

In another embodiment, p and m are 0, $R_1$ is -halo, x is 0, $R_4$ is —H, $R_8$ is -tert-butyl, and $R_9$ is —H.

In another embodiment, p and m are 0, $R_1$ is —Cl, x is 0, $R_4$ is —H, $R_8$ is -tert-butyl, and $R_9$ is —H.

In another embodiment, p and m are 0, $R_1$ is -halo, x is 0, $R_4$ is —H, $R_8$ is —H, and $R_9$ is -tert-butyl.

In another embodiment, p and m are 0, $R_1$ is —Cl, x is 0, $R_4$ is —H, $R_8$ is —H, and $R_9$ is -tert-butyl.

In another embodiment, p and m are 0, $R_1$ is —CH$_3$, x is 0, $R_4$ is —H, $R_8$ is -tert-butyl, and $R_9$ is —H.

In another embodiment, p and m are 0, $R_1$ is —CH$_3$, x is 0, $R_4$ is —H, $R_8$ is —H, and $R_9$ is -tert-butyl.

In another embodiment, p and m are 0, $R_1$ is —CH$_3$, x is 0, $R_4$ is —H, $R_8$ is —CH$_3$, and $R_9$ is —CH$_3$.

In another embodiment, p is 0, m is 1, $R_1$ is -halo, x is 0, $R_4$ is —H, $R_3$ is —CH$_3$ and is attached to the carbon atom adjacent to the nitrogen attached to the benzoimidazolyl group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —CH$_3$ and is attached to the carbon atom adjacent to the nitrogen attached to the benzoimidazolyl group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_4$ is —H, $R_3$ is —CH$_3$ and is attached to the carbon atom adjacent to the nitrogen attached to the benzoimidazolyl group, $R_8$ is —H, and $R_9$ is -halo. In another embodiment, $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —CH$_3$ and is attached to the carbon atom adjacent to the nitrogen attached to the benzoimidazolyl group, $R_8$ is —H, and $R_9$ is -halo. In another embodiment, $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_4$ is —H, $R_3$ is —CH$_3$ and is attached to the carbon atom adjacent to the nitrogen attached to the benzoimidazolyl group, $R_8$ is -halo, and $R_9$ is —H. In another embodiment, $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —CH$_3$ and is attached to the carbon atom adjacent to the nitrogen attached to the benzoimidazolyl group, $R_8$ is -halo, and $R_9$ is —H. In another embodiment, $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_4$ is —H, $R_3$ is —CH$_3$ and is attached to the carbon atom adjacent to the nitrogen attached to the benzoimidazolyl group, $R_8$ is —H, and $R_9$ is —CH$_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —CH$_3$ and is attached to the carbon atom adjacent to the nitrogen attached to the benzoimidazolyl group, $R_8$ is —H, and $R_9$ is —CH$_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_4$ is —H, $R_3$ is —CH$_3$ and is attached to the carbon atom adjacent to the nitrogen attached to the benzoimidazolyl group, $R_8$ is —CH$_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —CH$_3$ and is attached to the carbon atom adjacent to the nitrogen attached to the benzoimidazolyl group, $R_8$ is —CH$_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_4$ is —H, $R_3$ is —CH$_3$ and is attached to the carbon atom adjacent to the nitrogen attached to the benzoimidazolyl group, $R_8$ is —H, and $R_9$ is —CF$_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —CH$_3$ and is attached to the carbon atom adjacent to the nitrogen attached to the benzoimidazolyl group, $R_8$ is —H, and $R_9$ is —CF$_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_4$ is —H, $R_3$ is —CH$_3$ and is attached to the carbon atom adjacent to the nitrogen attached to the benzoimidazolyl group, $R_8$ is —CF$_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —CH$_3$ and is attached to the carbon atom adjacent to the nitrogen attached to the benzoimidazolyl group, $R_8$ is —CF$_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_4$ is —H, $R_3$ is —CH$_3$ and is attached to the carbon atom adjacent to the nitrogen attached to the benzoimidazolyl group, $R_8$ is —H, and $R_9$ is —OCH$_2$CH$_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —CH$_3$ and is attached to the carbon atom adjacent to the nitrogen attached to the benzoimidazolyl group, $R_8$ is —H, and $R_9$ is —OCH$_2$CH$_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_4$ is —H, $R_3$ is —CH$_3$ and is attached to the carbon atom adjacent to the nitrogen attached to the benzoimidazolyl group, $R_8$ is —OCH$_2$CH$_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —CH$_3$ and is attached to the carbon atom adjacent to the nitrogen attached to the benzoimidazolyl group, $R_8$ is —OCH$_2$CH$_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —CH$_3$, x is 0, $R_4$ is —H, $R_3$ is —CH$_3$ and is attached to the carbon atom adjacent to the nitrogen attached to the benzoimidazolyl group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —CH$_3$, x is 0, $R_4$ is —H, $R_3$ is —CH$_3$ and is attached to the carbon atom adjacent to the nitrogen attached to the benzoimidazolyl group, $R_8$ is —H, and $R_9$ is -halo. In another embodiment, $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —CH$_3$, x is 0, $R_4$ is —H, $R_3$ is —CH$_3$ and is attached to the carbon atom adjacent to the nitrogen attached to the benzoimidazolyl group, $R_8$ is -halo, and $R_9$ is —H. In another embodiment, $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —CH$_3$, x is 0, $R_4$ is —H, $R_3$ is —CH$_3$ and is attached to the carbon atom adjacent to the nitrogen attached to the benzoimidazolyl group, $R_8$ is —H, and $R_9$ is —CH$_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_4$ is —H, $R_3$ is —$CH_3$ and is attached to the carbon atom adjacent to the nitrogen attached to the benzoimidazolyl group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_4$ is —H, $R_3$ is —$CH_3$ and is attached to the carbon atom adjacent to the nitrogen attached to the benzoimidazolyl group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_4$ is —H, $R_3$ is —$CH_3$ and is attached to the carbon atom adjacent to the nitrogen attached to the benzoimidazolyl group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_4$ is —H, $R_3$ is —$CH_3$ and is attached to the carbon atom adjacent to the nitrogen attached to the benzoimidazolyl group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_4$ is —H, $R_3$ is —$CH_3$ and is attached to the carbon atom adjacent to the nitrogen attached to the benzoimidazolyl group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 0, $R_4$ is —H, $R_3$ is —$CH_3$ and is attached to the carbon atom adjacent to the nitrogen attached to the benzoimidazolyl group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 0, $R_4$ is —H, $R_3$ is —$CH_3$ and is attached to the carbon atom adjacent to the nitrogen attached to the benzoimidazolyl group, $R_8$ is —H, and $R_9$ is -halo. In another embodiment, $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 0, $R_4$ is —H, $R_3$ is —$CH_3$ and is attached to the carbon atom adjacent to the nitrogen attached to the benzoimidazolyl group, $R_8$ is -halo, and $R_9$ is —H. In another embodiment, $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 0, $R_4$ is —H, $R_3$ is —$CH_3$ and is attached to the carbon atom adjacent to the nitrogen attached to the benzoimidazolyl group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 0, $R_4$ is —H, $R_3$ is —$CH_3$ and is attached to the carbon atom adjacent to the nitrogen attached to the benzoimidazolyl group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 0, $R_4$ is —H, $R_3$ is —$CH_3$ and is attached to the carbon atom adjacent to the nitrogen attached to the benzoimidazolyl group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 0, $R_4$ is —H, $R_3$ is —$CH_3$ and is attached to the carbon atom adjacent to the nitrogen attached to the benzoimidazolyl group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 0, $R_4$ is —H, $R_3$ is —$CH_3$ and is attached to the carbon atom adjacent to the nitrogen attached to the benzoimidazolyl group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 0, $R_4$ is —H, $R_3$ is —$CH_3$ and is attached to the carbon atom adjacent to the nitrogen attached to the benzoimidazolyl group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_3$ is —$CH_3$ and is attached to the carbon atom adjacent to the nitrogen attached to the benzoimidazolyl group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_3$ is —$CH_3$ and is attached to the carbon atom adjacent to the nitrogen attached to the benzoimidazolyl group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_3$ is —$CH_3$ and is attached to the carbon atom adjacent to the nitrogen attached to the benzoimidazolyl group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_3$ is —$CH_3$ and is attached to the carbon atom adjacent to the nitrogen attached to the benzoimidazolyl group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_3$ is —$CH_3$ and is attached to the carbon atom adjacent to the nitrogen attached to the benzoimidazolyl group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_3$ is —$CH_3$ and is attached to the carbon atom adjacent to the nitrogen attached to the benzoimidazolyl group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_3$ is —$CH_3$ and is attached to the carbon atom adjacent to the nitrogen attached to the benzoimidazolyl group, $R_4$ is —H, $R_8$ is —$CH_3$, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is —$CH_3$ or -halo, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Cl. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is -halo, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is —Cl, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —F. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is —$CH_3$ or -halo, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Cl. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is -halo, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is —Cl, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —F. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is —$CH_3$ or -halo, x is 0, $R_3$ is —$CH_3$ and is attached to the carbon atom adjacent to the nitrogen attached to the benzoimidazolyl group, $R_4$ is —H, $R_8$ is —H, and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is —$CH_3$, x is 0, $R_3$ is —$CH_3$ and is attached to the carbon atom adjacent to the nitrogen attached to the benzoimidazolyl group, $R_4$ is —H, $R_8$ is —H, and $R_9$ is —Cl. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is -halo, x is 0, $R_3$ is —$CH_3$ and is attached to the carbon atom adjacent to the nitrogen attached to the benzoimidazolyl group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is —Cl, x is 0, $R_3$ is —$CH_3$ and is attached to the carbon atom adjacent to the nitrogen attached to the benzoimidazolyl group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is —$CH_3$, x is 0, $R_3$ is —$CH_3$ and is attached to the carbon atom adjacent to the nitrogen attached to the benzoimidazolyl group, $R_4$ is —H, $R_8$ is —H, and $R_9$ is —F. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is —$CH_3$ or -halo, x is 0, $R_3$ is —$CH_3$ and is attached to the carbon atom adjacent to the nitrogen attached to the benzoimidazolyl group, $R_4$ is —H, $R_8$ is —H, and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is —$CH_3$, x is 0, $R_3$ is —$CH_3$ and is attached to the carbon atom adjacent to the nitrogen attached to the benzoimidazolyl group, $R_4$ is —H, $R_8$ is —H, and $R_9$ is —Cl. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is -halo, x is 0, $R_3$ is —$CH_3$ and is attached to the carbon atom adjacent to the nitrogen attached to the benzoimidazolyl group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is —Cl, x is 0, $R_3$ is —$CH_3$ and is attached to the carbon atom adjacent to the nitrogen attached to the benzoimidazolyl group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is —$CH_3$, x is 0, $R_3$ is —$CH_3$ and is attached to the carbon atom adjacent to the nitrogen attached to the benzoimidazolyl group, $R_4$ is —H, $R_8$ is —H, and $R_9$ is —F. In another embodiment, the carbon atom to which the $R_3$ group is attached has the R configuration. In another embodiment, the carbon atom to which the $R_3$ group is attached has the S configuration.

In another embodiment, m is 1 and $R_3$ is —$(C_1-C_4)$alkyl and is attached to the carbon atom adjacent to the nitrogen attached to the —C(O)—N($R_4$)— when x is 1 or the benzoimidazolyl group when x is 0. In another embodiment, m is 1 and $R_3$ is —$(C_1-C_4)$alkyl and is attached to the carbon atom adjacent to the nitrogen attached to the —C(O)—N($R_4$)— when x is 1 or the benzoimidazolyl group when x is 0 and the carbon to which the $R_3$ group is attached is in the R configuration.

In another embodiment, m is 1 and $R_3$ is —$CH_3$ and is attached to the carbon atom adjacent to the nitrogen attached to the —C(O)—N($R_4$)— when x is 1 or the benzoimidazolyl group when x is 0. In another embodiment, m is 1 and $R_3$ is —$CH_3$ and is attached to the carbon atom adjacent to the nitrogen attached to the —C(O)—N($R_4$)— when x is 1 or the benzoimidazolyl group when x is 0 and the carbon to which the $R_3$ group is attached is in the R configuration.

In another embodiment, m is 1 and $R_3$ is —$CH_3$ and is attached to the carbon atom adjacent to the nitrogen attached to the —C(O)—N($R_4$)— when x is 1 or the benzoimidazolyl group when x is 0. In another embodiment, m is 1 and $R_3$ is —$CH_3$ and is attached to the carbon atom adjacent to the nitrogen attached to the —C(O)—N($R_4$)— when x is 1 or the benzoimidazolyl group when x is 0 and the carbon to which the $R_3$ group is attached is in the S configuration.

In another embodiment, m is 1 and $R_3$ is —$(C_1-C_4)$alkyl and is attached to the carbon atom adjacent to the nitrogen attached to the pyridazinyl group or thiazanyl group. In another embodiment, m is 1 and $R_3$ is —$(C_1-C_4)$alkyl and is attached to the carbon atom adjacent to the nitrogen attached to the pyridazinyl group or thiazanyl group and the carbon to which the $R_3$ group is attached is in the R configuration.

In another embodiment, m is 1 and $R_3$ is —$CH_3$ and is attached to the carbon atom adjacent to the nitrogen attached to the pyridazinyl group or thiazanyl group. In another embodiment, m is 1 and $R_3$ is —$CH_3$ and is attached to the carbon atom adjacent to the nitrogen attached to the pyridazinyl group or thiazanyl group and the carbon to which the $R_3$ group is attached is in the R configuration.

In another embodiment, m is 1 and $R_3$ is —$(C_1-C_4)$alkyl and is attached to the carbon atom adjacent to the nitrogen attached to the pyridazinyl group or thiazanyl group. In another embodiment, m is 1 and $R_3$ is —$(C_1-C_4)$alkyl and is attached to the carbon atom adjacent to the nitrogen attached to the pyridazinyl group or thiazanyl group and the carbon to which the $R_3$ group is attached is in the S configuration.

In another embodiment, m is 1 and $R_3$ is —$CH_3$ and is attached to the carbon atom adjacent to the nitrogen attached to the pyridazinyl group or thiazanyl group. In another embodiment, m is 1 and $R_3$ is —$CH_3$ and is attached to the carbon atom adjacent to the nitrogen attached to the pyridazinyl group or thiazanyl group and the carbon to which the $R_3$ group is attached is in the S configuration.

4.5 The Compounds of Formula (IIIa)

The present invention encompasses compounds of Formula (IIIa)

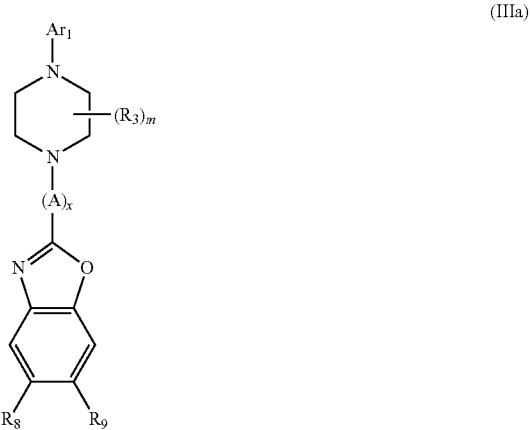

(IIIa)

and pharmaceutically acceptable salts thereof, where $Ar_1$, $R_3$, $R_8$, $R_9$, A, x, and m, are defined above for the Benzoazolylpiperazine Compounds of formula (IIIa).

In one embodiment, $Ar_1$ is a pyridyl group.

In another embodiment, $Ar_1$ is a pyrimidinyl group.

In another embodiment, x is 1 and A is —C(O)—N($R_4$)—.

In another embodiment, x is 1 and A is —C(S)—N($R_4$)—.

In another embodiment x is 0.

In another embodiment x is 1.

In another embodiment n or p is 0.

In another embodiment n or p is 1.

In another embodiment m is 0.

In another embodiment m is 1.

In another embodiment, $Ar_1$ is a pyridyl group, x is 1, and A is —C(O)N($R_4$)—.

In another embodiment, $Ar_1$ is a pyridyl group, x is 1, and A is —C(S)N($R_4$)—.

In another embodiment, $Ar_1$ is a pyrimidinyl group, x is 1, and A is —C(O)N($R_4$)—.

In another embodiment, $Ar_1$ is a pyrimidinyl group, x is 1, and A is —C(S)N($R_4$)—.

In another embodiment, $R_1$ is —Cl.

In another embodiment, $R_1$ is —Br.

In another embodiment, $R_1$ is —I.

In another embodiment, $R_1$ is —($C_1$-$C_6$)alkyl.

In another embodiment, $R_1$ is —$CH_3$.

In another embodiment, $R_1$ is —$NO_2$.

In another embodiment, $R_1$ is —CN.

In another embodiment, $R_1$ is —OH.

In another embodiment, $R_1$ is —$OCH_3$.

In another embodiment, $R_1$ is —$NH_2$.

In another embodiment, $R_1$ is —C(halo)$_3$.

In another embodiment, $R_1$ is —CH(halo)$_2$.

In another embodiment, $R_1$ is —$CH_2$(halo).

In another embodiment, n and p are 1 and $R_2$ is -halo, —CN, —OH, —O($C_1$-$C_6$)alkyl, —$NO_2$, or —$NH_2$.

In another embodiment, n and p are 1 and $R_2$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups.

In another embodiment, n and p are 1 and $R_2$ is -phenyl, -naphthyl, —($C_{14}$)aryl, or -(5- to 10-membered)heteroaryl, each of which is unsubstituted or substituted with one or more $R_6$ groups;

In another embodiment, m is 1 and $R_3$ is -halo, —CN, —OH, —O($C_1$-$C_6$)alkyl, —$NO_2$, or —$NH_2$.

In another embodiment, m is 1 and $R_3$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups.

In another embodiment, m is 1 and $R_3$ is -phenyl, -naphthyl, —($C_{14}$)aryl or -(5- to 10-membered)heteroaryl, each of which is unsubstituted or substituted with one or more $R_6$ groups.

In another embodiment, $R_4$ is —H.

In another embodiment, $R_4$ is —($C_1$-$C_6$)alkyl.

In another embodiment, $R_8$ and $R_9$ are each independently —H, halo, —($C_1$-$C_6$)alkyl, —O($C_1$-$C_6$)alkyl, —C(halo)$_3$, —CH(halo)$_2$, or —$CH_2$(halo).

In another embodiment, at least one of $R_8$ or $R_9$ is —H.

In another embodiment, n, p, and m are 0; $R_1$ is —Cl, —Br, or —I; x is 1; A is —C(O)—N($R_4$)—; $R_4$ is —H; and $R_8$ and $R_9$ are —H.

In another embodiment, n, p, and m are 0; $R_1$ is —Cl; x is 1; A is —C(O)—N($R_4$)—; $R_4$ is —H; and $R_8$ and $R_9$ are —H.

In another embodiment, n, p, and m are 0; $R_1$ is —Cl, —Br, or —I; x is 1; A is —C(O)—N($R_4$)—; $R_4$ is —H; $R_8$ is —H; and $R_9$ is -halo. In another embodiment, $R_9$ is —Cl. In another embodiment, $R_9$ is —Br. In another embodiment, $R_9$ is —F.

In another embodiment, n, p, and m are 0; $R_1$ is —Cl; x is 1; A is —C(O)—N($R_4$)—; $R_4$ is —H; $R_8$ is —H; and $R_9$ is -halo. In another embodiment, $R_9$ is —Cl. In another embodiment, $R_9$ is —Br. In another embodiment, $R_9$ is —F.

In another embodiment, n, p, and m are 0; $R_1$ is —Cl, —Br, or —I; x is 1; A is —C(O)—N($R_4$)—; $R_4$ is —H; $R_8$ is -halo; and $R_9$ is —H. In another embodiment, $R_8$ is —Cl. In another embodiment, $R_8$ is —Br. In another embodiment, $R_8$ is —F.

In another embodiment, n, p, and m are 0; $R_1$ is —Cl; x is 1; A is —C(O)—N($R_4$)—; $R_4$ is —H; $R_8$ is -halo; and $R_9$ is —H. In another embodiment, $R_8$ is —Cl. In another embodiment, $R_8$ is —Br. In another embodiment, $R_8$ is —F.

In another embodiment, n, p, and m are 0; $R_1$ is —Cl, —Br, or —I; x is 1; A is —C(O)—N($R_4$)—; $R_4$ is —H; $R_8$ is —H; and $R_9$ is —$CH_3$.

In another embodiment, n, p, and m are 0; $R_1$ is —Cl; x is 1; A is —C(O)—N($R_4$)—; $R_4$ is —H; $R_8$ is —H; and $R_9$ is —$CH_3$.

In another embodiment, n, p, and m are 0; $R_1$ is —Cl, —Br, or —I; x is 1; A is —C(O)—N($R_4$)—; $R_4$ is —H; $R_8$ is —$CH_3$; and $R_9$ is —H.

In another embodiment, n, p, and m are 0; $R_1$ is —Cl; x is 1; A is —C(O)—N($R_4$)—; $R_4$ is —H; $R_8$ is —$CH_3$; and $R_9$ is —H.

In another embodiment, n, p, and m are 0; $R_1$ is —Cl, —Br, or —I; x is 1; A is —C(O)—N($R_4$)—; $R_4$ is —H, $R_8$ is —H; and $R_9$ is —$CF_3$.

In another embodiment, n, p, and m are 0; $R_1$ is —Cl; x is 1; A is —C(O)—N($R_4$)—; $R_4$ is —H; $R_8$ is —H; and $R_9$ is —$CF_3$.

In another embodiment, n, p, and m are 0; $R_1$ is —Cl, —Br, or —I; x is 1; A is —C(O)—N($R_4$)—; $R_4$ is —H; $R_8$ is —$CF_3$; and $R_9$ is —H.

In another embodiment, n, p, and m are 0; $R_1$ is —Cl; x is 1; A is —C(O)—N($R_4$)—; $R_4$ is —H; $R_8$ is —$CF_3$; and $R_9$ is —H.

In another embodiment, n, p, and m are 0; $R_1$ is —Cl, —Br, or —I; x is 1; A is —C(O)—N($R_4$)—; $R_4$ is —H; $R_8$ is —H; and $R_9$ is —$OCH_2CH_3$.

In another embodiment, n, p, and m are 0; $R_1$ is —Cl; x is 1; A is —C(O)—N($R_4$)—; $R_4$ is —H; $R_8$ is —H; and $R_9$ is —$OCH_2CH_3$.

In another embodiment, n, p, and m are 0; $R_1$ is —Cl, —Br, or —I; x is 1; A is —C(O)—N($R_4$)—; $R_4$ is —H; $R_8$ is —$OCH_2CH_3$; and $R_9$ is —H.

In another embodiment, n, p, and m are 0; $R_1$ is —Cl; x is 1; A is —C(O)—N($R_4$)—; $R_4$ is —H; $R_8$ is —$OCH_2CH_3$; and $R_9$ is —H.

In another embodiment, n, p, and m are 0, $R_1$ is —$CH_3$, x is 1, A is —C(O)—N($R_4$)—, $R_4$ is —H, and $R_8$ and $R_9$ are —H.

In another embodiment, n, p, and m are 0, $R_1$ is —$CH_3$, x is 1, A is —C(O)—N($R_4$)—, $R_4$ is —H, $R_8$ is —H, and $R_9$ is -halo. In another embodiment, $R_9$ is —Cl. In another embodiment, $R_9$ is —Br. In another embodiment, $R_9$ is —F.

In another embodiment, n, p, and m are 0, $R_1$ is —$CH_3$, x is 1, A is —C(O)—N($R_4$)—, $R_4$ is —H, $R_8$ is -halo, and $R_9$ is —H. In another embodiment, $R_8$ is —Cl. In another embodiment, $R_8$ is —Br. In another embodiment, $R_8$ is —F.

In another embodiment, n, p, and m are 0, $R_1$ is —$CH_3$, x is 1, A is —C(O)—N($R_4$)—, $R_4$ is —H, $R_8$ is —H, and $R_9$ is —$CH_3$.

In another embodiment, n, p, and m are 0, $R_1$ is —$CH_3$, x is 1, A is —C(O)—N($R_4$)—, $R_4$ is —H, $R_8$ is —$CH_3$, and $R_9$ is —H.

In another embodiment, n, p, and m are 0, $R_1$ is —$CH_3$, x is 1, A is —C(O)—N($R_4$)—, $R_4$ is —H, $R_8$ is —H, and $R_9$ is —$CF_3$.

In another embodiment, n, p, and m are 0, $R_1$ is —$CH_3$, x is 1, A is —C(O)—N($R_4$)—, $R_4$ is —H, $R_8$ is —$CF_3$, and $R_9$ is —H.

In another embodiment, n, p, and m are 0, $R_1$ is —$CH_3$, x is 1, A is —C(O)—N($R_4$)—, $R_4$ is —H, $R_8$ is —H, and $R_9$ is —$OCH_2CH_3$.

In another embodiment, n, p, and m are 0, $R_1$ is —$CH_3$, x is 1, A is —C(O)—N($R_4$)—, $R_4$ is —H, $R_8$ is —$OCH_2CH_3$, and $R_9$ is —H.

In another embodiment, n, p, and m are 0, $R_1$ is —$CF_3$, x is 1, A is —C(O)—N($R_4$)—, $R_4$ is —H, and $R_8$ and $R_9$ are —H.

In another embodiment, n, p, and m are 0, $R_1$ is —$CF_3$, x is 1, A is —C(O)—N($R_4$)—, $R_4$ is —H, $R_8$ is —H, and $R_9$ is -halo. In another embodiment, $R_9$ is —Cl. In another embodiment, $R_9$ is —Br. In another embodiment, $R_9$ is —F.

In another embodiment, n, p, and m are 0, $R_1$ is —$CF_3$, x is 1, A is —C(O)—N($R_4$)—, $R_4$ is —H, $R_8$ is -halo, and $R_9$ is —H. In another embodiment, $R_8$ is —Cl. In another embodiment, $R_8$ is —Br. In another embodiment, $R_8$ is —F.

In another embodiment, n, p, and m are 0, $R_1$ is —$CF_3$, x is 1, A is —C(O)—N($R_4$)—, $R_4$ is —H, $R_8$ is —H, and $R_9$ is —$CH_3$.

In another embodiment, n, p, and m are 0, $R_1$ is —$CF_3$, x is 1, A is —C(O)—N($R_4$)—, $R_4$ is —H, $R_8$ is —$CH_3$, and $R_9$ is —H.

In another embodiment, n, p, and m are 0, $R_1$ is —$CF_3$, x is 1, A is —C(O)—N($R_4$)—, $R_4$ is —H, $R_8$ is —H, and $R_9$ is —$CF_3$.

In another embodiment, n, p, and m are 0, $R_1$ is —$CF_3$, x is 1, A is —C(O)—N($R_4$)—, $R_4$ is —H, $R_8$ is —$CF_3$, and $R_9$ is —H.

In another embodiment, n, p, and m are 0, $R_1$ is —$CF_3$, x is 1, A is —C(O)—N($R_4$)—, $R_4$ is —H, $R_8$ is —H, and $R_9$ is —$OCH_2CH_3$.

In another embodiment, n, p, and m are 0, $R_1$ is —$CF_3$, x is 1, A is —C(O)—N($R_4$)—, $R_4$ is —H, $R_8$ is —$OCH_2CH_3$, and $R_9$ is —H.

In another embodiment, n, p, and m are 0; $R_1$ is —Cl, —Br, or —I; x is 1; A is —C(O)—N($R_4$)—; $R_4$ is —H; $R_8$ is -tert-butyl; and $R_9$ is —H.

In another embodiment, n, p, and m are 0; $R_1$ is —Cl; x is 1; A is —C(O)—N($R_4$)—; $R_4$ is —H; $R_8$ is -tert-butyl; and $R_9$ is —H.

In another embodiment, n, p, and m are 0; $R_1$ is —Cl, —Br, or —I; x is 1; A is —C(O)—N($R_4$)—; $R_4$ is —H; $R_8$ is —H; and $R_9$ is -tert-butyl.

In another embodiment, n, p, and m are 0; $R_1$ is —Cl; x is 1; A is —C(O)—N($R_4$)—; $R_4$ is —H; $R_8$ is —H; and $R_9$ is -tert-butyl.

In another embodiment, n, p, and m are 0; $R_1$ is —$CH_3$; x is 1, A is —C(O)—N($R_4$)—, $R_4$ is —H, $R_8$ is -tert-butyl, and $R_9$ is —H.

In another embodiment, n, p, and m are 0, $R_1$ is —$CH_3$, x is 1, A is —C(O)—N($R_4$)—, $R_4$ is —H, $R_8$ is —H, and $R_9$ is -tert-butyl.

In another embodiment, n, p, and m are 0, $R_1$ is —$CH_3$, x is 1, A is —C(O)—N($R_4$)—, $R_4$ is —H, $R_8$ is —$CH_3$, and $R_9$ is —$CH_3$.

In another embodiment, n is 0, $Ar_1$ is -2-(3-nitropyridyl)-, m is 0, x is 0, and $R_8$ and $R_9$ are —H.

In another embodiment, n and p are 0; m is 1; $R_1$ is —Cl, —Br, or —I; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, n and p are 0; m is 1, $R_1$ is —Cl; x is 1, A is —C(O)—N($R_4$)—; $R_4$ is —H; $R_3$ is —$CH_3$ and is attached to the carbon atom adjacent to the nitrogen attached to the —C(O)—N($R_4$)— group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; $R_8$ is —H; and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; $R_8$ is —H; and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; $R_8$ is -halo; and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; $R_8$ is -halo; and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; $R_3$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; $R_3$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; x is 1; A is —C(O)—N($R_4$)—; $R_4$ is —H; $R_3$ is —$CH_3$ and is attached to the carbon atom adjacent to the nitrogen attached to the —C(O)—N($R_4$)— group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is -halo, and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is -halo, and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 1; A is —C(O)—N($R_4$)—; $R_3$ is —$CH_3$ and is attached to the carbon atom adjacent to the nitrogen attached to the —C(O)—N($R_4$)— group; $R_4$ is —H; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; x is 1; A is —C(O)—N($R_4$)—; $R_3$ is —$CH_3$ and is attached to the carbon atom adjacent to the nitrogen attached to the —C(O)—N($R_4$)— group; $R_4$ is —H; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 1; A is —C(O)—N($R_4$)—; $R_3$ is —$CH_3$ and is attached to the carbon atom adjacent to the nitrogen attached to the —C(O)—N($R_4$)— group; $R_4$ is —H; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; x is 1; A is —C(O)—N($R_4$)—; $R_3$ is —$CH_3$ and is attached to the carbon atom adjacent to the nitrogen attached to the —C(O)—N($R_4$)— group; $R_4$ is —H; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —$CH_3$, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, n, p, and m are 0; $R_1$ is —Cl, —Br, or —I; x is 0; $R_4$ is —H; and $R_8$ and $R_9$ are —H.

In another embodiment, n, p, and m are 0; $R_1$ is —Cl; x is 0; $R_4$ is —H; and $R_8$ and $R_9$ are —H.

In another embodiment, n, p, and m are 0; $R_1$ is —Cl, —Br, or —I; x is 0; $R_4$ is —H; $R_8$ is —H; and $R_9$ is -halo. In another embodiment, $R_9$ is —Cl. In another embodiment, $R_9$ is —Br. In another embodiment, $R_9$ is —F.

In another embodiment, n, p, and m are 0; $R_1$ is —Cl; x is 0; $R_4$ is —H; $R_8$ is —H; and $R_9$ is -halo. In another embodiment, $R_9$ is —Cl. In another embodiment, $R_9$ is —Br. In another embodiment, $R_9$ is —F.

In another embodiment, n, p, and m are 0; $R_1$ is —Cl, —Br, or —I; x is 0; $R_4$ is —H; $R_8$ is -halo; and $R_9$ is —H. In another embodiment, $R_8$ is —Cl. In another embodiment, $R_8$ is —Br. In another embodiment, $R_8$ is —F.

In another embodiment, n, p, and m are 0; $R_1$ is —Cl, x is 0; $R_4$ is —H; $R_8$ is -halo; and $R_9$ is —H. In another embodiment, $R_8$ is —Cl. In another embodiment, $R_8$ is —Br. In another embodiment, $R_8$ is —F.

In another embodiment, n, p, and m are 0; $R_1$ is —Cl, —Br, or —I; x is 0; $R_4$ is —H; $R_8$ is —H; and $R_9$ is —$CH_3$.

In another embodiment, n, p, and m are 0; $R_1$ is —Cl; x is 0; $R_4$ is —H; $R_8$ is —H; and $R_9$ is —$CH_3$.

In another embodiment, n, p, and m are 0; $R_1$ is —Cl, —Br, or —I; x is 0; $R_4$ is —H; $R_8$ is —$CH_3$; and $R_9$ is —H.

In another embodiment, n, p, and m are 0; $R_1$ is —Cl; x is 0; $R_4$ is —H; $R_8$ is —$CH_3$; and $R_9$ is —H.

In another embodiment, n, p, and m are 0; $R_1$ is —Cl, —Br, or —I; x is 0; $R_4$ is —H; $R_8$ is —H; and $R_9$ is —$CF_3$.

In another embodiment, n, p, and m are 0; $R_1$ is —Cl; x is 0; $R_4$ is —H; $R_8$ is —H; and $R_9$ is —$CF_3$.

In another embodiment, n, p, and m are 0; $R_1$ is —Cl, —Br, or —I; x is 0; $R_4$ is —H; $R_8$ is —$CF_3$; and $R_9$ is —H.

In another embodiment, n, p, and m are 0; $R_1$ is —Cl; x is 0; $R_4$ is —H; $R_8$ is —$CF_3$; and $R_9$ is —H.

In another embodiment, n, p, and m are 0; $R_1$ is —Cl, —Br, or —I; x is 0; $R_4$ is —H; $R_8$ is —H; and $R_9$ is —$OCH_2CH_3$.

In another embodiment, n, p, and m are 0; $R_1$ is —Cl; x is 0; $R_4$ is —H; $R_8$ is —H; and $R_9$ is —$OCH_2CH_3$.

In another embodiment, n, p, and m are 0; $R_1$ is —Cl, —Br, or —I; x is 0; $R_4$ is —H; $R_8$ is —$OCH_2CH_3$; and $R_9$ is —H.

In another embodiment, n, p, and m are 0; $R_1$ is —Cl; x is 0; $R_4$ is —H; $R_8$ is —$OCH_2CH_3$; and $R_9$ is —H.

In another embodiment, n, p, and m are 0; $R_1$ is —$CH_3$, x is 0; $R_4$ is —H, and $R_8$ and $R_9$ are —H.

In another embodiment, n, p, and m are 0; $R_1$ is —$CH_3$, x is 0; $R_4$ is —H, $R_8$ is —H, and $R_9$ is -halo. In another embodiment, $R_9$ is —Cl. In another embodiment, $R_9$ is —Br. In another embodiment, $R_9$ is —F.

In another embodiment, n, p, and m are 0; $R_1$ is —$CH_3$, x is 0; $R_4$ is —H, $R_8$ is -halo, and $R_9$ is —H. In another embodiment, $R_8$ is —Cl. In another embodiment, $R_8$ is —Br. In another embodiment, $R_8$ is —F.

In another embodiment, n, p, and m are 0; $R_1$ is —$CH_3$, x is 0; $R_4$ is —H, $R_8$ is —H, and $R_9$ is —$CH_3$.

In another embodiment, n, p, and m are 0, $R_1$ is —$CH_3$, x is 0, $R_4$ is —H, $R_8$ is —$CH_3$, and $R_9$ is —H.

In another embodiment, n, p, and m are 0, $R_1$ is —$CH_3$, x is 0, $R_4$ is —H, $R_8$ is —H, and $R_9$ is —$CF_3$.

In another embodiment, n, p, and m are 0, $R_1$ is —$CH_3$, x is 0, $R_4$ is —H, $R_8$ is —$CF_3$, and $R_9$ is —H.

In another embodiment, n, p, and m are 0, $R_1$ is —$CH_3$, x is 0, $R_4$ is —H, $R_8$ is —H, and $R_9$ is —$OCH_2CH_3$.

In another embodiment, n, p, and m are 0, $R_1$ is —$CH_3$, x is 0, $R_4$ is —H, $R_8$ is —$OCH_2CH_3$, and $R_9$ is —H.

In another embodiment, n, p, and m are 0, $R_1$ is —$CF_3$, x is 0, $R_4$ is —H, and $R_8$ and $R_9$ are —H.

In another embodiment, n, p, and m are 0, $R_1$ is —$CF_3$, x is 0, $R_4$ is —H, $R_8$ is —H, and $R_9$ is -halo. In another embodiment, $R_9$ is —Cl. In another embodiment, $R_9$ is —Br. In another embodiment, $R_9$ is —F.

In another embodiment, n, p, and m are 0, $R_1$ is —$CF_3$, x is 0, $R_4$ is —H, $R_8$ is -halo, and $R_9$ is —H. In another embodiment, $R_8$ is —Cl. In another embodiment, $R_8$ is —Br. In another embodiment, $R_8$ is —F.

In another embodiment, n, p, and m are 0, $R_1$ is —$CF_3$, x is 0, $R_4$ is —H, $R_8$ is —H, and $R_9$ is —$CH_3$.

In another embodiment, n, p, and m are 0, $R_1$ is —$CF_3$, x is 0, $R_4$ is —H, $R_8$ is —$CH_3$, and $R_9$ is —H.

In another embodiment, n, p, and m are 0, $R_1$ is —$CF_3$, x is 0, $R_4$ is —H, $R_8$ is —H, and $R_9$ is —$CF_3$.

In another embodiment, n, p, and m are 0, $R_1$ is —$CF_3$, x is 0, $R_4$ is —H, $R_8$ is —$CF_3$, and $R_9$ is —H.

In another embodiment, n, p, and m are 0, $R_1$ is —$CF_3$, x is 0, $R_4$ is —H, $R_8$ is —H, and $R_9$ is —$OCH_2CH_3$.

In another embodiment, n, p, and m are 0, $R_1$ is —$CF_3$, x is 0, $R_4$ is —H, $R_8$ is —$OCH_2CH_3$, and $R_9$ is —H.

In another embodiment, n, p, and m are 0; $R_1$ is —Cl, —Br, or —I; x is 0; $R_4$ is —H; $R_8$ is -tert-butyl; and $R_9$ is —H.

In another embodiment, n, p, and m are 0; $R_1$ is —Cl; x is 0; $R_4$ is —H; $R_8$ is -tert-butyl; and $R_9$ is —H.

In another embodiment, n, p, and m are 0; $R_1$ is —Cl, —Br, or —I; x is 0; $R_4$ is —H; $R_8$ is —H; and $R_9$ is -tert-butyl.

In another embodiment, n, p, and m are 0; $R_1$ is —Cl; x is 0; $R_4$ is —H; $R_8$ is —H; and $R_9$ is -tert-butyl.

In another embodiment, n, p, and m are 0, $R_1$ is —$CH_3$, x is 0, $R_4$ is —H, $R_8$ is -tert-butyl, and $R_9$ is —H.

In another embodiment, n, p, and m are 0, $R_1$ is —$CH_3$, x is 0, $R_4$ is —H, $R_8$ is —H, and $R_9$ is -tert-butyl.

In another embodiment, n, p, and m are 0, $R_1$ is —$CH_3$, x is 0, $R_4$ is —H, $R_8$ is —$CH_3$, and $R_9$ is —$CH_3$.

In another embodiment, n and p are 0; m is 1; $R_1$ is —Br, or —I; x is 0; $R_4$ is —H; $R_3$ is —$CH_3$ and is attached to the carbon atom adjacent to the nitrogen attached to the benzooxazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, n and p are 0; m is 1, $R_1$ is —Cl; x is 0; $R_4$ is —H; $R_3$ is —$CH_3$ and is attached to the carbon atom adjacent to the nitrogen attached to the benzooxazolyl group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 0; $R_4$ is —H; $R_3$ is —CH$_3$ and is attached to the carbon atom adjacent to the nitrogen attached to the benzooxazolyl group; $R_8$ is —H; and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; x is 0; $R_4$ is —H; $R_3$ is —CH$_3$ and is attached to the carbon atom adjacent to the nitrogen attached to the benzooxazolyl group; $R_8$ is —H; and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 0; $R_4$ is —H; $R_3$ is —CH$_3$ and is attached to the carbon atom adjacent to the nitrogen attached to the benzooxazolyl group; $R_8$ is -halo; and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, n and p are 0; m is 1, $R_1$ is —Cl; x is 0; $R_4$ is —H; $R_3$ is —CH$_3$ and is attached to the carbon atom adjacent to the nitrogen attached to the benzooxazolyl group; $R_8$ is -halo; and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 0; $R_4$ is —H; $R_3$ is —CH$_3$ and is attached to the carbon atom adjacent to the nitrogen attached to the benzooxazolyl group; $R_8$ is —H; and $R_9$ is —CH$_3$. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; x is 0; $R_4$ is —H; $R_3$ is —CH$_3$ and is attached to the carbon atom adjacent to the nitrogen attached to the benzooxazolyl group; $R_8$ is —H; and $R_9$ is —CH$_3$. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 0; $R_4$ is —H; $R_3$ is —CH$_3$ and is attached to the carbon atom adjacent to the nitrogen attached to the benzooxazolyl group; $R_8$ is —CH$_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; x is 0; $R_4$ is —H; $R_3$ is —CH$_3$ and is attached to the carbon atom adjacent to the nitrogen attached to the benzooxazolyl group; $R_8$ is —CH$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, n and p 0; m is 1; $R_1$ is —Cl, —Br, or —I; x is 0; $R_4$ is —H; $R_3$ is —CH$_3$ and is attached to the carbon atom adjacent to the nitrogen attached to the benzooxazolyl group; $R_8$ is —H; and $R_9$ is —CF$_3$. In another embodiment, the carbon atom to which the $R_3$ group is attached has the R configuration. In another embodiment, the carbon atom to which the $R_3$ group is attached has the S configuration.

In another embodiment, n and p 0; m is 1; $R_1$ is —Cl; x is 0; $R_4$ is —H; $R_3$ is —CH$_3$ and is attached to the carbon atom adjacent to the nitrogen attached to the benzooxazolyl group; $R_8$ is —H; and $R_9$ is —CF$_3$. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 0; $R_4$ is —H; $R_3$ is —CH$_3$ and is attached to the carbon atom adjacent to the nitrogen attached to the benzooxazolyl group; $R_8$ is —CF$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; x is 0; $R_4$ is —H; $R_3$ is —CH$_3$ and is attached to the carbon atom adjacent to the nitrogen attached to the benzooxazolyl group; $R_8$ is —CF$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 0; $R_4$ is —H; $R_3$ is —CH$_3$ and is attached to the carbon atom adjacent to the nitrogen attached to the benzooxazolyl group; $R_8$ is —H; and $R_9$ is —OCH$_2$CH$_3$. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; x is 0; $R_4$ is —H; $R_3$ is —CH$_3$ and is attached to the carbon atom adjacent to the nitrogen attached to the benzooxazolyl group; $R_8$ is —H; and $R_9$ is —OCH$_2$CH$_3$. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 0; $R_4$ is —H; $R_3$ is —CH$_3$ and is attached to the carbon atom adjacent to the nitrogen attached to the benzooxazolyl group; $R_8$ is —OCH$_2$CH$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; x is 0; $R_4$ is —H; $R_3$ is —CH$_3$ and is attached to the carbon atom adjacent to the nitrogen attached to the benzooxazolyl group; $R_8$ is —OCH$_2$CH$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —CH$_3$, x is 0, $R_4$ is —H, $R_3$ is —CH$_3$ and is attached to the carbon atom adjacent to the nitrogen attached to the benzooxazolyl group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 0, $R_4$ is —H, $R_3$ is —$CH_3$ and is attached to the carbon atom adjacent to the nitrogen attached to the benzooxazolyl group, $R_8$ is —H, and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 0, $R_4$ is —H, $R_3$ is —$CH_3$ and is attached to the carbon atom adjacent to the nitrogen attached to the benzooxazolyl group, $R_8$ is -halo, and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 0, $R_4$ is —H, $R_3$ is —$CH_3$ and is attached to the carbon atom adjacent to the nitrogen attached to the benzooxazolyl group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 0, $R_4$ is —H, $R_3$ is —$CH_3$ and is attached to the carbon atom adjacent to the nitrogen attached to the benzooxazolyl group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 0, $R_4$ is —H, $R_3$ is —$CH_3$ and is attached to the carbon atom adjacent to the nitrogen attached to the benzooxazolyl group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 0, $R_4$ is —H, $R_3$ is —$CH_3$ and is attached to the carbon atom adjacent to the nitrogen attached to the benzooxazolyl group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 0, $R_4$ is —H, $R_3$ is —$CH_3$ and is attached to the carbon atom adjacent to the nitrogen attached to the benzooxazolyl group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CH_3$, x is 0, $R_4$ is —H, $R_3$ is —$CH_3$ and is attached to the carbon atom adjacent to the nitrogen attached to the benzooxazolyl group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 0, $R_4$ is —H, $R_3$ is —$CH_3$ and is attached to the carbon atom adjacent to the nitrogen attached to the benzooxazolyl group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 0, $R_4$ is —H, $R_3$ is —$CH_3$ and is attached to the carbon atom adjacent to the nitrogen attached to the benzooxazolyl group, $R_8$ is —H, and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 0, $R_4$ is —H, $R_3$ is —$CH_3$ and is attached to the carbon atom adjacent to the nitrogen attached to the benzooxazolyl group, $R_8$ is -halo, and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 0, $R_4$ is —H, $R_3$ is —$CH_3$ and is attached to the carbon atom adjacent to the nitrogen attached to the benzooxazolyl group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 0, $R_4$ is —H, $R_3$ is —$CH_3$ and is attached to the carbon atom adjacent to the nitrogen attached to the benzooxazolyl group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 0, $R_4$ is —H, $R_3$ is —$CH_3$ and is attached to the carbon atom adjacent to the nitrogen attached to the benzooxazolyl group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 0, $R_1$ is —H, $R_3$ is —$CH_3$ and is attached to the carbon atom adjacent to the nitrogen attached to the benzooxazolyl group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 0, $R_4$ is —H, $R_3$ is —$CH_3$ and is attached to the carbon atom adjacent to the nitrogen attached to the benzooxazolyl group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —$CF_3$, x is 0, $R_4$ is —H, $R_3$ is —$CH_3$ and is attached to the carbon atom adjacent to the nitrogen attached to the benzooxazolyl group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 0; $R_3$ is —$CH_3$ and is attached to the carbon atom adjacent to the nitrogen attached to the benzooxazolyl group; $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; x is 0; $R_3$ is —CH$_3$ and is attached to the carbon atom adjacent to the nitrogen attached to the benzooxazolyl group; $R_4$ is —H; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl, —Br, or —I; x is 0; $R_3$ is —CH$_3$ and is attached to the carbon atom adjacent to the nitrogen attached to the benzooxazolyl group; $R_4$ is —H; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, n and p are 0; m is 1; $R_1$ is —Cl; x is 0; $R_3$ is —CH$_3$ and is attached to the carbon atom adjacent to the nitrogen attached to the benzooxazolyl group; $R_4$ is —H; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —CH$_3$, x is 0, $R_3$ is —CH$_3$ and is attached to the carbon atom adjacent to the nitrogen attached to the benzooxazolyl group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —CH$_3$, x is 0, $R_3$ is —CH$_3$ and is attached to the carbon atom adjacent to the nitrogen attached to the benzooxazolyl group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, n and p are 0, m is 1, $R_1$ is —CH$_3$, x is 0, $R_3$ is —CH$_3$ and is attached to the carbon atom adjacent to the nitrogen attached to the benzooxazolyl group, $R_4$ is —H, $R_8$ is —CH$_3$, and $R_9$ is —CH$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group; n is 0; m is 1; $R_1$ is —CH$_3$, —Cl, —Br, or —I; x is 1; A is —C(O)—N($R_4$)—; $R_3$ is —CH$_3$ and is attached to the carbon atom adjacent to the nitrogen attached to the —C(O)—N($R_4$)— group; $R_4$ is —H; $R_8$ is —H; and $R_9$ is -halo. In another embodiment, the carbon atom to which the $R_3$ group is attached has the R configuration.

In another embodiment, $Ar_1$ is a pyridyl group, n is 0, m is 1, $R_1$ is —CH$_3$, x is 1, A is —C(O)—N($R_4$)—, $R_3$ is —CH$_3$ and is attached to the carbon atom adjacent to the nitrogen attached to the —C(O)—N($R_4$)— group, $R_4$ is —H, $R_8$ is —H, and $R_9$ is —Cl. In another embodiment, the carbon atom to which the $R_3$ group is attached has the R configuration.

In another embodiment, $Ar_1$ is a pyridyl group; n is 0; m is 1; $R_1$ is —Cl, —Br, or —I; x is 1; A is —C(O)—N($R_4$)—; $R_3$ is —CH$_3$ and is attached to the carbon atom adjacent to the nitrogen attached to the —C(O)—N($R_4$)— group; $R_4$ is —H; $R_8$ is —H; and $R_9$ is —Br. In another embodiment, the carbon atom to which the $R_3$ group is attached has the R configuration.

In another embodiment, $Ar_1$ is a pyridyl group, n is 0, m is 1, $R_1$ is —Cl, x is 1, A is —C(O)—N($R_4$)—, $R_3$ is —CH$_3$ and is attached to the carbon atom adjacent to the nitrogen attached to the —C(O)—N($R_4$)— group, $R_4$ is —H, $R_8$ is —H, and $R_9$ is —Br. In another embodiment, the carbon atom to which the $R_3$ group is attached has the R configuration.

In another embodiment, $Ar_1$ is a pyridyl group, n is 0, m is 1, $R_1$ is —CH$_3$, x is 1, A is —C(O)—N($R_4$)—, $R_3$ is —CH$_3$ and is attached to the carbon atom adjacent to the nitrogen attached to the —C(O)—N($R_4$)— group, $R_4$ is —H, $R_8$ is —H, and $R_9$ is —F. In another embodiment, the carbon atom to which the $R_3$ group is attached has the R configuration.

In another embodiment, $Ar_1$ is a pyrimidinyl group; p is 0; m is 1; $R_1$ is —CH$_3$, —Cl, —Br, —I; x is 1; A is —C(O)—N($R_4$)—; $R_3$ is —CH$_3$ and is attached to the carbon atom adjacent to the nitrogen attached to the —C(O)—N($R_4$)— group; $R_4$ is —H; $R_8$ is —H; and $R_9$ is -halo. In another embodiment, the carbon atom to which the $R_3$ group is attached has the R configuration.

In another embodiment, $Ar_1$ is a pyrimidinyl group, p is 0, m is 1, $R_1$ is —CH$_3$, x is 1, A is —C(O)—N($R_4$)—, $R_3$ is —CH$_3$ and is attached to the carbon atom adjacent to the nitrogen attached to the —C(O)—N($R_4$)— group, $R_4$ is —H, $R_8$ is —H, and $R_9$ is —Cl. In another embodiment, the carbon atom to which the $R_3$ group is attached has the R configuration.

In another embodiment, $Ar_1$ is a pyrimidinyl group; p is 0; m is 1; $R_1$ is —Cl, —Br, or —I; x is 1; A is —C(O)—N($R_4$)—; $R_3$ is —CH$_3$ and is attached to the carbon atom adjacent to the nitrogen attached to the —C(O)—N($R_4$)— group; $R_4$ is —H; $R_8$ is —H; and $R_9$ is —Br. In another embodiment, the carbon atom to which the $R_3$ group is attached has the R configuration.

In another embodiment, $Ar_1$ is a pyrimidinyl group, p is 0, m is 1, $R_1$ is —Cl, x is 1, A is —C(O)—N($R_4$)—, $R_3$ is —CH$_3$ and is attached to the carbon atom adjacent to the nitrogen attached to the —C(O)—N($R_4$)— group, $R_4$ is —H, $R_8$ is —H, and $R_9$ is —Br. In another embodiment, the carbon atom to which the $R_3$ group is attached has the R configuration.

In another embodiment, $Ar_1$ is a pyrimidinyl group, p is 0, m is 1, $R_1$ is —CH$_3$, x is 1, A is —C(O)—N($R_4$)—, $R_3$ is —CH$_3$ and is attached to the carbon atom adjacent to the nitrogen attached to the —C(O)—N($R_4$)— group, $R_4$ is —H, $R_8$ is —H, and $R_9$ is —F. In another embodiment, the carbon atom to which the $R_3$ group is attached has the R configuration.

In another embodiment, $Ar_1$ is a pyridyl group; n is 0; m is 1; $R_1$ is —CH$_3$, —Cl, —Br, or —I; x is 0; $R_3$ is —CH$_3$ and is attached to the carbon atom adjacent to the nitrogen attached to the benzooxazolyl group; $R_4$ is —H; $R_8$ is —H; and $R_9$ is -halo. In another embodiment, the carbon atom to which the $R_3$ group is attached has the R configuration.

In another embodiment, $Ar_1$ is a pyridyl group, n is 0, m is 1, $R_1$ is —CH$_3$, x is 0, $R_3$ is —CH$_3$ and is attached to the carbon atom adjacent to the nitrogen attached to the benzooxazolyl group, $R_4$ is —H, $R_8$ is —H, and $R_9$ is —Cl. In another embodiment, the carbon atom to which the $R_3$ group is attached has the R configuration.

In another embodiment, $Ar_1$ is a pyridyl group; n is 0; m is 1; $R_1$ is —Cl, —Br, or —I; x is 0; $R_3$ is —CH$_3$ and is attached to the carbon atom adjacent to the nitrogen attached to the benzooxazolyl group; $R_4$ is —H; $R_8$ is —H; and $R_9$ is —Br. In another embodiment, the carbon atom to which the $R_3$ group is attached has the R configuration.

In another embodiment, $Ar_1$ is a pyridyl group, n is 0, m is 1, $R_1$ is —Cl, x is 0, $R_3$ is —CH$_3$ and is attached to the carbon atom adjacent to the nitrogen attached to the benzooxazolyl group, $R_4$ is —H, $R_8$ is —H, and $R_9$ is —Br. In another embodiment, the carbon atom to which the $R_3$ group is attached has the R configuration.

In another embodiment, $Ar_1$ is a pyridyl group, n is 0, m is 1, $R_1$ is —$CH_3$, x is 0, $R_3$ is —$CH_3$ and is attached to the carbon atom adjacent to the nitrogen attached to the benzooxazolyl group, $R_4$ is —H, $R_8$ is —H, and $R_9$ is —F. In another embodiment, the carbon atom to which the $R_3$ group is attached has the R configuration.

In another embodiment, $Ar_1$ is a pyrimidinyl group; p is 0; m is 1; $R_1$ is —$CH_3$, —Cl, —Br, or —I; x is 0; $R_3$ is —$CH_3$ and is attached to the carbon atom adjacent to the nitrogen attached to the benzooxazolyl group; $R_4$ is —H; $R_8$ is —H; and $R_9$ is -halo. In another embodiment, the carbon atom to which the $R_3$ group is attached has the R configuration.

In another embodiment, $Ar_1$ is a pyrimidinyl group, p is 0, m is 1, $R_1$ is —$CH_3$, x is 0, $R_3$ is —$CH_3$ and is attached to the carbon atom adjacent to the nitrogen attached to the benzooxazolyl group, $R_4$ is —H, $R_8$ is —H, and $R_9$ is —Cl. In another embodiment, the carbon atom to which the $R_3$ group is attached has the R configuration.

In another embodiment, $Ar_1$ is a pyrimidinyl group; p is 0; m is 1; $R_1$ is —Cl, —Br, or —I; x is 0; $R_3$ is —$CH_3$ and is attached to the carbon atom adjacent to the nitrogen attached to the benzooxazolyl group; $R_4$ is —H; $R_8$ is —H; and $R_9$ is —Br. In another embodiment, the carbon atom to which the $R_3$ group is attached has the R configuration.

In another embodiment, $Ar_1$ is a pyrimidinyl group, p is 0, m is 1, $R_1$ is —Cl, x is 0, $R_3$ is —$CH_3$ and is attached to the carbon atom adjacent to the nitrogen attached to the benzooxazolyl group, $R_4$ is —H, $R_8$ is —H, and $R_9$ is —Br. In another embodiment, the carbon atom to which the $R_3$ group is attached has the R configuration.

In another embodiment, $Ar_1$ is a pyrimidinyl group, p is 0, m is 1, $R_1$ is —$CH_3$, x is 0, $R_3$ is —$CH_3$ and is attached to the carbon atom adjacent to the nitrogen attached to the benzooxazolyl group, $R_4$ is —H, $R_8$ is —H, and $R_9$ is —F. In another embodiment, the carbon atom to which the $R_3$ group is attached has the R configuration.

In another embodiment, m is 1 and $R_3$ is —($C_1$-$C_4$)alkyl and is attached to the carbon atom adjacent to the nitrogen attached to the —C(O)—N($R_4$)— or the benzooxazolyl group. In another embodiment, m is 1 and $R_3$ is —($C_1$-$C_4$)alkyl and is attached to the carbon atom adjacent to the nitrogen attached to the —C(O)—N($R_4$)— or the benzooxazolyl group and the carbon to which the $R_3$ group is attached is in the R configuration.

In another embodiment, m is 1 and $R_3$ is —$CH_3$ and is attached to the carbon atom adjacent to the nitrogen attached to the —C(O)—N($R_4$)— or the benzooxazolyl group. In another embodiment, m is 1 and $R_3$ is —$CH_3$ and is attached to the carbon atom adjacent to the nitrogen attached to the —C(O)—N($R_4$)— or the benzooxazolyl group and the carbon to which the $R_3$ group is attached is in the R configuration.

In another embodiment, m is 1 and $R_3$ is —($C_1$-$C_4$)alkyl and is attached to the carbon atom adjacent to the nitrogen attached to the —C(O)—N($R_4$)— or the benzooxazolyl group. In another embodiment, m is 1 and $R_3$ is —($C_1$-$C_4$)alkyl and is attached to the carbon atom adjacent to the nitrogen attached to the —C(O)—N($R_4$)— or the benzooxazolyl group and the carbon to which the $R_3$ group is attached is in the S configuration.

In another embodiment, m is 1 and $R_3$ is —$CH_3$ and is attached to the carbon atom adjacent to the nitrogen attached to the —C(O)—N($R_4$)— or the benzooxazolyl group. In another embodiment, m is 1 and $R_3$ is —$CH_3$ and is attached to the carbon atom adjacent to the nitrogen attached to the —C(O)—N($R_4$)— or the benzooxazolyl group and the carbon to which the $R_3$ group is attached is in the S configuration.

In another embodiment, m is 1 and $R_3$ is —($C_1$-$C_4$)alkyl and is attached to the carbon atom adjacent to the nitrogen attached to the pyridyl group or pyrimidinyl group. In another embodiment, m is 1 and $R_3$ is —($C_1$-$C_4$)alkyl and is attached to the carbon atom adjacent to the nitrogen attached to the pyridyl group or pyrimidinyl group and the carbon to which the $R_3$ group is attached is in the R configuration.

In another embodiment, m is 1 and $R_3$ is —$CH_3$ and is attached to the carbon atom adjacent to the nitrogen attached to the pyridyl group or pyrimidinyl group. In another embodiment, m is 1 and $R_3$ is —$CH_3$ and is attached to the carbon atom adjacent to the nitrogen attached to the pyridyl group or pyrimidinyl group and the carbon to which the $R_3$ group is attached is in the R configuration.

In another embodiment, m is 1 and $R_3$ is —($C_1$-$C_4$)alkyl and is attached to the carbon atom adjacent to the nitrogen attached to the pyridyl group or pyrimidinyl group. In another embodiment, m is 1 and $R_3$ is —($C_1$-$C_4$)alkyl and is attached to the carbon atom adjacent to the nitrogen attached to the pyridyl group or pyrimidinyl group and the carbon to which the $R_3$ group is attached is in the S configuration.

In another embodiment, m is 1 and $R_3$ is —$CH_3$ and is attached to the carbon atom adjacent to the nitrogen attached to the pyridyl group or pyrimidinyl group. In another embodiment, m is 1 and $R_3$ is —$CH_3$ and is attached to the carbon atom adjacent to the nitrogen attached to the pyridyl group or pyrimidinyl group and the carbon to which the $R_3$ group is attached is in the S configuration.

4.6 The Compounds of Formula (IIIb)

The present invention also encompasses compounds of formula (IIIb):

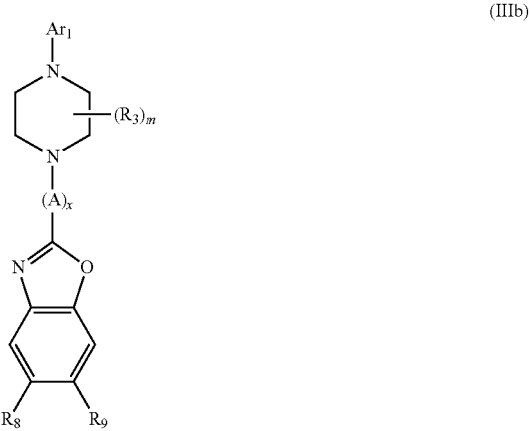

and pharmaceutically acceptable salts thereof, where $Ar_1$, $R_3$, $R_8$, $R_9$, A, x, and m, are defined above for the Benzoazolylpiperazine Compounds of formula (IIIb).

In one embodiment, $Ar_1$ is a pyrazinyl group.
In another embodiment, $Ar_1$ is a pyridazinyl group.
In another embodiment, $Ar_1$ is a thiazanyl group.
In another embodiment, x is 1 and A is —C(O)—N($R_4$)—.
In another embodiment, x is 1 and A is —C(S)—N($R_4$)—.
In another embodiment, x is 0.
In another embodiment, x is 1.
In another embodiment, p is 0.

In another embodiment, p is 1.

In another embodiment, m is 0.

In another embodiment, m is 1.

In another embodiment, $Ar_1$ is a pyrazinyl group, x is 1, and A is —C(O)N($R_4$)—.

In another embodiment, $Ar_1$ is a pyrazinyl group, x is 1, and A is —C(S)N($R_4$)—.

In another embodiment, $Ar_1$ is a pyridazinyl group, x is 1, and A is —C(O)N($R_4$)—.

In another embodiment, $Ar_1$ is a pyridazinyl group, x is 1, and A is —C(S)N($R_4$)—.

In another embodiment, $Ar_1$ is a thiazanyl group, x is 1, and A is —C(O)N($R_4$)—.

In another embodiment, $Ar_1$ is a thiazanyl group, x is 1, and A is —C(S)N($R_4$)—.

In another embodiment, $R_1$ is —H.

In another embodiment, $R_1$ is —Cl.

In another embodiment, $R_1$ is —Br.

In another embodiment, $R_1$ is —I.

In another embodiment, $R_1$ is —F.

In another embodiment, $R_1$ is —($C_1$-$C_6$)alkyl.

In another embodiment, $R_1$ is —$CH_3$.

In another embodiment, $R_1$ is —$NO_2$.

In another embodiment, $R_1$ is —CN.

In another embodiment, $R_1$ is —OH.

In another embodiment, $R_1$ is —$OCH_3$.

In another embodiment, $R_1$ is —$NH_2$.

In another embodiment, $R_1$ is —C(halo)$_3$.

In another embodiment, $R_1$ is —CH(halo)$_2$.

In another embodiment, $R_1$ is —$CH_2$(halo).

In another embodiment, p is 1 and $R_2$ is -halo, —CN, —OH, —O($C_1$-$C_6$)alkyl, —$NO_2$, or —$NH_2$.

In another embodiment, p is 1 and $R_2$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups.

In another embodiment, p is 1 and $R_2$ is -phenyl, -naphthyl, —($C_{14}$)aryl, or -(5- to 10-membered)heteroaryl, each of which is unsubstituted or substituted with one or more $R_6$ groups;

In another embodiment, m is 1 and $R_3$ is -halo, —CN, —OH, —O($C_1$-$C_6$)alkyl, —$NO_2$, or —$NH_2$.

In another embodiment, m is 1 and $R_3$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups.

In another embodiment, m is 1 and $R_3$ is -phenyl, -naphthyl, —($C_{14}$)aryl or -(5- to 10-membered)heteroaryl, each of which is unsubstituted or substituted with one or more $R_6$ groups.

In another embodiment, $R_4$ is —H.

In another embodiment, $R_4$ is —($C_1$-$C_6$)alkyl.

In another embodiment, $R_8$ and $R_9$ are each independently —H, halo, —($C_1$-$C_6$)alkyl, —O($C_1$-$C_6$)alkyl, —C(halo)$_3$, —CH(halo)$_2$, or —$CH_2$(halo).

In another embodiment, at least one of $R_8$ or $R_9$ is —H.

In another embodiment, p and m are 0, $R_1$ is -halo, x is 1, A is —C(O)—N($R_4$)—, $R_4$ is —H, and $R_8$ and $R_9$ are —H.

In another embodiment, p and m are 0, $R_1$ is —Cl, x is 1, A is —C(O)—N($R_4$)—, $R_4$ is —H, and $R_8$ and $R_9$ are —H.

In another embodiment, p and m are 0, $R_1$ is -halo, x is 1, A is —C(O)—N($R_4$)—, $R_4$ is —H, $R_8$ is —H, and $R_9$ is -halo. In another embodiment, $R_9$ is —Cl. In another embodiment, $R_9$ is —Br. In another embodiment, $R_9$ is —F.

In another embodiment, p and m are 0, $R_1$ is —Cl, x is 1, A is —C(O)—N($R_4$)—, $R_4$ is —H, $R_8$ is —H, and $R_9$ is -halo. In another embodiment, $R_9$ is —Cl. In another embodiment, $R_9$ is —Br. In another embodiment, $R_9$ is —F.

In another embodiment, p and m are 0, $R_1$ is -halo, x is 1, A is —C(O)—N($R_4$)—, $R_4$ is —H, $R_8$ is -halo, and $R_9$ is —H. In another embodiment, $R_8$ is —Cl. In another embodiment, $R_8$ is —Br. In another embodiment, $R_8$ is —F.

In another embodiment, p and m are 0, $R_1$ is —Cl, x is 1, A is —C(O)—N($R_4$)—, $R_4$ is —H, $R_8$ is -halo, and $R_9$ is —H. In another embodiment, $R_8$ is —Cl. In another embodiment, $R_8$ is —Br. In another embodiment, $R_8$ is —F.

In another embodiment, p and m are 0, $R_1$ is -halo, x is 1, A is —C(O)—N($R_4$)—, $R_4$ is —H, $R_8$ is —H, and $R_9$ is —$CH_3$.

In another embodiment, p and m are 0, $R_1$ is —Cl, x is 1, A is —C(O)—N($R_4$)—, $R_4$ is —H, $R_8$ is —H, and $R_9$ is —$CH_3$.

In another embodiment, p and m are 0, $R_1$ is -halo, x is 1, A is —C(O)—N($R_4$)—, $R_4$ is —H, $R_8$ is —$CH_3$, and $R_9$ is —H.

In another embodiment, p and m are 0, $R_1$ is —Cl, x is 1, A is —C(O)—N($R_4$)—, $R_4$ is —H, $R_8$ is —$CH_3$, and $R_9$ is —H.

In another embodiment, p and m are 0, $R_1$ is -halo, x is 1, A is —C(O)—N($R_4$)—, $R_4$ is —H, $R_8$ is —H, and $R_9$ is —$CF_3$.

In another embodiment, p and m are 0, $R_1$ is —Cl, x is 1, A is —C(O)—N($R_4$)—, $R_4$ is —H, $R_8$ is —H, and $R_9$ is —$CF_3$.

In another embodiment, p and m are 0, $R_1$ is -halo, x is 1, A is —C(O)—N($R_4$)—, $R_4$ is —H, $R_8$ is —$CF_3$, and $R_9$ is —H.

In another embodiment, p and m are 0, $R_1$ is —Cl, x is 1, A is —C(O)—N($R_4$)—, $R_4$ is —H, $R_8$ is —$CF_3$, and $R_9$ is —H.

In another embodiment, p and m are 0, $R_1$ is -halo, x is 1, A is —C(O)—N($R_4$)—, $R_4$ is —H, $R_8$ is —H, and $R_9$ is —$OCH_2CH_3$.

In another embodiment, p and m are 0, $R_1$ is —Cl, x is 1, A is —C(O)—N($R_4$)—, $R_4$ is —H, $R_8$ is —H, and $R_9$ is —$OCH_2CH_3$.

In another embodiment, p and m are 0, $R_1$ is -halo, x is 1, A is —C(O)—N($R_4$)—, $R_4$ is —H, $R_8$ is —$OCH_2CH_3$, and $R_9$ is —H.

In another embodiment, p and m are 0, $R_1$ is —Cl, x is 1, A is —C(O)—N($R_4$)—, $R_4$ —H, $R_g$ is —$OCH_2CH_3$, and $R_9$ is —H.

In another embodiment, p and m are 0, $R_1$ is —$CH_3$, x is 1, A is —C(O)—N($R_4$)—, $R_4$ is —H, and $R_8$ and $R_9$ are —H.

In another embodiment, p and m are 0, $R_1$ is —$CH_3$, x is 1, A is —C(O)—N($R_4$)—, $R_4$ is —H, $R_8$ is —H, and $R_9$ is -halo. In another embodiment, $R_9$ is —Cl. In another embodiment, $R_9$ is —Br. In another embodiment, $R_9$ is —F.

In another embodiment, p and m are 0, $R_1$ is —$CH_3$, x is 1, A is —C(O)—N($R_4$)—, $R_4$ is —H, $R_8$ is -halo, and $R_9$ is —H. In another embodiment, $R_8$ is —Cl. In another embodiment, $R_8$ is —Br. In another embodiment, $R_8$ is —F.

In another embodiment, p and m are 0, $R_1$ is —$CH_3$, x is 1, A is —C(O)—N($R_4$)—, $R_4$ is —H, $R_8$ is —H, and $R_9$ is —$CH_3$.

In another embodiment, p and m are 0, $R_1$ is —$CH_3$, x is 1, A is —C(O)—N($R_4$)—, $R_4$ is —H, $R_8$ is —$CH_3$, and $R_9$ is —H.

In another embodiment, p and m are 0, $R_1$ is —$CH_3$, x is 1, A is —C(O)—N($R_4$)—, $R_4$ is —H, $R_8$ is —H, and $R_9$ is —$CF_3$.

In another embodiment, p and m are 0, $R_1$ is —$CH_3$, x is 1, A is —C(O)—N($R_4$)—, $R_4$ is —H, $R_8$ is —$CF_3$, and $R_9$ is —H.

In another embodiment, p and m are 0, $R_1$ is —$CH_3$, x is 1, A is —C(O)—N($R_4$)—, $R_4$ is —H, $R_8$ is —H, and $R_9$ is —$OCH_2CH_3$.

In another embodiment, p and m are 0, $R_1$ is —$CH_3$, x is 1, A is —C(O)—N($R_4$)—, $R_4$ is —H, $R_8$ is —$OCH_2CH_3$, and $R_9$ is —H.

In another embodiment, p and m are 0, $R_1$ is —$CF_3$, x is 1, A is —C(O)—N($R_4$)—, $R_4$ is —H, and $R_8$ and $R_9$ are —H.

In another embodiment, p and m are 0, $R_1$ is —$CF_3$, x is 1, A is —C(O)—N($R_4$)—, $R_4$ is —H, $R_8$ is —H, and $R_9$ is -halo. In another embodiment, $R_9$ is —Cl. In another embodiment, $R_9$ is —Br. In another embodiment, $R_9$ is —F.

In another embodiment, p and m are 0, $R_1$ is —$CF_3$, x is 1, A is —C(O)—N($R_4$)—, $R_4$ is —H, $R_8$ is -halo, and $R_9$ is —H. In another embodiment, $R_8$ is —Cl. In another embodiment, $R_8$ is —Br. In another embodiment, $R_8$ is —F.

In another embodiment, p and m are 0, $R_1$ is —$CF_3$, x is 1, A is —C(O)—N($R_4$)—, $R_4$ is —H, $R_8$ is —H, and $R_9$ is —$CH_3$.

In another embodiment, p and m are 0, $R_1$ is —$CF_3$, x is 1, A is —C(O)—N($R_4$)—, $R_4$ is —H, $R_8$ is —$CH_3$, and $R_9$ is —H.

In another embodiment, p and m are 0, $R_1$ is —$CF_3$, x is 1, A is —C(O)—N($R_4$)—, $R_4$ is —H, $R_8$ is —H, and $R_9$ is —$CF_3$.

In another embodiment, p and m are 0, $R_1$ is —$CF_3$, x is 1, A is —C(O)—N($R_4$)—, $R_4$ is —H, $R_8$ is —$CF_3$, and $R_9$ is —H.

In another embodiment, p and m are 0, $R_1$ is —$CF_3$, x is 1, A is —C(O)—N($R_4$)—, $R_4$ is —H, $R_8$ is —H, and $R_9$ is —$OCH_2CH_3$.

In another embodiment, p and m are 0, $R_1$ is —$CF_3$, x is 1, A is —C(O)—N($R_4$)—, $R_4$ is —H, $R_8$ is —$OCH_2CH_3$, and $R_9$ is —H.

In another embodiment, p and m are 0, $R_1$ is -halo, x is 1, A is —C(O)—N($R_4$)—, $R_4$ is —H, $R_8$ is -tert-butyl, and $R_9$ is —H.

In another embodiment, p and m are 0, $R_1$ is —Cl, x is 1, A is —C(O)—N($R_4$)—, $R_4$ is —H, $R_8$ is -tert-butyl, and $R_9$ is —H.

In another embodiment, p and m are 0, $R_1$ is -halo, x is 1, A is —C(O)—N($R_4$)—, $R_4$ is —H, $R_8$ is —H, and $R_9$ is -tert-butyl.

In another embodiment, p and m are 0, $R_1$ is —Cl, x is 1, A is —C(O)—N($R_4$)—, $R_4$ is —H, $R_8$ is —H, and $R_9$ is -tert-butyl.

In another embodiment, p and m are 0, $R_1$ is —$CH_3$, x is 1, A is —C(O)—N($R_4$)—, $R_4$ is —H, $R_8$ is -tert-butyl, and $R_9$ is —H.

In another embodiment, p and m are 0, $R_1$ is —$CH_3$, x is 1, A is —C(O)—N($R_4$)—, $R_4$ is —H, $R_8$ is —H, and $R_9$ is -tert-butyl.

In another embodiment, p and m are 0, $R_1$ is —$CH_3$, x is 1, A is —C(O)—N($R_4$)—, $R_4$ is —H, $R_8$ is —$CH_3$, and $R_9$ is —$CH_3$.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is -halo. In another embodiment, $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is -halo. In another embodiment, $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is -halo, and $R_9$ is —H. In another embodiment, $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is -halo, and $R_9$ is —H. In another embodiment, $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_3$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is -halo, and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is -halo, and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CF_3$, x is 1, A is —C(O)—N($R_4$)—, $R_4$ is —H, $R_3$ is —$CH_3$ and is attached to the carbon atom adjacent to the nitrogen attached to the —C(O)—N($R_4$)— group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is halo, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N(R$_4$)— group, R$_4$ is —H, R$_8$ is —H, and R$_9$ is -tert-butyl. In another embodiment, the carbon atom to which the R$_3$ group is attached has the R configuration. In another embodiment, the carbon atom to which the R$_3$ group is attached has the S configuration.

In another embodiment, p is 0, m is 1, R$_1$ is —CH$_3$, x is 1, A is —C(O)—N(R$_4$)—, R$_3$ is —CH$_3$ and is attached to the carbon atom adjacent to the nitrogen attached to the —C(O)—N(R$_4$)— group, R$_4$ is —H, R$_8$ is —CH$_3$, and R$_9$ is —CH$_3$. In another embodiment, the carbon atom to which the R$_3$ group is attached has the R configuration. In another embodiment, the carbon atom to which the R$_3$ group is attached has the S configuration.

In another embodiment, p and m are 0, R$_1$ is -halo, x is 0, R$_4$ is —H, and R$_8$ and R$_9$ are —H.

In another embodiment, p and m are 0, R$_1$ is —Cl, x is 0, R$_4$ is —H, and R$_8$ and R$_9$ are —H.

In another embodiment, p and m are 0, R$_1$ is -halo, x is 0, R$_4$ is —H, R$_8$ is —H, and R$_9$ is -halo. In another embodiment, R$_9$ is —Cl. In another embodiment, R$_9$ is —Br. In another embodiment, R$_9$ is —F.

In another embodiment, p and m are 0, R$_1$ is —Cl, x is 0, R$_4$ is —H, R$_8$ is —H, and R$_9$ is -halo. In another embodiment, R$_9$ is —Cl. In another embodiment, R$_9$ is —Br. In another embodiment, R$_9$ is —F.

In another embodiment, p and m are 0, R$_1$ is -halo, x is 0, R$_4$ is —H, R$_8$ is -halo, and R$_9$ is —H. In another embodiment, R$_8$ is —Cl. In another embodiment, R$_8$ is —Br. In another embodiment, R$_8$ is —F.

In another embodiment, p and m are 0, R$_1$ is —Cl, x is 0, R$_4$ is —H, R$_8$ is -halo, and R$_9$ is —H. In another embodiment, R$_8$ is —Cl. In another embodiment, R$_8$ is —Br. In another embodiment, R$_8$ is —F.

In another embodiment, p and m are 0, R$_1$ is -halo, x is 0, R$_4$ is —H, R$_8$ is —H, and R$_9$ is —CH$_3$.

In another embodiment, p and m are 0, R$_1$ is —Cl, x is 0, R$_4$ is —H, R$_8$ is —H, and R$_9$ is —CH$_3$.

In another embodiment, p and m are 0, R$_1$ is -halo, x is 0, R$_4$ is —H, R$_8$ is —CH$_3$, and R$_9$ is —H.

In another embodiment, p and m are 0, R$_1$ is —Cl, x is 0, R$_4$ is —H, R$_8$ is —CH$_3$, and R$_9$ is —H.

In another embodiment, p and m are 0, R$_1$ is -halo, x is 0, R$_4$ is —H, R$_8$ is —H, and R$_9$ is —CF$_3$.

In another embodiment, p and m are 0, R$_1$ is —Cl, x is 0, R$_4$ is —H, R$_8$ is —H, and R$_9$ is —CF$_3$.

In another embodiment, p and m are 0, R$_1$ is -halo, x is 0, R$_4$ is —H, R$_8$ is —CF$_3$, and R$_9$ is —H.

In another embodiment, p and m are 0, R$_1$ is —Cl, x is 0, R$_4$ is —H, R$_8$ is —CF$_3$, and R$_9$ is —H.

In another embodiment, p and m are 0, R$_1$ is -halo, x is 0, R$_4$ is —H, R$_8$ is —H, and R$_9$ is —OCH$_2$CH$_3$.

In another embodiment, p and m are 0, R$_1$ is —Cl, x is 0, R$_4$ is —H, R$_8$ is —H, and R$_9$ is —OCH$_2$CH$_3$.

In another embodiment, p and m are 0, R$_1$ is -halo, x is 0, R$_4$ is —H, R$_8$ is —OCH$_2$CH$_3$, and R$_9$ is —H.

In another embodiment, p and m are 0, R$_1$ is —Cl, x is 0, R$_4$ is —H, R$_8$ is —OCH$_2$CH$_3$, and R$_9$ is —H.

In another embodiment, p and m are 0, R$_1$ is —CH$_3$, x is 0, R$_4$ is —H, and R$_8$ and R$_9$ are —H.

In another embodiment, p and m are 0, R$_1$ is —CH$_3$, x is 0, R$_4$ is —H, R$_8$ is —H, and R$_9$ is -halo. In another embodiment, R$_9$ is —Cl. In another embodiment, R$_9$ is —Br. In another embodiment, R$_9$ is —F.

In another embodiment, p and m are 0, R$_1$ is —CH$_3$, x is 0, R$_4$ is —H, R$_8$ is -halo, and R$_9$ is —H. In another embodiment, R$_8$ is —Cl. In another embodiment, R$_8$ is —Br. In another embodiment, R$_8$ is —F.

In another embodiment, p and m are 0, R$_1$ is —CH$_3$, x is 0, R$_4$ is —H, R$_8$ is —H, and R$_9$ is —CH$_3$.

In another embodiment, p and m are 0, R$_1$ is —CH$_3$, x is 0, R$_4$ is —H, R$_8$ is —CH$_3$, and R$_9$ is —H.

In another embodiment, p and m are 0, R$_1$ is —CH$_3$, x is 0, R$_4$ is —H, R$_8$ is —H, and R$_9$ is —CF$_3$.

In another embodiment, p and m are 0, R$_1$ is —CH$_3$, x is 0, R$_4$ is —H, R$_8$ is —CF$_3$, and R$_9$ is —H.

In another embodiment, p and m are 0, R$_1$ is —CH$_3$, x is 0, R$_4$ is —H, R$_8$ is —H, and R$_9$ is —OCH$_2$CH$_3$.

In another embodiment, p and m are 0, R$_1$ is —CH$_3$, x is 0, R$_4$ is —H, R$_8$ is —OCH$_2$CH$_3$, and R$_9$ is —H.

In another embodiment, p and m are 0, R$_1$ is —CF$_3$, x is 0, R$_4$ is —H, and R$_8$ and R$_9$ are —H.

In another embodiment, p and m are 0, R$_1$ is —CF$_3$, x is 0, R$_4$ is —H, R$_8$ is —H, and R$_9$ is -halo. In another embodiment, R$_9$ is —Cl. In another embodiment, R$_9$ is —Br. In another embodiment, R$_9$ is —F.

In another embodiment, p and m are 0, R$_1$ is —CF$_3$, x is 0, R$_4$ is —H, R$_8$ is -halo, and R$_9$ is —H. In another embodiment, R$_8$ is —Cl. In another embodiment, R$_8$ is —Br. In another embodiment, R$_8$ is —F.

In another embodiment, p and m are 0, R$_1$ is —CF$_3$, x is 0, R$_4$ is —H, R$_8$ is —H, and R$_9$ is —CH$_3$.

In another embodiment, p and m are 0, R$_1$ is —CF$_3$, x is 0, R$_4$ is —H, R$_8$ is —CH$_3$, and R$_9$ is —H.

In another embodiment, p and m are 0, R$_1$ is —CF$_3$, x is 0, R$_4$ is —H, R$_8$ is —H, and R$_9$ is —CF$_3$.

In another embodiment, p and m are 0, R$_1$ is —CF$_3$, x is 0, R$_4$ is —H, R$_8$ is —CF$_3$, and R$_9$ is —H.

In another embodiment, p and m are 0, R$_1$ is —CF$_3$, x is 0, R$_4$ is —H, R$_8$ is —H, and R$_9$ is —OCH$_2$CH$_3$.

In another embodiment, p and m are 0, R$_1$ is —CF$_3$, x is 0, R$_4$ is —H, R$_8$ is —OCH$_2$CH$_3$, and R$_9$ is —H.

In another embodiment, p and m are 0, R$_1$ is -halo, x is 0, R$_4$ is —H, R$_8$ is -ten-butyl, and R$_9$ is —H.

In another embodiment, p and m are 0, R$_1$ is —Cl, x is 0, R$_4$ is —H, R$_8$ is -tert-butyl, and R$_9$ is —H.

In another embodiment, p and m are 0, R$_1$ is -halo, x is 0, R$_4$ is —H, R$_8$ is —H, and R$_9$ is -tert-butyl.

In another embodiment, p and m are 0, R$_1$ is —Cl, x is 0, R$_4$ is —H, R$_8$ is —H, and R$_9$ is -tert-butyl.

In another embodiment, p and m are 0, R$_1$ is —CH$_3$, x is 0, R$_4$ is —H, R$_8$ is -tert-butyl, and R$_9$ is —H.

In another embodiment, p and m are 0, R$_1$ is —CH$_3$, x is 0, R$_4$ is —H, R$_8$ is —H, and R$_9$ is -tert-butyl.

In another embodiment, p and m are 0, R$_1$ is —CH$_3$, x is 0, R$_4$ is —H, R$_8$ is —CH$_3$, and R$_9$ is —CH$_3$.

In another embodiment, p is 0, m is 1, R$_1$ is -halo, x is 0, R$_4$ is —H, R$_3$ is —CH$_3$ and is attached to the carbon atom adjacent to the nitrogen attached to the benzooxazolyl group, and R$_8$ and R$_9$ are —H. In another embodiment, the carbon atom to which the R$_3$ group is attached has the R configuration. In another embodiment, the carbon atom to which the R$_3$ group is attached has the S configuration.

In another embodiment, p is 0, m is 1, R$_1$ is —Cl, x is 0, R$_4$ is —H, R$_3$ is —CH$_3$ and is attached to the carbon atom adjacent to the nitrogen attached to the benzooxazolyl group, and R$_8$ and R$_9$ are —H. In another embodiment, the carbon atom to which the R$_3$ group is attached has the R configuration. In another embodiment, the carbon atom to which the R$_3$ group is attached has the S configuration.

In another embodiment, p is 0, m is 1, R$_1$ is -halo, x is 0, R$_4$ is —H, R$_3$ is —CH$_3$ and is attached to the carbon atom adjacent to the nitrogen attached to the benzooxazolyl group, R$_8$ is —H, and R$_9$ is -halo. In another embodiment, R$_9$ is —Cl. In another embodiment, R$_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —$CH_3$ and is attached to the carbon atom adjacent to the nitrogen attached to the benzooxazolyl group, $R_8$ is —H, and $R_9$ is -halo. In another embodiment, $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_4$ is —H, $R_3$ is —$CH_3$ and is attached to the carbon atom adjacent to the nitrogen attached to the benzooxazolyl group, $R_8$ is -halo, and $R_9$ is —H. In another embodiment, $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —$CH_3$ and is attached to the carbon atom adjacent to the nitrogen attached to the benzooxazolyl group, $R_8$ is -halo, and $R_9$ is —H. In another embodiment, $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_4$ is —H, $R_3$ is —$CH_3$ and is attached to the carbon atom adjacent to the nitrogen attached to the benzooxazolyl group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —$CH_3$ and is attached to the carbon atom adjacent to the nitrogen attached to the benzooxazolyl group, $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_4$ is —H, $R_3$ is —$CH_3$ and is attached to the carbon atom adjacent to the nitrogen attached to the benzooxazolyl group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —$CH_3$ and is attached to the carbon atom adjacent to the nitrogen attached to the benzooxazolyl group, $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_4$ is —H, $R_3$ is —$CH_3$ and is attached to the carbon atom adjacent to the nitrogen attached to the benzooxazolyl group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —$CH_3$ and is attached to the carbon atom adjacent to the nitrogen attached to the benzooxazolyl group, $R_8$ is —H, and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_4$ is —H, $R_3$ is —$CH_3$ and is attached to the carbon atom adjacent to the nitrogen attached to the benzooxazolyl group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —$CH_3$ and is attached to the carbon atom adjacent to the nitrogen attached to the benzooxazolyl group, $R_8$ is —$CF_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_4$ is —H, $R_3$ is —$CH_3$ and is attached to the carbon atom adjacent to the nitrogen attached to the benzooxazolyl group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —$CH_3$ and is attached to the carbon atom adjacent to the nitrogen attached to the benzooxazolyl group, $R_8$ is —H, and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_4$ is —H, $R_3$ is —$CH_3$ and is attached to the carbon atom adjacent to the nitrogen attached to the benzooxazolyl group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_4$ is —H, $R_3$ is —$CH_3$ and is attached to the carbon atom adjacent to the nitrogen attached to the benzooxazolyl group, $R_8$ is —$OCH_2CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_4$ is —H, $R_3$ is —$CH_3$ and is attached to the carbon atom adjacent to the nitrogen attached to the benzooxazolyl group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_4$ is —H, $R_3$ is —$CH_3$ and is attached to the carbon atom adjacent to the nitrogen attached to the benzooxazolyl group, $R_8$ is —H, and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_4$ is —H, $R_3$ is —$CH_3$ and is attached to the carbon atom adjacent to the nitrogen attached to the benzooxazolyl group, $R_8$ is -halo, and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —CH$_3$, x is 0, $R_4$ is —H, $R_3$ is —CH$_3$ and is attached to the carbon atom adjacent to the nitrogen attached to the benzooxazolyl group, $R_8$ is —H, and $R_9$ is —CH$_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —CH$_3$, x is 0, $R_4$ is —H, $R_3$ is —CH$_3$ and is attached to the carbon atom adjacent to the nitrogen attached to the benzooxazolyl group, $R_8$ is —CH$_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —CH$_3$, x is 0, $R_4$ is —H, $R_3$ is —CH$_3$ and is attached to the carbon atom adjacent to the nitrogen attached to the benzooxazolyl group, $R_8$ is —H, and $R_9$ is —CF$_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —CH$_3$, x is 0, $R_4$ is —H, $R_3$ is —CH$_3$ and is attached to the carbon atom adjacent to the nitrogen attached to the benzooxazolyl group, $R_8$ is —CF$_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —CH$_3$, x is 0, $R_4$ is —H, $R_3$ is —CH$_3$ and is attached to the carbon atom adjacent to the nitrogen attached to the benzooxazolyl group, $R_8$ is —H, and $R_9$ is —OCH$_2$CH$_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —CH$_3$, x is 0, $R_4$ is —H, $R_3$ is —CH$_3$ and is attached to the carbon atom adjacent to the nitrogen attached to the benzooxazolyl group, $R_8$ is —OCH$_2$CH$_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —CF$_3$, x is 0, $R_4$ is —H, $R_3$ is —CH$_3$ and is attached to the carbon atom adjacent to the nitrogen attached to the benzooxazolyl group, and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —CF$_3$, x is 0, $R_4$ is —H, $R_3$ is —CH$_3$ and is attached to the carbon atom adjacent to the nitrogen attached to the benzooxazolyl group, $R_8$ is —H, and $R_9$ is -halo. In another embodiment $R_9$ is —Cl. In another embodiment, $R_9$ is —Br. In another embodiment, $R_9$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —CF$_3$, x is 0, $R_4$ is —H, $R_3$ is —CH$_3$ and is attached to the carbon atom adjacent to the nitrogen attached to the benzooxazolyl group, $R_8$ is -halo, and $R_9$ is —H. In another embodiment $R_8$ is —Cl. In another embodiment, $R_8$ is —Br. In another embodiment, $R_8$ is —F. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —CF$_3$, x is 0, $R_4$ is —H, $R_3$ is —CH$_3$ and is attached to the carbon atom adjacent to the nitrogen attached to the benzooxazolyl group, $R_8$ is —H, and $R_9$ is —CH$_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —CF$_3$, x is 0, $R_4$ is —H, $R_3$ is —CH$_3$ and is attached to the carbon atom adjacent to the nitrogen attached to the benzooxazolyl group, $R_8$ is —CH$_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —CF$_3$, x is 0, $R_4$ is —H, $R_3$ is —CH$_3$ and is attached to the carbon atom adjacent to the nitrogen attached to the benzooxazolyl group, $R_8$ is —H, and $R_9$ is —CF$_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —CF$_3$, x is 0, $R_4$ is —H, $R_3$ is —CH$_3$ and is attached to the carbon atom adjacent to the nitrogen attached to the benzooxazolyl group, $R_8$ is —CF$_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —CF$_3$, x is 0, $R_4$ is —H, $R_3$ is —CH$_3$ and is attached to the carbon atom adjacent to the nitrogen attached to the benzooxazolyl group, $R_8$ is —H, and $R_9$ is —OCH$_2$CH$_3$. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —CF$_3$, x is 0, $R_4$ is —H, $R_3$ is —CH$_3$ and is attached to the carbon atom adjacent to the nitrogen attached to the benzooxazolyl group, $R_8$ is —OCH$_2$CH$_3$, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_3$ is —CH$_3$ and is attached to the carbon atom adjacent to the nitrogen attached to the benzooxazolyl group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —Cl, x is 0, $R_3$ is —CH$_3$ and is attached to the carbon atom adjacent to the nitrogen attached to the benzooxazolyl group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is -halo, x is 0, $R_3$ is —CH$_3$ and is attached to the carbon atom adjacent to the nitrogen attached to the benzooxazolyl group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration In another embodiment, p is 0, m is 1, $R_1$ is —Cl, x is 0, $R_3$ is —$CH_3$ and is attached to the carbon atom adjacent to the nitrogen attached to the benzooxazolyl group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_3$ is —$CH_3$ and is attached to the carbon atom adjacent to the nitrogen attached to the benzooxazolyl group, $R_4$ is —H, $R_8$ is -tert-butyl, and $R_9$ is —H. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_3$ is —$CH_3$ and is attached to the carbon atom adjacent to the nitrogen attached to the benzooxazolyl group, $R_4$ is —H, $R_8$ is —H, and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, p is 0, m is 1, $R_1$ is —$CH_3$, x is 0, $R_3$ is —$CH_3$ and is attached to the carbon atom adjacent to the nitrogen attached to the benzooxazolyl group, $R_4$ is —H, $R_8$ is —$CH_3$, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group, p is 0, m is 1, $R_1$ is —$CH_3$ or -halo, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Cl. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group, p is 0, m is 1, $R_1$ is -halo, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group, p is 0, m is 1, $R_1$ is —Cl, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —F. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is —$CH_3$ or -halo, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Cl. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is -halo, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is —Cl, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —F. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is —$CH_3$ or -halo, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is —$CH_3$, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Cl. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is -halo, x is 1, A is —C(O)—N($R_4$)—, $R_3$ is —$CH_3$ and is attached to the carbon atom adjacent to the nitrogen attached to the —C(O)—N($R_4$)— group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is —Cl, x is 1, A is —C(O)—N($R_4$)—, $R_3$ is —CH$_3$ and is attached to the carbon atom adjacent to the nitrogen attached to the —C(O)—N($R_4$)— group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is —CH$_3$, x is 1, A is —C(O)—N($R_4$)—, $R_3$ is —CH$_3$ and is attached to the carbon atom adjacent to the nitrogen attached to the —C(O)—N($R_4$)— group, $R_4$ is —H, $R_8$ is —H, and $R_9$ is —F. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group, p is 0, m is 1, $R_1$ is —CH$_3$ or -halo, x is 0, $R_3$ is —CH$_3$ and is attached to the carbon atom adjacent to the nitrogen attached to the benzooxazolyl group, $R_4$ is —H, $R_8$ is —H, and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group, p is 0, m is 1, $R_1$ is —CH$_3$, x is 0, $R_3$ is —CH$_3$ and is attached to the carbon atom adjacent to the nitrogen attached to the benzooxazolyl group, $R_4$ is —H, $R_8$ is —H, and $R_9$ is —Cl. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group, p is 0, m is 1, $R_1$ is -halo, x is 0, $R_3$ is —CH$_3$ and is attached to the carbon atom adjacent to the nitrogen attached to the benzooxazolyl group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group, p is 0, m is 1, $R_1$ is —Cl, x is 0, $R_3$ is —CH$_3$ and is attached to the carbon atom adjacent to the nitrogen attached to the benzooxazolyl group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyrazinyl group, p is 0, m is 1, $R_1$ is —CH$_3$, x is 0, $R_3$ is —CH$_3$ and is attached to the carbon atom adjacent to the nitrogen attached to the benzooxazolyl group, $R_4$ is —H, $R_8$ is —H, and $R_9$ is —F. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is —CH$_3$ or -halo, x is 0, $R_3$ is —CH$_3$ and is attached to the carbon atom adjacent to the nitrogen attached to the benzooxazolyl group, $R_4$ is —H, $R_8$ is —H, and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is —CH$_3$, x is 0, $R_3$ is —CH$_3$ and is attached to the carbon atom adjacent to the nitrogen attached to the benzooxazolyl group, $R_4$ is —H, $R_8$ is —H, and $R_9$ is —Cl. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is -halo, x is 0, $R_3$ is —CH$_3$ and is attached to the carbon atom adjacent to the nitrogen attached to the benzooxazolyl group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is —Cl, x is 0, $R_3$ is —CH$_3$ and is attached to the carbon atom adjacent to the nitrogen attached to the benzooxazolyl group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a pyridazinyl group, p is 0, m is 1, $R_1$ is —CH$_3$, x is 0, $R_3$ is —CH$_3$ and is attached to the carbon atom adjacent to the nitrogen attached to the benzooxazolyl group, $R_4$ is —H, $R_8$ is —H, and $R_9$ is —F. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is —CH$_3$ or -halo, x is 0, $R_3$ is —CH$_3$ and is attached to the carbon atom adjacent to the nitrogen attached to the benzooxazolyl group, $R_4$ is —H, $R_8$ is —H, and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is —CH$_3$, x is 0, $R_3$ is —CH$_3$ and is attached to the carbon atom adjacent to the nitrogen attached to the benzooxazolyl group, $R_4$ is —H, $R_8$ is —H, and $R_9$ is —Cl. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is -halo, x is 0, $R_3$ is —CH$_3$ and is attached to the carbon atom adjacent to the nitrogen attached to the benzooxazolyl group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is —Cl, x is 0, $R_3$ is —CH$_3$ and is attached to the carbon atom adjacent to the nitrogen attached to the benzooxazolyl group, $R_4$ is —H, $R_8$ is —H, and $R_9$ is —Br. In another embodiment, the carbon atom to which the $R_3$ group is attached has the R configuration. In another embodiment, the carbon atom to which the $R_3$ group is attached has the S configuration.

In another embodiment, $Ar_1$ is a thiazanyl group, p is 0, m is 1, $R_1$ is —CH$_3$, x is 0, $R_3$ is —CH$_3$ and is attached to the carbon atom adjacent to the nitrogen attached to the benzooxazolyl group, $R_4$ is —H, $R_8$ is —H, and $R_9$ is —F. In another embodiment, the carbon atom to which the $R_3$ group is attached has the R configuration. In another embodiment, the carbon atom to which the $R_3$ group is attached has the S configuration.

In another embodiment, m is 1 and $R_3$ is —$(C_1$-$C_4)$alkyl and is attached to the carbon atom adjacent to the nitrogen attached to the —C(O)—N($R_4$)— when x is 1 or the benzooxazolyl group when x is 0. In another embodiment, m is 1 and $R_3$ is —$(C_1$-$C_4)$alkyl and is attached to the carbon atom adjacent to the nitrogen attached to the —C(O)—N($R_4$)— when x is 1 or the benzooxazolyl group when x is 0 and the carbon to which the $R_3$ group is attached is in the R configuration.

In another embodiment, m is 1 and $R_3$ is —$CH_3$ and is attached to the carbon atom adjacent to the nitrogen attached to the —C(O)—N($R_4$)— when x is 1 or the benzooxazolyl group when x is 0. In another embodiment, m is 1 and $R_3$ is —$CH_3$ and is attached to the carbon atom adjacent to the nitrogen attached to the —C(O)—N($R_4$)— when x is 1 or the benzooxazolyl group when x is 0 and the carbon to which the $R_3$ group is attached is in the R configuration.

In another embodiment, m is 1 and $R_3$ is —$(C_1$-$C_4)$alkyl and is attached to the carbon atom adjacent to the nitrogen attached to the —C(O)—N($R_4$)— when x is 1 or the benzooxazolyl group when x is 0. In another embodiment, m is 1 and $R_3$ is —$(C_1$-$C_4)$alkyl and is attached to the carbon atom adjacent to the nitrogen attached to the —C(O)—N($R_4$)— when x is 1 or the benzooxazolyl group when x is 0 and the carbon to which the $R_3$ group is attached is in the S configuration.

In another embodiment, m is 1 and $R_3$ is —$CH_3$ and is attached to the carbon atom adjacent to the nitrogen attached to the —C(O)—N($R_4$)— when x is 1 or the benzooxazolyl group when x is 0. In another embodiment, m is 1 and $R_3$ is —$CH_3$ and is attached to the carbon atom adjacent to the nitrogen attached to the —C(O)—N($R_4$)— when x is 1 or the benzooxazolyl group when x is 0 and the carbon to which the $R_3$ group is attached is in the S configuration.

In another embodiment, m is 1 and $R_3$ is —$(C_1$-$C_4)$alkyl and is attached to the carbon atom adjacent to the nitrogen attached to the pyrazinyl group, pyridazinyl group, or thiazanyl group. In another embodiment, m is 1 and $R_3$ is —$(C_1$-$C_4)$alkyl and is attached to the carbon atom adjacent to the nitrogen attached to the pyrazinyl group, pyridazinyl group, or thiazanyl group and the carbon to which the $R_3$ group is attached is in the R configuration.

In another embodiment, m is 1 and $R_3$ is —$CH_3$ and is attached to the carbon atom adjacent to the nitrogen attached to the pyrazinyl group, pyridazinyl group, or thiazanyl group. In another embodiment, m is 1 and $R_3$ is —$CH_3$ and is attached to the carbon atom adjacent to the nitrogen attached to the pyrazinyl group, pyridazinyl group, or thiazanyl group and the carbon to which the $R_3$ group is attached is in the R configuration.

In another embodiment, m is 1 and $R_3$ is —$(C_1$-$C_4)$alkyl and is attached to the carbon atom adjacent to the nitrogen attached to the pyrazinyl group, pyridazinyl group, or thiazanyl group. In another embodiment, m is 1 and $R_3$ is —$(C_1$-$C_4)$alkyl and is attached to the carbon atom adjacent to the nitrogen attached to the pyrazinyl group, pyridazinyl group, or thiazanyl group and the carbon to which the $R_3$ group is attached is in the S configuration.

In another embodiment, m is 1 and $R_3$ is —$CH_3$ and is attached to the carbon atom adjacent to the nitrogen attached to the pyrazinyl group, pyridazinyl group, or thiazanyl group. In another embodiment, m is 1 and $R_3$ is —$CH_3$ and is attached to the carbon atom adjacent to the nitrogen attached to the pyrazinyl group, pyridazinyl group, or thiazanyl group and the carbon to which the $R_3$ group is attached is in the S configuration.

4.7 The Compounds of Formula (IVa)

The present invention also encompasses compounds of formula (IVa):

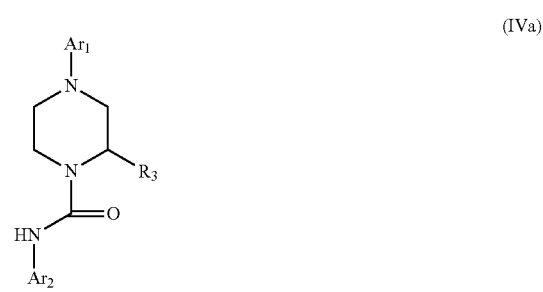

and pharmaceutically acceptable salts thereof, where $Ar_1$, $Ar_2$, and $R_3$, are defined above for the Benzoazolylpiperazine Compounds of formula (IVa).

In one embodiment, $Ar_1$ is a pyridyl group.
In another embodiment, $Ar_1$ is a pyrimidinyl group.
In another embodiment, $Ar_2$ is a benzothiazolyl group.
In another embodiment, $Ar_2$ is a benzooxazolyl group.
In another embodiment, $Ar_2$ is a benzoimidazolyl group.
In another embodiment, n or p is 0.
In another embodiment, n or p is 1.
In another embodiment, $R_1$ is —Cl.
In another embodiment, $R_1$ is —Br.
In another embodiment, $R_1$ is —I.
In another embodiment, $R_1$ is —F.
In another embodiment, $R_1$ is —$(C_1$-$C_6)$alkyl.
In another embodiment, $R_1$ is —$CH_3$.
In another embodiment, $R_1$ is —$NO_2$.
In another embodiment, $R_1$ is —CN.
In another embodiment, $R_1$ is —OH.
In another embodiment, $R_1$ is —$OCH_3$.
In another embodiment, $R_1$ is —$NH_2$.
In another embodiment, $R_1$ is —C(halo)$_3$.
In another embodiment, $R_1$ is —CH(halo)$_2$.
In another embodiment, $R_1$ is —$CH_2$(halo).
In another embodiment, n and p are 1 and $R_2$ is -halo, —CN, —OH, —O($C_1$-$C_6$)alkyl, —$NO_2$, or —$NH_2$.

In another embodiment, n and p are 1 and $R_2$ is —$(C_1$-$C_{10})$alkyl, —$(C_2$-$C_{10})$alkenyl, —$(C_2$-$C_{10})$alkynyl, —$(C_3$-$C_{10})$cycloalkyl, —$(C_8$-$C_{14})$bicycloalkyl, —$(C_8$-$C_{14})$tricycloalkyl, —$(C_5$-$C_{10})$cycloalkenyl, —$(C_8$-$C_{14})$bicycloalkenyl, —$(C_8$-$C_{14})$tricycloalkenyl, -(3- to 7-membered)heterocycle, or -(7- to 10-membered)bicycloheterocycle, each of which is unsubstituted or substituted with one or more $R_5$ groups.

In another embodiment, n and p are 1 and $R_2$ is -phenyl, -naphthyl, —$(C_{14})$aryl, or -(5- to 10-membered)heteroaryl, each of which is unsubstituted or substituted with one or more $R_6$ groups;

In another embodiment, $R_3$ is —H.
In another embodiment, $R_3$ is —$CH_3$.
In another embodiment, $R_8$ and $R_9$ are each independently —H, halo, —$(C_1$-$C_6)$alkyl, —O$(C_1$-$C_6)$alkyl, —C(halo)$_3$, —CH(halo)$_2$, or —$CH_2$(halo).
In another embodiment, at least one of $R_8$ and $R_9$ is —H.

In another embodiment, $Ar_1$ is a pyridyl group, n is 0; $R_3$ is —H; $R_1$ is —F, —Cl, —Br, or, —I; $Ar_2$ is a benzothiazolyl group; and $R_8$ and $R_9$ are —H.

In another embodiment, $Ar_1$ is a pyridyl group, n is 0; $R_3$ is —H; $R_1$ is —F; $Ar_2$ is a benzothiazolyl group; and $R_8$ and $R_9$ are —H.

In another embodiment, $Ar_1$ is a pyridyl group, n is 0; $R_3$ is —H; $R_1$ is —F, —Cl, —Br, or —I; $Ar_2$ is a benzothiazolyl group; $R_8$ is —H; and $R_9$ is -halo.

In another embodiment, $Ar_1$ is a pyridyl group, n is 0; $R_3$ is —H; $R_1$ is —F, $Ar_2$ is a benzothiazolyl group; $R_8$ is —H; and $R_9$ is -chloro.

In another embodiment, $Ar_1$ is a pyridyl group, n is 0; $R_3$ is —H; $R_1$ is —F, $Ar_2$ is a benzothiazolyl group; $R_8$ is —H; and $R_9$ is -bromo.

In another embodiment, $Ar_1$ is a pyridyl group, n is 0; $R_3$ is —H; $R_1$ is —F, $Ar_2$ is a benzothiazolyl group; $R_8$ is —H; and $R_9$ is -fluoro.

In another embodiment, $Ar_1$ is a pyridyl group, n is 0; $R_3$ is —H; $R_1$ is —F, $Ar_2$ is a benzothiazolyl group; $R_8$ is —H; and $R_9$ is -iodo.

In another embodiment, $Ar_1$ is a pyridyl group, n is 0; $R_3$ is —H; $R_1$ is —F, —Cl, —Br, or —I; $Ar_2$ is a benzothiazolyl group; $R_8$ is -halo; and $R_9$ is —H.

In another embodiment, $Ar_1$ is a pyridyl group, n is 0; $R_3$ is —H; $R_1$ is —F, —Cl, —Br, or —I; $Ar_2$ is a benzothiazolyl group; $R_8$ is -chloro; and $R_9$ is —H.

In another embodiment, $Ar_1$ is a pyridyl group, n is 0; $R_3$ is —H; $R_1$ is —F, —Cl, —Br, or —I; $Ar_2$ is a benzothiazolyl group; $R_8$ is -bromo; and $R_9$ is —H.

In another embodiment, $Ar_1$ is a pyridyl group, n is 0; $R_3$ is —H; $R_1$ is —F, —Cl, —Br, or —I; $Ar_2$ is a benzothiazolyl group; $R_8$ is -fluoro; and $R_9$ is —H.

In another embodiment, $Ar_1$ is a pyridyl group, n is 0; $R_3$ is —H; $R_1$ is —F, —Cl, —Br, or —I; $Ar_2$ is a benzothiazolyl group; $R_8$ is -iodo; and $R_9$ is —H.

In another embodiment, $Ar_1$ is a pyridyl group, n is 0; $R_3$ is —H; $R_1$ is —F; $Ar_2$ is a benzothiazolyl group; $R_8$ is -halo, and $R_9$ is —H.

In another embodiment, $Ar_1$ is a pyridyl group, n is 0; $R_3$ is —H; $R_1$ is —F; $Ar_2$ is a benzothiazolyl group; $R_8$ is -chloro, and $R_9$ is —H.

In another embodiment, $Ar_1$ is a pyridyl group, n is 0; $R_3$ is —H; $R_1$ is —F; $Ar_2$ is a benzothiazolyl group; $R_8$ is -bromo, and $R_9$ is —H.

In another embodiment, $Ar_1$ is a pyridyl group, n is 0; $R_3$ is —H; $R_1$ is —F; $Ar_2$ is a benzothiazolyl group; $R_8$ is -fluoro, and $R_9$ is —H.

In another embodiment, $Ar_1$ is a pyridyl group, n is 0; $R_3$ is —H; $R_1$ is —F; $Ar_2$ is a benzothiazolyl group; $R_8$ is -iodo, and $R_9$ is —H.

In another embodiment, $Ar_1$ is a pyridyl group, n is 0; $R_3$ is —H; $R_1$ is —F, —Cl, —Br, or —I; $Ar_2$ is a benzothiazolyl group; $R_8$ is —H; and $R_9$ is —$CH_3$.

In another embodiment, $Ar_1$ is a pyridyl group, n is 0; $R_3$ is —H; $R_1$ is —F; $Ar_2$ is a benzothiazolyl group; $R_8$ is —H, and $R_9$ is —$CH_3$.

In another embodiment, $Ar_1$ is a pyridyl group, n is 0; $R_3$ is —H; $R_1$ is —F, —Cl, —Br, or —I; $Ar_2$ is a benzothiazolyl group; $R_8$ is —$CH_3$; and $R_9$ is —H.

In another embodiment, $Ar_1$ is a pyridyl group, n is 0; $R_3$ is —H; $R_1$ is —F; $Ar_2$ is a benzothiazolyl group; $R_8$ is —$CH_3$, and $R_9$ is —H.

In another embodiment, $Ar_1$ is a pyridyl group, n is 0; $R_3$ is —H; $R_1$ is —F, —Cl, —Br, or —I; $Ar_2$ is a benzothiazolyl group; $R_8$ is —H; and $R_9$ is —$CF_3$.

In another embodiment, $Ar_1$ is a pyridyl group, n is 0; $R_3$ is —H; $R_1$ is —F; $Ar_2$ is a benzothiazolyl group; $R_8$ is —H; and $R_9$ is —$CF_3$.

In another embodiment, $Ar_1$ is a pyridyl group, n is 0; $R_3$ is —H; $R_1$ is —F, —Cl; —Br, or —I; $Ar_2$ is a benzothiazolyl group; $R_8$ is —$CF_3$; and $R_9$ is —H.

In another embodiment, $Ar_1$ is a pyridyl group, n is 0; $R_3$ is —H; $R_1$ is —F. $Ar_2$ is a benzothiazolyl group; $R_8$ is —$CF_3$; and $R_9$ is —H.

In another embodiment, $Ar_1$ is a pyridyl group, n is 0; $R_3$ is —H; $R_1$ is —F, —Cl, —Br, or —I; $Ar_2$ is a benzothiazolyl group; $R_8$ is —H; and $R_9$ is —$OCH_2CH_3$.

In another embodiment, $Ar_1$ is a pyridyl group, n is 0; $R_3$ is —H; $R_1$ is —F; $Ar_2$ is a benzothiazolyl group; $R_8$ is —H; and $R_9$ is —$OCH_2CH_3$.

In another embodiment $Ar_1$ is a pyridyl group, n is 0; $R_3$ is —H; $R_1$ is —F, —Cl; —Br, or —I; $Ar_2$ is a benzothiazolyl group; $R_8$ is —$OCH_2CH_3$; and $R_9$ is —H.

In another embodiment, $Ar_1$ $Ar_1$ is a pyridyl group, n is 0; $R_3$ is —H; $R_1$ is —F; $Ar_2$ is a benzothiazolyl group; $R_8$ is —$OCH_2CH_3$; and $R_9$ is —H.

In another embodiment, $Ar_1$ is a pyridyl group, n is 0; $R_3$ is —H; $R_1$ is —F, —Cl, —Br, or —I; $Ar_2$ is a benzothiazolyl group; $R_8$ is -tert-butyl; and $R_9$ is —H.

In another embodiment, $Ar_1$ is a pyridyl group, n is 0; $R_3$ is —H; $R_1$ is —F; $Ar_2$ is a benzothiazolyl group; $R_8$ is -tert-butyl; and $R_9$ is —H.

In another embodiment, $Ar_1$ is a pyridyl group, n is 0; $R_3$ is —H; $R_1$ is $R_1$ is —F, —Cl, —Br, or —I; $Ar_2$ is a benzothiazolyl group; $R_8$ is —H; and $R_9$ is -tert-butyl.

In another embodiment, $Ar_1$ is a pyridyl group, n is 0; $R_3$ is —H; $R_1$ is $R_1$ is —F; $Ar_2$ is a benzothiazolyl group; $R_8$ is —H; and $R_9$ is -tert-butyl.

In another embodiment, $Ar_1$ is a pyridyl group, n is 0; $R_3$ is —$CH_3$; $R_1$ is —F, —Cl, —Br, or, —I; $Ar_2$ is a benzothiazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzothiazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl; —Br, or —I; $Ar_2$ is a benzothiazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, $Ar_2$ is a benzothiazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, $Ar_2$ is a benzothiazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, $Ar_2$ is a benzothiazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, $Ar_2$ is a benzothiazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzothiazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzothiazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzothiazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzothiazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzothiazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzothiazolyl group; $R_8$ is -halo, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzothiazolyl group; $R_8$ is -chloro, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzothiazolyl group; $R_8$ is -bromo, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzothiazolyl group; $R_8$ is -fluoro, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzothiazolyl group; $R_8$ is -iodo, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzothiazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzothiazolyl group; $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzothiazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzothiazolyl group; $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzothiazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, $Ar_2$ is a benzothiazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzothiazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzothiazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzothiazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzothiazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment $Ar_1$ is a pyridyl group, n is 0; $R_3$ is —$CH_3$; $R_1$ is —F, —Cl, —Br, or —I; $Ar_2$ is a benzothiazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzothiazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzothiazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is $R_1$ is —F, —Cl, —Br, or —I; $Ar_2$ is a benzothiazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is $R_1$ is —F; $Ar_2$ is a benzothiazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —H; $R_1$ is —F, —Cl, —Br, or, —I; $Ar_2$ is a benzothiazolyl group; and $R_8$ and $R_9$ are —H.

In another embodiment, $Ar_1$ is a pyrimidinyl group, p is 0; $R_3$ is —H; $R_1$ is —F; $Ar_2$ is a benzothiazolyl group; and $R_8$ and $R_9$ are —H.

In another embodiment, $Ar_1$ is a pyrimidinyl group, p is 0; $R_3$ is —H; $R_1$ is —F, —Cl, —Br, or —I; $Ar_2$ is a benzothiazolyl group; $R_8$ is —H; and $R_9$ is -halo.

In another embodiment, $Ar_1$ is a pyrimidinyl group, p is 0; $R_3$ is —H; $R_1$ is —F, $Ar_2$ is a benzothiazolyl group; $R_8$ is —H; and $R_9$ is -chloro.

In another embodiment, $Ar_1$ is a pyrimidinyl group, p is 0; $R_3$ is —H; $R_1$ is —F, $Ar_2$ is a benzothiazolyl group; $R_8$ is —H; and $R_9$ is -bromo.

In another embodiment, $Ar_1$ is a pyrimidinyl group, p is 0; $R_3$ is —H; $R_1$ is —F, $Ar_2$ is a benzothiazolyl group; $R_8$ is —H; and $R_9$ is -fluoro.

In another embodiment, $Ar_1$ is a pyrimidinyl group, p is 0; $R_3$ is —H; $R_1$ is —F, $Ar_2$ is a benzothiazolyl group; $R_8$ is —H; and $R_9$ is -iodo.

In another embodiment, $Ar_1$ is a pyrimidinyl group, p is 0; $R_3$ is —H; $R_1$ is —F, —Cl, —Br, or —I; $Ar_2$ is a benzothiazolyl group; $R_8$ is -halo; and $R_9$ is —H.

In another embodiment, $Ar_1$ is a pyrimidinyl group, p is 0; $R_3$ is —H; $R_1$ is —F, —Cl, —Br, or —I; $Ar_2$ is a benzothiazolyl group; $R_8$ is -chloro; and $R_9$ is —H.

In another embodiment, $Ar_1$ is a pyrimidinyl group, p is 0; $R_3$ is —H; $R_1$ is —F, —Cl, —Br, or —I; $Ar_2$ is a benzothiazolyl group; $R_8$ is -bromo; and $R_9$ is —H.

In another embodiment, $Ar_1$ is a pyrimidinyl group, p is 0; $R_3$ is —H; $R_1$ is —F, —Cl, —Br, or —I; $Ar_2$ is a benzothiazolyl group; $R_8$ is -fluoro; and $R_9$ is —H.

In another embodiment, $Ar_1$ is a pyrimidinyl group, p is 0; $R_3$ is —H; $R_1$ is —F, —Cl, —Br, or —I; $Ar_2$ is a benzothiazolyl group; $R_8$ is -iodo; and $R_9$ is —H.

In another embodiment, $Ar_1$ is a pyrimidinyl group, p is 0; $R_3$ is —H; $R_1$ is —F; $Ar_2$ is a benzothiazolyl group; $R_8$ is -halo, and $R_9$ is —H.

In another embodiment, $Ar_1$ is a pyrimidinyl group, p is 0; $R_3$ is —H; $R_1$ is —F; $Ar_2$ is a benzothiazolyl group; $R_8$ is -chloro, and $R_9$ is —H.

In another embodiment, $Ar_1$ is a pyrimidinyl group, p is 0; $R_3$ is —H; $R_1$ is —F; $Ar_2$ is a benzothiazolyl group; $R_8$ is -bromo, and $R_9$ is —H.

In another embodiment, $Ar_1$ is a pyrimidinyl group, p is 0; $R_3$ is —H; $R_1$ is —F; $Ar_2$ is a benzothiazolyl group; $R_8$ is -fluoro, and $R_9$ is —H.

In another embodiment, $Ar_1$ is a pyrimidinyl group, p is 0; $R_3$ is —H; $R_1$ is —F; $Ar_2$ is a benzothiazolyl group; $R_8$ is -iodo, and $R_9$ is —H.

In another embodiment, $Ar_1$ is a pyrimidinyl group, p is 0; $R_3$ is —H; $R_1$ is —F, —Cl, —Br, or —I; $Ar_2$ is a benzothiazolyl group; $R_8$ is —H; and $R_9$ is —$CH_3$.

In another embodiment, $Ar_1$ is a pyrimidinyl group, p is 0; $R_3$ is —H; $R_1$ is —F; $Ar_2$ is a benzothiazolyl group; $R_8$ is —H, and $R_9$ is —$CH_3$.

In another embodiment, $Ar_1$ is a pyrimidinyl group, p is 0; $R_3$ is —H; $R_1$ is —F, —Cl, —Br, or —I; $Ar_2$ is a benzothiazolyl group; $R_8$ is —$CH_3$; and $R_9$ is —H.

In another embodiment, $Ar_1$ is a pyrimidinyl group, p is 0; $R_3$ is —H; $R_1$ is —F; $Ar_2$ is a benzothiazolyl group; $R_8$ is —$CH_3$, and $R_9$ is —H.

In another embodiment, $Ar_1$ is a pyrimidinyl group, p is 0; $R_3$ is —H; $R_1$ is —F, —Cl, —Br, or —I; $Ar_2$ is a benzothiazolyl group; $R_8$ is —H; and $R_9$ is —$CF_3$.

In another embodiment, $Ar_1$ is a pyrimidinyl group, p is 0; $R_3$ is —H; $R_1$ is —F. $Ar_2$ is a benzothiazolyl group; $R_8$ is —H; and $R_9$ is —$CF_3$.

In another embodiment, $Ar_1$ is a pyrimidinyl group, p is 0; $R_3$ is —H; $R_1$ is —F, —Cl, —Br, or —I; $Ar_2$ is a benzothiazolyl group; $R_8$ is —$CF_3$; and $R_9$ is —H.

In another embodiment, $Ar_1$ is a pyrimidinyl group, p is 0; $R_3$ is —H; $R_1$ is —F; $Ar_2$ is a benzothiazolyl group; $R_8$ is —$CF_3$; and $R_9$ is —H.

In another embodiment, $Ar_1$ is a pyrimidinyl group, p is 0; $R_3$ is —H; $R_1$ is —F, —Cl, —Br, or —I; $Ar_2$ is a benzothiazolyl group; $R_8$ is —H; and $R_9$ is —$OCH_2CH_3$.

In another embodiment, $Ar_1$ is a pyrimidinyl group, p is 0; $R_3$ is —H; $R_1$ is —F; $Ar_2$ is a benzothiazolyl group; $R_8$ is —H; and $R_9$ is —$OCH_2CH_3$.

In another embodiment $Ar_1$ is a pyrimidinyl group, p is 0; $R_3$ is —H; $R_1$ is —F, —Cl, —Br, or —I; $Ar_2$ is a benzothiazolyl group; $R_8$ is —$OCH_2CH_3$; and $R_9$ is —H.

In another embodiment, $Ar_1$ $Ar_1$ is a pyrimidinyl group, p is 0; $R_3$ is —H; $R_1$ is —F; $Ar_2$ is a benzothiazolyl group; $R_8$ is —$OCH_2CH_3$; and $R_9$ is —H.

In another embodiment, $Ar_1$ is a pyrimidinyl group, p is 0; $R_3$ is —H; $R_1$ is —F, —Cl, —Br, or —I; $Ar_2$ is a benzothiazolyl group; $R_8$ is -tert-butyl; and $R_9$ is —H.

In another embodiment, $Ar_1$ is a pyrimidinyl group, p is 0; $R_3$ is —H; $R_1$ is —F; $Ar_2$ is a benzothiazolyl group; $R_8$ is -tert-butyl; and $R_9$ is —H.

In another embodiment, $Ar_1$ is a pyrimidinyl group, p is 0; $R_3$ is —H; $R_1$ is $R_1$ is —F, —Cl, —Br, or —I; $Ar_2$ is a benzothiazolyl group; $R_8$ is —H; and $R_9$ is -tert-butyl.

In another embodiment, $Ar_1$ is a pyrimidinyl group, p is 0; $R_3$ is —H; $R_1$ is $R_1$ is —F; $Ar_2$ is a benzothiazolyl group; $R_8$ is —H; and $R_9$ is -tert-butyl.

In another embodiment, $Ar_1$ is a pyrimidinyl group, p is 0; $R_3$ is —$CH_3$; $R_1$ is —F, —Cl, —Br, or, —I; $Ar_2$ is a benzothiazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzothiazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzothiazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, $Ar_2$ is a benzothiazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, $Ar_2$ is a benzothiazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, $Ar_2$ is a benzothiazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, $Ar_2$ is a benzothiazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzothiazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzothiazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzothiazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzothiazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzothiazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzothiazolyl group; $R_8$ is -halo, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzothiazolyl group; $R_8$ is -chloro, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzothiazolyl group; $R_8$ is -bromo, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzothiazolyl group; $R_8$ is -fluoro, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzothiazolyl group; $R_8$ is -iodo, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzothiazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzothiazolyl group; $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzothiazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzothiazolyl group; $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzothiazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzothiazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzothiazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzothiazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzothiazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzothiazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment $Ar_1$ is a pyrimidinyl group, p is 0; $R_3$ is —$CH_3$; $R_1$ is —F, —Cl, —Br, or —I; $Ar_2$ is a benzothiazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzothiazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzothiazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is $R_1$ is —F, —Cl, —Br, or —I; $Ar_2$ is a benzothiazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is $R_1$ is —F; $Ar_2$ is a benzothiazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —H; $R_1$ is —F, —Cl, —Br, or, —I; $Ar_2$ is a benzoimidazolyl group; and $R_8$ and $R_9$ are —H.

In another embodiment, $Ar_1$ is a pyridyl group, n is 0; $R_3$ is —H; $R_1$ is —F; $Ar_2$ is a benzoimidazolyl group, and $R_8$ and $R_9$ are —H.

In another embodiment, $Ar_1$ is a pyridyl group, n is 0; $R_3$ is —H; $R_1$ is —F, —Cl, —Br, or —I; $Ar_2$ is a benzoimidazolyl group; $R_8$ is —H; and $R_9$ is -halo.

In another embodiment, $Ar_1$ is a pyridyl group, n is 0; $R_3$ is —H; $R_1$ is —F, $Ar_2$ is a benzoimidazolyl group; $R_8$ is —H; and $R_9$ is -chloro.

In another embodiment, $Ar_1$ is a pyridyl group, n is 0; $R_3$ is —H; $R_1$ is —F, $Ar_2$ is a benzoimidazolyl group; $R_8$ is —H; and $R_9$ is -bromo.

In another embodiment, $Ar_1$ is a pyridyl group, n is 0; $R_3$ is —H; $R_1$ is —F, $Ar_2$ is a benzoimidazolyl group; $R_8$ is —H; and $R_9$ is -fluoro.

In another embodiment, $Ar_1$ is a pyridyl group, n is 0; $R_3$ is —H; $R_1$ is —F, $Ar_2$ is a benzoimidazolyl group; $R_8$ is —H; and $R_9$ is -iodo.

In another embodiment, $Ar_1$ is a pyridyl group, n is 0; $R_3$ is —H; $R_1$ is —F, —Cl, —Br, or —I; $Ar_2$ is a benzoimidazolyl group; $R_8$ is -halo; and $R_9$ is —H.

In another embodiment, $Ar_1$ is a pyridyl group, n is 0; $R_3$ is —H; $R_1$ is —F, —Cl, —Br, or —I; $Ar_2$ is a benzoimidazolyl group; $R_8$ is -chloro; and $R_9$ is —H.

In another embodiment, $Ar_1$ is a pyridyl group, n is 0; $R_3$ is —H; $R_1$ is —F, —Cl, —Br, or —I; $Ar_2$ is a benzoimidazolyl group; $R_8$ is -bromo; and $R_9$ is —H.

In another embodiment, $Ar_1$ is a pyridyl group, n is 0; $R_3$ is —H; $R_1$ is —F, —Cl, —Br, or —I; $Ar_2$ is a benzoimidazolyl group; $R_8$ is -fluoro; and $R_9$ is —H.

In another embodiment, $Ar_1$ is a pyridyl group, n is 0; $R_3$ is —H; $R_1$ is —F, —Cl, —Br, or —I; $Ar_2$ is a benzoimidazolyl group; $R_8$ is -iodo; and $R_9$ is —H.

In another embodiment, $Ar_1$ is a pyridyl group, n is 0; $R_3$ is —H; $R_1$ is —F; $Ar_2$ is a benzoimidazolyl group; $R_8$ is -halo, and $R_9$ is —H.

In another embodiment, $Ar_1$ is a pyridyl group, n is 0; $R_3$ is —H; $R_1$ is —F; $Ar_2$ is a benzoimidazolyl group; $R_8$ is -chloro, and $R_9$ is —H.

In another embodiment, $Ar_1$ is a pyridyl group, n is 0; $R_3$ is —H; $R_1$ is —F; $Ar_2$ is a benzoimidazolyl group; $R_8$ is -bromo, and $R_9$ is —H.

In another embodiment, $Ar_1$ is a pyridyl group, n is 0; $R_3$ is —H; $R_1$ is —F; $Ar_2$ is a benzoimidazolyl group; $R_8$ is -fluoro, and $R_9$ is —H.

In another embodiment, $Ar_1$ is a pyridyl group, n is 0; $R_3$ is —H; $R_1$ is —F; $Ar_2$ is a benzoimidazolyl group; $R_8$ is -iodo, and $R_9$ is —H.

In another embodiment, $Ar_1$ is a pyridyl group, n is 0; $R_3$ is —H; $R_1$ is —F, —Cl, —Br, or —I; $Ar_2$ is a benzoimidazolyl group; $R_8$ is —H; and $R_9$ is —$CH_3$.

In another embodiment, $Ar_1$ is a pyridyl group, n is 0; $R_3$ is —H; $R_1$ is —F; $Ar_2$ is a benzoimidazolyl group; $R_8$ is —H, and $R_9$ is —$CH_3$.

In another embodiment, $Ar_1$ is a pyridyl group, n is 0; $R_3$ is —H; $R_1$ is —F, —Cl; —Br, or —I; $Ar_2$ is a benzoimidazolyl group; $R_8$ is —$CH_3$; and $R_9$ is —H.

In another embodiment, $Ar_1$ is a pyridyl group, n is 0; $R_3$ is —H; $R_1$ is —F; $Ar_2$ is a benzoimidazolyl group; $R_8$ is —$CH_3$, and $R_9$ is —H.

In another embodiment, $Ar_1$ is a pyridyl group, n is 0; $R_3$ is —H; $R_1$ is —F, —Cl; —Br, or —I; $Ar_2$ is a benzoimidazolyl group; $R_8$ is —H; and $R_9$ is —$CF_3$.

In another embodiment, $Ar_1$ is a pyridyl group, n is 0; $R_3$ is —H; $R_1$ is —F; $Ar_2$ is a benzoimidazolyl group; $R_8$ is —H; and $R_9$ is —$CF_3$.

In another embodiment, $Ar_1$ is a pyridyl group, n is 0; $R_3$ is —H; $R_1$ is —F, —Cl; —Br, or —I; $Ar_2$ is a benzoimidazolyl group; $R_8$ is —$CF_3$; and $R_9$ is —H.

In another embodiment, $Ar_1$ is a pyridyl group, n is 0; $R_3$ is —H; $R_1$ is —F; $Ar_2$ is a benzoimidazolyl group; $R_8$ is —$CF_3$; and $R_9$ is —H.

In another embodiment, $Ar_1$ is a pyridyl group, n is 0; $R_3$ is —H; $R_1$ is —F, —Cl, —Br, or —I; $Ar_2$ is a benzoimidazolyl group; $R_8$ is —H; and $R_9$ is —$OCH_2CH_3$.

In another embodiment, $Ar_1$ is a pyridyl group, n is 0; $R_3$ is —H; $R_1$ is —F; $Ar_2$ is a benzoimidazolyl group; $R_8$ is —H; and $R_9$ is —$OCH_2CH_3$.

In another embodiment $Ar_1$ is a pyridyl group, n is 0; $R_3$ is —H; $R_1$ is —F, —Cl, —Br, or —I; $Ar_2$ is a benzoimidazolyl group; $R_8$ is —$OCH_2CH_3$; and $R_9$ is —H.

In another embodiment, $Ar_1$ $Ar_1$ is a pyridyl group, n is 0; $R_3$ is —H; $R_1$ is —F; $Ar_2$ is a benzoimidazolyl group; $R_8$ is —$OCH_2CH_3$; and $R_9$ is —H.

In another embodiment, $Ar_1$ is a pyridyl group, n is 0; $R_3$ is —H; $R_1$ is —F, —Cl, —Br, or —I; $Ar_2$ is a benzoimidazolyl group; $R_8$ is -tert-butyl; and $R_9$ is —H.

In another embodiment, $Ar_1$ is a pyridyl group, n is 0; $R_3$ is —H; $R_1$ is —F. $Ar_2$ is a benzoimidazolyl group; $R_8$ is -tert-butyl; and $R_9$ is —H.

In another embodiment, $Ar_1$ is a pyridyl group, n is 0; $R_3$ is —H; $R_1$ is $R_1$ is —F, —Cl, —Br, or —I; $Ar_2$ is a benzoimidazolyl group; $R_8$ is —H; and $R_9$ is -tert-butyl.

In another embodiment, $Ar_1$ is a pyridyl group, n is 0; $R_3$ is —H; $R_1$ is $R_1$ is —F; $Ar_2$ is a benzoimidazolyl group; $R_8$ is —H; and $R_9$ is -tert-butyl.

In another embodiment, $Ar_1$ is a pyridyl group, n is 0; $R_3$ is —$CH_3$; $R_1$ is —F, —Cl, —Br, or, —I; $Ar_2$ is a benzoimidazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzoimidazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzoimidazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, $Ar_2$ is a benzoimidazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, $Ar_2$ is a benzoimidazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, $Ar_2$ is a benzoimidazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, $Ar_2$ is a benzoimidazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzoimidazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzoimidazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzoimidazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Az_1$ is a pyridyl group, n is 0; $R_3$ is —$CH_3$; $R_1$ is —F, —Cl, —Br, or —I; $Ar_2$ is a benzoimidazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzoimidazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzoimidazolyl group; $R_8$ is -halo, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzoimidazolyl group; $R_8$ is -chloro, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzoimidazolyl group; $R_8$ is -bromo, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzoimidazolyl group; $R_8$ is -fluoro, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzoimidazolyl group; $R_8$ is -iodo, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzoimidazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzoimidazolyl group; $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzoimidazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzoimidazolyl group; $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzoimidazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzoimidazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzoimidazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzoimidazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzoimidazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzoimidazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment $Ar_1$ is a pyridyl group, n is 0; $R_3$ is —$CH_3$; $R_1$ is —F, —Cl, —Br, or —I; $Ar_2$ is a benzoimidazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzoimidazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzoimidazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is $R_1$ is —F, —Cl, —Br, or —I; $Ar_2$ is a benzoimidazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is $R_1$ is —F; $Ar_2$ is a benzoimidazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —H; $R_1$ is —F, —Cl, —Br, or, —I; $Ar_2$ is a benzoimidazolyl group; and $R_8$ and $R_9$ are —H.

In another embodiment, $Ar_1$ is a pyrimidinyl group, p is 0; $R_3$ is —H; $R_1$ is —F; $Ar_2$ is a benzoimidazolyl group; and $R_8$ and $R_9$ are —H.

In another embodiment, $Ar_1$ is a pyrimidinyl group, p is 0; $R_3$ is —H; $R_1$ is —F, —Cl, —Br, or —I; $Ar_2$ is a benzoimidazolyl group; $R_8$ is —H; and $R_9$ is -halo.

In another embodiment, $Ar_1$ is a pyrimidinyl group, p is 0; $R_3$ is —H; $R_1$ is —F, $Ar_2$ is a benzoimidazolyl group; $R_8$ is —H; and $R_9$ is -chloro.

In another embodiment, $Ar_1$ is a pyrimidinyl group, p is 0; $R_3$ is —H; $R_1$ is —F, $Ar_2$ is a benzoimidazolyl group; $R_8$ is —H; and $R_9$ is -bromo.

In another embodiment, $Ar_1$ is a pyrimidinyl group, p is 0; $R_3$ is —H; $R_1$ is —F, $Ar_2$ is a benzoimidazolyl group; $R_8$ is —H; and $R_9$ is -fluoro.

In another embodiment, $Ar_1$ is a pyrimidinyl group, p is 0; $R_3$ is —H; $R_1$ is —F, $Ar_2$ is a benzoimidazolyl group; $R_8$ is —H; and $R_9$ is -iodo.

In another embodiment, $Ar_1$ is a pyrimidinyl group, p is 0; $R_3$ is —H; $R_1$ is —F, —Cl, —Br, or —I; $Ar_2$ is a benzoimidazolyl group; $R_8$ is -halo; and $R_9$ is —H.

In another embodiment, $Ar_1$ is a pyrimidinyl group, p is 0; $R_3$ is —H; $R_1$ is —F, —Cl, —Br, or —I; $Ar_2$ is a benzoimidazolyl group; $R_8$ is -chloro; and $R_9$ is —H.

In another embodiment, $Ar_1$ is a pyrimidinyl group, p is 0; $R_3$ is —H; $R_1$ is —F, —Cl, —Br, or —I; $Ar_2$ is a benzoimidazolyl group; $R_8$ is -bromo; and $R_9$ is —H.

In another embodiment, $Ar_1$ is a pyrimidinyl group, p is 0; $R_3$ is —H; $R_1$ is —F, —Cl, —Br, or —I; $Ar_2$ is a benzoimidazolyl group; $R_8$ is -fluoro; and $R_9$ is —H.

In another embodiment, $Ar_1$ is a pyrimidinyl group, p is 0; $R_3$ is —H; $R_1$ is —F, —Cl, —Br, or —I; $Ar_2$ is a benzoimidazolyl group; $R_8$ is -iodo; and $R_9$ is —H.

In another embodiment, $Ar_1$ is a pyrimidinyl group, p is 0; $R_3$ is —H; $R_1$ is —F; $Ar_2$ is a benzoimidazolyl group; $R_8$ is -halo, and $R_9$ is —H.

In another embodiment, $Ar_1$ is a pyrimidinyl group, p is 0; $R_3$ is —H; $R_1$ is —F; $Ar_2$ is a benzoimidazolyl group; $R_8$ is -chloro, and $R_9$ is —H.

In another embodiment, $Ar_1$ is a pyrimidinyl group, p is 0; $R_3$ is —H; $R_1$ is —F; $Ar_2$ is a benzoimidazolyl group; $R_8$ is -bromo, and $R_9$ is —H.

In another embodiment, $Ar_1$ is a pyrimidinyl group, p is 0; $R_3$ is —H; $R_1$ is —F; $Ar_2$ is a benzoimidazolyl group; $R_8$ is -fluoro, and $R_9$ is —H.

In another embodiment, $Ar_1$ is a pyrimidinyl group, p is 0; $R_3$ is —H; $R_1$ is —F; $Ar_2$ is a benzoimidazolyl group; $R_8$ is -iodo, and $R_9$ is —H.

In another embodiment, $Ar_1$ is a pyrimidinyl group, p is 0; $R_3$ is —H; $R_1$ is —F, —Cl, —Br, or —I; $Ar_2$ is a benzoimidazolyl group; $R_8$ is —H; and $R_9$ is —$CH_3$.

In another embodiment, $Ar_1$ is a pyrimidinyl group, p is 0; $R_3$ is —H; $R_1$ is —F; $Ar_2$ is a benzoimidazolyl group; $R_8$ is —H, and $R_9$ is —$CH_3$.

In another embodiment, $Ar_1$ is a pyrimidinyl group, p is 0; $R_3$ is —H; $R_1$ is —F, —Cl, —Br, or —I; $Ar_2$ is a benzoimidazolyl group; $R_8$ is —$CH_3$; and $R_9$ is —H.

In another embodiment, $Ar_1$ is a pyrimidinyl group, p is 0; $R_3$ is —H; $R_1$ is —F; $Ar_2$ is a benzoimidazolyl group; $R_8$ is —$CH_3$, and $R_9$ is —H.

In another embodiment, $Ar_1$ is a pyrimidinyl group, p is 0; $R_3$ is —H; $R_1$ is —F, —Cl, —Br, or —I; $Ar_2$ is a benzoimidazolyl group; $R_8$ is —H; and $R_9$ is —$CF_3$.

In another embodiment, $Ar_1$ is a pyrimidinyl group, p is 0; $R_3$ is —H; $R_1$ is —F; $Ar_2$ is a benzoimidazolyl group; $R_8$ is —H; and $R_9$ is —$CF_3$.

In another embodiment, $Ar_1$ is a pyrimidinyl group, p is 0; $R_3$ is —H; $R_1$ is —F, —Cl, —Br, or —I; $Ar_2$ is a benzoimidazolyl group; $R_8$ is —$CF_3$; and $R_9$ is —H.

In another embodiment, $Ar_1$ is a pyrimidinyl group, p is 0; $R_3$ is —H; $R_1$ is —F; $Ar_2$ is a benzoimidazolyl group; $R_8$ is —$CF_3$; and $R_9$ is —H.

In another embodiment, $Ar_1$ is a pyrimidinyl group, p is 0; $R_3$ is —H; $R_1$ is —F, —Cl, —Br, or —I; $Ar_2$ is a benzoimidazolyl group; $R_8$ is —H; and $R_9$ is —$OCH_2CH_3$.

In another embodiment, $Ar_1$ is a pyrimidinyl group, p is 0; $R_3$ is —H; $R_1$ is —F; $Ar_2$ is a benzoimidazolyl group; $R_8$ is —H; and $R_9$ is —$OCH_2CH_3$.

In another embodiment $Ar_1$ is a pyrimidinyl group, p is 0; $R_3$ is —H; $R_1$ is —F, —Cl, —Br, or —I; $Ar_2$ is a benzoimidazolyl group; $R_8$ is —$OCH_2CH_3$; and $R_9$ is —H.

In another embodiment, $Ar_1$ $Ar_1$ is a pyrimidinyl group, p is 0; $R_3$ is —H; $R_1$ is —F; $Ar_2$ is a benzoimidazolyl group; $R_8$ is —$OCH_2CH_3$; and $R_9$ is —H.

In another embodiment, $Ar_1$ is a pyrimidinyl group, p is 0; $R_3$ is —H; $R_1$ is —F, —Cl, —Br, or —I; $Ar_2$ is a benzoimidazolyl group; $R_8$ is -tert-butyl; and $R_9$ is —H.

In another embodiment, $Ar_1$ is a pyrimidinyl group, p is 0; $R_3$ is —H; $R_1$ is —F; $Ar_2$ is a benzoimidazolyl group; $R_8$ is -tert-butyl; and $R_9$ is —H.

In another embodiment, $Ar_1$ is a pyrimidinyl group, p is 0; $R_3$ is —H; $R_1$ is $R_1$ is —F, —Cl, —Br, or —I; $Ar_2$ is a benzoimidazolyl group; $R_8$ is —H; and $R_9$ is -tert-butyl.

In another embodiment, $Ar_1$ is a pyrimidinyl group, p is 0; $R_3$ is —H; $R_1$ is $R_1$ is —F; $Ar_2$ is a benzoimidazolyl group; $R_8$ is —H; and $R_9$ is -tert-butyl.

In another embodiment, $Ar_1$ is a pyrimidinyl group, p is 0; $R_3$ is —$CH_3$; $R_1$ is —F, —Cl, —Br, or, —I; $Ar_2$ is a benzoimidazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, $Ar_2$ is a benzoimidazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzoimidazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, $Ar_2$ is a benzoimidazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, $Ar_2$ is a benzoimidazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, $Ar_2$ is a benzoimidazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, $Ar_2$ is a benzoimidazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzoimidazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzoimidazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzoimidazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzoimidazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzoimidazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzoimidazolyl group; $R_8$ is -halo, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzoimidazolyl group; $R_8$ is -chloro, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzoimidazolyl group; $R_8$ is -bromo, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzoimidazolyl group; $R_8$ is -fluoro, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzoimidazolyl group; $R_8$ is -iodo, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzoimidazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzoimidazolyl group; $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzoimidazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzoimidazolyl group; $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzoimidazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzoimidazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzoimidazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzoimidazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzoimidazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzoimidazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment $Ar_1$ is a pyrimidinyl group, p is 0; $R_3$ is —$CH_3$; $R_1$ is —F, —Cl, —Br, or —I; $Ar_2$ is a benzoimidazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzoimidazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzoimidazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is $R_1$ is —F, —Cl, —Br, or —I; $Ar_2$ is a benzoimidazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is $R_1$ is —F; $Ar_2$ is a benzoimidazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —H; $R_1$ is —F, —Cl, —Br, or, —I; $Ar_2$ is a benzooxazolyl group; and $R_8$ and $R_9$ are —H.

In another embodiment, $Ar_1$ is a pyridyl group, n is 0; $R_3$ is —H; $R_1$ is —F; $Ar_2$ is a benzooxazolyl group, and $R_8$ and $R_9$ are —H.

In another embodiment, $Ar_1$ is a pyridyl group, n is 0; $R_3$ is —H; $R_1$ is —F, —Cl, —Br, or —I; $Ar_2$ is a benzooxazolyl group; $R_8$ is —H; and $R_9$ is -halo.

In another embodiment, $Ar_1$ is a pyridyl group, n is 0; $R_3$ is —H; $R_1$ is —F, $Ar_2$ is a benzooxazolyl group; $R_8$ is —H; and $R_9$ is -chloro.

In another embodiment, $Ar_1$ is a pyridyl group, n is 0; $R_3$ is —H; $R_1$ is —F, $Ar_2$ is a benzooxazolyl group; $R_8$ is —H; and $R_9$ is -bromo.

In another embodiment, $Ar_1$ is a pyridyl group, n is 0; $R_3$ is —H; $R_1$ is —F, $Ar_2$ is a benzooxazolyl group; $R_8$ is —H; and $R_9$ is -fluoro.

In another embodiment, $Ar_1$ is a pyridyl group, n is 0; $R_3$ is —H; $R_1$ is —F, $Ar_2$ is a benzooxazolyl group; $R_8$ is —H; and $R_9$ is -iodo.

In another embodiment, $Ar_1$ is a pyridyl group, n is 0; $R_3$ is —H; $R_1$ is —F, —Cl, —Br, or —I; $Ar_2$ is a benzooxazolyl group; $R_8$ is -halo; and $R_9$ is —H.

In another embodiment, $Ar_1$ is a pyridyl group, n is 0; $R_3$ is —H; $R_1$ is —F, —Cl, —Br, or —I; $Ar_2$ is a benzooxazolyl group; $R_8$ is -chloro; and $R_9$ is —H.

In another embodiment, $Ar_1$ is a pyridyl group, n is 0; $R_3$ is —H; $R_1$ is —F, —Cl, —Br, or —I; $Ar_2$ is a benzooxazolyl group; $R_8$ is -bromo; and $R_9$ is —H.

In another embodiment, $Ar_1$ is a pyridyl group, n is 0; $R_3$ is —H; $R_1$ is —F, —Cl, —Br, or —I; $Ar_2$ is a benzooxazolyl group; $R_8$ is -fluoro; and $R_9$ is —H.

In another embodiment, $Ar_1$ is a pyridyl group, n is 0; $R_3$ is —H; $R_1$ is —F, —Cl, —Br, or —I; $Ar_2$ is a benzooxazolyl group; $R_8$ is -iodo; and $R_9$ is —H.

In another embodiment, $Ar_1$ is a pyridyl group, n is 0; $R_3$ is —H; $R_1$ is —F; $Ar_2$ is a benzooxazolyl group; $R_8$ is -halo, and $R_9$ is —H.

In another embodiment, $Ar_1$ is a pyridyl group, n is 0; $R_3$ is —H; $R_1$ is —F; $Ar_2$ is a benzooxazolyl group; $R_8$ is -chloro, and $R_9$ is —H.

In another embodiment, $Ar_1$ is a pyridyl group, n is 0; $R_3$ is —H; $R_1$ is —F; $Ar_2$ is a benzooxazolyl group; $R_8$ is -bromo, and $R_9$ is —H.

In another embodiment, $Ar_1$ is a pyridyl group, n is 0; $R_3$ is —H; $R_1$ is —F; $Ar_2$ is a benzooxazolyl group; $R_8$ is -fluoro, and $R_9$ is —H.

In another embodiment, $Ar_1$ is a pyridyl group, n is 0; $R_3$ is —H; $R_1$ is —F; $Ar_2$ is a benzooxazolyl group; $R_8$ is -iodo, and $R_9$ is —H.

In another embodiment, $Ar_1$ is a pyridyl group, n is 0; $R_3$ is —H; $R_1$ is —F, —Cl, —Br, or —I; $Ar_2$ is a benzooxazolyl group; $R_8$ is —H; and $R_9$ is —$CH_3$.

In another embodiment, $Ar_1$ is a pyridyl group, n is 0; $R_3$ is —H; $R_1$ is —F; $Ar_2$ is a benzooxazolyl group; $R_8$ is —H, and $R_9$ is —$CH_3$.

In another embodiment, $Ar_1$ is a pyridyl group, n is 0; $R_3$ is —H; $R_1$ is —F, —Cl, —Br, or —I; $Ar_2$ is a benzooxazolyl group; $R_8$ is —$CH_3$; and $R_9$ is —H.

In another embodiment, $Ar_1$ is a pyridyl group, n is 0; $R_3$ is —H; $R_1$ is —F; $Ar_2$ is a benzooxazolyl group; $R_8$ is —$CH_3$, and $R_9$ is —H.

In another embodiment, $Ar_1$ is a pyridyl group, n is 0; $R_3$ is —H; $R_1$ is —F, —Cl, —Br, or —I; $Ar_2$ is a benzooxazolyl group; $R_8$ is —H; and $R_9$ is —$CF_3$.

In another embodiment, $Ar_1$ is a pyridyl group, n is 0; $R_3$ is —H; $R_1$ is —F. $Ar_2$ is a benzooxazolyl group; $R_8$ is —H; and $R_9$ is —$CF_3$.

In another embodiment, $Ar_1$ is a pyridyl group, n is 0; $R_3$ is —H; $R_1$ is —F, —Cl, —Br, or —I; $Ar_2$ is a benzooxazolyl group; $R_8$ is —$CF_3$; and $R_9$ is —H.

In another embodiment, $Ar_1$ is a pyridyl group, n is 0; $R_3$ is —H; $R_1$ is $Ar_2$ is a benzooxazolyl group; $R_8$ is —$CF_3$; and $R_9$ is —H.

In another embodiment, $Ar_1$ is a pyridyl group, n is 0; $R_3$ is —H; $R_1$ is —F, —Cl, —Br, or —I; $Ar_2$ is a benzooxazolyl group; $R_8$ is —H; and $R_9$ is —$OCH_2CH_3$.

In another embodiment, $Ar_1$ is a pyridyl group, n is 0; $R_3$ is —H; $R_1$ is —F; $Ar_2$ is a benzooxazolyl group; $R_8$ is —H; and $R_9$ is —$OCH_2CH_3$.

In another embodiment $Ar_1$ is a pyridyl group, n is 0; $R_3$ is —H; $R_1$ is —F, —Cl, —Br, or —I; $Ar_2$ is a benzooxazolyl group; $R_8$ is —$OCH_2CH_3$; and $R_9$ is —H.

In another embodiment, $Ar_1$ $Ar_1$ is a pyridyl group, n is 0; $R_3$ is —H; $R_1$ is —F; $Ar_2$ is a benzooxazolyl group; $R_8$ is —$OCH_2CH_3$; and $R_9$ is —H.

In another embodiment, $Ar_1$ is a pyridyl group, n is 0; $R_3$ is —H; $R_1$ is —F, —Cl, —Br, or —I; $Ar_2$ is a benzooxazolyl group; $R_8$ is -tert-butyl; and $R_9$ is —H.

In another embodiment, $Ar_1$ is a pyridyl group, n is 0; $R_3$ is —H; $R_1$ is —F; $Ar_2$ is a benzooxazolyl group; $R_8$ is -tert-butyl; and $R_9$ is —H.

In another embodiment, $Ar_1$ is a pyridyl group, n is 0; $R_3$ is —H; $R_1$ is $R_1$ is —F, —Cl, —Br, or —I; $Ar_2$ is a benzooxazolyl group; $R_8$ is —H; and $R_9$ is -tert-butyl.

In another embodiment, $Ar_1$ is a pyridyl group, n is 0; $R_3$ is —H; $R_1$ is $R_1$ is —F; $Ar_2$ is a benzooxazolyl group; $R_8$ is —H; and $R_9$ is -tert-butyl.

In another embodiment, $Ar_1$ is a pyridyl group, n is 0; $R_3$ is —$CH_3$; $R_1$ is —F, —Cl, —Br, or, —I; $Ar_2$ is a benzooxazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzooxazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzooxazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, $Ar_2$ is a benzooxazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, $Ar_2$ is a benzooxazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, $Ar_2$ is a benzooxazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, $Ar_2$ is a benzooxazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzooxazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzooxazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzooxazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzooxazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzooxazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzooxazolyl group; $R_8$ is -halo, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzooxazolyl group; $R_8$ is -chloro, and $R_9$ is —H. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzooxazolyl group; $R_8$ is -bromo, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzooxazolyl group; $R_8$ is -fluoro, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzooxazolyl group; $R_8$ is -iodo, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzooxazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzooxazolyl group; $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzooxazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzooxazolyl group; $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzooxazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzooxazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzooxazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzooxazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzooxazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzooxazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment $Ar_1$ is a pyridyl group, n is 0; $R_3$ is —$CH_3$; $R_1$ is —F, —Cl, —Br, or —I; $Ar_2$ is a benzooxazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $Ar_2$ is a benzooxazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F, —Cl, —Br, or —I; $Ar_2$ is a benzooxazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is —F; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is $R_1$ is —F, —Cl, —Br, or —I; $Ar_2$ is a benzooxazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_3$ is —$CH_3$; $R_1$ is $R_1$ is —F; $Ar_2$ is a benzooxazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —H; $R_1$ is —F, —Cl, —Br, or, —I; $Ar_2$ is a benzooxazolyl group; and $R_8$ and $R_9$ are —H.

In another embodiment, $Ar_1$ is a pyrimidinyl group, p is 0; $R_3$ is —H; $R_1$ is —F; $Ar_2$ is a benzooxazolyl group; and $R_8$ and $R_9$ are —H.

In another embodiment, $Ar_1$ is a pyrimidinyl group, p is 0; $R_3$ is —H; $R_1$ is —F, —Cl, —Br, or —I; $Ar_2$ is a benzooxazolyl group; $R_8$ is —H; and $R_9$ is -halo.

In another embodiment, $Ar_1$ is a pyrimidinyl group, p is 0; $R_3$ is —H; $R_1$ is —F, $Ar_2$ is a benzooxazolyl group; $R_8$ is —H; and $R_9$ is -chloro.

In another embodiment, $Ar_1$ is a pyrimidinyl group, p is 0; $R_3$ is —H; $R_1$ is —F; $Ar_2$ is a benzooxazolyl group; $R_8$ is —H; and $R_9$ is -bromo.

In another embodiment, $Ar_1$ is a pyrimidinyl group, p is 0; $R_3$ is —H; $R_1$ is —F, $Ar_2$ is a benzooxazolyl group; $R_8$ is —H; and $R_9$ is -fluoro.

In another embodiment, $Ar_1$ is a pyrimidinyl group, p is 0; $R_3$ is —H; $R_1$ is —F, $Ar_2$ is a benzooxazolyl group; $R_8$ is —H; and $R_9$ is -iodo.

In another embodiment, $Ar_1$ is a pyrimidinyl group, p is 0; $R_3$ is —H; $R_1$ is —F, —Cl, —Br, or —I; $Ar_2$ is a benzooxazolyl group; $R_8$ is -halo; and $R_9$ is —H.

In another embodiment, $Ar_1$ is a pyrimidinyl group, p is 0; $R_3$ is —H; $R_1$ is —F, —Cl, —Br, or —I; $Ar_2$ is a benzooxazolyl group; $R_8$ is -chloro; and $R_9$ is —H.

In another embodiment, $Ar_1$ is a pyrimidinyl group, p is 0; $R_3$ is —H; $R_1$ is —F, —Cl, —Br, or —I; $Ar_2$ is a benzooxazolyl group; $R_8$ is -bromo; and $R_9$ is —H.

In another embodiment, $Ar_1$ is a pyrimidinyl group, p is 0; $R_3$ is —H; $R_1$ is —F, —Cl, —Br, or —I; $Ar_2$ is a benzooxazolyl group; $R_8$ is -fluoro; and $R_9$ is —H.

In another embodiment, $Ar_1$ is a pyrimidinyl group, p is 0; $R_3$ is —H; $R_1$ is —F, —Cl, —Br, or —I; $Ar_2$ is a benzooxazolyl group; $R_8$ is -iodo; and $R_9$ is —H.

In another embodiment, $Ar_1$ is a pyrimidinyl group, p is 0; $R_3$ is —H; $R_1$ is —F; $Ar_2$ is a benzooxazolyl group; $R_8$ is -halo, and $R_9$ is —H.

In another embodiment, $Ar_1$ is a pyrimidinyl group, p is 0; $R_3$ is —H; $R_1$ is —F; $Ar_2$ is a benzooxazolyl group; $R_8$ is -chloro, and $R_9$ is —H.

In another embodiment, $Ar_1$ is a pyrimidinyl group, p is 0; $R_3$ is —H; $R_1$ is —F; $Ar_2$ is a benzooxazolyl group; $R_8$ is -bromo, and $R_9$ is —H.

In another embodiment, $Ar_1$ is a pyrimidinyl group, p is 0; $R_3$ is —H; $R_1$ is —F; $Ar_2$ is a benzooxazolyl group; $R_8$ is -fluoro, and $R_9$ is —H.

In another embodiment, $Ar_1$ is a pyrimidinyl group, p is 0; $R_3$ is —H; $R_1$ is —F; $Ar_2$ is a benzooxazolyl group; $R_8$ is -iodo, and $R_9$ is —H.

In another embodiment, $Ar_1$ is a pyrimidinyl group, p is 0; $R_3$ is —H; $R_1$ is —F, —Cl, —Br, or —I; $Ar_2$ is a benzooxazolyl group; $R_8$ is —H; and $R_9$ is —$CH_3$.

In another embodiment, $Ar_1$ is a pyrimidinyl group, p is 0; $R_3$ is —H; $R_1$ is —F; $Ar_2$ is a benzooxazolyl group; $R_8$ is —H, and $R_9$ is —$CH_3$.

In another embodiment, $Ar_1$ is a pyrimidinyl group, p is 0; $R_3$ is —H; $R_1$ is —F, —Cl, —Br, or —I; $Ar_2$ is a benzooxazolyl group; $R_8$ is —$CH_3$; and $R_9$ is —H.

In another embodiment, $Ar_1$ is a pyrimidinyl group, p is 0; $R_3$ is —H; $R_1$ is —F; $Ar_2$ is a benzooxazolyl group; $R_8$ is —$CH_3$, and $R_9$ is —H.

In another embodiment, $Ar_1$ is a pyrimidinyl group, p is 0; $R_3$ is —H; $R_1$ is —F, —Cl, —Br, or —I; $Ar_2$ is a benzooxazolyl group; $R_8$ is —H; and $R_9$ is —$CF_3$.

In another embodiment, $Ar_1$ is a pyrimidinyl group, p is 0; $R_3$ is —H; $R_1$ is —F; $Ar_2$ is a benzooxazolyl group; $R_8$ is —H; and $R_9$ is —$CF_3$.

In another embodiment, $Ar_1$ is a pyrimidinyl group, p is 0; $R_3$ is —H; $R_1$ is —F, —Cl, —Br, or —I; $Ar_2$ is a benzooxazolyl group; $R_8$ is —$CF_3$; and $R_9$ is —H.

In another embodiment, $Ar_1$ is a pyrimidinyl group, p is 0; $R_3$ is —H; $R_1$ is —F; $Ar_2$ is a benzooxazolyl group; $R_8$ is —$CF_3$; and $R_9$ is —H.

In another embodiment, $Ar_1$ is a pyrimidinyl group, p is 0; $R_3$ is —H; $R_1$ is —F, —Cl, —Br, or —I; $Ar_2$ is a benzooxazolyl group; $R_8$ is —H; and $R_9$ is —$OCH_2CH_3$.

In another embodiment, $Ar_1$ is a pyrimidinyl group, p is 0; $R_3$ is —H; $R_1$ is —F; $Ar_2$ is a benzooxazolyl group; $R_8$ is —H; and $R_9$ is —$OCH_2CH_3$.

In another embodiment $Ar_1$ is a pyrimidinyl group, p is 0; $R_3$ is —H; $R_1$ is —F, —Cl, —Br, or —I; $Ar_2$ is a benzooxazolyl group; $R_8$ is —OCH$_2$CH$_3$; and $R_9$ is —H.

In another embodiment, $Ar_1$ $Ar_1$ is a pyrimidinyl group, p is 0; $R_3$ is —H; $R_1$ is —F; $Ar_2$ is a benzooxazolyl group; $R_8$ is —OCH$_2$CH$_3$; and $R_9$ is —H.

In another embodiment, $Ar_1$ is a pyrimidinyl group, p is 0; $R_3$ is —H; $R_1$ is —F, —Cl, —Br, or —I; $Ar_2$ is a benzooxazolyl group; $R_8$ is -tert-butyl; and $R_9$ is —H.

In another embodiment, $Ar_1$ is a pyrimidinyl group, p is 0; $R_3$ is —H; $R_1$ is —F; $Ar_2$ is a benzooxazolyl group; $R_8$ is -tert-butyl; and $R_9$ is —H.

In another embodiment, $Ar_1$ is a pyrimidinyl group, p is 0; $R_3$ is —H; $R_1$ is $R_1$ is —F, —Cl, —Br, or —I; $Ar_2$ is a benzooxazolyl group; $R_8$ is —H; and $R_9$ is -tert-butyl.

In another embodiment, $Ar_1$ is a pyrimidinyl group, p is 0; $R_3$ is —H; $R_1$ is $R_1$ is —F; $Ar_2$ is a benzooxazolyl group; $R_8$ is —H; and $R_9$ is -tert-butyl.

In another embodiment, $Ar_1$ is a pyrimidinyl group, p is 0; $R_3$ is —CH$_3$; $R_1$ is —F, —Cl, —Br, or, —I; $Ar_2$ is a benzooxazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —CH$_3$; $R_1$ is —F; $Ar_2$ is a benzooxazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —CH$_3$; $R_1$ is —F, —Cl, —Br, or —I; $Ar_2$ is a benzooxazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —CH$_3$; $R_1$ is —F, —Cl, —Br, or —I; $Ar_2$ is a benzooxazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —CH$_3$; $R_1$ is —F, —Cl, —Br, or —I; $Ar_2$ is a benzooxazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —CH$_3$; $R_1$ is —F, —Cl, —Br, or —I; $Ar_2$ is a benzooxazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —CH$_3$; $R_1$ is —F, —Cl, —Br, or —I; $Ar_2$ is a benzooxazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —CH$_3$; $R_1$ is —F, $Ar_2$ is a benzooxazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —CH$_3$; $R_1$ is —F, $Ar_2$ is a benzooxazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —CH$_3$; $R_1$ is —F, $Ar_2$ is a benzooxazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —CH$_3$; $R_1$ is —F, $Ar_2$ is a benzooxazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —CH$_3$; $R_1$ is —F, —Cl, —Br, or —I; $Ar_2$ is a benzooxazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —CH$_3$; $R_1$ is —F, —Cl, —Br, or —I; $Ar_2$ is a benzooxazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —CH$_3$; $R_1$ is —F, —Cl, —Br, or —I; $Ar_2$ is a benzooxazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —CH$_3$; $R_1$ is —F, —Cl, —Br, or —I; $Ar_2$ is a benzooxazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —CH$_3$; $R_1$ is —F, —Cl, —Br, or —I; $Ar_2$ is a benzooxazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —CH$_3$; $R_1$ is —F; $Ar_2$ is a benzooxazolyl group; $R_8$ is -halo, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —CH$_3$; $R_1$ is —F; $Ar_2$ is a benzooxazolyl group; $R_8$ is -chloro, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —CH$_3$; $R_1$ is —F; $Ar_2$ is a benzooxazolyl group; $R_8$ is -bromo, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzooxazolyl group; $R_8$ is -fluoro, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzooxazolyl group; $R_8$ is -iodo, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzooxazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzooxazolyl group; $R_8$ is —H, and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzooxazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzooxazolyl group; $R_8$ is —$CH_3$, and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzooxazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzooxazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzooxazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzooxazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzooxazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzooxazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment $Ar_1$ is a pyrimidinyl group, p is 0; $R_3$ is —$CH_3$; $R_1$ is —F, —Cl, —Br, or —I; $Ar_2$ is a benzooxazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $Ar_2$ is a benzooxazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F, —Cl, —Br, or —I; $Ar_2$ is a benzooxazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is —F; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is $R_1$ is —F, —Cl, —Br, or —I; $Ar_2$ is a benzooxazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_3$ is —$CH_3$; $R_1$ is $R_1$ is —F; $Ar_2$ is a benzooxazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

4.8 The Compounds of Formula (IVb)

The present invention also encompasses compounds of formula (IVb):

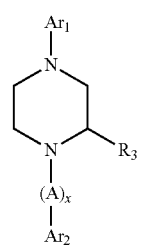

(IVb)

and pharmaceutically acceptable salts thereof, where $Ar_1$, $Ar_2$, A, $R_3$ and x are defined above for the Benzoazolylpiperazine Compounds of formula (IVb).

In one embodiment, $Ar_1$ is a pyridyl group.

In another embodiment, $Ar_1$ is a pyrimidinyl group.

In another embodiment, n or p is 0.

In another embodiment, n or p is 1.

In another embodiment, x is 0.

In another embodiment, x is 1.

In another embodiment, $R_1$ is —F.

In another embodiment, $R_1$ is —Cl.

In another embodiment, $R_1$ is —Br.

In another embodiment, $R_1$ is —I.

In another embodiment, $R_1$ is —$(C_1$-$C_6)$alkyl.

In another embodiment, $R_1$ is —$CH_3$.

In another embodiment, $R_1$ is —$NO_2$.

In another embodiment, $R_1$ is —CN.

In another embodiment, $R_1$ is —OH.

In another embodiment, $R_1$ is —$OCH_3$.

In another embodiment, $R_1$ is —$NH_2$.

In another embodiment, $R_1$ is —$C(halo)_3$.

In another embodiment, $R_1$ is —$CH(halo)_2$.

In another embodiment, $R_1$ is —$CH_2(halo)$.

In another embodiment, n and p are 1 and $R_2$ is -halo, —CN, —OH, —$O(C_1$-$C_6)$alkyl, —$NO_2$, or —$NH_2$.

In another embodiment, n and p are 1 and $R_2$ is —$(C_1$-$C_{10})$alkyl, —$(C_2$-$C_{10})$alkenyl, —$(C_2$-$C_{10})$alkynyl, —$(C_3$-$C_{10})$cycloalkyl, —$(C_8$-$C_{14})$bicycloalkyl, —$(C_8$-$C_{14})$tricycloalkyl, —$(C_5$-$C_{10})$cycloalkenyl, —$(C_8$-$C_{14})$bicycloalkenyl, -$(C_8$-$C_{14})$tricycloalkenyl, -(3- to 7-membered)heterocycle, or -(7- to 10-membered)bicycloheterocycle, each of which is unsubstituted or substituted with one or more $R_5$ groups.

In another embodiment, n and p are 1 and $R_2$ is -phenyl, -naphthyl, —$(C_{14})$aryl, or -(5- to 10-membered)heteroaryl, each of which is unsubstituted or substituted with one or more $R_6$ groups;

In another embodiment, x is 1 and A is —$C(O)N(R_4)$—.

In another embodiment, x is 1, A is —$C(O)N(R_4)$—, and $R_4$ is —H.

In another embodiment, x is 1, A is —$C(O)N(R_4)$—, and $R_4$ is —$CH_3$.

In another embodiment, x is 1 and A is —$C(S)N(R_4)$—.

In another embodiment, x is 1, A is —$C(S)N(R_4)$—, and $R_4$ is —H.

In another embodiment, x is 1, A is —$C(S)N(R_4)$—, and $R_4$ is —$CH_3$.

In another embodiment, $Ar_2$ is a benzothiazolyl group.

In another embodiment, $Ar_2$ is a benzoimidazolyl group.

In another embodiment, $Ar_2$ is a benzooxazolyl group.

In another embodiment, $R_8$ and $R_9$ are each independently —H, halo, —$(C_1$-$C_6)$alkyl, —$O(C_1$-$C_6)$alkyl, —$C(halo)_3$, —$CH(halo)_2$, or —$CH_2(halo)$.

In another embodiment, at least one of $R_8$ or $R_9$ is —H.

In another embodiment, $Ar_1$ is a pyridyl group, n is 0; $R_1$ is —F, —Cl, —Br, or —I; $R_4$ is —H; $Ar_2$ is a benzothiazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $R_4$ is —H; $Ar_2$ is a benzothiazolyl group and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzothiazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzothiazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzothiazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzothiazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzothiazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzothiazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzothiazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzothiazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzothiazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzothiazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzothiazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzothiazolyl group; $R_8$ is -chloro; and $R_9$ is —H.

In another embodiment, $Ar_1$ is a pyridyl group, n is 0; $R_1$ is —F, —Cl, —Br, or —I; $Ar_2$ is a benzothiazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzothiazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzothiazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzothiazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzothiazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzothiazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzothiazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzothiazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, Br, or —I; $Ar_2$ is a benzothiazolyl group; $R_8$ is —H; and $R_9$ is —CH$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzothiazolyl group; $R_8$ is —H; and $R_9$ is —CH$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, Br, or —I; $Ar_2$ is a benzothiazolyl group; $R_8$ is —CH$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, Ar1 is a pyridyl group, n is 0; $R_1$ is —F; $Ar_2$ is a benzothiazolyl group; $R_8$ is —CH$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, Br, or —I; $Ar_2$ is a benzothiazolyl group; $R_8$ is —H; and $R_9$ is —CF$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzothiazolyl group; $R_8$ is —H; and $R_9$ is —CF$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, Br, or —I; $Ar_2$ is a benzothiazolyl group; $R_8$ is —CF$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzothiazolyl group; $R_8$ is —CF$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, Br, or —I; $Ar_2$ is a benzothiazolyl group; $R_8$ is —H; and $R_9$ is —OCH$_2$CH$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzothiazolyl group; $R_8$ is —H; and $R_9$ is —OCH$_2$CH$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, Br, or —I; $Ar_2$ is a benzothiazolyl group; $R_8$ is —OCH$_2$CH$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzothiazolyl group; $R_8$ is —OCH$_2$CH$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —CH$_3$; $Ar_2$ is a benzothiazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —CH$_3$; $Ar_2$ is a benzothiazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —CH$_3$; $Ar_2$ is a benzothiazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzothiazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzothiazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzothiazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzothiazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzothiazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzothiazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzothiazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzothiazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzothiazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzothiazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzothiazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzothiazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzothiazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzothiazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzothiazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzothiazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzothiazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzothiazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzothiazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzothiazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzothiazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzothiazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzothiazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzothiazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzothiazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzothiazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzothiazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzothiazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzothiazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzothiazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzothiazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzothiazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzothiazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzothiazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzothiazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzothiazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzothiazolyl group; $R_8$ is —$CH_3$; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $R_4$ is —H; $Ar_2$ is a benzothiazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $R_4$ is —H; $Ar_2$ is a benzothiazolyl group and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzothiazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzothiazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzothiazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzothiazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzothiazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —Cl; $Ar_2$ is a benzothiazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —Cl; $Ar_2$ is a benzothiazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —Cl; $Ar_2$ is a benzothiazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —Cl; $Ar_2$ is a benzothiazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —Cl; $Ar_2$ is a benzothiazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzothiazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzothiazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzothiazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzothiazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzothiazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzothiazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzothiazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzothiazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzothiazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzothiazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, Br, or —I; $Ar_2$ is a benzothiazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzothiazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, Br, or —I; $Ar_2$ is a benzothiazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, Ar1 is a pyrimidinyl group, p is 0; $R_1$ is —F; $Ar_2$ is a benzothiazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, Br, or —I; $Ar_2$ is a benzothiazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzothiazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, Br, or —I; $Ar_2$ is a benzothiazolyl group; $R_8$ is —$CF_3$; and $R_9$ is —H. In another embodiment, the carbon atom to which the $R_3$ group is attached has the R configura- In another embodiment, the carbon atom to which the $R_3$ group is attached has the S configuration.

In another embodiment, $Ar_1$ is a pyrimidinyl group, p is 0; $R_1$ is —F; $Ar_2$ is a benzothiazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, Br, or —I; $Ar_2$ is a benzothiazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzothiazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, Br, or —I; $Ar_2$ is a benzothiazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzothiazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzothiazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzothiazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzothiazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzothiazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzothiazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzothiazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzothiazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzothiazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzothiazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzothiazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzothiazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzothiazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzothiazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzothiazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzothiazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzothiazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzothiazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzothiazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzothiazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzothiazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzothiazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzothiazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzothiazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzothiazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzothiazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzothiazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzothiazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzothiazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzothiazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzothiazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzothiazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzothiazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzothiazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzothiazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzothiazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzothiazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzothiazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzothiazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzothiazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzothiazolyl group; $R_8$ is —$CH_3$; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $R_4$ is —H; $Ar_2$ is a benzoimidazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ $R_4$ is —H; $Ar_2$ is a benzoimidazolyl group and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzoimidazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzoimidazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzoimidazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzoimidazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzoimidazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —Cl; $Ar_2$ is a benzoimidazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —Cl; $Ar_2$ is a benzoimidazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —Cl; $Ar_2$ is a benzoimidazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —Cl; $Ar_2$ is a benzoimidazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —Cl; $Ar_2$ is a benzoimidazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzoimidazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzoimidazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzoimidazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzoimidazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzoimidazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzoimidazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzoimidazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzoimidazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzoimidazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzoimidazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, Br, or —I; $Ar_2$ is a benzoimidazolyl group; $R_8$ is —H; and $R_9$ is —CH$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzoimidazolyl group; $R_8$ is —H; and $R_9$ is —CH$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, Br, or —I; $Ar_2$ is a benzoimidazolyl group; $R_8$ is —CH$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, Ar1 is a pyridyl group, n is 0; $R_1$ is —F; $Ar_2$ is a benzoimidazolyl group; $R_8$ is —CH$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, Br, or —I; $Ar_2$ is a benzoimidazolyl group; $R_8$ is —H; and $R_9$ is —CF$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzoimidazolyl group; $R_8$ is —H; and $R_9$ is —CF$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, Br, or —I; $Ar_2$ is a benzoimidazolyl group; $R_8$ is —CF$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzoimidazolyl group; $R_8$ is —CF$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, Br, or —I; $Ar_2$ is a benzoimidazolyl group; $R_8$ is —H; and $R_9$ is —OCH$_2$CH$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzoimidazolyl group; $R_8$ is —H; and $R_9$ is —OCH$_2$CH$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, Br, or —I; $Ar_1$ is a benzoimidazolyl group; $R_8$ is —OCH$_2$CH$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzoimidazolyl group; $R_8$ is —OCH$_2$CH$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —CH$_3$; $Ar_2$ is a benzoimidazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —CH$_3$; $Ar_2$ is a benzoimidazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —CH$_3$; $Ar_2$ is a benzoimidazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —CH$_3$; $Ar_2$ is a benzoimidazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —CH$_3$; $Ar_2$ is a benzoimidazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —CH$_3$; $Ar_2$ is a benzoimidazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —CH$_3$; $Ar_2$ is a benzoimidazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —CH$_3$; $Ar_2$ is a benzoimidazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —CH$_3$; $Ar_2$ is a benzoimidazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzoimidazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzoimidazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzoimidazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzoimidazolyl group; $R_8$ is —H; and $H_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzoimidazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzoimidazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzoimidazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzoimidazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzoimidazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzoimidazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzoimidazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzoimidazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzoimidazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzoimidazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzoimidazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzoimidazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzoimidazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzoimidazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzoimidazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzoimidazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzoimidazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzoimidazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzoimidazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzoimidazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzoimidazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzoimidazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzoimidazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzoimidazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzoimidazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzoimidazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzoimidazolyl group; $R_8$ is —$CH_3$; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $R_4$ is —H; $Ar_2$ is a benzoimidazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $R_4$ is —H; $Ar_2$ is a benzoimidazolyl group and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzoimidazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzoimidazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzoimidazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzoimidazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzoimidazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —Cl; $Ar_2$ is a benzoimidazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —Cl; $Ar_2$ is a benzoimidazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —Cl; $Ar_2$ is a benzoimidazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —Cl; $Ar_2$ is a benzoimidazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —Cl; $Ar_2$ is a benzoimidazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzoimidazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzoimidazolyl group; $R_8$ is -chloro; and $R_9$ is —H.

In another embodiment, $Ar_1$ is a pyrimidinyl group, p is 0; $R_1$ is —F, —Cl, —Br, or —I; $Ar_2$ is a benzoimidazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzoimidazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzoimidazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzoimidazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzoimidazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzoimidazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzoimidazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzoimidazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, Br, or —I; $Ar_2$ is a benzoimidazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzoimidazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzoimidazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar1$ is a pyrimidinyl group, p is 0; $R_1$ is —F; $Ar_2$ is a benzoimidazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, Br, or —I; $Ar_2$ is a benzoimidazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzoimidazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, Br, or —I; $Ar_2$ is a benzoimidazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzoimidazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, Br, or —I; $Ar_2$ is a benzoimidazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzoimidazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, Br, or —I; $Ar_2$ is a benzoimidazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzoimidazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzoimidazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzoimidazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzoimidazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzoimidazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzoimidazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzoimidazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzoimidazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzoimidazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzoimidazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzoimidazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzoimidazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzoimidazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzoimidazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzoimidazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzoimidazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzoimidazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzoimidazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzoimidazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzoimidazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzoimidazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzoimidazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzoimidazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzoimidazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzoimidazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzoimidazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzoimidazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzoimidazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzoimidazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzoimidazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzoimidazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzoimidazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzoimidazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzoimidazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzoimidazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzoimidazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzoimidazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzoimidazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzoimidazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzoimidazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzoimidazolyl group; $R_8$ is —$CH_3$; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $R_4$ is —H; $Ar_2$ is a benzooxazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $R_4$ is —H; $Ar_2$ is a benzooxazolyl group and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzooxazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzooxazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzooxazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzooxazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzooxazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —Cl; $Ar_2$ is a benzooxazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —Cl; $Ar_2$ is a benzooxazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —Cl; $Ar_2$ is a benzooxazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —Cl; $Ar_2$ is a benzooxazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —Cl; $Ar_2$ is a benzooxazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzooxazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzooxazolyl group; $R_8$ is -chloro; and $R_9$ is —H.

In another embodiment, $Ar_1$ is a pyridyl group, n is 0; $R_1$ is —F, —Cl, —Br, or —I; $Ar_2$ is a benzooxazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzooxazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzooxazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzooxazolyl group; $R_8$ is -halo; and $R_9$ is —H.

In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzooxazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzooxazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzooxazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzooxazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, Br, or —I; $Ar_2$ is a benzooxazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzooxazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, Br, or —I; $Ar_2$ is a benzooxazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, Ar1 is a pyridyl group, n is 0; $R_1$ is —F; $Ar_2$ is a benzooxazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, Br, or —I; $Ar_2$ is a benzooxazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzooxazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, Br, or —I; $Ar_2$ is a benzooxazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzooxazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, Br, or —I; $Ar_2$ is a benzooxazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzooxazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, Br, or —I; $Ar_2$ is a benzooxazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzooxazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzooxazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzooxazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzooxazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzooxazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzooxazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzooxazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzooxazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzooxazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzooxazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzooxazolyl group; $R_8$ is -iodo; and $R_1$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzooxazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzooxazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzooxazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzooxazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzooxazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzooxazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzooxazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzooxazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzooxazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzooxazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzooxazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzooxazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzooxazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzooxazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzooxazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzooxazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzooxazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzooxazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzooxazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzooxazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzooxazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzooxazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CF_3$; $Ar_2$ is a benzooxazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzooxazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzooxazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F, —Cl, —Br, or —I; $Ar_2$ is a benzooxazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —F; $Ar_2$ is a benzooxazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzooxazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzooxazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group, n is 0; $R_1$ is —$CH_3$; $Ar_2$ is a benzooxazolyl group; $R_8$ is —$CH_3$; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $R_4$ is —H; $Ar_2$ is a benzooxazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $R_4$ is —H; $Ar_2$ is a benzooxazolyl group and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzooxazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzooxazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzooxazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzooxazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzooxazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —Cl; $Ar_2$ is a benzooxazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —Cl; $Ar_2$ is a benzooxazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —Cl; $Ar_2$ is a benzooxazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —Cl; $Ar_2$ is a benzooxazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —Cl; $Ar_2$ is a benzooxazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Br, or —I; $Ar_2$ is a benzooxazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzooxazolyl group; $R_8$ is -chloro; and $R_9$ is —H.

In another embodiment, $Ar_1$ is a pyrimidinyl group, p is 0; $R_1$ is —F, —Cl, —Br, or —I; $Ar_2$ is a benzooxazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzooxazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzooxazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzooxazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzooxazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzooxazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzooxazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzooxazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, Br, or —I; $Ar_2$ is a benzooxazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzooxazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, Br, or —I; $Ar_2$ is a benzooxazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, Ar1 is a pyrimidinyl group, p is 0; $R_1$ is —F; $Ar_2$ is a benzooxazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, Br, or —I; $Ar_2$ is a benzooxazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzooxazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, Br, or —I; $Ar_2$ is a benzooxazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzooxazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, Br, or —I; $Ar_2$ is a benzooxazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzooxazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, Br, or —I; $Ar_2$ is a benzooxazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzooxazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzooxazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzooxazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzooxazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzooxazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzooxazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzooxazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzooxazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzooxazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzooxazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzooxazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzooxazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzooxazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzooxazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzooxazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzooxazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzooxazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzooxazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzooxazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzooxazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzooxazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzooxazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzooxazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzooxazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzooxazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzooxazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzooxazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzooxazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzooxazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzooxazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzooxazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzooxazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzooxazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CF_3$; $Ar_2$ is a benzooxazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzooxazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzooxazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F, —Cl, —Br, or —I; $Ar_2$ is a benzooxazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —F; $Ar_2$ is a benzooxazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzooxazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl group, p is 0; $R_1$ is —$CH_3$; $Ar_2$ is a benzooxazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyrimidinyl, p is 0; $R_1$ is —$CH_3$; $Ar_2$ is a benzooxazolyl group; $R_8$ is —$CH_3$; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $R_4$ is —H; $Ar_2$ is a benzothiazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $R_4$ is —H; $Ar_2$ is a benzothiazolyl group and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzothiazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzothiazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzothiazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzothiazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzothiazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —Cl; $Ar_2$ is a benzothiazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —Cl; $Ar_2$ is a benzothiazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —Cl; $Ar_2$ is a benzothiazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —Cl; $Ar_2$ is a benzothiazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —Cl; $Ar_2$ is a benzothiazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzothiazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzothiazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzothiazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzothiazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzothiazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzothiazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzothiazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzothiazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzothiazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzothiazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, Br, or —I; $Ar_2$ is a benzothiazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzothiazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, Br, or —I; $Ar_2$ is a benzothiazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, Ar1 is a pyridyl group and n is 0; $R_1$ is —F; $Ar_2$ is a benzothiazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, Br, or —I; $Ar_2$ is a benzothiazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzothiazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, Br, or —I; $Ar_2$ is a benzothiazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzothiazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, Br, or —I; $Ar_2$ is a benzothiazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzothiazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, Br, or —I; $Ar_2$ is a benzothiazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzothiazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzothiazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzothiazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzothiazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzothiazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzothiazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzothiazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzothiazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzothiazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzothiazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzothiazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzothiazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzothiazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzothiazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzothiazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzothiazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzothiazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzothiazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzothiazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzothiazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzothiazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzothiazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzothiazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzothiazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzothiazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzothiazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzothiazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzothiazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzothiazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzothiazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzothiazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzothiazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzothiazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzothiazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzothiazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzothiazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzothiazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzothiazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzothiazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzothiazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzothiazolyl group; $R_8$ is —$CH_3$; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $R_4$ is —H; $Ar_2$ is a benzothiazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $R_4$ is —H; $Ar_2$ is a benzothiazolyl group and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzothiazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzothiazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzothiazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzothiazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzothiazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —Cl; $Ar_2$ is a benzothiazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —Cl; $Ar_2$ is a benzothiazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —Cl; $Ar_2$ is a benzothiazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —Cl; $Ar_2$ is a benzothiazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —Cl; $Ar_2$ is a benzothiazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzothiazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzothiazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzothiazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzothiazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzothiazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzothiazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzothiazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzothiazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzothiazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzothiazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, Br, or —I; $Ar_2$ is a benzothiazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzothiazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, Br, or —I; $Ar_2$ is a benzothiazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, Ar1 is a pyriminidyl group and p is 0; $R_1$ is —F; $Ar_2$ is a benzothiazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, Br, or —I; $Ar_2$ is a benzothiazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzothiazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, Br, or —I; $Ar_2$ is a benzothiazolyl group; $R_8$ is —CF$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzothiazolyl group; $R_8$ is —CF$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, Br, or —I; $Ar_2$ is a benzothiazolyl group; $R_8$ is —H; and $R_9$ is —OCH$_2$CH$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzothiazolyl group; $R_8$ is —H; and $R_9$ is —OCH$_2$CH$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, Br, or —I; $Ar_2$ is a benzothiazolyl group; $R_8$ is —OCH$_2$CH$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzothiazolyl group; $R_8$ is —OCH$_2$CH$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —CH$_3$; $Ar_2$ is a benzothiazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —CH$_3$; $Ar_2$ is a benzothiazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —CH$_3$; $Ar_2$ is a benzothiazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —CH$_3$; $Ar_2$ is a benzothiazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —CH$_3$; $Ar_2$ is a benzothiazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —CH$_3$; $Ar_2$ is a benzothiazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —CH$_3$; $Ar_2$ is a benzothiazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —CH$_3$; $Ar_2$ is a benzothiazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —CH$_3$; $Ar_2$ is a benzothiazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —CH$_3$; $Ar_2$ is a benzothiazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —CH$_3$; $Ar_2$ is a benzothiazolyl group; $R_8$ is —H; and $R_9$ is —CH$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —CH$_3$; $Ar_2$ is a benzothiazolyl group; $R_8$ is —CH$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —CH$_3$; $Ar_2$ is a benzothiazolyl group; $R_8$ is —H; and $R_9$ is —CF$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —CH$_3$; $Ar_2$ is a benzothiazolyl group; $R_8$ is —CF$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —CH$_3$; $Ar_2$ is a benzothiazolyl group; $R_8$ is —H; and $R_9$ is —OCH$_2$CH$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —CH$_3$; $Ar_2$ is a benzothiazolyl group; $R_8$ is —OCH$_2$CH$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzothiazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzothiazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzothiazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzothiazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzothiazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzothiazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzothiazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzothiazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzothiazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzothiazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzothiazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzothiazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzothiazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzothiazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzothiazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzothiazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzothiazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzothiazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzothiazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzothiazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzothiazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzothiazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzothiazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzothiazolyl group; $R_8$ is —$CH_3$; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $R_4$ is —H; $Ar_2$ is a benzoimidazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is $R_4$ is —H; $Ar_2$ is a benzoimidazolyl group and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzoimidazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzoimidazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzoimidazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzoimidazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzoimidazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —Cl; $Ar_2$ is a benzoimidazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —Cl; $Ar_2$ is a benzoimidazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —Cl; $Ar_2$ is a benzoimidazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —Cl; $Ar_2$ is a benzoimidazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —Cl; $Ar_2$ is a benzoimidazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzoimidazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzoimidazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzoimidazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzoimidazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzoimidazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzoimidazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzoimidazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzoimidazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzoimidazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzoimidazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, Br, or —I; $Ar_2$ is a benzoimidazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzoimidazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, Br, or —I; $Ar_2$ is a benzoimidazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, Ar1 is a pyridyl group and n is 0; $R_1$ is —F; $Ar_2$ is a benzoimidazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, Br, or —I; $Ar_2$ is a benzoimidazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzoimidazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, Br, or —I; $Ar_2$ is a benzoimidazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzoimidazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, Br, or —I; $Ar_2$ is a benzoimidazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzoimidazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, Br, or —I; $Ar_2$ is a benzoimidazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzoimidazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzoimidazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzoimidazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzoimidazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzoimidazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzoimidazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzoimidazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzoimidazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzoimidazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzoimidazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzoimidazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzoimidazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzoimidazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzoimidazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzoimidazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzoimidazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzoimidazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzoimidazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzoimidazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzoimidazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzoimidazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzoimidazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzoimidazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzoimidazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzoimidazolyl group; $R_s$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzoimidazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzoimidazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzoimidazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzoimidazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzoimidazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzoimidazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzoimidazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzoimidazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzoimidazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzoimidazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzoimidazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzoimidazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzoimidazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzoimidazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzoimidazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzoimidazolyl group; $R_8$ is —$CH_3$; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $R_4$ is —H; $Ar_2$ is a benzoimidazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $R_4$ is —H; $Ar_2$ is a benzoimidazolyl group and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzoimidazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzoimidazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzoimidazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzoimidazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzoimidazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —Cl; $Ar_2$ is a benzoimidazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —Cl; $Ar_2$ is a benzoimidazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —Cl; $Ar_2$ is a benzoimidazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —Cl; $Ar_2$ is a benzoimidazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —Cl; $Ar_2$ is a benzoimidazolyl group; $R_8$ is —H; and $R_9$ is -iodo. In another embodiment, the carbon atom to which the $R_3$ group is attached has the R configuration. In another In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzoimidazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzoimidazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzoimidazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzoimidazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzoimidazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzoimidazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzoimidazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzoimidazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzoimidazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzoimidazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, Br, or —I; $Ar_2$ is a benzoimidazolyl group; $R_8$ is —H; and $R_9$ is —CH_3. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzoimidazolyl group; $R_8$ is —H; and $R_9$ is —CH_3. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, Br, or —I; $Ar_2$ is a benzoimidazolyl group; $R_8$ is —CH_3; and $R_9$ is —H. In another embodiment, the carbon atom to which the $R_3$ group is attached has the R configuration. In another embodiment, the carbon atom to which the $R_3$ group is attached has the S configuration.

In another embodiment, Ar1 is a pyriminidyl group and p is 0; $R_1$ is —F; $Ar_2$ is a benzoimidazolyl group; $R_8$ is —CH_3; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, Br, or —I; $Ar_2$ is a benzoimidazolyl group; $R_8$ is —H; and $R_9$ is —CF_3. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzoimidazolyl group; $R_8$ is —H; and $R_9$ is —CF_3. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, Br, or —I; $Ar_2$ is a benzoimidazolyl group; $R_8$ is —CF_3; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzoimidazolyl group; $R_8$ is —CF_3; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, Br, or —I; $Ar_2$ is a benzoimidazolyl group; $R_8$ is —H; and $R_9$ is —OCH_2CH_3. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzoimidazolyl group; $R_8$ is —H; and $R_9$ is —OCH_2CH_3. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, Br, or —I; $Ar_2$ is a benzoimidazolyl group; $R_8$ is —OCH_2CH_3; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzoimidazolyl group; $R_8$ is —OCH_2CH_3; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzoimidazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzoimidazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzoimidazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzoimidazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzoimidazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzoimidazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzoimidazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzoimidazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzoimidazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzoimidazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzoimidazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzoimidazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzoimidazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzoimidazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzoimidazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzoimidazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzoimidazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzoimidazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzoimidazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzoimidazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzoimidazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzoimidazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzoimidazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzoimidazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzoimidazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzoimidazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzoimidazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzoimidazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzoimidazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzoimidazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzoimidazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzoimidazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzoimidazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzoimidazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzoimidazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzoimidazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzoimidazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzoimidazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzoimidazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzoimidazolyl group; $R_8$ is —$CH_3$; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $R_4$ is —H; $Ar_2$ is a benzooxazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $R_4$ is —H; $Ar_2$ is a benzooxazolyl group and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzooxazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzooxazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzooxazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzooxazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzooxazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —Cl; $Ar_2$ is a benzooxazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —Cl; $Ar_2$ is a benzooxazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —Cl; $Ar_2$ is a benzooxazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —Cl; $Ar_2$ is a benzooxazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —Cl; $Ar_2$ is a benzooxazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzooxazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzooxazolyl group; $R_8$ is -chloro; and $R_9$ is —H.

In another embodiment, $Ar_1$ is a pyridyl group and n is 0; $R_1$ is —F, —Cl, —Br, or —I; $Ar_2$ is a benzooxazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzooxazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzooxazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzooxazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzooxazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzooxazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzooxazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzooxazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, Br, or —I; $Ar_2$ is a benzooxazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzooxazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, Br, or —I; $Ar_2$ is a benzooxazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, Ar1 is a pyridyl group and n is 0; $R_1$ is —F; $Ar_2$ is a benzooxazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, Br, or —I; $Ar_2$ is a benzooxazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzooxazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, Br, or —I; $Ar_2$ is a benzooxazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzooxazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, Br, or —I; $Ar_2$ is a benzooxazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzooxazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, Br, or —I; $Ar_2$ is a benzooxazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzooxazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzooxazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzooxazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzooxazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzooxazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzooxazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzooxazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzooxazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzooxazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzooxazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzooxazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzooxazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzooxazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzooxazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzooxazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzooxazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzooxazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzooxazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzooxazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzooxazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzooxazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzooxazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzooxazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzooxazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzooxazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzooxazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzooxazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzooxazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzooxazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzooxazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzooxazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzooxazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzooxazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CF_3$; $Ar_2$ is a benzooxazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzooxazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzooxazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F, —Cl, —Br, or —I; $Ar_2$ is a benzooxazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —F; $Ar_2$ is a benzooxazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzooxazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzooxazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyridyl group and n is 0; $R_1$ is —$CH_3$; $Ar_2$ is a benzooxazolyl group; $R_8$ is —$CH_3$; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $R_4$ is —H; $Ar_2$ is a benzooxazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $R_4$ is —H; $Ar_2$ is a benzooxazolyl group and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzooxazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzooxazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzooxazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzooxazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzooxazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —Cl; $Ar_2$ is a benzooxazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —Cl; $Ar_2$ is a benzooxazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —Cl; $Ar_2$ is a benzooxazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —Cl; $Ar_2$ is a benzooxazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —Cl; $Ar_2$ is a benzooxazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzooxazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzooxazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzooxazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzooxazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzooxazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzooxazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzooxazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzooxazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzooxazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzooxazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, Br, or —I; $Ar_2$ is a benzooxazolyl group; $R_8$ is —H; and $R_9$ is —CH$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzooxazolyl group; $R_8$ is —H; and $R_9$ is —CH$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, Br, or —I; $Ar_2$ is a benzooxazolyl group; $R_8$ is —CH$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, Ar1 is a pyriminidyl group and p is 0; $R_1$ is —F; $Ar_2$ is a benzooxazolyl group; $R_8$ is —CH$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, Br, or —I; $Ar_2$ is a benzooxazolyl group; $R_8$ is —H; and $R_9$ is —CF$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzooxazolyl group; $R_8$ is —H; and $R_9$ is —CF$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, Br, or —I; $Ar_2$ is a benzooxazolyl group; $R_8$ is —CF$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzooxazolyl group; $R_8$ is —CF$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, Br, or —I; $Ar_2$ is a benzooxazolyl group; $R_8$ is —H; and $R_9$ is —OCH$_2$CH$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzooxazolyl group; $R_8$ is —H; and $R_9$ is —OCH$_2$CH$_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, Br, or —I; $Ar_2$ is a benzooxazolyl group; $R_8$ is —OCH$_2$CH$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzooxazolyl group; $R_8$ is —OCH$_2$CH$_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —CH$_3$; $Ar_2$ is a benzooxazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —CH$_3$; $Ar_2$ is a benzooxazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —CH$_3$; $Ar_2$ is a benzooxazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —CH$_3$; $Ar_2$ is a benzooxazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —CH$_3$; $Ar_2$ is a benzooxazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —CH$_3$; $Ar_2$ is a benzooxazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —CH$_3$; $Ar_2$ is a benzooxazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzooxazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzooxazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzooxazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzooxazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzooxazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzooxazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzooxazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzooxazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzooxazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzooxazolyl group; and $R_8$ and $R_9$ are —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzooxazolyl group; $R_8$ is —H; and $R_9$ is -halo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzooxazolyl group; $R_8$ is —H; and $R_9$ is -chloro. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzooxazolyl group; $R_8$ is —H; and $R_9$ is -bromo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzooxazolyl group; $R_8$ is —H; and $R_9$ is -fluoro. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzooxazolyl group; $R_8$ is —H; and $R_9$ is -iodo. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzooxazolyl group; $R_8$ is -halo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzooxazolyl group; $R_8$ is -chloro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzooxazolyl group; $R_8$ is -bromo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzooxazolyl group; $R_8$ is -fluoro; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzooxazolyl group; $R_8$ is -iodo; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzooxazolyl group; $R_8$ is —H; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzooxazolyl group; $R_8$ is —$CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzooxazolyl group; $R_8$ is —H; and $R_9$ is —$CF_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzooxazolyl group; $R_8$ is —$CF_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzooxazolyl group; $R_8$ is —H; and $R_9$ is —$OCH_2CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CF_3$; $Ar_2$ is a benzooxazolyl group; $R_8$ is —$OCH_2CH_3$; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzooxazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzooxazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F, —Cl, —Br, or —I; $Ar_2$ is a benzooxazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —F; $Ar_2$ is a benzooxazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzooxazolyl group; $R_8$ is -tert-butyl; and $R_9$ is —H. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group and p is 0; $R_1$ is —$CH_3$; $Ar_2$ is a benzooxazolyl group; $R_8$ is —H; and $R_9$ is -tert-butyl. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group, p is 0; $R_1$ is —$CH_3$; $Ar_2$ is a benzooxazolyl group; $R_8$ is —$CH_3$; and $R_9$ is —$CH_3$. In another embodiment, the carbon atom to which the $R_3$ group is attached has the R configuration. In another embodiment, the carbon atom to which the $R_3$ group is attached has the S configuration.

In another embodiment, $Ar_1$ is a pyriminidyl group, p is 0; $R_1$ is —$CH_3$; $Ar_2$ is a benzooxazolyl group; $R_8$ is —$CH_3$; and $R_9$ is —$CH_3$. In another embodiment, the carbon atom to which the $R_3$ group is attached has the R configuration. In another embodiment, the carbon atom to which the $R_3$ group is attached has the S configuration.

In the Benzoazolylpiperazine Compounds the $R_3$ group can be on any carbon of the piperazine ring. In one embodiment, the $R_3$ group is attached to a carbon atom adjacent to the nitrogen atom attached to the pyridyl group, pyrimidinyl group, pyrazinyl group, pyridazinyl group, or thiazanyl group. In another embodiment, the $R_3$ group is attached to a carbon atom adjacent to the nitrogen atom attached to the -(A)- group, when x is 1; or the $R_3$ group is attached to the carbon atom adjacent to the nitrogen atom attached to the benzothiazolyl group, the benzoimidazolyl group, or the benzooxazolyl group, when x is 0.

In one embodiment, wherein the Benzoazolylpiperazine Compound has an $R_3$ group, the carbon atom to which the $R_3$ group is attached has the (R) configuration. In another embodiment, wherein the Benzoazolylpiperazine Compound has an $R_3$ group, the carbon atom to which the $R_3$ group is attached has the (S) configuration.

In another embodiment, the Benzoazolylpiperazine Compound has an $R_3$ group; the $R_3$ group is attached to a carbon atom adjacent to a nitrogen atom attached to the pyridyl group, pyrimidinyl group, pyrazinyl group, pyridazinyl group, or thiazanyl group; and the carbon to which the $R_3$ group is attached is in the (R) configuration. In another embodiment, the Benzoazolylpiperazine Compound has an $R_3$ group; the $R_3$ group is attached to a carbon atom adjacent to a nitrogen attached to the pyridyl group, pyrimidinyl group, pyrazinyl group, pyridazinyl group, or thiazanyl group; the carbon to which the $R_3$ group is attached is in the (R) configuration; and $R_3$ is —$(C_1$-$C_4)$alkyl unsubstituted or substituted with one or more halo groups. In another embodiment, the Benzoazolylpiperazine Compound has an $R_3$ group; the $R_3$ group is attached to a carbon atom adjacent to a nitrogen attached to the pyridyl group, pyrimidinyl group, pyrazinyl group, pyridazinyl group, or thiazanyl group; the carbon to which the $R_3$ group is attached is in the (R) configuration; and $R_3$ is —$CH_3$. In another embodiment, the Benzoazolylpiperazine Compound has an $R_3$ group; the $R_3$ group is attached to a carbon atom adjacent to a nitrogen attached to the pyridyl group, pyrimidinyl group, pyrazinyl group, pyridazinyl group, or thiazanyl group; the carbon to which the $R_3$ group is attached is in the (R) configuration; and $R_3$ is —$CF_3$. In another embodiment, the Benzoazolylpiperazine Compound has an $R_3$ group; the $R_3$ group is attached to a carbon atom adjacent to a nitrogen attached to the pyridyl group, pyrimidinyl group, pyrazinyl group, pyridazinyl group, or thiazanyl group; the carbon to which the $R_3$ group is attached is in the (R) configuration; and $R_3$ is —$CH_2CH_3$.

In another embodiment, the Benzoazolylpiperazine Compound has an $R_3$ group; the $R_3$ group is attached to a carbon atom adjacent to a nitrogen atom attached to the -(A)- group, when x is 1; or the $R_3$ group is attached to the carbon atom adjacent to the nitrogen atom attached to the benzothiazolyl group, the benzoimidazolyl group, or the benzooxazolyl group when x is 0; and the carbon to which the $R_3$ group is attached is in the (R) configuration. In another embodiment, the Benzoazolylpiperazine Compound has an $R_3$ group; the $R_3$ group is attached to a carbon atom adjacent to a nitrogen attached to the -(A)- group, when x is 1; or the $R_3$ group is attached to the carbon atom adjacent to the nitrogen atom attached to the benzothiazolyl group, the benzoimidazolyl group, or the benzooxazolyl group, when x is 0; the carbon to which the $R_3$ group is attached is in the (R) configuration; and $R_3$ is —($C_1$-$C_4$)alkyl unsubstituted or substituted with one or more halo groups. In another embodiment, the Benzoazolylpiperazine Compound has an $R_3$ group; the $R_3$ group is attached to a carbon atom adjacent to a nitrogen attached to the -(A)- group, when x is 1; or the $R_3$ group is attached to the carbon atom adjacent to the nitrogen atom attached to the benzothiazolyl group, the benzoimidazolyl group, or the benzooxazolyl group when x is 0; the carbon to which the $R_3$ group is attached is in the (R) configuration; and $R_3$ is —$CH_3$. In another embodiment, the Benzoazolylpiperazine Compound has an $R_3$ group; the $R_3$ group is attached to a carbon atom adjacent to a nitrogen attached to the -(A)- group, when x is 1; or the $R_3$ group is attached to the carbon atom adjacent to the nitrogen atom attached to the benzothiazolyl group, the benzoimidazolyl group, or the benzooxazolyl group, when x is 0; the carbon to which the $R_3$ group is attached is in the (R) configuration; and $R_3$ is —$CF_3$. In another embodiment, the Benzoazolylpiperazine Compound has an $R_3$ group; the $R_3$ group is attached to a carbon atom adjacent to a nitrogen attached to the -(A)- group, when x is 1; or the $R_3$ group is attached to the carbon atom adjacent to the nitrogen atom attached to the benzothiazolyl group, the benzoimidazolyl group, or the benzooxazolyl group, when x is 0; the carbon to which the $R_3$ group is attached is in the (R) configuration; and $R_3$ is —$CH_2CH_3$.

In another embodiment, the Benzoazolylpiperazine Compound has an $R_3$ group; the $R_3$ group is attached to a carbon atom adjacent to a nitrogen atom attached to the pyridyl group, pyrimidinyl group, pyrazinyl group, pyridazinyl group, or thiazanyl group; and the carbon to which the $R_3$ group is attached is in the (S) configuration. In another embodiment, the Benzoazolylpiperazine Compound has an $R_3$ group; the $R_3$ group is attached to a carbon atom adjacent to a nitrogen attached to the pyridyl group, pyrimidinyl group, pyrazinyl group, pyridazinyl group, or thiazanyl group; the carbon to which the $R_3$ group is attached is in the (S) configuration; and $R_3$ is —($C_1$-$C_4$)alkyl unsubstituted or substituted with one or more halo groups. In another embodiment, the Benzoazolylpiperazine Compound has an $R_3$ group; the $R_3$ group is attached to a carbon atom adjacent to a nitrogen attached to the pyridyl group, pyrimidinyl group, pyrazinyl group, pyridazinyl group, or thiazanyl group; the carbon to which the $R_3$ group is attached is in the (S) configuration; and $R_3$ is —$CH_3$. In another embodiment, the Benzoazolylpiperazine Compound has an $R_3$ group; the $R_3$ group is attached to a carbon atom adjacent to a nitrogen attached to the pyridyl group, pyrimidinyl group, pyrazinyl group, pyridazinyl group, or thiazanyl group; the carbon to which the $R_3$ group is attached is in the (S) configuration; and $R_3$ is —$CF_3$. In another embodiment, the Benzoazolylpiperazine Compound has an $R_3$ group; the $R_3$ group is attached to a carbon atom adjacent to a nitrogen attached to the pyridyl group, pyrimidinyl group, pyrazinyl group, pyridazinyl group, or thiazanyl group; the carbon to which the $R_3$ group is attached is in the (S) configuration; and $R_3$ is —$CH_2CH_3$.

In another embodiment, the Benzoazolylpiperazine Compound has an $R_3$ groups; the $R_3$ group is attached to a carbon atom adjacent to a nitrogen atom attached to the -(A)- group, when x is 1; or the $R_3$ group is attached to the carbon atom adjacent to the nitrogen atom attached to the benzothiazolyl group, the benzoazolyl group, or the benzooxazolyl group, when x is 0; and the carbon to which the $R_3$ group is attached is in the (S) configuration. In another embodiment, the Benzoazolylpiperazine Compound has an $R_3$ group; the $R_3$ group is attached to a carbon atom adjacent to a nitrogen attached to the -(A)- group, when x is 1; or the $R_3$ group is attached to the carbon atom adjacent to the nitrogen atom attached to the benzothiazolyl group, the benzoimidazolyl group, or the benzooxazolyl group, when x is 0; the carbon to which the $R_3$ group is attached is in the (S) configuration; and $R_3$ is —($C_1$-$C_4$)alkyl unsubstituted or substituted with one or more halo groups. In another embodiment, the Benzoazolylpiperazine Compound has an $R_3$ group; the $R_3$ group is attached to a carbon atom adjacent to a nitrogen attached to the -(A)- group, when x is 1; or the $R_3$ group is attached to the carbon atom adjacent to the nitrogen atom attached to the benzothiazolyl group, the benzoimidazolyl group, or the benzooxazolyl group, when x is 0; the carbon to which the $R_3$ group is attached is in the (S) configuration; and $R_3$ is —$CH_3$. In another embodiment, the Benzoazolylpiperazine Compound has an $R_3$ group; the $R_3$ group is attached to a carbon atom adjacent to a nitrogen attached to the -(A)- group, when x is 1; or the $R_3$ group is attached to the carbon atom adjacent to the nitrogen atom attached to the benzothiazolyl group, the benzoimidazolyl group, or the benzooxazolyl group, when x is 0; the carbon to which the $R_3$ group is attached is in the (S) configuration; and $R_3$ is —$CF_3$. In another embodiment, the Benzoazolylpiperazine Compound has an $R_3$ group; the $R_3$ group is attached to a carbon atom adjacent to a nitrogen attached to the -(A)- group, when x is 1; or the $R_3$ group is attached to the carbon atom adjacent to the nitrogen atom attached to the benzothiazolyl group, the benzoimidazolyl group, or the benzooxazolyl group, when x is 0; the carbon to which the $R_3$ group is attached is in the (S) configuration; and $R_3$ is —$CH_2CH_3$ In a preferred embodiment, the $R_3$ group is attached to a carbon atom adjacent to a nitrogen attached to the -(A)- group, when x is 1; or the $R_3$ group is attached to the carbon atom adjacent to the nitrogen atom attached to the benzothiazolyl group, the benzoimidazolyl group, or the benzooxazolyl group, when x is 0; and the $R_3$ group is a —$CH_3$. In another preferred embodiment, the $R_3$ group is attached to a carbon atom adjacent to a nitrogen attached to the -(A)- group, when x is 1; or the $R_3$ group is attached to the carbon atom adjacent to the nitrogen atom attached to the benzothiazolyl group, the benzoimidazolyl group, or the benzooxazolyl group, when x is 0 and the $R_3$ group is a —$CF_3$. In another preferred embodiment, the $R_3$ group is attached to a carbon atom adjacent to a nitrogen attached to the -(A)- group, when x is 1; or the $R_3$ group is attached to the carbon atom adjacent to the nitrogen atom attached to the benzothiazolyl group, the benzoimidazolyl group, or the benzooxazolyl group, when x is 0; and the $R_3$ group is a —$CH_2CH_3$. In another preferred embodiment, the $R_3$ group is attached to a carbon atom adjacent to a nitrogen attached to the -(A)- group, when x is 1; or the $R_3$ group is attached to the carbon atom adjacent to the nitrogen atom attached to the benzothiazolyl group, the benzoimidazolyl group, or the benzooxazolyl group, when x is 0; and the carbon to which the $R_3$ group is attached is in the (R) configuration. In another preferred embodiment, the $R_3$ group is attached to a carbon atom adjacent to a nitrogen attached to the -(A)- group, when x is 1; or the $R_3$ group is attached to the carbon atom adjacent to the nitrogen atom attached to the benzothiazolyl group, the benzoimidazolyl group, or the benzooxazolyl group, when x is 0; the carbon to which the $R_3$ group is attached is in the (R) configuration; and the $R_3$ group is a —$CH_3$. In another preferred embodiment, the $R_3$ group is attached to a carbon atom adjacent to a nitrogen attached to the -(A)- group, when x is 1; or the $R_3$ group is attached to the carbon atom adjacent to the nitrogen atom attached to the benzothiazolyl group, the benzoimidazolyl group, or the benzooxazolyl group, when x is 0; the carbon to which the $R_3$ group is attached is in the (R) configuration; and the $R_3$ group is a —$CF_3$. In another preferred embodiment, the $R_3$ group is attached to a carbon atom adjacent to a nitrogen attached to the -(A)- group, when x is 1; or the $R_3$ group is attached to the carbon atom adjacent to the nitrogen atom attached to the benzothiazolyl group, the benzoimidazolyl group, or the benzooxazolyl group, when x is 0; the carbon to which the $R_3$ group is attached is in the (R) configuration; and the $R_3$ group is a —$CH_2CH_3$.

Illustrative Benzoazolylpiperazine Compounds are listed below in Tables I-XXII:

TABLE I

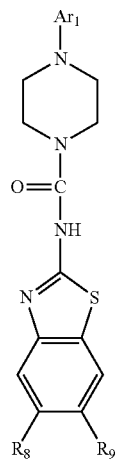

and pharmaceutically acceptable salts thereof, wherein:

| Compound | $Ar_1$ | $R_8$ | $R_9$ |
|---|---|---|---|
| AAA | -2-(3-chloropyridyl) | —Cl | —H |
| AAB | -2-(3-chloropyridyl) | —Br | —H |
| AAC | -2-(3-chloropyridyl) | —F | —H |
| AAD | -2-(3-chloropyridyl) | —$CH_3$ | —H |
| AAE | -2-(3-chloropyridyl) | —$CF_3$ | —H |
| AAF | -2-(3-chloropyridyl) | —$OCH_3$ | —H |
| AAG | -2-(3-chloropyridyl) | —$OCH_2CH_3$ | —H |
| AAH | -2-(3-chloropyridyl) | —$OCF_3$ | —H |
| AAI | -2-(3-chloropyridyl) | -tert-butyl | —H |
| AAJ | -2-(3-chloropyridyl) | -iso-propyl | —H |
| AAK | -2-(3-chloropyridyl) | —$CH_3$ | —$CH_3$ |
| AAL | -2-(3-chloropyridyl) | —H | —H |
| AAM | -2-(3-chloropyridyl) | —H | —Cl |
| AAN | -2-(3-chloropyridyl) | —H | —Br |
| AAO | -2-(3-chloropyridyl) | —H | —F |
| AAP | -2-(3-chloropyridyl) | —H | —$CH_3$ |
| AAQ | -2-(3-chloropyridyl) | —H | —$CF_3$ |
| AAR | -2-(3-chloropyridyl) | —H | —$OCH_3$ |
| AAS | -2-(3-chloropyridyl) | —H | —$OCH_2CH_3$ |
| AAT | -2-(3-chloropyridyl) | —H | —$OCF_3$ |
| AAU | -2-(3-chloropyridyl) | —H | -tert-butyl |
| AAV | -2-(3-chloropyridyl) | —H | -iso-propyl |
| AAW | -2-(3-methylpyridyl) | —Cl | —H |
| AAX | -2-(3-methylpyridyl) | —Br | —H |
| AAY | -2-(3-methylpyridyl) | —F | —H |
| AAZ | -2-(3-methylpyridyl) | —$CH_3$ | —H |
| ABA | -2-(3-methylpyridyl) | —$CF_3$ | —H |
| ABB | -2-(3-methylpyridyl) | —$OCH_3$ | —H |
| ABC | -2-(3-methylpyridyl) | —$OCH_2CH_3$ | —H |
| ABD | -2-(3-methylpyridyl) | —$OCF_3$ | —H |
| ABE | -2-(3-methylpyridyl) | -tert-butyl | —H |
| ABF | -2-(3-methylpyridyl) | -iso-propyl | —H |
| ABG | -2-(3-methylpyridyl) | —$CH_3$ | —$CH_3$ |
| ABH | -2-(3-methylpyridyl) | —H | —H |
| ABI | -2-(3-methylpyridyl) | —H | —Cl |
| ABJ | -2-(3-methylpyridyl) | —H | —Br |
| ABK | -2-(3-methylpyridyl) | —H | —F |
| ABL | -2-(3-methylpyridyl) | —H | —$CH_3$ |
| ABM | -2-(3-methylpyridyl) | —H | —$CF_3$ |

TABLE I-continued

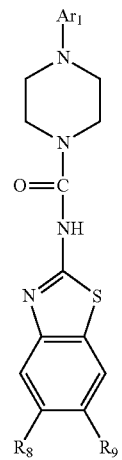

and pharmaceutically acceptable salts thereof, wherein:

| Compound | $Ar_1$ | $R_8$ | $R_9$ |
|---|---|---|---|
| ABN | -2-(3-methylpyridyl) | —H | —$OCH_3$ |
| ABO | -2-(3-methylpyridyl) | —H | —$OCH_2CH_3$ |
| ABP | -2-(3-methylpyridyl) | —H | —$OCF_3$ |
| ABQ | -2-(3-methylpyridyl) | —H | -tert-butyl |
| ABR | -2-(3-methylpyridyl) | —H | -iso-propyl |
| ABS | -2-(3-$CF_3$-pyridyl) | —Cl | —H |
| ABT | -2-(3-$CF_3$-pyridyl) | —Br | —H |
| ABU | -2-(3-$CF_3$-pyridyl) | —F | —H |
| ABV | -2-(3-$CF_3$-pyridyl) | —$CH_3$ | —H |
| ABW | -2-(3-$CF_3$-pyridyl) | —$CF_3$ | —H |
| ABX | -2-(3-$CF_3$-pyridyl) | —$OCH_3$ | —H |
| ABY | -2-(3-$CF_3$-pyridyl) | —$OCH_2CH_3$ | —H |
| ABZ | -2-(3-$CF_3$-pyridyl) | —$OCF_3$ | —H |
| ACA | -2-(3-$CF_3$-pyridyl) | -tert-butyl | —H |
| ACB | -2-(3-$CF_3$-pyridyl) | -iso-propyl | —H |
| ACC | -2-(3-$CF_3$-pyridyl) | —$CH_3$ | —$CH_3$ |
| ACD | -2-(3-$CF_3$-pyridyl) | —H | —H |
| ACE | -2-(3-$CF_3$-pyridyl) | —H | —Cl |
| ACF | -2-(3-$CF_3$-pyridyl) | —H | —Br |
| ACG | -2-(3-$CF_3$-pyridyl) | —H | —F |
| ACH | -2-(3-$CF_3$-pyridyl) | —H | —$CH_3$ |
| ACI | -2-(3-$CF_3$-pyridyl) | —H | —$CF_3$ |
| ACJ | -2-(3-$CF_3$-pyridyl) | —H | —$OCH_3$ |
| ACK | -2-(3-$CF_3$-pyridyl) | —H | —$OCH_2CH_3$ |
| ACL | -2-(3-$CF_3$-pyridyl) | —H | —$OCF_3$ |
| ACM | -2-(3-$CF_3$-pyridyl) | —H | -tert-butyl |
| ACN | -2-(3-$CF_3$-pyridyl) | —H | -iso-propyl |
| ACO | -4-(5-chloropyrimidinyl) | —Cl | —H |
| ACP | -4-(5-chloropyrimidinyl) | —Br | —H |
| ACQ | -4-(5-chloropyrimidinyl) | —F | —H |
| ACR | -4-(5-chloropyrimidinyl) | —$CH_3$ | —H |
| ACS | -4-(5-chloropyrimidinyl) | —$CF_3$ | —H |
| ACT | -4-(5-chloropyrimidinyl) | —$OCH_3$ | —H |
| ACU | -4-(5-chloropyrimidinyl) | —$OCH_2CH_3$ | —H |
| ACV | -4-(5-chloropyrimidinyl) | —$OCF_3$ | —H |
| ACW | -4-(5-chloropyrimidinyl) | -tert-butyl | —H |
| ACX | -4-(5-chloropyrimidinyl) | -iso-propyl | —H |
| ACY | -4-(5-chloropyrimidinyl) | —$CH_3$ | —$CH_3$ |
| ACZ | -4-(5-chloropyrimidinyl) | —H | —H |
| ADA | -4-(5-chloropyrimidinyl) | —H | —Cl |
| ADB | -4-(5-chloropyrimidinyl) | —H | —Br |
| ADC | -4-(5-chloropyrimidinyl) | —H | —F |
| ADD | -4-(5-chloropyrimidinyl) | —H | —$CH_3$ |
| ADE | -4-(5-chloropyrimidinyl) | —H | —$CF_3$ |
| ADF | -4-(5-chloropyrimidinyl) | —H | —$OCH_3$ |
| ADG | -4-(5-chloropyrimidinyl) | —H | —$OCH_2CH_3$ |
| ADH | -4-(5-chloropyrimidinyl) | —H | —$OCF_3$ |
| ADI | -4-(5-chloropyrimidinyl) | —H | -tert-butyl |
| ADJ | -4-(5-chloropyrimidinyl) | —H | -iso-propyl |
| ADK | -4-(5-methylpyrimidinyl) | —Cl | —H |
| ADL | -4-(5-methylpyrimidinyl) | —Br | —H |
| ADM | -4-(5-methylpyrimidinyl) | —F | —H |
| ADN | -4-(5-methylpyrimidinyl) | —$CH_3$ | —H |
| ADO | -4-(5-methylpyrimidinyl) | —$CF_3$ | —H |

TABLE I-continued

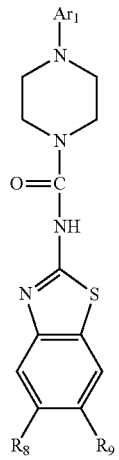

and pharmaceutically acceptable salts thereof, wherein:

| Compound | Ar₁ | R₈ | R₉ |
|---|---|---|---|
| ADP | -4-(5-methylpyrimidinyl) | —OCH₃ | —H |
| ADQ | -4-(5-methylpyrimidinyl) | —OCH₂CH₃ | —H |
| ADR | -4-(5-methylpyrimidinyl) | —OCF₃ | —H |
| ADS | -4-(5-methylpyrimidinyl) | -tert-butyl | —H |
| ADT | -4-(5-methylpyrimidinyl) | -iso-propyl | —H |
| ADU | -4-(5-methylpyrimidinyl) | —CH₃ | —CH₃ |
| ADV | -4-(5-methylpyrimidinyl) | —H | —H |
| ADW | -4-(5-methylpyrimidinyl) | —H | —Cl |
| ADX | -4-(5-methylpyrimidinyl) | —H | —Br |
| ADY | -4-(5-methylpyrimidinyl) | —H | —F |
| ADZ | -4-(5-methylpyrimidinyl) | —H | —CH₃ |
| AEA | -4-(5-methylpyrimidinyl) | —H | —CF₃ |
| AEB | -4-(5-methylpyrimidinyl) | —H | —OCH₃ |
| AEC | -4-(5-methylpyrimidinyl) | —H | —OCH₂CH₃ |
| AED | -4-(5-methylpyrimidinyl) | —H | —OCF₃ |
| AEE | -4-(5-methylpyrimidinyl) | —H | -tert-butyl |
| AEF | -4-(5-methylpyrimidinyl) | —H | -iso-propyl |
| AEG | -2-pyrazinyl | —Cl | —H |
| AEH | -2-pyrazinyl | —Br | —H |
| AEI | -2-pyrazinyl | —F | —H |
| AEJ | -2-pyrazinyl | —CH₃ | —H |
| AEK | -2-pyrazinyl | —CF₃ | —H |
| AEL | -2-pyrazinyl | —OCH₃ | —H |
| AEM | -2-pyrazinyl | —OCH₂CH₃ | —H |
| AEN | -2-pyrazinyl | —OCF₃ | —H |
| AEO | -2-pyrazinyl | -tert-butyl | —H |
| AEP | -2-pyrazinyl | -iso-propyl | —H |
| AEQ | -2-pyrazinyl | —CH₃ | —CH₃ |
| AER | -2-pyrazinyl | —H | —H |
| AES | -2-pyrazinyl | —H | —Cl |
| AET | -2-pyrazinyl | —H | —Br |
| AEU | -2-pyrazinyl | —H | —F |
| AEV | -2-pyrazinyl | —H | —CH₃ |
| AEW | -2-pyrazinyl | —H | —CF₃ |
| AEX | -2-pyrazinyl | —H | —OCH₃ |
| AEY | -2-pyrazinyl | —H | —OCH₂CH₃ |
| AEZ | -2-pyrazinyl | —H | —OCF₃ |
| AFA | -2-pyrazinyl | —H | -tert-butyl |
| AFB | -2-pyrazinyl | —H | -iso-propyl |
| AFC | -2-(3-chloropyrazinyl) | —Cl | —H |
| AFD | -2-(3-chloropyrazinyl) | —Br | —H |
| AFE | -2-(3-chloropyrazinyl) | —F | —H |
| AFF | -2-(3-chloropyrazinyl) | —CH₃ | —H |
| AFG | -2-(3-chloropyrazinyl) | —CF₃ | —H |
| AFH | -2-(3-chloropyrazinyl) | —OCH₃ | —H |
| AFI | -2-(3-chloropyrazinyl) | —OCH₂CH₃ | —H |
| AFJ | -2-(3-chloropyrazinyl) | —OCF₃ | —H |
| AFK | -2-(3-chloropyrazinyl) | -tert-butyl | —H |
| AFL | -2-(3-chloropyrazinyl) | -iso-propyl | —H |
| AFM | -2-(3-chloropyrazinyl) | —CH₃ | —CH₃ |
| AFN | -2-(3-chloropyrazinyl) | —H | —H |
| AFO | -2-(3-chloropyrazinyl) | —H | —Cl |
| AFP | -2-(3-chloropyrazinyl) | —H | —Br |
| AFQ | -2-(3-chloropyrazinyl) | —H | —F |

TABLE I-continued

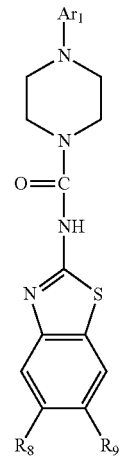

and pharmaceutically acceptable salts thereof, wherein:

| Compound | Ar₁ | R₈ | R₉ |
|---|---|---|---|
| AFR | -2-(3-chloropyrazinyl) | —H | —CH₃ |
| AFS | -2-(3-chloropyrazinyl) | —H | —CF₃ |
| AFT | -2-(3-chloropyrazinyl) | —H | —OCH₃ |
| AFU | -2-(3-chloropyrazinyl) | —H | —OCH₂CH₃ |
| AFV | -2-(3-chloropyrazinyl) | —H | —OCF₃ |
| AFW | -2-(3-chloropyrazinyl) | —H | -tert-butyl |
| AFX | -2-(3-chloropyrazinyl) | —H | -iso-propyl |
| AFY | -2-(3-methylpyrazinyl) | —Cl | —H |
| AFZ | -2-(3-methylpyrazinyl) | —Br | —H |
| AGA | -2-(3-methylpyrazinyl) | —F | —H |
| AGB | -2-(3-methylpyrazinyl) | —CH₃ | —H |
| AGC | -2-(3-methylpyrazinyl) | —CF₃ | —H |
| AGD | -2-(3-methylpyrazinyl) | —OCH₃ | —H |
| AGE | -2-(3-methylpyrazinyl) | —OCH₂CH₃ | —H |
| AGF | -2-(3-methylpyrazinyl) | —OCF₃ | —H |
| AGG | -2-(3-methylpyrazinyl) | -tert-butyl | —H |
| AGH | -2-(3-methylpyrazinyl) | -iso-propyl | —H |
| AGI | -2-(3-methylpyrazinyl) | —CH₃ | —CH₃ |
| AGJ | -2-(3-methylpyrazinyl) | —H | —H |
| AGK | -2-(3-methylpyrazinyl) | —H | —Cl |
| AGL | -2-(3-methylpyrazinyl) | —H | —Br |
| AGM | -2-(3-methylpyrazinyl) | —H | —F |
| AGN | -2-(3-methylpyrazinyl) | —H | —CH₃ |
| AGO | -2-(3-methylpyrazinyl) | —H | —CF₃ |
| AGP | -2-(3-methylpyrazinyl) | —H | —OCH₃ |
| AGQ | -2-(3-methylpyrazinyl) | —H | —OCH₂CH₃ |
| AGR | -2-(3-methylpyrazinyl) | —H | —OCF₃ |
| AGS | -2-(3-methylpyrazinyl) | —H | -tert-butyl |
| AGT | -2-(3-methylpyrazinyl) | —H | -iso-propyl |
| AGU | -2-pyridazinyl | —Cl | —H |
| AGV | -2-pyridazinyl | —Br | —H |
| AGW | -2-pyridazinyl | —F | —H |
| AGX | -2-pyridazinyl | —CH₃ | —H |
| AGY | -2-pyridazinyl | —CF₃ | —H |
| AGZ | -2-pyridazinyl | —OCH₃ | —H |
| AHA | -2-pyridazinyl | —OCH₂CH₃ | —H |
| AHB | -2-pyridazinyl | —OCF₃ | —H |
| AHC | -2-pyridazinyl | -tert-butyl | —H |
| AHD | -2-pyridazinyl | -iso-propyl | —H |
| AHE | -2-pyridazinyl | —CH₃ | —CH₃ |
| AHF | -2-pyridazinyl | —H | —H |
| AHG | -2-pyridazinyl | —H | —Cl |
| AHH | -2-pyridazinyl | —H | —Br |
| AHI | -2-pyridazinyl | —H | —F |
| AHJ | -2-pyridazinyl | —H | —CH₃ |
| AHK | -2-pyridazinyl | —H | —CF₃ |
| AHL | -2-pyridazinyl | —H | —OCH₃ |
| AHM | -2-pyridazinyl | —H | —OCH₂CH₃ |
| AHN | -2-pyridazinyl | —H | —OCF₃ |
| AHO | -2-pyridazinyl | —H | -tert-butyl |
| AHP | -2-pyridazinyl | —H | -iso-propyl |
| AHQ | -3-(4-chloropyridazinyl) | —Cl | —H |
| AHR | -3-(4-chloropyridazinyl) | —Br | —H |
| AHS | -3-(4-chloropyridazinyl) | —F | —H |

TABLE I-continued

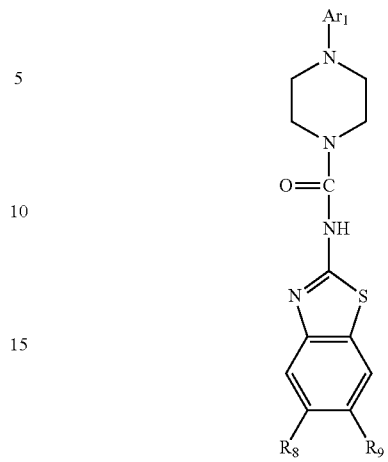

and pharmaceutically acceptable salts thereof, wherein:

| Compound | Ar$_1$ | R$_8$ | R$_9$ |
|---|---|---|---|
| AHT | -3-(4-chloropyridazinyl) | —CH$_3$ | —H |
| AHU | -3-(4-chloropyridazinyl) | —CF$_3$ | —H |
| AHV | -3-(4-chloropyridazinyl) | —OCH$_3$ | —H |
| AHW | :3-(4-chloropyridazinyl) | —OCH$_2$CH$_3$ | —H |
| AHX | -3-(4-chloropyridazinyl) | —OCF$_3$ | —H |
| AHY | -3-(4-chloropyridazinyl) | -tert-butyl | —H |
| AHZ | -3-(4-chloropyridazinyl) | -iso-propyl | —H |
| AIA | -3-(4-chloropyridazinyl) | —CH$_3$ | —CH$_3$ |
| AIB | -3-(4-chloropyridazinyl) | —H | —H |
| AIC | -3-(4-chloropyridazinyl) | —H | —Cl |
| AID | -3-(4-chloropyridazinyl) | —H | —Br |
| AIE | -3-(4-chloropyridazinyl) | —H | —F |
| AIF | -3-(4-chloropyridazinyl) | —H | —CH$_3$ |
| AIG | -3-(4-chloropyridazinyl) | —H | —CF$_3$ |
| AIH | -3-(4-chloropyridazinyl) | —H | —OCH$_3$ |
| AII | -3-(4-chloropyridazinyl) | —H | —OCH$_2$CH$_3$ |
| AIJ | -3-(4-chloropyridazinyl) | —H | —OCF$_3$ |
| AIK | -3-(4-chloropyridazinyl) | —H | -tert-butyl |
| AIL | -3-(4-chloropyridazinyl) | —H | -iso-propyl |
| AIM | -3-(4-methylpyridazinyl) | —Cl | —H |
| AIN | -3-(4-methylpyridazinyl) | —Br | —H |
| AIO | -3-(4-methylpyridazinyl) | —F | —H |
| AIP | -3-(4-methylpyridazinyl) | —CH$_3$ | —H |
| AIQ | -3-(4-methylpyridazinyl) | —CF$_3$ | —H |
| AIR | -3-(4-methylpyridazinyl) | —OCH$_3$ | —H |
| AIS | -3-(4-methylpyridazinyl) | —OCH$_2$CH$_3$ | —H |
| AIT | -3-(4-methylpyridazinyl) | —OCF$_3$ | —H |
| AIU | -3-(4-methylpyridazinyl) | -tert-butyl | —H |
| AIV | -3-(4-methylpyridazinyl) | -iso-propyl | —H |
| AIW | -3-(4-methylpyridazinyl) | —CH$_3$ | —CH$_3$ |
| AIX | -3-(4-methylpyridazinyl) | —H | —H |
| AIY | -3-(4-methylpyridazinyl) | —H | —Cl |
| AIZ | -3-(4-methylpyridazinyl) | —H | —Br |
| AJA | -3-(4-methylpyridazinyl) | —H | —F |
| AJB | -3-(4-methylpyridazinyl) | —H | —CH$_3$ |
| AJC | -3-(4-methylpyridazinyl) | —H | —CF$_3$ |
| AJD | -3-(4-methylpyridazinyl) | —H | —OCH$_3$ |
| AJE | -3-(4-methylpyridazinyl) | —H | —OCH$_2$CH$_3$ |
| AJF | -3-(4-methylpyridazinyl) | —H | —OCF$_3$ |
| AJG | -3-(4-methylpyridazinyl) | —H | -tert-butyl |
| AJH | -3-(4-methylpyridazinyl) | —H | -iso-propyl |
| AJI | -4-thiazanyl | —Cl | —H |
| AJJ | -4-thiazanyl | —Br | —H |
| AJK | -4-thiazanyl | —F | —H |
| AJL | -4-thiazanyl | —CH$_3$ | —H |
| AJM | -4-thiazanyl | —CF$_3$ | —H |
| AJN | -4-thiazanyl | —OCH$_3$ | —H |
| AJO | -4-thiazanyl | —OCH$_2$CH$_3$ | —H |
| AJP | -4-thiazanyl | —OCF$_3$ | —H |
| AJQ | -4-thiazanyl | -tert-butyl | —H |
| AJR | -4-thiazanyl | -iso-propyl | —H |
| AJS | -4-thiazanyl | —CH$_3$ | —CH$_3$ |
| AJT | -4-thiazanyl | —H | —H |
| AJU | -4-thiazanyl | —H | —Cl |
| AJV | -4-thiazanyl | —H | —Br |
| AJW | -4-thiazanyl | —H | —F |
| AJX | -4-thiazanyl | —H | —CH$_3$ |
| AJY | -4-thiazanyl | —H | —CF$_3$ |
| AJZ | -4-thiazanyl | —H | —OCH$_3$ |
| AKA | -4-thiazanyl | —H | —OCH$_2$CH$_3$ |
| AKB | -4-thiazanyl | —H | —OCF$_3$ |
| AKC | -4-thiazanyl | —H | -tert-butyl |
| AKD | -4-thiazanyl | —H | -iso-propyl |
| AKE | -5-(4-chlorothiazanyl) | —Cl | —H |
| AKF | -5-(4-chlorothiazanyl) | —Br | —H |
| AKG | -5-(4-chlorothiazanyl) | —F | —H |
| AKH | -5-(4-chlorothiazanyl) | —CH$_3$ | —H |
| AKI | -5-(4-chlorothiazanyl) | —CF$_3$ | —H |
| AKJ | -5-(4-chlorothiazanyl) | —OCH$_3$ | —H |
| AKK | -5-(4-chlorothiazanyl) | —OCH$_2$CH$_3$ | —H |
| AKL | -5-(4-chlorothiazanyl) | —OCF$_3$ | —H |
| AKM | -5-(4-chlorothiazanyl) | -tert-butyl | —H |
| AKN | -5-(4-chlorothiazanyl) | -iso-propyl | —H |
| AKO | -5-(4-chlorothiazanyl) | —CH$_3$ | —CH$_3$ |
| AKP | -5-(4-chlorothiazanyl) | —H | —H |
| AKQ | -5-(4-chlorothiazanyl) | —H | —Cl |
| AKR | -5-(4-chlorothiazanyl) | —H | —Br |
| AKS | -5-(4-chlorothiazanyl) | —H | —F |
| AKT | -5-(4-chlorothiazanyl) | —H | —CH$_3$ |
| AKU | -5-(4-chlorothiazanyl) | —H | —CF$_3$ |
| AKV | -5-(4-chlorothiazanyl) | —H | —OCH$_3$ |
| AKW | -5-(4-chlorothiazanyl) | —H | —OCH$_2$CH$_3$ |
| AKX | -5-(4-chlorothiazanyl) | —H | —OCF$_3$ |
| AKY | -5-(4-chlorothiazanyl) | —H | -tert-butyl |
| AKZ | -5-(4-chlorothiazanyl) | —H | -iso-propyl |
| ALA | -5-(4-methylthiazanyl) | —Cl | —H |
| ALB | -5-(4-methylthiazanyl) | —Br | —H |
| ALC | -5-(4-methylthiazanyl) | —F | —H |
| ALD | -5-(4-methylthiazanyl) | —CH$_3$ | —H |
| ALE | -5-(4-methylthiazanyl) | —CF$_3$ | —H |
| ALF | -5-(4-methylthiazanyl) | —OCH$_3$ | —H |
| ALG | -5-(4-methylthiazanyl) | —OCH$_2$CH$_3$ | —H |
| ALH | -5-(4-methylthiazanyl) | —OCF$_3$ | —H |
| ALI | -5-(4-methylthiazanyl) | -tert-butyl | —H |
| ALJ | -5-(4-methylthiazanyl) | -iso-propyl | —H |
| ALK | -5-(4-methylthiazanyl) | —CH$_3$ | —CH$_3$ |
| ALL | -5-(4-methylthiazanyl) | —H | —H |
| ALM | -5-(4-methylthiazanyl) | —H | —Cl |
| ALN | -5-(4-methylthiazanyl) | —H | —Br |
| ALO | -5-(4-methylthiazanyl) | —H | —F |
| ALP | -5-(4-methylthiazanyl) | —H | —CH$_3$ |
| ALQ | -5-(4-methylthiazanyl) | —H | —CF$_3$ |
| ALR | -5-(4-methylthiazanyl) | —H | —OCH$_3$ |
| ALS | -5-(4-methylthiazanyl) | —H | —OCH$_2$CH$_3$ |
| ALT | -5-(4-methylthiazanyl) | —H | —OCF$_3$ |
| ALU | -5-(4-methylthiazanyl) | —H | -tert-butyl |
| ALV | -5-(4-methylthiazanyl) | —H | -iso-propyl |

TABLE II

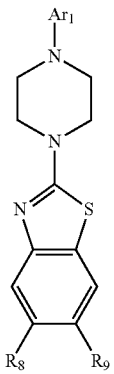

and pharmaceutically acceptable salts thereof, wherein:

| Compound | Ar$_1$ | R$_8$ | R$_9$ |
|---|---|---|---|
| ALW | -2-(3-chloropyridyl) | —Cl | —H |
| ALX | -2-(3-chloropyridyl) | —Br | —H |
| ALY | -2-(3-chloropyridyl) | —F | —H |
| ALZ | -2-(3-chloropyridyl) | —CH$_3$ | —H |
| AMA | -2-(3-chloropyridyl) | —CF$_3$ | —H |
| AMB | -2-(3-chloropyridyl) | —OCH$_3$ | —H |
| AMC | -2-(3-chloropyridyl) | —OCH$_2$CH$_3$ | —H |
| AMD | -2-(3-chloropyridyl) | —OCF$_3$ | —H |
| AME | -2-(3-chloropyridyl) | -tert-butyl | —H |
| AMF | -2-(3-chloropyridyl) | -iso-propyl | —H |
| AMG | -2-(3-chloropyridyl) | —CH$_3$ | —CH$_3$ |
| AMH | -2-(3-chloropyridyl) | —H | —H |
| AMI | -2-(3-chloropyridyl) | —H | —Cl |
| AMJ | -2-(3-chloropyridyl) | —H | —Br |
| AMK | -2-(3-chloropyridyl) | —H | —F |
| AML | -2-(3-chloropyridyl) | —H | —CH$_3$ |
| AMM | -2-(3-chloropyridyl) | —H | —CF$_3$ |
| AMN | -2-(3-chloropyridyl) | —H | —OCH$_3$ |
| AMO | -2-(3-chloropyridyl) | —H | —OCH$_2$CH$_3$ |
| AMP | -2-(3-chloropyridyl) | —H | —OCF$_3$ |
| AMQ | -2-(3-chloropyridyl) | —H | -tert-butyl |
| AMR | -2-(3-chloropyridyl) | —H | -iso-propyl |
| AMS | -2-(3-methylpyridyl) | —Cl | —H |
| AMT | -2-(3-methylpyridyl) | —Br | —H |
| AMU | -2-(3-methylpyridyl) | —F | —H |
| AMV | -2-(3-methylpyridyl) | —CH$_3$ | —H |
| AMW | -2-(3-methylpyridyl) | —CF$_3$ | —H |
| AMX | -2-(3-methylpyridyl) | —OCH$_3$ | —H |
| AMY | -2-(3-methylpyridyl) | —OCH$_2$CH$_3$ | —H |
| AMZ | -2-(3-methylpyridyl) | —OCF$_3$ | —H |
| ANA | -2-(3-methylpyridyl) | -tert-butyl | —H |
| ANB | -2-(3-methylpyridyl) | -iso-propyl | —H |
| ANC | -2-(3-methylpyridyl) | —CH$_3$ | —CH$_3$ |
| AND | -2-(3-methylpyridyl) | —H | —H |
| ANE | -2-(3-methylpyridyl) | —H | —Cl |
| ANF | -2-(3-methylpyridyl) | —H | —Br |
| ANG | -2-(3-methylpyridyl) | —H | —F |
| ANH | -2-(3-methylpyridyl) | —H | —CH$_3$ |
| ANI | -2-(3-methylpyridyl) | —H | —CF$_3$ |
| ANJ | -2-(3-methylpyridyl) | —H | —OCH$_3$ |
| ANK | -2-(3-methylpyridyl) | —H | —OCH$_2$CH$_3$ |
| ANL | -2-(3-methylpyridyl) | —H | —OCF$_3$ |
| ANM | -2-(3-methylpyridyl) | —H | -tert-butyl |
| ANN | -2-(3-methylpyridyl) | —H | -iso-propyl |
| ANO | -2-(3-CF$_3$-pyridyl) | —Cl | —H |
| ANP | -2-(3-CF$_3$-pyridyl) | —Br | —H |
| ANQ | -2-(3-CF$_3$-pyridyl) | —F | —H |
| ANR | -2-(3-CF$_3$-pyridyl) | —CH$_3$ | —H |
| ANS | -2-(3-CF$_3$-pyridyl) | —CF$_3$ | —H |
| ANT | -2-(3-CF$_3$-pyridyl) | —OCH$_3$ | —H |
| ANU | -2-(3-CF$_3$-pyridyl) | —OCH$_2$CH$_3$ | —H |
| ANV | -2-(3-CF$_3$-pyridyl) | —OCF$_3$ | —H |
| ANW | -2-(3-CF$_3$-pyridyl) | -tert-butyl | —H |
| ANX | -2-(3-CF$_3$-pyridyl) | -iso-propyl | —H |
| ANY | -2-(3-CF$_3$-pyridyl) | —CH$_3$ | —CH$_3$ |
| ANZ | -2-(3-CF$_3$-pyridyl) | —H | —H |
| AOA | -2-(3-CF$_3$-pyridyl) | —H | —Cl |
| AOB | -2-(3-CF$_3$-pyridyl) | —H | —Br |

TABLE II-continued

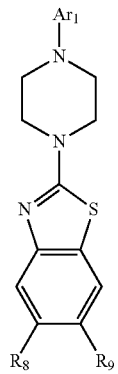

and pharmaceutically acceptable salts thereof, wherein:

| Compound | Ar$_1$ | R$_8$ | R$_9$ |
|---|---|---|---|
| AOC | -2-(3-CF$_3$-pyridyl) | —H | —F |
| AOD | -2-(3-CF$_3$-pyridyl) | —H | —CH$_3$ |
| AOE | -2-(3-CF$_3$-pyridyl) | —H | —CF$_3$ |
| AOF | -2-(3-CF$_3$-pyridyl) | —H | —OCH$_3$ |
| AOG | -2-(3-CF$_3$-pyridyl) | —H | —OCH$_2$CH$_3$ |
| AOH | -2-(3-CF$_3$-pyridyl) | —H | —OCF$_3$ |
| AOI | -2-(3-CF$_3$-pyridyl) | —H | -tert-butyl |
| AOJ | -2-(3-CF$_3$-pyridyl) | —H | -iso-propyl |
| AOK | 4-(5-chloropyrimidinyl) | —Cl | —H |
| AOL | 4-(5-chloropyrimidinyl) | —Br | —H |
| AOM | 4-(5-chloropyrimidinyl) | —F | —H |
| AON | 4-(5-chloropyrimidinyl) | —CH$_3$ | —H |
| AOO | 4-(5-chloropyrimidinyl) | —CF$_3$ | —H |
| AOP | 4-(5-chloropyrimidinyl) | —OCH$_3$ | —H |
| AOQ | 4-(5-chloropyrimidinyl) | —OCH$_2$CH$_3$ | —H |
| AOR | 4-(5-chloropyrimidinyl) | —OCF$_3$ | —H |
| AOS | 4-(5-chloropyrimidinyl) | -tert-butyl | —H |
| AOT | 4-(5-chloropyrimidinyl) | -iso-propyl | —H |
| AOU | 4-(5-chloropyrimidinyl) | —CH$_3$ | —CH$_3$ |
| AOV | 4-(5-chloropyrimidinyl) | —H | —H |
| AOW | 4-(5-chloropyrimidinyl) | —H | —Cl |
| AOX | 4-(5-chloropyrimidinyl) | —H | —Br |
| AOY | 4-(5-chloropyrimidinyl) | —H | —F |
| AOZ | 4-(5-chloropyrimidinyl) | —H | —CH$_3$ |
| APA | 4-(5-chloropyrimidinyl) | —H | —CF$_3$ |
| APB | 4-(5-chloropyrimidinyl) | —H | —OCH$_3$ |
| APC | 4-(5-chloropyrimidinyl) | —H | —OCH$_2$CH$_3$ |
| APD | 4-(5-chloropyrimidinyl) | —H | —OCF$_3$ |
| APE | 4-(5-chloropyrimidinyl) | —H | -tert-butyl |
| APF | 4-(5-chloropyrimidinyl) | —H | -iso-propyl |
| APG | 4-(5-methylpyrimidinyl) | —Cl | —H |
| APH | 4-(5-methylpyrimidinyl) | —Br | —H |
| API | 4-(5-methylpyrimidinyl) | —F | —H |
| APJ | 4-(5-methylpyrimidinyl) | —CH$_3$ | —H |
| APK | 4-(5-methylpyrimidinyl) | —CF$_3$ | —H |
| APL | 4-(5-methylpyrimidinyl) | —OCH$_3$ | —H |
| APM | 4-(5-methylpyrimidinyl) | —OCH$_2$CH$_3$ | —H |
| APN | 4-(5-methylpyrimidinyl) | —OCF$_3$ | —H |
| APO | 4-(5-methylpyrimidinyl) | -tert-butyl | —H |
| APP | 4-(5-methylpyrimidinyl) | -iso-propyl | —H |
| APQ | 4-(5-methylpyrimidinyl) | —CH$_3$ | —CH$_3$ |
| APR | 4-(5-methylpyrimidinyl) | —H | —H |
| APS | 4-(5-methylpyrimidinyl) | —H | —Cl |
| APT | 4-(5-methylpyrimidinyl) | —H | —Br |
| APU | 4-(5-methylpyrimidinyl) | —H | —F |
| APV | 4-(5-methylpyrimidinyl) | —H | —CH$_3$ |
| APW | 4-(5-methylpyrimidinyl) | —H | —CF$_3$ |
| APX | 4-(5-methylpyrimidinyl) | —H | —OCH$_3$ |
| APY | 4-(5-methylpyrimidinyl) | —H | —OCH$_2$CH$_3$ |
| APZ | 4-(5-methylpyrimidinyl) | —H | —OCF$_3$ |
| AQA | 4-(5-methylpyrimidinyl) | —H | -tert-butyl |
| AQB | 4-(5-methylpyrimidinyl) | —H | -iso-propyl |
| AQC | -2-pyrazinyl | —Cl | —H |
| AQD | -2-pyrazinyl | —Br | —H |
| AQE | -2-pyrazinyl | —F | —H |
| AQF | -2-pyrazinyl | —CH$_3$ | —H |
| AQG | -2-pyrazinyl | —CF$_3$ | —H |
| AQH | -2-pyrazinyl | —OCH$_3$ | —H |

TABLE II-continued

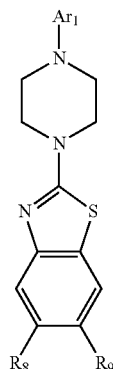

and pharmaceutically acceptable salts thereof, wherein:

| Compound | Ar₁ | R₈ | R₉ |
|---|---|---|---|
| AQI | -2-pyrazinyl | —OCH₂CH₃ | —H |
| AQJ | -2-pyrazinyl | —OCF₃ | —H |
| AQK | -2-pyrazinyl | -tert-butyl | —H |
| AQL | -2-pyrazinyl | -iso-propyl | —H |
| AQM | -2-pyrazinyl | —CH₃ | —CH₃ |
| AQN | -2-pyrazinyl | —H | —H |
| AQO | -2-pyrazinyl | —H | —Cl |
| AQP | -2-pyrazinyl | —H | —Br |
| AQQ | -2-pyrazinyl | —H | —F |
| AQR | -2-pyrazinyl | —H | —CH₃ |
| AQS | -2-pyrazinyl | —H | —CF₃ |
| AQT | -2-pyrazinyl | —H | —OCH₃ |
| AQU | -2-pyrazinyl | —H | —OCH₂CH₃ |
| AQV | -2-pyrazinyl | —H | —OCF₃ |
| AQW | -2-pyrazinyl | —H | -tert-butyl |
| AQX | -2-pyrazinyl | —H | -iso-propyl |
| AQY | -2-(3-chloropyrazinyl) | —Cl | —H |
| AQZ | -2-(3-chloropyrazinyl) | —Br | —H |
| ARA | -2-(3-chloropyrazinyl) | —F | —H |
| ARB | -2-(3-chloropyrazinyl) | —CH₃ | —H |
| ARC | -2-(3-chloropyrazinyl) | —CF₃ | —H |
| ARD | -2-(3-chloropyrazinyl) | —OCH₃ | —H |
| ARE | -2-(3-chloropyrazinyl) | —OCH₂CH₃ | —H |
| ARF | -2-(3-chloropyrazinyl) | —OCF₃ | —H |
| ARG | -2-(3-chloropyrazinyl) | -tert-butyl | —H |
| ARH | -2-(3-chloropyrazinyl) | -iso-propyl | —H |
| ARI | -2-(3-chloropyrazinyl) | —CH₃ | —CH₃ |
| ARJ | -2-(3-chloropyrazinyl) | —H | —H |
| ARK | -2-(3-chloropyrazinyl) | —H | —Cl |
| ARL | -2-(3-chloropyrazinyl) | —H | —Br |
| ARM | -2-(3-chloropyrazinyl) | —H | —F |
| ARN | -2-(3-chloropyrazinyl) | —H | —CH₃ |
| ARO | -2-(3-chloropyrazinyl) | —H | —CF₃ |
| ARP | -2-(3-chloropyrazinyl) | —H | —OCH₃ |
| ARQ | -2-(3-chloropyrazinyl) | —H | —OCH₂CH₃ |
| ARR | -2-(3-chloropyrazinyl) | —H | —OCF₃ |
| ARS | -2-(3-chloropyrazinyl) | —H | -tert-butyl |
| ART | -2-(3-chloropyrazinyl) | —H | -iso-propyl |
| ARU | -2-(3-methylpyrazinyl) | —Cl | —H |
| ARV | -2-(3-methylpyrazinyl) | —Br | —H |
| ARW | -2-(3-methylpyrazinyl) | —F | —H |
| ARX | -2-(3-methylpyrazinyl) | —CH₃ | —H |
| ARY | -2-(3-methylpyrazinyl) | —CF₃ | —H |
| ARZ | -2-(3-methylpyrazinyl) | —OCH₃ | —H |
| ASA | -2-(3-methylpyrazinyl) | —OCH₂CH₃ | —H |
| ASB | -2-(3-methylpyrazinyl) | —OCF₃ | —H |
| ASC | -2-(3-methylpyrazinyl) | -tert-butyl | —H |
| ASD | -2-(3-methylpyrazinyl) | -iso-propyl | —H |
| ASE | -2-(3-methylpyrazinyl) | —CH₃ | —CH₃ |
| ASF | -2-(3-methylpyrazinyl) | —H | —H |
| ASG | -2-(3-methylpyrazinyl) | —H | —Cl |
| ASH | -2-(3-methylpyrazinyl) | —H | —Br |
| ASI | -2-(3-methylpyrazinyl) | —H | —F |
| ASJ | -2-(3-methylpyrazinyl) | —H | —CH₃ |
| ASK | -2-(3-methylpyrazinyl) | —H | —CF₃ |
| ASL | -2-(3-methylpyrazinyl) | —H | —OCH₃ |
| ASM | -2-(3-methylpyrazinyl) | —H | —OCH₂CH₃ |
| ASN | -2-(3-methylpyrazinyl) | —H | —OCF₃ |

TABLE II-continued

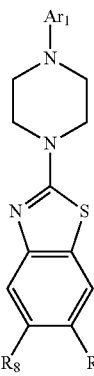

and pharmaceutically acceptable salts thereof, wherein:

| Compound | Ar₁ | R₈ | R₉ |
|---|---|---|---|
| ASO | -2-(3-methylpyrazinyl) | —H | -tert-butyl |
| ASP | -2-(3-methylpyrazinyl) | —H | -iso-propyl |
| ASQ | -2-pyridazinyl | —Cl | —H |
| ASR | -2-pyridazinyl | —Br | —H |
| ASS | -2-pyridazinyl | —F | —H |
| AST | -2-pyridazinyl | —CH₃ | —H |
| ASU | -2-pyridazinyl | —CF₃ | —H |
| ASV | -2-pyridazinyl | —OCH₃ | —H |
| ASW | -2-pyridazinyl | —OCH₂CH₃ | —H |
| ASX | -2-pyridazinyl | —OCF₃ | —H |
| ASY | -2-pyridazinyl | -tert-butyl | —H |
| ASZ | -2-pyridazinyl | -iso-propyl | —H |
| ATA | -2-pyridazinyl | —CH₃ | —CH₃ |
| ATB | -2-pyridazinyl | —H | —H |
| ATC | -2-pyridazinyl | —H | —Cl |
| ATD | -2-pyridazinyl | —H | —Br |
| ATE | -2-pyridazinyl | —H | —F |
| ATF | -2-pyridazinyl | —H | —CH₃ |
| ATG | -2-pyridazinyl | —H | —CF₃ |
| ATH | -2-pyridazinyl | —H | —OCH₃ |
| ATI | -2-pyridazinyl | —H | —OCH₂CH₃ |
| ATJ | -2-pyridazinyl | —H | —OCF₃ |
| ATK | -2-pyridazinyl | —H | -tert-butyl |
| ATL | -2-pyridazinyl | —H | -iso-propyl |
| ATM | -3-(4-chloropyridazinyl) | —Cl | —H |
| ATN | -3-(4-chloropyridazinyl) | —Br | —H |
| ATO | -3-(4-chloropyridazinyl) | —F | —H |
| ATP | -3-(4-chloropyridazinyl) | —CH₃ | —H |
| ATQ | -3-(4-chloropyridazinyl) | —CF₃ | —H |
| ATR | -3-(4-chloropyridazinyl) | —OCH₃ | —H |
| ATS | -3-(4-chloropyridazinyl) | —OCH₂CH₃ | —H |
| ATT | -3-(4-chloropyridazinyl) | —OCF₃ | —H |
| ATU | -3-(4-chloropyridazinyl) | -tert-butyl | —H |
| ATV | -3-(4-chloropyridazinyl) | -iso-propyl | —H |
| ATW | -3-(4-chloropyridazinyl) | —CH₃ | —CH₃ |
| ATX | -3-(4-chloropyridazinyl) | —H | —H |
| ATY | -3-(4-chloropyridazinyl) | —H | —Cl |
| ATZ | -3-(4-chloropyridazinyl) | —H | —Br |
| AUA | -3-(4-chloropyridazinyl) | —H | —F |
| AUB | -3-(4-chloropyridazinyl) | —H | —CH₃ |
| AUC | -3-(4-chloropyridazinyl) | —H | —CF₃ |
| AUD | -3-(4-chloropyridazinyl) | —H | —OCH₃ |
| AUE | -3-(4-chloropyridazinyl) | —H | —OCH₂CH₃ |
| AUF | -3-(4-chloropyridazinyl) | —H | —OCF₃ |
| AUG | -3-(4-chloropyridazinyl) | —H | -tert-butyl |
| AUH | -3-(4-chloropyridazinyl) | —H | -iso-propyl |
| AUI | -3-(4-methylpyridazinyl) | —Cl | —H |
| AUJ | -3-(4-methylpyridazinyl) | —Br | —H |
| AUK | -3-(4-methylpyridazinyl) | —F | —H |
| AUL | -3-(4-methylpyridazinyl) | —CH₃ | —H |
| AUM | -3-(4-methylpyridazinyl) | —CF₃ | —H |
| AUN | -3-(4-methylpyridazinyl) | —OCH₃ | —H |
| AUO | -3-(4-methylpyridazinyl) | —OCH₂CH₃ | —H |
| AUP | -3-(4-methylpyridazinyl) | —OCF₃ | —H |
| AUQ | -3-(4-methylpyridazinyl) | -tert-butyl | —H |
| AUR | -3-(4-methylpyridazinyl) | -iso-propyl | —H |
| AUS | -3-(4-methylpyridazinyl) | —CH₃ | —CH₃ |
| AUT | -3-(4-methylpyridazinyl) | —H | —H |

TABLE II-continued

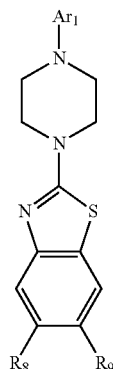

and pharmaceutically acceptable salts thereof, wherein:

| Compound | Ar$_1$ | R$_8$ | R$_9$ |
|---|---|---|---|
| AUU | -3-(4-methylpyridazinyl) | —H | —Cl |
| AUV | -3-(4-methylpyridazinyl) | —H | —Br |
| AUW | -3-(4-methylpyridazinyl) | —H | —F |
| AUX | -3-(4-methylpyridazinyl) | —H | —CH$_3$ |
| AUY | -3-(4-methylpyridazinyl) | —H | —CF$_3$ |
| AUZ | -3-(4-methylpyridazinyl) | —H | —OCH$_3$ |
| AVA | -3-(4-methylpyridazinyl) | —H | —OCH$_2$CH$_3$ |
| AVB | -3-(4-methylpyridazinyl) | —H | —OCF$_3$ |
| AVC | -3-(4-methylpyridazinyl) | —H | -tert-butyl |
| AVD | -3-(4-methylpyridazinyl) | —H | -iso-propyl |
| AVE | -4-thiazanyl | —Cl | —H |
| AVF | -4-thiazanyl | —Br | —H |
| AVG | -4-thiazanyl | —F | —H |
| AVH | -4-thiazanyl | —CH$_3$ | —H |
| AVI | -4-thiazanyl | —CF$_3$ | —H |
| AVJ | -4-thiazanyl | —OCH$_3$ | —H |
| AVK | -4-thiazanyl | —OCH$_2$CH$_3$ | —H |
| AVL | -4-thiazanyl | —OCF$_3$ | —H |
| AVM | -4-thiazanyl | -tert-butyl | —H |
| AVN | -4-thiazanyl | -iso-propyl | —H |
| AVO | -4-thiazanyl | —CH$_3$ | —CH$_3$ |
| AVP | -4-thiazanyl | —H | —H |
| AVQ | -4-thiazanyl | —H | —Cl |
| AVR | -4-thiazanyl | —H | —Br |
| AVS | -4-thiazanyl | —H | —F |
| AVT | -4-thiazanyl | —H | —CH$_3$ |
| AVU | -4-thiazanyl | —H | —CF$_3$ |
| AVV | -4-thiazanyl | —H | —OCH$_3$ |
| AVW | -4-thiazanyl | —H | —OCH$_2$CH$_3$ |
| AVX | -4-thiazanyl | —H | —OCF$_3$ |
| AVY | -4-thiazanyl | —H | -tert-butyl |
| AVZ | -4-thiazanyl | —H | -iso-propyl |
| AWA | -5-(4-chlorothiazanyl) | —Cl | —H |
| AWB | -5-(4-chlorothiazanyl) | —Br | —H |
| AWC | -5-(4-chlorothiazanyl) | —F | —H |
| AWD | -5-(4-chlorothiazanyl) | —CH$_3$ | —H |
| AWE | -5-(4-chlorothiazanyl) | —CF$_3$ | —H |
| AWF | -5-(4-chlorothiazanyl) | —OCH$_3$ | —H |
| AWG | -5-(4-chlorothiazanyl) | —OCH$_2$CH$_3$ | —H |
| AWH | -5-(4-chlorothiazanyl) | —OCF$_3$ | —H |
| AWI | -5-(4-chlorothiazanyl) | -tert-butyl | —H |
| AWJ | -5-(4-chlorothiazanyl) | -iso-propyl | —H |
| AWK | -5-(4-chlorothiazanyl) | —CH$_3$ | —CH$_3$ |
| AWL | -5-(4-chlorothiazanyl) | —H | —H |
| AWM | -5-(4-chlorothiazanyl) | —H | —Cl |
| AWN | -5-(4-chlorothiazanyl) | —H | —Br |
| AWO | -5-(4-chlorothiazanyl) | —H | —F |
| AWP | -5-(4-chlorothiazanyl) | —H | —CH$_3$ |
| AWQ | -5-(4-chlorothiazanyl) | —H | —CF$_3$ |
| AWR | -5-(4-chlorothiazanyl) | —H | —OCH$_3$ |
| AWS | -5-(4-chlorothiazanyl) | —H | —OCH$_2$CH$_3$ |
| AWT | -5-(4-chlorothiazanyl) | —H | —OCF$_3$ |
| AWU | -5-(4-chlorothiazanyl) | —H | -tert-butyl |
| AWV | -5-(4-chlorothiazanyl) | —H | -iso-propyl |
| AWW | -5-(4-methylthiazanyl) | —Cl | —H |
| AWX | -5-(4-methylthiazanyl) | —Br | —H |
| AWY | -5-(4-methylthiazanyl) | —F | —H |
| AWZ | -5-(4-methylthiazanyl) | —CH$_3$ | —H |

TABLE II-continued

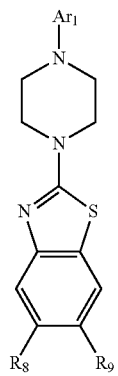

and pharmaceutically acceptable salts thereof, wherein:

| Compound | Ar$_1$ | R$_8$ | R$_9$ |
|---|---|---|---|
| AXA | -5-(4-methylthiazanyl) | —CF$_3$ | —H |
| AXB | -5-(4-methylthiazanyl) | —OCH$_3$ | —H |
| AXC | -5-(4-methylthiazanyl) | —OCH$_2$CH$_3$ | —H |
| AXD | -5-(4-methylthiazanyl) | —OCF$_3$ | —H |
| AXE | -5-(4-methylthiazanyl) | -tert-butyl | —H |
| AXF | -5-(4-methylthiazanyl) | -iso-propyl | —H |
| AXG | -5-(4-methylthiazanyl) | —CH$_3$ | —CH$_3$ |
| AXH | -5-(4-methylthiazanyl) | —H | —H |
| AXI | -5-(4-methylthiazanyl) | —H | —Cl |
| AXJ | -5-(4-methylthiazanyl) | —H | —Br |
| AXK | -5-(4-methylthiazanyl) | —H | —F |
| AXL | -5-(4-methylthiazanyl) | —H | —CH$_3$ |
| AXM | -5-(4-methylthiazanyl) | —H | —CF$_3$ |
| AXN | -5-(4-methylthiazanyl) | —H | —OCH$_3$ |
| AXO | -5-(4-methylthiazanyl) | —H | —OCH$_2$CH$_3$ |
| AXP | -5-(4-methylthiazanyl) | —H | —OCF$_3$ |
| AXQ | -5-(4-methylthiazanyl) | —H | -tert-butyl |
| AXR | -5-(4-methylthiazanyl) | —H | -iso-propyl |

TABLE III

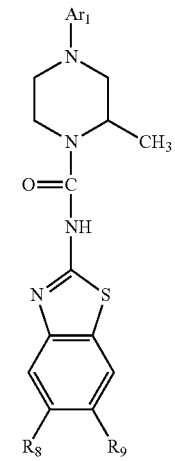

and pharmaceutically acceptable salts thereof, wherein:

| Compound | Ar$_1$ | R$_8$ | R$_9$ |
|---|---|---|---|
| AXS (a, b, and c) | -2-(3-chloropyridyl) | —Cl | —H |
| AXT (a, b, and c) | -2-(3-chloropyridyl) | —Br | —H |
| AXU (a, b, and c) | -2-(3-chloropyridyl) | —F | —H |
| AXV (a, b, and c) | -2-(3-chloropyridyl) | —CH$_3$ | —H |
| AXW (a, b, and c) | -2-(3-chloropyridyl) | —CF$_3$ | —H |
| AXX (a, b, and c) | -2-(3-chloropyridyl) | —OCH$_3$ | —H |
| AXY (a, b, and c) | -2-(3-chloropyridyl) | —OCH$_2$CH$_3$ | —H |
| AXZ (a, b, and c) | -2-(3-chloropyridyl) | —OCF$_3$ | —H |
| AYA (a, b, and c) | -2-(3-chloropyridyl) | -tert-butyl | —H |

TABLE III-continued

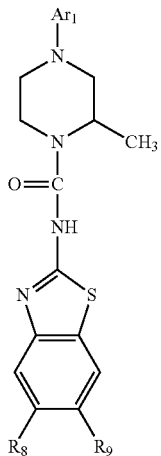

and pharmaceutically acceptable salts thereof, wherein:

| Compound | $Ar_1$ | $R_8$ | $R_9$ |
|---|---|---|---|
| AYB (a, b, and c) | -2-(3-chloropyridyl) | -iso-propyl | —H |
| AYC (a, b, and c) | -2-(3-chloropyridyl) | —$CH_3$ | —$CH_3$ |
| AYD (a, b, and c) | -2-(3-chloropyridyl) | —H | —H |
| AYE (a, b, and c) | -2-(3-chloropyridyl) | —H | —Cl |
| AYF (a, b, and c) | -2-(3-chloropyridyl) | —H | —Br |
| AYG (a, b, and c) | -2-(3-chloropyridyl) | —H | —F |
| AYH (a, b, and c) | -2-(3-chloropyridyl) | —H | —$CH_3$ |
| AYI (a, b, and c) | -2-(3-chloropyridyl) | —H | —$CF_3$ |
| AYJ (a, b, and c) | -2-(3-chloropyridyl) | —H | —$OCH_3$ |
| AYK (a, b, and c) | -2-(3-chloropyridyl) | —H | —$OCH_2CH_3$ |
| AYL (a, b, and c) | -2-(3-chloropyridyl) | —H | —$OCF_3$ |
| AYM (a, b, and c) | -2-(3-chloropyridyl) | —H | -tert-butyl |
| AYN (a, b, and c) | -2-(3-chloropyridyl) | —H | -iso-propyl |
| AYO (a, b, and c) | -2-(3-methylpyridyl) | —Cl | —H |
| AYP (a, b, and c) | -2-(3-methylpyridyl) | —Br | —H |
| AYQ (a, b, and c) | -2-(3-methylpyridyl) | —F | —H |
| AYR (a, b, and c) | -2-(3-methylpyridyl) | —$CH_3$ | —H |
| AYS (a, b, and c) | -2-(3-methylpyridyl) | —$CF_3$ | —H |
| AYT (a, b, and c) | -2-(3-methylpyridyl) | —$OCH_3$ | —H |
| AYU (a, b, and c) | -2-(3-methylpyridyl) | —$OCH_2CH_3$ | —H |
| AYV (a, b, and c) | -2-(3-methylpyridyl) | —$OCF_3$ | —H |
| AYW (a, b, and c) | -2-(3-methylpyridyl) | -tert-butyl | —H |
| AYX (a, b, and c) | -2-(3-methylpyridyl) | -iso-propyl | —H |
| AYY (a, b, and c) | -2-(3-methylpyridyl) | —$CH_3$ | —$CH_3$ |
| AYZ (a, b, and c) | -2-(3-methylpyridyl) | —H | —H |
| AZA (a, b, and c) | -2-(3-methylpyridyl) | —H | —Cl |
| AZB (a, b, and c) | -2-(3-methylpyridyl) | —H | —Br |
| AZC (a, b, and c) | -2-(3-methylpyridyl) | —H | —F |
| AZD (a, b, and c) | -2-(3-methylpyridyl) | —H | —$CH_3$ |
| AZE (a, b, and c) | -2-(3-methylpyridyl) | —H | —$CF_3$ |
| AZF (a, b, and c) | -2-(3-methylpyridyl) | —H | —$OCH_3$ |
| AZG (a, b, and c) | -2-(3-methylpyridyl) | —H | —$OCH_2CH_3$ |
| AZH (a, b, and c) | -2-(3-methylpyridyl) | —H | —$OCF_3$ |
| AZI (a, b, and c) | -2-(3-methylpyridyl) | —H | -tert-butyl |
| AZJ (a, b, and c) | -2-(3-methylpyridyl) | —H | -iso-propyl |
| AZK (a, b, and c) | -2-(3-$CF_3$-pyridyl) | —Cl | —H |
| AZL (a, b, and c) | -2-(3-$CF_3$-pyridyl) | —Br | —H |
| AZM (a, b, and c) | -2-(3-$CF_3$-pyridyl) | —F | —H |
| AZN (a, b, and c) | -2-(3-$CF_3$-pyridyl) | —$CH_3$ | —H |
| AZO (a, b, and c) | -2-(3-$CF_3$-pyridyl) | —$CF_3$ | —H |
| AZP (a, b, and c) | -2-(3-$CF_3$-pyridyl) | —$OCH_3$ | —H |
| AZQ (a, b, and c) | -2-(3-$CF_3$-pyridyl) | —$OCH_2CH_3$ | —H |
| AZR (a, b, and c) | -2-(3-$CF_3$-pyridyl) | —$OCF_3$ | —H |
| AZS (a, b, and c) | -2-(3-$CF_3$-pyridyl) | -tert-butyl | —H |
| AZT (a, b, and c) | -2-(3-$CF_3$-pyridyl) | -iso-propyl | —H |
| AZU (a, b, and c) | -2-(3-$CF_3$-pyridyl) | —$CH_3$ | —$CH_3$ |
| AZV (a, b, and c) | -2-(3-$CF_3$-pyridyl) | —H | —H |
| AZW (a, b, and c) | -2-(3-$CF_3$-pyridyl) | —H | —Cl |
| AZX (a, b, and c) | -2-(3-$CF_3$-pyridyl) | —H | —Br |
| AZY (a, b, and c) | -2-(3-$CF_3$-pyridyl) | —H | —F |
| AZZ (a, b, and c) | -2-(3-$CF_3$-pyridyl) | —H | —$CH_3$ |
| BAA (a, b, and c) | -2-(3-$CF_3$-pyridyl) | —H | —$CF_3$ |
| BAB (a, b, and c) | -2-(3-$CF_3$-pyridyl) | —H | —$OCH_3$ |
| BAC (a, b, and c) | -2-(3-$CF_3$-pyridyl) | —H | —$OCH_2CH_3$ |
| BAD (a, b, and c) | -2-(3-$CF_3$-pyridyl) | —H | —$OCF_3$ |
| BAE (a, b, and c) | -2-(3-$CF_3$-pyridyl) | —H | -tert-butyl |
| BAF (a, b, and c) | -2-(3-$CF_3$-pyridyl) | —H | -iso-propyl |
| BAG (a, b, and c) | -4-(5-chloropyrimidinyl) | —Cl | —H |
| BAH (a, b, and c) | -4-(5-chloropyrimidinyl) | —Br | —H |
| BAI (a, b, and c) | -4-(5-chloropyrimidinyl) | —F | —H |
| BAJ (a, b, and c) | -4-(5-chloropyrimidinyl) | —$CH_3$ | —H |
| BAK (a, b, and c) | -4-(5-chloropyrimidinyl) | —$CF_3$ | —H |
| BAL (a, b, and c) | -4-(5-chloropyrimidinyl) | —$OCH_3$ | —H |
| BAM (a, b, and c) | -4-(5-chloropyrimidinyl) | —$OCH_2CH_3$ | —H |
| BAN (a, b, and c) | -4-(5-chloropyrimidinyl) | —$OCF_3$ | —H |
| BAO (a, b, and c) | -4-(5-chloropyrimidinyl) | -tert-butyl | —H |
| BAP (a, b, and c) | -4-(5-chloropyrimidinyl) | -iso-propyl | —H |
| BAQ (a, b, and c) | -4-(5-chloropyrimidinyl) | —$CH_3$ | —$CH_3$ |
| BAR (a, b, and c) | -4-(5-chloropyrimidinyl) | —H | —H |
| BAS (a, b, and c) | -4-(5-chloropyrimidinyl) | —H | —Cl |
| BAT (a, b, and c) | -4-(5-chloropyrimidinyl) | —H | —Br |
| BAU (a, b, and c) | -4-(5-chloropyrimidinyl) | —H | —F |
| BAV (a, b, and c) | -4-(5-chloropyrimidinyl) | —H | —$CH_3$ |
| BAW (a, b, and c) | -4-(5-chloropyrimidinyl) | —H | —$CF_3$ |
| BAX (a, b, and c) | -4-(5-chloropyrimidinyl) | —H | —$OCH_3$ |
| BAY (a, b, and c) | -4-(5-chloropyrimidinyl) | —H | —$OCH_2CH_3$ |
| BAZ (a, b, and c) | -4-(5-chloropyrimidinyl) | —H | —$OCF_3$ |
| BBA (a, b, and c) | -4-(5-chloropyrimidinyl) | —H | -tert-butyl |
| BBB (a, b, and c) | -4-(5-chloropyrimidinyl) | —H | -iso-propyl |
| BBC (a, b, and c) | -4-(5-methylpyrimidinyl) | —Cl | —H |
| BBD (a, b, and c) | -4-(5-methylpyrimidinyl) | —Br | —H |
| BBE (a, b, and c) | -4-(5-methylpyrimidinyl) | —F | —H |
| BBF (a, b, and c) | -4-(5-methylpyrimidinyl) | —$CH_3$ | —H |
| BBG (a, b, and c) | -4-(5-methylpyrimidinyl) | —$CF_3$ | —H |
| BBH (a, b, and c) | -4-(5-methylpyrimidinyl) | —$OCH_3$ | —H |
| BBI (a, b, and c) | -4-(5-methylpyrimidinyl) | —$OCH_2CH_3$ | —H |
| BBJ (a, b, and c) | -4-(5-methylpyrimidinyl) | —$OCF_3$ | —H |
| BBK (a, b, and c) | -4-(5-methylpyrimidinyl) | -tert-butyl | —H |
| BBL (a, b, and c) | -4-(5-methylpyrimidinyl) | -iso-propyl | —H |
| BBM (a, b, and c) | -4-(5-methylpyrimidinyl) | —$CH_3$ | —$CH_3$ |
| BBN (a, b, and c) | -4-(5-methylpyrimidinyl) | —H | —H |
| BBO (a, b, and c) | -4-(5-methylpyrimidinyl) | —H | —Cl |
| BBP (a, b, and c) | -4-(5-methylpyrimidinyl) | —H | —Br |
| BBQ (a, b, and c) | -4-(5-methylpyrimidinyl) | —H | —F |
| BBR (a, b, and c) | -4-(5-methylpyrimidinyl) | —H | —$CH_3$ |
| BBS (a, b, and c) | -4-(5-methylpyrimidinyl) | —H | —$CF_3$ |
| BBT (a, b, and c) | -4-(5-methylpyrimidinyl) | —H | —$OCH_3$ |
| BBU (a, b, and c) | -4-(5-methylpyrimidinyl) | —H | —$OCH_2CH_3$ |
| BBV (a, b, and c) | -4-(5-methylpyrimidinyl) | —H | —$OCF_3$ |
| BBW (a, b, and c) | -4-(5-methylpyrimidinyl) | —H | -tert-butyl |
| BBX (a, b, and c) | -4-(5-methylpyrimidinyl) | —H | -iso-propyl |
| BBY (a, b, and c) | -2-pyrazinyl | —Cl | —H |
| BBZ (a, b, and c) | -2-pyrazinyl | —Br | —H |
| BCA (a, b, and c) | -2-pyrazinyl | —F | —H |
| BCB (a, b, and c) | -2-pyrazinyl | —$CH_3$ | —H |
| BCC (a, b, and c) | -2-pyrazinyl | —$CF_3$ | —H |
| BCD (a, b, and c) | -2-pyrazinyl | —$OCH_3$ | —H |
| BCE (a, b, and c) | -2-pyrazinyl | —$OCH_2CH_3$ | —H |

TABLE III-continued

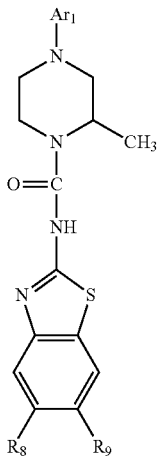

and pharmaceutically acceptable salts thereof, wherein:

| Compound | Ar₁ | R₈ | R₉ |
|---|---|---|---|
| BCF (a, b, and c) | -2-pyrazinyl | —OCF₃ | —H |
| BCG (a, b, and c) | -2-pyrazinyl | -tert-butyl | —H |
| BCH (a, b, and c) | -2-pyrazinyl | -iso-propyl | —H |
| BCI (a, b, and c) | -2-pyrazinyl | —CH₃ | —CH₃ |
| BCJ (a, b, and c) | -2-pyrazinyl | —H | —H |
| BCK (a, b, and c) | -2-pyrazinyl | —H | —Cl |
| BCL (a, b, and c) | -2-pyrazinyl | —H | —Br |
| BCM (a, b, and c) | -2-pyrazinyl | —H | —F |
| BCN (a, b, and c) | -2-pyrazinyl | —H | —CH₃ |
| BCO (a, b, and c) | -2-pyrazinyl | —H | —CF₃ |
| BCP (a, b, and c) | -2-pyrazinyl | —H | —OCH₃ |
| BCQ (a, b, and c) | -2-pyrazinyl | —H | —OCH₂CH₃ |
| BCR (a, b, and c) | -2-pyrazinyl | —H | —OCF₃ |
| BCS (a, b, and c) | -2-pyrazinyl | —H | -tert-butyl |
| BCT (a, b, and c) | -2-pyrazinyl | —H | -iso-propyl |
| BCU (a, b, and c) | -2-(3-chloropyrazinyl) | —Cl | —H |
| BCV (a, b, and c) | -2-(3-chloropyrazinyl) | —Br | —H |
| BCW (a, b, and c) | -2-(3-chloropyrazinyl) | —F | —H |
| BCX (a, b, and c) | -2-(3-chloropyrazinyl) | —CH₃ | —H |
| BCY (a, b, and c) | -2-(3-chloropyrazinyl) | —CF₃ | —H |
| BCZ (a, b, and c) | -2-(3-chloropyrazinyl) | —OCH₃ | —H |
| BDA (a, b, and c) | -2-(3-chloropyrazinyl) | —OCH₂CH₃ | —H |
| BDB (a, b, and c) | -2-(3-chloropyrazinyl) | —OCF₃ | —H |
| BDC (a, b, and c) | -2-(3-chloropyrazinyl) | -tert-butyl | —H |
| BDD (a, b, and c) | -2-(3-chloropyrazinyl) | -iso-propyl | —H |
| BDE (a, b, and c) | -2-(3-chloropyrazinyl) | —CH₃ | —CH₃ |
| BDF (a, b, and c) | -2-(3-chloropyrazinyl) | —H | —H |
| BDG (a, b, and c) | -2-(3-chloropyrazinyl) | —H | —Cl |
| BDH (a, b, and c) | -2-(3-chloropyrazinyl) | —H | —Br |
| BDI (a, b, and c) | -2-(3-chloropyrazinyl) | —H | —F |
| BDJ (a, b, and c) | -2-(3-chloropyrazinyl) | —H | —CH₃ |
| BDK (a, b, and c) | -2-(3-chloropyrazinyl) | —H | —CF₃ |
| BDL (a, b, and c) | -2-(3-chloropyrazinyl) | —H | —OCH₃ |
| BDM (a, b, and c) | -2-(3-chloropyrazinyl) | —H | —OCH₂CH₃ |
| BDN (a, b, and c) | -2-(3-chloropyrazinyl) | —H | —OCF₃ |
| BDO (a, b, and c) | -2-(3-chloropyrazinyl) | —H | -tert-butyl |
| BDP (a, b, and c) | -2-(3-chloropyrazinyl) | —H | -iso-propyl |
| BDQ (a, b, and c) | -2-(3-methylpyrazinyl) | —Cl | —H |
| BDR (a, b, and c) | -2-(3-methylpyrazinyl) | —Br | —H |
| BDS (a, b, and c) | -2-(3-methylpyrazinyl) | —F | —H |
| BDT (a, b, and c) | -2-(3-methylpyrazinyl) | —CH₃ | —H |
| BDU (a, b, and c) | -2-(3-methylpyrazinyl) | —CF₃ | —H |
| BDV (a, b, and c) | -2-(3-methylpyrazinyl) | —OCH₃ | —H |
| BDW (a, b, and c) | -2-(3-methylpyrazinyl) | —OCH₂CH₃ | —H |
| BDX (a, b, and c) | -2-(3-methylpyrazinyl) | —OCF₃ | —H |
| BDY (a, b, and c) | -2-(3-methylpyrazinyl) | -tert-butyl | —H |
| BDZ (a, b, and c) | -2-(3-methylpyrazinyl) | -iso-propyl | —H |
| BEA (a, b, and c) | -2-(3-methylpyrazinyl) | —CH₃ | —CH₃ |
| BEB (a, b, and c) | -2-(3-methylpyrazinyl) | —H | —H |
| BEC (a, b, and c) | -2-(3-methylpyrazinyl) | —H | —Cl |
| BED (a, b, and c) | -2-(3-methylpyrazinyl) | —H | —Br |
| BEE (a, b, and c) | -2-(3-methylpyrazinyl) | —H | —F |
| BEF (a, b, and c) | -2-(3-methylpyrazinyl) | —H | —CH₃ |
| BEG (a, b, and c) | -2-(3-methylpyrazinyl) | —H | —CF₃ |

TABLE III-continued

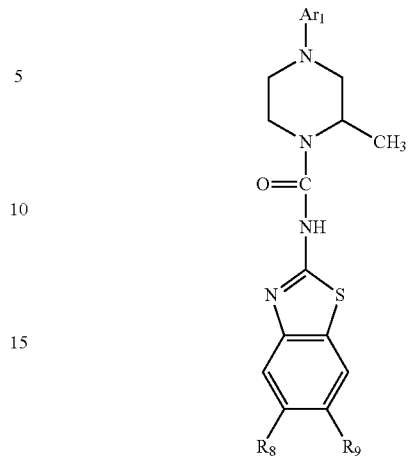

and pharmaceutically acceptable salts thereof, wherein:

| Compound | Ar₁ | R₈ | R₉ |
|---|---|---|---|
| BEH (a, b, and c) | -2-(3-methylpyrazinyl) | —H | —OCH₃ |
| BEI (a, b, and c) | -2-(3-methylpyrazinyl) | —H | —OCH₂CH₃ |
| BEJ (a, b, and c) | -2-(3-methylpyrazinyl) | —H | —OCF₃ |
| BEK (a, b, and c) | -2-(3-methylpyrazinyl) | —H | -tert-butyl |
| BEL (a, b, and c) | -2-(3-methylpyrazinyl) | —H | -iso-propyl |
| BEM (a, b, and c) | -2-pyridazinyl | —Cl | —H |
| BEN (a, b, and c) | -2-pyridazinyl | —Br | —H |
| BEO (a, b, and c) | -2-pyridazinyl | —F | —H |
| BEP (a, b, and c) | -2-pyridazinyl | —CH₃ | —H |
| BEQ (a, b, and c) | -2-pyridazinyl | —CF₃ | —H |
| BER (a, b, and c) | -2-pyridazinyl | —OCH₃ | —H |
| BES (a, b, and c) | -2-pyridazinyl | —OCH₂CH₃ | —H |
| BET (a, b, and c) | -2-pyridazinyl | —OCF₃ | —H |
| BEU (a, b, and c) | -2-pyridazinyl | -tert-butyl | —H |
| BEV (a, b, and c) | -2-pyridazinyl | -iso-propyl | —H |
| BEW (a, b, and c) | -2-pyridazinyl | —CH₃ | —CH₃ |
| BEX (a, b, and c) | -2-pyridazinyl | —H | —H |
| BEY (a, b, and c) | -2-pyridazinyl | —H | —Cl |
| BEZ (a, b, and c) | -2-pyridazinyl | —H | —Br |
| BFA (a, b, and c) | -2-pyridazinyl | —H | —F |
| BFB (a, b, and c) | -2-pyridazinyl | —H | —CH₃ |
| BFC (a, b, and c) | -2-pyridazinyl | —H | —CF₃ |
| BFD (a, b, and c) | -2-pyridazinyl | —H | —OCH₃ |
| BFE (a, b, and c) | -2-pyridazinyl | —H | —OCH₂CH₃ |
| BFF (a, b, and c) | -2-pyridazinyl | —H | —OCF₃ |
| BFG (a, b, and c) | -2-pyridazinyl | —H | -tert-butyl |
| BFH (a, b, and c) | -2-pyridazinyl | —H | -iso-propyl |
| BFI (a, b, and c) | -3-(4-chloropyridazinyl) | —Cl | —H |
| BFJ (a, b, and c) | -3-(4-chloropyridazinyl) | —Br | —H |
| BFK (a, b, and c) | -3-(4-chloropyridazinyl) | —F | —H |
| BFL (a, b, and c) | -3-(4-chloropyridazinyl) | —CH₃ | —H |
| BFM (a, b, and c) | -3-(4-chloropyridazinyl) | —CF₃ | —H |
| BFN (a, b, and c) | -3-(4-chloropyridazinyl) | —OCH₃ | —H |
| BFO (a, b, and c) | -3-(4-chloropyridazinyl) | —OCH₂CH₃ | —H |
| BFP (a, b, and c) | -3-(4-chloropyridazinyl) | —OCF₃ | —H |
| BFQ (a, b, and c) | -3-(4-chloropyridazinyl) | -tert-butyl | —H |
| BFR (a, b, and c) | -3-(4-chloropyridazinyl) | -iso-propyl | —H |
| BFS (a, b, and c) | -3-(4-chloropyridazinyl) | —CH₃ | —CH₃ |
| BFT (a, b, and c) | -3-(4-chloropyridazinyl) | —H | —H |
| BFU (a, b, and c) | -3-(4-chloropyridazinyl) | —H | —Cl |
| BFV (a, b, and c) | -3-(4-chloropyridazinyl) | —H | —Br |
| BFW (a, b, and c) | -3-(4-chloropyridazinyl) | —H | —F |
| BFX (a, b, and c) | -3-(4-chloropyridazinyl) | —H | —CH₃ |
| BFY (a, b, and c) | -3-(4-chloropyridazinyl) | —H | —CF₃ |
| BFZ (a, b, and c) | -3-(4-chloropyridazinyl) | —H | —OCH₃ |
| BGA (a, b, and c) | -3-(4-chloropyridazinyl) | —H | —OCH₂CH₃ |
| BGB (a, b, and c) | -3-(4-chloropyridazinyl) | —H | —OCF₃ |
| BGC (a, b, and c) | -3-(4-chloropyridazinyl) | —H | -tert-butyl |
| BGD (a, b, and c) | -3-(4-chloropyridazinyl) | —H | -iso-propyl |
| BGE (a, b, and c) | -3-(4-methylpyridazinyl) | —Cl | —H |
| BGF (a, b, and c) | -3-(4-methylpyridazinyl) | —Br | —H |
| BGG (a, b, and c) | -3-(4-methylpyridazinyl) | —F | —H |
| BGH (a, b, and c) | -3-(4-methylpyridazinyl) | —CH₃ | —H |
| BGI (a, b, and c) | -3-(4-methylpyridazinyl) | —CF₃ | —H |

TABLE III-continued

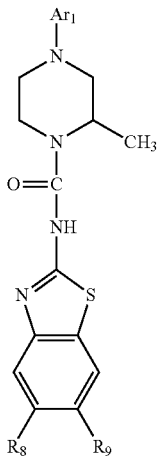

and pharmaceutically acceptable salts thereof, wherein:

| Compound | $Ar_1$ | $R_8$ | $R_9$ |
|---|---|---|---|
| BGJ (a, b, and c) | -3-(4-methylpyridazinyl) | —$OCH_3$ | —H |
| BGK (a, b, and c) | -3-(4-methylpyridazinyl) | —$OCH_2CH_3$ | —H |
| BGL (a, b, and c) | -3-(4-methylpyridazinyl) | —$OCF_3$ | —H |
| BGM (a, b, and c) | -3-(4-methylpyridazinyl) | -tert-butyl | —H |
| BGN (a, b, and c) | -3-(4-methylpyridazinyl) | -iso-propyl | —H |
| BGO (a, b, and c) | -3-(4-methylpyridazinyl) | —$CH_3$ | —$CH_3$ |
| BGP (a, b, and c) | -3-(4-methylpyridazinyl) | —H | —H |
| BGQ (a, b, and c) | -3-(4-methylpyridazinyl) | —H | —Cl |
| BGR (a, b, and c) | -3-(4-methylpyridazinyl) | —H | —Br |
| BGS (a, b, and c) | -3-(4-methylpyridazinyl) | —H | —F |
| BGT (a, b, and c) | -3-(4-methylpyridazinyl) | —H | —$CH_3$ |
| BGU (a, b, and c) | -3-(4-methylpyridazinyl) | —H | —$CF_3$ |
| BGV (a, b, and c) | -3-(4-methylpyridazinyl) | —H | —$OCH_3$ |
| BGW (a, b, and c) | -3-(4-methylpyridazinyl) | —H | —$OCH_2CH_3$ |
| BGX (a, b, and c) | -3-(4-methylpyridazinyl) | —H | —$OCF_3$ |
| BGY (a, b, and c) | -3-(4-methylpyridazinyl) | —H | -tert-butyl |
| BGZ (a, b, and c) | -3-(4-methylpyridazinyl) | —H | -iso-propyl |
| BHA (a, b, and c) | -4-thiazanyl | —Cl | —H |
| BHB (a, b, and c) | -4-thiazanyl | —Br | —H |
| BHC (a, b, and c) | -4-thiazanyl | —F | —H |
| BHD (a, b, and c) | -4-thiazanyl | —$CH_3$ | —H |
| BHE (a, b, and c) | -4-thiazanyl | —$CF_3$ | —H |
| BHF (a, b, and c) | -4-thiazanyl | —$OCH_3$ | —H |
| BHG (a, b, and c) | -4-thiazanyl | —$OCH_2CH_3$ | —H |
| BHH (a, b, and c) | -4-thiazanyl | —$OCF_3$ | —H |
| BHI (a, b, and c) | -4-thiazanyl | -tert-butyl | —H |
| BHJ (a, b, and c) | -4-thiazanyl | -iso-propyl | —H |
| BHK (a, b, and c) | -4-thiazanyl | —$CH_3$ | —$CH_3$ |
| BHL (a, b, and c) | -4-thiazanyl | —H | —H |
| BHM (a, b, and c) | -4-thiazanyl | —H | —Cl |
| BHN (a, b, and c) | -4-thiazanyl | —H | —Br |
| BHO (a, b, and c) | -4-thiazanyl | —H | —F |
| BHP (a, b, and c) | -4-thiazanyl | —H | —$CH_3$ |
| BHQ (a, b, and c) | -4-thiazanyl | —H | —$CF_3$ |
| BHR (a, b, and c) | -4-thiazanyl | —H | —$OCH_3$ |
| BHS (a, b, and c) | -4-thiazanyl | —H | —$OCH_2CH_3$ |
| BHT (a, b, and c) | -4-thiazanyl | —H | —$OCF_3$ |
| BHU (a, b, and c) | -4-thiazanyl | —H | -tert-butyl |
| BHV (a, b, and c) | -4-thiazanyl | —H | -iso-propyl |
| BHW (a, b, and c) | -5-(4-chlorothiazanyl) | —Cl | —H |
| BHX (a, b, and c) | -5-(4-chlorothiazanyl) | —Br | —H |
| BHY (a, b, and c) | -5-(4-chlorothiazanyl) | —F | —H |
| BHZ (a, b, and c) | -5-(4-chlorothiazanyl) | —$CH_3$ | —H |
| BIA (a, b, and c) | -5-(4-chlorothiazanyl) | —$CF_3$ | —H |
| BIB (a, b, and c) | -5-(4-chlorothiazanyl) | —$OCH_3$ | —H |
| BIC (a, b, and c) | -5-(4-chlorothiazanyl) | —$OCH_2CH_3$ | —H |
| BID (a, b, and c) | -5-(4-chlorothiazanyl) | —$OCF_3$ | —H |
| BIE (a, b, and c) | -5-(4-chlorothiazanyl) | -tert-butyl | —H |
| BIF (a, b, and c) | -5-(4-chlorothiazanyl) | -iso-propyl | —H |
| BIG (a, b, and c) | -5-(4-chlorothiazanyl) | —$CH_3$ | —$CH_3$ |
| BIH (a, b, and c) | -5-(4-chlorothiazanyl) | —H | —H |
| BII (a, b, and c) | -5-(4-chlorothiazanyl) | —H | —Cl |

TABLE III-continued

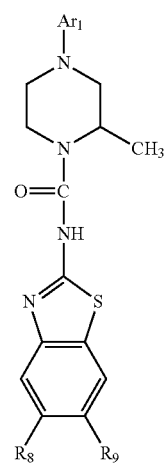

and pharmaceutically acceptable salts thereof, wherein:

| Compound | $Ar_1$ | $R_8$ | $R_9$ |
|---|---|---|---|
| BIJ (a, b, and c) | -5-(4-chlorothiazanyl) | —H | —Br |
| BIK (a, b, and c) | -5-(4-chlorothiazanyl) | —H | —F |
| BIL (a, b, and c) | -5-(4-chlorothiazanyl) | —H | —$CH_3$ |
| BIM (a, b, and c) | -5-(4-chlorothiazanyl) | —H | —$CF_3$ |
| BIN (a, b, and c) | -5-(4-chlorothiazanyl) | —H | —$OCH_3$ |
| BIO (a, b, and c) | -5-(4-chlorothiazanyl) | —H | —$OCH_2CH_3$ |
| BIP (a, b, and c) | -5-(4-chlorothiazanyl) | —H | —$OCF_3$ |
| BIQ (a, b, and c) | -5-(4-chlorothiazanyl) | —H | -tert-butyl |
| BIR (a, b, and c) | -5-(4-chlorothiazanyl) | —H | -iso-propyl |
| BIS (a, b, and c) | -5-(4-methylthiazanyl) | —Cl | —H |
| BIT (a, b, and c) | -5-(4-methylthiazanyl) | —Br | —H |
| BIU (a, b, and c) | -5-(4-methylthiazanyl) | —F | —H |
| BIV (a, b, and c) | -5-(4-methylthiazanyl) | —$CH_3$ | —H |
| BIW (a, b, and c) | -5-(4-methylthiazanyl) | —$CF_3$ | —H |
| BIX (a, b, and c) | -5-(4-methylthiazanyl) | —$OCH_3$ | —H |
| BIY (a, b, and c) | -5-(4-methylthiazanyl) | —$OCH_2CH_3$ | —H |
| BIZ (a, b, and c) | -5-(4-methylthiazanyl) | —$OCF_3$ | —H |
| BJA (a, b, and c) | -5-(4-methylthiazanyl) | -tert-butyl | —H |
| BJB (a, b, and c) | -5-(4-methylthiazanyl) | -iso-propyl | —H |
| BJC (a, b, and c) | -5-(4-methylthiazanyl) | —$CH_3$ | —$CH_3$ |
| BJD (a, b, and c) | -5-(4-methylthiazanyl) | —H | —H |
| BJE (a, b, and c) | -5-(4-methylthiazanyl) | —H | —Cl |
| BJF (a, b, and c) | -5-(4-methylthiazanyl) | —H | —Br |
| BJG (a, b, and c) | -5-(4-methylthiazanyl) | —H | —F |
| BJH (a, b, and c) | -5-(4-methylthiazanyl) | —H | —$CH_3$ |
| BJI (a, b, and c) | -5-(4-methylthiazanyl) | —H | —$CF_3$ |
| BJJ (a, b, and c) | -5-(4-methylthiazanyl) | —H | —$OCH_3$ |
| BJK (a, b, and c) | -5-(4-methylthiazanyl) | —H | —$OCH_2CH_3$ |
| BJL (a, b, and c) | -5-(4-methylthiazanyl) | —H | —$OCF_3$ |
| BJM (a, b, and c) | -5-(4-methylthiazanyl) | —H | -tert-butyl |
| BJN (a, b, and c) | -5-(4-methylthiazanyl) | —H | -iso-propyl |

"a" means the Benzoazolylpiperazine Compound is racemic.

"b" means the carbon atom of the piperazine ring attached to the methyl group is in the R configuration.

"c" means the carbon atom of the piperazine ring attached to the methyl group is in the S configuration.

TABLE IV

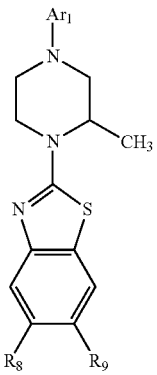

and pharmaceutically acceptable salts thereof, wherein:

| Compound | Ar$_1$ | R$_8$ | R$_9$ |
|---|---|---|---|
| BJO (a, b, and c) | -2-(3-chloropyridyl) | —Cl | —H |
| BJP (a, b, and c) | -2-(3-chloropyridyl) | —Br | —H |
| BJQ (a, b, and c) | -2-(3-chloropyridyl) | —F | —H |
| BJR (a, b, and c) | -2-(3-chloropyridyl) | —CH$_3$ | —H |
| BJS (a, b, and c) | -2-(3-chloropyridyl) | —CF$_3$ | —H |
| BJT (a, b, and c) | -2-(3-chloropyridyl) | —OCH$_3$ | —H |
| BJU (a, b, and c) | -2-(3-chloropyridyl) | —OCH$_2$CH$_3$ | —H |
| BJV (a, b, and c) | -2-(3-chloropyridyl) | —OCF$_3$ | —H |
| BJW (a, b, and c) | -2-(3-chloropyridyl) | -tert-butyl | —H |
| BJX (a, b, and c) | -2-(3-chloropyridyl) | -iso-propyl | —H |
| BJY (a, b, and c) | -2-(3-chloropyridyl) | —CH$_3$ | —CH$_3$ |
| BJZ (a, b, and c) | -2-(3-chloropyridyl) | —H | —H |
| BKA (a, b, and c) | -2-(3-chloropyridyl) | —H | —Cl |
| BKB (a, b, and c) | -2-(3-chloropyridyl) | —H | —Br |
| BKC (a, b, and c) | -2-(3-chloropyridyl) | —H | —F |
| BKD (a, b, and c) | -2-(3-chloropyridyl) | —H | —CH$_3$ |
| BKE (a, b, and c) | -2-(3-chloropyridyl) | —H | —CF$_3$ |
| BKF (a, b, and c) | -2-(3-chloropyridyl) | —H | —OCH$_3$ |
| BKG (a, b, and c) | -2-(3-chloropyridyl) | —H | —OCH$_2$CH$_3$ |
| BKH (a, b, and c) | -2-(3-chloropyridyl) | —H | —OCF$_3$ |
| BKI (a, b, and c) | -2-(3-chloropyridyl) | —H | -tert-butyl |
| BKJ (a, b, and c) | -2-(3-chloropyridyl) | —H | -iso-propyl |
| BKK (a, b, and c) | -2-(3-methylpyridyl) | —Cl | —H |
| BKL (a, b, and c) | -2-(3-methylpyridyl) | —Br | —H |
| BKM (a, b, and c) | -2-(3-methylpyridyl) | —F | —H |
| BKN (a, b, and c) | -2-(3-methylpyridyl) | —CH$_3$ | —H |
| BKO (a, b, and c) | -2-(3-methylpyridyl) | —CF$_3$ | —H |
| BKP (a, b, and c) | -2-(3-methylpyridyl) | —OCH$_3$ | —H |
| BKQ (a, b, and c) | -2-(3-methylpyridyl) | —OCH$_2$CH$_3$ | —H |
| BKR (a, b, and c) | -2-(3-methylpyridyl) | —OCF$_3$ | —H |
| BKS (a, b, and c) | -2-(3-methylpyridyl) | -tert-butyl | —H |
| BKT (a, b, and c) | -2-(3-methylpyridyl) | -iso-propyl | —H |
| BKU (a, b, and c) | -2-(3-methylpyridyl) | —CH$_3$ | —CH$_3$ |
| BKV (a, b, and c) | -2-(3-methylpyridyl) | —H | —H |
| BKW (a, b, and c) | -2-(3-methylpyridyl) | —H | —Cl |
| BKX (a, b, and c) | -2-(3-methylpyridyl) | —H | —Br |
| BKY (a, b, and c) | -2-(3-methylpyridyl) | —H | —F |
| BKZ (a, b, and c) | -2-(3-methylpyridyl) | —H | —CH$_3$ |
| BLA (a, b, and c) | -2-(3-methylpyridyl) | —H | —CF$_3$ |
| BLB (a, b, and c) | -2-(3-methylpyridyl) | —H | —OCH$_3$ |
| BLC (a, b, and c) | -2-(3-methylpyridyl) | —H | —OCH$_2$CH$_3$ |
| BLD (a, b, and c) | -2-(3-methylpyridyl) | —H | —OCF$_3$ |
| BLE (a, b, and c) | -2-(3-methylpyridyl) | —H | -tert-butyl |
| BLF (a, b, and c) | -2-(3-methylpyridyl) | —H | -iso-propyl |
| BLG (a, b, and c) | -2-(3-CF$_3$-pyridyl) | —Cl | —H |
| BLH (a, b, and c) | -2-(3-CF$_3$-pyridyl) | —Br | —H |
| BLI (a, b, and c) | -2-(3-CF$_3$-pyridyl) | —F | —H |
| BLJ (a, b, and c) | -2-(3-CF$_3$-pyridyl) | —CH$_3$ | —H |
| BLK (a, b, and c) | -2-(3-CF$_3$-pyridyl) | —CF$_3$ | —H |
| BLL (a, b, and c) | -2-(3-CF$_3$-pyridyl) | —OCH$_3$ | —H |
| BLM (a, b, and c) | -2-(3-CF$_3$-pyridyl) | —OCH$_2$CH$_3$ | —H |
| BLN (a, b, and c) | -2-(3-CF$_3$-pyridyl) | —OCF$_3$ | —H |
| BLO (a, b, and c) | -2-(3-CF$_3$-pyridyl) | -tert-butyl | —H |
| BLP (a, b, and c) | -2-(3-CF$_3$-pyridyl) | -iso-propyl | —H |
| BLQ (a, b, and c) | -2-(3-CF$_3$-pyridyl) | —CH$_3$ | —CH$_3$ |
| BLR (a, b, and c) | -2-(3-CF$_3$-pyridyl) | —H | —H |
| BLS (a, b, and c) | -2-(3-CF$_3$-pyridyl) | —H | —Cl |
| BLT (a, b, and c) | -2-(3-CF$_3$-pyridyl) | —H | —Br |

TABLE IV-continued

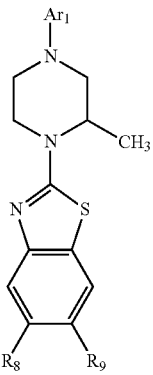

and pharmaceutically acceptable salts thereof, wherein:

| Compound | Ar$_1$ | R$_8$ | R$_9$ |
|---|---|---|---|
| BLU (a, b, and c) | -2-(3-CF$_3$-pyridyl) | —H | —F |
| BLV (a, b, and c) | -2-(3-CF$_3$-pyridyl) | —H | —CH$_3$ |
| BLW (a, b, and c) | -2-(3-CF$_3$-pyridyl) | —H | —CF$_3$ |
| BLX (a, b, and c) | -2-(3-CF$_3$-pyridyl) | —H | —OCH$_3$ |
| BLY (a, b, and c) | -2-(3-CF$_3$-pyridyl) | —H | —OCH$_2$CH$_3$ |
| BLZ (a, b, and c) | -2-(3-CF$_3$-pyridyl) | —H | —OCF$_3$ |
| BMA (a, b, and c) | -2-(3-CF$_3$-pyridyl) | —H | -tert-butyl |
| BMB (a, b, and c) | -2-(3-CF$_3$-pyridyl) | —H | -iso-propyl |
| BMC (a, b, and c) | -4-(5-chloropyrimidinyl) | —Cl | —H |
| BMD (a, b, and c) | -4-(5-chloropyrimidinyl) | —Br | —H |
| BME (a, b, and c) | -4-(5-chloropyrimidinyl) | —F | —H |
| BMF (a, b, and c) | -4-(5-chloropyrimidinyl) | —CH$_3$ | —H |
| BMG (a, b, and c) | -4-(5-chloropyrimidinyl) | —CF$_3$ | —H |
| BMH (a, b, and c) | -4-(5-chloropyrimidinyl) | —OCH$_3$ | —H |
| BMI (a, b, and c) | -4-(5-chloropyrimidinyl) | —OCH$_2$CH$_3$ | —H |
| BMJ (a, b, and c) | -4-(5-chloropyrimidinyl) | —OCF$_3$ | —H |
| BMK (a, b, and c) | -4-(5-chloropyrimidinyl) | -tert-butyl | —H |
| BML (a, b, and c) | -4-(5-chloropyrimidinyl) | -iso-propyl | —H |
| BMM (a, b, and c) | -4-(5-chloropyrimidinyl) | —CH$_3$ | —CH$_3$ |
| BMN (a, b, and c) | -4-(5-chloropyrimidinyl) | —H | —H |
| BMO (a, b, and c) | -4-(5-chloropyrimidinyl) | —H | —Cl |
| BMP (a, b, and c) | -4-(5-chloropyrimidinyl) | —H | —Br |
| BMQ (a, b, and c) | -4-(5-chloropyrimidinyl) | —H | —F |
| BMR (a, b, and c) | -4-(5-chloropyrimidinyl) | —H | —CH$_3$ |
| BMS (a, b, and c) | -4-(5-chloropyrimidinyl) | —H | —CF$_3$ |
| BMT (a, b, and c) | -4-(5-chloropyrimidinyl) | —H | —OCH$_3$ |
| BMU (a, b, and c) | -4-(5-chloropyrimidinyl) | —H | —OCH$_2$CH$_3$ |
| BMV (a, b, and c) | -4-(5-chloropyrimidinyl) | —H | —OCF$_3$ |
| BMW (a, b, and c) | -4-(5-chloropyrimidinyl) | —H | -tert-butyl |
| BMX (a, b, and c) | -4-(5-chloropyrimidinyl) | —H | -iso-propyl |
| BMY (a, b, and c) | -4-(5-methylpyrimidinyl) | —Cl | —H |
| BMZ (a, b, and c) | -4-(5-methylpyrimidinyl) | —Br | —H |
| BNA (a, b, and c) | -4-(5-methylpyrimidinyl) | —F | —H |
| BNB (a, b, and c) | -4-(5-methylpyrimidinyl) | —CH$_3$ | —H |
| BNC (a, b, and c) | -4-(5-methylpyrimidinyl) | —CF$_3$ | —H |
| BND (a, b, and c) | -4-(5-methylpyrimidinyl) | —OCH$_3$ | —H |
| BNE (a, b, and c) | -4-(5-methylpyrimidinyl) | —OCH$_2$CH$_3$ | —H |
| BNF (a, b, and c) | -4-(5-methylpyrimidinyl) | —OCF$_3$ | —H |
| BNG (a, b, and c) | -4-(5-methylpyrimidinyl) | -tert-butyl | —H |
| BNH (a, b, and c) | -4-(5-methylpyrimidinyl) | -iso-propyl | —H |
| BNI (a, b, and c) | -4-(5-methylpyrimidinyl) | —CH$_3$ | —CH$_3$ |
| BNJ (a, b, and c) | -4-(5-methylpyrimidinyl) | —H | —H |
| BNK (a, b, and c) | -4-(5-methylpyrimidinyl) | —H | —Cl |
| BNL (a, b, and c) | -4-(5-methylpyrimidinyl) | —H | —Br |
| BNM (a, b, and c) | -4-(5-methylpyrimidinyl) | —H | —F |
| BNN (a, b, and c) | -4-(5-methylpyrimidinyl) | —H | —CH$_3$ |
| BNO (a, b, and c) | -4-(5-methylpyrimidinyl) | —H | —CF$_3$ |
| BNP (a, b, and c) | -4-(5-methylpyrimidinyl) | —H | —OCH$_3$ |
| BNQ (a, b, and c) | -4-(5-methylpyrimidinyl) | —H | —OCH$_2$CH$_3$ |
| BNR (a, b, and c) | -4-(5-methylpyrimidinyl) | —H | —OCF$_3$ |
| BNS (a, b, and c) | -4-(5-methylpyrimidinyl) | —H | -tert-butyl |
| BNT (a, b, and c) | -4-(5-methylpyrimidinyl) | —H | -iso-propyl |
| BNU (a, b, and c) | -2-pyrazinyl | —Cl | —H |
| BNV (a, b, and c) | -2-pyrazinyl | —Br | —H |
| BNW (a, b, and c) | -2-pyrazinyl | —F | —H |
| BNX (a, b, and c) | -2-pyrazinyl | —CH$_3$ | —H |
| BNY (a, b, and c) | -2-pyrazinyl | —CF$_3$ | —H |
| BNZ (a, b, and c) | -2-pyrazinyl | —OCH$_3$ | —H |

TABLE IV-continued

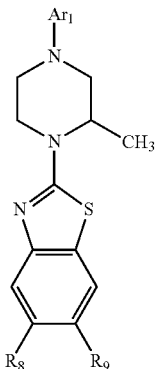

and pharmaceutically acceptable salts thereof, wherein:

| Compound | Ar₁ | R₈ | R₉ |
|---|---|---|---|
| BOA (a, b, and c) | -2-pyrazinyl | —OCH₂CH₃ | —H |
| BOB (a, b, and c) | -2-pyrazinyl | —OCF₃ | —H |
| BOC (a, b, and c) | -2-pyrazinyl | -tert-butyl | —H |
| BOD (a, b, and c) | -2-pyrazinyl | -iso-propyl | —H |
| BOE (a, b, and c) | -2-pyrazinyl | —CH₃ | —CH₃ |
| BOF (a, b, and c) | -2-pyrazinyl | —H | —H |
| BOG (a, b, and c) | -2-pyrazinyl | —H | —Cl |
| BOH (a, b, and c) | -2-pyrazinyl | —H | —Br |
| BOI (a, b, and c) | -2-pyrazinyl | —H | —F |
| BOJ (a, b, and c) | -2-pyrazinyl | —H | —CH₃ |
| BOK (a, b, and c) | -2-pyrazinyl | —H | —CF₃ |
| BOL (a, b, and c) | -2-pyrazinyl | —H | —OCH₃ |
| BOM (a, b, and c) | -2-pyrazinyl | —H | —OCH₂CH₃ |
| BON (a, b, and c) | -2-pyrazinyl | —H | —OCF₃ |
| BOO (a, b, and c) | -2-pyrazinyl | —H | -tert-butyl |
| BOP (a, b, and c) | -2-pyrazinyl | —H | -iso-propyl |
| BOQ (a, b, and c) | -2-(3-chloropyrazinyl) | —Cl | —H |
| BOR (a, b, and c) | -2-(3-chloropyrazinyl) | —Br | —H |
| BOS (a, b, and c) | -2-(3-chloropyrazinyl) | —F | —H |
| BOT (a, b, and c) | -2-(3-chloropyrazinyl) | —CH₃ | —H |
| BOU (a, b, and c) | -2-(3-chloropyrazinyl) | —CF₃ | —H |
| BOV (a, b, and c) | -2-(3-chloropyrazinyl) | —OCH₃ | —H |
| BOW (a, b, and c) | -2-(3-chloropyrazinyl) | —OCH₂CH₃ | —H |
| BOX (a, b, and c) | -2-(3-chloropyrazinyl) | —OCF₃ | —H |
| BOY (a, b, and c) | -2-(3-chloropyrazinyl) | -tert-butyl | —H |
| BOZ (a, b, and c) | -2-(3-chloropyrazinyl) | -iso-propyl | —H |
| BPA (a, b, and c) | -2-(3-chloropyrazinyl) | —CH₃ | —CH₃ |
| BPB (a, b, and c) | -2-(3-chloropyrazinyl) | —H | —H |
| BPC (a, b, and c) | -2-(3-chloropyrazinyl) | —H | —Cl |
| BPD (a, b, and c) | -2-(3-chloropyrazinyl) | —H | —Br |
| BPE (a, b, and c) | -2-(3-chloropyrazinyl) | —H | —F |
| BPF (a, b, and c) | -2-(3-chloropyrazinyl) | —H | —CH₃ |
| BPG (a, b, and c) | -2-(3-chloropyrazinyl) | —H | —CF₃ |
| BPH (a, b, and c) | -2-(3-chloropyrazinyl) | —H | —OCH₃ |
| BPI (a, b, and c) | -2-(3-chloropyrazinyl) | —H | —OCH₂CH₃ |
| BPJ (a, b, and c) | -2-(3-chloropyrazinyl) | —H | —OCF₃ |
| BPK (a, b, and c) | -2-(3-chloropyrazinyl) | —H | -tert-butyl |
| BPL (a, b, and c) | -2-(3-chloropyrazinyl) | —H | -iso-propyl |
| BPM (a, b, and c) | -2-(3-methylpyrazinyl) | —Cl | —H |
| BPN (a, b, and c) | -2-(3-methylpyrazinyl) | —Br | —H |
| BPO (a, b, and c) | -2-(3-methylpyrazinyl) | —F | —H |
| BPP (a, b, and c) | -2-(3-methylpyrazinyl) | —CH₃ | —H |
| BPQ (a, b, and c) | -2-(3-methylpyrazinyl) | —CF₃ | —H |
| BPR (a, b, and c) | -2-(3-methylpyrazinyl) | —OCH₃ | —H |
| BPS (a, b, and c) | -2-(3-methylpyrazinyl) | —OCH₂CH₃ | —H |
| BPT (a, b, and c) | -2-(3-methylpyrazinyl) | —OCF₃ | —H |
| BPU (a, b, and c) | -2-(3-methylpyrazinyl) | -tert-butyl | —H |
| BPV (a, b, and c) | -2-(3-methylpyrazinyl) | -iso-propyl | —H |
| BPW (a, b, and c) | -2-(3-methylpyrazinyl) | —CH₃ | —CH₃ |
| BPX (a, b, and c) | -2-(3-methylpyrazinyl) | —H | —H |
| BPY (a, b, and c) | -2-(3-methylpyrazinyl) | —H | —Cl |
| BPZ (a, b, and c) | -2-(3-methylpyrazinyl) | —H | —Br |
| BQA (a, b, and c) | -2-(3-methylpyrazinyl) | —H | —F |
| BQB (a, b, and c) | -2-(3-methylpyrazinyl) | —H | —CH₃ |
| BQC (a, b, and c) | -2-(3-methylpyrazinyl) | —H | —CF₃ |
| BQD (a, b, and c) | -2-(3-methylpyrazinyl) | —H | —OCH₃ |
| BQE (a, b, and c) | -2-(3-methylpyrazinyl) | —H | —OCH₂CH₃ |
| BQF (a, b, and c) | -2-(3-methylpyrazinyl) | —H | —OCF₃ |

TABLE IV-continued

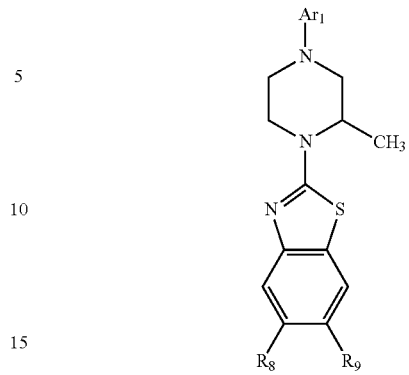

and pharmaceutically acceptable salts thereof, wherein:

| Compound | Ar₁ | R₈ | R₉ |
|---|---|---|---|
| BQG (a, b, and c) | -2-(3-methylpyrazinyl) | —H | -tert-butyl |
| BQH (a, b, and c) | -2-(3-methylpyrazinyl) | —H | -iso-propyl |
| BQI (a, b, and c) | -2-pyridazinyl | —Cl | —H |
| BQJ (a, b, and c) | -2-pyridazinyl | —Br | —H |
| BQK (a, b, and c) | -2-pyridazinyl | —F | —H |
| BQL (a, b, and c) | -2-pyridazinyl | —CH₃ | —H |
| BQM (a, b, and c) | -2-pyridazinyl | —CF₃ | —H |
| BQN (a, b, and c) | -2-pyridazinyl | —OCH₃ | —H |
| BQO (a, b, and c) | -2-pyridazinyl | —OCH₂CH₃ | —H |
| BQP (a, b, and c) | -2-pyridazinyl | —OCF₃ | —H |
| BQQ (a, b, and c) | -2-pyridazinyl | -tert-butyl | —H |
| BQR (a, b, and c) | -2-pyridazinyl | -iso-propyl | —H |
| BQS (a, b, and c) | -2-pyridazinyl | —CH₃ | —CH₃ |
| BQT (a, b, and c) | -2-pyridazinyl | —H | —H |
| BQU (a, b, and c) | -2-pyridazinyl | —H | —Cl |
| BQV (a, b, and c) | -2-pyridazinyl | —H | —Br |
| BQW (a, b, and c) | -2-pyridazinyl | —H | —F |
| BQX (a, b, and c) | -2-pyridazinyl | —H | —CH₃ |
| BQY (a, b, and c) | -2-pyridazinyl | —H | —CF₃ |
| BQZ (a, b, and c) | -2-pyridazinyl | —H | —OCH₃ |
| BRA (a, b, and c) | -2-pyridazinyl | —H | —OCH₂CH₃ |
| BRB (a, b, and c) | -2-pyridazinyl | —H | —OCF₃ |
| BRC (a, b, and c) | -2-pyridazinyl | —H | -tert-butyl |
| BRD (a, b, and c) | -2-pyridazinyl | —H | -iso-propyl |
| BRE (a, b, and c) | -3-(4-chloropyridazinyl) | —Cl | —H |
| BRF (a, b, and c) | -3-(4-chloropyridazinyl) | —Br | —H |
| BRG (a, b, and c) | -3-(4-chloropyridazinyl) | —F | —H |
| BRH (a, b, and c) | -3-(4-chloropyridazinyl) | —CH₃ | —H |
| BRI (a, b, and c) | -3-(4-chloropyridazinyl) | —CF₃ | —H |
| BRJ (a, b, and c) | -3-(4-chloropyridazinyl) | —OCH₃ | —H |
| BRK (a, b, and c) | -3-(4-chloropyridazinyl) | —OCH₂CH₃ | —H |
| BRL (a, b, and c) | -3-(4-chloropyridazinyl) | —OCF₃ | —H |
| BRM (a, b, and c) | -3-(4-chloropyridazinyl) | -tert-butyl | —H |
| BRN (a, b, and c) | -3-(4-chloropyridazinyl) | -iso-propyl | —H |
| BRO (a, b, and c) | -3-(4-chloropyridazinyl) | —CH₃ | —CH₃ |
| BRP (a, b, and c) | -3-(4-chloropyridazinyl) | —H | —H |
| BRQ (a, b, and c) | -3-(4-chloropyridazinyl) | —H | —Cl |
| BRR (a, b, and c) | -3-(4-chloropyridazinyl) | —H | —Br |
| BRS (a, b, and c) | -3-(4-chloropyridazinyl) | —H | —F |
| BRT (a, b, and c) | -3-(4-chloropyridazinyl) | —H | —CH₃ |
| BRU (a, b, and c) | -3-(4-chloropyridazinyl) | —H | —CF₃ |
| BRV (a, b, and c) | -3-(4-chloropyridazinyl) | —H | —OCH₃ |
| BRW (a, b, and c) | -3-(4-chloropyridazinyl) | —H | —OCH₂CH₃ |
| BRX (a, b, and c) | -3-(4-chloropyridazinyl) | —H | —OCF₃ |
| BRY (a, b, and c) | -3-(4-chloropyridazinyl) | —H | -tert-butyl |
| BRZ (a, b, and c) | -3-(4-chloropyridazinyl) | —H | -iso-propyl |
| BSA (a, b, and c) | -3-(4-methylpyridazinyl) | —Cl | —H |
| BSB (a, b, and c) | -3-(4-methylpyridazinyl) | —Br | —H |
| BSC (a, b, and c) | -3-(4-methylpyridazinyl) | —F | —H |
| BSD (a, b, and c) | -3-(4-methylpyridazinyl) | —CH₃ | —H |
| BSE (a, b, and c) | -3-(4-methylpyridazinyl) | —CF₃ | —H |
| BSF (a, b, and c) | -3-(4-methylpyridazinyl) | —OCH₃ | —H |
| BSG (a, b, and c) | -3-(4-methylpyridazinyl) | —OCH₂CH₃ | —H |
| BSH (a, b, and c) | -3-(4-methylpyridazinyl) | —OCF₃ | —H |
| BSI (a, b, and c) | -3-(4-methylpyridazinyl) | -tert-butyl | —H |
| BSJ (a, b, and c) | -3-(4-methylpyridazinyl) | -iso-propyl | —H |
| BSK (a, b, and c) | -3-(4-methylpyridazinyl) | —CH₃ | —CH₃ |
| BSL (a, b, and c) | -3-(4-methylpyridazinyl) | —H | —H |

TABLE IV-continued

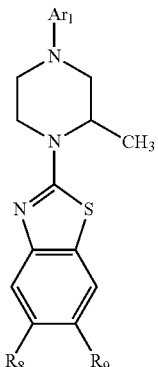

and pharmaceutically acceptable salts thereof, wherein:

| Compound | Ar₁ | R₈ | R₉ |
|---|---|---|---|
| BSM (a, b, and c) | -3-(4-methylpyridazinyl) | —H | —Cl |
| BSN (a, b, and c) | -3-(4-methylpyridazinyl) | —H | —Br |
| BSO (a, b, and c) | -3-(4-methylpyridazinyl) | —H | —F |
| BSP (a, b, and c) | -3-(4-methylpyridazinyl) | —H | —CH₃ |
| BSQ (a, b, and c) | -3-(4-methylpyridazinyl) | —H | —CF₃ |
| BSR (a, b, and c) | -3-(4-methylpyridazinyl) | —H | —OCH₃ |
| BSS (a, b, and c) | -3-(4-methylpyridazinyl) | —H | —OCH₂CH₃ |
| BST (a, b, and c) | -3-(4-methylpyridazinyl) | —H | —OCF₃ |
| BSU (a, b, and c) | -3-(4-methylpyridazinyl) | —H | -tert-butyl |
| BSV (a, b, and c) | -3-(4-methylpyridazinyl) | —H | -iso-propyl |
| BSW (a, b, and c) | -4-thiazanyl | —Cl | —H |
| BSX (a, b, and c) | -4-thiazanyl | —Br | —H |
| BSY (a, b, and c) | -4-thiazanyl | —F | —H |
| BSZ (a, b, and c) | -4-thiazanyl | —CH₃ | —H |
| BTA (a, b, and c) | -4-thiazanyl | —CF₃ | —H |
| BTB (a, b, and c) | -4-thiazanyl | —OCH₃ | —H |
| BTC (a, b, and c) | -4-thiazanyl | —OCH₂CH₃ | —H |
| BTD (a, b, and c) | -4-thiazanyl | —OCF₃ | —H |
| BTE (a, b, and c) | -4-thiazanyl | -tert-butyl | —H |
| BTF (a, b, and c) | -4-thiazanyl | -iso-propyl | —H |
| BTG (a, b, and c) | -4-thiazanyl | —CH₃ | —CH₃ |
| BTH (a, b, and c) | -4-thiazanyl | —H | —H |
| BTI (a, b, and c) | -4-thiazanyl | —H | —Cl |
| BTJ (a, b, and c) | -4-thiazanyl | —H | —Br |
| BTK (a, b, and c) | -4-thiazanyl | —H | —F |
| BTL (a, b, and c) | -4-thiazanyl | —H | —CH₃ |
| BTM (a, b, and c) | -4-thiazanyl | —H | —CF₃ |
| BTN (a, b, and c) | -4-thiazanyl | —H | —OCH₃ |
| BTO (a, b, and c) | -4-thiazanyl | —H | —OCH₂CH₃ |
| BTP (a, b, and c) | -4-thiazanyl | —H | —OCF₃ |
| BTQ (a, b, and c) | -4-thiazanyl | —H | -tert-butyl |
| BTR (a, b, and c) | -4-thiazanyl | —H | -iso-propyl |
| BTS (a, b, and c) | -5-(4-chlorothiazanyl) | —Cl | —H |
| BTT (a, b, and c) | -5-(4-chlorothiazanyl) | —Br | —H |
| BTU (a, b, and c) | -5-(4-chlorothiazanyl) | —F | —H |
| BTV (a, b, and c) | -5-(4-chlorothiazanyl) | —CH₃ | —H |
| BTW (a, b, and c) | -5-(4-chlorothiazanyl) | —CF₃ | —H |
| BTX (a, b, and c) | -5-(4-chlorothiazanyl) | —OCH₃ | —H |
| BTY (a, b, and c) | -5-(4-chlorothiazanyl) | —OCH₂CH₃ | —H |
| BTZ (a, b, and c) | -5-(4-chlorothiazanyl) | —OCF₃ | —H |
| BUA (a, b, and c) | -5-(4-chlorothiazanyl) | -tert-butyl | —H |
| BUB (a, b, and c) | -5-(4-chlorothiazanyl) | -iso-propyl | —H |
| BUC (a, b, and c) | -5-(4-chlorothiazanyl) | —CH₃ | —CH₃ |
| BUD (a, b, and c) | -5-(4-chlorothiazanyl) | —H | —H |
| BUE (a, b, and c) | -5-(4-chlorothiazanyl) | —H | —Cl |
| BUF (a, b, and c) | -5-(4-chlorothiazanyl) | —H | —Br |
| BUG (a, b, and c) | -5-(4-chlorothiazanyl) | —H | —F |
| BUH (a, b, and c) | -5-(4-chlorothiazanyl) | —H | —CH₃ |
| BUI (a, b, and c) | -5-(4-chlorothiazanyl) | —H | —CF₃ |
| BUJ (a, b, and c) | -5-(4-chlorothiazanyl) | —H | —OCH₃ |
| BUK (a, b, and c) | -5-(4-chlorothiazanyl) | —H | —OCH₂CH₃ |
| BUL (a, b, and c) | -5-(4-chlorothiazanyl) | —H | —OCF₃ |
| BUM (a, b, and c) | -5-(4-chlorothiazanyl) | —H | -tert-butyl |
| BUN (a, b, and c) | -5-(4-chlorothiazanyl) | —H | -iso-propyl |
| BUO (a, b, and c) | -5-(4-methylthiazanyl) | —Cl | —H |
| BUP (a, b, and c) | -5-(4-methylthiazanyl) | —Br | —H |
| BUQ (a, b, and c) | -5-(4-methylthiazanyl) | —F | —H |
| BUR (a, b, and c) | -5-(4-methylthiazanyl) | —CH₃ | —H |

TABLE IV-continued

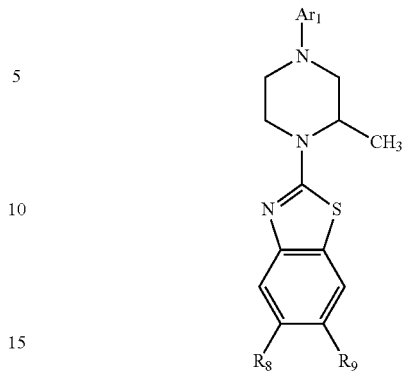

and pharmaceutically acceptable salts thereof, wherein:

| Compound | Ar₁ | R₈ | R₉ |
|---|---|---|---|
| BUS (a, b, and c) | -5-(4-methylthiazanyl) | —CF₃ | —H |
| BUT (a, b, and c) | -5-(4-methylthiazanyl) | —OCH₃ | —H |
| BUU (a, b, and c) | -5-(4-methylthiazanyl) | —OCH₂CH₃ | —H |
| BUV (a, b, and c) | -5-(4-methylthiazanyl) | —OCF₃ | —H |
| BUW (a, b, and c) | -5-(4-methylthiazanyl) | -tert-butyl | —H |
| BUX (a, b, and c) | -5-(4-methylthiazanyl) | -iso-propyl | —H |
| BUY (a, b, and c) | -5-(4-methylthiazanyl) | —CH₃ | —CH₃ |
| BUZ (a, b, and c) | -5-(4-methylthiazanyl) | —H | —H |
| BVA (a, b, and c) | -5-(4-methylthiazanyl) | —H | —Cl |
| BVB (a, b, and c) | -5-(4-methylthiazanyl) | —H | —Br |
| BVC (a, b, and c) | -5-(4-methylthiazanyl) | —H | —F |
| BVD (a, b, and c) | -5-(4-methylthiazanyl) | —H | —CH₃ |
| BVE (a, b, and c) | -5-(4-methylthiazanyl) | —H | —CF₃ |
| BVF (a, b, and c) | -5-(4-methylthiazanyl) | —H | —OCH₃ |
| BVG (a, b, and c) | -5-(4-methylthiazanyl) | —H | —OCH₂CH₃ |
| BVH (a, b, and c) | -5-(4-methylthiazanyl) | —H | —OCF₃ |
| BVI (a, b, and c) | -5-(4-methylthiazanyl) | —H | -tert-butyl |
| BVJ (a, b, and c) | -5-(4-methylthiazanyl) | —H | -iso-propyl |

"a" means the Benzoazolylpiperazine Compound is racemic.
"b" means the carbon atom of the piperazine ring attached to the methyl group is in the R configuration.
"c" means the carbon atom of the piperazine ring attached to the methyl groupis in the S configuration.

TABLE V

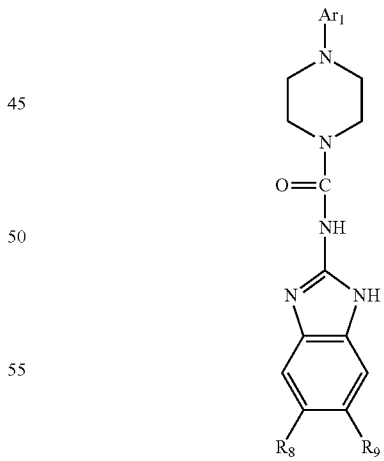

and pharmaceutically acceptable salts thereof, wherein:

| Compound | Ar₁ | R₈ | R₉ |
|---|---|---|---|
| BVK | -2-pyridazinyl | —Cl | —H |
| BVL | -2-pyridazinyl | —Br | —H |
| BVM | -2-pyridazinyl | —F | —H |
| BVN | -2-pyridazinyl | —CH₃ | —H |
| BVO | -2-pyridazinyl | —CF₃ | —H |
| BVP | -2-pyridazinyl | —OCH₃ | —H |

TABLE V-continued

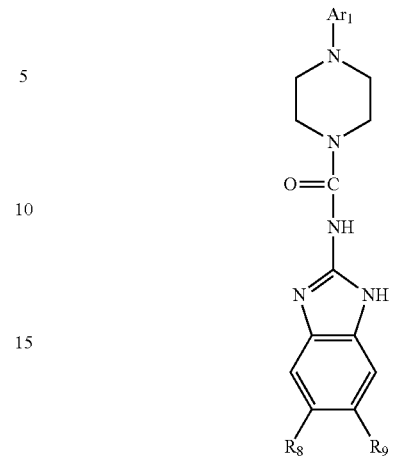

and pharmaceutically acceptable salts thereof, wherein:

| Compound | Ar₁ | R₈ | R₉ |
|---|---|---|---|
| BVQ | -2-pyridazinyl | —OCH₂CH₃ | —H |
| BVR | -2-pyridazinyl | —OCF₃ | —H |
| BVS | -2-pyridazinyl | -tert-butyl | —H |
| BVT | -2-pyridazinyl | -iso-propyl | —H |
| BVU | -2-pyridazinyl | —CH₃ | —CH₃ |
| BVV | -2-pyridazinyl | —H | —H |
| BVW | -2-pyridazinyl | —H | —Cl |
| BVX | -2-pyridazinyl | —H | —Br |
| BVY | -2-pyridazinyl | —H | —F |
| BVZ | -2-pyridazinyl | —H | —CH₃ |
| BWA | -2-pyridazinyl | —H | —CF₃ |
| BWB | -2-pyridazinyl | —H | —OCH₃ |
| BWC | -2-pyridazinyl | —H | —OCH₂CH₃ |
| BWD | -2-pyridazinyl | —H | —OCF₃ |
| BWE | -2-pyridazinyl | —H | -tert-butyl |
| BWF | -2-pyridazinyl | —H | -iso-propyl |
| BWG | -3-(4-chloropyridazinyl) | —Cl | —H |
| BWH | -3-(4-chloropyridazinyl) | —Br | —H |
| BWI | -3-(4-chloropyridazinyl) | —F | —H |
| BWJ | -3-(4-chloropyridazinyl) | —CH₃ | —H |
| BWK | -3-(4-chloropyridazinyl) | —CF₃ | —H |
| BWL | -3-(4-chloropyridazinyl) | —OCH₃ | —H |
| BWM | -3-(4-chloropyridazinyl) | —OCH₂CH₃ | —H |
| BWN | -3-(4-chloropyridazinyl) | —OCF₃ | —H |
| BWO | -3-(4-chloropyridazinyl) | -tert-butyl | —H |
| BWP | -3-(4-chloropyridazinyl) | -iso-propyl | —H |
| BWQ | -3-(4-chloropyridazinyl) | —CH₃ | —CH₃ |
| BWR | -3-(4-chloropyridazinyl) | —H | —H |
| BWS | -3-(4-chloropyridazinyl) | —H | —Cl |
| BWT | -3-(4-chloropyridazinyl) | —H | —Br |
| BWU | -3-(4-chloropyridazinyl) | —H | —F |
| BWV | -3-(4-chloropyridazinyl) | —H | —CH₃ |
| BWW | -3-(4-chloropyridazinyl) | —H | —CF₃ |
| BWX | -3-(4-chloropyridazinyl) | —H | —OCH₃ |
| BWY | -3-(4-chloropyridazinyl) | —H | —OCH₂CH₃ |
| BWZ | -3-(4-chloropyridazinyl) | —H | —OCF₃ |
| BXA | -3-(4-chloropyridazinyl) | —H | -tert-butyl |
| BXB | -3-(4-chloropyridazinyl) | —H | -iso-propyl |
| BXC | -3-(4-methylpyridazinyl) | —Cl | —H |
| BXD | -3-(4-methylpyridazinyl) | —Br | —H |
| BXE | -3-(4-methylpyridazinyl) | —F | —H |
| BXF | -3-(4-methylpyridazinyl) | —CH₃ | —H |
| BXG | -3-(4-methylpyridazinyl) | —CF₃ | —H |
| BXH | -3-(4-methylpyridazinyl) | —OCH₃ | —H |
| BXI | -3-(4-methylpyridazinyl) | —OCH₂CH₃ | —H |
| BXJ | -3-(4-methylpyridazinyl) | —OCF₃ | —H |
| BXK | -3-(4-methylpyridazinyl) | -tert-butyl | —H |
| BXL | -3-(4-methylpyridazinyl) | -iso-propyl | —H |
| BXM | -3-(4-methylpyridazinyl) | —CH₃ | —CH₃ |
| BXN | -3-(4-methylpyridazinyl) | —H | —H |
| BXO | -3-(4-methylpyridazinyl) | —H | —Cl |
| BXP | -3-(4-methylpyridazinyl) | —H | —Br |
| BXQ | -3-(4-methylpyridazinyl) | —H | —F |
| BXR | -3-(4-methylpyridazinyl) | —H | —CH₃ |
| BXS | -3-(4-methylpyridazinyl) | —H | —CF₃ |
| BXT | -3-(4-methylpyridazinyl) | —H | —OCH₃ |
| BXU | -3-(4-methylpyridazinyl) | —H | —OCH₂CH₃ |
| BXV | -3-(4-methylpyridazinyl) | —H | —OCF₃ |
| BXW | -3-(4-methylpyridazinyl) | —H | -tert-butyl |
| BXX | -3-(4-methylpyridazinyl) | —H | -iso-propyl |
| BXY | -4-thiazanyl | —Cl | —H |
| BXZ | -4-thiazanyl | —Br | —H |
| BYA | -4-thiazanyl | —F | —H |
| BYB | -4-thiazanyl | —CH₃ | —H |
| BYC | -4-thiazanyl | —CF₃ | —H |
| BYD | -4-thiazanyl | —OCH₃ | —H |
| BYE | -4-thiazanyl | —OCH₂CH₃ | —H |
| BYF | -4-thiazanyl | —OCF₃ | —H |
| BYG | -4-thiazanyl | -tert-butyl | —H |
| BYH | -4-thiazanyl | -iso-propyl | —H |
| BYI | -4-thiazanyl | —CH₃ | —CH₃ |
| BYJ | -4-thiazanyl | —H | —H |
| BYK | -4-thiazanyl | —H | —Cl |
| BYL | -4-thiazanyl | —H | —Br |
| BYM | -4-thiazanyl | —H | —F |
| BYN | -4-thiazanyl | —H | —CH₃ |
| BYO | -4-thiazanyl | —H | —CF₃ |
| BYP | -4-thiazanyl | —H | —OCH₃ |
| BYQ | -4-thiazanyl | —H | —OCH₂CH₃ |
| BYR | -4-thiazanyl | —H | —OCF₃ |
| BYS | -4-thiazanyl | —H | -tert-butyl |
| BYT | -4-thiazanyl | —H | -iso-propyl |
| BYU | -5-(4-chlorothiazanyl) | —Cl | —H |
| BYV | -5-(4-chlorothiazanyl) | —Br | —H |
| BYW | -5-(4-chlorothiazanyl) | —F | —H |
| BYX | -5-(4-chlorothiazanyl) | —CH₃ | —H |
| BYY | -5-(4-chlorothiazanyl) | —CF₃ | —H |
| BYZ | -5-(4-chlorothiazanyl) | —OCH₃ | —H |
| BZA | -5-(4-chlorothiazanyl) | —OCH₂CH₃ | —H |
| BZB | -5-(4-chlorothiazanyl) | —OCF₃ | —H |
| BZC | -5-(4-chlorothiazanyl) | -tert-butyl | —H |
| BZD | -5-(4-chlorothiazanyl) | -iso-propyl | —H |
| BZE | -5-(4-chlorothiazanyl) | —CH₃ | —CH₃ |
| BZF | -5-(4-chlorothiazanyl) | —H | —H |
| BZG | -5-(4-chlorothiazanyl) | —H | —Cl |
| BZH | -5-(4-chlorothiazanyl) | —H | —Br |
| BZI | -5-(4-chlorothiazanyl) | —H | —F |
| BZJ | -5-(4-chlorothiazanyl) | —H | —CH₃ |
| BZK | -5-(4-chlorothiazanyl) | —H | —CF₃ |
| BZL | -5-(4-chlorothiazanyl) | —H | —OCH₃ |
| BZM | -5-(4-chlorothiazanyl) | —H | —OCH₂CH₃ |
| BZN | -5-(4-chlorothiazanyl) | —H | —OCF₃ |
| BZO | -5-(4-chlorothiazanyl) | —H | -tert-butyl |
| BZP | -5-(4-chlorothiazanyl) | —H | -iso-propyl |
| BZQ | -5-(4-methylthiazanyl) | —Cl | —H |
| BZR | -5-(4-methylthiazanyl) | —Br | —H |
| BZS | -5-(4-methylthiazanyl) | —F | —H |
| BZT | -5-(4-methylthiazanyl) | —CH₃ | —H |

TABLE V-continued

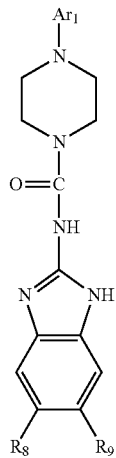

and pharmaceutically acceptable salts thereof, wherein:

| Compound | Ar₁ | R₈ | R₉ |
|---|---|---|---|
| BZU | -5-(4-methylthiazanyl) | —CF₃ | —H |
| BZV | -5-(4-methylthiazanyl) | —OCH₃ | —H |
| BZW | -5-(4-methylthiazanyl) | —OCH₂CH₃ | —H |
| BZX | -5-(4-methylthiazanyl) | —OCF₃ | —H |
| BZY | -5-(4-methylthiazanyl) | -tert-butyl | —H |
| BZZ | -5-(4-methylthiazanyl) | -iso-propyl | —H |
| CAA | -5-(4-methylthiazanyl) | —CH₃ | —CH₃ |
| CAB | -5-(4-methylthiazanyl) | —H | —H |
| CAC | -5-(4-methylthiazanyl) | —H | —Cl |
| CAD | -5-(4-methylthiazanyl) | —H | —Br |
| CAE | -5-(4-methylthiazanyl) | —H | —F |
| CAF | -5-(4-methylthiazanyl) | —H | —CH₃ |
| CAG | -5-(4-methylthiazanyl) | —H | —CF₃ |
| CAH | -5-(4-methylthiazanyl) | —H | —OCH₃ |
| CAI | -5-(4-methylthiazanyl) | —H | —OCH₂CH₃ |
| CAJ | -5-(4-methylthiazanyl) | —H | —OCF₃ |
| CAK | -5-(4-methylthiazanyl) | —H | -tert-butyl |
| CAL | -5-(4-methylthiazanyl) | —H | -iso-propyl |

TABLE VI

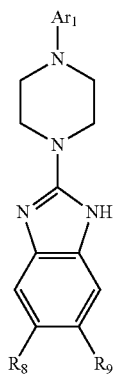

and pharmaceutically acceptable salts thereof, wherein:

| Compound | Ar₁ | R₈ | R₉ |
|---|---|---|---|
| CAM | -2-(3-chloropyridyl) | —Cl | —H |
| CAN | -2-(3-chloropyridyl) | —Br | —H |
| CAO | -2-(3-chloropyridyl) | —F | —H |
| CAP | -2-(3-chloropyridyl) | —CH₃ | —H |
| CAQ | -2-(3-chloropyridyl) | —CF₃ | —H |
| CAR | -2-(3-chloropyridyl) | —OCH₃ | —H |
| CAS | -2-(3-chloropyridyl) | —OCH₂CH₃ | —H |
| CAT | -2-(3-chloropyridyl) | —OCF₃ | —H |
| CAU | -2-(3-chloropyridyl) | -tert-butyl | —H |
| CAV | -2-(3-chloropyridyl) | -iso-propyl | —H |

TABLE VI-continued

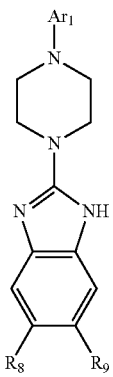

and pharmaceutically acceptable salts thereof, wherein:

| Compound | Ar₁ | R₈ | R₉ |
|---|---|---|---|
| CAW | -2-(3-chloropyridyl) | —CH₃ | —CH₃ |
| CAX | -2-(3-chloropyridyl) | —H | —H |
| CAY | -2-(3-chloropyridyl) | —H | —Cl |
| CAZ | -2-(3-chloropyridyl) | —H | —Br |
| CBA | -2-(3-chloropyridyl) | —H | —F |
| CBB | -2-(3-chloropyridyl) | —H | —CH₃ |
| CBC | -2-(3-chloropyridyl) | —H | —CF₃ |
| CBD | -2-(3-chloropyridyl) | —H | —OCH₃ |
| CBE | -2-(3-chloropyridyl) | —H | —OCH₂CH₃ |
| CBF | -2-(3-chloropyridyl) | —H | —OCF₃ |
| CBG | -2-(3-chloropyridyl) | —H | -tert-butyl |
| CBH | -2-(3-chloropyridyl) | —H | -iso-propyl |
| CBI | -2-(3-methylpyridyl) | —Cl | —H |
| CBJ | -2-(3-methylpyridyl) | —Br | —H |
| CBK | -2-(3-methylpyridyl) | —F | —H |
| CBL | -2-(3-methylpyridyl) | —CH₃ | —H |
| CBM | -2-(3-methylpyridyl) | —CF₃ | —H |
| CBN | -2-(3-methylpyridyl) | —OCH₃ | —H |
| CBO | -2-(3-methylpyridyl) | —OCH₂CH₃ | —H |
| CBP | -2-(3-methylpyridyl) | —OCF₃ | —H |
| CBQ | -2-(3-methylpyridyl) | -tert-butyl | —H |
| CBR | -2-(3-methylpyridyl) | -iso-propyl | —H |
| CBS | -2-(3-methylpyridyl) | —CH₃ | —CH₃ |
| CBT | -2-(3-methylpyridyl) | —H | —H |
| CBU | -2-(3-methylpyridyl) | —H | —Cl |
| CBV | -2-(3-methylpyridyl) | —H | —Br |
| CBW | -2-(3-methylpyridyl) | —H | —F |
| CBX | -2-(3-methylpyridyl) | —H | —CH₃ |
| CBY | -2-(3-methylpyridyl) | —H | —CF₃ |
| CBZ | -2-(3-methylpyridyl) | —H | —OCH₃ |
| CCA | -2-(3-methylpyridyl) | —H | —OCH₂CH₃ |
| CCB | -2-(3-methylpyridyl) | —H | —OCF₃ |
| CCC | -2-(3-methylpyridyl) | —H | -tert-butyl |
| CCD | -2-(3-methylpyridyl) | —H | -iso-propyl |
| CCE | -2-(3-CF₃-pyridyl) | —Cl | —H |
| CCF | -2-(3-CF₃-pyridyl) | —Br | —H |
| CCG | -2-(3-CF₃-pyridyl) | —F | —H |
| CCH | -2-(3-CF₃-pyridyl) | —CH₃ | —H |
| CCI | -2-(3-CF₃-pyridyl) | —CF₃ | —H |
| CCJ | -2-(3-CF₃-pyridyl) | —OCH₃ | —H |
| CCK | -2-(3-CF₃-pyridyl) | —OCH₂CH₃ | —H |
| CCL | -2-(3-CF₃-pyridyl) | —OCF₃ | —H |
| CCM | -2-(3-CF₃-pyridyl) | -tert-butyl | —H |
| CCN | -2-(3-CF₃-pyridyl) | -iso-propyl | —H |
| CCO | -2-(3-CF₃-pyridyl) | —CH₃ | —CH₃ |
| CCP | -2-(3-CF₃-pyridyl) | —H | —H |
| CCQ | -2-(3-CF₃-pyridyl) | —H | —Cl |
| CCR | -2-(3-CF₃-pyridyl) | —H | —Br |
| CCS | -2-(3-CF₃-pyridyl) | —H | —F |
| CCT | -2-(3-CF₃-pyridyl) | —H | —CH₃ |
| CCU | -2-(3-CF₃-pyridyl) | —H | —CF₃ |
| CCV | -2-(3-CF₃-pyridyl) | —H | —OCH₃ |
| CCW | -2-(3-CF₃-pyridyl) | —H | —OCH₂CH₃ |
| CCX | -2-(3-CF₃-pyridyl) | —H | —OCF₃ |
| CCY | -2-(3-CF₃-pyridyl) | —H | -tert-butyl |
| CCZ | -2-(3-CF₃-pyridyl) | —H | -iso-propyl |
| CDA | -4-(5-chloropyrimidinyl) | —Cl | —H |
| CDB | -4-(5-chloropyrimidinyl) | —Br | —H |

TABLE VI-continued

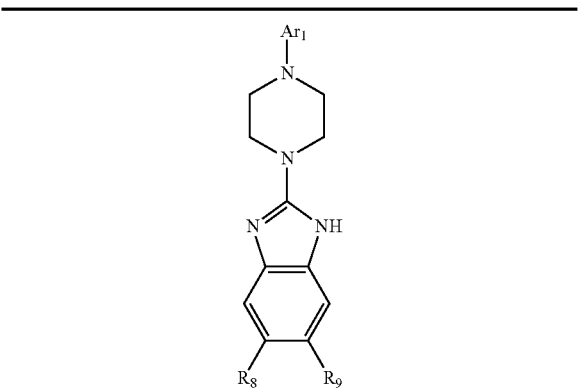

and pharmaceutically acceptable salts thereof, wherein:

| Compound | Ar₁ | R₈ | R₉ |
|---|---|---|---|
| CDC | -4-(5-chloropyrimidinyl) | —F | —H |
| CDD | -4-(5-chloropyrimidinyl) | —CH₃ | —H |
| CDE | -4-(5-chloropyrimidinyl) | —CF₃ | —H |
| CDF | -4-(5-chloropyrimidinyl) | —OCH₃ | —H |
| CDG | -4-(5-chloropyrimidinyl) | —OCH₂CH₃ | —H |
| CDH | -4-(5-chloropyrimidinyl) | —OCF₃ | —H |
| CDI | -4-(5-chloropyrimidinyl) | -tert-butyl | —H |
| CDJ | -4-(5-chloropyrimidinyl) | -iso-propyl | —H |
| CDK | -4-(5-chloropyrimidinyl) | —CH₃ | —CH₃ |
| CDL | -4-(5-chloropyrimidinyl) | —H | —H |
| CDM | -4-(5-chloropyrimidinyl) | —H | —Cl |
| CDN | -4-(5-chloropyrimidinyl) | —H | —Br |
| CDO | -4-(5-chloropyrimidinyl) | —H | —F |
| CDP | -4-(5-chloropyrimidinyl) | —H | —CH₃ |
| CDQ | -4-(5-chloropyrimidinyl) | —H | —CF₃ |
| CDR | -4-(5-chloropyrimidinyl) | —H | —OCH₃ |
| CDS | -4-(5-chloropyrimidinyl) | —H | —OCH₂CH₃ |
| CDT | -4-(5-chloropyrimidinyl) | —H | —OCF₃ |
| CDU | -4-(5-chloropyrimidinyl) | —H | -tert-butyl |
| CDV | -4-(5-chloropyrimidinyl) | —H | -iso-propyl |
| CDW | -4-(5-methylpyrimidinyl) | —Cl | —H |
| CDX | -4-(5-methylpyrimidinyl) | —Br | —H |
| CDY | -4-(5-methylpyrimidinyl) | —F | —H |
| CDZ | -4-(5-methylpyrimidinyl) | —CH₃ | —H |
| CEA | -4-(5-methylpyrimidinyl) | —CF₃ | —H |
| CEB | -4-(5-methylpyrimidinyl) | —OCH₃ | —H |
| CEC | -4-(5-methylpyrimidinyl) | —OCH₂CH₃ | —H |
| CED | -4-(5-methylpyrimidinyl) | —OCF₃ | —H |
| CEE | -4-(5-methylpyrimidinyl) | -tert-butyl | —H |
| CEF | -4-(5-methylpyrimidinyl) | -iso-propyl | —H |
| CEG | -4-(5-methylpyrimidinyl) | —CH₃ | —CH₃ |
| CEH | -4-(5-methylpyrimidinyl) | —H | —H |
| CEI | -4-(5-methylpyrimidinyl) | —H | —Cl |
| CEJ | -4-(5-methylpyrimidinyl) | —H | —Br |
| CEK | -4-(5-methylpyrimidinyl) | —H | —F |
| CEL | -4-(5-methylpyrimidinyl) | —H | —CH₃ |
| CEM | -4-(5-methylpyrimidinyl) | —H | —CF₃ |
| CEN | -4-(5-methylpyrimidinyl) | —H | —OCH₃ |
| CEO | -4-(5-methylpyrimidinyl) | —H | —OCH₂CH₃ |
| CEP | -4-(5-methylpyrimidinyl) | —H | —OCF₃ |
| CEQ | -4-(5-methylpyrimidinyl) | —H | -tert-butyl |
| CER | -4-(5-methylpyrimidinyl) | —H | -iso-propyl |
| CES | -2-pyrazinyl | —Cl | —H |
| CET | -2-pyrazinyl | —Br | —H |
| CEU | -2-pyrazinyl | —F | —H |
| CEV | -2-pyrazinyl | —CH₃ | —H |
| CEW | -2-pyrazinyl | —CF₃ | —H |
| CEX | -2-pyrazinyl | —OCH₃ | —H |
| CEY | -2-pyrazinyl | —OCH₂CH₃ | —H |
| CEZ | -2-pyrazinyl | —OCF₃ | —H |
| CFA | -2-pyrazinyl | -tert-butyl | —H |
| CFB | -2-pyrazinyl | -iso-propyl | —H |
| CFC | -2-pyrazinyl | —CH₃ | —CH₃ |
| CFD | -2-pyrazinyl | —H | —H |
| CFE | -2-pyrazinyl | —H | —Cl |
| CFF | -2-pyrazinyl | —H | —Br |
| CFG | -2-pyrazinyl | —H | —F |
| CFH | -2-pyrazinyl | —H | —CH₃ |

TABLE VI-continued

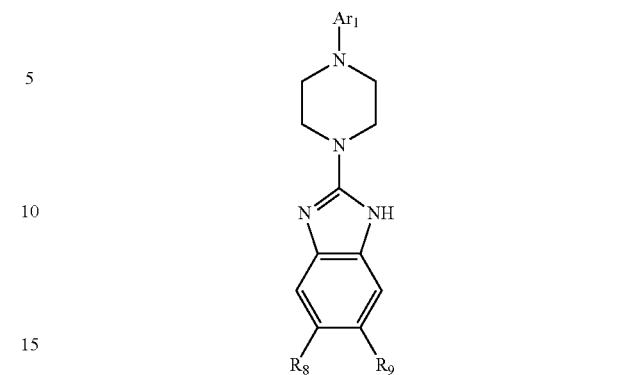

and pharmaceutically acceptable salts thereof, wherein:

| Compound | Ar₁ | R₈ | R₉ |
|---|---|---|---|
| CFI | -2-pyrazinyl | —H | —CF₃ |
| CFJ | -2-pyrazinyl | —H | —OCH₃ |
| CFK | -2-pyrazinyl | —H | —OCH₂CH₃ |
| CFL | -2-pyrazinyl | —H | —OCF₃ |
| CFM | -2-pyrazinyl | —H | -tert-butyl |
| CFN | -2-pyrazinyl | —H | -iso-propyl |
| CFO | -2-(3-chloropyrazinyl) | —Cl | —H |
| CFP | -2-(3-chloropyrazinyl) | —Br | —H |
| CFQ | -2-(3-chloropyrazinyl) | —F | —H |
| CFR | -2-(3-chloropyrazinyl) | —CH₃ | —H |
| CFS | -2-(3-chloropyrazinyl) | —CF₃ | —H |
| CFT | -2-(3-chloropyrazinyl) | —OCH₃ | —H |
| CFU | -2-(3-chloropyrazinyl) | —OCH₂CH₃ | —H |
| CFV | -2-(3-chloropyrazinyl) | —OCF₃ | —H |
| CFW | -2-(3-chloropyrazinyl) | -tert-butyl | —H |
| CFX | -2-(3-chloropyrazinyl) | -iso-propyl | —H |
| CFY | -2-(3-chloropyrazinyl) | —CH₃ | —CH₃ |
| CFZ | -2-(3-chloropyrazinyl) | —H | —H |
| CGA | -2-(3-chloropyrazinyl) | —H | —Cl |
| CGB | -2-(3-chloropyrazinyl) | —H | —Br |
| CGC | -2-(3-chloropyrazinyl) | —H | —F |
| CGD | -2-(3-chloropyrazinyl) | —H | —CH₃ |
| CGE | -2-(3-chloropyrazinyl) | —H | —CF₃ |
| CGF | -2-(3-chloropyrazinyl) | —H | —OCH₃ |
| CGG | -2-(3-chloropyrazinyl) | —H | —OCH₂CH₃ |
| CGH | -2-(3-chloropyrazinyl) | —H | —OCF₃ |
| CGI | -2-(3-chloropyrazinyl) | —H | -tert-butyl |
| CGJ | -2-(3-chloropyrazinyl) | —H | -iso-propyl |
| CGK | -2-(3-methylpyrazinyl) | —Cl | —H |
| CGL | -2-(3-methylpyrazinyl) | —Br | —H |
| CGM | -2-(3-methylpyrazinyl) | —F | —H |
| CGN | -2-(3-methylpyrazinyl) | —CH₃ | —H |
| CGO | -2-(3-methylpyrazinyl) | —CF₃ | —H |
| CGP | -2-(3-methylpyrazinyl) | —OCH₃ | —H |
| CGQ | -2-(3-methylpyrazinyl) | —OCH₂CH₃ | —H |
| CGR | -2-(3-methylpyrazinyl) | —OCF₃ | —H |
| CGS | -2-(3-methylpyrazinyl) | -tert-butyl | —H |
| CGT | -2-(3-methylpyrazinyl) | -iso-propyl | —H |
| CGU | -2-(3-methylpyrazinyl) | —CH₃ | —CH₃ |
| CGV | -2-(3-methylpyrazinyl) | —H | —H |
| CGW | -2-(3-methylpyrazinyl) | —H | —Cl |
| CGX | -2-(3-methylpyrazinyl) | —H | —Br |
| CGY | -2-(3-methylpyrazinyl) | —H | —F |
| CGZ | -2-(3-methylpyrazinyl) | —H | —CH₃ |
| CHA | -2-(3-methylpyrazinyl) | —H | —CF₃ |
| CHB | -2-(3-methylpyrazinyl) | —H | —OCH₃ |
| CHC | -2-(3-methylpyrazinyl) | —H | —OCH₂CH₃ |
| CHD | -2-(3-methylpyrazinyl) | —H | —OCF₃ |
| CHE | -2-(3-methylpyrazinyl) | —H | -tert-butyl |
| CHF | -2-(3-methylpyrazinyl) | —H | -iso-propyl |
| CHG | -2-pyridazinyl | —Cl | —H |
| CHH | -2-pyridazinyl | —Br | —H |
| CHI | -2-pyridazinyl | —F | —H |
| CHJ | -2-pyridazinyl | —CH₃ | —H |
| CHK | -2-pyridazinyl | —CF₃ | —H |
| CHL | -2-pyridazinyl | —OCH₃ | —H |
| CHM | -2-pyridazinyl | —OCH₂CH₃ | —H |
| CHN | -2-pyridazinyl | —OCF₃ | —H |

TABLE VI-continued

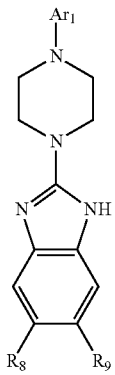

and pharmaceutically acceptable salts thereof, wherein:

| Compound | $Ar_1$ | $R_8$ | $R_9$ |
|---|---|---|---|
| CHO | -2-pyridazinyl | -tert-butyl | —H |
| CHP | -2-pyridazinyl | -iso-propyl | —H |
| CHQ | -2-pyridazinyl | —$CH_3$ | —$CH_3$ |
| CHR | -2-pyridazinyl | —H | —H |
| CHS | -2-pyridazinyl | —H | —Cl |
| CHT | -2-pyridazinyl | —H | —Br |
| CHU | -2-pyridazinyl | —H | —F |
| CHV | -2-pyridazinyl | —H | —$CH_3$ |
| CHW | -2-pyridazinyl | —H | —$CF_3$ |
| CHX | -2-pyridazinyl | —H | —$OCH_3$ |
| CHY | -2-pyridazinyl | —H | —$OCH_2CH_3$ |
| CHZ | -2-pyridazinyl | —H | —$OCF_3$ |
| CIA | -2-pyridazinyl | —H | -tert-butyl |
| CIB | -2-pyridazinyl | —H | -iso-propyl |
| CIC | -3-(4-chloropyridazinyl) | —Cl | —H |
| CID | -3-(4-chloropyridazinyl) | —Br | —H |
| CIE | -3-(4-chloropyridazinyl) | —F | —H |
| CIF | -3-(4-chloropyridazinyl) | —$CH_3$ | —H |
| CIG | -3-(4-chloropyridazinyl) | —$CF_3$ | —H |
| CIH | -3-(4-chloropyridazinyl) | —$OCH_3$ | —H |
| CII | -3-(4-chloropyridazinyl) | —$OCH_2CH_3$ | —H |
| CIJ | -3-(4-chloropyridazinyl) | —$OCF_3$ | —H |
| CIK | -3-(4-chloropyridazinyl) | -tert-butyl | —H |
| CIL | -3-(4-chloropyridazinyl) | -iso-propyl | —H |
| CIM | -3-(4-chloropyridazinyl) | —$CH_3$ | —$CH_3$ |
| CIN | -3-(4-chloropyridazinyl) | —H | —H |
| CIO | -3-(4-chloropyridazinyl) | —H | —Cl |
| CIP | -3-(4-chloropyridazinyl) | —H | —Br |
| CIQ | -3-(4-chloropyridazinyl) | —H | —F |
| CIR | -3-(4-chloropyridazinyl) | —H | —$CH_3$ |
| CIS | -3-(4-chloropyridazinyl) | —H | —$CF_3$ |
| CIT | -3-(4-chloropyridazinyl) | —H | —$OCH_3$ |
| CIU | -3-(4-chloropyridazinyl) | —H | —$OCH_2CH_3$ |
| CIV | -3-(4-chloropyridazinyl) | —H | —$OCF_3$ |
| CIW | -3-(4-chloropyridazinyl) | —H | -tert-butyl |
| CIX | -3-(4-chloropyridazinyl) | —H | -iso-propyl |
| CIY | -3-(4-methylpyridazinyl) | —Cl | —H |
| CIZ | -3-(4-methylpyridazinyl) | —Br | —H |
| CJA | -3-(4-methylpyridazinyl) | —F | —H |
| CJB | -3-(4-methylpyridazinyl) | —$CH_3$ | —H |
| CJC | -3-(4-methylpyridazinyl) | —$CF_3$ | —H |
| CJD | -3-(4-methylpyridazinyl) | —$OCH_3$ | —H |
| CJE | -3-(4-methylpyridazinyl) | —$OCH_2CH_3$ | —H |
| CJF | -3-(4-methylpyridazinyl) | —$OCF_3$ | —H |
| CJG | -3-(4-methylpyridazinyl) | -tert-butyl | —H |
| CJH | -3-(4-methylpyridazinyl) | -iso-propyl | —H |
| CJI | -3-(4-methylpyridazinyl) | —$CH_3$ | —$CH_3$ |
| CJJ | -3-(4-methylpyridazinyl) | —H | —H |
| CJK | -3-(4-methylpyridazinyl) | —H | —Cl |
| CJL | -3-(4-methylpyridazinyl) | —H | —Br |
| CJM | -3-(4-methylpyridazinyl) | —H | —F |
| CJN | -3-(4-methylpyridazinyl) | —H | —$CH_3$ |
| CJO | -3-(4-methylpyridazinyl) | —H | —$CF_3$ |
| CJP | -3-(4-methylpyridazinyl) | —H | —$OCH_3$ |
| CJQ | -3-(4-methylpyridazinyl) | —H | —$OCH_2CH_3$ |
| CJR | -3-(4-methylpyridazinyl) | —H | —$OCF_3$ |
| CJS | -3-(4-methylpyridazinyl) | —H | -tert-butyl |
| CJT | -3-(4-methylpyridazinyl) | —H | -iso-propyl |

TABLE VI-continued

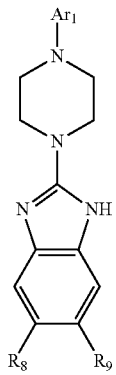

and pharmaceutically acceptable salts thereof, wherein:

| Compound | $Ar_1$ | $R_8$ | $R_9$ |
|---|---|---|---|
| CJU | -4-thiazanyl | —Cl | —H |
| CJV | -4-thiazanyl | —Br | —H |
| CJW | -4-thiazanyl | —F | —H |
| CJX | -4-thiazanyl | —$CH_3$ | —H |
| CJY | -4-thiazanyl | —$CF_3$ | —H |
| CJZ | -4-thiazanyl | —$OCH_3$ | —H |
| CKA | -4-thiazanyl | —$OCH_2CH_3$ | —H |
| CKB | -4-thiazanyl | —$OCF_3$ | —H |
| CKC | -4-thiazanyl | -tert-butyl | —H |
| CKD | -4-thiazanyl | -iso-propyl | —H |
| CKE | -4-thiazanyl | —$CH_3$ | —$CH_3$ |
| CKF | -4-thiazanyl | —H | —H |
| CKG | -4-thiazanyl | —H | —Cl |
| CKH | -4-thiazanyl | —H | —Br |
| CKI | -4-thiazanyl | —H | —F |
| CKJ | -4-thiazanyl | —H | —$CH_3$ |
| CKK | -4-thiazanyl | —H | —$CF_3$ |
| CKL | -4-thiazanyl | —H | —$OCH_3$ |
| CKM | -4-thiazanyl | —H | —$OCH_2CH_3$ |
| CKN | -4-thiazanyl | —H | —$OCF_3$ |
| CKO | -4-thiazanyl | —H | -tert-butyl |
| CKP | -4-thiazanyl | —H | -iso-propyl |
| CKQ | -5-(4-chlorothiazanyl) | —Cl | —H |
| CKR | -5-(4-chlorothiazanyl) | —Br | —H |
| CKS | -5-(4-chlorothiazanyl) | —F | —H |
| CKT | -5-(4-chlorothiazanyl) | —$CH_3$ | —H |
| CKU | -5-(4-chlorothiazanyl) | —$CF_3$ | —H |
| CKV | -5-(4-chlorothiazanyl) | —$OCH_3$ | —H |
| CKW | -5-(4-chlorothiazanyl) | —$OCH_2CH_3$ | —H |
| CKX | -5-(4-chlorothiazanyl) | —$OCF_3$ | —H |
| CKY | -5-(4-chlorothiazanyl) | -tert-butyl | —H |
| CKZ | -5-(4-chlorothiazanyl) | -iso-propyl | —H |
| CLA | -5-(4-chlorothiazanyl) | —$CH_3$ | —$CH_3$ |
| CLB | -5-(4-chlorothiazanyl) | —H | —H |
| CLC | -5-(4-chlorothiazanyl) | —H | —Cl |
| CLD | -5-(4-chlorothiazanyl) | —H | —Br |
| CLE | -5-(4-chlorothiazanyl) | —H | —F |
| CLF | -5-(4-chlorothiazanyl) | —H | —$CH_3$ |
| CLG | -5-(4-chlorothiazanyl) | —H | —$CF_3$ |
| CLH | -5-(4-chlorothiazanyl) | —H | —$OCH_3$ |
| CLI | -5-(4-chlorothiazanyl) | —H | —$OCH_2CH_3$ |
| CLJ | -5-(4-chlorothiazanyl) | —H | —$OCF_3$ |
| CLK | -5-(4-chlorothiazanyl) | —H | -tert-butyl |
| CLL | -5-(4-chlorothiazanyl) | —H | -iso-propyl |
| CLM | -5-(4-methylthiazanyl) | —Cl | —H |
| CLN | -5-(4-methylthiazanyl) | —Br | —H |
| CLO | -5-(4-methylthiazanyl) | —F | —H |
| CLP | -5-(4-methylthiazanyl) | —$CH_3$ | —H |
| CLQ | -5-(4-methylthiazanyl) | —$CF_3$ | —H |
| CLR | -5-(4-methylthiazanyl) | —$OCH_3$ | —H |
| CLS | -5-(4-methylthiazanyl) | —$OCH_2CH_3$ | —H |
| CLT | -5-(4-methylthiazanyl) | —$OCF_3$ | —H |
| CLU | -5-(4-methylthiazanyl) | -tert-butyl | —H |
| CLV | -5-(4-methylthiazanyl) | -iso-propyl | —H |
| CLW | -5-(4-methylthiazanyl) | —$CH_3$ | —$CH_3$ |
| CLX | -5-(4-methylthiazanyl) | —H | —H |
| CLY | -5-(4-methylthiazanyl) | —H | —Cl |
| CLZ | -5-(4-methylthiazanyl) | —H | —Br |

TABLE VI-continued

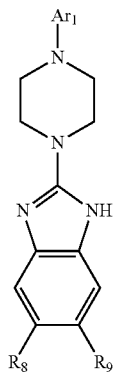

and pharmaceutically acceptable salts thereof, wherein:

| Compound | Ar$_1$ | R$_8$ | R$_9$ |
|---|---|---|---|
| CMA | -5-(4-methylthiazanyl) | —H | —F |
| CMB | -5-(4-methylthiazanyl) | —H | —CH$_3$ |
| CMC | -5-(4-methylthiazanyl) | —H | —CF$_3$ |
| CMD | -5-(4-methylthiazanyl) | —H | —OCH$_3$ |
| CME | -5-(4-methylthiazanyl) | —H | —OCH$_2$CH$_3$ |
| CMF | -5-(4-methylthiazanyl) | —H | —OCF$_3$ |
| CMG | -5-(4-methylthiazanyl) | —H | -tert-butyl |
| CMH | -5-(4-methylthiazanyl) | —H | -iso-propyl |

TABLE VII

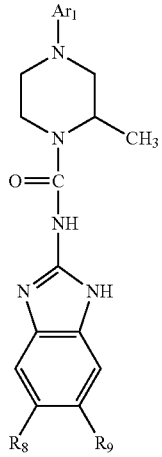

and pharmaceutically acceptable salts thereof, wherein:

| Compound | Ar$_1$ | R$_8$ | R$_9$ |
|---|---|---|---|
| CMI (a, b, and c) | -2-pyridazinyl | —Cl | —H |
| CMJ (a, b, and c) | -2-pyridazinyl | —Br | —H |
| CMK (a, b, and c) | -2-pyridazinyl | —F | —H |
| CML (a, b, and c) | -2-pyridazinyl | —CH$_3$ | —H |
| CMM (a, b, and c) | -2-pyridazinyl | —CF$_3$ | —H |
| CMN (a, b, and c) | -2-pyridazinyl | —OCH$_3$ | —H |
| CMO (a, b, and c) | -2-pyridazinyl | —OCH$_2$CH$_3$ | —H |
| CMP (a, b, and c) | -2-pyridazinyl | —OCF$_3$ | —H |
| CMQ (a, b, and c) | -2-pyridazinyl | -tert-butyl | —H |
| CMR (a, b, and c) | -2-pyridazinyl | -iso-propyl | —H |
| CMS (a, b, and c) | -2-pyridazinyl | —CH$_3$ | —CH$_3$ |
| CMT (a, b, and c) | -2-pyridazinyl | —H | —H |
| CMU (a, b, and c) | -2-pyridazinyl | —H | —Cl |
| CMV (a, b, and c) | -2-pyridazinyl | —H | —Br |
| CMW (a, b, and c) | -2-pyridazinyl | —H | —F |
| CMX (a, b, and c) | -2-pyridazinyl | —H | —CH$_3$ |
| CMY (a, b, and c) | -2-pyridazinyl | —H | —CF$_3$ |
| CMZ (a, b, and c) | -2-pyridazinyl | —H | —OCH$_3$ |
| CNA (a, b, and c) | -2-pyridazinyl | —H | —OCH$_2$CH$_3$ |

TABLE VII-continued

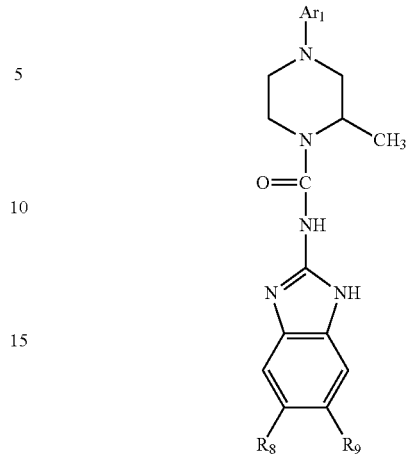

and pharmaceutically acceptable salts thereof, wherein:

| Compound | Ar$_1$ | R$_8$ | R$_9$ |
|---|---|---|---|
| CNB (a, b, and c) | -2-pyridazinyl | —H | —OCF$_3$ |
| CNC (a, b, and c) | -2-pyridazinyl | —H | -tert-butyl |
| CND (a, b, and c) | -2-pyridazinyl | —H | -iso-propyl |
| CNE (a, b, and c) | -3-(4-chloropyridazinyl) | —Cl | —H |
| CNF (a, b, and c) | -3-(4-chloropyridazinyl) | —Br | —H |
| CNG (a, b, and c) | -3-(4-chloropyridazinyl) | —F | —H |
| CNH (a, b, and c) | -3-(4-chloropyridazinyl) | —CH$_3$ | —H |
| CNI (a, b, and c) | -3-(4-chloropyridazinyl) | —CF$_3$ | —H |
| CNJ (a, b, and c) | -3-(4-chloropyridazinyl) | —OCH$_3$ | —H |
| CNK (a, b, and c) | -3-(4-chloropyridazinyl) | —OCH$_2$CH$_3$ | —H |
| CNL (a, b, and c) | -3-(4-chloropyridazinyl) | —OCF$_3$ | —H |
| CNM (a, b, and c) | -3-(4-chloropyridazinyl) | -tert-butyl | —H |
| CNN (a, b, and c) | -3-(4-chloropyridazinyl) | -iso-propyl | —H |
| CNO (a, b, and c) | -3-(4-chloropyridazinyl) | —CH$_3$ | —CH$_3$ |
| CNP (a, b, and c) | -3-(4-chloropyridazinyl) | —H | —H |
| CNQ (a, b, and c) | -3-(4-chloropyridazinyl) | —H | —Cl |
| CNR (a, b, and c) | -3-(4-chloropyridazinyl) | —H | —Br |
| CNS (a, b, and c) | -3-(4-chloropyridazinyl) | —H | —F |
| CNT (a, b, and c) | -3-(4-chloropyridazinyl) | —H | —CH$_3$ |
| CNU (a, b, and c) | -3-(4-chloropyridazinyl) | —H | —CF$_3$ |
| CNV (a, b, and c) | -3-(4-chloropyridazinyl) | —H | —OCH$_3$ |
| CNW (a, b, and c) | -3-(4-chloropyridazinyl) | —H | —OCH$_2$CH$_3$ |
| CNX (a, b, and c) | -3-(4-chloropyridazinyl) | —H | —OCF$_3$ |
| CNY (a, b, and c) | -3-(4-chloropyridazinyl) | —H | -tert-butyl |
| CNZ (a, b, and c) | -3-(4-chloropyridazinyl) | —H | -iso-propyl |
| COA (a, b, and c) | -3-(4-methylpyridazinyl) | —Cl | —H |
| COB (a, b, and c) | -3-(4-methylpyridazinyl) | —Br | —H |
| COC (a, b, and c) | -3-(4-methylpyridazinyl) | —F | —H |
| COD (a, b, and c) | -3-(4-methylpyridazinyl) | —CH$_3$ | —H |
| COE (a, b, and c) | -3-(4-methylpyridazinyl) | —CF$_3$ | —H |
| COF (a, b, and c) | -3-(4-methylpyridazinyl) | —OCH$_3$ | —H |
| COG (a, b, and c) | -3-(4-methylpyridazinyl) | —OCH$_2$CH$_3$ | —H |
| COH (a, b, and c) | -3-(4-methylpyridazinyl) | —OCF$_3$ | —H |
| COI (a, b, and c) | -3-(4-methylpyridazinyl) | -tert-butyl | —H |
| COJ (a, b, and c) | -3-(4-methylpyridazinyl) | -iso-propyl | —H |
| COK (a, b, and c) | -3-(4-methylpyridazinyl) | —CH$_3$ | —CH$_3$ |
| COL (a, b, and c) | -3-(4-methylpyridazinyl) | —H | —H |
| COM (a, b, and c) | -3-(4-methylpyridazinyl) | —H | —Cl |
| CON (a, b, and c) | -3-(4-methylpyridazinyl) | —H | —Br |
| COO (a, b, and c) | -3-(4-methylpyridazinyl) | —H | —F |
| COP (a, b, and c) | -3-(4-methylpyridazinyl) | —H | —CH$_3$ |
| COQ (a, b, and c) | -3-(4-methylpyridazinyl) | —H | —CF$_3$ |
| COR (a, b, and c) | -3-(4-methylpyridazinyl) | —H | —OCH$_3$ |
| COS (a, b, and c) | -3-(4-methylpyridazinyl) | —H | —OCH$_2$CH$_3$ |
| COT (a, b, and c) | -3-(4-methylpyridazinyl) | —H | —OCF$_3$ |
| COU (a, b, and c) | -3-(4-methylpyridazinyl) | —H | -tert-butyl |
| COV (a, b, and c) | -3-(4-methylpyridazinyl) | —H | -iso-propyl |
| COW (a, b, and c) | -4-thiazanyl | —Cl | —H |
| COX (a, b, and c) | -4-thiazanyl | —Br | —H |
| COY (a, b, and c) | -4-thiazanyl | —F | —H |
| COZ (a, b, and c) | -4-thiazanyl | —CH$_3$ | —H |
| CPA (a, b, and c) | -4-thiazanyl | —CF$_3$ | —H |
| CPB (a, b, and c) | -4-thiazanyl | —OCH$_3$ | —H |
| CPC (a, b, and c) | -4-thiazanyl | —OCH$_2$CH$_3$ | —H |

TABLE VII-continued

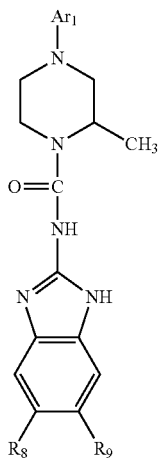

and pharmaceutically acceptable salts thereof, wherein:

| Compound | Ar₁ | R₈ | R₉ |
|---|---|---|---|
| CPD (a, b, and c) | -4-thiazanyl | —OCF₃ | —H |
| CPE (a, b, and c) | -4-thiazanyl | -tert-butyl | —H |
| CPF (a, b, and c) | -4-thiazanyl | -iso-propyl | —H |
| CPG (a, b, and c) | -4-thiazanyl | —CH₃ | —CH₃ |
| CPH (a, b, and c) | -4-thiazanyl | —H | —H |
| CPI (a, b, and c) | -4-thiazanyl | —H | —Cl |
| CPJ (a, b, and c) | -4-thiazanyl | —H | —Br |
| CPK (a, b, and c) | -4-thiazanyl | —H | —F |
| CPL (a, b, and c) | -4-thiazanyl | —H | —CH₃ |
| CPM (a, b, and c) | -4-thiazanyl | —H | —CF₃ |
| CPN (a, b, and c) | -4-thiazanyl | —H | —OCH₃ |
| CPO (a, b, and c) | -4-thiazanyl | —H | —OCH₂CH₃ |
| CPP (a, b, and c) | -4-thiazanyl | —H | —OCF₃ |
| CPQ (a, b, and c) | -4-thiazanyl | —H | -tert-butyl |
| CPR (a, b, and c) | -4-thiazanyl | —H | -iso-propyl |
| CPS (a, b, and c) | -5-(4-chlorothiazanyl) | —Cl | —H |
| CPT (a, b, and c) | -5-(4-chlorothiazanyl) | —Br | —H |
| CPU (a, b, and c) | -5-(4-chlorothiazanyl) | —F | —H |
| CPV (a, b, and c) | -5-(4-chlorothiazanyl) | —CH₃ | —H |
| CPW (a, b, and c) | -5-(4-chlorothiazanyl) | —CF₃ | —H |
| CPX (a, b, and c) | -5-(4-chlorothiazanyl) | —OCH₃ | —H |
| CPY (a, b, and c) | -5-(4-chlorothiazanyl) | —OCH₂CH₃ | —H |
| CPZ (a, b, and c) | -5-(4-chlorothiazanyl) | —OCF₃ | —H |
| CQA (a, b, and c) | -5-(4-chlorothiazanyl) | -tert-butyl | —H |
| CQB (a, b, and c) | -5-(4-chlorothiazanyl) | -iso-propyl | —H |
| CQC (a, b, and c) | -5-(4-chlorothiazanyl) | —CH₃ | —CH₃ |
| CQD (a, b, and c) | -5-(4-chlorothiazanyl) | —H | —H |
| CQE (a, b, and c) | -5-(4-chlorothiazanyl) | —H | —Cl |
| CQF (a, b, and c) | -5-(4-chlorothiazanyl) | —H | —Br |
| CQG (a, b, and c) | -5-(4-chlorothiazanyl) | —H | —F |
| CQH (a, b, and c) | -5-(4-chlorothiazanyl) | —H | —CH₃ |
| CQI (a, b, and c) | -5-(4-chlorothiazanyl) | —H | —CF₃ |
| CQJ (a, b, and c) | -5-(4-chlorothiazanyl) | —H | —OCH₃ |
| CQK (a, b, and c) | -5-(4-chlorothiazanyl) | —H | —OCH₂CH₃ |
| CQL (a, b, and c) | -5-(4-chlorothiazanyl) | —H | —OCF₃ |
| CQM (a, b, and c) | -5-(4-chlorothiazanyl) | —H | -tert-butyl |
| CQN (a, b, and c) | -5-(4-chlorothiazanyl) | —H | -iso-propyl |
| CQO (a, b, and c) | -5-(4-methylthiazanyl) | —Cl | —H |
| CQP (a, b, and c) | -5-(4-methylthiazanyl) | —Br | —H |
| CQQ (a, b, and c) | -5-(4-methylthiazanyl) | —F | —H |
| CQR (a, b, and c) | -5-(4-methylthiazanyl) | —CH₃ | —H |
| CQS (a, b, and c) | -5-(4-methylthiazanyl) | —CF₃ | —H |
| CQT (a, b, and c) | -5-(4-methylthiazanyl) | —OCH₃ | —H |
| CQU (a, b, and c) | -5-(4-methylthiazanyl) | —OCH₂CH₃ | —H |
| CQV (a, b, and c) | -5-(4-methylthiazanyl) | —OCF₃ | —H |
| CQW (a, b, and c) | -5-(4-methylthiazanyl) | -tert-butyl | —H |
| CQX (a, b, and c) | -5-(4-methylthiazanyl) | -iso-propyl | —H |
| CQY (a, b, and c) | -5-(4-methylthiazanyl) | —CH₃ | —CH₃ |
| CQZ (a, b, and c) | -5-(4-methylthiazanyl) | —H | —H |
| CRA (a, b, and c) | -5-(4-methylthiazanyl) | —H | —Cl |
| CRB (a, b, and c) | -5-(4-methylthiazanyl) | —H | —Br |
| CRC (a, b, and c) | -5-(4-methylthiazanyl) | —H | —F |
| CRD (a, b, and c) | -5-(4-methylthiazanyl) | —H | —CH₃ |
| CRE (a, b, and c) | -5-(4-methylthiazanyl) | —H | —CF₃ |

TABLE VII-continued

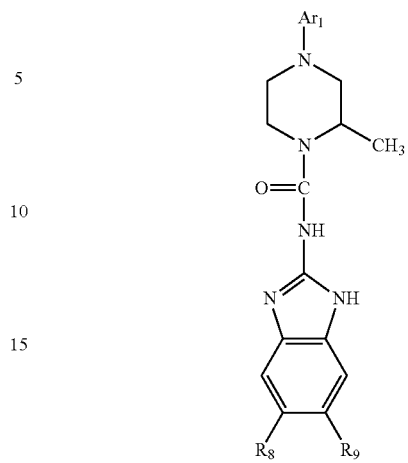

and pharmaceutically acceptable salts thereof, wherein:

| Compound | Ar₁ | R₈ | R₉ |
|---|---|---|---|
| CRF (a, b, and c) | -5-(4-methylthiazanyl) | —H | —OCH₃ |
| CRG (a, b, and c) | -5-(4-methylthiazanyl) | —H | —OCH₂CH₃ |
| CRH (a, b, and c) | -5-(4-methylthiazanyl) | —H | —OCF₃ |
| CRI (a, b, and c) | -5-(4-methylthiazanyl) | —H | -tert-butyl |
| CRJ (a, b, and c) | -5-(4-methylthiazanyl) | —H | -iso-propyl |

"a" means the Benzoazolylpiperazine Compound is racemic.
"b" means the carbon atom of the piperazine ring attached to the methyl group is in the R configuration.
"c" means the carbon atom of the piperazine ring attached to the methyl group is in the S configuration.

TABLE VIII

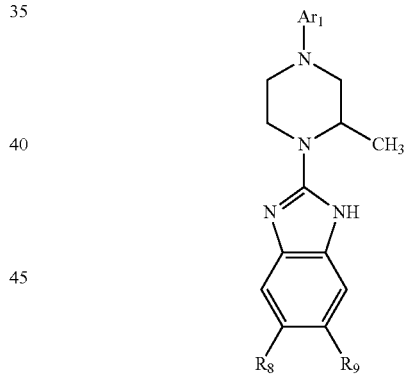

and pharmaceutically acceptable salts thereof, wherein:

| Compound | Ar₁ | R₈ | R₉ |
|---|---|---|---|
| CRK (a, b, and c) | -2-(3-chloropyridyl) | —Cl | —H |
| CRL (a, b, and c) | -2-(3-chloropyridyl) | —Br | —H |
| CRM (a, b, and c) | -2-(3-chloropyridyl) | —F | —H |
| CRN (a, b, and c) | -2-(3-chloropyridyl) | —CH₃ | —H |
| CRO (a, b, and c) | -2-(3-chloropyridyl) | —CF₃ | —H |
| CRP (a, b, and c) | -2-(3-chloropyridyl) | —OCH₃ | —H |
| CRQ (a, b, and c) | -2-(3-chloropyridyl) | —OCH₂CH₃ | —H |
| CRR (a, b, and c) | -2-(3-chloropyridyl) | —OCF₃ | —H |
| CRS (a, b, and c) | -2-(3-chloropyridyl) | -tert-butyl | —H |
| CRT (a, b, and c) | -2-(3-chloropyridyl) | -iso-propyl | —H |
| CRU (a, b, and c) | -2-(3-chloropyridyl) | —CH₃ | —CH₃ |
| CRV (a, b, and c) | -2-(3-chloropyridyl) | —H | —H |
| CRW (a, b, and c) | -2-(3-chloropyridyl) | —H | —Cl |
| CRX (a, b, and c) | -2-(3-chloropyridyl) | —H | —Br |
| CRY (a, b, and c) | -2-(3-chloropyridyl) | —H | —F |
| CRZ (a, b, and c) | -2-(3-chloropyridyl) | —H | —CH₃ |
| CSA (a, b, and c) | -2-(3-chloropyridyl) | —H | —CF₃ |
| CSB (a, b, and c) | -2-(3-chloropyridyl) | —H | —OCH₃ |

TABLE VIII-continued

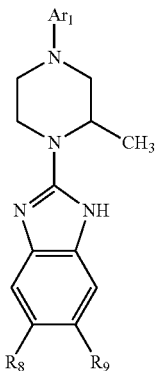

and pharmaceutically acceptable salts thereof, wherein:

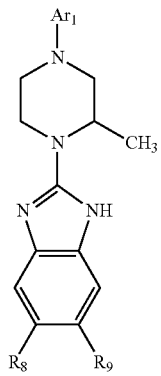

and pharmaceutically acceptable salts thereof, wherein:

| Compound | Ar₁ | R₈ | R₉ |
|---|---|---|---|
| CSC (a, b, and c) | -2-(3-chloropyridyl) | —H | —OCH₂CH₃ |
| CSD (a, b, and c) | -2-(3-chloropyridyl) | —H | —OCF₃ |
| CSE (a, b, and c) | -2-(3-chloropyridyl) | —H | -tert-butyl |
| CSF (a, b, and c) | -2-(3-chloropyridyl) | —H | -iso-propyl |
| CSG (a, b, and c) | -2-(3-methylpyridyl) | —Cl | —H |
| CSH (a, b, and c) | -2-(3-methylpyridyl) | —Br | —H |
| CSI (a, b, and c) | -2-(3-methylpyridyl) | —F | —H |
| CSJ (a, b, and c) | -2-(3-methylpyridyl) | —CH₃ | —H |
| CSK (a, b, and c) | -2-(3-methylpyridyl) | —CF₃ | —H |
| CSL (a, b, and c) | -2-(3-methylpyridyl) | —OCH₃ | —H |
| CSM (a, b, and c) | -2-(3-methylpyridyl) | —OCH₂CH₃ | —H |
| CSN (a, b, and c) | -2-(3-methylpyridyl) | —OCF₃ | —H |
| CSO (a, b, and c) | -2-(3-methylpyridyl) | -tert-butyl | —H |
| CSP (a, b, and c) | -2-(3-methylpyridyl) | -iso-propyl | —H |
| CSQ (a, b, and c) | -2-(3-methylpyridyl) | —CH₃ | —CH₃ |
| CSR (a, b, and c) | -2-(3-methylpyridyl) | —H | —H |
| CSS (a, b, and c) | -2-(3-methylpyridyl) | —H | —Cl |
| CST (a, b, and c) | -2-(3-methylpyridyl) | —H | —Br |
| CSU (a, b, and c) | -2-(3-methylpyridyl) | —H | —F |
| CSV (a, b, and c) | -2-(3-methylpyridyl) | —H | —CH₃ |
| CSW (a, b, and c) | -2-(3-methylpyridyl) | —H | —CF₃ |
| CSX (a, b, and c) | -2-(3-methylpyridyl) | —H | —OCH₃ |
| CSY (a, b, and c) | -2-(3-methylpyridyl) | —H | —OCH₂CH₃ |
| CSZ (a, b, and c) | -2-(3-methylpyridyl) | —H | —OCF₃ |
| CTA (a, b, and c) | -2-(3-methylpyridyl) | —H | -tert-butyl |
| CTB (a, b, and c) | -2-(3-methylpyridyl) | —H | -iso-propyl |
| CTC (a, b, and c) | -2-(3-CF₃-pyridyl) | —Cl | —H |
| CTD (a, b, and c) | -2-(3-CF₃-pyridyl) | —Br | —H |
| CTE (a, b, and c) | -2-(3-CF₃-pyridyl) | —F | —H |
| CTF (a, b, and c) | -2-(3-CF₃-pyridyl) | —CH₃ | —H |
| CTG (a, b, and c) | -2-(3-CF₃-pyridyl) | —CF₃ | —H |
| CTH (a, b, and c) | -2-(3-CF₃-pyridyl) | —OCH₃ | —H |
| CTI (a, b, and c) | -2-(3-CF₃-pyridyl) | —OCH₂CH₃ | —H |
| CTJ (a, b, and c) | -2-(3-CF₃-pyridyl) | —OCF₃ | —H |
| CTK (a, b, and c) | -2-(3-CF₃-pyridyl) | -tert-butyl | —H |
| CTL (a, b, and c) | -2-(3-CF₃-pyridyl) | -iso-propyl | —H |
| CTM (a, b, and c) | -2-(3-CF₃-pyridyl) | —CH₃ | —CH₃ |
| CTN (a, b, and c) | -2-(3-CF₃-pyridyl) | —H | —H |
| CTO (a, b, and c) | -2-(3-CF₃-pyridyl) | —H | —Cl |
| CTP (a, b, and c) | -2-(3-CF₃-pyridyl) | —H | —Br |
| CTQ (a, b, and c) | -2-(3-CF₃-pyridyl) | —H | —F |
| CTR (a, b, and c) | -2-(3-CF₃-pyridyl) | —H | —CH₃ |
| CTS (a, b, and c) | -2-(3-CF₃-pyridyl) | —H | —CF₃ |
| CTT (a, b, and c) | -2-(3-CF₃-pyridyl) | —H | —OCH₃ |
| CTU (a, b, and c) | -2-(3-CF₃-pyridyl) | —H | —OCH₂CH₃ |
| CTV (a, b, and c) | -2-(3-CF₃-pyridyl) | —H | —OCF₃ |
| CTW (a, b, and c) | -2-(3-CF₃-pyridyl) | —H | -tert-butyl |
| CTX (a, b, and c) | -2-(3-CF₃-pyridyl) | —H | -iso-propyl |
| CTY (a, b, and c) | -4-(5-chloropyrimidinyl) | —Cl | —H |
| CTZ (a, b, and c) | -4-(5-chloropyrimidinyl) | —Br | —H |
| CUA (a, b, and c) | -4-(5-chloropyrimidinyl) | —F | —H |
| CUB (a, b, and c) | -4-(5-chloropyrimidinyl) | —CH₃ | —H |
| CUC (a, b, and c) | -4-(5-chloropyrimidinyl) | —CF₃ | —H |
| CUD (a, b, and c) | -4-(5-chloropyrimidinyl) | —OCH₃ | —H |
| CUE (a, b, and c) | -4-(5-chloropyrimidinyl) | —OCH₂CH₃ | —H |
| CUF (a, b, and c) | -4-(5-chloropyrimidinyl) | —OCF₃ | —H |
| CUG (a, b, and c) | -4-(5-chloropyrimidinyl) | -tert-butyl | —H |
| CUH (a, b, and c) | -4-(5-chloropyrimidinyl) | -iso-propyl | —H |
| CUI (a, b, and c) | -4-(5-chloropyrimidinyl) | —CH₃ | —CH₃ |
| CUJ (a, b, and c) | -4-(5-chloropyrimidinyl) | —H | —H |
| CUK (a, b, and c) | -4-(5-chloropyrimidinyl) | —H | —Cl |
| CUL (a, b, and c) | -4-(5-chloropyrimidinyl) | —H | —Br |
| CUM (a, b, and c) | -4-(5-chloropyrimidinyl) | —H | —F |
| CUN (a, b, and c) | -4-(5-chloropyrimidinyl) | —H | —CH₃ |
| CUO (a, b, and c) | -4-(5-chloropyrimidinyl) | —H | —CF₃ |
| CUP (a, b, and c) | -4-(5-chloropyrimidinyl) | —H | —OCH₃ |
| CUQ (a, b, and c) | -4-(5-chloropyrimidinyl) | —H | —OCH₂CH₃ |
| CUR (a, b, and c) | -4-(5-chloropyrimidinyl) | —H | —OCF₃ |
| CUS (a, b, and c) | -4-(5-chloropyrimidinyl) | —H | -tert-butyl |
| CUT (a, b, and c) | -4-(5-chloropyrimidinyl) | —H | -iso-propyl |
| CUU (a, b, and c) | -4-(5-methylpyrimidinyl) | —Cl | —H |
| CUV (a, b, and c) | -4-(5-methylpyrimidinyl) | —Br | —H |
| CUW (a, b, and c) | -4-(5-methylpyrimidinyl) | —F | —H |
| CUX (a, b, and c) | -4-(5-methylpyrimidinyl) | —CH₃ | —H |
| CUY (a, b, and c) | -4-(5-methylpyrimidinyl) | —CF₃ | —H |
| CUZ (a, b, and c) | -4-(5-methylpyrimidinyl) | —OCH₃ | —H |
| CVA (a, b, and c) | -4-(5-methylpyrimidinyl) | —OCH₂CH₃ | —H |
| CVB (a, b, and c) | -4-(5-methylpyrimidinyl) | —OCF₃ | —H |
| CVC (a, b, and c) | -4-(5-methylpyrimidinyl) | -tert-butyl | —H |
| CVD (a, b, and c) | -4-(5-methylpyrimidinyl) | -iso-propyl | —H |
| CVE (a, b, and c) | -4-(5-methylpyrimidinyl) | —CH₃ | —CH₃ |
| CVF (a, b, and c) | -4-(5-methylpyrimidinyl) | —H | —H |
| CVG (a, b, and c) | -4-(5-methylpyrimidinyl) | —H | —Cl |
| CVH (a, b, and c) | -4-(5-methylpyrimidinyl) | —H | —Br |
| CVI (a, b, and c) | -4-(5-methylpyrimidinyl) | —H | —F |
| CVJ (a, b, and c) | -4-(5-methylpyrimidinyl) | —H | —CH₃ |
| CVK (a, b, and c) | -4-(5-methylpyrimidinyl) | —H | —CF₃ |
| CVL (a, b, and c) | -4-(5-methylpyrimidinyl) | —H | —OCH₃ |
| CVM (a, b, and c) | -4-(5-methylpyrimidinyl) | —H | —OCH₂CH₃ |
| CVN (a, b, and c) | -4-(5-methylpyrimidinyl) | —H | —OCF₃ |
| CVO (a, b, and c) | -4-(5-methylpyrimidinyl) | —H | -tert-butyl |
| CVP (a, b, and c) | -4-(5-methylpyrimidinyl) | —H | -iso-propyl |
| CVQ (a, b, and c) | -2-pyrazinyl | —Cl | —H |
| CVR (a, b, and c) | -2-pyrazinyl | —Br | —H |
| CVS (a, b, and c) | -2-pyrazinyl | —F | —H |
| CVT (a, b, and c) | -2-pyrazinyl | —CH₃ | —H |
| CVU (a, b, and c) | -2-pyrazinyl | —CF₃ | —H |
| CVV (a, b, and c) | -2-pyrazinyl | —OCH₃ | —H |
| CVW (a, b, and c) | -2-pyrazinyl | —OCH₂CH₃ | —H |
| CVX (a, b, and c) | -2-pyrazinyl | —OCF₃ | —H |
| CVY (a, b, and c) | -2-pyrazinyl | -tert-butyl | —H |
| CVZ (a, b, and c) | -2-pyrazinyl | -iso-propyl | —H |
| CWA (a, b, and c) | -2-pyrazinyl | —CH₃ | —CH₃ |
| CWB (a, b, and c) | -2-pyrazinyl | —H | —H |
| CWC (a, b, and c) | -2-pyrazinyl | —H | —Cl |
| CWD (a, b, and c) | -2-pyrazinyl | —H | —Br |
| CWE (a, b, and c) | -2-pyrazinyl | —H | —F |
| CWF (a, b, and c) | -2-pyrazinyl | —H | —CH₃ |
| CWG (a, b, and c) | -2-pyrazinyl | —H | —CF₃ |
| CWH (a, b, and c) | -2-pyrazinyl | —H | —OCH₃ |
| CWI (a, b, and c) | -2-pyrazinyl | —H | —OCH₂CH₃ |
| CWJ (a, b, and c) | -2-pyrazinyl | —H | —OCF₃ |
| CWK (a, b, and c) | -2-pyrazinyl | —H | -tert-butyl |
| CWL (a, b, and c) | -2-pyrazinyl | —H | -iso-propyl |
| CWM (a, b, and c) | -2-(3-chloropyrazinyl) | —Cl | —H |
| CWN (a, b, and c) | -2-(3-chloropyrazinyl) | —Br | —H |

TABLE VIII-continued

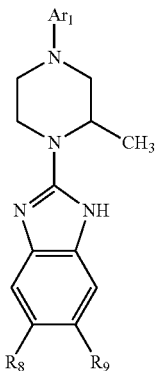

and pharmaceutically acceptable salts thereof, wherein:

| Compound | Ar₁ | R₈ | R₉ |
|---|---|---|---|
| CWO (a, b, and c) | -2-(3-chloropyrazinyl) | —F | —H |
| CWP (a, b, and c) | -2-(3-chloropyrazinyl) | —CH₃ | —H |
| CWQ (a, b, and c) | -2-(3-chloropyrazinyl) | —CF₃ | —H |
| CWR (a, b, and c) | -2-(3-chloropyrazinyl) | —OCH₃ | —H |
| CWS (a, b, and c) | -2-(3-chloropyrazinyl) | —OCH₂CH₃ | —H |
| CWT (a, b, and c) | -2-(3-chloropyrazinyl) | —OCF₃ | —H |
| CWU (a, b, and c) | -2-(3-chloropyrazinyl) | -tert-butyl | —H |
| CWV (a, b, and c) | -2-(3-chloropyrazinyl) | -iso-propyl | —H |
| CWW (a, b, and c) | -2-(3-chloropyrazinyl) | —CH₃ | —CH₃ |
| CWX (a, b, and c) | -2-(3-chloropyrazinyl) | —H | —H |
| CWY (a, b, and c) | -2-(3-chloropyrazinyl) | —H | —Cl |
| CWZ (a, b, and c) | -2-(3-chloropyrazinyl) | —H | —Br |
| CXA (a, b, and c) | -2-(3-chloropyrazinyl) | —H | —F |
| CXB (a, b, and c) | -2-(3-chloropyrazinyl) | —H | —CH₃ |
| CXC (a, b, and c) | -2-(3-chloropyrazinyl) | —H | —CF₃ |
| CXD (a, b, and c) | -2-(3-chloropyrazinyl) | —H | —OCH₃ |
| CXE (a, b, and c) | -2-(3-chloropyrazinyl) | —H | —OCH₂CH₃ |
| CXF (a, b, and c) | -2-(3-chloropyrazinyl) | —H | —OCF₃ |
| CXG (a, b, and c) | -2-(3-chloropyrazinyl) | —H | -tert-butyl |
| CXH (a, b, and c) | -2-(3-chloropyrazinyl) | —H | -iso-propyl |
| CXI (a, b, and c) | -2-(3-methylpyrazinyl) | —Cl | —H |
| CXJ (a, b, and c) | -2-(3-methylpyrazinyl) | —Br | —H |
| CXK (a, b, and c) | -2-(3-methylpyrazinyl) | —F | —H |
| CXL (a, b, and c) | -2-(3-methylpyrazinyl) | —CH₃ | —H |
| CXM (a, b, and c) | -2-(3-methylpyrazinyl) | —CF₃ | —H |
| CXN (a, b, and c) | -2-(3-methylpyrazinyl) | —OCH₃ | —H |
| CXO (a, b, and c) | -2-(3-methylpyrazinyl) | —OCH₂CH₃ | —H |
| CXP (a, b, and c) | -2-(3-methylpyrazinyl) | —OCF₃ | —H |
| CXQ (a, b, and c) | -2-(3-methylpyrazinyl) | -tert-butyl | —H |
| CXR (a, b, and c) | -2-(3-methylpyrazinyl) | -iso-propyl | —H |
| CXS (a, b, and c) | -2-(3-methylpyrazinyl) | —CH₃ | —CH₃ |
| CXT (a, b, and c) | -2-(3-methylpyrazinyl) | —H | —H |
| CXU (a, b, and c) | -2-(3-methylpyrazinyl) | —H | —Cl |
| CXV (a, b, and c) | -2-(3-methylpyrazinyl) | —H | —Br |
| CXW (a, b, and c) | -2-(3-methylpyrazinyl) | —H | —F |
| CXX (a, b, and c) | -2-(3-methylpyrazinyl) | —H | —CH₃ |
| CXY (a, b, and c) | -2-(3-methylpyrazinyl) | —H | —CF₃ |
| CXZ (a, b, and c) | -2-(3-methylpyrazinyl) | —H | —OCH₃ |
| CYA (a, b, and c) | -2-(3-methylpyrazinyl) | —H | —OCH₂CH₃ |
| CYB (a, b, and c) | -2-(3-methylpyrazinyl) | —H | —OCF₃ |
| CYC (a, b, and c) | -2-(3-methylpyrazinyl) | —H | -tert-butyl |
| CYD (a, b, and c) | -2-(3-methylpyrazinyl) | —H | -iso-propyl |
| CYE (a, b, and c) | -2-pyridazinyl | —Cl | —H |
| CYF (a, b, and c) | -2-pyridazinyl | —Br | —H |
| CYG (a, b, and c) | -2-pyridazinyl | —F | —H |
| CYH (a, b, and c) | -2-pyridazinyl | —CH₃ | —H |
| CYI (a, b, and c) | -2-pyridazinyl | —CF₃ | —H |
| CYJ (a, b, and c) | -2-pyridazinyl | —OCH₃ | —H |
| CYK (a, b, and c) | -2-pyridazinyl | —OCH₂CH₃ | —H |
| CYL (a, b, and c) | -2-pyridazinyl | —OCF₃ | —H |
| CYM (a, b, and c) | -2-pyridazinyl | -tert-butyl | —H |
| CYN (a, b, and c) | -2-pyridazinyl | -iso-propyl | —H |
| CYO (a, b, and c) | -2-pyridazinyl | —CH₃ | —CH₃ |
| CYP (a, b, and c) | -2-pyridazinyl | —H | —H |
| CYQ (a, b, and c) | -2-pyridazinyl | —H | —Cl |
| CYR (a, b, and c) | -2-pyridazinyl | —H | —Br |
| CYS (a, b, and c) | -2-pyridazinyl | —H | —F |
| CYT (a, b, and c) | -2-pyridazinyl | —H | —CH₃ |

TABLE VIII-continued

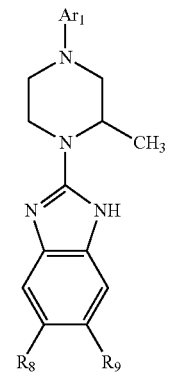

and pharmaceutically acceptable salts thereof, wherein:

| Compound | Ar₁ | R₈ | R₉ |
|---|---|---|---|
| CYU (a, b, and c) | -2-pyridazinyl | —H | —CF₃ |
| CYV (a, b, and c) | -2-pyridazinyl | —H | —OCH₃ |
| CYW (a, b, and c) | -2-pyridazinyl | —H | —OCH₂CH₃ |
| CYX (a, b, and c) | -2-pyridazinyl | —H | —OCF₃ |
| CYY (a, b, and c) | -2-pyridazinyl | —H | -tert-butyl |
| CYZ (a, b, and c) | -2-pyridazinyl | —H | -iso-propyl |
| CZA (a, b, and c) | -3-(4-chloropyridazinyl) | —Cl | —H |
| CZB (a, b, and c) | -3-(4-chloropyridazinyl) | —Br | —H |
| CZC (a, b, and c) | -3-(4-chloropyridazinyl) | —F | —H |
| CZD (a, b, and c) | -3-(4-chloropyridazinyl) | —CH₃ | —H |
| CZE (a, b, and c) | -3-(4-chloropyridazinyl) | —CF₃ | —H |
| CZF (a, b, and c) | -3-(4-chloropyridazinyl) | —OCH₃ | —H |
| CZG (a, b, and c) | -3-(4-chloropyridazinyl) | —OCH₂CH₃ | —H |
| CZH (a, b, and c) | -3-(4-chloropyridazinyl) | —OCF₃ | —H |
| CZI (a, b, and c) | -3-(4-chloropyridazinyl) | -tert-butyl | —H |
| CZJ (a, b, and c) | -3-(4-chloropyridazinyl) | -iso-propyl | —H |
| CZK (a, b, and c) | -3-(4-chloropyridazinyl) | —CH₃ | —CH₃ |
| CZL (a, b, and c) | -3-(4-chloropyridazinyl) | —H | —H |
| CZM (a, b, and c) | -3-(4-chloropyridazinyl) | —H | —Cl |
| CZN (a, b, and c) | -3-(4-chloropyridazinyl) | —H | —Br |
| CZO (a, b, and c) | -3-(4-chloropyridazinyl) | —H | —F |
| CZP (a, b, and c) | -3-(4-chloropyridazinyl) | —H | —CH₃ |
| CZQ (a, b, and c) | -3-(4-chloropyridazinyl) | —H | —CF₃ |
| CZR (a, b, and c) | -3-(4-chloropyridazinyl) | —H | —OCH₃ |
| CZS (a, b, and c) | -3-(4-chloropyridazinyl) | —H | —OCH₂CH₃ |
| CZT (a, b, and c) | -3-(4-chloropyridazinyl) | —H | —OCF₃ |
| CZU (a, b, and c) | -3-(4-chloropyridazinyl) | —H | -tert-butyl |
| CZV (a, b, and c) | -3-(4-chloropyridazinyl) | —H | -iso-propyl |
| CZW (a, b, and c) | -3-(4-methylpyridazinyl) | —Cl | —H |
| CZX (a, b, and c) | -3-(4-methylpyridazinyl) | —Br | —H |
| CZY (a, b, and c) | -3-(4-methylpyridazinyl) | —F | —H |
| CZZ (a, b, and c) | -3-(4-methylpyridazinyl) | —CH₃ | —H |
| DAA (a, b, and c) | -3-(4-methylpyridazinyl) | —CF₃ | —H |
| DAB (a, b, and c) | -3-(4-methylpyridazinyl) | —OCH₃ | —H |
| DAC (a, b, and c) | -3-(4-methylpyridazinyl) | —OCH₂CH₃ | —H |
| DAD (a, b, and c) | -3-(4-methylpyridazinyl) | —OCF₃ | —H |
| DAE (a, b, and c) | -3-(4-methylpyridazinyl) | -tert-butyl | —H |
| DAF (a, b, and c) | -3-(4-methylpyridazinyl) | -iso-propyl | —H |
| DAG (a, b, and c) | -3-(4-methylpyridazinyl) | —CH₃ | —CH₃ |
| DAH (a, b, and c) | -3-(4-methylpyridazinyl) | —H | —H |
| DAI (a, b, and c) | -3-(4-methylpyridazinyl) | —H | —Cl |
| DAJ (a, b, and c) | -3-(4-methylpyridazinyl) | —H | —Br |
| DAK (a, b, and c) | -3-(4-methylpyridazinyl) | —H | —F |
| DAL (a, b, and c) | -3-(4-methylpyridazinyl) | —H | —CH₃ |
| DAM (a, b, and c) | -3-(4-methylpyridazinyl) | —H | —CF₃ |
| DAN (a, b, and c) | -3-(4-methylpyridazinyl) | —H | —OCH₃ |
| DAO (a, b, and c) | -3-(4-methylpyridazinyl) | —H | —OCH₂CH₃ |
| DAP (a, b, and c) | -3-(4-methylpyridazinyl) | —H | —OCF₃ |
| DAQ (a, b, and c) | -3-(4-methylpyridazinyl) | —H | -tert-butyl |
| DAR (a, b, and c) | -3-(4-methylpyridazinyl) | —H | -iso-propyl |
| DAS (a, b, and c) | -4-thiazanyl | —Cl | —H |
| DAT (a, b, and c) | -4-thiazanyl | —Br | —H |
| DAU (a, b, and c) | -4-thiazanyl | —F | —H |
| DAV (a, b, and c) | -4-thiazanyl | —CH₃ | —H |
| DAW (a, b, and c) | -4-thiazanyl | —CF₃ | —H |
| DAX (a, b, and c) | -4-thiazanyl | —OCH₃ | —H |
| DAY (a, b, and c) | -4-thiazanyl | —OCH₂CH₃ | —H |
| DAZ (a, b, and c) | -4-thiazanyl | —OCF₃ | —H |

TABLE VIII-continued

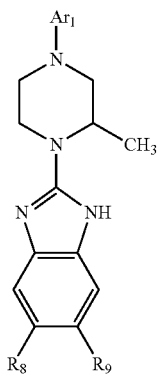

and pharmaceutically acceptable salts thereof, wherein:

| Compound | $Ar_1$ | $R_8$ | $R_9$ |
|---|---|---|---|
| DBA (a, b, and c) | -4-thiazanyl | -tert-butyl | —H |
| DBB (a, b, and c) | -4-thiazanyl | -iso-propyl | —H |
| DBC (a, b, and c) | -4-thiazanyl | —CH$_3$ | —CH$_3$ |
| DBD (a, b, and c) | -4-thiazanyl | —H | —H |
| DBE (a, b, and c) | -4-thiazanyl | —H | —Cl |
| DBF (a, b, and c) | -4-thiazanyl | —H | —Br |
| DBG (a, b, and c) | -4-thiazanyl | —H | —F |
| DBH (a, b, and c) | -4-thiazanyl | —H | —CH$_3$ |
| DBI (a, b, and c) | -4-thiazanyl | —H | —CF$_3$ |
| DBJ (a, b, and c) | -4-thiazanyl | —H | —OCH$_3$ |
| DBK (a, b, and c) | -4-thiazanyl | —H | —OCH$_2$CH$_3$ |
| DBL (a, b, and c) | -4-thiazanyl | —H | —OCF$_3$ |
| DBM (a, b, and c) | -4-thiazanyl | —H | -tert-butyl |
| DBN (a, b, and c) | -4-thiazanyl | —H | -iso-propyl |
| DBO (a, b, and c) | -5-(4-chlorothiazanyl) | —Cl | —H |
| DBP (a, b, and c) | -5-(4-chlorothiazanyl) | —Br | —H |
| DBQ (a, b, and c) | -5-(4-chlorothiazanyl) | —F | —H |
| DBR (a, b, and c) | -5-(4-chlorothiazanyl) | —CH$_3$ | —H |
| DBS (a, b, and c) | -5-(4-chlorothiazanyl) | —CF$_3$ | —H |
| DBT (a, b, and c) | -5-(4-chlorothiazariyl) | —OCH$_3$ | —H |
| DBU (a, b, and c) | -5-(4-chlorothiazanyl) | —OCH$_2$CH$_3$ | —H |
| DBV (a, b, and c) | -5-(4-chlorothiazanyl) | —OCF$_3$ | —H |
| DBW (a, b, and c) | -5-(4-chlorothiazanyl) | -tert-butyl | —H |
| DBX (a, b, and c) | -5-(4-chlorothiazanyl) | -iso-propyl | —H |
| DBY (a, b, and c) | -5-(4-chlorothiazanyl) | —CH$_3$ | —CH$_3$ |
| DBZ (a, b, and c) | -5-(4-chlorothiazanyl) | —H | —H |
| DCA (a, b, and c) | -5-(4-chlorothiazanyl) | —H | —Cl |
| DCB (a, b, and c) | -5-(4-chlorothiazanyl) | —H | —Br |
| DCC (a, b, and c) | -5-(4-chlorothiazanyl) | —H | —F |
| DCD (a, b, and c) | -5-(4-chlorothiazanyl) | —H | —CH$_3$ |
| DCE (a, b, and c) | -5-(4-chlorothiazanyl) | —H | —CF$_3$ |
| DCF (a, b, and c) | -5-(4-chlorothiazanyl) | —H | —OCH$_3$ |
| DCG (a, b, and c) | -5-(4-chlorothiazanyl) | —H | —OCH$_2$CH$_3$ |
| DCH (a, b, and c) | -5-(4-chlorothiazanyl) | —H | —OCF$_3$ |
| DCI (a, b, and c) | -5-(4-chlorothiazanyl) | —H | -tert-butyl |
| DCJ (a, b, and c) | -5-(4-chlorothiazanyl) | —H | -iso-propyl |
| DCK (a, b, and c) | -5-(4-methylthiazanyl) | —Cl | —H |
| DCL (a, b, and c) | -5-(4-methylthiazanyl) | —Br | —H |
| DCM (a, b, and c) | -5-(4-methylthiazanyl) | —F | —H |
| DCN (a, b, and c) | -5-(4-methylthiazanyl) | —CH$_3$ | —H |
| DCO (a, b, and c) | -5-(4-methylthiazanyl) | —CF$_3$ | —H |
| DCP (a, b, and c) | -5-(4-methylthiazanyl) | —OCH$_3$ | —H |
| DCQ (a, b, and c) | -5-(4-methylthiazanyl) | —OCH$_2$CH$_3$ | —H |
| DCR (a, b, and c) | -5-(4-methylthiazanyl) | —OCF$_3$ | —H |
| DCS (a, b, and c) | -5-(4-methylthiazanyl) | -tert-butyl | —H |
| DCT (a, b, and c) | -5-(4-methylthiazanyl) | -iso-propyl | —H |
| DCU (a, b, and c) | -5-(4-methylthiazanyl) | —CH$_3$ | —CH$_3$ |
| DCV (a, b, and c) | -5-(4-methylthiazanyl) | —H | —H |
| DCW (a, b, and c) | -5-(4-methylthiazanyl) | —H | —Cl |
| DCX (a, b, and c) | -5-(4-methylthiazanyl) | —H | —Br |
| DCY (a, b, and c) | -5-(4-methylthiazanyl) | —H | —F |
| DCZ (a, b, and c) | -5-(4-methylthiazanyl) | —H | —CH$_3$ |
| DDA (a, b, and c) | -5-(4-methylthiazanyl) | —H | —CF$_3$ |
| DDB (a, b, and c) | -5-(4-methylthiazanyl) | —H | —OCH$_3$ |
| DDC (a, b, and c) | -5-(4-methylthiazanyl) | —H | —OCH$_2$CH$_3$ |
| DDD (a, b, and c) | -5-(4-methylthiazanyl) | —H | —OCF$_3$ |

TABLE VIII-continued

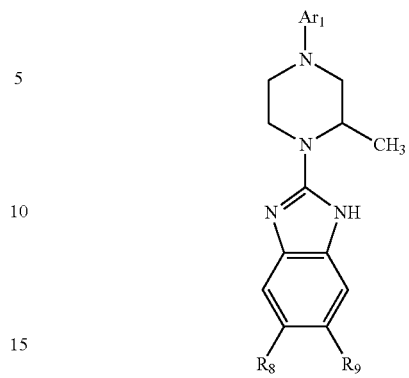

and pharmaceutically acceptable salts thereof, wherein:

| Compound | $Ar_1$ | $R_8$ | $R_9$ |
|---|---|---|---|
| DDE (a, b, and c) | -5-(4-methylthiazanyl) | —H | -tert-butyl |
| DDF (a, b, and c) | -5-(4-methylthiazanyl) | —H | -iso-propyl |

"a" means the Benzoazolylpiperazine Compound is racemic.
"b" means the carbon atom of the piperazine ring attached to the methyl group is in the R configuration.
"c" means the carbon atom of the piperazine ring attached to the methyl group is in the S configuration.

TABLE IX

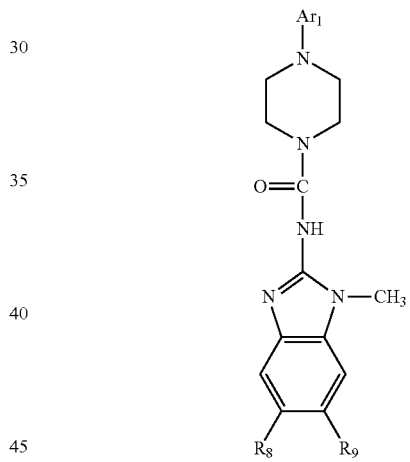

and pharmaceutically acceptable salts thereof, wherein:

| Compound | $Ar_1$ | $R_8$ | $R_9$ |
|---|---|---|---|
| DDG | -2-pyridazinyl | —Cl | —H |
| DDH | -2-pyridazinyl | —Br | —H |
| DDI | -2-pyridazinyl | —F | —H |
| DDJ | -2-pyridazinyl | —CH$_3$ | —H |
| DDK | -2-pyridazinyl | —CF$_3$ | —H |
| DDL | -2-pyridazinyl | —OCH$_3$ | —H |
| DDM | -2-pyridazinyl | —OCH$_2$CH$_3$ | —H |
| DDN | -2-pyridazinyl | —OCF$_3$ | —H |
| DDO | -2-pyridazinyl | -tert-butyl | —H |
| DDP | -2-pyridazinyl | -iso-propyl | —H |
| DDQ | -2-pyridazinyl | —CH$_3$ | —CH$_3$ |
| DDR | -2-pyridazinyl | —H | —H |
| DDS | -2-pyridazinyl | —H | —Cl |
| DDT | -2-pyridazinyl | —H | —Br |
| DDU | -2-pyridazinyl | —H | —F |
| DDV | -2-pyridazinyl | —H | —CH$_3$ |
| DDW | -2-pyridazinyl | —H | —CF$_3$ |
| DDX | -2-pyridazinyl | —H | —OCH$_3$ |
| DDY | -2-pyridazinyl | —H | —OCH$_2$CH$_3$ |
| DDZ | -2-pyridazinyl | —H | —OCF$_3$ |
| DEA | -2-pyridazinyl | —H | -tert-butyl |
| DEB | -2-pyridazinyl | —H | -iso-propyl |

TABLE IX-continued

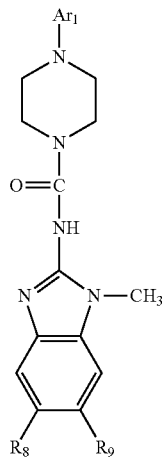

and pharmaceutically acceptable salts thereof, wherein:

| Compound | Ar₁ | R₈ | R₉ |
|---|---|---|---|
| DEC | -3-(4-chloropyridazanyl) | —Cl | —H |
| DED | -3-(4-chloropyridazanyl) | —Br | —H |
| DEE | -3-(4-chloropyridazanyl) | —F | —H |
| DEF | -3-(4-chloropyridazanyl) | —CH₃ | —H |
| DEG | -3-(4-chloropyridazanyl) | —CF₃ | —H |
| DEH | -3-(4-chloropyridazanyl) | —OCH₃ | —H |
| DEI | -3-(4-chloropyridazanyl) | —OCH₂CH₃ | —H |
| DEJ | -3-(4-chloropyridazanyl) | —OCF₃ | —H |
| DEK | -3-(4-chloropyridazanyl) | -tert-butyl | —H |
| DEL | -3-(4-chloropyridazanyl) | -iso-propyl | —H |
| DEM | -3-(4-chloropyridazanyl) | —CH₃ | —CH₃ |
| DEN | -3-(4-chloropyridazanyl) | —H | —H |
| DEO | -3-(4-chloropyridazanyl) | —H | —Cl |
| DEP | -3-(4-chloropyridazanyl) | —H | —Br |
| DEQ | -3-(4-chloropyridazanyl) | —H | —F |
| DER | -3-(4-chloropyridazanyl) | —H | —CH₃ |
| DES | -3-(4-chloropyridazanyl) | —H | —CF₃ |
| DET | -3-(4-chloropyridazanyl) | —H | —OCH₃ |
| DEU | -3-(4-chloropyridazanyl) | —H | —OCH₂CH₃ |
| DEV | -3-(4-chloropyridazanyl) | —H | —OCF₃ |
| DEW | -3-(4-chloropyridazanyl) | —H | -tert-butyl |
| DEX | -3-(4-chloropyridazanyl) | —H | -iso-propyl |
| DEY | -3-(4-methylpyridazinyl) | —Cl | —H |
| DEZ | -3-(4-methylpyridazinyl) | —Br | —H |
| DFA | -3-(4-methylpyridazinyl) | —F | —H |
| DFB | -3-(4-methylpyridazinyl) | —CH₃ | —H |
| DFC | -3-(4-methylpyridazinyl) | —CF₃ | —H |
| DFD | -3-(4-methylpyridazinyl) | —OCH₃ | —H |
| DFE | -3-(4-methylpyridazinyl) | —OCH₂CH₃ | —H |
| DFF | -3-(4-methylpyridazinyl) | —OCF₃ | —H |
| DFG | -3-(4-methylpyridazinyl) | -tert-butyl | —H |
| DFH | -3-(4-methylpyridazinyl) | -iso-propyl | —H |
| DFI | -3-(4-methylpyridazinyl) | —CH₃ | —CH₃ |
| DFJ | -3-(4-methylpyridazinyl) | —H | —H |
| DFK | -3-(4-methylpyridazinyl) | —H | —Cl |
| DFL | -3-(4-methylpyridazinyl) | —H | —Br |
| DFM | -3-(4-methylpyridazinyl) | —H | —F |
| DFN | -3-(4-methylpyridazinyl) | —H | —CH₃ |
| DFO | -3-(4-methylpyridazinyl) | —H | —CF₃ |
| DFP | -3-(4-methylpyridazinyl) | —H | —OCH₃ |
| DFQ | -3-(4-methylpyridazinyl) | —H | —OCH₂CH₃ |
| DFR | -3-(4-methylpyridazinyl) | —H | —OCF₃ |
| DFS | -3-(4-methylpyridazinyl) | —H | -tert-butyl |
| DFT | -3-(4-methylpyridazinyl) | —H | -iso-propyl |
| DFU | -4-thiazanyl | —Cl | —H |
| DFV | -4-thiazanyl | —Br | —H |
| DFW | -4-thiazanyl | —F | —H |
| DFX | -4-thiazanyl | —CH₃ | —H |
| DFY | -4-thiazanyl | —CF₃ | —H |
| DFZ | -4-thiazanyl | —OCH₃ | —H |
| DGA | -4-thiazanyl | —OCH₂CH₃ | —H |
| DGB | -4-thiazanyl | —OCF₃ | —H |
| DGC | -4-thiazanyl | -tert-butyl | —H |
| DGD | -4-thiazanyl | -iso-propyl | —H |

TABLE IX-continued

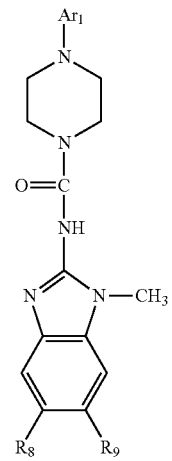

and pharmaceutically acceptable salts thereof, wherein:

| Compound | Ar₁ | R₈ | R₉ |
|---|---|---|---|
| DGE | -4-thiazanyl | —CH₃ | —CH₃ |
| DGF | -4-thiazanyl | —H | —H |
| DGG | -4-thiazanyl | —H | —Cl |
| DGH | -4-thiazanyl | —H | —Br |
| DGI | -4-thiazanyl | —H | —F |
| DGJ | -4-thiazanyl | —H | —CH₃ |
| DGK | -4-thiazanyl | —H | —CF₃ |
| DGL | -4-thiazanyl | —H | —OCH₃ |
| DGM | -4-thiazanyl | —H | —OCH₂CH₃ |
| DGN | -4-thiazanyl | —H | —OCF₃ |
| DGO | -4-thiazanyl | —H | -tert-butyl |
| DGP | -4-thiazanyl | —H | -iso-propyl |
| DGQ | -5-(4-chlorothiazanyl) | —Cl | —H |
| DGR | -5-(4-chlorothiazanyl) | —Br | —H |
| DGS | -5-(4-chlorothiazanyl) | —F | —H |
| DGT | -5-(4-chlorothiazanyl) | —CH₃ | —H |
| DGU | -5-(4-chlorothiazanyl) | —CF₃ | —H |
| DGV | -5-(4-chlorothiazanyl) | —OCH₃ | —H |
| DGW | -5-(4-chlorothiazanyl) | —OCH₂CH₃ | —H |
| DGX | -5-(4-chlorothiazanyl) | —OCF₃ | —H |
| DGY | -5-(4-chlorothiazanyl) | -tert-butyl | —H |
| DGZ | -5-(4-chlorothiazanyl) | -iso-propyl | —H |
| DHA | -5-(4-chlorothiazanyl) | —CH₃ | —CH₃ |
| DHB | -5-(4-chlorothiazanyl) | —H | —H |
| DHC | -5-(4-chlorothiazanyl) | —H | —Cl |
| DHD | -5-(4-chlorothiazanyl) | —H | —Br |
| DHE | -5-(4-chlorothiazanyl) | —H | —F |
| DHF | -5-(4-chlorothiazanyl) | —H | —CH₃ |
| DHG | -5-(4-chlorothiazanyl) | —H | —CF₃ |
| DHH | -5-(4-chlorothiazanyl) | —H | —OCH₃ |
| DHI | -5-(4-chlorothiazanyl) | —H | —OCH₂CH₃ |
| DHJ | -5-(4-chlorothiazanyl) | —H | —OCF₃ |
| DHK | -5-(4-chlorothiazanyl) | —H | -tert-butyl |
| DHL | -5-(4-chlorothiazanyl) | —H | -iso-propyl |
| DHM | -5-(4-methylthiazanyl) | —Cl | —H |
| DHN | -5-(4-methylthiazanyl) | —Br | —H |
| DHO | -5-(4-methylthiazanyl) | —F | —H |
| DHP | -5-(4-methylthiazanyl) | —CH₃ | —H |
| DHQ | -5-(4-methylthiazanyl) | —CF₃ | —H |
| DHR | -5-(4-methylthiazanyl) | —OCH₃ | —H |
| DHS | -5-(4-methylthiazanyl) | —OCH₂CH₃ | —H |
| DHT | -5-(4-methylthiazanyl) | —OCF₃ | —H |
| DHU | -5-(4-methylthiazanyl) | -tert-butyl | —H |
| DHV | -5-(4-methylthiazanyl) | -iso-propyl | —H |
| DHW | -5-(4-methylthiazanyl) | —CH₃ | —CH₃ |
| DHX | -5-(4-methylthiazanyl) | —H | —H |
| DHY | -5-(4-methylthiazanyl) | —H | —Cl |
| DHZ | -5-(4-methylthiazanyl) | —H | —Br |
| DIA | -5-(4-methylthiazanyl) | —H | —F |
| DIB | -5-(4-methylthiazanyl) | —H | —CH₃ |
| DIC | -5-(4-methylthiazanyl) | —H | —CF₃ |
| DID | -5-(4-methylthiazanyl) | —H | —OCH₃ |
| DIE | -5-(4-methylthiazanyl) | —H | —OCH₂CH₃ |
| DIF | -5-(4-methylthiazanyl) | —H | —OCF₃ |

TABLE IX-continued

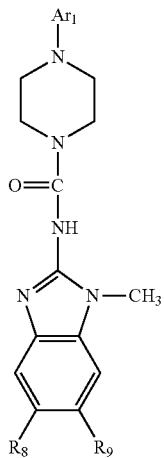

and pharmaceutically acceptable salts thereof, wherein:

| Compound | Ar₁ | R₈ | R₉ |
|---|---|---|---|
| DIG | -5-(4-methylthiazanyl) | —H | -tert-butyl |
| DIH | -5-(4-methylthiazanyl) | —H | -iso-propyl |

TABLE X

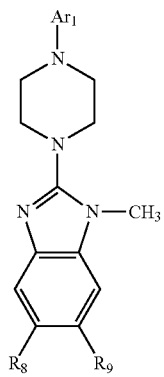

and pharmaceutically acceptable salts thereof, wherein:

| Compound | Ar₁ | R₈ | R₉ |
|---|---|---|---|
| DII | -2-(3-chloropyridyl) | —Cl | —H |
| DIJ | -2-(3-chloropyridyl) | —Br | —H |
| DIK | -2-(3-chloropyridyl) | —F | —H |
| DIL | -2-(3-chloropyridyl) | —CH₃ | —H |
| DIM | -2-(3-chloropyridyl) | —CF₃ | —H |
| DIN | -2-(3-chloropyridyl) | —OCH₃ | —H |
| DIO | -2-(3-chloropyridyl) | —OCH₂CH₃ | —H |
| DIP | -2-(3-chloropyridyl) | —OCF₃ | —H |
| DIQ | -2-(3-chloropyridyl) | -tert-butyl | —H |
| DIR | -2-(3-chloropyridyl) | -iso-propyl | —H |
| DIS | -2-(3-chloropyridyl) | —CH₃ | —CH₃ |
| DIT | -2-(3-chloropyridyl) | —H | —H |
| DIU | -2-(3-chloropyridyl) | —H | —Cl |
| DIV | -2-(3-chloropyridyl) | —H | —Br |
| DIW | -2-(3-chloropyridyl) | —H | —F |
| DIX | -2-(3-chloropyridyl) | —H | —CH₃ |
| DIY | -2-(3-chloropyridyl) | —H | —CF₃ |
| DIZ | -2-(3-chloropyridyl) | —H | —OCH₃ |
| DJA | -2-(3-chloropyridyl) | —H | —OCH₂CH₃ |
| DJB | -2-(3-chloropyridyl) | —H | —OCF₃ |
| DJC | -2-(3-chloropyridyl) | —H | -tert-butyl |
| DJD | -2-(3-chloropyridyl) | —H | -iso-propyl |
| DJE | -2-(3-methylpyridyl) | —Cl | —H |
| DJF | -2-(3-methylpyridyl) | —Br | —H |
| DJG | -2-(3-methylpyridyl) | —F | —H |
| DJH | -2-(3-methylpyridyl) | —CH₃ | —H |

TABLE X-continued

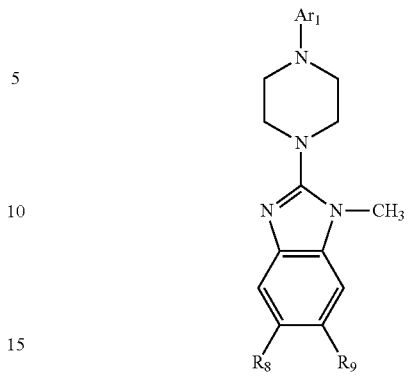

and pharmaceutically acceptable salts thereof, wherein:

| Compound | Ar₁ | R₈ | R₉ |
|---|---|---|---|
| DJI | -2-(3-methylpyridyl) | —CF₃ | —H |
| DJJ | -2-(3-methylpyridyl) | —OCH₃ | —H |
| DJK | -2-(3-methylpyridyl) | —OCH₂CH₃ | —H |
| DJL | -2-(3-methylpyridyl) | —OCF₃ | —H |
| DJM | -2-(3-methylpyridyl) | -tert-butyl | —H |
| DJN | -2-(3-methylpyridyl) | -iso-propyl | —H |
| DJO | -2-(3-methylpyridyl) | —CH₃ | —CH₃ |
| DJP | -2-(3-methylpyridyl) | —H | —H |
| DJQ | -2-(3-methylpyridyl) | —H | —Cl |
| DJR | -2-(3-methylpyridyl) | —H | —Br |
| DJS | -2-(3-methylpyridyl) | —H | —F |
| DJT | -2-(3-methylpyridyl) | —H | —CH₃ |
| DJU | -2-(3-methylpyridyl) | —H | —CF₃ |
| DJV | -2-(3-methylpyridyl) | —H | —OCH₃ |
| DJW | -2-(3-methylpyridyl) | —H | —OCH₂CH₃ |
| DJX | -2-(3-methylpyridyl) | —H | —OCF₃ |
| DJY | -2-(3-methylpyridyl) | —H | -tert-butyl |
| DJZ | -2-(3-methylpyridyl) | —H | -iso-propyl |
| DKA | -2-(3-CF₃-pyridyl) | —Cl | —H |
| DKB | -2-(3-CF₃-pyridyl) | —Br | —H |
| DKC | -2-(3-CF₃-pyridyl) | —F | —H |
| DKD | -2-(3-CF₃-pyridyl) | —CH₃ | —H |
| DKE | -2-(3-CF₃-pyridyl) | —CF₃ | —H |
| DKF | -2-(3-CF₃-pyridyl) | —OCH₃ | —H |
| DKG | -2-(3-CF₃-pyridyl) | —OCH₂CH₃ | —H |
| DKH | -2-(3-CF₃-pyridyl) | —OCF₃ | —H |
| DKI | -2-(3-CF₃-pyridyl) | -tert-butyl | —H |
| DKJ | -2-(3-CF₃-pyridyl) | -iso-propyl | —H |
| DKK | -2-(3-CF₃-pyridyl) | —CH₃ | —CH₃ |
| DKL | -2-(3-CF₃-pyridyl) | —H | —H |
| DKM | -2-(3-CF₃-pyridyl) | —H | —Cl |
| DKN | -2-(3-CF₃-pyridyl) | —H | —Br |
| DKO | -2-(3-CF₃-pyridyl) | —H | —F |
| DKP | -2-(3-CF₃-pyridyl) | —H | —CH₃ |
| DKQ | -2-(3-CF₃-pyridyl) | —H | —CF₃ |
| DKR | -2-(3-CF₃-pyridyl) | —H | —OCH₃ |
| DKS | -2-(3-CF₃-pyridyl) | —H | —OCH₂CH₃ |
| DKT | -2-(3-CF₃-pyridyl) | —H | —OCF₃ |
| DKU | -2-(3-CF₃-pyridyl) | —H | -tert-butyl |
| DKV | -2-(3-CF₃-pyridyl) | —H | -iso-propyl |
| DKW | -4-(5-chloropyrimidinyl) | —Cl | —H |
| DKX | -4-(5-chloropyrimidinyl) | —Br | —H |
| DKY | -4-(5-chloropyrimidinyl) | —F | —H |
| DKZ | -4-(5-chloropyrimidinyl) | —CH₃ | —H |
| DLA | -4-(5-chloropyrimidinyl) | —CF₃ | —H |
| DLB | -4-(5-chloropyrimidinyl) | —OCH₃ | —H |
| DLC | -4-(5-chloropyrimidinyl) | —OCH₂CH₃ | —H |
| DLD | -4-(5-chloropyrimidinyl) | —OCF₃ | —H |
| DLE | -4-(5-chloropyrimidinyl) | -tert-butyl | —H |
| DLF | -4-(5-chloropyrimidinyl) | -iso-propyl | —H |
| DLG | -4-(5-chloropyrimidinyl) | —CH₃ | —CH₃ |
| DLH | -4-(5-chloropyrimidinyl) | —H | —H |
| DLI | -4-(5-chloropyrimidinyl) | —H | —Cl |
| DLJ | -4-(5-chloropyrimidinyl) | —H | —Br |
| DLK | -4-(5-chloropyrimidinyl) | —H | —F |
| DLL | -4-(5-chloropyrimidinyl) | —H | —CH₃ |
| DLM | -4-(5-chloropyrimidinyl) | —H | —CF₃ |
| DLN | -4-(5-chloropyrimidinyl) | —H | —OCH₃ |

TABLE X-continued

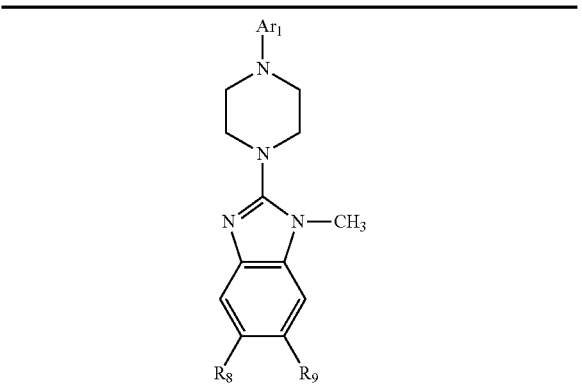

and pharmaceutically acceptable salts thereof, wherein:

| Compound | $Ar_1$ | $R_8$ | $R_9$ |
|---|---|---|---|
| DLO | -4-(5-chloropyrimidinyl) | —H | —OCH$_2$CH$_3$ |
| DLP | -4-(5-chloropyrimidinyl) | —H | —OCF$_3$ |
| DLQ | -4-(5-chloropyrimidinyl) | —H | -tert-butyl |
| DLR | -4-(5-chloropyrimidinyl) | —H | -iso-propyl |
| DLS | -4-(5-methylpyrimidinyl) | —Cl | —H |
| DLT | -4-(5-methylpyrimidinyl) | —Br | —H |
| DLU | -4-(5-methylpyrimidinyl) | —F | —H |
| DLV | -4-(5-methylpyrimidinyl) | —CH$_3$ | —H |
| DLW | -4-(5-methylpyrimidinyl) | —CF$_3$ | —H |
| DLX | -4-(5-methylpyrimidinyl) | —OCH$_3$ | —H |
| DLY | -4-(5-methylpyrimidinyl) | —OCH$_2$CH$_3$ | —H |
| DLZ | -4-(5-methylpyrimidinyl) | —OCF$_3$ | —H |
| DMA | -4-(5-methylpyrimidinyl) | -tert-butyl | —H |
| DMB | -4-(5-methylpyrimidinyl) | -iso-propyl | —H |
| DMC | -4-(5-methylpyrimidinyl) | —CH$_3$ | —CH$_3$ |
| DMD | -4-(5-methylpyrimidinyl) | —H | —H |
| DME | -4-(5-methylpyrimidinyl) | —H | —Cl |
| DMF | -4-(5-methylpyrimidinyl) | —H | —Br |
| DMG | -4-(5-methylpyrimidinyl) | —H | —F |
| DMH | -4-(5-methylpyrimidinyl) | —H | —CH$_3$ |
| DMI | -4-(5-methylpyrimidinyl) | —H | —CF$_3$ |
| DMJ | -4-(5-methylpyrimidinyl) | —H | —OCH$_3$ |
| DMK | -4-(5-methylpyrimidinyl) | —H | —OCH$_2$CH$_3$ |
| DML | -4-(5-methylpyrimidinyl) | —H | —OCF$_3$ |
| DMM | -4-(5-methylpyrimidinyl) | —H | -tert-butyl |
| DMN | -4-(5-methylpyrimidinyl) | —H | -iso-propyl |
| DMO | -2-pyrazinyl | —Cl | —H |
| DMP | -2-pyrazinyl | —Br | —H |
| DMQ | -2-pyrazinyl | —F | —H |
| DMR | -2-pyrazinyl | —CH$_3$ | —H |
| DMS | -2-pyrazinyl | —CF$_3$ | —H |
| DMT | -2-pyrazinyl | —OCH$_3$ | —H |
| DMU | -2-pyrazinyl | —OCH$_2$CH$_3$ | —H |
| DMV | -2-pyrazinyl | —OCF$_3$ | —H |
| DMW | -2-pyrazinyl | -tert-butyl | —H |
| DMX | -2-pyrazinyl | -iso-propyl | —H |
| DMY | -2-pyrazinyl | —CH$_3$ | —CH$_3$ |
| DMZ | -2-pyrazinyl | —H | —H |
| DNA | -2-pyrazinyl | —H | —Cl |
| DNB | -2-pyrazinyl | —H | —Br |
| DNC | -2-pyrazinyl | —H | —F |
| DND | -2-pyrazinyl | —H | —CH$_3$ |
| DNE | -2-pyrazinyl | —H | —CF$_3$ |
| DNF | -2-pyrazinyl | —H | —OCH$_3$ |
| DNG | -2-pyrazinyl | —H | —OCH$_2$CH$_3$ |
| DNH | -2-pyrazinyl | —H | —OCF$_3$ |
| DNI | -2-pyrazinyl | —H | -tert-butyl |
| DNJ | -2-pyrazinyl | —H | -iso-propyl |
| DNK | -2-(3-chloropyrazinyl) | —Cl | —H |
| DNL | -2-(3-chloropyrazinyl) | —Br | —H |
| DNM | -2-(3-chloropyrazinyl) | —F | —H |
| DNN | -2-(3-chloropyrazinyl) | —CH$_3$ | —H |
| DNO | -2-(3-chloropyrazinyl) | —CF$_3$ | —H |
| DNP | -2-(3-chloropyrazinyl) | —OCH$_3$ | —H |
| DNQ | -2-(3-chloropyrazinyl) | —OCH$_2$CH$_3$ | —H |
| DNR | -2-(3-chloropyrazinyl) | —OCF$_3$ | —H |
| DNS | -2-(3-chloropyrazinyl) | -tert-butyl | —H |
| DNT | -2-(3-chloropyrazinyl) | -iso-propyl | —H |

TABLE X-continued

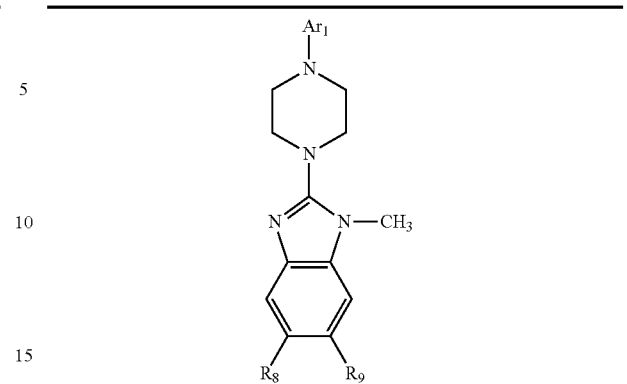

and pharmaceutically acceptable salts thereof, wherein:

| Compound | $Ar_1$ | $R_8$ | $R_9$ |
|---|---|---|---|
| DNU | -2-(3-chloropyrazinyl) | —CH$_3$ | —CH$_3$ |
| DNV | -2-(3-chloropyrazinyl) | —H | —H |
| DNW | -2-(3-chloropyrazinyl) | —H | —Cl |
| DNX | -2-(3-chloropyrazinyl) | —H | —Br |
| DNY | -2-(3-chloropyrazinyl) | —H | —F |
| DNZ | -2-(3-chloropyrazinyl) | —H | —CH$_3$ |
| DOA | -2-(3-chloropyrazinyl) | —H | —CF$_3$ |
| DOB | -2-(3-chloropyrazinyl) | —H | —OCH$_3$ |
| DOC | -2-(3-chloropyrazinyl) | —H | —OCH$_2$CH$_3$ |
| DOD | -2-(3-chloropyrazinyl) | —H | —OCF$_3$ |
| DOE | -2-(3-chloropyrazinyl) | —H | -tert-butyl |
| DOF | -2-(3-chloropyrazinyl) | —H | -iso-propyl |
| DOG | -2-(3-methylpyrazinyl) | —Cl | —H |
| DOH | -2-(3-methylpyrazinyl) | —Br | —H |
| DOI | -2-(3-methylpyrazinyl) | —F | —H |
| DOJ | -2-(3-methylpyrazinyl) | —CH$_3$ | —H |
| DOK | -2-(3-methylpyrazinyl) | —CF$_3$ | —H |
| DOL | -2-(3-methylpyrazinyl) | —OCH$_3$ | —H |
| DOM | -2-(3-methylpyrazinyl) | —OCH$_2$CH$_3$ | —H |
| DON | -2-(3-methylpyrazinyl) | —OCF$_3$ | —H |
| DOO | -2-(3-methylpyrazinyl) | -tert-butyl | —H |
| DOP | -2-(3-methylpyrazinyl) | -iso-propyl | —H |
| DOQ | -2-(3-methylpyrazinyl) | —CH$_3$ | —CH$_3$ |
| DOR | -2-(3-methylpyrazinyl) | —H | —H |
| DOS | -2-(3-methylpyrazinyl) | —H | —Cl |
| DOT | -2-(3-methylpyrazinyl) | —H | —Br |
| DOU | -2-(3-methylpyrazinyl) | —H | —F |
| DOV | -2-(3-methylpyrazinyl) | —H | —CH$_3$ |
| DOW | -2-(3-methylpyrazinyl) | —H | —CF$_3$ |
| DOX | -2-(3-methylpyrazinyl) | —H | —OCH$_3$ |
| DOY | -2-(3-methylpyrazinyl) | —H | —OCH$_2$CH$_3$ |
| DOZ | -2-(3-methylpyrazinyl) | —H | —OCF$_3$ |
| DPA | -2-(3-methylpyrazinyl) | —H | -tert-butyl |
| DPB | -2-(3-methylpyrazinyl) | —H | -iso-propyl |
| DPC | -2-pyridazinyl | —Cl | —H |
| DPD | -2-pyridazinyl | —Br | —H |
| DPE | -2-pyridazinyl | —F | —H |
| DPF | -2-pyridazinyl | —CH$_3$ | —H |
| DPG | -2-pyridazinyl | —CF$_3$ | —H |
| DPH | -2-pyridazinyl | —OCH$_3$ | —H |
| DPI | -2-pyridazinyl | —OCH$_2$CH$_3$ | —H |
| DPJ | -2-pyridazinyl | —OCF$_3$ | —H |
| DPK | -2-pyridazinyl | -tert-butyl | —H |
| DPL | -2-pyridazinyl | -iso-propyl | —H |
| DPM | -2-pyridazinyl | —CH$_3$ | —CH$_3$ |
| DPN | -2-pyridazinyl | —H | —H |
| DPO | -2-pyridazinyl | —H | —Cl |
| DPP | -2-pyridazinyl | —H | —Br |
| DPQ | -2-pyridazinyl | —H | —F |
| DPR | -2-pyridazinyl | —H | —CH$_3$ |
| DPS | -2-pyridazinyl | —H | —CF$_3$ |
| DPT | -2-pyridazinyl | —H | —OCH$_3$ |
| DPU | -2-pyridazinyl | —H | —OCH$_2$CH$_3$ |
| DPV | -2-pyridazinyl | —H | —OCF$_3$ |
| DPW | -2-pyridazinyl | —H | -tert-butyl |
| DPX | -2-pyridazinyl | —H | -iso-propyl |
| DPY | -3-(4-chloropyridazinyl) | —Cl | —H |
| DPZ | -3-(4-chloropyridazinyl) | —Br | —H |

TABLE X-continued

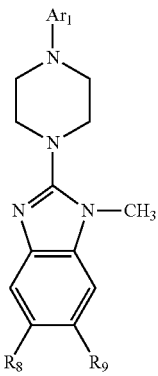

and pharmaceutically acceptable salts thereof, wherein:

| Compound | Ar$_1$ | R$_8$ | R$_9$ |
|---|---|---|---|
| DQA | -3-(4-chloropyridazinyl) | —F | —H |
| DQB | -3-(4-chloropyridazinyl) | —CH$_3$ | —H |
| DQC | -3-(4-chloropyridazinyl) | —CF$_3$ | —H |
| DQD | -3-(4-chloropyridazinyl) | —OCH$_3$ | —H |
| DQE | -3-(4-chloropyridazinyl) | —OCH$_2$CH$_3$ | —H |
| DQF | -3-(4-chloropyridazinyl) | —OCF$_3$ | —H |
| DQG | -3-(4-chloropyridazinyl) | -tert-butyl | —H |
| DQH | -3-(4-chloropyridazinyl) | -iso-propyl | —H |
| DQI | -3-(4-chloropyridazinyl) | —CH$_3$ | —CH$_3$ |
| DQJ | -3-(4-chloropyridazinyl) | —H | —H |
| DQK | -3-(4-chloropyridazinyl) | —H | —Cl |
| DQL | -3-(4-chloropyridazinyl) | —H | —Br |
| DQM | -3-(4-chloropyridazinyl) | —H | —F |
| DQN | -3-(4-chloropyridazinyl) | —H | —CH$_3$ |
| DQO | -3-(4-chloropyridazinyl) | —H | —CF$_3$ |
| DQP | -3-(4-chloropyridazinyl) | —H | —OCH$_3$ |
| DQQ | -3-(4-chloropyridazinyl) | —H | —OCH$_2$CH$_3$ |
| DQR | -3-(4-chloropyridazinyl) | —H | —OCF$_3$ |
| DQS | -3-(4-chloropyridazinyl) | —H | -tert-butyl |
| DQT | -3-(4-chloropyridazinyl) | —H | -iso-propyl |
| DQU | -3-(4-methylpyridazinyl) | —Cl | —H |
| DQV | -3-(4-methylpyridazinyl) | —Br | —H |
| DQW | -3-(4-methylpyridazinyl) | —F | —H |
| DQX | -3-(4-methylpyridazinyl) | —CH$_3$ | —H |
| DQY | -3-(4-methylpyridazinyl) | —CF$_3$ | —H |
| DQZ | -3-(4-methylpyridazinyl) | —OCH$_3$ | —H |
| DRA | -3-(4-methylpyridazinyl) | —OCH$_2$CH$_3$ | —H |
| DRB | -3-(4-methylpyridazinyl) | —OCF$_3$ | —H |
| DRC | -3-(4-methylpyridazinyl) | -tert-butyl | —H |
| DRD | -3-(4-methylpyridazinyl) | -iso-propyl | —H |
| DRE | -3-(4-methylpyridazinyl) | —CH$_3$ | —CH$_3$ |
| DRF | -3-(4-methylpyridazinyl) | —H | —H |
| DRG | -3-(4-methylpyridazinyl) | —H | —Cl |
| DRH | -3-(4-methylpyridazinyl) | —H | —Br |
| DRI | -3-(4-methylpyridazinyl) | —H | —F |
| DRJ | -3-(4-methylpyridazinyl) | —H | —CH$_3$ |
| DRK | -3-(4-methylpyridazinyl) | —H | —CF$_3$ |
| DRL | -3-(4-methylpyridazinyl) | —H | —OCH$_3$ |
| DRM | -3-(4-methylpyridazinyl) | —H | —OCH$_2$CH$_3$ |
| DRN | -3-(4-methylpyridazinyl) | —H | —OCF$_3$ |
| DRO | -3-(4-methylpyridazinyl) | —H | -tert-butyl |
| DRP | -3-(4-methylpyridazinyl) | —H | -iso-propyl |
| DRQ | -4-thiazanyl | —Cl | —H |
| DRR | -4-thiazanyl | —Br | —H |
| DRS | -4-thiazanyl | —F | —H |
| DRT | -4-thiazanyl | —CH$_3$ | —H |
| DRU | -4-thiazanyl | —CF$_3$ | —H |
| DRV | -4-thiazanyl | —OCH$_3$ | —H |
| DRW | -4-thiazanyl | —OCH$_2$CH$_3$ | —H |
| DRX | -4-thiazanyl | —OCF$_3$ | —H |
| DRY | -4-thiazanyl | -tert-butyl | —H |
| DRZ | -4-thiazanyl | -iso-propyl | —H |
| DSA | -4-thiazanyl | —CH$_3$ | —CH$_3$ |
| DSB | -4-thiazanyl | —H | —H |
| DSC | -4-thiazanyl | —H | —Cl |
| DSD | -4-thiazanyl | —H | —Br |
| DSE | -4-thiazanyl | —H | —F |
| DSF | -4-thiazanyl | —H | —CH$_3$ |
| DSG | -4-thiazanyl | —H | —CF$_3$ |
| DSH | -4-thiazanyl | —H | —OCH$_3$ |
| DSI | -4-thiazanyl | —H | —OCH$_2$CH$_3$ |
| DSJ | -4-thiazanyl | —H | —OCF$_3$ |
| DSK | -4-thiazanyl | —H | -tert-butyl |
| DSL | -4-thiazanyl | —H | -iso-propyl |
| DSM | -5-(4-chlorothiazanyl) | —Cl | —H |
| DSN | -5-(4-chlorothiazanyl) | —Br | —H |
| DSO | -5-(4-chlorothiazanyl) | —F | —H |
| DSP | -5-(4-chlorothiazanyl) | —CH$_3$ | —H |
| DSQ | -5-(4-chlorothiazanyl) | —CF$_3$ | —H |
| DSR | -5-(4-chlorothiazanyl) | —OCH$_3$ | —H |
| DSS | -5-(4-chlorothiazanyl) | —OCH$_2$CH$_3$ | —H |
| DST | -5-(4-chlorothiazanyl) | —OCF$_3$ | —H |
| DSU | -5-(4-chlorothiazanyl) | -tert-butyl | —H |
| DSV | -5-(4-chlorothiazanyl) | -iso-propyl | —H |
| DSW | -5-(4-chlorothiazanyl) | —CH$_3$ | —CH$_3$ |
| DSX | -5-(4-chlorothiazanyl) | —H | —H |
| DSY | -5-(4-chlorothiazanyl) | —H | —Cl |
| DSZ | -5-(4-chlorothiazanyl) | —H | —Br |
| DTA | -5-(4-chlorothiazanyl) | —H | —F |
| DTB | -5-(4-chlorothiazanyl) | —H | —CH$_3$ |
| DTC | -5-(4-chlorothiazanyl) | —H | —CF$_3$ |
| DTD | -5-(4-chlorothiazanyl) | —H | —OCH$_3$ |
| DTE | -5-(4-chlorothiazanyl) | —H | —OCH$_2$CH$_3$ |
| DTF | -5-(4-chlorothiazanyl) | —H | —OCF$_3$ |
| DTG | -5-(4-chlorothiazanyl) | —H | -tert-butyl |
| DTH | -5-(4-chlorothiazanyl) | —H | -iso-propyl |
| DTI | -5-(4-methylthiazanyl) | —Cl | —H |
| DTJ | -5-(4-methylthiazanyl) | —Br | —H |
| DTK | -5-(4-methylthiazanyl) | —F | —H |
| DTL | -5-(4-methylthiazanyl) | —CH$_3$ | —H |
| DTM | -5-(4-methylthiazanyl) | —CF$_3$ | —H |
| DTN | -5-(4-methylthiazanyl) | —OCH$_3$ | —H |
| DTO | -5-(4-methylthiazanyl) | —OCH$_2$CH$_3$ | —H |
| DTP | -5-(4-methylthiazanyl) | —OCF$_3$ | —H |
| DTQ | -5-(4-methylthiazanyl) | -tert-butyl | —H |
| DTR | -5-(4-methylthiazanyl) | -iso-propyl | —H |
| DTS | -5-(4-methylthiazanyl) | —CH$_3$ | —CH$_3$ |
| DTT | -5-(4-methylthiazanyl) | —H | —H |
| DTU | -5-(4-methylthiazanyl) | —H | —Cl |
| DTV | -5-(4-methylthiazanyl) | —H | —Br |
| DTW | -5-(4-methylthiazanyl) | —H | —F |
| DTX | -5-(4-methylthiazanyl) | —H | —CH$_3$ |
| DTY | -5-(4-methylthiazanyl) | —H | —CF$_3$ |
| DTZ | -5-(4-methylthiazanyl) | —H | —OCH$_3$ |
| DUA | -5-(4-methylthiazanyl) | —H | —OCH$_2$CH$_3$ |
| DUB | -5-(4-methylthiazanyl) | —H | —OCF$_3$ |
| DUC | -5-(4-methylthiazanyl) | —H | -tert-butyl |
| DUD | -5-(4-methylthiazanyl) | —H | -iso-propyl |

TABLE XI

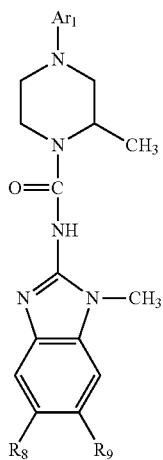

and pharmaceutically acceptable salts thereof, wherein:

| Compound | Ar$_1$ | R$_8$ | R$_9$ |
|---|---|---|---|
| DUE (a, b, and c) | -2-pyridazinyl | —Cl | —H |
| DUF (a, b, and c) | -2-pyridazinyl | —Br | —H |
| DUG (a, b, and c) | -2-pyridazinyl | —F | —H |
| DUH (a, b, and c) | -2-pyridazinyl | —CH$_3$ | —H |
| DUI (a, b, and c) | -2-pyridazinyl | —CF$_3$ | —H |
| DUJ (a, b, and c) | -2-pyridazinyl | —OCH$_3$ | —H |
| DUK (a, b, and c) | -2-pyridazinyl | —OCH$_2$CH$_3$ | —H |
| DUL (a, b, and c) | -2-pyridazinyl | —OCF$_3$ | —H |
| DUM (a, b, and c) | -2-pyridazinyl | -tert-butyl | —H |
| DUN (a, b, and c) | -2-pyridazinyl | -iso-propyl | —H |
| DUO (a, b, and c) | -2-pyridazinyl | —CH$_3$ | —CH$_3$ |
| DUP (a, b, and c) | -2-pyridazinyl | —H | —H |
| DUQ (a, b, and c) | -2-pyridazinyl | —H | —Cl |
| DUR (a, b, and c) | -2-pyridazinyl | —H | —Br |
| DUS (a, b, and c) | -2-pyridazinyl | —H | —F |
| DUT (a, b, and c) | -2-pyridazinyl | —H | —CH$_3$ |
| DUU (a, b, and c) | -2-pyridazinyl | —H | —CF$_3$ |
| DUV (a, b, and c) | -2-pyridazinyl | —H | —OCH$_3$ |
| DUW (a, b, and c) | -2-pyridazinyl | —H | —OCH$_2$CH$_3$ |
| DUX (a, b, and c) | -2-pyridazinyl | —H | —OCF$_3$ |
| DUY (a, b, and c) | -2-pyridazinyl | —H | -tert-butyl |
| DUZ (a, b, and c) | -2-pyridazinyl | —H | -iso-propyl |
| DVA (a, b, and c) | -3-(4-chloropyridazinyl) | —Cl | —H |
| DVB (a, b, and c) | -3-(4-chloropyridazinyl) | —Br | —H |
| DVC (a, b, and c) | -3-(4-chloropyridazinyl) | —F | —H |
| DVD (a, b, and c) | -3-(4-chloropyridazinyl) | —CH$_3$ | —H |
| DVE (a, b, and c) | -3-(4-chloropyridazinyl) | —CF$_3$ | —H |
| DVF (a, b, and c) | -3-(4-chloropyridazinyl) | —OCH$_3$ | —H |
| DVG (a, b, and c) | -3-(4-chloropyridazinyl) | —OCH$_2$CH$_3$ | —H |
| DVH (a, b, and c) | -3-(4-chloropyridazinyl) | —OCF$_3$ | —H |
| DVI (a, b, and c) | -3-(4-chloropyridazinyl) | -tert-butyl | —H |
| DVJ (a, b, and c) | -3-(4-chloropyridazinyl) | -iso-propyl | —H |
| DVK (a, b, and c) | -3-(4-chloropyridazinyl) | —CH$_3$ | —CH$_3$ |
| DVL (a, b, and c) | -3-(4-chloropyridazinyl) | —H | —H |
| DVM (a, b, and c) | -3-(4-chloropyridazinyl) | —H | —Cl |
| DVN (a, b, and c) | -3-(4-chloropyridazinyl) | —H | —Br |
| DVO (a, b, and c) | -3-(4-chloropyridazinyl) | —H | —F |
| DVP (a, b, and c) | -3-(4-chloropyridazinyl) | —H | —CH$_3$ |
| DVQ (a, b, and c) | -3-(4-chloropyridazinyl) | —H | —CF$_3$ |
| DVR (a, b, and c) | -3-(4-chloropyridazinyl) | —H | —OCH$_3$ |
| DVS (a, b, and c) | -3-(4-chloropyridazinyl) | —H | —OCH$_2$CH$_3$ |
| DVT (a, b, and c) | -3-(4-chloropyridazinyl) | —H | —OCF$_3$ |
| DVU (a, b, and c) | -3-(4-chloropyridazinyl) | —H | -tert-butyl |
| DVV (a, b, and c) | -3-(4-chloropyridazinyl) | —H | -iso-propyl |
| DVW (a, b, and c) | -3-(4-methylpyridazinyl) | —Cl | —H |
| DVX (a, b, and c) | -3-(4-methylpyridazinyl) | —Br | —H |
| DVY (a, b, and c) | -3-(4-methylpyridazinyl) | —F | —H |
| DVZ (a, b, and c) | -3-(4-methylpyridazinyl) | —CH$_3$ | —H |
| DWA (a, b, and c) | -3-(4-methylpyridazinyl) | —CF$_3$ | —H |
| DWB (a, b, and c) | -3-(4-methylpyridazinyl) | —OCH$_3$ | —H |
| DWC (a, b, and c) | -3-(4-methylpyridazinyl) | —OCH$_2$CH$_3$ | —H |

TABLE XI-continued

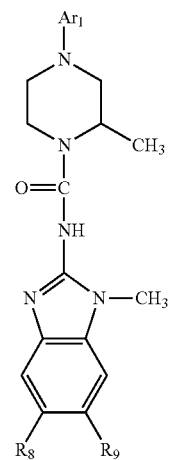

and pharmaceutically acceptable salts thereof, wherein:

| Compound | Ar$_1$ | R$_8$ | R$_9$ |
|---|---|---|---|
| DWD (a, b, and c) | -3-(4-methylpyridazinyl) | —OCF$_3$ | —H |
| DWE (a, b, and c) | -3-(4-methylpyridazinyl) | -tert-butyl | —H |
| DWF (a, b, and c) | -3-(4-methylpyridazinyl) | -iso-propyl | —H |
| DWG (a, b, and c) | -3-(4-methylpyridazinyl) | —CH$_3$ | —CH$_3$ |
| DWH (a, b, and c) | -3-(4-methylpyridazinyl) | —H | —H |
| DWI (a, b, and c) | -3-(4-methylpyridazinyl) | —H | —Cl |
| DWJ (a, b, and c) | -3-(4-methylpyridazinyl) | —H | —Br |
| DWK (a, b, and c) | -3-(4-methylpyridazinyl) | —H | —F |
| DWL (a, b, and c) | -3-(4-methylpyridazinyl) | —H | —CH$_3$ |
| DWM (a, b, and c) | -3-(4-methylpyridazinyl) | —H | —CF$_3$ |
| DWN (a, b, and c) | -3-(4-methylpyridazinyl) | —H | —OCH$_3$ |
| DWO (a, b, and c) | -3-(4-methylpyridazinyl) | —H | —OCH$_2$CH$_3$ |
| DWP (a, b, and c) | -3-(4-methylpyridazinyl) | —H | —OCF$_3$ |
| DWQ (a, b, and c) | -3-(4-methylpyridazinyl) | —H | -tert-butyl |
| DWR (a, b, and c) | -3-(4-methylpyridazinyl) | —H | -iso-propyl |
| DWS (a, b, and c) | -4-thiazanyl | —Cl | —H |
| DWT (a, b, and c) | -4-thiazanyl | —Br | —H |
| DWU (a, b, and c) | -4-thiazanyl | —F | —H |
| DWV (a, b, and c) | -4-thiazanyl | —CH$_3$ | —H |
| DWW (a, b, and c) | -4-thiazanyl | —CF$_3$ | —H |
| DWX (a, b, and c) | -4-thiazanyl | —OCH$_3$ | —H |
| DWY (a, b, and c) | -4-thiazanyl | —OCH$_2$CH$_3$ | —H |
| DWZ (a, b, and c) | -4-thiazanyl | —OCF$_3$ | —H |
| DXA (a, b, and c) | -4-thiazanyl | -tert-butyl | —H |
| DXB (a, b, and c) | -4-thiazanyl | -iso-propyl | —H |
| DXC (a, b, and c) | -4-thiazanyl | —CH$_3$ | —CH$_3$ |
| DXD (a, b, and c) | -4-thiazanyl | —H | —H |
| DXE (a, b, and c) | -4-thiazanyl | —H | —Cl |
| DXF (a, b, and c) | -4-thiazanyl | —H | —Br |
| DXG (a, b, and c) | -4-thiazanyl | —H | —F |
| DXH (a, b, and c) | -4-thiazanyl | —H | —CH$_3$ |
| DXI (a, b, and c) | -4-thiazanyl | —H | —CF$_3$ |
| DXJ (a, b, and c) | -4-thiazanyl | —H | —OCH$_3$ |
| DXK (a, b, and c) | -4-thiazanyl | —H | —OCH$_2$CH$_3$ |
| DXL (a, b, and c) | -4-thiazanyl | —H | —OCF$_3$ |
| DXM (a, b, and c) | -4-thiazanyl | —H | -tert-butyl |
| DXN (a, b, and c) | -4-thiazanyl | —H | -iso-propyl |
| DXO (a, b, and c) | -5-(4-chlorothiazanyl) | —Cl | —H |
| DXP (a, b, and c) | -5-(4-chlorothiazanyl) | —Br | —H |
| DXQ (a, b, and c) | -5-(4-chlorothiazanyl) | —F | —H |
| DXR (a, b, and c) | -5-(4-chlorothiazanyl) | —CH$_3$ | —H |
| DXS (a, b, and c) | -5-(4-chlorothiazanyl) | —CF$_3$ | —H |
| DXT (a, b, and c) | -5-(4-chlorothiazanyl) | —OCH$_3$ | —H |
| DXU (a, b, and c) | -5-(4-chlorothiazanyl) | —OCH$_2$CH$_3$ | —H |
| DXV (a, b, and c) | -5-(4-chlorothiazanyl) | —OCF$_3$ | —H |
| DXW (a, b, and c) | -5-(4-chlorothiazanyl) | -tert-butyl | —H |
| DXX (a, b, and c) | -5-(4-chlorothiazanyl) | -iso-propyl | —H |
| DXY (a, b, and c) | -5-(4-chlorothiazanyl) | —CH$_3$ | —CH$_3$ |
| DXZ (a, b, and c) | -5-(4-chlorothiazanyl) | —H | —H |
| DYA (a, b, and c) | -5-(4-chlorothiazanyl) | —H | —Cl |
| DYB (a, b, and c) | -5-(4-chlorothiazanyl) | —H | —Br |

303

TABLE XI-continued

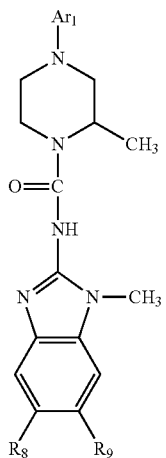

and pharmaceutically acceptable salts thereof, wherein:

| Compound | Ar₁ | R₈ | R₉ |
|---|---|---|---|
| DYC (a, b, and c) | -5-(4-chlorothiazanyl) | —H | —F |
| DYD (a, b, and c) | -5-(4-chlorothiazanyl) | —H | —CH₃ |
| DYE (a, b, and c) | -5-(4-chlorothiazanyl) | —H | —CF₃ |
| DYF (a, b, and c) | -5-(4-chlorothiazanyl) | —H | —OCH₃ |
| DYG (a, b, and c) | -5-(4-chlorothiazanyl) | —H | —OCH₂CH₃ |
| DYH (a, b, and c) | -5-(4-chlorothiazanyl) | —H | —OCF₃ |
| DYI (a, b, and c) | -5-(4-chlorothiazanyl) | —H | -tert-butyl |
| DYJ (a, b, and c) | -5-(4-chlorothiazanyl) | —H | -iso-propyl |
| DYK (a, b, and c) | -5-(4-methylthiazanyl) | —Cl | —H |
| DYL (a, b, and c) | -5-(4-methylthiazanyl) | —Br | —H |
| DYM (a, b, and c) | -5-(4-methylthiazanyl) | —F | —H |
| DYN (a, b, and c) | -5-(4-methylthiazanyl) | —CH₃ | —H |
| DYO (a, b, and c) | -5-(4-methylthiazanyl) | —CF₃ | —H |
| DYP (a, b, and c) | -5-(4-methylthiazanyl) | —OCH₃ | —H |
| DYQ (a, b, and c) | -5-(4-methylthiazanyl) | —OCH₂CH₃ | —H |
| DYR (a, b, and c) | -5-(4-methylthiazanyl) | —OCF₃ | —H |
| DYS (a, b, and c) | -5-(4-methylthiazanyl) | -tert-butyl | —H |
| DYT (a, b, and c) | -5-(4-methylthiazanyl) | -iso-propyl | —H |
| DYU (a, b, and c) | -5-(4-methylthiazanyl) | —CH₃ | —CH₃ |
| DYV (a, b, and c) | -5-(4-methylthiazanyl) | —H | —H |
| DYW (a, b, and c) | -5-(4-methylthiazanyl) | —H | —Cl |
| DYX (a, b, and c) | -5-(4-methylthiazanyl) | —H | —Br |
| DYY (a, b, and c) | -5-(4-methylthiazanyl) | —H | —F |
| DYZ (a, b, and c) | -5-(4-methylthiazanyl) | —H | —CH₃ |
| DZA (a, b, and c) | -5-(4-methylthiazanyl) | —H | —CF₃ |
| DZB (a, b, and c) | -5-(4-methylthiazanyl) | —H | —OCH₃ |
| DZC (a, b, and c) | -5-(4-methylthiazanyl) | —H | —OCH₂CH₃ |
| DZD (a, b, and c) | -5-(4-methylthiazanyl) | —H | —OCF₃ |
| DZE (a, b, and c) | -5-(4-methylthiazanyl) | —H | -tert-butyl |
| DZF (a, b, and c) | -5-(4-methylthiazanyl) | —H | -iso-propyl |

"a" means the Benzoazolylpiperazine Compound is racemic.

"b" means the carbon atom of the piperazine ring attached to the methyl group is in the R configuration.

"c" means the carbon atom of the piperazine ring attached to the methyl group is in the S configuration.

304

TABLE XII

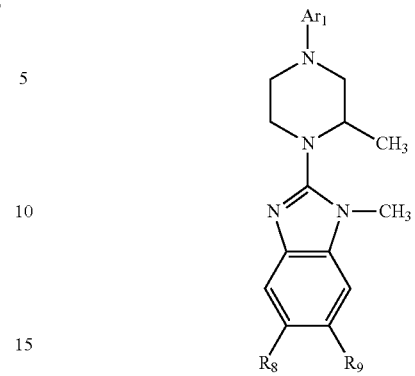

and pharmaceutically acceptable salts thereof, wherein:

| Compound | Ar₁ | R₈ | R₉ |
|---|---|---|---|
| DZG (a, b, and c) | -2-(3-chloropyridyl) | —Cl | —H |
| DZH (a, b, and c) | -2-(3-chloropyridyl) | —Br | —H |
| DZI (a, b, and c) | -2-(3-chloropyridyl) | —F | —H |
| DZJ (a, b, and c) | -2-(3-chloropyridyl) | —CH₃ | —H |
| DZK (a, b, and c) | -2-(3-chloropyridyl) | —CF₃ | —H |
| DZL (a, b, and c) | -2-(3-chloropyridyl) | —OCH₃ | —H |
| DZM (a, b, and c) | -2-(3-chloropyridyl) | —OCH₂CH₃ | —H |
| DZN (a, b, and c) | -2-(3-chloropyridyl) | —OCF₃ | —H |
| DZO (a, b, and c) | -2-(3-chloropyridyl) | -tert-butyl | —H |
| DZP (a, b, and c) | -2-(3-chloropyridyl) | -iso-propyl | —H |
| DZQ (a, b, and c) | -2-(3-chloropyridyl) | —CH₃ | —CH₃ |
| DZR (a, b, and c) | -2-(3-chloropyridyl) | —H | —H |
| DZS (a, b, and c) | -2-(3-chloropyridyl) | —H | —Cl |
| DZT (a, b, and c) | -2-(3-chloropyridyl) | —H | —Br |
| DZU (a, b, and c) | -2-(3-chloropyridyl) | —H | —F |
| DZV (a, b, and c) | -2-(3-chloropyridyl) | —H | —CH₃ |
| DZW (a, b, and c) | -2-(3-chloropyridyl) | —H | —CF₃ |
| DZX (a, b, and c) | -2-(3-chloropyridyl) | —H | —OCH₃ |
| DZY (a, b, and c) | -2-(3-chloropyridyl) | —H | —OCH₂CH₃ |
| DZZ (a, b, and c) | -2-(3-chloropyridyl) | —H | —OCF₃ |
| EAA (a, b, and c) | -2-(3-chloropyridyl) | —H | -tert-butyl |
| EAB (a, b, and c) | -2-(3-chloropyridyl) | —H | -iso-propyl |
| EAC (a, b, and c) | -2-(3-methylpyridyl) | —Cl | —H |
| EAD (a, b, and c) | -2-(3-methylpyridyl) | —Br | —H |
| EAE (a, b, and c) | -2-(3-methylpyridyl) | —F | —H |
| EAF (a, b, and c) | -2-(3-methylpyridyl) | —CH₃ | —H |
| EAG (a, b, and c) | -2-(3-methylpyridyl) | —CF₃ | —H |
| EAH (a, b, and c) | -2-(3-methylpyridyl) | —OCH₃ | —H |
| EAI (a, b, and c) | -2-(3-methylpyridyl) | —OCH₂CH₃ | —H |
| EAJ (a, b, and c) | -2-(3-methylpyridyl) | —OCF₃ | —H |
| EAK (a, b, and c) | -2-(3-methylpyridyl) | -tert-butyl | —H |
| EAL (a, b, and c) | -2-(3-methylpyridyl) | -iso-propyl | —H |
| EAM (a, b, and c) | -2-(3-methylpyridyl) | —CH₃ | —CH₃ |
| EAN (a, b, and c) | -2-(3-methylpyridyl) | —H | —H |
| EAO (a, b, and c) | -2-(3-methylpyridyl) | —H | —Cl |
| EAP (a, b, and c) | -2-(3-methylpyridyl) | —H | —Br |
| EAQ (a, b, and c) | -2-(3-methylpyridyl) | —H | —F |
| EAR (a, b, and c) | -2-(3-methylpyridyl) | —H | —CH₃ |
| EAS (a, b, and c) | -2-(3-methylpyridyl) | —H | —CF₃ |
| EAT (a, b, and c) | -2-(3-methylpyridyl) | —H | —OCH₃ |
| EAU (a, b, and c) | -2-(3-methylpyridyl) | —H | —OCH₂CH₃ |
| EAV (a, b, and c) | -2-(3-methylpyridyl) | —H | —OCF₃ |
| EAW (a, b, and c) | -2-(3-methylpyridyl) | —H | -tert-butyl |
| EAX (a, b, and c) | -2-(3-methylpyridyl) | —H | -iso-propyl |
| EAY (a, b, and c) | -2-(3-CF₃-pyridyl) | —Cl | —H |
| EAZ (a, b, and c) | -2-(3-CF₃-pyridyl) | —Br | —H |
| EBA (a, b, and c) | -2-(3-CF₃-pyridyl) | —F | —H |
| EBB (a, b, and c) | -2-(3-CF₃-pyridyl) | —CH₃ | —H |
| EBC (a, b, and c) | -2-(3-CF₃-pyridyl) | —CF₃ | —H |
| EBD (a, b, and c) | -2-(3-CF₃-pyridyl) | —OCH₃ | —H |
| EBE (a, b, and c) | -2-(3-CF₃-pyridyl) | —OCH₂CH₃ | —H |
| EBF (a, b, and c) | -2-(3-CF₃-pyridyl) | —OCF₃ | —H |
| EBG (a, b, and c) | -2-(3-CF₃-pyridyl) | -tert-butyl | —H |
| EBH (a, b, and c) | -2-(3-CF₃-pyridyl) | -iso-propyl | —H |
| EBI (a, b, and c) | -2-(3-CF₃-pyridyl) | —CH₃ | —CH₃ |
| EBJ (a, b, and c) | -2-(3-CF₃-pyridyl) | —H | —H |
| EBK (a, b, and c) | -2-(3-CF₃-pyridyl) | —H | —Cl |
| EBL (a, b, and c) | -2-(3-CF₃-pyridyl) | —H | —Br |

TABLE XII-continued

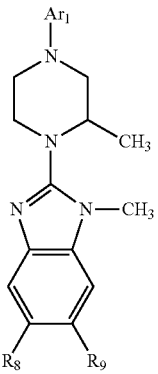

and pharmaceutically acceptable salts thereof, wherein:

| Compound | Ar₁ | R₈ | R₉ |
|---|---|---|---|
| EBM (a, b, and c) | -2-(3-CF₃-pyridyl) | —H | —F |
| EBN (a, b, and c) | -2-(3-CF₃-pyridyl) | —H | —CH₃ |
| EBO (a, b, and c) | -2-(3-CF₃-pyridyl) | —H | —CF₃ |
| EBP (a, b, and c) | -2-(3-CF₃-pyridyl) | —H | —OCH₃ |
| EBQ (a, b, and c) | -2-(3-CF₃-pyridyl) | —H | —OCH₂CH₃ |
| EBR (a, b, and c) | -2-(3-CF₃-pyridyl) | —H | —OCF₃ |
| EBS (a, b, and c) | -2-(3-CF₃-pyridyl) | —H | -tert-butyl |
| EBT (a, b, and c) | -2-(3-CF₃-pyridyl) | —H | -iso-propyl |
| EBU (a, b, and c) | -4-(5-chloropyrimidinyl) | —Cl | —H |
| EBV (a, b, and c) | -4-(5-chloropyrimidinyl) | —Br | —H |
| EBW (a, b, and c) | -4-(5-chloropyrimidinyl) | —F | —H |
| EBX (a, b, and c) | -4-(5-chloropyrimidinyl) | —CH₃ | —H |
| EBY (a, b, and c) | -4-(5-chloropyrimidinyl) | —CF₃ | —H |
| EBZ (a, b, and c) | -4-(5-chloropyrimidinyl) | —OCH₃ | —H |
| ECA (a, b, and c) | -4-(5-chloropyrimidinyl) | —OCH₂CH₃ | —H |
| ECB (a, b, and c) | -4-(5-chloropyrimidinyl) | —OCF₃ | —H |
| ECC (a, b, and c) | -4-(5-chloropyrimidinyl) | -tert-butyl | —H |
| ECD (a, b, and c) | -4-(5-chloropyrimidinyl) | -iso-propyl | —H |
| ECE (a, b, and c) | -4-(5-chloropyrimidinyl) | —CH₃ | —CH₃ |
| ECF (a, b, and c) | -4-(5-chloropyrimidinyl) | —H | —H |
| ECG (a, b, and c) | -4-(5-chloropyrimidinyl) | —H | —Cl |
| ECH (a, b, and c) | -4-(5-chloropyrimidinyl) | —H | —Br |
| ECI (a, b, and c) | -4-(5-chloropyrimidinyl) | —H | —F |
| ECJ (a, b, and c) | -4-(5-chloropyrimidinyl) | —H | —CH₃ |
| ECK (a, b, and c) | -4-(5-chloropyrimidinyl) | —H | —CF₃ |
| ECL (a, b, and c) | -4-(5-chloropyrimidinyl) | —H | —OCH₃ |
| ECM (a, b, and c) | -4-(5-chloropyrimidinyl) | —H | —OCH₂CH₃ |
| ECN (a, b, and c) | -4-(5-chloropyrimidinyl) | —H | —OCF₃ |
| ECO (a, b, and c) | -4-(5-chloropyrimidinyl) | —H | -tert-butyl |
| ECP (a, b, and c) | -4-(5-chloropyrimidinyl) | —H | -iso-propyl |
| ECQ (a, b, and c) | -4-(5-methylpyrimidinyl) | —Cl | —H |
| ECR (a, b, and c) | -4-(5-methylpyrimidinyl) | —Br | —H |
| ECS (a, b, and c) | -4-(5-methylpyrimidinyl) | —F | —H |
| ECT (a, b, and c) | -4-(5-methylpyrimidinyl) | —CH₃ | —H |
| ECU (a, b, and c) | -4-(5-methylpyrimidinyl) | —CF₃ | —H |
| ECV (a, b, and c) | -4-(5-methylpyrimidinyl) | —OCH₃ | —H |
| ECW (a, b, and c) | -4-(5-methylpyrimidinyl) | —OCH₂CH₃ | —H |
| ECX (a, b, and c) | -4-(5-methylpyrimidinyl) | —OCF₃ | —H |
| ECY (a, b, and c) | -4-(5-methylpyrimidinyl) | -tert-butyl | —H |
| ECZ (a, b, and c) | -4-(5-methylpyrimidinyl) | -iso-propyl | —H |
| EDA (a, b, and c) | -4-(5-methylpyrimidinyl) | —CH₃ | —CH₃ |
| EDB (a, b, and c) | -4-(5-methylpyrimidinyl) | —H | —H |
| EDC (a, b, and c) | -4-(5-methylpyrimidinyl) | —H | —Cl |
| EDD (a, b, and c) | -4-(5-methylpyrimidinyl) | —H | —Br |
| EDE (a, b, and c) | -4-(5-methylpyrimidinyl) | —H | —F |
| EDF (a, b, and c) | -4-(5-methylpyrimidinyl) | —H | —CH₃ |
| EDG (a, b, and c) | -4-(5-methylpyrimidinyl) | —H | —CF₃ |
| EDH (a, b, and c) | -4-(5-methylpyrimidinyl) | —H | —OCH₃ |
| EDI (a, b, and c) | -4-(5-methylpyrimidinyl) | —H | —OCH₂CH₃ |
| EDJ (a, b, and c) | -4-(5-methylpyrimidinyl) | —H | —OCF₃ |
| EDK (a, b, and c) | -4-(5-methylpyrimidinyl) | —H | -tert-butyl |
| EDL (a, b, and c) | -4-(5-methylpyrimidinyl) | —H | -iso-propyl |
| EDM (a, b, and c) | -2-pyrazinyl | —Cl | —H |
| EDN (a, b, and c) | -2-pyrazinyl | —Br | —H |
| EDO (a, b, and c) | -2-pyrazinyl | —F | —H |
| EDP (a, b, and c) | -2-pyrazinyl | —CH₃ | —H |
| EDQ (a, b, and c) | -2-pyrazinyl | —CF₃ | —H |
| EDR (a, b, and c) | -2-pyrazinyl | —OCH₃ | —H |

TABLE XII-continued

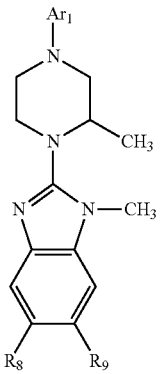

and pharmaceutically acceptable salts thereof, wherein:

| Compound | Ar₁ | R₈ | R₉ |
|---|---|---|---|
| EDS (a, b, and c) | -2-pyrazinyl | —OCH₂CH₃ | —H |
| EDT (a, b, and c) | -2-pyrazinyl | —OCF₃ | —H |
| EDU (a, b, and c) | -2-pyrazinyl | -tert-butyl | —H |
| EDV (a, b, and c) | -2-pyrazinyl | -iso-propyl | —H |
| EDW (a, b, and c) | -2-pyrazinyl | —CH₃ | —CH₃ |
| EDX (a, b, and c) | -2-pyrazinyl | —H | —H |
| EDY (a, b, and c) | -2-pyrazinyl | —H | —Cl |
| EDZ (a, b, and c) | -2-pyrazinyl | —H | —Br |
| EEA (a, b, and c) | -2-pyrazinyl | —H | —F |
| EEB (a, b, and c) | -2-pyrazinyl | —H | —CH₃ |
| EEC (a, b, and c) | -2-pyrazinyl | —H | —CF₃ |
| EED (a, b, and c) | -2-pyrazinyl | —H | —OCH₃ |
| EEE (a, b, and c) | -2-pyrazinyl | —H | —OCH₂CH₃ |
| EEF (a, b, and c) | -2-pyrazinyl | —H | —OCF₃ |
| EEG (a, b, and c) | -2-pyrazinyl | —H | -tert-butyl |
| EEH (a, b, and c) | -2-pyrazinyl | —H | -iso-propyl |
| EEI (a, b, and c) | -2-(3-chloropyrazinyl) | —Cl | —H |
| EEJ (a, b, and c) | -2-(3-chloropyrazinyl) | —Br | —H |
| EEK (a, b, and c) | -2-(3-chloropyrazinyl) | —F | —H |
| EEL (a, b, and c) | -2-(3-chloropyrazinyl) | —CH₃ | —H |
| EEM (a, b, and c) | -2-(3-chloropyrazinyl) | —CF₃ | —H |
| EEN (a, b, and c) | -2-(3-chloropyrazinyl) | —OCH₃ | —H |
| EEO (a, b, and c) | -2-(3-chloropyrazinyl) | —OCH₂CH₃ | —H |
| EEP (a, b, and c) | -2-(3-chloropyrazinyl) | —OCF₃ | —H |
| EEQ (a, b, and c) | -2-(3-chloropyrazinyl) | -tert-butyl | —H |
| EER (a, b, and c) | -2-(3-chloropyrazinyl) | -iso-propyl | —H |
| EES (a, b, and c) | -2-(3-chloropyrazinyl) | —CH₃ | —CH₃ |
| EET (a, b, and c) | -2-(3-chloropyrazinyl) | —H | —H |
| EEU (a, b, and c) | -2-(3-chloropyrazinyl) | —H | —Cl |
| EEV (a, b, and c) | -2-(3-chloropyrazinyl) | —H | —Br |
| EEW (a, b, and c) | -2-(3-chloropyrazinyl) | —H | —F |
| EEX (a, b, and c) | -2-(3-chloropyrazinyl) | —H | —CH₃ |
| EEY (a, b, and c) | -2-(3-chloropyrazinyl) | —H | —CF₃ |
| EEZ (a, b, and c) | -2-(3-chloropyrazinyl) | —H | —OCH₃ |
| EFA (a, b, and c) | -2-(3-chloropyrazinyl) | —H | —OCH₂CH₃ |
| EFB (a, b, and c) | -2-(3-chloropyrazinyl) | —H | —OCF₃ |
| EFC (a, b, and c) | -2-(3-chloropyrazinyl) | —H | -tert-butyl |
| EFD (a, b, and c) | -2-(3-chloropyrazinyl) | —H | -iso-propyl |
| EFE (a, b, and c) | -2-(3-methylpyrazinyl) | —Cl | —H |
| EFF (a, b, and c) | -2-(3-methylpyrazinyl) | —Br | —H |
| EFG (a, b, and c) | -2-(3-methylpyrazinyl) | —F | —H |
| EFH (a, b, and c) | -2-(3-methylpyrazinyl) | —CH₃ | —H |
| EFI (a, b, and c) | -2-(3-methylpyrazinyl) | —CF₃ | —H |
| EFJ (a, b, and c) | -2-(3-methylpyrazinyl) | —OCH₃ | —H |
| EFK (a, b, and c) | -2-(3-methylpyrazinyl) | —OCH₂CH₃ | —H |
| EFL (a, b, and c) | -2-(3-methylpyrazinyl) | —OCF₃ | —H |
| EFM (a, b, and c) | -2-(3-methylpyrazinyl) | -tert-butyl | —H |
| EFN (a, b, and c) | -2-(3-methylpyrazinyl) | -iso-propyl | —H |
| EFO (a, b, and c) | -2-(3-methylpyrazinyl) | —CH₃ | —CH₃ |
| EFP (a, b, and c) | -2-(3-methylpyrazinyl) | —H | —H |
| EFQ (a, b, and c) | -2-(3-methylpyrazinyl) | —H | —Cl |
| EFR (a, b, and c) | -2-(3-methylpyrazinyl) | —H | —Br |
| EFS (a, b, and c) | -2-(3-methylpyrazinyl) | —H | —F |
| EFT (a, b, and c) | -2-(3-methylpyrazinyl) | —H | —CH₃ |
| EFU (a, b, and c) | -2-(3-methylpyrazinyl) | —H | —CF₃ |
| EFV (a, b, and c) | -2-(3-methylpyrazinyl) | —H | —OCH₃ |
| EFW (a, b, and c) | -2-(3-methylpyrazinyl) | —H | —OCH₂CH₃ |
| EFX (a, b, and c) | -2-(3-methylpyrazinyl) | —H | —OCF₃ |

TABLE XII-continued

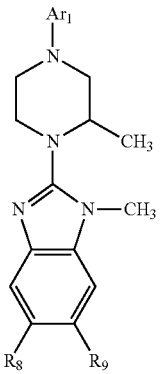

and pharmaceutically acceptable salts thereof, wherein:

| Compound | Ar₁ | R₈ | R₉ |
|---|---|---|---|
| EFY (a, b, and c) | -2-(3-methylpyrazinyl) | —H | -tert-butyl |
| EFZ (a, b, and c) | -2-(3-methylpyrazinyl) | —H | -iso-propyl |
| EGA (a, b, and c) | -2-pyridazinyl | —Cl | —H |
| EGB (a, b, and c) | -2-pyridazinyl | —Br | —H |
| EGC (a, b, and c) | -2-pyridazinyl | —F | —H |
| EGD (a, b, and c) | -2-pyridazinyl | —CH₃ | —H |
| EGE (a, b, and c) | -2-pyridazinyl | —CF₃ | —H |
| EGF (a, b, and c) | -2-pyridazinyl | —OCH₃ | —H |
| EGG (a, b, and c) | -2-pyridazinyl | —OCH₂CH₃ | —H |
| EGH (a, b, and c) | -2-pyridazinyl | —OCF₃ | —H |
| EGI (a, b, and c) | -2-pyridazinyl | -tert-butyl | —H |
| EGJ (a, b, and c) | -2-pyridazinyl | -iso-propyl | —H |
| EGK (a, b, and c) | -2-pyridazinyl | —CH₃ | —CH₃ |
| EGL (a, b, and c) | -2-pyridazinyl | —H | —H |
| EGM (a, b, and c) | -2-pyridazinyl | —H | —Cl |
| EGN (a, b, and c) | -2-pyridazinyl | —H | —Br |
| EGO (a, b, and c) | -2-pyridazinyl | —H | —F |
| EGP (a, b, and c) | -2-pyridazinyl | —H | —CH₃ |
| EGQ (a, b, and c) | -2-pyridazinyl | —H | —CF₃ |
| EGR (a, b, and c) | -2-pyridazinyl | —H | —OCH₃ |
| EGS (a, b, and c) | -2-pyridazinyl | —H | —OCH₂CH₃ |
| EGT (a, b, and c) | -2-pyridazinyl | —H | —OCF₃ |
| EGU (a, b, and c) | -2-pyridazinyl | —H | -tert-butyl |
| EGV (a, b, and c) | -2-pyridazinyl | —H | -iso-propyl |
| EGW (a, b, and c) | -3-(4-chloropyridazinyl) | —Cl | —H |
| EGX (a, b, and c) | -3-(4-chloropyridazinyl) | —Br | —H |
| EGY (a, b, and c) | -3-(4-chloropyridazinyl) | —F | —H |
| EGZ (a, b, and c) | -3-(4-chloropyridazinyl) | —CH₃ | —H |
| EHA (a, b, and c) | -3-(4-chloropyridazinyl) | —CF₃ | —H |
| EHB (a, b, and c) | -3-(4-chloropyridazinyl) | —OCH₃ | —H |
| EHC (a, b, and c) | -3-(4-chloropyridazinyl) | —OCH₂CH₃ | —H |
| EHD (a, b, and c) | -3-(4-chloropyridazinyl) | —OCF₃ | —H |
| EHE (a, b, and c) | -3-(4-chloropyridazinyl) | -tert-butyl | —H |
| EHF (a, b, and c) | -3-(4-chloropyridazinyl) | -iso-propyl | —H |
| EHG (a, b, and c) | -3-(4-chloropyridazinyl) | —CH₃ | —CH₃ |
| EHH (a, b, and c) | -3-(4-chloropyridazinyl) | —H | —H |
| EHI (a, b, and c) | -3-(4-chloropyridazinyl) | —H | —Cl |
| EHJ (a, b, and c) | -3-(4-chloropyridazinyl) | —H | —Br |
| EHK (a, b, and c) | -3-(4-chloropyridazinyl) | —H | —F |
| EHL (a, b, and c) | -3-(4-chloropyridazinyl) | —H | —CH₃ |
| EHM (a, b, and c) | -3-(4-chloropyridazinyl) | —H | —CF₃ |
| EHN (a, b, and c) | -3-(4-chloropyridazinyl) | —H | —OCH₃ |
| EHO (a, b, and c) | -3-(4-chloropyridazinyl) | —H | —OCH₂CH₃ |
| EHP (a, b, and c) | -3-(4-chloropyridazinyl) | —H | —OCF₃ |
| EHQ (a, b, and c) | -3-(4-chloropyridazinyl) | —H | -tert-butyl |
| EHR (a, b, and c) | -3-(4-chloropyridazinyl) | —H | -iso-propyl |
| EHS (a, b, and c) | -3-(4-methylpyridazinyl) | —Cl | —H |
| EHT (a, b, and c) | -3-(4-methylpyridazinyl) | —Br | —H |
| EHU (a, b, and c) | -3-(4-methylpyridazinyl) | —F | —H |
| EHV (a, b, and c) | -3-(4-methylpyridazinyl) | —CH₃ | —H |
| EHW (a, b, and c) | -3-(4-methylpyridazinyl) | —CF₃ | —H |
| EHX (a, b, and c) | -3-(4-methylpyridazinyl) | —OCH₃ | —H |
| EHY (a, b, and c) | -3-(4-methylpyridazinyl) | —OCH₂CH₃ | —H |
| EHZ (a, b, and c) | -3-(4-methylpyridazinyl) | —OCF₃ | —H |
| EIA (a, b, and c) | -3-(4-methylpyridazinyl) | -tert-butyl | —H |
| EIB (a, b, and c) | -3-(4-methylpyridazinyl) | -iso-propyl | —H |
| EIC (a, b, and c) | -3-(4-methylpyridazinyl) | —CH₃ | —CH₃ |
| EID (a, b, and c) | -3-(4-methylpyridazinyl) | —H | —H |

TABLE XII-continued

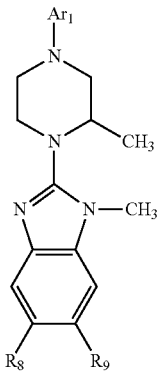

and pharmaceutically acceptable salts thereof, wherein:

| Compound | Ar₁ | R₈ | R₉ |
|---|---|---|---|
| EIE (a, b, and c) | -3-(4-methylpyridazinyl) | —H | —Cl |
| EIF (a, b, and c) | -3-(4-methylpyridazinyl) | —H | —Br |
| EIG (a, b, and c) | -3-(4-methylpyridazinyl) | —H | —F |
| EIH (a, b, and c) | -3-(4-methylpyridazinyl) | —H | —CH₃ |
| EII (a, b, and c) | -3-(4-methylpyridazinyl) | —H | —CF₃ |
| EIJ (a, b, and c) | -3-(4-methylpyridazinyl) | —H | —OCH₃ |
| EIK (a, b, and c) | -3-(4-methylpyridazinyl) | —H | —OCH₂CH₃ |
| EIL (a, b, and c) | -3-(4-methylpyridazinyl) | —H | —OCF₃ |
| EIM (a, b, and c) | -3-(4-methylpyridazinyl) | —H | -tert-butyl |
| EIN (a, b, and c) | -3-(4-methylpyridazinyl) | —H | -iso-propyl |
| EIO (a, b, and c) | -4-thiazanyl | —Cl | —H |
| EIP (a, b, and c) | -4-thiazanyl | —Br | —H |
| EIQ (a, b, and c) | -4-thiazanyl | —F | —H |
| EIR (a, b, and c) | -4-thiazanyl | —CH₃ | —H |
| EIS (a, b, and c) | -4-thiazanyl | —CF₃ | —H |
| EIT (a, b, and c) | -4-thiazanyl | —OCH₃ | —H |
| EIU (a, b, and c) | -4-thiazanyl | —OCH₂CH₃ | —H |
| EIV (a, b, and c) | -4-thiazanyl | —OCF₃ | —H |
| EIW (a, b, and c) | -4-thiazanyl | -tert-butyl | —H |
| EIX (a, b, and c) | -4-thiazanyl | -iso-propyl | —H |
| EIY (a, b, and c) | -4-thiazanyl | —CH₃ | —CH₃ |
| EIZ (a, b, and c) | -4-thiazanyl | —H | —H |
| EJA (a, b, and c) | -4-thiazanyl | —H | —Cl |
| EJB (a, b, and c) | -4-thiazanyl | —H | —Br |
| EJC (a, b, and c) | -4-thiazanyl | —H | —F |
| EJD (a, b, and c) | -4-thiazanyl | —H | —CH₃ |
| EJE (a, b, and c) | -4-thiazanyl | —H | —CF₃ |
| EJF (a, b, and c) | -4-thiazanyl | —H | —OCH₃ |
| EJG (a, b, and c) | -4-thiazanyl | —H | —OCH₂CH₃ |
| EJH (a, b, and c) | -4-thiazanyl | —H | —OCF₃ |
| EJI (a, b, and c) | -4-thiazanyl | —H | -tert-butyl |
| EJJ (a, b, and c) | -4-thiazanyl | —H | -iso-propyl |
| EJK (a, b, and c) | -5-(4-chlorothiazanyl) | —Cl | —H |
| EJL (a, b, and c) | -5-(4-chlorothiazanyl) | —Br | —H |
| EJM (a, b, and c) | -5-(4-chlorothiazanyl) | —F | —H |
| EJN (a, b, and c) | -5-(4-chlorothiazanyl) | —CH₃ | —H |
| EJO (a, b, and c) | -5-(4-chlorothiazanyl) | —CF₃ | —H |
| EJP (a, b, and c) | -5-(4-chlorothiazanyl) | —OCH₃ | —H |
| EJQ (a, b, and c) | -5-(4-chlorothiazanyl) | —OCH₂CH₃ | —H |
| EJR (a, b, and c) | -5-(4-chlorothiazanyl) | —OCF₃ | —H |
| EJS (a, b, and c) | -5-(4-chlorothiazanyl) | -tert-butyl | —H |
| EJT (a, b, and c) | -5-(4-chlorothiazanyl) | -iso-propyl | —H |
| EJU (a, b, and c) | -5-(4-chlorothiazanyl) | —CH₃ | —CH₃ |
| EJV (a, b, and c) | -5-(4-chlorothiazanyl) | —H | —H |
| EJW (a, b, and c) | -5-(4-chlorothiazanyl) | —H | —Cl |
| EJX (a, b, and c) | -5-(4-chlorothiazanyl) | —H | —Br |
| EJY (a, b, and c) | -5-(4-chlorothiazanyl) | —H | —F |
| EJZ (a, b, and c) | -5-(4-chlorothiazanyl) | —H | —CH₃ |
| EKA (a, b, and c) | -5-(4-chlorothiazanyl) | —H | —CF₃ |
| EKB (a, b, and c) | -5-(4-chlorothiazanyl) | —H | —OCH₃ |
| EKC (a, b, and c) | -5-(4-chlorothiazanyl) | —H | —OCH₂CH₃ |
| EKD (a, b, and c) | -5-(4-chlorothiazanyl) | —H | —OCF₃ |
| EKE (a, b, and c) | -5-(4-chlorothiazanyl) | —H | -tert-butyl |
| EKF (a, b, and c) | -5-(4-chlorothiazanyl) | —H | -iso-propyl |
| EKG (a, b, and c) | -5-(4-methylthiazanyl) | —Cl | —H |
| EKH (a, b, and c) | -5-(4-methylthiazanyl) | —Br | —H |
| EKI (a, b, and c) | -5-(4-methylthiazanyl) | —F | —H |
| EKJ (a, b, and c) | -5-(4-methylthiazanyl) | —CH₃ | —H |

TABLE XII-continued

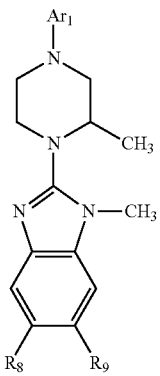

and pharmaceutically acceptable salts thereof, wherein:

| Compound | Ar₁ | R₈ | R₉ |
|---|---|---|---|
| EKK (a, b, and c) | -5-(4-methylthiazanyl) | —CF₃ | —H |
| EKL (a, b, and c) | -5-(4-methylthiazanyl) | —OCH₃ | —H |
| EKM (a, b, and c) | -5-(4-methylthiazanyl) | —OCH₂CH₃ | —H |
| EKN (a, b, and c) | -5-(4-methylthiazanyl) | —OCF₃ | —H |
| EKO (a, b, and c) | -5-(4-methylthiazanyl) | -tert-butyl | —H |
| EKP (a, b, and c) | -5-(4-methylthiazanyl) | -iso-propyl | —H |
| EKQ (a, b, and c) | -5-(4-methylthiazanyl) | —CH₃ | —CH₃ |
| EKR (a, b, and c) | -5-(4-methylthiazanyl) | —H | —H |
| EKS (a, b, and c) | -5-(4-methylthiazanyl) | —H | —Cl |
| EKT (a, b, and c) | -5-(4-methylthiazanyl) | —H | —Br |
| EKU (a, b, and c) | -5-(4-methylthiazanyl) | —H | —F |
| EKV (a, b, and c) | -5-(4-methylthiazanyl) | —H | —CH₃ |
| EKW (a, b, and c) | -5-(4-methylthiazanyl) | —H | —CF₃ |
| EKX (a, b, and c) | -5-(4-methylthiazanyl) | —H | —OCH₃ |
| EKY (a, b, and c) | -5-(4-methylthiazanyl) | —H | —OCH₂CH₃ |
| EKZ (a, b, and c) | -5-(4-methylthiazanyl) | —H | —OCF₃ |
| ELA (a, b, and c) | -5-(4-methylthiazanyl) | —H | -tert-butyl |
| ELB (a, b, and c) | -5-(4-methylthiazanyl) | —H | -iso-propyl |

"a" means the Benzoazolylpiperazine Compound is racemic.
"b" means the carbon atom of the piperazine ring attached to the methyl group is in the R configuration.
"c" means the carbon atom of the piperazine ring attached to the methyl group is in the S configuration.

TABLE XIII

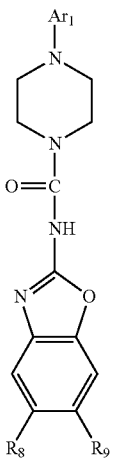

and pharmaceutically acceptable salts thereof, wherein:

| Compound | Ar₁ | R₈ | R₉ |
|---|---|---|---|
| ELC | -2-(3-chloropyridyl) | —Cl | —H |
| ELD | -2-(3-chloropyridyl) | —Br | —H |
| ELE | -2-(3-chloropyridyl) | —F | —H |
| ELF | -2-(3-chloropyridyl) | —CH₃ | —H |
| ELG | -2-(3-chloropyridyl) | —CF₃ | —H |
| ELH | -2-(3-chloropyridyl) | —OCH₃ | —H |

TABLE XIII-continued

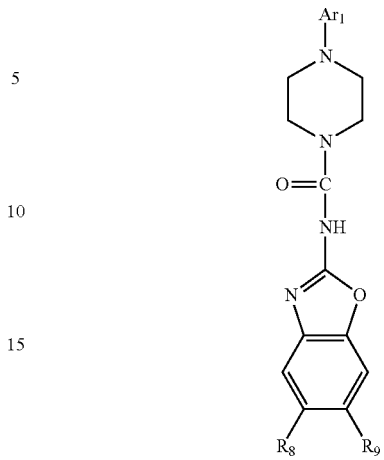

and pharmaceutically acceptable salts thereof, wherein:

| Compound | Ar₁ | R₈ | R₉ |
|---|---|---|---|
| ELI | -2-(3-chloropyridyl) | —OCH₂CH₃ | —H |
| ELJ | -2-(3-chloropyridyl) | —OCF₃ | —H |
| ELK | -2-(3-chloropyridyl) | -tert-butyl | —H |
| ELL | -2-(3-chloropyridyl) | -iso-propyl | —H |
| ELM | -2-(3-chloropyridyl) | —CH₃ | —CH₃ |
| ELN | -2-(3-chloropyridyl) | —H | —H |
| ELO | -2-(3-chloropyridyl) | —H | —Cl |
| ELP | -2-(3-chloropyridyl) | —H | —Br |
| ELQ | -2-(3-chloropyridyl) | —H | —F |
| ELR | -2-(3-chloropyridyl) | —H | —CH₃ |
| ELS | -2-(3-chloropyridyl) | —H | —CF₃ |
| ELT | -2-(3-chloropyridyl) | —H | —OCH₃ |
| ELU | -2-(3-chloropyridyl) | —H | —OCH₂CH₃ |
| ELV | -2-(3-chloropyridyl) | —H | —OCF₃ |
| ELW | -2-(3-chloropyridyl) | —H | -tert-butyl |
| ELX | -2-(3-chloropyridyl) | —H | -iso-propyl |
| ELY | -2-(3-methylpyridyl) | —Cl | —H |
| ELZ | -2-(3-methylpyridyl) | —Br | —H |
| EMA | -2-(3-methylpyridyl) | —F | —H |
| EMB | -2-(3-methylpyridyl) | —CH₃ | —H |
| EMC | -2-(3-methylpyridyl) | —CF₃ | —H |
| EMD | -2-(3-methylpyridyl) | —OCH₃ | —H |
| EME | -2-(3-methylpyridyl) | —OCH₂CH₃ | —H |
| EMF | -2-(3-methylpyridyl) | —OCF₃ | —H |
| EMG | -2-(3-methylpyridyl) | -tert-butyl | —H |
| EMH | -2-(3-methylpyridyl) | -iso-propyl | —H |
| EMI | -2-(3-methylpyridyl) | —CH₃ | —CH₃ |
| EMJ | -2-(3-methylpyridyl) | —H | —H |
| EMK | -2-(3-methylpyridyl) | —H | —Cl |
| EML | -2-(3-methylpyridyl) | —H | —Br |
| EMM | -2-(3-methylpyridyl) | —H | —F |
| EMN | -2-(3-methylpyridyl) | —H | —CH₃ |
| EMO | -2-(3-methylpyridyl) | —H | —CF₃ |
| EMP | -2-(3-methylpyridyl) | —H | —OCH₃ |
| EMQ | -2-(3-methylpyridyl) | —H | —OCH₂CH₃ |
| EMR | -2-(3-methylpyridyl) | —H | —OCF₃ |
| EMS | -2-(3-methylpyridyl) | —H | -tert-butyl |
| EMT | -2-(3-methylpyridyl) | —H | -iso-propyl |
| EMU | -2-(3-CF₃-pyridyl) | —Cl | —H |
| EMV | -2-(3-CF₃-pyridyl) | —Br | —H |
| EMW | -2-(3-CF₃-pyridyl) | —F | —H |
| EMX | -2-(3-CF₃-pyridyl) | —CH₃ | —H |
| EMY | -2-(3-CF₃-pyridyl) | —CF₃ | —H |
| EMZ | -2-(3-CF₃-pyridyl) | —OCH₃ | —H |
| ENA | -2-(3-CF₃-pyridyl) | —OCH₂CH₃ | —H |
| ENB | -2-(3-CF₃-pyridyl) | —OCF₃ | —H |
| ENC | -2-(3-CF₃-pyridyl) | -tert-butyl | —H |
| END | -2-(3-CF₃-pyridyl) | -iso-propyl | —H |
| ENE | -2-(3-CF₃-pyridyl) | —CH₃ | —CH₃ |
| ENF | -2-(3-CF₃-pyridyl) | —H | —H |
| ENG | -2-(3-CF₃-pyridyl) | —H | —Cl |
| ENH | -2-(3-CF₃-pyridyl) | —H | —Br |
| ENI | -2-(3-CF₃-pyridyl) | —H | —F |
| ENJ | -2-(3-CF₃-pyridyl) | —H | —CH₃ |

TABLE XIII-continued

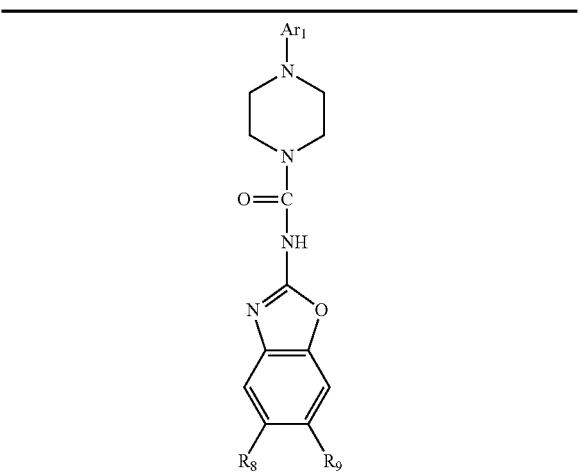

and pharmaceutically acceptable salts thereof, wherein:

| Compound | Ar₁ | R₈ | R₉ |
|---|---|---|---|
| ENK | -2-(3-CF₃-pyridyl) | —H | —CF₃ |
| ENL | -2-(3-CF₃-pyridyl) | —H | —OCH₃ |
| ENM | -2-(3-CF₃-pyridyl) | —H | —OCH₂CH₃ |
| ENN | -2-(3-CF₃-pyridyl) | —H | —OCF₃ |
| ENO | -2-(3-CF₃-pyridyl) | —H | -tert-butyl |
| ENP | -2-(3-CF₃-pyridyl) | —H | -iso-propyl |
| ENQ | 4-(5-chloropyrimidinyl) | —Cl | —H |
| ENR | 4-(5-chloropyrimidinyl) | —Br | —H |
| ENS | 4-(5-chloropyrimidinyl) | —F | —H |
| ENT | 4-(5-chloropyrimidinyl) | —CH₃ | —H |
| ENU | 4-(5-chloropyrimidinyl) | —CF₃ | —H |
| ENV | 4-(5-chloropyrimidinyl) | —OCH₃ | —H |
| ENW | 4-(5-chloropyrimidinyl) | —OCH₂CH₃ | —H |
| ENX | 4-(5-chloropyrimidinyl) | —OCF₃ | —H |
| ENY | 4-(5-chloropyrimidinyl) | -tert-butyl | —H |
| ENZ | 4-(5-chloropyrimidinyl) | -iso-propyl | —H |
| EOA | 4-(5-chloropyrimidinyl) | —CH₃ | —CH₃ |
| EOB | 4-(5-chloropyrimidinyl) | —H | —H |
| EOC | 4-(5-chloropyrimidinyl) | —H | —Cl |
| EOD | 4-(5-chloropyrimidinyl) | —H | —Br |
| EOE | 4-(5-chloropyrimidinyl) | —H | —F |
| EOF | 4-(5-chloropyrimidinyl) | —H | —CH₃ |
| EOG | 4-(5-chloropyrimidinyl) | —H | —CF₃ |
| EOH | 4-(5-chloropyrimidinyl) | —H | —OCH₃ |
| EOI | 4-(5-chloropyrimidinyl) | —H | —OCH₂CH₃ |
| EOJ | 4-(5-chloropyrimidinyl) | —H | —OCF₃ |
| EOK | 4-(5-chloropyrimidinyl) | —H | -tert-butyl |
| EOL | 4-(5-chloropyrimidinyl) | —H | -iso-propyl |
| EOM | 4-(5-methylpyrimidinyl) | —Cl | —H |
| EON | 4-(5-methylpyrimidinyl) | —Br | —H |
| EOO | 4-(5-methylpyrimidinyl) | —F | —H |
| EOP | 4-(5-methylpyrimidinyl) | —CH₃ | —H |
| EOQ | 4-(5-methylpyrimidinyl) | —CF₃ | —H |
| EOR | 4-(5-methylpyrimidinyl) | —OCH₃ | —H |
| EOS | 4-(5-methylpyrimidinyl) | —OCH₂CH₃ | —H |
| EOT | 4-(5-methylpyrimidinyl) | —OCF₃ | —H |
| EOU | 4-(5-methylpyrimidinyl) | -tert-butyl | —H |
| EOV | 4-(5-methylpyrimidinyl) | -iso-propyl | —H |
| EOW | 4-(5-methylpyrimidinyl) | —CH₃ | —CH₃ |
| EOX | 4-(5-methylpyrimidinyl) | —H | —H |
| EOY | 4-(5-methylpyrimidinyl) | —H | —Cl |
| EOZ | 4-(5-methylpyrimidinyl) | —H | —Br |
| EPA | 4-(5-methylpyrimidinyl) | —H | —F |
| EPB | 4-(5-methylpyrimidinyl) | —H | —CH₃ |
| EPC | 4-(5-methylpyrimidinyl) | —H | —CF₃ |
| EPD | 4-(5-methylpyrimidinyl) | —H | —OCH₃ |
| EPE | 4-(5-methylpyrimidinyl) | —H | —OCH₂CH₃ |
| EPF | 4-(5-methylpyrimidinyl) | —H | —OCF₃ |
| EPG | 4-(5-methylpyrimidinyl) | —H | -tert-butyl |
| EPH | 4-(5-methylpyrimidinyl) | —H | -iso-propyl |
| EPI | -2-pyrazinyl | —Cl | —H |
| EPJ | -2-pyrazinyl | —Br | —H |
| EPK | -2-pyrazinyl | —F | —H |
| EPL | -2-pyrazinyl | —CH₃ | —H |

TABLE XIII-continued

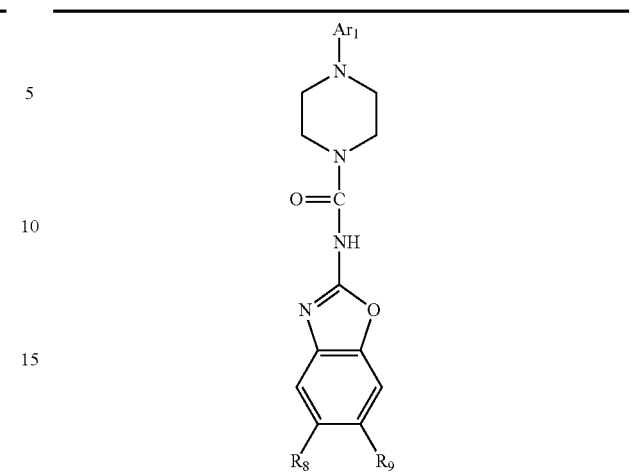

and pharmaceutically acceptable salts thereof, wherein:

| Compound | Ar₁ | R₈ | R₉ |
|---|---|---|---|
| EPM | -2-pyrazinyl | —CF₃ | —H |
| EPN | -2-pyrazinyl | —OCH₃ | —H |
| EPO | -2-pyrazinyl | —OCH₂CH₃ | —H |
| EPP | -2-pyrazinyl | —OCF₃ | —H |
| EPQ | -2-pyrazinyl | -tert-butyl | —H |
| EPR | -2-pyrazinyl | -iso-propyl | —H |
| EPS | -2-pyrazinyl | —CH₃ | —CH₃ |
| EPT | -2-pyrazinyl | —H | —H |
| EPU | -2-pyrazinyl | —H | —Cl |
| EPV | -2-pyrazinyl | —H | —Br |
| EPW | -2-pyrazinyl | —H | —F |
| EPX | -2-pyrazinyl | —H | —CH₃ |
| EPY | -2-pyrazinyl | —H | —CF₃ |
| EPZ | -2-pyrazinyl | —H | —OCH₃ |
| EQA | -2-pyrazinyl | —H | —OCH₂CH₃ |
| EQB | -2-pyrazinyl | —H | —OCF₃ |
| EQC | -2-pyrazinyl | —H | -tert-butyl |
| EQD | -2-pyrazinyl | —H | -iso-propyl |
| EQE | -2-(3-chloropyrazinyl) | —Cl | —H |
| EQF | -2-(3-chloropyrazinyl) | —Br | —H |
| EQG | -2-(3-chloropyrazinyl) | —F | —H |
| EQH | -2-(3-chloropyrazinyl) | —CH₃ | —H |
| EQI | -2-(3-chloropyrazinyl) | —CF₃ | —H |
| EQJ | -2-(3-chloropyrazinyl) | —OCH₃ | —H |
| EQK | -2-(3-chloropyrazinyl) | —OCH₂CH₃ | —H |
| EQL | -2-(3-chloropyrazinyl) | —OCF₃ | —H |
| EQM | -2-(3-chloropyrazinyl) | -tert-butyl | —H |
| EQN | -2-(3-chloropyrazinyl) | -iso-propyl | —H |
| EQO | -2-(3-chloropyrazinyl) | —CH₃ | —CH₃ |
| EQP | -2-(3-chloropyrazinyl) | —H | —H |
| EQQ | -2-(3-chloropyrazinyl) | —H | —Cl |
| EQR | -2-(3-chloropyrazinyl) | —H | —Br |
| EQS | -2-(3-chloropyrazinyl) | —H | —F |
| EQT | -2-(3-chloropyrazinyl) | —H | —CH₃ |
| EQU | -2-(3-chloropyrazinyl) | —H | —CF₃ |
| EQV | -2-(3-chloropyrazinyl) | —H | —OCH₃ |
| EQW | -2-(3-chloropyrazinyl) | —H | —OCH₂CH₃ |
| EQX | -2-(3-chloropyrazinyl) | —H | —OCF₃ |
| EQY | -2-(3-chloropyrazinyl) | —H | -tert-butyl |
| EQZ | -2-(3-chloropyrazinyl) | —H | -iso-propyl |
| ERA | -2-(3-methylpyrazinyl) | —Cl | —H |
| ERB | -2-(3-methylpyrazinyl) | —Br | —H |
| ERC | -2-(3-methylpyrazinyl) | —F | —H |
| ERD | -2-(3-methylpyrazinyl) | —CH₃ | —H |
| ERE | -2-(3-methylpyrazinyl) | —CF₃ | —H |
| ERF | -2-(3-methylpyrazinyl) | —OCH₃ | —H |
| ERG | -2-(3-methylpyrazinyl) | —OCH₂CH₃ | —H |
| ERH | -2-(3-methylpyrazinyl) | —OCF₃ | —H |
| ERI | -2-(3-methylpyrazinyl) | -tert-butyl | —H |
| ERJ | -2-(3-methylpyrazinyl) | -iso-propyl | —H |
| ERK | -2-(3-methylpyrazinyl) | —CH₃ | —CH₃ |
| ERL | -2-(3-methylpyrazinyl) | —H | —H |
| ERM | -2-(3-methylpyrazinyl) | —H | —Cl |
| ERN | -2-(3-methylpyrazinyl) | —H | —Br |

TABLE XIII-continued

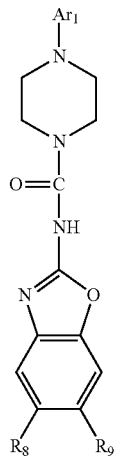

and pharmaceutically acceptable salts thereof, wherein:

| Compound | Ar₁ | R₈ | R₉ |
|---|---|---|---|
| ERO | -2-(3-methylpyrazinyl) | —H | —F |
| ERP | -2-(3-methylpyrazinyl) | —H | —CH₃ |
| ERQ | -2-(3-methylpyrazinyl) | —H | —CF₃ |
| ERR | -2-(3-methylpyrazinyl) | —H | —OCH₃ |
| ERS | -2-(3-methylpyrazinyl) | —H | —OCH₂CH₃ |
| ERT | -2-(3-methylpyrazinyl) | —H | —OCF₃ |
| ERU | -2-(3-methylpyrazinyl) | —H | -tert-butyl |
| ERV | -2-(3-methylpyrazinyl) | —H | -iso-propyl |
| ERW | -2-pyridazinyl | —Cl | —H |
| ERX | -2-pyridazinyl | —Br | —H |
| ERY | -2-pyridazinyl | —F | —H |
| ERZ | -2-pyridazinyl | —CH₃ | —H |
| ESA | -2-pyridazinyl | —CF₃ | —H |
| ESB | -2-pyridazinyl | —OCH₃ | —H |
| ESC | -2-pyridazinyl | —OCH₂CH₃ | —H |
| ESD | -2-pyridazinyl | —OCF₃ | —H |
| ESE | -2-pyridazinyl | -tert-butyl | —H |
| ESF | -2-pyridazinyl | -iso-propyl | —H |
| ESG | -2-pyridazinyl | —CH₃ | —CH₃ |
| ESH | -2-pyridazinyl | —H | —H |
| ESI | -2-pyridazinyl | —H | —Cl |
| ESJ | -2-pyridazinyl | —H | —Br |
| ESK | -2-pyridazinyl | —H | —F |
| ESL | -2-pyridazinyl | —H | —CH₃ |
| ESM | -2-pyridazinyl | —H | —CF₃ |
| ESN | -2-pyridazinyl | —H | —OCH₃ |
| ESO | -2-pyridazinyl | —H | —OCH₂CH₃ |
| ESP | -2-pyridazinyl | —H | —OCF₃ |
| ESQ | -2-pyridazinyl | —H | -tert-butyl |
| ESR | -2-pyridazinyl | —H | -iso-propyl |
| ESS | -3-(4-chloropyridazinyl) | —Cl | —H |
| EST | -3-(4-chloropyridazinyl) | —Br | —H |
| ESU | -3-(4-chloropyridazinyl) | —F | —H |
| ESV | -3-(4-chloropyridazinyl) | —CH₃ | —H |
| ESW | -3-(4-chloropyridazinyl) | —CF₃ | —H |
| ESX | -3-(4-chloropyridazinyl) | —OCH₃ | —H |
| ESY | -3-(4-chloropyridazinyl) | —OCH₂CH₃ | —H |
| ESZ | -3-(4-chloropyridazinyl) | —OCF₃ | —H |
| ETA | -3-(4-chloropyridazinyl) | -tert-butyl | —H |
| ETB | -3-(4-chloropyridazinyl) | -iso-propyl | —H |
| ETC | -3-(4-chloropyridazinyl) | —CH₃ | —CH₃ |
| ETD | -3-(4-chloropyridazinyl) | —H | —H |
| ETE | -3-(4-chloropyridazinyl) | —H | —Cl |
| ETF | -3-(4-chloropyridazinyl) | —H | —Br |
| ETG | -3-(4-chloropyridazinyl) | —H | —F |
| ETH | -3-(4-chloropyridazinyl) | —H | —CH₃ |
| ETI | -3-(4-chloropyridazinyl) | —H | —CF₃ |
| ETJ | -3-(4-chloropyridazinyl) | —H | —OCH₃ |
| ETK | -3-(4-chloropyridazinyl) | —H | —OCH₂CH₃ |
| ETL | -3-(4-chloropyridazinyl) | —H | —OCF₃ |
| ETM | -3-(4-chloropyridazinyl) | —H | -tert-butyl |
| ETN | -3-(4-chloropyridazinyl) | —H | -iso-propyl |

TABLE XIII-continued

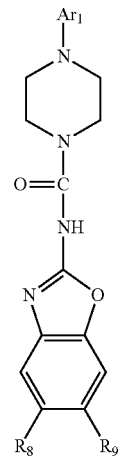

and pharmaceutically acceptable salts thereof, wherein:

| Compound | Ar₁ | R₈ | R₉ |
|---|---|---|---|
| ETO | -3-(4-methylpyridazinyl) | —Cl | —H |
| ETP | -3-(4-methylpyridazinyl) | —Br | —H |
| ETQ | -3-(4-methylpyridazinyl) | —F | —H |
| ETR | -3-(4-methylpyridazinyl) | —CH₃ | —H |
| ETS | -3-(4-methylpyridazinyl) | —CF₃ | —H |
| ETT | -3-(4-methylpyridazinyl) | —OCH₃ | —H |
| ETU | -3-(4-methylpyridazinyl) | —OCH₂CH₃ | —H |
| ETV | -3-(4-methylpyridazinyl) | —OCF₃ | —H |
| ETW | -3-(4-methylpyridazinyl) | -tert-butyl | —H |
| ETX | -3-(4-methylpyridazinyl) | -iso-propyl | —H |
| ETY | -3-(4-methylpyridazinyl) | —CH₃ | —CH₃ |
| ETZ | -3-(4-methylpyridazinyl) | —H | —H |
| EUA | -3-(4-methylpyridazinyl) | —H | —Cl |
| EUB | -3-(4-methylpyridazinyl) | —H | —Br |
| EUC | -3-(4-methylpyridazinyl) | —H | —F |
| EUD | -3-(4-methylpyridazinyl) | —H | —CH₃ |
| EUE | -3-(4-methylpyridazinyl) | —H | —CF₃ |
| EUF | -3-(4-methylpyridazinyl) | —H | —OCH₃ |
| EUG | -3-(4-methylpyridazinyl) | —H | —OCH₂CH₃ |
| EUH | -3-(4-methylpyridazinyl) | —H | —OCF₃ |
| EUI | -3-(4-methylpyridazinyl) | —H | -tert-butyl |
| EUJ | -3-(4-methylpyridazinyl) | —H | -iso-propyl |
| EUK | -4-thiazanyl | —Cl | —H |
| EUL | -4-thiazanyl | —Br | —H |
| EUM | -4-thiazanyl | —F | —H |
| EUN | -4-thiazanyl | —CH₃ | —H |
| EUO | -4-thiazanyl | —CF₃ | —H |
| EUP | -4-thiazanyl | —OCH₃ | —H |
| EUQ | -4-thiazanyl | —OCH₂CH₃ | —H |
| EUR | -4-thiazanyl | —OCF₃ | —H |
| EUS | -4-thiazanyl | -tert-butyl | —H |
| EUT | -4-thiazanyl | -iso-propyl | —H |
| EUU | -4-thiazanyl | —CH₃ | —CH₃ |
| EUV | -4-thiazanyl | —H | —H |
| EUW | -4-thiazanyl | —H | —Cl |
| EUX | -4-thiazanyl | —H | —Br |
| EUY | -4-thiazanyl | —H | —F |
| EUZ | -4-thiazanyl | —H | —CH₃ |
| EVA | -4-thiazanyl | —H | —CF₃ |
| EVB | -4-thiazanyl | —H | —OCH₃ |
| EVC | -4-thiazanyl | —H | —OCH₂CH₃ |
| EVD | -4-thiazanyl | —H | —OCF₃ |
| EVE | -4-thiazanyl | —H | -tert-butyl |
| EVF | -4-thiazanyl | —H | -iso-propyl |
| EVG | -5-(4-chlorothiazanyl) | —Cl | —H |
| EVH | -5-(4-chlorothiazanyl) | —Br | —H |
| EVI | -5-(4-chlorothiazanyl) | —F | —H |
| EVJ | -5-(4-chlorothiazanyl) | —CH₃ | —H |
| EVK | -5-(4-chlorothiazanyl) | —CF₃ | —H |
| EVL | -5-(4-chlorothiazanyl) | —OCH₃ | —H |
| EVM | -5-(4-chlorothiazanyl) | —OCH₂CH₃ | —H |
| EVN | -5-(4-chlorothiazanyl) | —OCF₃ | —H |

TABLE XIII-continued

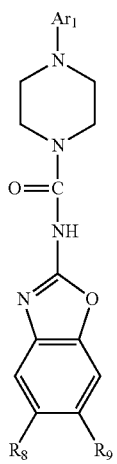

and pharmaceutically acceptable salts thereof, wherein:

| Compound | Ar₁ | R₈ | R₉ |
|---|---|---|---|
| EVO | -5-(4-chlorothiazanyl) | -tert-butyl | —H |
| EVP | -5-(4-chlorothiazanyl) | -iso-propyl | —H |
| EVQ | -5-(4-chlorothiazanyl) | —CH₃ | —CH₃ |
| EVR | -5-(4-chlorothiazanyl) | —H | —H |
| EVS | -5-(4-chlorothiazanyl) | —H | —Cl |
| EVT | -5-(4-chlorothiazanyl) | —H | —Br |
| EVU | -5-(4-chlorothiazanyl) | —H | —F |
| EVV | -5-(4-chlorothiazanyl) | —H | —CH₃ |
| EVW | -5-(4-chlorothiazanyl) | —H | —CF₃ |
| EVX | -5-(4-chlorothiazanyl) | —H | —OCH₃ |
| EVY | -5-(4-chlorothiazanyl) | —H | —OCH₂CH₃ |
| EVZ | -5-(4-chlorothiazanyl) | —H | —OCF₃ |
| EWA | -5-(4-chlorothiazanyl) | —H | -tert-butyl |
| EWB | -5-(4-chlorothiazanyl) | —H | -iso-propyl |
| EWC | -5-(4-methylthiazanyl) | —Cl | —H |
| EWD | -5-(4-methylthiazanyl) | —Br | —H |
| EWE | -5-(4-methylthiazanyl) | —F | —H |
| EWF | -5-(4-methylthiazanyl) | —CH₃ | —H |
| EWG | -5-(4-methylthiazanyl) | —CF₃ | —H |
| EWH | -5-(4-methylthiazanyl) | —OCH₃ | —H |
| EWI | -5-(4-methylthiazanyl) | —OCH₂CH₃ | —H |
| EWJ | -5-(4-methylthiazanyl) | —OCF₃ | —H |
| EWK | -5-(4-methylthiazanyl) | -tert-butyl | —H |
| EWL | -5-(4-methylthiazanyl) | -iso-propyl | —H |
| EWM | -5-(4-methylthiazanyl) | —CH₃ | —CH₃ |
| EWN | -5-(4-methylthiazanyl) | —H | —H |
| EWO | -5-(4-methylthiazanyl) | —H | —Cl |
| EWP | -5-(4-methylthiazanyl) | —H | —Br |
| EWQ | -5-(4-methylthiazanyl) | —H | —F |
| EWR | -5-(4-methylthiazanyl) | —H | —CH₃ |
| EWS | -5-(4-methylthiazanyl) | —H | —CF₃ |
| EWT | -5-(4-methylthiazanyl) | —H | —OCH₃ |
| EWU | -5-(4-methylthiazanyl) | —H | —OCH₂CH₃ |
| EWV | -5-(4-methylthiazanyl) | —H | —OCF₃ |
| EWW | -5-(4-methylthiazanyl) | —H | -tert-butyl |
| EWX | -5-(4-methylthiazanyl) | —H | -iso-propyl |

TABLE XIV

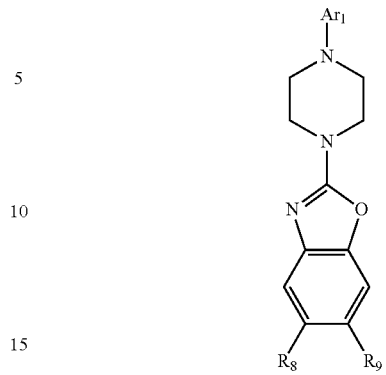

and pharmaceutically acceptable salts thereof, wherein:

| Compound | Ar₁ | R₈ | R₉ |
|---|---|---|---|
| EWY | -2-(3-chloropyridyl) | —Cl | —H |
| EWZ | -2-(3-chloropyridyl) | —Br | —H |
| EXA | -2-(3-chloropyridyl) | —F | —H |
| EXB | -2-(3-chloropyridyl) | —CH₃ | —H |
| EXC | -2-(3-chloropyridyl) | —CF₃ | —H |
| EXD | -2-(3-chloropyridyl) | —OCH₃ | —H |
| EXE | -2-(3-chloropyridyl) | —OCH₂CH₃ | —H |
| EXF | -2-(3-chloropyridyl) | —OCF₃ | —H |
| EXG | -2-(3-chloropyridyl) | -tert-butyl | —H |
| EXH | -2-(3-chloropyridyl) | -iso-propyl | —H |
| EXI | -2-(3-chloropyridyl) | —CH₃ | —CH₃ |
| EXJ | -2-(3-chloropyridyl) | —H | —H |
| EXK | -2-(3-chloropyridyl) | —H | —Cl |
| EXL | -2-(3-chloropyridyl) | —H | —Br |
| EXM | -2-(3-chloropyridyl) | —H | —F |
| EXN | -2-(3-chloropyridyl) | —H | —CH₃ |
| EXO | -2-(3-chloropyridyl) | —H | —CF₃ |
| EXP | -2-(3-chloropyridyl) | —H | —OCH₃ |
| EXQ | -2-(3-chloropyridyl) | —H | —OCH₂CH₃ |
| EXR | -2-(3-chloropyridyl) | —H | —OCF₃ |
| EXS | -2-(3-chloropyridyl) | —H | -tert-butyl |
| EXT | -2-(3-chloropyridyl) | —H | -iso-propyl |
| EXU | -2-(3-methylpyridyl) | —Cl | —H |
| EXV | -2-(3-methylpyridyl) | —Br | —H |
| EXW | -2-(3-methylpyridyl) | —F | —H |
| EXX | -2-(3-methylpyridyl) | —CH₃ | —H |
| EXY | -2-(3-methylpyridyl) | —CF₃ | —H |
| EXZ | -2-(3-methylpyridyl) | —OCH₃ | —H |
| EYA | -2-(3-methylpyridyl) | —OCH₂CH₃ | —H |
| EYB | -2-(3-methylpyridyl) | —OCF₃ | —H |
| EYC | -2-(3-methylpyridyl) | -tert-butyl | —H |
| EYD | -2-(3-methylpyridyl) | -iso-propyl | —H |
| EYE | -2-(3-methylpyridyl) | —CH₃ | —CH₃ |
| EYF | -2-(3-methylpyridyl) | —H | —H |
| EYG | -2-(3-methylpyridyl) | —H | —Cl |
| EYH | -2-(3-methylpyridyl) | —H | —Br |
| EYI | -2-(3-methylpyridyl) | —H | —F |
| EYJ | -2-(3-methylpyridyl) | —H | —CH₃ |
| EYK | -2-(3-methylpyridyl) | —H | —CF₃ |
| EYL | -2-(3-methylpyridyl) | —H | —OCH₃ |
| EYM | -2-(3-methylpyridyl) | —H | —OCH₂CH₃ |
| EYN | -2-(3-methylpyridyl) | —H | —OCF₃ |
| EYO | -2-(3-methylpyridyl) | —H | -tert-butyl |
| EYP | -2-(3-methylpyridyl) | —H | -iso-propyl |
| EYQ | -2-(3-CF₃-pyridyl) | —Cl | —H |
| EYR | -2-(3-CF₃-pyridyl) | —Br | —H |
| EYS | -2-(3-CF₃-pyridyl) | —F | —H |
| EYT | -2-(3-CF₃-pyridyl) | —CH₃ | —H |
| EYU | -2-(3-CF₃-pyridyl) | —CF₃ | —H |
| EYV | -2-(3-CF₃-pyridyl) | —OCH₃ | —H |
| EYW | -2-(3-CF₃-pyridyl) | —OCH₂CH₃ | —H |
| EYX | -2-(3-CF₃-pyridyl) | —OCF₃ | —H |
| EYY | -2-(3-CF₃-pyridyl) | -tert-butyl | —H |
| EYZ | -2-(3-CF₃-pyridyl) | -iso-propyl | —H |
| EZA | -2-(3-CF₃-pyridyl) | —CH₃ | —CH₃ |
| EZB | -2-(3-CF₃-pyridyl) | —H | —H |
| EZC | -2-(3-CF₃-pyridyl) | —H | —Cl |
| EZD | -2-(3-CF₃-pyridyl) | —H | —Br |

TABLE XIV-continued

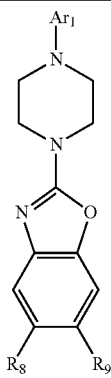

and pharmaceutically acceptable salts thereof, wherein:

| Compound | Ar₁ | R₈ | R₉ |
|---|---|---|---|
| EZE | -2-(3-CF₃-pyridyl) | —H | —F |
| EZF | -2-(3-CF₃-pyridyl) | —H | —CH₃ |
| EZG | -2-(3-CF₃-pyridyl) | —H | —CF₃ |
| EZH | -2-(3-CF₃-pyridyl) | —H | —OCH₃ |
| EZI | -2-(3-CF₃-pyridyl) | —H | —OCH₂CH₃ |
| EZJ | -2-(3-CF₃-pyridyl) | —H | —OCF₃ |
| EZK | -2-(3-CF₃-pyridyl) | —H | -tert-butyl |
| EZL | -2-(3-CF₃-pyridyl) | —H | -iso-propyl |
| EZM | 4-(5-chloropyrimidinyl) | —Cl | —H |
| EZN | 4-(5-chloropyrimidinyl) | —Br | —H |
| EZO | 4-(5-chloropyrimidinyl) | —F | —H |
| EZP | 4-(5-chloropyrimidinyl) | —CH₃ | —H |
| EZQ | 4-(5-chloropyrimidinyl) | —CF₃ | —H |
| EZR | 4-(5-chloropyrimidinyl) | —OCH₃ | —H |
| EZS | 4-(5-chloropyrimidinyl) | —OCH₂CH₃ | —H |
| EZT | 4-(5-chloropyrimidinyl) | —OCF₃ | —H |
| EZU | 4-(5-chloropyrimidinyl) | -tert-butyl | —H |
| EZV | 4-(5-chloropyrimidinyl) | -iso-propyl | —H |
| EZW | 4-(5-chloropyrimidinyl) | —CH₃ | —CH₃ |
| EZX | 4-(5-chloropyrimidinyl) | —H | —H |
| EZY | 4-(5-chloropyrimidinyl) | —H | —Cl |
| EZZ | 4-(5-chloropyrimidinyl) | —H | —Br |
| FAA | 4-(5-chloropyrimidinyl) | —H | —F |
| FAB | 4-(5-chloropyrimidinyl) | —H | —CH₃ |
| FAC | 4-(5-chloropyrimidinyl) | —H | —CF₃ |
| FAD | 4-(5-chloropyrimidinyl) | —H | —OCH₃ |
| FAE | 4-(5-chloropyrimidinyl) | —H | —OCH₂CH₃ |
| FAF | 4-(5-chloropyrimidinyl) | —H | —OCF₃ |
| FAG | 4-(5-chloropyrimidinyl) | —H | -tert-butyl |
| FAH | 4-(5-chloropyrimidinyl) | —H | -iso-propyl |
| FAI | 4-(5-methylpyrimidinyl) | —Cl | —H |
| FAJ | 4-(5-methylpyrimidinyl) | —Br | —H |
| FAK | 4-(5-methylpyrimidinyl) | —F | —H |
| FAL | 4-(5-methylpyrimidinyl) | —CH₃ | —H |
| FAM | 4-(5-methylpyrimidinyl) | —CF₃ | —H |
| FAN | 4-(5-methylpyrimidinyl) | —OCH₃ | —H |
| FAO | 4-(5-methylpyrimidinyl) | —OCH₂CH₃ | —H |
| FAP | 4-(5-methylpyrimidinyl) | —OCF₃ | —H |
| FAQ | 4-(5-methylpyrimidinyl) | -tert-butyl | —H |
| FAR | 4-(5-methylpyrimidinyl) | -iso-propyl | —H |
| FAS | 4-(5-methylpyrimidinyl) | —CH₃ | —CH₃ |
| FAT | 4-(5-methylpyrimidinyl) | —H | —H |
| FAU | 4-(5-methylpyrimidinyl) | —H | —Cl |
| FAV | 4-(5-methylpyrimidinyl) | —H | —Br |
| FAW | 4-(5-methylpyrimidinyl) | —H | —F |
| FAX | 4-(5-methylpyrimidinyl) | —H | —CH₃ |
| FAY | 4-(5-methylpyrimidinyl) | —H | —CF₃ |
| FAZ | 4-(5-methylpyrimidinyl) | —H | —OCH₃ |
| FBA | 4-(5-methylpyrimidinyl) | —H | —OCH₂CH₃ |
| FBB | 4-(5-methylpyrimidinyl) | —H | —OCF₃ |
| FBC | 4-(5-methylpyrimidinyl) | —H | -tert-butyl |
| FBD | 4-(5-methylpyrimidinyl) | —H | -iso-propyl |
| FBE | -2-pyrazinyl | —Cl | —H |
| FBF | -2-pyrazinyl | —Br | —H |
| FBG | -2-pyrazinyl | —F | —H |
| FBH | -2-pyrazinyl | —CH₃ | —H |
| FBI | -2-pyrazinyl | —CF₃ | —H |
| FBJ | -2-pyrazinyl | —OCH₃ | —H |

TABLE XIV-continued

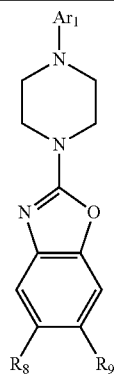

and pharmaceutically acceptable salts thereof, wherein:

| Compound | Ar₁ | R₈ | R₉ |
|---|---|---|---|
| FBK | -2-pyrazinyl | —OCH₂CH₃ | —H |
| FBL | -2-pyrazinyl | —OCF₃ | —H |
| FBM | -2-pyrazinyl | -tert-butyl | —H |
| FBN | -2-pyrazinyl | -iso-propyl | —H |
| FBO | -2-pyrazinyl | —CH₃ | —CH₃ |
| FBP | -2-pyrazinyl | —H | —H |
| FBQ | -2-pyrazinyl | —H | —Cl |
| FBR | -2-pyrazinyl | —H | —Br |
| FBS | -2-pyrazinyl | —H | —F |
| FBT | -2-pyrazinyl | —H | —CH₃ |
| FBU | -2-pyrazinyl | —H | —CF₃ |
| FBV | -2-pyrazinyl | —H | —OCH₃ |
| FBW | -2-pyrazinyl | —H | —OCH₂CH₃ |
| FBX | -2-pyrazinyl | —H | —OCF₃ |
| FBY | -2-pyrazinyl | —H | -tert-butyl |
| FBZ | -2-pyrazinyl | —H | -iso-propyl |
| FCA | -2-(3-chloropyrazinyl) | —Cl | —H |
| FCB | -2-(3-chloropyrazinyl) | —Br | —H |
| FCC | -2-(3-chloropyrazinyl) | —F | —H |
| FCD | -2-(3-chloropyrazinyl) | —CH₃ | —H |
| FCE | -2-(3-chloropyrazinyl) | —CF₃ | —H |
| FCF | -2-(3-chloropyrazinyl) | —OCH₃ | —H |
| FCG | -2-(3-chloropyrazinyl) | —OCH₂CH₃ | —H |
| FCH | -2-(3-chloropyrazinyl) | —OCF₃ | —H |
| FCI | -2-(3-chloropyrazinyl) | -tert-butyl | —H |
| FCJ | -2-(3-chloropyrazinyl) | -iso-propyl | —H |
| FCK | -2-(3-chloropyrazinyl) | —CH₃ | —CH₃ |
| FCL | -2-(3-chloropyrazinyl) | —H | —H |
| FCM | -2-(3-chloropyrazinyl) | —H | —Cl |
| FCN | -2-(3-chloropyrazinyl) | —H | —Br |
| FCO | -2-(3-chloropyrazinyl) | —H | —F |
| FCP | -2-(3-chloropyrazinyl) | —H | —CH₃ |
| FCQ | -2-(3-chloropyrazinyl) | —H | —CF₃ |
| FCR | -2-(3-chloropyrazinyl) | —H | —OCH₃ |
| FCS | -2-(3-chloropyrazinyl) | —H | —OCH₂CH₃ |
| FCT | -2-(3-chloropyrazinyl) | —H | —OCF₃ |
| FCU | -2-(3-chloropyrazinyl) | —H | -tert-butyl |
| FCV | -2-(3-chloropyrazinyl) | —H | -iso-propyl |
| FCW | -2-(3-methylpyrazinyl) | —Cl | —H |
| FCX | -2-(3-methylpyrazinyl) | —Br | —H |
| FCY | -2-(3-methylpyrazinyl) | —F | —H |
| FCZ | -2-(3-methylpyrazinyl) | —CH₃ | —H |
| FDA | -2-(3-methylpyrazinyl) | —CF₃ | —H |
| FDB | -2-(3-methylpyrazinyl) | —OCH₃ | —H |
| FDC | -2-(3-methylpyrazinyl) | —OCH₂CH₃ | —H |
| FDD | -2-(3-methylpyrazinyl) | —OCF₃ | —H |
| FDE | -2-(3-methylpyrazinyl) | -tert-butyl | —H |
| FDF | -2-(3-methylpyrazinyl) | -iso-propyl | —H |
| FDG | -2-(3-methylpyrazinyl) | —CH₃ | —CH₃ |
| FDH | -2-(3-methylpyrazinyl) | —H | —H |
| FDI | -2-(3-methylpyrazinyl) | —H | —Cl |
| FDJ | -2-(3-methylpyrazinyl) | —H | —Br |
| FDK | -2-(3-methylpyrazinyl) | —H | —F |
| FDL | -2-(3-methylpyrazinyl) | —H | —CH₃ |
| FDM | -2-(3-methylpyrazinyl) | —H | —CF₃ |
| FDN | -2-(3-methylpyrazinyl) | —H | —OCH₃ |
| FDO | -2-(3-methylpyrazinyl) | —H | —OCH₂CH₃ |
| FDP | -2-(3-methylpyrazinyl) | —H | —OCF₃ |

TABLE XIV-continued

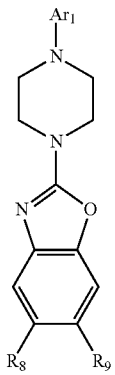

and pharmaceutically acceptable salts thereof, wherein:

| Compound | Ar₁ | R₈ | R₉ |
|---|---|---|---|
| FDQ | -2-(3-methylpyrazinyl) | —H | -tert-butyl |
| FDR | -2-(3-methylpyrazinyl) | —H | -iso-propyl |
| FDS | -2-pyridazinyl | —Cl | —H |
| FDT | -2-pyridazinyl | —Br | —H |
| FDU | -2-pyridazinyl | —F | —H |
| FDV | -2-pyridazinyl | —CH₃ | —H |
| FDW | -2-pyridazinyl | —CF₃ | —H |
| FDX | -2-pyridazinyl | —OCH₃ | —H |
| FDY | -2-pyridazinyl | —OCH₂CH₃ | —H |
| FDZ | -2-pyridazinyl | —OCF₃ | —H |
| FEA | -2-pyridazinyl | -tert-butyl | —H |
| FEB | -2-pyridazinyl | -iso-propyl | —H |
| FEC | -2-pyridazinyl | —CH₃ | —CH₃ |
| FED | -2-pyridazinyl | —H | —H |
| FEE | -2-pyridazinyl | —H | —Cl |
| FEF | -2-pyridazinyl | —H | —Br |
| FEG | -2-pyridazinyl | —H | —F |
| FEH | -2-pyridazinyl | —H | —CH₃ |
| FEI | -2-pyridazinyl | —H | —CF₃ |
| FEJ | -2-pyridazinyl | —H | —OCH₃ |
| FEK | -2-pyridazinyl | —H | —OCH₂CH₃ |
| FEL | -2-pyridazinyl | —H | —OCF₃ |
| FEM | -2-pyridazinyl | —H | -tert-butyl |
| FEN | -2-pyridazinyl | —H | -iso-propyl |
| FEO | -3-(4-chloropyridazinyl) | —Cl | —H |
| FEP | -3-(4-chloropyridazinyl) | —Br | —H |
| FEQ | -3-(4-chloropyridazinyl) | —F | —H |
| FER | -3-(4-chloropyridazinyl) | —CH₃ | —H |
| FES | -3-(4-chloropyridazinyl) | —CF₃ | —H |
| FET | -3-(4-chloropyridazinyl) | —OCH₃ | —H |
| FEU | -3-(4-chloropyridazinyl) | —OCH₂CH₃ | —H |
| FEV | -3-(4-chloropyridazinyl) | —OCF₃ | —H |
| FEW | -3-(4-chloropyridazinyl) | -tert-butyl | —H |
| FEX | -3-(4-chloropyridazinyl) | -iso-propyl | —H |
| FEY | -3-(4-chloropyridazinyl) | —CH₃ | —CH₃ |
| FEZ | -3-(4-chloropyridazinyl) | —H | —H |
| FFA | -3-(4-chloropyridazinyl) | —H | —Cl |
| FFB | -3-(4-chloropyridazinyl) | —H | —Br |
| FFC | -3-(4-chloropyridazinyl) | —H | —F |
| FFD | -3-(4-chloropyridazinyl) | —H | —CH₃ |
| FFE | -3-(4-chloropyridazinyl) | —H | —CF₃ |
| FFF | -3-(4-chloropyridazinyl) | —H | —OCH₃ |
| FFG | -3-(4-chloropyridazinyl) | —H | —OCH₂CH₃ |
| FFH | -3-(4-chloropyridazinyl) | —H | —OCF₃ |
| FFI | -3-(4-chloropyridazinyl) | —H | -tert-butyl |
| FFJ | -3-(4-chloropyridazinyl) | —H | -iso-propyl |
| FFK | -3-(4-methylpyridazinyl) | —Cl | —H |
| FFL | -3-(4-methylpyridazinyl) | —Br | —H |
| FFM | -3-(4-methylpyridazinyl) | —F | —H |
| FFN | -3-(4-methylpyridazinyl) | —CH₃ | —H |
| FFO | -3-(4-methylpyridazinyl) | —CF₃ | —H |
| FFP | -3-(4-methylpyridazinyl) | —OCH₃ | —H |
| FFQ | -3-(4-methylpyridazinyl) | —OCH₂CH₃ | —H |
| FFR | -3-(4-methylpyridazinyl) | —OCF₃ | —H |
| FFS | -3-(4-methylpyridazinyl) | -tert-butyl | —H |
| FFT | -3-(4-methylpyridazinyl) | -iso-propyl | —H |
| FFU | -3-(4-methylpyridazinyl) | —CH₃ | —CH₃ |
| FFV | -3-(4-methylpyridazinyl) | —H | —H |
| FFW | -3-(4-methylpyridazinyl) | —H | —Cl |
| FFX | -3-(4-methylpyridazinyl) | —H | —Br |
| FFY | -3-(4-methylpyridazinyl) | —H | —F |
| FFZ | -3-(4-methylpyridazinyl) | —H | —CH₃ |
| FGA | -3-(4-methylpyridazinyl) | —H | —CF₃ |
| FGB | -3-(4-methylpyridazinyl) | —H | —OCH₃ |
| FGC | -3-(4-methylpyridazinyl) | —H | —OCH₂CH₃ |
| FGD | -3-(4-methylpyridazinyl) | —H | —OCF₃ |
| FGE | -3-(4-methylpyridazinyl) | —H | -tert-butyl |
| FGF | -3-(4-methylpyridazinyl) | —H | -iso-propyl |
| FGG | -4-thiazanyl | —Cl | —H |
| FGH | -4-thiazanyl | —Br | —H |
| FGI | -4-thiazanyl | —F | —H |
| FGJ | -4-thiazanyl | —CH₃ | —H |
| FGK | -4-thiazanyl | —CF₃ | —H |
| FGL | -4-thiazanyl | —OCH₃ | —H |
| FGM | -4-thiazanyl | —OCH₂CH₃ | —H |
| FGN | -4-thiazanyl | —OCF₃ | —H |
| FGO | -4-thiazanyl | -tert-butyl | —H |
| FGP | -4-thiazanyl | -iso-propyl | —H |
| FGQ | -4-thiazanyl | —CH₃ | —CH₃ |
| FGR | -4-thiazanyl | —H | —H |
| FGS | -4-thiazanyl | —H | —Cl |
| FGT | -4-thiazanyl | —H | —Br |
| FGU | -4-thiazanyl | —H | —F |
| FGV | -4-thiazanyl | —H | —CH₃ |
| FGW | -4-thiazanyl | —H | —CF₃ |
| FGX | -4-thiazanyl | —H | —OCH₃ |
| FGY | -4-thiazanyl | —H | —OCH₂CH₃ |
| FGZ | -4-thiazanyl | —H | —OCF₃ |
| FHA | -4-thiazanyl | —H | -tert-butyl |
| FHB | -4-thiazanyl | —H | -iso-propyl |
| FHC | -5-(4-chlorothiazanyl) | —Cl | —H |
| FHD | -5-(4-chlorothiazanyl) | —Br | —H |
| FHE | -5-(4-chlorothiazanyl) | —F | —H |
| FHF | -5-(4-chlorothiazanyl) | —CH₃ | —H |
| FHG | -5-(4-chlorothiazanyl) | —CF₃ | —H |
| FHH | -5-(4-chlorothiazanyl) | —OCH₃ | —H |
| FHI | -5-(4-chlorothiazanyl) | —OCH₂CH₃ | —H |
| FHJ | -5-(4-chlorothiazanyl) | —OCF₃ | —H |
| FHK | -5-(4-chlorothiazanyl) | -tert-butyl | —H |
| FHL | -5-(4-chlorothiazanyl) | -iso-propyl | —H |
| FHM | -5-(4-chlorothiazanyl) | —CH₃ | —CH₃ |
| FHN | -5-(4-chlorothiazanyl) | —H | —H |
| FHO | -5-(4-chlorothiazanyl) | —H | —Cl |
| FHP | -5-(4-chlorothiazanyl) | —H | —Br |
| FHQ | -5-(4-chlorothiazanyl) | —H | —F |
| FHR | -5-(4-chlorothiazanyl) | —H | —CH₃ |
| FHS | -5-(4-chlorothiazanyl) | —H | —CF₃ |
| FHT | -5-(4-chlorothiazanyl) | —H | —OCH₃ |
| FHU | -5-(4-chlorothiazanyl) | —H | —OCH₂CH₃ |
| FHV | -5-(4-chlorothiazanyl) | —H | —OCF₃ |
| FHW | -5-(4-chlorothiazanyl) | —H | -tert-butyl |
| FHX | -5-(4-chlorothiazanyl) | —H | -iso-propyl |
| FHY | -5-(4-methylthiazanyl) | —Cl | —H |
| FHZ | -5-(4-methylthiazanyl) | —Br | —H |
| FIA | -5-(4-methylthiazanyl) | —F | —H |
| FIB | -5-(4-methylthiazanyl) | —CH₃ | —H |

TABLE XIV-continued

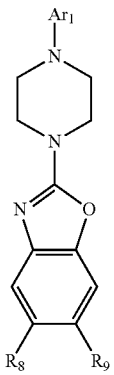

and pharmaceutically acceptable salts thereof, wherein:

| Compound | Ar$_1$ | R$_8$ | R$_9$ |
|---|---|---|---|
| FIC | -5-(4-methylthiazanyl) | —CF$_3$ | —H |
| FID | -5-(4-methylthiazanyl) | —OCH$_3$ | —H |
| FIE | -5-(4-methylthiazanyl) | —OCH$_2$CH$_3$ | —H |
| FIF | -5-(4-methylthiazanyl) | —OCF$_3$ | —H |
| FIG | -5-(4-methylthiazanyl) | -tert-butyl | —H |
| FIH | -5-(4-methylthiazanyl) | -iso-propyl | —H |
| FII | -5-(4-methylthiazanyl) | —CH$_3$ | —CH$_3$ |
| FIJ | -5-(4-methylthiazanyl) | —H | —H |
| FIK | -5-(4-methylthiazanyl) | —H | —Cl |
| FIL | -5-(4-methylthiazanyl) | —H | —Br |
| FIM | -5-(4-methylthiazanyl) | —H | —F |
| FIN | -5-(4-methylthiazanyl) | —H | —CH$_3$ |
| FIO | -5-(4-methylthiazanyl) | —H | —CF$_3$ |
| FIP | -5-(4-methylthiazanyl) | —H | —OCH$_3$ |
| FIQ | -5-(4-methylthiazanyl) | —H | —OCH$_2$CH$_3$ |
| FIR | -5-(4-methylthiazanyl) | —H | —OCF$_3$ |
| FIS | -5-(4-methylthiazanyl) | —H | -tert-butyl |
| FIT | -5-(4-methylthiazanyl) | —H | -iso-propyl |

TABLE XV

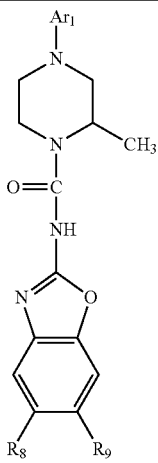

and pharmaceutically acceptable salts thereof, wherein:

| Compound | Ar$_1$ | R$_8$ | R$_9$ |
|---|---|---|---|
| FIU (a, b, and c) | -2-(3-chloropyridyl) | —Cl | —H |
| FIV (a, b, and c) | -2-(3-chloropyridyl) | —Br | —H |
| FIW (a, b, and c) | -2-(3-chloropyridyl) | —F | —H |
| FIX (a, b, and c) | -2-(3-chloropyridyl) | —CH$_3$ | —H |
| FIY (a, b, and c) | -2-(3-chloropyridyl) | —CF$_3$ | —H |
| FIZ (a, b, and c) | -2-(3-chloropyridyl) | —OCH$_3$ | —H |
| FJA (a, b, and c) | -2-(3-chloropyridyl) | —OCH$_2$CH$_3$ | —H |
| FJB (a, b, and c) | -2-(3-chloropyridyl) | —OCF$_3$ | —H |
| FJC (a, b, and c) | -2-(3-chloropyridyl) | -tert-butyl | —H |
| FJD (a, b, and c) | -2-(3-chloropyridyl) | -iso-propyl | —H |

TABLE XV-continued

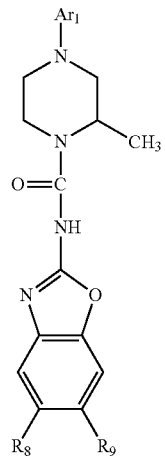

and pharmaceutically acceptable salts thereof, wherein:

| Compound | Ar$_1$ | R$_8$ | R$_9$ |
|---|---|---|---|
| FJE (a, b, and c) | -2-(3-chloropyridyl) | —CH$_3$ | —CH$_3$ |
| FJF (a, b, and c) | -2-(3-chloropyridyl) | —H | —H |
| FJG (a, b, and c) | -2-(3-chloropyridyl) | —H | —Cl |
| FJH (a, b, and c) | -2-(3-chloropyridyl) | —H | —Br |
| FJI (a, b, and c) | -2-(3-chloropyridyl) | —H | —F |
| FJJ (a, b, and c) | -2-(3-chloropyridyl) | —H | —CH$_3$ |
| FJK (a, b, and c) | -2-(3-chloropyridyl) | —H | —CF$_3$ |
| FJL (a, b, and c) | -2-(3-chloropyridyl) | —H | —OCH$_3$ |
| FJM (a, b, and c) | -2-(3-chloropyridyl) | —H | —OCH$_2$CH$_3$ |
| FJN (a, b, and c) | -2-(3-chloropyridyl) | —H | —OCF$_3$ |
| FJO (a, b, and c) | -2-(3-chloropyridyl) | —H | -tert-butyl |
| FJP (a, b, and c) | -2-(3-chloropyridyl) | —H | -iso-propyl |
| FJQ (a, b, and c) | -2-(3-methylpyridyl) | —Cl | —H |
| FJR (a, b, and c) | -2-(3-methylpyridyl) | —Br | —H |
| FJS (a, b, and c) | -2-(3-methylpyridyl) | —F | —H |
| FJT (a, b, and c) | -2-(3-methylpyridyl) | —CH$_3$ | —H |
| FJU (a, b, and c) | -2-(3-methylpyridyl) | —CF$_3$ | —H |
| FJV (a, b, and c) | -2-(3-methylpyridyl) | —OCH$_3$ | —H |
| FJW (a, b, and c) | -2-(3-methylpyridyl) | —OCH$_2$CH$_3$ | —H |
| FJX (a, b, and c) | -2-(3-methylpyridyl) | —OCF$_3$ | —H |
| FJY (a, b, and c) | -2-(3-methylpyridyl) | -tert-butyl | —H |
| FJZ (a, b, and c) | -2-(3-methylpyridyl) | -iso-propyl | —H |
| FKA (a, b, and c) | -2-(3-methylpyridyl) | —CH$_3$ | —CH$_3$ |
| FKB (a, b, and c) | -2-(3-methylpyridyl) | —H | —H |
| FKC (a, b, and c) | -2-(3-methylpyridyl) | —H | —Cl |
| FKD (a, b, and c) | -2-(3-methylpyridyl) | —H | —Br |
| FKE (a, b, and c) | -2-(3-methylpyridyl) | —H | —F |
| FKF (a, b, and c) | -2-(3-methylpyridyl) | —H | —CH$_3$ |
| FKG (a, b, and c) | -2-(3-methylpyridyl) | —H | —CF$_3$ |
| FKH (a, b, and c) | -2-(3-methylpyridyl) | —H | —OCH$_3$ |
| FKI (a, b, and c) | -2-(3-methylpyridyl) | —H | —OCH$_2$CH$_3$ |
| FKJ (a, b, and c) | -2-(3-methylpyridyl) | —H | —OCF$_3$ |
| FKK (a, b, and c) | -2-(3-methylpyridyl) | —H | -tert-butyl |
| FKL (a, b, and c) | -2-(3-methylpyridyl) | —H | -iso-propyl |
| FKM (a, b, and c) | -2-(3-CF$_3$-pyridyl) | —Cl | —H |
| FKN (a, b, and c) | -2-(3-CF$_3$-pyridyl) | —Br | —H |
| FKO (a, b, and c) | -2-(3-CF$_3$-pyridyl) | —F | —H |
| FKP (a, b, and c) | -2-(3-CF$_3$-pyridyl) | —CH$_3$ | —H |
| FKQ (a, b, and c) | -2-(3-CF$_3$-pyridyl) | —CF$_3$ | —H |
| FKR (a, b, and c) | -2-(3-CF$_3$-pyridyl) | —OCH$_3$ | —H |
| FKS (a, b, and c) | -2-(3-CF$_3$-pyridyl) | —OCH$_2$CH$_3$ | —H |
| FKT (a, b, and c) | -2-(3-CF$_3$-pyridyl) | —OCF$_3$ | —H |
| FKU (a, b, and c) | -2-(3-CF$_3$-pyridyl) | -tert-butyl | —H |
| FKV (a, b, and c) | -2-(3-CF$_3$-pyridyl) | -iso-propyl | —H |
| FKW (a, b, and c) | -2-(3-CF$_3$-pyridyl) | —CH$_3$ | —CH$_3$ |
| FKX (a, b, and c) | -2-(3-CF$_3$-pyridyl) | —H | —H |
| FKY (a, b, and c) | -2-(3-CF$_3$-pyridyl) | —H | —Cl |
| FKZ (a, b, and c) | -2-(3-CF$_3$-pyridyl) | —H | —Br |
| FLA (a, b, and c) | -2-(3-CF$_3$-pyridyl) | —H | —F |
| FLB (a, b, and c) | -2-(3-CF$_3$-pyridyl) | —H | —CH$_3$ |
| FLC (a, b, and c) | -2-(3-CF$_3$-pyridyl) | —H | —CF$_3$ |
| FLD (a, b, and c) | -2-(3-CF$_3$-pyridyl) | —H | —OCH$_3$ |
| FLE (a, b, and c) | -2-(3-CF$_3$-pyridyl) | —H | —OCH$_2$CH$_3$ |
| FLF (a, b, and c) | -2-(3-CF$_3$-pyridyl) | —H | —OCF$_3$ |

TABLE XV-continued

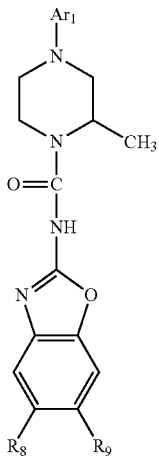

and pharmaceutically acceptable salts thereof, wherein:

| Compound | Ar$_1$ | R$_8$ | R$_9$ |
|---|---|---|---|
| FLG (a, b, and c) | -2-(3-CF$_3$-pyridyl) | —H | -tert-butyl |
| FLH (a, b, and c) | -2-(3-CF$_3$-pyridyl) | —H | -iso-propyl |
| FLI (a, b, and c) | -4-(5-chloropyrimidinyl) | —Cl | —H |
| FLJ (a, b, and c) | -4-(5-chloropyrimidinyl) | —Br | —H |
| FLK (a, b, and c) | -4-(5-chloropyrimidinyl) | —F | —H |
| FLL (a, b, and c) | -4-(5-chloropyrimidinyl) | —CH$_3$ | —H |
| FLM (a, b, and c) | -4-(5-chloropyrimidinyl) | —CF$_3$ | —H |
| FLN (a, b, and c) | -4-(5-chloropyrimidinyl) | —OCH$_3$ | —H |
| FLO (a, b, and c) | -4-(5-chloropyrimidinyl) | —OCH$_2$CH$_3$ | —H |
| FLP (a, b, and c) | -4-(5-chloropyrimidinyl) | —OCF$_3$ | —H |
| FLQ (a, b, and c) | -4-(5-chloropyrimidinyl) | -tert-butyl | —H |
| FLR (a, b, and c) | -4-(5-chloropyrimidinyl) | -iso-propyl | —H |
| FLS (a, b, and c) | -4-(5-chloropyrimidinyl) | —CH$_3$ | —CH$_3$ |
| FLT (a, b, and c) | -4-(5-chloropyrimidinyl) | —H | —H |
| FLU (a, b, and c) | -4-(5-chloropyrimidinyl) | —H | —Cl |
| FLV (a, b, and c) | -4-(5-chloropyrimidinyl) | —H | —Br |
| FLW (a, b, and c) | -4-(5-chloropyrimidinyl) | —H | —F |
| FLX (a, b, and c) | -4-(5-chloropyrimidinyl) | —H | —CH$_3$ |
| FLY (a, b, and c) | -4-(5-chloropyrimidinyl) | —H | —CF$_3$ |
| FLZ (a, b, and c) | -4-(5-chloropyrimidinyl) | —H | —OCH$_3$ |
| FMA (a, b, and c) | -4-(5-chloropyrimidinyl) | —H | —OCH$_2$CH$_3$ |
| FMB (a, b, and c) | -4-(5-chloropyrimidinyl) | —H | —OCF$_3$ |
| FMC (a, b, and c) | -4-(5-chloropyrimidinyl) | —H | -tert-butyl |
| FMD (a, b, and c) | -4-(5-chloropyrimidinyl) | —H | -iso-propyl |
| FME (a, b, and c) | -4-(5-methylpyrimidinyl) | —Cl | —H |
| FMF (a, b, and c) | -4-(5-methylpyrimidinyl) | —Br | —H |
| FMG (a, b, and c) | -4-(5-methylpyrimidinyl) | —F | —H |
| FMH (a, b, and c) | -4-(5-methylpyrimidinyl) | —CH$_3$ | —H |
| FMI (a, b, and c) | -4-(5-methylpyrimidinyl) | —CF$_3$ | —H |
| FMJ (a, b, and c) | -4-(5-methylpyrimidinyl) | —OCH$_3$ | —H |
| FMK (a, b, and c) | -4-(5-methylpyrimidinyl) | —OCH$_2$CH$_3$ | —H |
| FML (a, b, and c) | -4-(5-methylpyrimidinyl) | —OCF$_3$ | —H |
| FMM (a, b, and c) | -4-(5-methylpyrimidinyl) | -tert-butyl | —H |
| FMN (a, b, and c) | -4-(5-methylpyrimidinyl) | -iso-propyl | —H |
| FMO (a, b, and c) | -4-(5-methylpyrimidinyl) | —CH$_3$ | —CH$_3$ |
| FMP (a, b, and c) | -4-(5-methylpyrimidinyl) | —H | —H |
| FMQ (a, b, and c) | -4-(5-methylpyrimidinyl) | —H | —Cl |
| FMR (a, b, and c) | -4-(5-methylpyrimidinyl) | —H | —Br |
| FMS (a, b, and c) | -4-(5-methylpyrimidinyl) | —H | —F |
| FMT (a, b, and c) | -4-(5-methylpyrimidinyl) | —H | —CH$_3$ |
| FMU (a, b, and c) | -4-(5-methylpyrimidinyl) | —H | —CF$_3$ |
| FMV (a, b, and c) | -4-(5-methylpyrimidinyl) | —H | —OCH$_3$ |
| FMW (a, b, and c) | -4-(5-methylpyrimidinyl) | —H | —OCH$_2$CH$_3$ |
| FMX (a, b, and c) | -4-(5-methylpyrimidinyl) | —H | —OCF$_3$ |
| FMY (a, b, and c) | -4-(5-methylpyrimidinyl) | —H | -tert-butyl |
| FMZ (a, b, and c) | -4-(5-methylpyrimidinyl) | —H | -iso-propyl |
| FNA (a, b, and c) | -2-pyrazinyl | —Cl | —H |
| FNB (a, b, and c) | -2-pyrazinyl | —Br | —H |
| FNC (a, b, and c) | -2-pyrazinyl | —F | —H |
| FND (a, b, and c) | -2-pyrazinyl | —CH$_3$ | —H |
| FNE (a, b, and c) | -2-pyrazinyl | —CF$_3$ | —H |
| FNF (a, b, and c) | -2-pyrazinyl | —OCH$_3$ | —H |
| FNG (a, b, and c) | -2-pyrazinyl | —OCH$_2$CH$_3$ | —H |
| FNH (a, b, and c) | -2-pyrazinyl | —OCF$_3$ | —H |
| FNI (a, b, and c) | -2-pyrazinyl | -tert-butyl | —H |
| FNJ (a, b, and c) | -2-pyrazinyl | -iso-propyl | —H |
| FNK (a, b, and c) | -2-pyrazinyl | —CH$_3$ | —CH$_3$ |
| FNL (a, b, and c) | -2-pyrazinyl | —H | —H |
| FNM (a, b, and c) | -2-pyrazinyl | —H | —Cl |
| FNN (a, b, and c) | -2-pyrazinyl | —H | —Br |
| FNO (a, b, and c) | -2-pyrazinyl | —H | —F |
| FNP (a, b, and c) | -2-pyrazinyl | —H | —CH$_3$ |
| FNQ (a, b, and c) | -2-pyrazinyl | —H | —CF$_3$ |
| FNR (a, b, and c) | -2-pyrazinyl | —H | —OCH$_3$ |
| FNS (a, b, and c) | -2-pyrazinyl | —H | —OCH$_2$CH$_3$ |
| FNT (a, b, and c) | -2-pyrazinyl | —H | —OCF$_3$ |
| FNU (a, b, and c) | -2-pyrazinyl | —H | -tert-butyl |
| FNV (a, b, and c) | -2-pyrazinyl | —H | -iso-propyl |
| FNW (a, b, and c) | -2-(3-chloropyrazinyl) | —Cl | —H |
| FNX (a, b, and c) | -2-(3-chloropyrazinyl) | —Br | —H |
| FNY (a, b, and c) | -2-(3-chloropyrazinyl) | —F | —H |
| FNZ (a, b, and c) | -2-(3-chloropyrazinyl) | —CH$_3$ | —H |
| FOA (a, b, and c) | -2-(3-chloropyrazinyl) | —CF$_3$ | —H |
| FOB (a, b, and c) | -2-(3-chloropyrazinyl) | —OCH$_3$ | —H |
| FOC (a, b, and c) | -2-(3-chloropyrazinyl) | —OCH$_2$CH$_3$ | —H |
| FOD (a, b, and c) | -2-(3-chloropyrazinyl) | —OCF$_3$ | —H |
| FOE (a, b, and c) | -2-(3-chloropyrazinyl) | -tert-butyl | —H |
| FOF (a, b, and c) | -2-(3-chloropyrazinyl) | -iso-propyl | —H |
| FOG (a, b, and c) | -2-(3-chloropyrazinyl) | —CH$_3$ | —CH$_3$ |
| FOH (a, b, and c) | -2-(3-chloropyrazinyl) | —H | —H |
| FOI (a, b, and c) | -2-(3-chloropyrazinyl) | —H | —Cl |
| FOJ (a, b, and c) | -2-(3-chloropyrazinyl) | —H | —Br |
| FOK (a, b, and c) | -2-(3-chloropyrazinyl) | —H | —F |
| FOL (a, b, and c) | -2-(3-chloropyrazinyl) | —H | —CH$_3$ |
| FOM (a, b, and c) | -2-(3-chloropyrazinyl) | —H | —CF$_3$ |
| FON (a, b, and c) | -2-(3-chloropyrazinyl) | —H | —OCH$_3$ |
| FOO (a, b, and c) | -2-(3-chloropyrazinyl) | —H | —OCH$_2$CH$_3$ |
| FOP (a, b, and c) | -2-(3-chloropyrazinyl) | —H | —OCF$_3$ |
| FOQ (a, b, and c) | -2-(3-chloropyrazinyl) | —H | -tert-butyl |
| FOR (a, b, and c) | -2-(3-chloropyrazinyl) | —H | -iso-propyl |
| FOS (a, b, and c) | -2-(3-methylpyrazinyl) | —Cl | —H |
| FOT (a, b, and c) | -2-(3-methylpyrazinyl) | —Br | —H |
| FOU (a, b, and c) | -2-(3-methylpyrazinyl) | —F | —H |
| FOV (a, b, and c) | -2-(3-methylpyrazinyl) | —CH$_3$ | —H |
| FOW (a, b, and c) | -2-(3-methylpyrazinyl) | —CF$_3$ | —H |
| FOX (a, b, and c) | -2-(3-methylpyrazinyl) | —OCH$_3$ | —H |
| FOY (a, b, and c) | -2-(3-methylpyrazinyl) | —OCH$_2$CH$_3$ | —H |
| FOZ (a, b, and c) | -2-(3-methylpyrazinyl) | —OCF$_3$ | —H |
| FPA (a, b, and c) | -2-(3-methylpyrazinyl) | -tert-butyl | —H |
| FPB (a, b, and c) | -2-(3-methylpyrazinyl) | -iso-propyl | —H |
| FPC (a, b, and c) | -2-(3-methylpyrazinyl) | —CH$_3$ | —CH$_3$ |
| FPD (a, b, and c) | -2-(3-methylpyrazinyl) | —H | —H |
| FPE (a, b, and c) | -2-(3-methylpyrazinyl) | —H | —Cl |
| FPF (a, b, and c) | -2-(3-methylpyrazinyl) | —H | —Br |
| FPG (a, b, and c) | -2-(3-methylpyrazinyl) | —H | —F |
| FPH (a, b, and c) | -2-(3-methylpyrazinyl) | —H | —CH$_3$ |
| FPI (a, b, and c) | -2-(3-methylpyrazinyl) | —H | —CF$_3$ |
| FPJ (a, b, and c) | -2-(3-methylpyrazinyl) | —H | —OCH$_3$ |

TABLE XV-continued

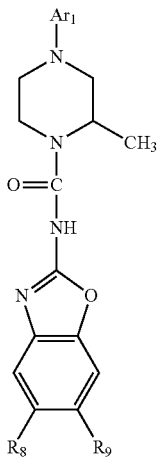

and pharmaceutically acceptable salts thereof, wherein:

| Compound | Ar$_1$ | R$_8$ | R$_9$ |
|---|---|---|---|
| FPK (a, b, and c) | -2-(3-methylpyrazinyl) | —H | —OCH$_2$CH$_3$ |
| FPL (a, b, and c) | -2-(3-methylpyrazinyl) | —H | —OCF$_3$ |
| FPM (a, b, and c) | -2-(3-methylpyrazinyl) | —H | -tert-butyl |
| FPN (a, b, and c) | -2-(3-methylpyrazinyl) | —H | -iso-propyl |
| FPO (a, b, and c) | -2-pyridazinyl | —Cl | —H |
| FPP (a, b, and c) | -2-pyridazinyl | —Br | —H |
| FPQ (a, b, and c) | -2-pyridazinyl | —F | —H |
| FPR (a, b, and c) | -2-pyridazinyl | —CH$_3$ | —H |
| FPS (a, b, and c) | -2-pyridazinyl | —CF$_3$ | —H |
| FPT (a, b, and c) | -2-pyridazinyl | —OCH$_3$ | —H |
| FPU (a, b, and c) | -2-pyridazinyl | —OCH$_2$CH$_3$ | —H |
| FPV (a, b, and c) | -2-pyridazinyl | —OCF$_3$ | —H |
| FPW (a, b, and c) | -2-pyridazinyl | -tert-butyl | —H |
| FPX (a, b, and c) | -2-pyridazinyl | -iso-propyl | —H |
| FPY (a, b, and c) | -2-pyridazinyl | —CH$_3$ | —CH$_3$ |
| FPZ (a, b, and c) | -2-pyridazinyl | —H | —H |
| FQA (a, b, and c) | -2-pyridazinyl | —H | —Cl |
| FQB (a, b, and c) | -2-pyridazinyl | —H | —Br |
| FQC (a, b, and c) | -2-pyridazinyl | —H | —F |
| FQD (a, b, and c) | -2-pyridazinyl | —H | —CH$_3$ |
| FQE (a, b, and c) | -2-pyridazinyl | —H | —CF$_3$ |
| FQF (a, b, and c) | -2-pyridazinyl | —H | —OCH$_3$ |
| FQG (a, b, and c) | -2-pyridazinyl | —H | —OCH$_2$CH$_3$ |
| FQH (a, b, and c) | -2-pyridazinyl | —H | —OCF$_3$ |
| FQI (a, b, and c) | -2-pyridazinyl | —H | -tert-butyl |
| FQJ (a, b, and c) | -2-pyridazinyl | —H | -iso-propyl |
| FQK (a, b, and c) | -3-(4-chloropyridazinyl) | —Cl | —H |
| FQL (a, b, and c) | -3-(4-chloropyridazinyl) | —Br | —H |
| FQM (a, b, and c) | -3-(4-chloropyridazinyl) | —F | —H |
| FQN (a, b, and c) | -3-(4-chloropyridazinyl) | —CH$_3$ | —H |
| FQO (a, b, and c) | -3-(4-chloropyridazinyl) | —CF$_3$ | —H |
| FQP (a, b, and c) | -3-(4-chloropyridazinyl) | —OCH$_3$ | —H |
| FQQ (a, b, and c) | -3-(4-chloropyridazinyl) | —OCH$_2$CH$_3$ | —H |
| FQR (a, b, and c) | -3-(4-chloropyridazinyl) | —OCF$_3$ | —H |
| FQS (a, b, and c) | -3-(4-chloropyridazinyl) | -tert-butyl | —H |
| FQT (a, b, and c) | -3-(4-chloropyridazinyl) | -iso-propyl | —H |
| FQU (a, b, and c) | -3-(4-chloropyridazinyl) | —CH$_3$ | —CH$_3$ |
| FQV (a, b, and c) | -3-(4-chloropyridazinyl) | —H | —H |
| FQW (a, b, and c) | -3-(4-chloropyridazinyl) | —H | —Cl |
| FQX (a, b, and c) | -3-(4-chloropyridazinyl) | —H | —Br |
| FQY (a, b, and c) | -3-(4-chloropyridazinyl) | —H | —F |
| FQZ (a, b, and c) | -3-(4-chloropyridazinyl) | —H | —CH$_3$ |
| FRA (a, b, and c) | -3-(4-chloropyridazinyl) | —H | —CF$_3$ |
| FRB (a, b, and c) | -3-(4-chloropyridazinyl) | —H | —OCH$_3$ |
| FRC (a, b, and c) | -3-(4-chloropyridazinyl) | —H | —OCH$_2$CH$_3$ |
| FRD (a, b, and c) | -3-(4-chloropyridazinyl) | —H | —OCF$_3$ |
| FRE (a, b, and c) | -3-(4-chloropyridazinyl) | —H | -tert-butyl |
| FRF (a, b, and c) | -3-(4-chloropyridazinyl) | —H | -iso-propyl |
| FRG (a, b, and c) | -3-(4-methylpyridazinyl) | —Cl | —H |
| FRH (a, b, and c) | -3-(4-methylpyridazinyl) | —Br | —H |
| FRI (a, b, and c) | -3-(4-methylpyridazinyl) | —F | —H |
| FRJ (a, b, and c) | -3-(4-methylpyridazinyl) | —CH$_3$ | —H |
| FRK (a, b, and c) | -3-(4-methylpyridazinyl) | —CF$_3$ | —H |
| FRL (a, b, and c) | -3-(4-methylpyridazinyl) | —OCH$_3$ | —H |
| FRM (a, b, and c) | -3-(4-methylpyridazinyl) | —OCH$_2$CH$_3$ | —H |
| FRN (a, b, and c) | -3-(4-methylpyridazinyl) | —OCF$_3$ | —H |
| FRO (a, b, and c) | -3-(4-methylpyridazinyl) | -tert-butyl | —H |
| FRP (a, b, and c) | -3-(4-methylpyridazinyl) | -iso-propyl | —H |
| FRQ (a, b, and c) | -3-(4-methylpyridazinyl) | —CH$_3$ | —CH$_3$ |
| FRR (a, b, and c) | -3-(4-methylpyridazinyl) | —H | —H |
| FRS (a, b, and c) | -3-(4-methylpyridazinyl) | —H | —Cl |
| FRT (a, b, and c) | -3-(4-methylpyridazinyl) | —H | —Br |
| FRU (a, b, and c) | -3-(4-methylpyridazinyl) | —H | —F |
| FRV (a, b, and c) | -3-(4-methylpyridazinyl) | —H | —CH$_3$ |
| FRW (a, b, and c) | -3-(4-methylpyridazinyl) | —H | —CF$_3$ |
| FRX (a, b, and c) | -3-(4-methylpyridazinyl) | —H | —OCH$_3$ |
| FRY (a, b, and c) | -3-(4-methylpyridazinyl) | —H | —OCH$_2$CH$_3$ |
| FRZ (a, b, and c) | -3-(4-methylpyridazinyl) | —H | —OCF$_3$ |
| FSA (a, b, and c) | -3-(4-methylpyridazinyl) | —H | -tert-butyl |
| FSB (a, b, and c) | -3-(4-methylpyridazinyl) | —H | -iso-propyl |
| FSC (a, b, and c) | -4-thiazanyl | —Cl | —H |
| FSD (a, b, and c) | -4-thiazanyl | —Br | —H |
| FSE (a, b, and c) | -4-thiazanyl | —F | —H |
| FSF (a, b, and c) | -4-thiazanyl | —CH$_3$ | —H |
| FSG (a, b, and c) | -4-thiazanyl | —CF$_3$ | —H |
| FSH (a, b, and c) | -4-thiazanyl | —OCH$_3$ | —H |
| FSI (a, b, and c) | -4-thiazanyl | —OCH$_2$CH$_3$ | —H |
| FSJ (a, b, and c) | -4-thiazanyl | —OCF$_3$ | —H |
| FSK (a, b, and c) | -4-thiazanyl | -tert-butyl | —H |
| FSL (a, b, and c) | -4-thiazanyl | -iso-propyl | —H |
| FSM (a, b, and c) | -4-thiazanyl | —CH$_3$ | —CH$_3$ |
| FSN (a, b, and c) | -4-thiazanyl | —H | —H |
| FSO (a, b, and c) | -4-thiazanyl | —H | —Cl |
| FSP (a, b, and c) | -4-thiazanyl | —H | —Br |
| FSQ (a, b, and c) | -4-thiazanyl | —H | —F |
| FSR (a, b, and c) | -4-thiazanyl | —H | —CH$_3$ |
| FSS (a, b, and c) | -4-thiazanyl | —H | —CF$_3$ |
| FST (a, b, and c) | -4-thiazanyl | —H | —OCH$_3$ |
| FSU (a, b, and c) | -4-thiazanyl | —H | —OCH$_2$CH$_3$ |
| FSV (a, b, and c) | -4-thiazanyl | —H | —OCF$_3$ |
| FSW (a, b, and c) | -4-thiazanyl | —H | -tert-butyl |
| FSX (a, b, and c) | -4-thiazanyl | —H | -iso-propyl |
| FSY (a, b, and c) | -5-(4-chlorothiazanyl) | —Cl | —H |
| FSZ (a, b, and c) | -5-(4-chlorothiazanyl) | —Br | —H |
| FTA (a, b, and c) | -5-(4-chlorothiazanyl) | —F | —H |
| FTB (a, b, and c) | -5-(4-chlorothiazanyl) | —CH$_3$ | —H |
| FTC (a, b, and c) | -5-(4-chlorothiazanyl) | —CF$_3$ | —H |
| FTD (a, b, and c) | -5-(4-chlorothiazanyl) | —OCH$_3$ | —H |
| FTE (a, b, and c) | -5-(4-chlorothiazanyl) | —OCH$_2$CH$_3$ | —H |
| FTF (a, b, and c) | -5-(4-chlorothiazanyl) | —OCF$_3$ | —H |
| FTG (a, b, and c) | -5-(4-chlorothiazanyl) | -tert-butyl | —H |
| FTH (a, b, and c) | -5-(4-chlorothiazanyl) | -iso-propyl | —H |
| FTI (a, b, and c) | -5-(4-chlorothiazanyl) | —CH$_3$ | —CH$_3$ |

TABLE XV-continued

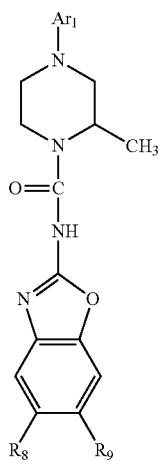

and pharmaceutically acceptable salts thereof, wherein:

| Compound | Ar₁ | R₈ | R₉ |
|---|---|---|---|
| FTJ (a, b, and c) | -5-(4-chlorothiazanyl) | —H | —H |
| FTK (a, b, and c) | -5-(4-chlorothiazanyl) | —H | —Cl |
| FTL (a, b, and c) | -5-(4-chlorothiazanyl) | —H | —Br |
| FTM (a, b, and c) | -5-(4-chlorothiazanyl) | —H | —F |
| FTN (a, b, and c) | -5-(4-chlorothiazanyl) | —H | —CH₃ |
| FTO (a, b, and c) | -5-(4-chlorothiazanyl) | —H | —CF₃ |
| FTP (a, b, and c) | -5-(4-chlorothiazanyl) | —H | —OCH₃ |
| FTQ (a, b, and c) | -5-(4-chlorothiazanyl) | —H | —OCH₂CH₃ |
| FTR (a, b, and c) | -5-(4-chlorothiazanyl) | —H | —OCF₃ |
| FTS (a, b, and c) | -5-(4-chlorothiazanyl) | —H | -tert-butyl |
| FTT (a, b, and c) | -5-(4-chlorothiazanyl) | —H | -iso-propyl |
| FTU (a, b, and c) | -5-(4-methylthiazanyl) | —Cl | —H |
| FTV (a, b, and c) | -5-(4-methylthiazanyl) | —Br | —H |
| FTW (a, b, and c) | -5-(4-methylthiazanyl) | —F | —H |
| FTX (a, b, and c) | -5-(4-methylthiazanyl) | —CH₃ | —H |
| FTY (a, b, and c) | -5-(4-methylthiazanyl) | —CF₃ | —H |
| FTZ (a, b, and c) | -5-(4-methylthiazanyl) | —OCH₃ | —H |
| FUA (a, b, and c) | -5-(4-methylthiazanyl) | —OCH₂CH₃ | —H |
| FUB (a, b, and c) | -5-(4-methylthiazanyl) | —OCF₃ | —H |
| FUC (a, b, and c) | -5-(4-methylthiazanyl) | -tert-butyl | —H |
| FUD (a, b, and c) | -5-(4-methylthiazanyl) | -iso-propyl | —H |
| FUE (a, b, and c) | -5-(4-methylthiazanyl) | —CH₃ | —CH₃ |
| FUF (a, b, and c) | -5-(4-methylthiazanyl) | —H | —H |
| FUG (a, b, and c) | -5-(4-methylthiazanyl) | —H | —Cl |
| FUH (a, b, and c) | -5-(4-methylthiazanyl) | —H | —Br |
| FUI (a, b, and c) | -5-(4-methylthiazanyl) | —H | —F |
| FUJ (a, b, and c) | -5-(4-methylthiazanyl) | —H | —CH₃ |
| FUK (a, b, and c) | -5-(4-methylthiazanyl) | —H | —CF₃ |
| FUL (a, b, and c) | -5-(4-methylthiazanyl) | —H | —OCH₃ |
| FUM (a, b, and c) | -5-(4-methylthiazanyl) | —H | —OCH₂CH₃ |
| FUN (a, b, and c) | -5-(4-methylthiazanyl) | —H | —OCF₃ |
| FUO (a, b, and c) | -5-(4-methylthiazanyl) | —H | -tert-butyl |
| FUP (a, b, and c) | -5-(4-methylthiazanyl) | —H | -iso-propyl |

"a" means the Benzoazolylpiperazine Compound is racemic.

"b" means the carbon atom of the piperazine ring attached to the methyl group is in the R configuration.

"c" means the carbon atom of the piperazine ring attached to the methyl group is in the S configuration.

TABLE XVI

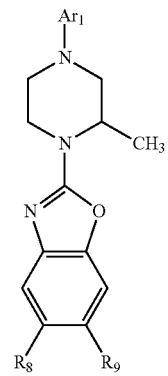

and pharmaceutically acceptable salts thereof, wherein:

| Compound | Ar₁ | R₈ | R₉ |
|---|---|---|---|
| FUQ (a, b, and c) | -2-(3-chloropyridyl) | —Cl | —H |
| FUR (a, b, and c) | -2-(3-chloropyridyl) | —Br | —H |
| FUS (a, b, and c) | -2-(3-chloropyridyl) | —F | —H |
| FUT (a, b, and c) | -2-(3-chloropyridyl) | —CH₃ | —H |
| FUU (a, b, and c) | -2-(3-chloropyridyl) | —CF₃ | —H |
| FUV (a, b, and c) | -2-(3-chloropyridyl) | —OCH₃ | —H |
| FUW (a, b, and c) | -2-(3-chloropyridyl) | —OCH₂CH₃ | —H |
| FUX (a, b, and c) | -2-(3-chloropyridyl) | —OCF₃ | —H |
| FUY (a, b, and c) | -2-(3-chloropyridyl) | -tert-butyl | —H |
| FUZ (a, b, and c) | -2-(3-chloropyridyl) | -iso-propyl | —H |
| FVA (a, b, and c) | -2-(3-chloropyridyl) | —CH₃ | —CH₃ |
| FVB (a, b, and c) | -2-(3-chloropyridyl) | —H | —H |
| FVC (a, b, and c) | -2-(3-chloropyridyl) | —H | —Cl |
| FVD (a, b, and c) | -2-(3-chloropyridyl) | —H | —Br |
| FVE (a, b, and c) | -2-(3-chloropyridyl) | —H | —F |
| FVF (a, b, and c) | -2-(3-chloropyridyl) | —H | —CH₃ |
| FVG (a, b, and c) | -2-(3-chloropyridyl) | —H | —CF₃ |
| FVH (a, b, and c) | -2-(3-chloropyridyl) | —H | —OCH₃ |
| FVI (a, b, and c) | -2-(3-chloropyridyl) | —H | —OCH₂CH₃ |
| FVJ (a, b, and c) | -2-(3-chloropyridyl) | —H | —OCF₃ |
| FVK (a, b, and c) | -2-(3-chloropyridyl) | —H | -tert-butyl |
| FVL (a, b, and c) | -2-(3-chloropyridyl) | —H | -iso-propyl |
| FVM (a, b, and c) | -2-(3-methylpyridyl) | —Cl | —H |
| FVN (a, b, and c) | -2-(3-methylpyridyl) | —Br | —H |
| FVO (a, b, and c) | -2-(3-methylpyridyl) | —F | —H |
| FVP (a, b, and c) | -2-(3-methylpyridyl) | —CH₃ | —H |
| FVQ (a, b, and c) | -2-(3-methylpyridyl) | —CF₃ | —H |
| FVR (a, b, and c) | -2-(3-methylpyridyl) | —OCH₃ | —H |
| FVS (a, b, and c) | -2-(3-methylpyridyl) | —OCH₂CH₃ | —H |
| FVT (a, b, and c) | -2-(3-methylpyridyl) | —OCF₃ | —H |
| FVU (a, b, and c) | -2-(3-methylpyridyl) | -tert-butyl | —H |
| FVV (a, b, and c) | -2-(3-methylpyridyl) | -iso-propyl | —H |
| FVW (a, b, and c) | -2-(3-methylpyridyl) | —CH₃ | —CH₃ |
| FVX (a, b, and c) | -2-(3-methylpyridyl) | —H | —H |
| FVY (a, b, and c) | -2-(3-methylpyridyl) | —H | —Cl |
| FVZ (a, b, and c) | -2-(3-methylpyridyl) | —H | —Br |
| FWA (a, b, and c) | -2-(3-methylpyridyl) | —H | —F |
| FWB (a, b, and c) | -2-(3-methylpyridyl) | —H | —CH₃ |
| FWC (a, b, and c) | -2-(3-methylpyridyl) | —H | —CF₃ |
| FWD (a, b, and c) | -2-(3-methylpyridyl) | —H | —OCH₃ |
| FWE (a, b, and c) | -2-(3-methylpyridyl) | —H | —OCH₂CH₃ |
| FWF (a, b, and c) | -2-(3-methylpyridyl) | —H | —OCF₃ |
| FWG (a, b, and c) | -2-(3-methylpyridyl) | —H | -tert-butyl |
| FWH (a, b, and c) | -2-(3-methylpyridyl) | —H | -iso-propyl |
| FWI (a, b, and c) | -2-(3-CF₃-pyridyl) | —Cl | —H |
| FWJ (a, b, and c) | -2-(3-CF₃-pyridyl) | —Br | —H |
| FWK (a, b, and c) | -2-(3-CF₃-pyridyl) | —F | —H |
| FWL (a, b, and c) | -2-(3-CF₃-pyridyl) | —CH₃ | —H |
| FWM (a, b, and c) | -2-(3-CF₃-pyridyl) | —CF₃ | —H |
| FWN (a, b, and c) | -2-(3-CF₃-pyridyl) | —OCH₃ | —H |
| FWO (a, b, and c) | -2-(3-CF₃-pyridyl) | —OCH₂CH₃ | —H |
| FWP (a, b, and c) | -2-(3-CF₃-pyridyl) | —OCF₃ | —H |
| FWQ (a, b, and c) | -2-(3-CF₃-pyridyl) | -tert-butyl | —H |
| FWR (a, b, and c) | -2-(3-CF₃-pyridyl) | -iso-propyl | —H |
| FWS (a, b, and c) | -2-(3-CF₃-pyridyl) | —CH₃ | —CH₃ |
| FWT (a, b, and c) | -2-(3-CF₃-pyridyl) | —H | —H |
| FWU (a, b, and c) | -2-(3-CF₃-pyridyl) | —H | —Cl |
| FWV (a, b, and c) | -2-(3-CF₃-pyridyl) | —H | —Br |

TABLE XVI-continued

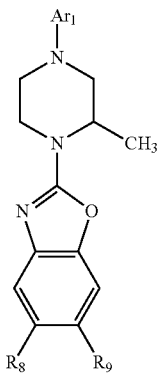

and pharmaceutically acceptable salts thereof, wherein:

| Compound | Ar₁ | R₈ | R₉ |
|---|---|---|---|
| FWW (a, b, and c) | -2-(3-CF₃-pyridyl) | —H | —F |
| FWX (a, b, and c) | -2-(3-CF₃-pyridyl) | —H | —CH₃ |
| FWY (a, b, and c) | -2-(3-CF₃-pyridyl) | —H | —CF₃ |
| FWZ (a, b, and c) | -2-(3-CF₃-pyridyl) | —H | —OCH₃ |
| FXA (a, b, and c) | -2-(3-CF₃-pyridyl) | —H | —OCH₂CH₃ |
| FXB (a, b, and c) | -2-(3-CF₃-pyridyl) | —H | —OCF₃ |
| FXC (a, b, and c) | -2-(3-CF₃-pyridyl) | —H | -tert-butyl |
| FXD (a, b, and c) | -2-(3-CF₃-pyridyl) | —H | -iso-propyl |
| FXE (a, b, and c) | -4-(5-chloropyrimidinyl) | —Cl | —H |
| FXF (a, b, and c) | -4-(5-chloropyrimidinyl) | —Br | —H |
| FXG (a, b, and c) | -4-(5-chloropyrimidinyl) | —F | —H |
| FXH (a, b, and c) | -4-(5-chloropyrimidinyl) | —CH₃ | —H |
| FXI (a, b, and c) | -4-(5-chloropyrimidinyl) | —CF₃ | —H |
| FXJ (a, b, and c) | -4-(5-chloropyrimidinyl) | —OCH₃ | —H |
| FXK (a, b, and c) | -4-(5-chloropyrimidinyl) | —OCH₂CH₃ | —H |
| FXL (a, b, and c) | -4-(5-chloropyrimidinyl) | —OCF₃ | —H |
| FXM (a, b, and c) | -4-(5-chloropyrimidinyl) | -tert-butyl | —H |
| FXN (a, b, and c) | -4-(5-chloropyrimidinyl) | -iso-propyl | —H |
| FXO (a, b, and c) | -4-(5-chloropyrimidinyl) | —CH₃ | —CH₃ |
| FXP (a, b, and c) | -4-(5-chloropyrimidinyl) | —H | —H |
| FXQ (a, b, and c) | -4-(5-chloropyrimidinyl) | —H | —Cl |
| FXR (a, b, and c) | -4-(5-chloropyrimidinyl) | —H | —Br |
| FXS (a, b, and c) | -4-(5-chloropyrimidinyl) | —H | —F |
| FXT (a, b, and c) | -4-(5-chloropyrimidinyl) | —H | —CH₃ |
| FXU (a, b, and c) | -4-(5-chloropyrimidinyl) | —H | —CF₃ |
| FXV (a, b, and c) | -4-(5-chloropyrimidinyl) | —H | —OCH₃ |
| FXW (a, b, and c) | -4-(5-chloropyrimidinyl) | —H | —OCH₂CH₃ |
| FXX (a, b, and c) | -4-(5-chloropyrimidinyl) | —H | —OCF₃ |
| FXY (a, b, and c) | -4-(5-chloropyrimidinyl) | —H | -tert-butyl |
| FXZ (a, b, and c) | -4-(5-chloropyrimidinyl) | —H | -iso-propyl |
| FYA (a, b, and c) | -4-(5-methylpyrimidinyl) | —Cl | —H |
| FYB (a, b, and c) | -4-(5-methylpyrimidinyl) | —Br | —H |
| FYC (a, b, and c) | -4-(5-methylpyrimidinyl) | —F | —H |
| FYD (a, b, and c) | -4-(5-methylpyrimidinyl) | —CH₃ | —H |
| FYE (a, b, and c) | -4-(5-methylpyrimidinyl) | —CF₃ | —H |
| FYF (a, b, and c) | -4-(5-methylpyrimidinyl) | —OCH₃ | —H |
| FYG (a, b, and c) | -4-(5-methylpyrimidinyl) | —OCH₂CH₃ | —H |
| FYH (a, b, and c) | -4-(5-methylpyrimidinyl) | —OCF₃ | —H |
| FYI (a, b, and c) | -4-(5-methylpyrimidinyl) | -tert-butyl | —H |
| FYJ (a, b, and c) | -4-(5-methylpyrimidinyl) | -iso-propyl | —H |
| FYK (a, b, and c) | -4-(5-methylpyrimidinyl) | —CH₃ | —CH₃ |
| FYL (a, b, and c) | -4-(5-methylpyrimidinyl) | —H | —H |
| FYM (a, b, and c) | -4-(5-methylpyrimidinyl) | —H | —Cl |
| FYN (a, b, and c) | -4-(5-methylpyrimidinyl) | —H | —Br |
| FYO (a, b, and c) | -4-(5-methylpyrimidinyl) | —H | —F |
| FYP (a, b, and c) | -4-(5-methylpyrimidinyl) | —H | —CH₃ |
| FYQ (a, b, and c) | -4-(5-methylpyrimidinyl) | —H | —CF₃ |
| FYR (a, b, and c) | -4-(5-methylpyrimidinyl) | —H | —OCH₃ |
| FYS (a, b, and c) | -4-(5-methylpyrimidinyl) | —H | —OCH₂CH₃ |
| FYT (a, b, and c) | -4-(5-methylpyrimidinyl) | —H | —OCF₃ |
| FYU (a, b, and c) | -4-(5-methylpyrimidinyl) | —H | -tert-butyl |
| FYV (a, b, and c) | -4-(5-methylpyrimidinyl) | —H | -iso-propyl |
| FYW (a, b, and c) | -2-pyrazinyl | —Cl | —H |
| FYX (a, b, and c) | -2-pyrazinyl | —Br | —H |
| FYY (a, b, and c) | -2-pyrazinyl | —F | —H |
| FYZ (a, b, and c) | -2-pyrazinyl | —CH₃ | —H |
| FZA (a, b, and c) | -2-pyrazinyl | —CF₃ | —H |
| FZB (a, b, and c) | -2-pyrazinyl | —OCH₃ | —H |
| FZC (a, b, and c) | -2-pyrazinyl | —OCH₂CH₃ | —H |
| FZD (a, b, and c) | -2-pyrazinyl | —OCF₃ | —H |
| FZE (a, b, and c) | -2-pyrazinyl | -tert-butyl | —H |
| FZF (a, b, and c) | -2-pyrazinyl | -iso-propyl | —H |
| FZG (a, b, and c) | -2-pyrazinyl | —CH₃ | —CH₃ |
| FZH (a, b, and c) | -2-pyrazinyl | —H | —H |
| FZI (a, b, and c) | -2-pyrazinyl | —H | —Cl |
| FZJ (a, b, and c) | -2-pyrazinyl | —H | —Br |
| FZK (a, b, and c) | -2-pyrazinyl | —H | —F |
| FZL (a, b, and c) | -2-pyrazinyl | —H | —CH₃ |
| FZM (a, b, and c) | -2-pyrazinyl | —H | —CF₃ |
| FZN (a, b, and c) | -2-pyrazinyl | —H | —OCH₃ |
| FZO (a, b, and c) | -2-pyrazinyl | —H | —OCH₂CH₃ |
| FZP (a, b, and c) | -2-pyrazinyl | —H | —OCF₃ |
| FZQ (a, b, and c) | -2-pyrazinyl | —H | -tert-butyl |
| FZR (a, b, and c) | -2-pyrazinyl | —H | -iso-propyl |
| FZS (a, b, and c) | -2-(3-chloropyrazinyl) | —Cl | —H |
| FZT (a, b, and c) | -2-(3-chloropyrazinyl) | —Br | —H |
| FZU (a, b, and c) | -2-(3-chloropyrazinyl) | —F | —H |
| FZV (a, b, and c) | -2-(3-chloropyrazinyl) | —CH₃ | —H |
| FZW (a, b, and c) | -2-(3-chloropyrazinyl) | —CF₃ | —H |
| FZX (a, b, and c) | -2-(3-chloropyrazinyl) | —OCH₃ | —H |
| FZY (a, b, and c) | -2-(3-chloropyrazinyl) | —OCH₂CH₃ | —H |
| FZZ (a, b, and c) | -2-(3-chloropyrazinyl) | —OCF₃ | —H |
| GAA (a, b, and c) | -2-(3-chloropyrazinyl) | -tert-butyl | —H |
| GAB (a, b, and c) | -2-(3-chloropyrazinyl) | -iso-propyl | —H |
| GAC (a, b, and c) | -2-(3-chloropyrazinyl) | —CH₃ | —CH₃ |
| GAD (a, b, and c) | -2-(3-chloropyrazinyl) | —H | —H |
| GAE (a, b, and c) | -2-(3-chloropyrazinyl) | —H | —Cl |
| GAF (a, b, and c) | -2-(3-chloropyrazinyl) | —H | —Br |
| GAG (a, b, and c) | -2-(3-chloropyrazinyl) | —H | —F |
| GAH (a, b, and c) | -2-(3-chloropyrazinyl) | —H | —CH₃ |
| GAI (a, b, and c) | -2-(3-chloropyrazinyl) | —H | —CF₃ |
| GAJ (a, b, and c) | -2-(3-chloropyrazinyl) | —H | —OCH₃ |
| GAK (a, b, and c) | -2-(3-chloropyrazinyl) | —H | —OCH₂CH₃ |
| GAL (a, b, and c) | -2-(3-chloropyrazinyl) | —H | —OCF₃ |
| GAM (a, b, and c) | -2-(3-chloropyrazinyl) | —H | -tert-butyl |
| GAN (a, b, and c) | -2-(3-chloropyrazinyl) | —H | -iso-propyl |
| GAO (a, b, and c) | -2-(3-methylpyrazinyl) | —Cl | —H |
| GAP (a, b, and c) | -2-(3-methylpyrazinyl) | —Br | —H |
| GAQ (a, b, and c) | -2-(3-methylpyrazinyl) | —F | —H |
| GAR (a, b, and c) | -2-(3-methylpyrazinyl) | —CH₃ | —H |
| GAS (a, b, and c) | -2-(3-methylpyrazinyl) | —CF₃ | —H |
| GAT (a, b, and c) | -2-(3-methylpyrazinyl) | —OCH₃ | —H |
| GAU (a, b, and c) | -2-(3-methylpyrazinyl) | —OCH₂CH₃ | —H |
| GAV (a, b, and c) | -2-(3-methylpyrazinyl) | —OCF₃ | —H |
| GAW (a, b, and c) | -2-(3-methylpyrazinyl) | -tert-butyl | —H |
| GAX (a, b, and c) | -2-(3-methylpyrazinyl) | -iso-propyl | —H |
| GAY (a, b, and c) | -2-(3-methylpyrazinyl) | —CH₃ | —CH₃ |
| GAZ (a, b, and c) | -2-(3-methylpyrazinyl) | —H | —H |
| GBA (a, b, and c) | -2-(3-methylpyrazinyl) | —H | —Cl |
| GBB (a, b, and c) | -2-(3-methylpyrazinyl) | —H | —Br |
| GBC (a, b, and c) | -2-(3-methylpyrazinyl) | —H | —F |
| GBD (a, b, and c) | -2-(3-methylpyrazinyl) | —H | —CH₃ |
| GBE (a, b, and c) | -2-(3-methylpyrazinyl) | —H | —CF₃ |
| GBF (a, b, and c) | -2-(3-methylpyrazinyl) | —H | —OCH₃ |
| GBG (a, b, and c) | -2-(3-methylpyrazinyl) | —H | —OCH₂CH₃ |
| GBH (a, b, and c) | -2-(3-methylpyrazinyl) | —H | —OCF₃ |

TABLE XVI-continued

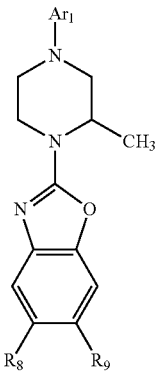

and pharmaceutically acceptable salts thereof, wherein:

| Compound | Ar₁ | R₈ | R₉ |
|---|---|---|---|
| GBI (a, b, and c) | -2-(3-methylpyrazinyl) | —H | -tert-butyl |
| GBJ (a, b, and c) | -2-(3-methylpyrazinyl) | —H | -iso-propyl |
| GBK (a, b, and c) | -2-pyridazinyl | —Cl | —H |
| GBL (a, b, and c) | -2-pyridazinyl | —Br | —H |
| GBM (a, b, and c) | -2-pyridazinyl | —F | —H |
| GBN (a, b, and c) | -2-pyridazinyl | —CH₃ | —H |
| GBO (a, b, and c) | -2-pyridazinyl | —CF₃ | —H |
| GBP (a, b, and c) | -2-pyridazinyl | —OCH₃ | —H |
| GBQ (a, b, and c) | -2-pyridazinyl | —OCH₂CH₃ | —H |
| GBR (a, b, and c) | -2-pyridazinyl | —OCF₃ | —H |
| GBS (a, b, and c) | -2-pyridazinyl | -tert-butyl | —H |
| GBT (a, b, and c) | -2-pyridazinyl | -iso-propyl | —H |
| GBU (a, b, and c) | -2-pyridazinyl | —CH₃ | —CH₃ |
| GBV (a, b, and c) | -2-pyridazinyl | —H | —H |
| GBW (a, b, and c) | -2-pyridazinyl | —H | —Cl |
| GBX (a, b, and c) | -2-pyridazinyl | —H | —Br |
| GBY (a, b, and c) | -2-pyridazinyl | —H | —F |
| GBZ (a, b, and c) | -2-pyridazinyl | —H | —CH₃ |
| GCA (a, b, and c) | -2-pyridazinyl | —H | —CF₃ |
| GCB (a, b, and c) | -2-pyridazinyl | —H | —OCH₃ |
| GCC (a, b, and c) | -2-pyridazinyl | —H | —OCH₂CH₃ |
| GCD (a, b, and c) | -2-pyridazinyl | —H | —OCF₃ |
| GCE (a, b, and c) | -2-pyridazinyl | —H | -tert-butyl |
| GCF (a, b, and c) | -2-pyridazinyl | —H | -iso-propyl |
| GCG (a, b, and c) | -3-(4-chloropyridazinyl) | —Cl | —H |
| GCH (a, b, and c) | -3-(4-chloropyridazinyl) | —Br | —H |
| GCI (a, b, and c) | -3-(4-chloropyridazinyl) | —F | —H |
| GCJ (a, b, and c) | -3-(4-chloropyridazinyl) | —CH₃ | —H |
| GCK (a, b, and c) | -3-(4-chloropyridazinyl) | —CF₃ | —H |
| GCL (a, b, and c) | -3-(4-chloropyridazinyl) | —OCH₃ | —H |
| GCM (a, b, and c) | -3-(4-chloropyridazinyl) | —OCH₂CH₃ | —H |
| GCN (a, b, and c) | -3-(4-chloropyridazinyl) | —OCF₃ | —H |
| GCO (a, b, and c) | -3-(4-chloropyridazinyl) | -tert-butyl | —H |
| GCP (a, b, and c) | -3-(4-chloropyridazinyl) | -iso-propyl | —H |
| GCQ (a, b, and c) | -3-(4-chloropyridazinyl) | —CH₃ | —CH₃ |
| GCR (a, b, and c) | -3-(4-chloropyridazinyl) | —H | —H |
| GCS (a, b, and c) | -3-(4-chloropyridazinyl) | —H | —Cl |
| GCT (a, b, and c) | -3-(4-chloropyridazinyl) | —H | —Br |
| GCU (a, b, and c) | -3-(4-chloropyridazinyl) | —H | —F |
| GCV (a, b, and c) | -3-(4-chloropyridazinyl) | —H | —CH₃ |
| GCW (a, b, and c) | -3-(4-chloropyridazinyl) | —H | —CF₃ |
| GCX (a, b, and c) | -3-(4-chloropyridazinyl) | —H | —OCH₃ |
| GCY (a, b, and c) | -3-(4-chloropyridazinyl) | —H | —OCH₂CH₃ |
| GCZ (a, b, and c) | -3-(4-chloropyridazinyl) | —H | —OCF₃ |
| GDA (a, b, and c) | -3-(4-chloropyridazinyl) | —H | -tert-butyl |
| GDB (a, b, and c) | -3-(4-chloropyridazinyl) | —H | -iso-propyl |
| GDC (a, b, and c) | -3-(4-methylpyridazinyl) | —Cl | —H |
| GDD (a, b, and c) | -3-(4-methylpyridazinyl) | —Br | —H |
| GDE (a, b, and c) | -3-(4-methylpyridazinyl) | —F | —H |
| GDF (a, b, and c) | -3-(4-methylpyridazinyl) | —CH₃ | —H |
| GDG (a, b, and c) | -3-(4-methylpyridazinyl) | —CF₃ | —H |
| GDH (a, b, and c) | -3-(4-methylpyridazinyl) | —OCH₃ | —H |
| GDI (a, b, and c) | -3-(4-methylpyridazinyl) | —OCH₂CH₃ | —H |
| GDJ (a, b, and c) | -3-(4-methylpyridazinyl) | —OCF₃ | —H |
| GDK (a, b, and c) | -3-(4-methylpyridazinyl) | -tert-butyl | —H |
| GDL (a, b, and c) | -3-(4-methylpyridazinyl) | -iso-propyl | —H |
| GDM (a, b, and c) | -3-(4-methylpyridazinyl) | —CH₃ | —CH₃ |
| GDN (a, b, and c) | -3-(4-methylpyridazinyl) | —H | —H |
| GDO (a, b, and c) | -3-(4-methylpyridazinyl) | —H | —Cl |
| GDP (a, b, and c) | -3-(4-methylpyridazinyl) | —H | —Br |
| GDQ (a, b, and c) | -3-(4-methylpyridazinyl) | —H | —F |
| GDR (a, b, and c) | -3-(4-methylpyridazinyl) | —H | —CH₃ |
| GDS (a, b, and c) | -3-(4-methylpyridazinyl) | —H | —CF₃ |
| GDT (a, b, and c) | -3-(4-methylpyridazinyl) | —H | —OCH₃ |
| GDU (a, b, and c) | -3-(4-methylpyridazinyl) | —H | —OCH₂CH₃ |
| GDV (a, b, and c) | -3-(4-methylpyridazinyl) | —H | —OCF₃ |
| GDW (a, b, and c) | -3-(4-methylpyridazinyl) | —H | -tert-butyl |
| GDX (a, b, and c) | -3-(4-methylpyridazinyl) | —H | -iso-propyl |
| GDY (a, b, and c) | -4-thiazanyl | —Cl | —H |
| GDZ (a, b, and c) | -4-thiazanyl | —Br | —H |
| GEA (a, b, and c) | -4-thiazanyl | —F | —H |
| GEB (a, b, and c) | -4-thiazanyl | —CH₃ | —H |
| GEC (a, b, and c) | -4-thiazanyl | —CF₃ | —H |
| GED (a, b, and c) | -4-thiazanyl | —OCH₃ | —H |
| GEE (a, b, and c) | -4-thiazanyl | —OCH₂CH₃ | —H |
| GEF (a, b, and c) | -4-thiazanyl | —OCF₃ | —H |
| GEG (a, b, and c) | -4-thiazanyl | -tert-butyl | —H |
| GEH (a, b, and c) | -4-thiazanyl | -iso-propyl | —H |
| GEI (a, b, and c) | -4-thiazanyl | —CH₃ | —CH₃ |
| GEJ (a, b, and c) | -4-thiazanyl | —H | —H |
| GEK (a, b, and c) | -4-thiazanyl | —H | —Cl |
| GEL (a, b, and c) | -4-thiazanyl | —H | —Br |
| GEM (a, b, and c) | -4-thiazanyl | —H | —F |
| GEN (a, b, and c) | -4-thiazanyl | —H | —CH₃ |
| GEO (a, b, and c) | -4-thiazanyl | —H | —CF₃ |
| GEP (a, b, and c) | -4-thiazanyl | —H | —OCH₃ |
| GEQ (a, b, and c) | -4-thiazanyl | —H | —OCH₂CH₃ |
| GER (a, b, and c) | -4-thiazanyl | —H | —OCF₃ |
| GES (a, b, and c) | -4-thiazanyl | —H | -tert-butyl |
| GET (a, b, and c) | -4-thiazanyl | —H | -iso-propyl |
| GEU (a, b, and c) | -5-(4-chlorothiazanyl) | —Cl | —H |
| GEV (a, b, and c) | -5-(4-chlorothiazanyl) | —Br | —H |
| GEW (a, b, and c) | -5-(4-chlorothiazanyl) | —F | —H |
| GEX (a, b, and c) | -5-(4-chlorothiazanyl) | —CH₃ | —H |
| GEY (a, b, and c) | -5-(4-chlorothiazanyl) | —CF₃ | —H |
| GEZ (a, b, and c) | -5-(4-chlorothiazanyl) | —OCH₃ | —H |
| GFA (a, b, and c) | -5-(4-chlorothiazanyl) | —OCH₂CH₃ | —H |
| GFB (a, b, and c) | -5-(4-chlorothiazanyl) | —OCF₃ | —H |
| GFC (a, b, and c) | -5-(4-chlorothiazanyl) | -tert-butyl | —H |
| GFD (a, b, and c) | -5-(4-chlorothiazanyl) | -iso-propyl | —H |
| GFE (a, b, and c) | -5-(4-chlorothiazanyl) | —CH₃ | —CH₃ |
| GFF (a, b, and c) | -5-(4-chlorothiazanyl) | —H | —H |
| GFG (a, b, and c) | -5-(4-chlorothiazanyl) | —H | —Cl |
| GFH (a, b, and c) | -5-(4-chlorothiazanyl) | —H | —Br |
| GFI (a, b, and c) | -5-(4-chlorothiazanyl) | —H | —F |
| GFJ (a, b, and c) | -5-(4-chlorothiazanyl) | —H | —CH₃ |
| GFK (a, b, and c) | -5-(4-chlorothiazanyl) | —H | —CF₃ |
| GFL (a, b, and c) | -5-(4-chlorothiazanyl) | —H | —OCH₃ |
| GFM (a, b, and c) | -5-(4-chlorothiazanyl) | —H | —OCH₂CH₃ |
| GFN (a, b, and c) | -5-(4-chlorothiazanyl) | —H | —OCF₃ |
| GFO (a, b, and c) | -5-(4-chlorothiazanyl) | —H | -tert-butyl |
| GFP (a, b, and c) | -5-(4-chlorothiazanyl) | —H | -iso-propyl |
| GFQ (a, b, and c) | -5-(4-methylthiazanyl) | —Cl | —H |
| GFR (a, b, and c) | -5-(4-methylthiazanyl) | —Br | —H |
| GFS (a, b, and c) | -5-(4-methylthiazanyl) | —F | —H |
| GFT (a, b, and c) | -5-(4-methylthiazanyl) | —CH₃ | —H |

TABLE XVI-continued

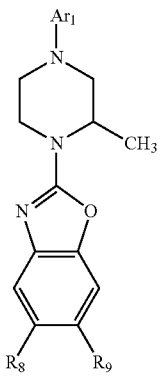

and pharmaceutically acceptable salts thereof, wherein:

| Compound | $Ar_1$ | $R_8$ | $R_9$ |
|---|---|---|---|
| GFU (a, b, and c) | -5-(4-methylthiazanyl) | —$CF_3$ | —H |
| GFV (a, b, and c) | -5-(4-methylthiazanyl) | —$OCH_3$ | —H |
| GFW (a, b, and c) | -5-(4-methylthiazanyl) | —$OCH_2CH_3$ | —H |
| GFX (a, b, and c) | -5-(4-methylthiazanyl) | —$OCF_3$ | —H |
| GFY (a, b, and c) | -5-(4-methylthiazanyl) | -tert-butyl | —H |
| GFZ (a, b, and c) | -5-(4-methylthiazanyl) | -iso-propyl | —H |
| GGA (a, b, and c) | -5-(4-methylthiazanyl) | —$CH_3$ | —$CH_3$ |
| GGB (a, b, and c) | -5-(4-methylthiazanyl) | —H | —H |
| GGC (a, b, and c) | -5-(4-methylthiazanyl) | —H | —Cl |
| GGD (a, b, and c) | -5-(4-methylthiazanyl) | —H | —Br |
| GGE (a, b, and c) | -5-(4-methylthiazanyl) | —H | —F |
| GGF (a, b, and c) | -5-(4-methylthiazanyl) | —H | —$CH_3$ |
| GGG (a, b, and c) | -5-(4-methylthiazanyl) | —H | —$CF_3$ |
| GGH (a, b, and c) | -5-(4-methylthiazanyl) | —H | —$OCH_3$ |
| GGI (a, b, and c) | -5-(4-methylthiazanyl) | —H | —$OCH_2CH_3$ |
| GGJ (a, b, and c) | -5-(4-methylthiazanyl) | —H | —$OCF_3$ |
| GGK (a, b, and c) | -5-(4-methylthiazanyl) | —H | -tert-butyl |
| GGL (a, b, and c) | -5-(4-methylthiazanyl) | —H | -iso-propyl |

"a" means the Benzoazolylpiperazine Compound is racemic.
"b" means the carbon atom of the piperazine ring attached to the methyl group is in the R configuration.
"c" means the carbon atom of the piperazine ring attached to the methyl group is in the S configuration.

TABLE XIX

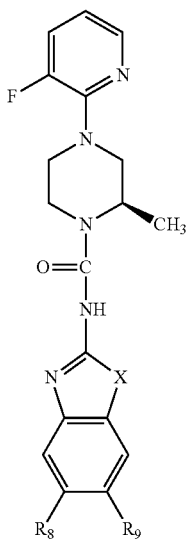

and pharmaceutically acceptable salts thereof, wherein:

| Compound | X | $R_8$ | $R_9$ |
|---|---|---|---|
| GGM | S | —Cl | —H |
| GGN | S | —Br | —H |

TABLE XIX-continued

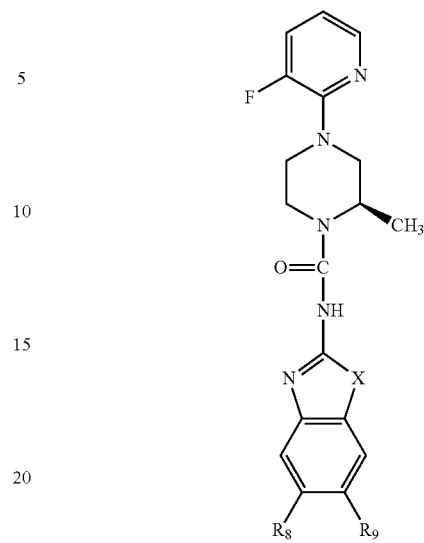

and pharmaceutically acceptable salts thereof, wherein:

| Compound | X | $R_8$ | $R_9$ |
|---|---|---|---|
| GGO | S | —F | —H |
| GGP | S | —$CH_3$ | —H |
| GGQ | S | —$CF_3$ | —H |
| GGR | S | —$OCH_3$ | —H |
| GGS | S | —$OCH_2CH_3$ | —H |
| GGT | S | —$OCF_3$ | —H |
| GGU | S | -tert-butyl | —H |
| GGV | S | -iso-propyl | —H |
| GGW | S | —$CH_3$ | —$CH_3$ |
| GGX | S | —H | —H |
| GGY | S | —H | —Cl |
| GGZ | S | —H | —Br |
| GHA | S | —H | —F |
| GHB | S | —H | —$CH_3$ |
| GHC | S | —H | —$CF_3$ |
| GHD | S | —H | —$OCH_3$ |
| GHE | S | —H | —$OCH_2CH_3$ |
| GHF | S | —H | —$OCF_3$ |
| GHG | S | —H | -tert-butyl |
| GHH | S | —H | -iso-propyl |
| GHI | O | —Cl | —H |
| GHJ | O | —Br | —H |
| GHK | O | —F | —H |
| GHL | O | —$CH_3$ | —H |
| GHM | O | —$CF_3$ | —H |
| GHN | O | —$OCH_3$ | —H |
| GHO | O | —$OCH_2CH_3$ | —H |
| GHP | O | —$OCF_3$ | —H |
| GHQ | O | -tert-butyl | —H |
| GHR | O | -iso-propyl | —H |
| GHS | O | —$CH_3$ | —$CH_3$ |
| GHT | O | —H | —H |
| GHU | O | —H | —Cl |
| GHV | O | —H | —Br |
| GHW | O | —H | —F |
| GHX | O | —H | —$CH_3$ |
| GHY | O | —H | —$CF_3$ |
| GHZ | O | —H | —$OCH_3$ |
| GIA | O | —H | —$OCH_2CH_3$ |
| GIB | O | —H | —$OCF_3$ |
| GIC | O | —H | -tert-butyl |
| GID | O | —H | -iso-propyl |
| GIE | NH | —Cl | —H |
| GIF | NH | —Br | —H |
| GIG | NH | —F | —H |
| GIH | NH | —$CH_3$ | —H |
| GII | NH | —$CF_3$ | —H |
| GIJ | NH | —$OCH_3$ | —H |
| GIK | NH | —$OCH_2CH_3$ | —H |
| GIL | NH | —$OCF_3$ | —H |

TABLE XIX-continued

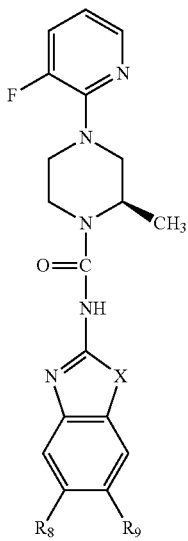

and pharmaceutically acceptable salts thereof, wherein:

| Compound | X | R8 | R9 |
|---|---|---|---|
| GIM | NH | -tert-butyl | —H |
| GIN | NH | -iso-propyl | —H |
| GIO | NH | —CH3 | —CH3 |
| GIP | NH | —H | —H |
| GIQ | NH | —H | —Cl |
| GIR | NH | —H | —Br |
| GIS | NH | —H | —F |
| GIT | NH | —H | —CH3 |
| GIU | NH | —H | —CF3 |
| GIV | NH | —H | —OCH3 |
| GIW | NH | —H | —OCH2CH3 |
| GIX | NH | —H | —OCF3 |
| GIY | NH | —H | -tert-butyl |
| GIZ | NH | —H | -iso-propyl |

TABLE XX

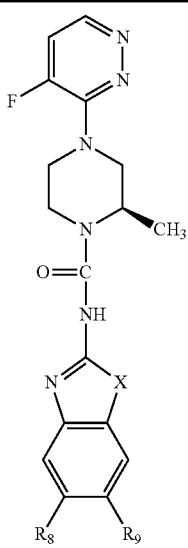

and pharmaceutically acceptable salts thereof, wherein:

| Compound | X | R8 | R9 |
|---|---|---|---|
| GJA | S | —Cl | —H |
| GJB | S | —Br | —H |

TABLE XX-continued

| Compound | X | R8 | R9 |
|---|---|---|---|
| GJC | S | —F | —H |
| GJD | S | —CH3 | —H |
| GJE | S | —CF3 | —H |
| GJF | S | —OCH3 | —H |
| GJG | S | —OCH2CH3 | —H |
| GJH | S | —OCF3 | —H |
| GJI | S | -tert-butyl | —H |
| GJJ | S | -iso-propyl | —H |
| GJK | S | —CH3 | —CH3 |
| GJL | S | —H | —H |
| GJM | S | —H | —Cl |
| GJN | S | —H | —Br |
| GJO | S | —H | —F |
| GJP | S | —H | —CH3 |
| GJQ | S | —H | —CF3 |
| GJR | S | —H | —OCH3 |
| GJS | S | —H | —OCH2CH3 |
| GJT | S | —H | —OCF3 |
| GJU | S | —H | -tert-butyl |
| GJV | S | —H | -iso-propyl |
| GJW | O | —Cl | —H |
| GJX | O | —Br | —H |
| GJY | O | —F | —H |
| GJZ | O | —CH3 | —H |
| GKA | O | —CF3 | —H |
| GKB | O | —OCH3 | —H |
| GKC | O | —OCH2CH3 | —H |
| GKD | O | —OCF3 | —H |
| GKE | O | -tert-butyl | —H |
| GKF | O | -iso-propyl | —H |
| GKG | O | —CH3 | —CH3 |
| GKH | O | —H | —H |
| GKI | O | —H | —Cl |
| GKJ | O | —H | —Br |
| GKK | O | —H | —F |
| GKL | O | —H | —CH3 |
| GKM | O | —H | —CF3 |
| GKN | O | —H | —OCH3 |
| GKO | O | —H | —OCH2CH3 |
| GKP | O | —H | —OCF3 |
| GKQ | O | —H | -tert-butyl |
| GKR | O | —H | -iso-propyl |
| GKS | N | —Cl | —H |
| GKT | N | —Br | —H |
| GKU | N | —F | —H |
| GKV | N | —CH3 | —H |
| GKW | N | —CF3 | —H |
| GKX | N | —OCH3 | —H |
| GKY | N | —OCH2CH3 | —H |
| GKZ | N | —OCF3 | —H |

TABLE XX-continued

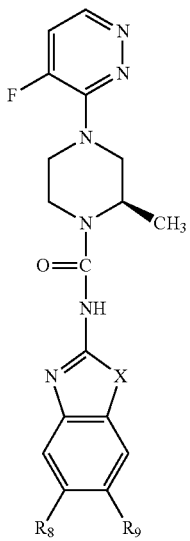

and pharmaceutically acceptable salts thereof, wherein:

| Compound | X | R8 | R9 |
|---|---|---|---|
| GLA | N | -tert-butyl | —H |
| GLB | N | -iso-propyl | —H |
| GLC | N | —CH3 | —CH3 |
| GLD | N | —H | —H |
| GLE | N | —H | —Cl |
| GLF | N | —H | —Br |
| GLG | N | —H | —F |
| GLH | N | —H | —CH3 |
| GLI | N | —H | —CF3 |
| GLJ | N | —H | —OCH3 |
| GLK | N | —H | —OCH2CH3 |
| GLL | N | —H | —OCF3 |
| GLM | N | —H | -tert-butyl |
| GLN | N | —H | -iso-propyl |

TABLE XXI

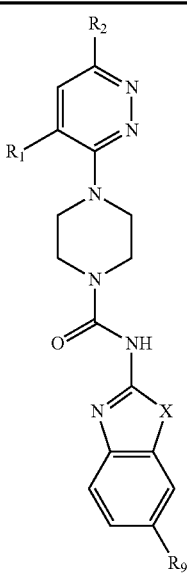

and pharmaceutically acceptable salts thereof, wherein:

| Compound | X | R1 | R2 | R9 |
|---|---|---|---|---|
| GLO | S | —CH3 | —Cl | —F |
| GLP | S | —CH3 | —Cl | —Cl |

TABLE XXI-continued

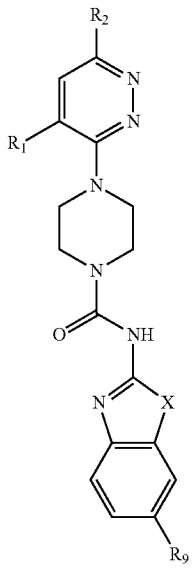

and pharmaceutically acceptable salts thereof, wherein:

| Compound | X | R1 | R2 | R9 |
|---|---|---|---|---|
| GLQ | S | —CH3 | —Cl | —CH3 |
| GLR | S | —CH3 | —F | —F |
| GLS | S | —CH3 | —F | —Cl |
| GLT | S | —CH3 | —F | —CH3 |
| GLU | S | —CF3 | —Cl | —F |
| GLV | S | —CF3 | —Cl | —Cl |
| GLW | S | —CF3 | —Cl | —CH3 |
| GLX | S | —CF3 | —F | —F |
| GLY | S | —CF3 | —F | —Cl |
| GLZ | S | —CF3 | —F | —CH3 |
| GMA | S | —Cl | —Cl | —F |
| GMB | S | —Cl | —Cl | —Cl |
| GMC | S | —Cl | —Cl | —CH3 |
| GMD | S | —Cl | —F | —F |
| GME | S | —Cl | —F | —Cl |
| GMF | S | —Cl | —F | —CH3 |
| GMG | NH | —CH3 | —Cl | —F |
| GMH | NH | —CH3 | —Cl | —Cl |
| GMI | NH | —CH3 | —Cl | —CH3 |
| GMJ | NH | —CH3 | —F | —F |
| GMK | NH | —CH3 | —F | —Cl |
| GML | NH | —CH3 | —F | —CH3 |
| GMM | NH | —CF3 | —Cl | —F |
| GMN | NH | —CF3 | —Cl | —Cl |
| GMO | NH | —CF3 | —Cl | —CH3 |
| GMP | NH | —CF3 | —F | —F |
| GMQ | NH | —CF3 | —F | —Cl |
| GMR | NH | —CF3 | —F | —CH3 |
| GMS | NH | —Cl | —Cl | —F |
| GMT | NH | —Cl | —Cl | —Cl |
| GMU | NH | —Cl | —Cl | —CH3 |
| GMV | NH | —Cl | —F | —F |
| GMW | NH | —Cl | —F | —Cl |
| GMX | NH | —Cl | —F | —CH3 |
| GMY | O | —CH3 | —Cl | —F |
| GMZ | O | —CH3 | —Cl | —Cl |
| GNA | O | —CH3 | —Cl | —CH3 |
| GNB | O | —CH3 | —F | —F |
| GNC | O | —CH3 | —F | —Cl |
| GND | O | —CH3 | —F | —CH3 |
| GNE | O | —CF3 | —Cl | —F |
| GNF | O | —CF3 | —Cl | —Cl |
| GNG | O | —CF3 | —Cl | —CH3 |
| GNH | O | —CF3 | —F | —F |
| GNI | O | —CF3 | —F | —Cl |
| GNJ | O | —CF3 | —F | —CH3 |
| GNK | O | —Cl | —Cl | —F |
| GNL | O | —Cl | —Cl | —Cl |
| GNM | O | —Cl | —Cl | —CH3 |

TABLE XXI-continued

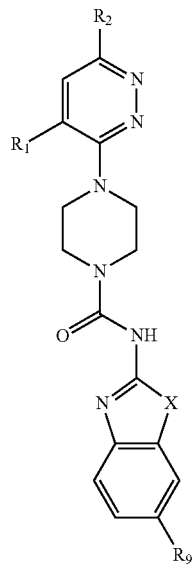

and pharmaceutically acceptable salts thereof, wherein:

| Compound | X | R₁ | R₂ | R₉ |
|---|---|---|---|---|
| GNN | O | —Cl | —F | —F |
| GNO | O | —Cl | —F | —Cl |
| GNP | O | —Cl | —F | —CH₃ |

TABLE XXII

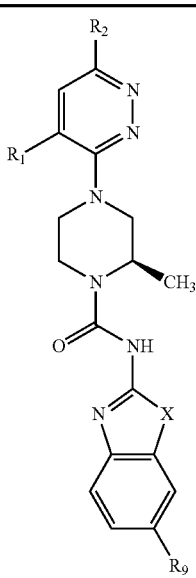

and pharmaceutically acceptable salts thereof, wherein:

| Compound | X | R₁ | R₂ | R₉ |
|---|---|---|---|---|
| GNQ | S | —CH₃ | —Cl | —F |
| GNR | S | —CH₃ | —Cl | —Cl |
| GNS | S | —CH₃ | —Cl | —CH₃ |
| GNT | S | —CH₃ | —F | —F |
| GNU | S | —CH₃ | —F | —Cl |
| GNV | S | —CH₃ | —F | —CH₃ |
| GNW | S | —CF₃ | —Cl | —F |
| GNX | S | —CF₃ | —Cl | —Cl |
| GNY | S | —CF₃ | —Cl | —CH₃ |
| GNZ | S | —CF₃ | —F | —F |

TABLE XXII-continued

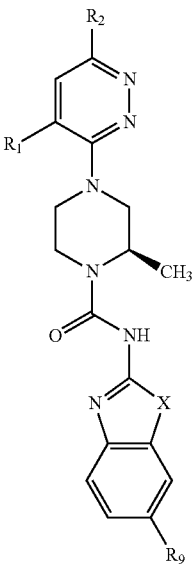

and pharmaceutically acceptable salts thereof, wherein:

| Compound | X | R₁ | R₂ | R₉ |
|---|---|---|---|---|
| GOA | S | —CF₃ | —F | —Cl |
| GOB | S | —CF₃ | —F | —CH₃ |
| GOC | S | —Cl | —Cl | —F |
| GOD | S | —Cl | —Cl | —Cl |
| GOE | S | —Cl | —Cl | —CH₃ |
| GOF | S | —Cl | —F | —F |
| GOG | S | —Cl | —F | —Cl |
| GOH | S | —Cl | —F | —CH₃ |
| GOI | NH | —CH₃ | —Cl | —F |
| GOJ | NH | —CH₃ | —Cl | —Cl |
| GOK | NH | —CH₃ | —Cl | —CH₃ |
| GOL | NH | —CH₃ | —F | —F |
| GOM | NH | —CH₃ | —F | —Cl |
| GON | NH | —CH₃ | —F | —CH₃ |
| GOO | NH | —CF₃ | —Cl | —F |
| GOP | NH | —CF₃ | —Cl | —Cl |
| GOQ | NH | —CF₃ | —Cl | —CH₃ |
| GOR | NH | —CF₃ | —F | —F |
| GOS | NH | —CF₃ | —F | —Cl |
| GOT | NH | —CF₃ | —F | —CH₃ |
| GOU | NH | —Cl | —Cl | —F |
| GOV | NH | —Cl | —Cl | —Cl |
| GOW | NH | —Cl | —Cl | —CH₃ |
| GOX | NH | —Cl | —F | —F |
| GOY | NH | —Cl | —F | —Cl |
| GOZ | NH | —Cl | —F | —CH₃ |
| GPA | O | —CH₃ | —Cl | —F |
| GPB | O | —CH₃ | —Cl | —Cl |
| GPC | O | —CH₃ | —Cl | —CH₃ |
| GPD | O | —CH₃ | —F | —F |
| GPE | O | —CH₃ | —F | —Cl |
| GPF | O | —CH₃ | —F | —CH₃ |
| GPG | O | —CF₃ | —Cl | —F |
| GPH | O | —CF₃ | —Cl | —Cl |
| GPI | O | —CF₃ | —Cl | —CH₃ |
| GPJ | O | —CF₃ | —F | —F |
| GPK | O | —CF₃ | —F | —Cl |
| GPL | O | —CF₃ | —F | —CH₃ |
| GPM | O | —Cl | —Cl | —F |
| GPN | O | —Cl | —Cl | —Cl |
| GPO | O | —Cl | —Cl | —CH₃ |
| GPP | O | —Cl | —F | —F |
| GPQ | O | —Cl | —F | —Cl |
| GPR | O | —Cl | —F | —CH₃ |

4.1 Definitions

As used herein, the terms used above having following meaning:

"—($C_1$-$C_{10}$)alkyl" means a straight chain or branched non-cyclic hydrocarbon having from 1 to 10 carbon atoms. Representative straight chain —($C_1$-$C_{10}$)alkyls include -methyl, -ethyl, -n-propyl, -n-butyl, -n-pentyl, -n-hexyl, -n-heptyl, -n-octyl, -n-nonyl, and -n-decyl. Representative branched —($C_1$-$C_{10}$)alkyls include -isopropyl, -sec-butyl, -isobutyl, -tert-butyl, -isopentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

"—($C_1$-$C_6$)alkyl" means a straight chain or branched non-cyclic hydrocarbon having from 1 to 6 carbon atoms. Representative straight chain —($C_1$-$C_6$)alkyls include -methyl, -ethyl, -n-propyl, -n-butyl, -n-pentyl, and -n-hexyl. Representative branched —($C_1$-$C_6$)alkyls include -isopropyl, -sec-butyl, -isobutyl, -tert-butyl, -isopentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, and 3,3-dimethylbutyl.

"—($C_1$-$C_4$)alkyl" means a straight chain or branched non-cyclic hydrocarbon having from 1 to 4 carbon atoms. Representative straight chain —($C_1$-$C_4$)alkyls include -methyl, -ethyl, -n-propyl, and -n-butyl. Representative branched —($C_1$-$C_4$)alkyls include -isopropyl, -sec-butyl, -isobutyl, and -tert-butyl.

"—($C_2$-$C_{10}$)alkenyl" means a straight chain or branched non-cyclic hydrocarbon having from 2 to 10 carbon atoms and including at least one carbon-carbon double bond. Representative straight chain and branched ($C_2$-$C_{10}$)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like.

"—($C_2$-$C_6$)alkenyl" means a straight chain or branched non-cyclic hydrocarbon having from 2 to 6 carbon atoms and including at least one carbon-carbon double bond. Representative straight chain and branched ($C_2$-$C_6$)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, 2-hexenyl, 3-hexenyl and the like.

"—($C_2$-$C_{10}$)alkynyl" means a straight chain or branched non-cyclic hydrocarbon having from 2 to 10 carbon atoms and including at least one carbon-carbon triple bond. Representative straight chain and branched —($C_2$-$C_{10}$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl and the like.

"—($C_2$-$C_6$)alkynyl" means a straight chain or branched non-cyclic hydrocarbon having from 2 to 6 carbon atoms and including at least one carbon-carbon triple bond. Representative straight chain and branched ($C_2$-$C_6$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl and the like.

"—($C_3$-$C_{10}$)cycloalkyl" means a saturated cyclic hydrocarbon having from 3 to 10 carbon atoms. Representative ($C_3$-$C_{10}$)cycloalkyls are -cyclopropyl, -cyclobutyl, -cyclopentyl, -cyclohexyl, -cycloheptyl, -cyclooctyl, -cyclononyl, and -cyclodecyl.

"—($C_3$-$C_8$)cycloalkyl" means a saturated cyclic hydrocarbon having from 3 to 8 carbon atoms. Representative ($C_3$-$C_8$) cycloalkyls include -cyclopropyl, -cyclobutyl, -cyclopentyl, -cyclohexyl, -cycloheptyl, and -cyclooctyl.

"—($C_8$-$C_{14}$)bicycloalkyl" means a bi-cyclic hydrocarbon ring system having from 8 to 14 carbon atoms and at least one saturated cyclic alkyl ring. Representative —($C_8$-$C_{14}$)bicycloalkyls include -indanyl, -1,2,3,4-tetrahydronaphthyl, -5,6,7,8-tetrahydronaphthyl, -perhydronaphthyl and the like.

"—($C_8$-$C_{14}$)tricycloalkyl" means a tri-cyclic hydrocarbon ring system having from 8 to 14 carbon atoms and at least one saturated ring. Representative —($C_8$-$C_{14}$) tricycloalkyls include -pyrenyl, -1,2,3,4-tetrahydroanthracenyl, -perhydroanthracenyl aceanthreneyl, -1,2,3,4-tetrahydropenanthrenyl, -5,6,7,8-tetrahydrophenanthrenyl, -perhydrophenanthrenyl and the like.

"—($C_5$-$C_{10}$)cycloalkenyl" means a cyclic non-aromatic hydrocarbon having at least one carbon-carbon double bond in the cyclic system and from 5 to 10 carbon atoms. Representative ($C_5$-$C_{10}$)cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl -cyclononadienyl, -cyclodecenyl, -cyclodecadienyl and the like.

"—($C_5$-$C_8$)cycloalkenyl" means a cyclic non-aromatic hydrocarbon having at least one carbon-carbon double bond in the cyclic system and from 5 to 8 carbon atoms. Representative ($C_5$-$C_8$)cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl and the like.

"—($C_8$-$C_{14}$)bicycloalkenyl" means a bi-cyclic hydrocarbon ring system having at least one carbon-carbon double bond in each ring and from 8 to 14 carbon atoms. Representative —($C_8$-$C_{14}$)bicycloalkenyls include -indenyl, -pentalenyl, -naphthalenyl, -azulenyl, -heptalenyl, -1,2,7,8-tetrahydronaphthalenyl and the like.

"—($C_8$-$C_{14}$)tricycloalkenyl" means a tri-cyclic hydrocarbon ring system having at least one carbon-carbon double bond in each ring and from 8 to 14 carbon atoms. Representative —($C_8$-$C_{14}$)tricycloalkenyls include -anthracenyl, -phenanthrenyl, -phenalenyl, -acenaphthalenyl, as-indacenyl, s-indacenyl and the like.

"-(3- to 7-membered)heterocycle" or "-(3- to 7-membered) heterocyclo" means a 3- to 7-membered monocyclic heterocyclic ring which is either saturated, unsaturated non-aromatic, or aromatic. A 3-membered -heterocycle can contain up to 3 heteroatoms, and a 4- to 7-membered heterocycle can contain up to 4 heteroatoms. Each heteroatom is independently selected from nitrogen, which can be quaternized; oxygen; and sulfur, including sulfoxide and sulfone. The -(3- to 7-membered)heterocycle can be attached via a nitrogen or carbon atom. Representative -(3- to 7-membered)heterocycles include pyridyl, furyl, thiophenyl, pyrrolyl, oxazolyl, imidazolyl, thiazolyl, thiadiazolyl, isoxazolyl, pyrazolyl, isothiazolyl, pyridazinyl, pyrimidinyl, pyrazinyl, triazinyl, morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl and the like.

"-(3- to 5-membered)heterocycle" or "-(3- to 5-membered)heterocyclo" means a 3- to 5-membered monocyclic heterocyclic ring which is either saturated, unsaturated non-aromatic, or aromatic. A 3-membered heterocycle can contain up to 3 heteroatoms, and a 4- to 5-membered heterocycle can contain up to 4 heteroatoms. Each heteroatom is independently selected from nitrogen, which can be quaternized; oxygen; and sulfur, including sulfoxide and sulfone. The -(3- to 5-membered)heterocycle can be attached via a nitrogen or carbon atom. Representative -(3- to 5-membered)heterocycles include furyl, thiophenyl, pyrrolyl, oxazolyl, imidazolyl, thiazolyl, isoxazolyl, pyrazolyl, isothiazolyl, triazinyl, pyrrolidinonyl, pyrrolidinyl, hydantoinyl, oxiranyl, oxetanyl, tetrahydrofuranyl, tetrahydrothiophenyl and the like.

"-(7- to 10-membered)bicycloheterocycle" or "-(7- to 10-membered)bicycloheterocyclo" means a 7- to 10-membered bicyclic, heterocyclic ring which is either saturated, unsaturated non-aromatic, or aromatic. A -(7- to 10-membered)bicycloheterocycle contains from 1 to 4 heteroatoms independently selected from nitrogen, which can be quaternized; oxygen; and sulfur, including sulfoxide and sulfone. The -(7- to 10-membered)bicycloheterocycle can be attached via a nitrogen or carbon atom. Representative -(7- to 10-membered)bicycloheterocycles include -quinolinyl, -isoquinolinyl, -chromonyl, -coumarinyl, -indolyl, -indolizinyl, -benzo[b]furanyl, -benzo[b]thiophenyl, -indazolyl, -purinyl, -4H-quinolizinyl, -isoquinolyl, -quinolyl, -phthalazinyl, -naphthyridinyl, -carbazolyl, -β-carbolinyl and the like.

"—($C_{14}$)aryl" means a 14-membered aromatic carbocyclic moiety such as -anthryl or -phenanthryl.

"-(5- to 10-membered)heteroaryl" means an aromatic heterocycle ring of 5 to 10 members, including both mono- and bicyclic ring systems, wherein at least one carbon atom of one or both of the rings is replaced with a heteroatom independently selected from nitrogen, oxygen, and sulfur. One or both of the -(5- to 10-membered)heteroaryl's rings contain at least one carbon atom. Representative -(5- to 10-membered)heteroaryls include pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, thiadiazolyl, triazinyl, cinnolinyl, phthalazinyl, and quinazolinyl.

"—$CH_2$(halo)" means a methyl group wherein one of the hydrogens of the methyl group has been replaced with a halogen. Representative —$CH_2$(halo) groups include —$CH_2F$, —$CH_2Cl$, —$CH_2Br$, and —$CH_2I$.

"—CH(halo)$_2$" means a methyl group wherein two of the hydrogens of the methyl group have been replaced with a halogen. Representative —CH(halo)$_2$ groups include —$CHF_2$, —$CHCl_2$, —$CHBr_2$, CHBrCl, CHClI, and —$CHI_2$.

"—C(halo)$_3$" means a methyl group wherein each of the hydrogens of the methyl group has been replaced with a halogen. Representative —C(halo)$_3$ groups include —$CF_3$, —$CCl_3$, —$CBr_3$, and —$CI_3$.

"-Halogen" or "-Halo" means —F, —Cl, —Br, or —I.

The phrase "pyridyl group" means

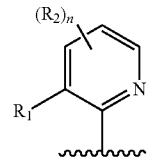

wherein $R_1$, $R_2$, and n are defined above for the Benzoazolylpiperazine Compounds of formula (Ia, IIa, and IIIa).

The phrase "pyrazinyl group" means,

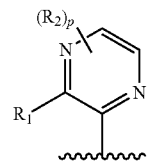

wherein $R_1$, $R_2$, and p are defined above for the Benzoazolylpiperazine Compounds of formula (Ib, IIa, and IIIb).

The phrase "pyrimidinyl group" means

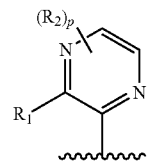

wherein $R_1$, $R_2$, and p are defined above for the Benzoazolylpiperazine Compounds of formula (Ia), (IIa), and (IIIa).

The phrase "pyridazinyl group" means

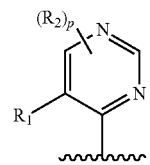

wherein $R_1$, $R_2$, and p are defined above for the Benzoazolylpiperazine Compounds of formula (Ib), (IIb), and (IIIb).

The phrase "thiazanyl group" means

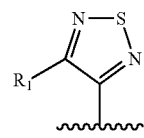

wherein $R_1$ is defined above for the Benzoazolylpiperazine Compounds of formula (Ib), (IIb), and (IIIb).

The phrase "2-(3-chloropyridyl)" means

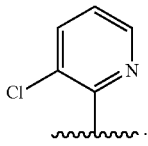

The phrase "2-(3-methylpyridyl)" means

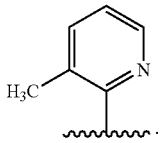 [SMILES: *c1ncccc1C(F)(F)F]

The phrase "2-(3-CF₃-pyridyl)" means

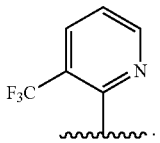

The phrase "2-(3-CHF₂-pyridyl)" means

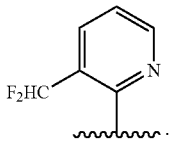 [SMILES: *c1ncccc1C(F)F]

The phrase "2-(3-hydroxypyridyl)" means

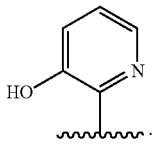

The phrase "2-(3-nitropyridyl)" means

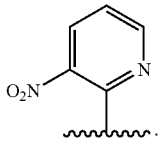

The phrase "2-(3-cyanopyridyl)" means

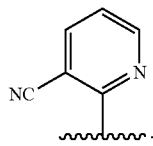

The phrase "2-(3-bromopyridyl)" means

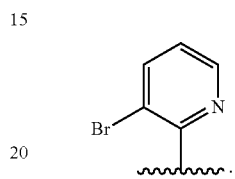

The phrase "2-(3-iodopyridyl)" means

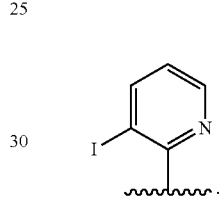

The phrase "4-(5-chloropyrimidinyl)" means

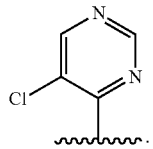

The phrase "4-(5-methylpyrimidinyl)" means

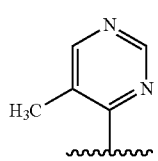

The phrase "4-(5-fluoropyrimidinyl)" means

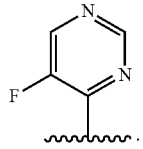

The phrase "2-(3-chloropyrazinyl)" means

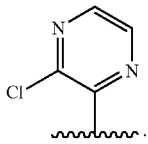

The phrase "2-(3-methylpyrazinyl)" means

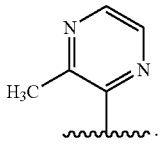

The phrase "2-(3-fluoropyrazinyl)" means

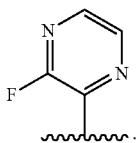

The phrase "3-(4-chloropyridazinyl)" means

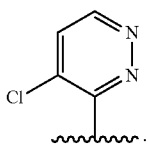

The phrase "3-(4-methylpyridazinyl)" means

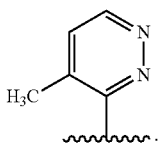

The phrase "3-(4-fluoropyridazinyl)" means

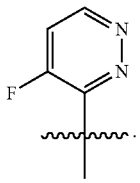

The phrase "5-(4-chlorothiazanyl)" means

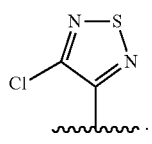 [SMILES: *c1nsnc1Cl]

The phrase "5-(4-methylthiazanyl)" means

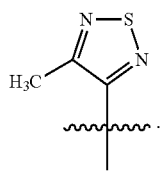

The phrase "2-pyrazinyl" means

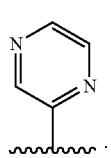

The phrase "2-pyridazinyl" means

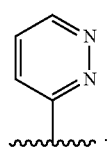

The phrase "4-thiazanyl" means

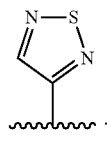

The phrase "5-(4-fluorothiazanyl)" means

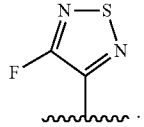

The phrase "benzoimidiazolyl group" means

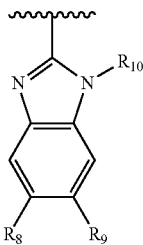

wherein $R_8$, $R_9$ and $R_{10}$ are defined above for the Benzoazolylpiperazine Compounds of formula (IIa) and (IIb).

The phrase "benzothiazolyl group" means

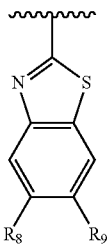

wherein $R_8$ and $R_9$ are defined above for the Benzoazolylpiperazine Compounds of formula (Ia) and (Ib).

The phrase "benzooxazolyl group" means

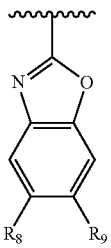

wherein $R_8$ and $R_9$ are defined above for the Benzoazolylpiperazine Compounds of formula (IIIa) and (IIIb).

The term "animal," includes, but is not limited to, a cow, monkey, baboon, chimpanzee, horse, sheep, pig, chicken, turkey, quail, cat, dog, mouse, rat, rabbit, guinea pig, and human.

The phrase "pharmaceutically acceptable salt," as used herein, includes a salt formed from an acid and a basic nitrogen group of one of the Benzoazolylpiperazine Compounds. Illustrative salts include, but are not limited, to sulfate, citrate, acetate, oxalate, chloride, bromide, iodide, nitrate, bisulfate, phosphate, acid phosphate, isonicotinate, lactate, salkylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also includes a salt prepared from a Benzoazolylpiperazine Compound having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; and amino acids such as arginine, lysine and the like.

The phrase "effective amount," when used in connection with a Benzoazolylpiperazine Compound means an amount effective for: (a) treating or preventing pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression; or (b) inhibiting VR1, mGluR1, or mGluR5 function in a cell.

The phrase "effective amount," when used in connection with the another therapeutic agent means an amount for providing the therapeutic effect of the therapeutic agent.

When a first group is "substituted with one or more" second groups, one or more hydrogen atoms of the first group is replaced with a corresponding number of second groups. When the number of second groups is two or greater, each second group can be the same or different. In one embodiment, the number of second groups is one or two. In another embodiment, the number of second groups is one.

The term "DMSO" means dimethyl sulfoxide.

The term "DCM" means dichloromethane.

The term "UI" means urinary incontinence.

The term "IBD" means inflammatory-bowel disease.

The term "IBS" means irritable-bowel syndrome.

The term "ALS" means amyotrophic lateral sclerosis.

The phrase "treatment of" and "treating" includes the amelioration or cessation of pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression, or a symptom thereof.

The phrase "prevention of" and "preventing" includes the avoidance of the onset of pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression, or a symptom thereof.

4.2 Methods for Making the Benzoazolylpiperazine Compounds

The Benzoazolylpiperazine Compounds can be made using conventional organic synthesis or by the following illustrative methods shown in the schemes below.

4.2.1 Methods for Making the Benzoazolylpiperazine Compounds of Formula (IA) and (IB) wherein x is 1 and A is —C(O)—NR₄

The Benzoazolylpiperazine Compounds of formula (Ia) and (Ib) wherein x is 1, A is —C(O)—NR₄—, and R₄ is —H, can be obtained by the following illustrative method shown in Scheme A:

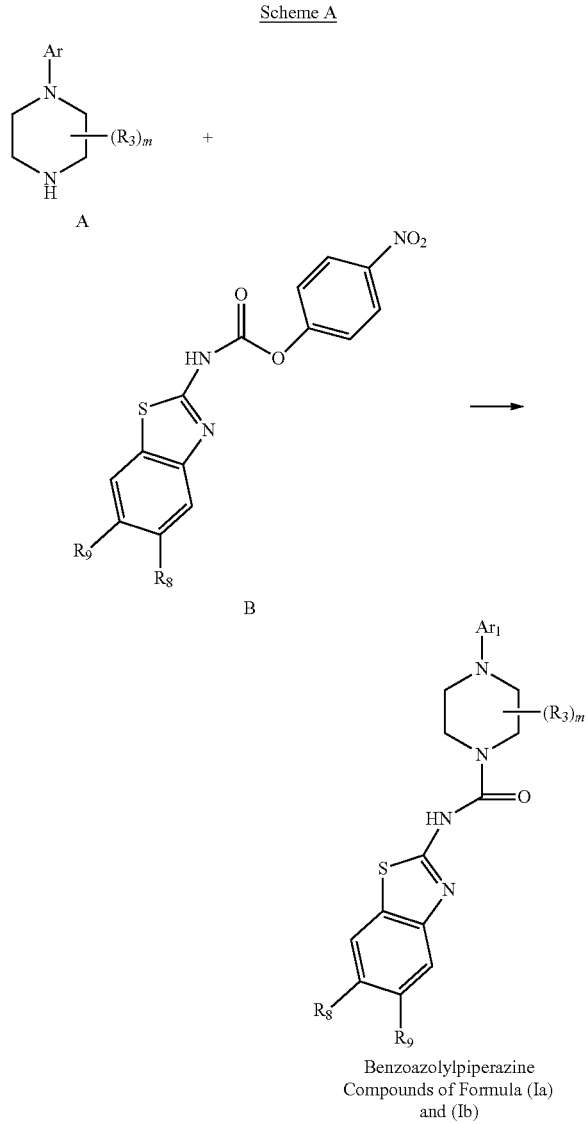

wherein $Ar_1$, $R_3$, $R_8$, $R_9$ and m are defined above for the Benzoazolylpiperazine Compounds of formula (Ia) and (Ib).

A compound of formula B (about 2 mmol) is dissolved in an aprotic organic solvent (about 3 mL). To the resulting solution is added a compound of formula A (about 2 mmol) and the resulting reaction mixture allowed to stir for about 10 min. The solvent is then removed under reduced pressure to provide the Benzoazolylpiperazine Compound of formula (Ia) or (Ib) wherein x is 1, A is —C(O)—NR₄—, and R₄ is —H. The Benzoazolylpiperazine Compounds of formula (Ia) and (Ib) can be purified on a silica column eluted with 5:95 ethyl acetate/hexane.

The compound of formula B can be obtained as shown below in Scheme B:

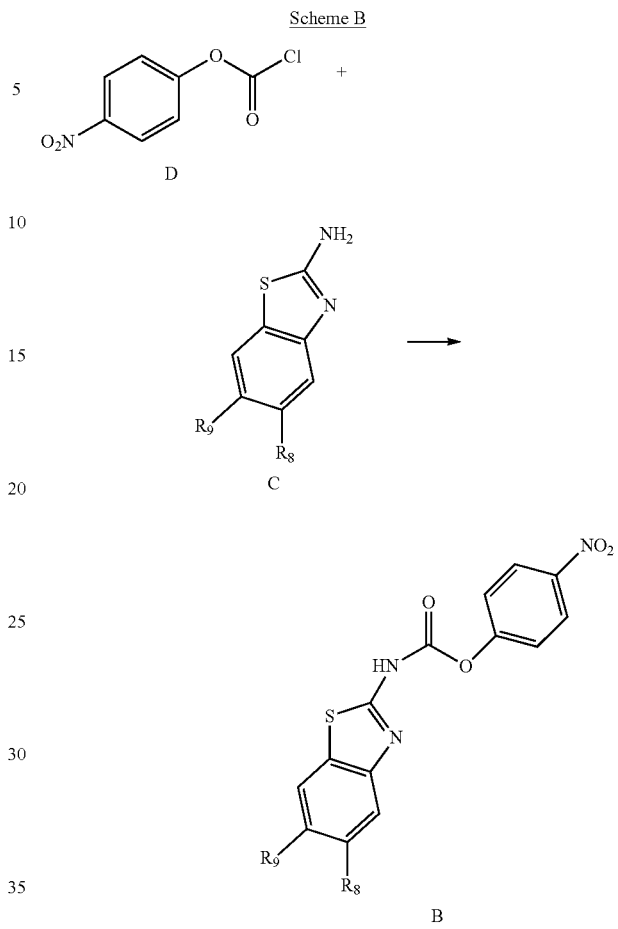

wherein $R_8$ and $R_9$ are defined above for the Benzoazolylpiperazine Compounds of formula (Ia) and (Ib).

A compound of formula D (about 0.75 eq.) in an aprotic organic solvent (about 0.04 M) is cooled to about 0° C. To the cooled solution is slowly added a solution of a compound of formula C (about 0.75 eq.) in an aprotic organic solvent (about 0.4 M). The resulting reaction mixture is stirred at 0° C. for about 5 min. and about 0.75 eq. of triethylamine are added to the reaction mixture. The reaction mixture is then allowed to warm to room temperature and the solvent is then removed under reduced pressure to provide the compound of formula B. The compound of formula D is commercially available from Sigma-Aldrich, St. Louis, Mo. (www.sigma-aldrich.com). Compounds of formula C are commercially available or can be prepared by the following illustrative method shown below in Scheme C.

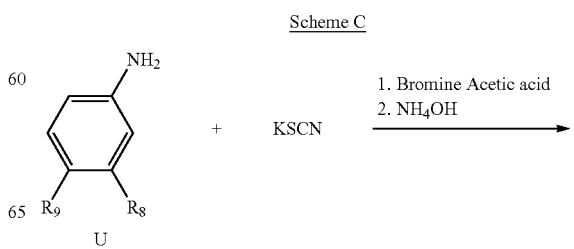

-continued

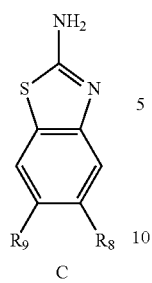

C wherein $R_8$ and $R_9$ are defined above for the Benzoazolylpiperazine Compounds of formula (Ia) and (Ib).

To a stirred solution of aniline U (about 74 mmol) and potassium thiocyanate (about 148 mmol) in about 100 mL of glacial acetic acid is added dropwise a solution of bromine (about 74 mmol) in about 25 mL of glacial acetic acid. The flask containing the bromine in acetic acid is then rinsed with about 15 mL of acetic acid which is combined with the solution of aniline U. The resulting reaction mixture is vigorously stirred at room temperature for between about 2 h and about 24 h. The reaction mixture is then poured over crushed ice (about 500 mL) and the pH of the resulting mixture adjusted to a value of about 10 using ammonium hydroxide to provide a precipitate. The resulting precipitate is collected by filtration and recrystallized from toluene to provide the compound of formula C. Compounds of formula U are commercially available or can be prepared by methods well known to those skilled in the art.

The compound of formula A can be obtained as shown below in Scheme D:

Scheme D

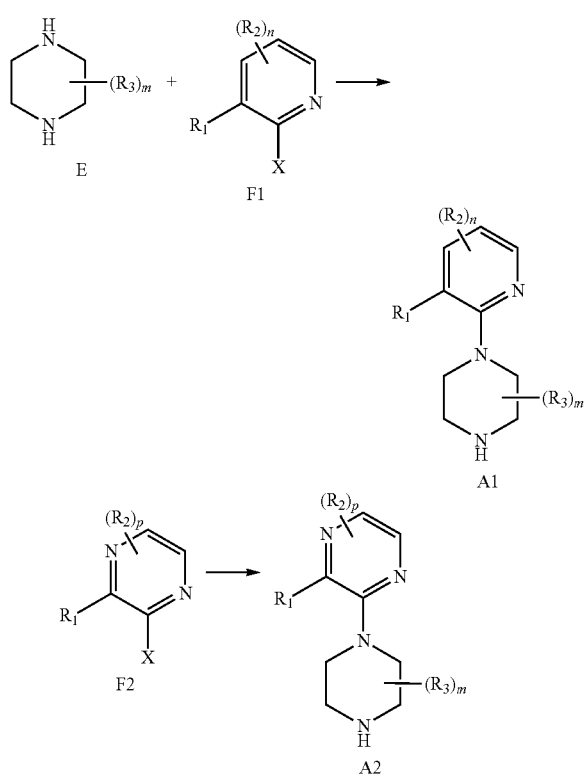

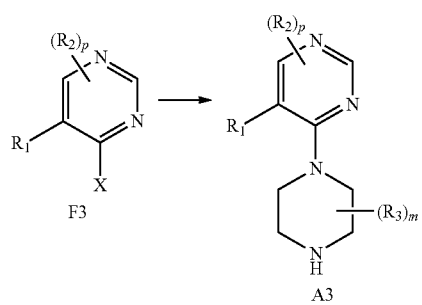

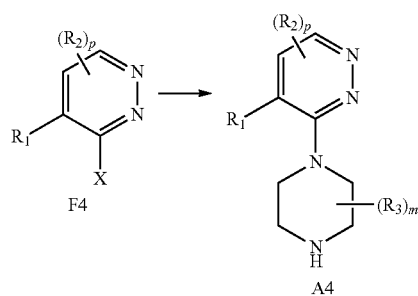

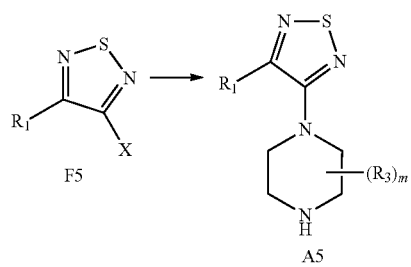

wherein $R_1$, $R_2$, $R_3$, m, n, and p are defined above for the Benzoazolylpiperazine Compounds of formula (Ia) and (Ib) and X is a halogen.

A compound of formula F1-F5 (about 20 mmol) is reacted with a compound of formula E (about 27.5 mmol) in about 15 mL of DMSO in the presence of triethylamine (about 30 mmol), optionally with heating, for about 24 h to provide a compound of formula A. The compound of formula A is isolated from the reaction mixture and purified. In one embodiment, the compound of formula A is purified using column chromatography or recrystallization.

Compounds of formula E and F are commercially available or can be prepared by methods well known to those skilled in the art. The compound of formula E wherein m is 0 and the compound of formula E wherein m is 1 and $R_3$ is (R) —$CH_3$ or (S) —$CH_3$ are commercially available from Sigma-Aldrich, St. Louis, Mo. (www.sigma-aldrich.com). In one embodiment, X is bromide, chloride, or iodide.

The Benzoazolylpiperazine Compounds of formula (Ia) and (Ib) wherein x is 1, A is —C(O)—$NR_4$—, and $R_4$ is —($C_1$-$C_6$)alkyl can be obtained by the following illustrative method shown below in Scheme E.

Scheme E

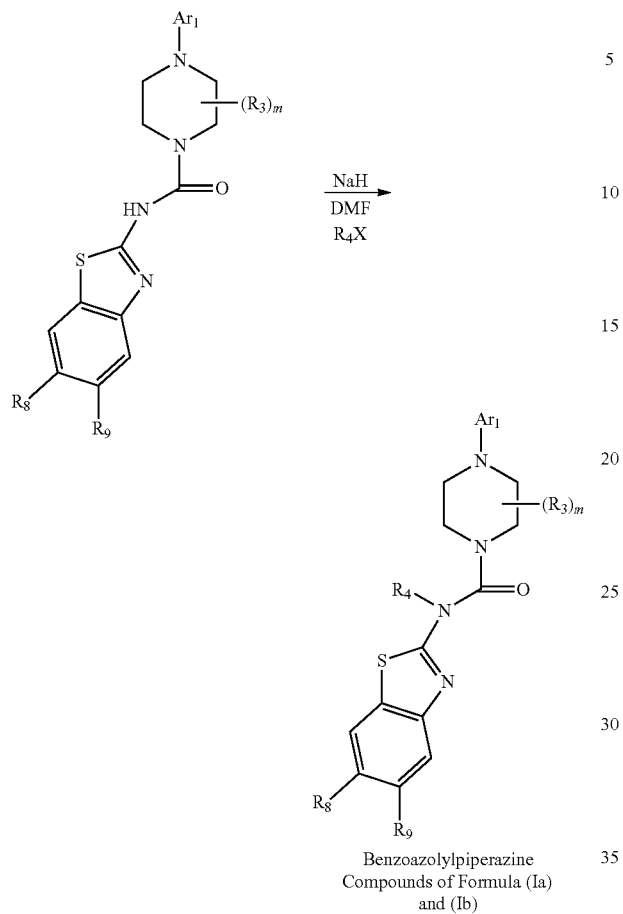

Benzoazolylpiperazine
Compounds of Formula (Ia)
and (Ib)

wherein $Ar_1$, $R_3$, $R_4$, $R_8$, $R_9$, and m are defined above for the Benzoazolylpiperazine Compounds of formula (Ia) and (Ib) and X is a halogen.

To a solution of a Benzoazolylpiperazine compound of formula (Ia) or (Ib) wherein x is 1, A is —C(O)—$NR_4$—, and $R_4$ is —H (about 1 eq.), obtained as described above in Scheme A, in DMF at 0° C., is added a DMF solution of NaH (about 2 eq.). The resulting reaction mixture is allowed to warm to room temperature over about 1 h. To the resulting mixture is added about 1.2 eq. of an alkyl halide, $R_4X$, and the resulting reaction mixture allowed to stir until the Benzoazolylpiperazine Compounds of formula (Ia) and (Ib) wherein x is 1, A is —C(O)—$NR_4$—, and $R_4$ is —($C_1$-$C_6$)alkyl is formed. The progress of the reaction can be monitored using conventional analytical techniques including, but not limited to, high pressure liquid chromatography (HPLC), column chromatography, thin-layer chromatography (TLC), column chromatography, gas chromatography, mass spectrometry, and nuclear magnetic resonance spectroscopy such as $^1$H and $^{13}$C NMR. The Benzoazolylpiperazine Compounds of formula (Ia) and (Ib) wherein x is 1, A is —C(O)—$NR_4$—, and $R_4$ is —($C_1$-$C_6$)alkyl is then isolated and purified. In one embodiment, the Benzoazolylpiperazine Compounds of formula (Ia) and (Ib) wherein x is 1, A is —C(O)—$NR_4$—, and $R_4$ is —($C_1$-$C_6$)alkyl is isolated by removing the solvent under reduced pressure. In another embodiment, the Benzoazolylpiperazine Compounds of formula (Ia) and (Ib) wherein x is 1, A is —C(O)—$NR_4$—, and $R_4$ is —($C_1$-$C_6$)alkyl is isolated by extraction. The Benzoazolylpiperazine Compounds of formula (Ia) and (Ib) wherein x is 1, A is —C(O)—$NR_4$—, and $R_4$ is —($C_1$-$C_6$)alkyl can be purified, for example, by column chromatography or recrystallization.

4.2.2 Methods for Making the Benzoazolylpiperazine Compounds of Formula (Ia) and (Ib) wherein x is 1 and A is —C(S)—$NR_4$ The Benzoazolylpiperazine Compounds of formula (Ia) and (Ib) wherein x is 1, A is —C(S)—$NR_4$—, and $R_4$ is —H can be obtained by the following illustrative method in Scheme F:

Scheme F

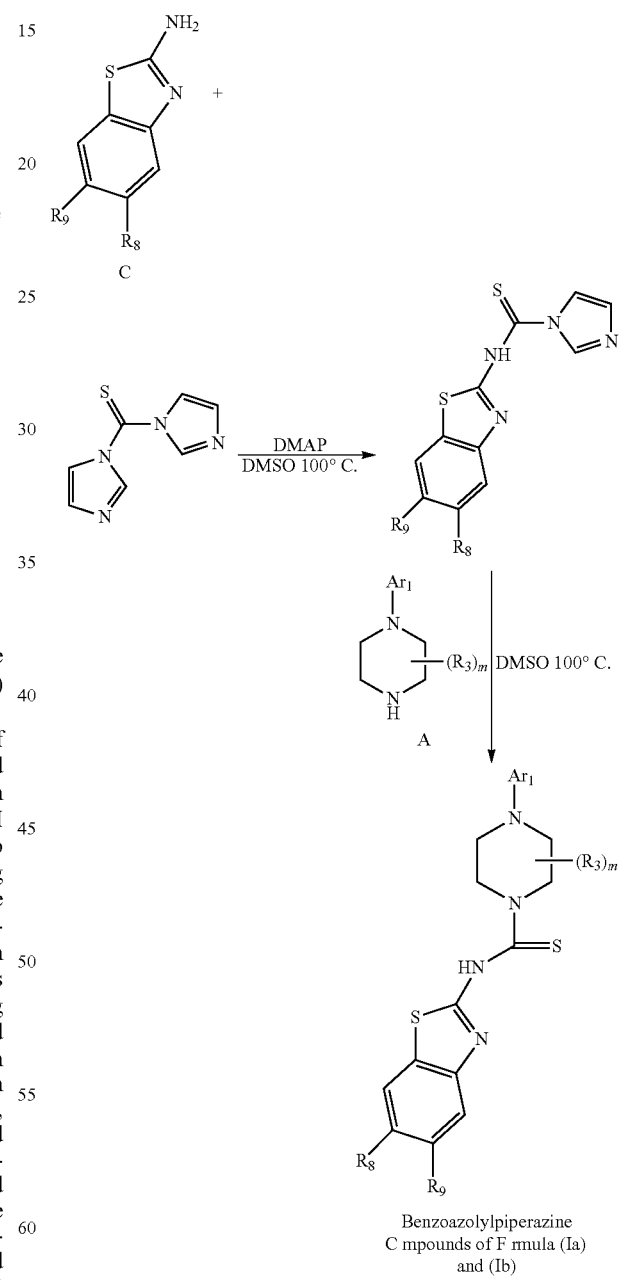

Benzoazolylpiperazine
Compounds of Formula (Ia)
and (Ib)

wherein $Ar_1$, $R_3$, $R_8$, $R_9$ and m are defined above for the Benzoazolylpiperazine Compounds of formula (Ia) and (Ib).

A Compound of Formula C (about 2 mmol), 1,1'-thiocarbonyldiimidazole (about 2 mmol) (commercially available from Sigma-Aldrich, St. Louis, Mo. (www.sigma-aldrich.com)), and 4-dimethylaminopyridine (DMAP) (commercially available from Sigma-Aldrich, St. Louis, Mo. (www.sigma-aldrich.com)) are suspended in DMSO (about 3 mL) at room temperature and the resulting mixture is heated at about 100° C. for about 6 h. The resulting reaction mixture is then cooled to room temperature and a compound of Formula A (about 2 mmol) is added to the reaction mixture and the reaction mixture is heated to about 100° C. for about 16 h. The solvent is then removed under reduced pressure to provide the Benzoazolylpiperazine Compound of formula (Ia) or (Ib) wherein x is 1, A is —C(S)—NR$_4$—, and R$_4$ is —H. The Benzoazolylpiperazine Compounds of formula (Ia) and (Ib) can be purified on a silica column eluted with 5:95 ethyl acetate/hexane.

The Benzoazolylpiperazine Compounds of formula (Ia) and (Ib) wherein x is 1, A is —C(S)—NR$_4$—, and R$_4$ is —(C$_1$-C$_6$)alkyl can be obtained by a method analogous to the method used to obtain the Benzoazolylpiperazine Compounds of formula (Ia) and (Ib) wherein x is 1, A is —C(O)—NR$_4$—, and R$_4$ is —(C$_1$-C$_6$)alkyl as described in Scheme E except that a Benzoazolylpiperazine Compound of formula (Ia) and (Ib) wherein x is 1, A is —C(S)—NR$_4$—, and R$_4$ is —H, obtained as described above in Scheme F, is used in place of the Benzoazolylpiperazine Compounds of formula (Ia) and (Ib) wherein x is 1, A is —C(O)—NR$_4$—, and R$_4$ is —H.

4.2.3 Methods for Making the Benzoazolylpiperazine Compounds of Formula (IA) and (IB) wherein x is 0

The Benzoazolylpiperazine Compounds of formula (Ia) and (Ib) wherein x is 0 can be obtained by the following illustrative method shown below in Scheme G:

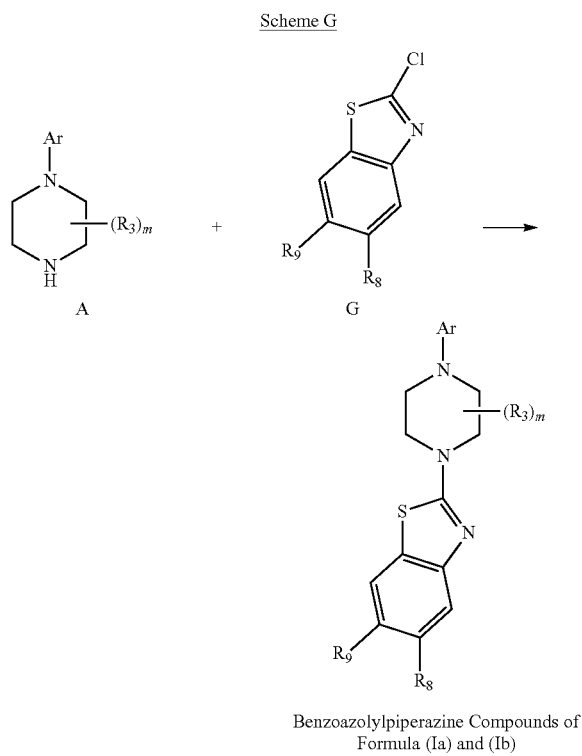

Benzoazolylpiperazine Compounds of Formula (Ia) and (Ib)

wherein Ar$_1$, R$_3$, R$_8$, R$_9$, and m are defined above for the Benzoazolylpiperazine Compounds of formula (Ia) and (Ib).

A compound of Formula A (about 1 mmol) and a compound of Formula G (about 1 mmol) are dissolved in DMSO (about 3 mL) and heated at a temperature of between about 140° C. and 150° C. for about 12 h. The mixture is cooled to room temperature and the solvent removed under reduced pressure to provide a residue that is purified using silica gel flash chromatography (gradient elution from 2:98 methanol:DCM to 6:94 methanol:DCM) to provide the Benzoazolylpiperazine Compound of formula (Ia) or (Ib) wherein x is 0.

The compound of Formula A can be obtained as shown above in Scheme D.

The compounds of Formula G are commercially available or can be prepared by procedures well known to those skilled in the art. An illustrative method for preparing compounds of Formula G is shown below in Scheme H.

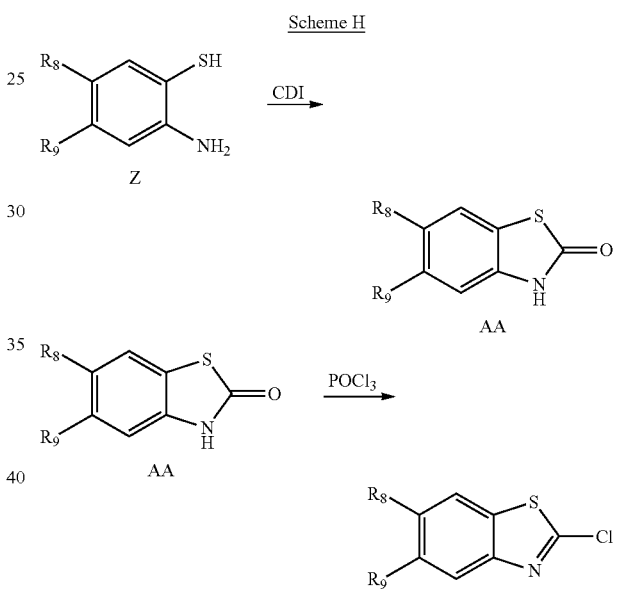

wherein R$_8$ and R$_9$ are defined above for the Benzoazolylpiperazine Compounds of formula (Ia) and (Ib).

A compound of Formula Z (about 5 to about 10 mmol) and carbodiimidazole (CDI) (commercially available from Sigma-Aldrich, St. Louis, Mo. (www.sigma-aldrich.com)) (about 2 eq) is dissolved in THF (about 50 to about 70 mL) and the resulting reaction mixture is heated at reflux temperature for about 4 hours. The reaction mixture is then concentrated under reduced pressure to provide a residue. Ethyl acetate (about 50 mL) is added to the residue and the resulting insoluble material is collected by filtration and washed with ethyl acetate to provide a compound of Formula AA. The compound of Formula AA is then reacted with POCl$_3$ according to the procedure described in *J. Med. Chem.* 40:586-593 (1997) to provide the compound of Formula BB. The compounds of Formula Z are commercially available or can be prepared by procedures well known to those skilled in the art. An illustrative procedure for obtaining a compound of Formula Z is shown below in Scheme I:

Scheme I

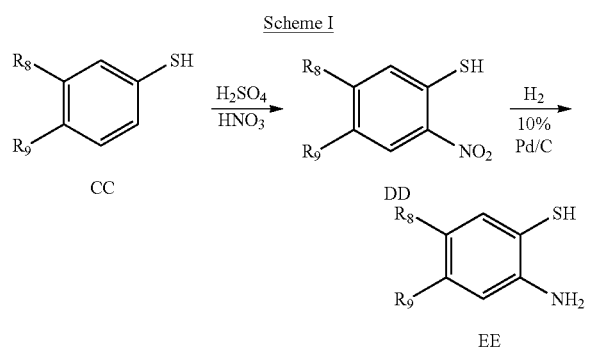

wherein $R_8$ and $R_9$ are defined above for the Benzoazolylpiperazine Compounds of formula (Ia) and (Ib).

Thiol CC (about 12 mmol) is dissolved in concentrated sulfuric acid (about 10 mL) at 0° C. and the resulting solution cooled to a temperature of about −13° C. to about −15° C. About 1 mL of 70% nitric acid is added to the resulting solution over a time period of about 30 min. and the resulting reaction mixture allowed to stir for about 2 h at a temperature of between about −13° C. to about −15° C. The reaction mixture is then poured into ice water (about 100 mL), neutralized with 5% to 10% aqueous sodium hydroxide, and extracted with about 50 mL of chloroform. The chloroform layer is separated from the aqueous layer and removed under reduced pressure to provide a residue that is purified using flash chromatography (silica column and chloroform eluant) to provide a compound of Formula DD. The compound of Formula DD is dissolved in ethanol (about 50 mL) and hydrogenated for about 12 h at room temperature using 10% palladium on carbon as a catalyst. The catalyst is removed by filtration and the ethanol is removed under reduced pressure to provide a residue that is purified using flash chromatography (silica gel eluted with 20:1 dichloromethane:methanol) to provide the compound of Formula EE. The compounds of Formula CC are commercially available or can be prepared by procedures well known to those skilled in the art.

4.2.4 Methods for Making the Benzoazolylpiperazine Compounds of Formula (IIa) and (IIb) wherein x is 0

The Benzoazolylpiperazine Compounds of formula (IIa) wherein $R_{10}$ is —H and formula (IIb) wherein x is 0 and $R_{10}$ is —H can be obtained by a method analogous to that used to obtain the Benzoazolylpiperazine Compounds of formula (Ia) and (Ib) wherein x is 0 as described above in section 4.2.3, Scheme G except that a compound of Formula H, shown below,

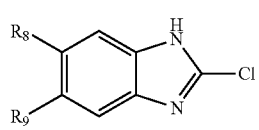

H wherein $R_8$ and $R_9$ are defined above for the Benzoazolylpiperazine Compounds of formula (IIa) and (IIb), is used in place of the compound of Formula G as illustrated below in Scheme J:

Scheme J

[Reaction scheme showing compound A (piperazine with $Ar_1$ and $(R_3)_m$) plus compound H (2-chloro-benzimidazole with $R_8$, $R_9$) giving Benzoazolylpiperazine Compounds of Formula (IIa) or (IIb)]

wherein $Ar_1$, $R_3$, $R_8$, $R_9$, and m are defined above for the Benzoazolylpiperazine Compounds of formula (IIa) and (IIb).

A compound of Formula A (about 1 mmol) and a compound of Formula H (about 1 mmol) are dissolved in toluene or p-xylene in a sealed tube and heated at a temperature of between about 140° C. and 150° C. for about 3 days. The mixture is cooled to room temperature and the solvent removed under reduced pressure to provide a residue that is purified using flash chromatography (silica gel with a gradient elution from 2% methanol:dichloromethane to 6% methanol:dichloromethane) to provide the Benzoazolylpiperazine Compound of formula (IIa) and formula (IIb) wherein x is 0.

The compound of Formula A can be obtained as shown above in Scheme D.

The compounds of Formula H are commercially available or can be prepared by procedures well known to those skilled in the art. An illustrative method for preparing the compound of Formula H is shown below in Scheme K:

Scheme K

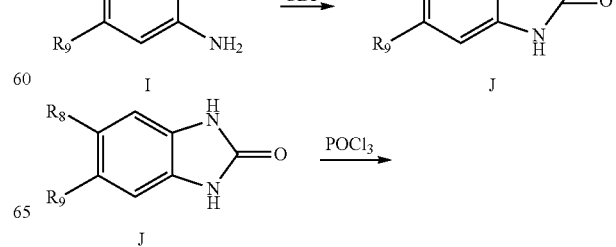

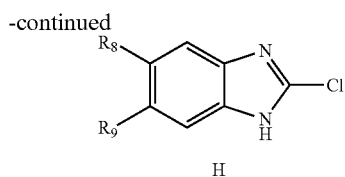

wherein $R_8$ and $R_9$ are defined above for the Benzoazolylpiperazine Compounds of formula (IIa) and (IIb).

A compound of Formula I (about 5 to about 10 mmol) and carbodiimidazole (CDI) (commercially available from Sigma-Aldrich, St. Louis, Mo. (www.sigma-aldrich.com)) (about 2 eq) is dissolved in THF (about 50 to about 70 mL) and the resulting reaction mixture is heated at reflux temperature for about 4 hours. The reaction mixture is then concentrated under reduced pressure to provide a residue. Ethyl acetate (about 50 mL) is added to the residue and the resulting insoluble material is collected by filtration and washed with ethyl acetate to provide a compound of Formula J. The compound of Formula J is then reacted with $POCl_3$ according to the procedure described in *J. Med. Chem.* 40:586-593 (1997) to provide the compound of Formula H. The compounds of Formula I are commercially available or can be prepared by procedures well known to those skilled in the art. An illustrative procedure for obtaining a compound of Formula I is shown below in Scheme L:

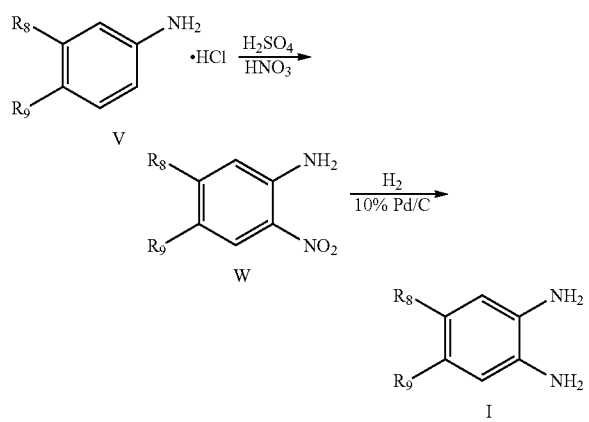

wherein $R_8$ and $R_9$ are defined above for the Benzoazolylpiperazine Compounds of formula (IIa) and (IIb).

Aniline hydrochloride V (about 12 mmol) is dissolved in concentrated sulfuric acid (about 10 mL) at 0° C. and the resulting solution cooled to a temperature of about −13° C. to about −15° C. About 1 mL of 70% nitric acid is added to the resulting solution over a time period of about 30 min. and the resulting reaction mixture allowed to stir for about 2 h at a temperature of between about −13° C. to about −15° C. The reaction mixture is then poured into ice water (about 100 mL), neutralized with 5% to 10% aqueous sodium hydroxide and extracted with about 50 mL of chloroform. The chloroform is separated from the aqueous layer and removed under reduced pressure to provide a residue that is purified using flash chromatography (silica column and chloroform eluant) to provide a compound of Formula W. The compound of Formula W is dissolved in ethanol (about 50 mL) and hydrogenated for about 12 h at room temperature using 10% palladium on carbon as a catalyst. The catalyst is removed by filtration and the ethanol is removed under reduced pressure to provide a residue that is purified using flash chromatography (silica gel eluted with 20:1 dichloromethane:methanol) to provide the compound of Formula I. The compounds of Formula V are commercially available or can be prepared by procedures well known to those skilled in the art.

The Benzoazolylpiperazine Compounds of formula (IIa) wherein $R_{10}$ is —$(C_1$-$C_4)$alkyl and formula (IIb) wherein x is 0 and $R_{10}$ is —$(C_1$-$C_4)$alkyl can be obtained by a method analogous to that used to obtain the Benzoazolylpiperazine Compounds of formula (IIa) and (IIb) wherein x is 0 and $R_{10}$ is —H, as described above in Scheme J, except that a compound of Formula K, shown below

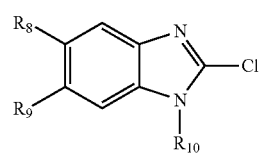

K wherein $R_8$ and $R_9$ are defined above for the Benzoazolylpiperazine Compounds of formula (IIa) and (IIb) and $R_{10}$ is a —$(C_1$-$C_6)$alkyl is used in place of the compound of Formula H. The compound of Formula K can be obtained as described below in Scheme M

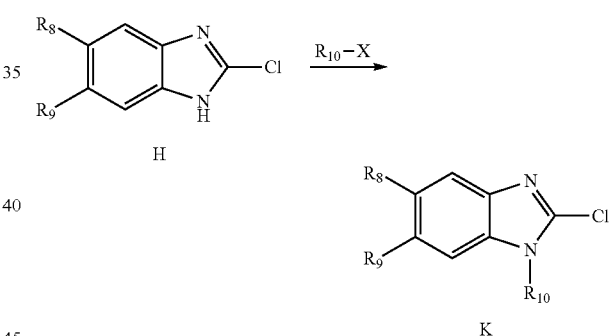

wherein $R_8$ and $R_9$ are defined above for the Benzoazolylpiperazine Compounds of formula (IIa) and (IIb), $R_{10}$ is a —$(C_1$-$C_6)$alkyl, and X is a halogen.

NaH (about 2 eq) is added to a solution of a compound of Formula H in DMF at 0° C. and the resulting mixture is allowed to stir and to warm to room temperature over a period of about one hour. An alkyl halide, $R_{10}$—X, (about 1.2 eq) is then added to the solution and the resulting reaction mixture allowed to stir until the compound of Formula K is produced. In one embodiment, the alkyl halide is an alkyl iodide. The formation of the compound of Formula K can be monitored by analytical methods well known to those skilled in the art including, but not limited to, liquid chromatography, column chromatography, gas chromatography, thin-layer chromatography, mass spectrometry, and nuclear magnetic resonance spectroscopy such as $^1H$ and $^{13}C$ NMR. Water is then added to the reaction mixture to produce a precipitate of the compound of Formula K which is filtered, collected, and dried.

The compound of Formula H can be obtained as described above in Scheme K.

4.2.5 Methods for Making the Benzoazolylpiperazine Compounds of Formula (IIb) wherein x is 1 and A is —C(O)—NR₄

The Benzoazolylpiperazine Compounds of formula (IIb) wherein x is 1, A is —C(O)—NR₄—, R₄ is —H, and R₁₀ is —H can be obtained by a method analogous to that used to obtain the Benzoazolylpiperazine Compounds of formula (Ia) and (Ib) wherein x is 1, A is —C(O)—NR₄—, and R₄ is —H as described above in Scheme A except that a compound of Formula L, shown below,

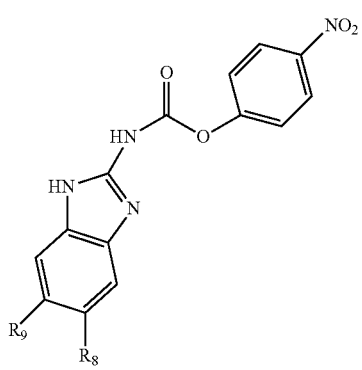

L wherein $R_8$ and $R_9$ are defined above for the Benzoazolylpiperazine Compounds of formula (IIb), is used in place of the compound of Formula B.

The Compound of Formula L can be obtained by a method analogous to that used to obtain the compound of Formula B as described in section 4.2.1, Scheme B, except that a compound of Formula M, shown below,

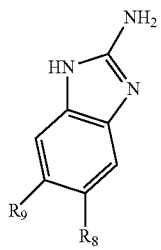

M wherein $R_8$ and $R_9$ are defined above for the Benzoazolylpiperazine Compounds of formula (IIb), is used in place of the compound of Formula C. Compounds of Formula M are commercially available or can be prepared by procedures well known to those skilled in the art. An illustrative procedure for obtaining a compound of Formula M is shown below in Scheme N:

Scheme N

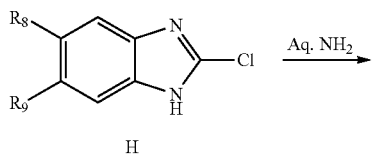

M wherein $R_8$ and $R_9$ are defined above for the Benzoazolylpiperazine Compounds of formula (IIb).

A compound of Formula H (about 1 mmol), prepared as described above in Scheme K, is dissolved in excess aqueous ammonia in a sealed tube and heated at a temperature of between about 140° C. and 150° C. for about 3 days. The mixture is cooled to room temperature and the solvent removed under reduced pressure to provide a residue. In another embodiment, the mixture is cooled to room temperature, extracted with an organic solvent, the organic phase separated from the aqueous phase, and the organic solvent removed under reduced pressure to provide a residue. The residue is then purified to provide the compound of Formula M. In one embodiment, the residue is purified by recrystallization. In another embodiment, the residue is purified using flash chromatography.

The Benzoazolylpiperazine Compounds of formula (IIb) wherein x is 1, A is —C(O)—NR₄—, R₄ is —H, and R₁₀ is —(C₁-C₄)alkyl can be obtained by a method analogous to that used to obtain the Benzoazolylpiperazine Compounds of formula (IIb) wherein x is 1, A is —C(O)—NR₄—, R₄ is —H, and R₁₀ is —H except that a compound of Formula N, shown below,

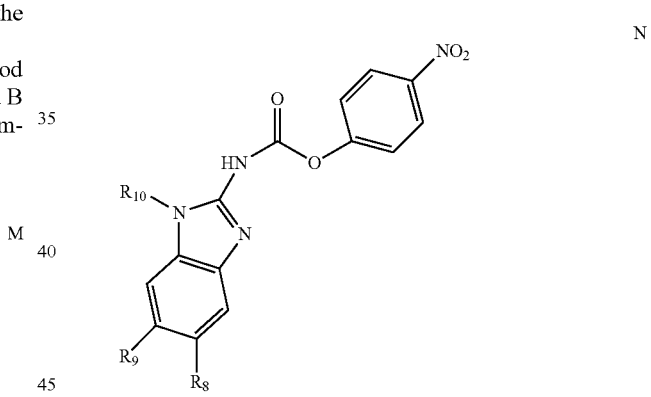

N wherein $R_8$, $R_9$, and $R_{10}$ are defined above for the Benzoazolylpiperazine Compounds of formula (IIb), is used in place of the Compound of Formula L. The compound of Formula N can be obtained by a method analogous to that used to obtain the compound of Formula L except that a compound of Formula O, shown below,

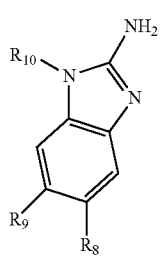

O wherein $R_8$, $R_9$, and $R_{10}$ are defined above for the Benzoazolylpiperazine Compounds of formula (IIb), is used in place of the compound of Formula M. The compound of Formula O can be obtained as shown below in Scheme N:

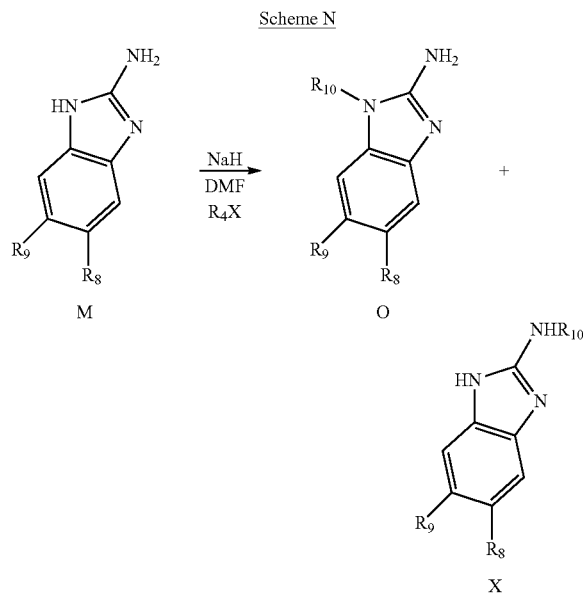

wherein $R_8$, $R_9$, and $R_{10}$ are defined above for the Benzoazolylpiperazine Compounds of formula (IIb).

NaH (about 2 eq) is added to a solution of a compound of Formula M in DMF at 0° C. and the resulting mixture is allowed to stir and to warm to room temperature over a period of about one hour. An alkyl halide, $R_{10}$—X, (about 1 eq.) is then added to the solution and the resulting reaction mixture allowed to stir until a mixture of a compound of Formula O and a compound of Formula X is produced. In one embodiment, the alkyl halide is an alkyl iodide. The formation of the compound of Formula O and the compound of Formula X can be monitored by analytical methods well known to those skilled in the art including, but not limited to, those described above. Water is then added to the reaction mixture to produce a precipitate of the compound of Formula O and the compound of Formula X which are collected by filtration. The compound of Formula O and the compound of Formula X are then separated to provide the compound of Formula O. The compound of Formula O and the compound of Formula X can be separated by analytical methods well known to those skilled in the art including, but not limited to, column chromatography, preparative TLC, preparative HPLC, and preparative GC.

The Benzoazolylpiperazine Compounds of formula (IIb) wherein x is 1, A is —C(O)—$NR_4$—, $R_4$ is —($C_1$-$C_6$)alkyl, and $R_{10}$ is —H can be obtained by a method analogous to that used to obtain the Benzoazolylpiperazine Compounds of formula (Ia) and (Ib) wherein x is 1, A is —C(O)—$NR_4$—, and $R_4$ is —($C_1$-$C_6$)alkyl as shown above in Scheme E except that the Benzoazolylpiperazine Compounds of formula (IIb) wherein x is 1, A is —C(O)—$NR_4$—, $R_4$ is —H, and $R_{10}$ is —H, prepared as described above, is used in place of the Benzoazolylpiperazine compound of formula (Ia) or (Ib) wherein x is 1, A is —C(O)—$NR_4$—, and $R_4$ is —H.

The Benzoazolylpiperazine Compounds of formula (IIb) wherein x is 1, A is —C(O)—$NR_4$—, $R_4$ is —($C_1$-$C_6$)alkyl, and $R_{10}$ is —($C_1$-$C_4$)alkyl can be obtained by a method analogous to that used to obtain the Benzoazolylpiperazine Compounds of formula (Ia) and (Ib) wherein x is 1, A is —C(O)—$NR_4$—, and $R_4$ is —($C_1$-$C_6$)alkyl as shown above in Scheme E except that the Benzoazolylpiperazine Compounds of formula (IIb) wherein x is 1, A is —C(O)—$NR_4$—, $R_4$ is —H, and $R_{10}$ is —($C_1$-$C_6$)alkyl, prepared as described above, is used in place of the Benzoazolylpiperazine compound of formula (Ia) or (Ib) wherein x is 1, A is —C(O)—$NR_4$—, and $R_4$ is —H.

4.2.6 Methods for Making the Benzoazolylpiperazine Compounds of Formula (IIb) wherein X is 1 and A is —C(S)—$NR_4$—

The Benzoazolylpiperazine Compounds of formula (IIb) wherein x is 1, A is —C(S)—$NR_4$—, $R_4$ is —H, and $R_{10}$ is —H can be obtained by a method analogous to that used to obtain the Benzoazolylpiperazine Compounds of formula (Ia) and (Ib) wherein x is 1 and A is —C(S)—$NR_4$—, and $R_4$ is —H as described above in Scheme F except that a compound of Formula M is used in place of the compound of Formula C. The compound of Formula M can be obtained as described above.

The Benzoazolylpiperazine Compounds of formula (IIb) wherein x is 1, A is —C(S)—$NR_4$—, $R_4$ is —H, and $R_{10}$ is —($C_1$-$C_4$)alkyl can be obtained by a method analogous to that used to obtain the Benzoazolylpiperazine Compounds of formula (Ia) and (Ib) wherein x is 1, A is —C(S)—$NR_4$—, and $R_4$ is —H, as described in section 4.2.2, Scheme F, except that a compound of Formula O is used in place of the compound of Formula C. The compound of Formula O can be obtained as described above.

The Benzoazolylpiperazine Compounds of formula (IIb) wherein x is 1, A is —C(S)—$NR_4$—, $R_4$ is —($C_1$-$C_6$)alkyl, and $R_{10}$ is —H can be obtained by a method analogous to that used to obtain the Benzoazolylpiperazine Compounds of formula (Ia) and (Ib) wherein x is 1, A is —C(O)—$NR_4$—, and $R_4$ is —($C_1$-$C_6$)alkyl as described above in Scheme E except that the Benzoylpiperazine Compound of Formula (IIa) wherein A is —C(S)—$NR_4$—, $R_4$ is —H, and $R_{10}$ is —H, prepared as described above, is used in place of the Benzoazolylpiperazine Compounds of formula (Ia) and (Ib) wherein x is 1, A is —C(O)—$NR_4$—, and $R_4$ is —H.

The Benzoazolylpiperazine Compounds of formula (IIb) wherein x is 1, A is —C(S)—$NR_4$—, $R_4$ is —($C_1$-$C_6$)alkyl, and $R_{10}$ is —($C_1$-$C_4$)alkyl can be obtained by a method analogous to that used to obtain the Benzoazolylpiperazine Compounds of formula (Ia) and (Ib) wherein x is 1, A is —C(O)—$NR_4$—, and $R_4$ is —($C_1$-$C_6$)alkyl as described above in Scheme E except that the Benzoylpiperazine Compound of Formula (IIa) wherein A is —C(S)—$NR_4$—, $R_4$ is —H, and $R_{10}$ is —($C_1$-$C_4$)alkyl, prepared as described above, is used in place of the Benzoazolylpiperazine Compounds of formula (Ia) and (Ib) wherein x is 1, A is —C(O)—$NR_4$—, and $R_4$ is —H.

4.2.7 Methods for Making the Benzoazolylpiperazine Compounds of Formula (IIIa) and (IIIb) wherein x is 1 and A is —C(O)$NR_4$ The Benzoazolylpiperazine Compounds of formula (IIIa) and (IIIb) wherein x is 1, A is —C(O)—$NR_4$—, and $R_4$ is —H can be obtained by a method analogous to that used to obtain the Benzoazolylpiperazine Compounds of formula (Ia) and (Ib) wherein x is 1 and A is —C(O)—$NR_4$ as described in section 4.2.1, Scheme A, except that a compound of Formula P, shown below,

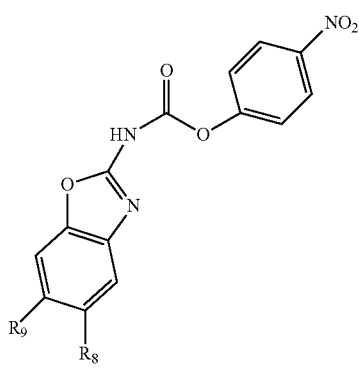

P wherein $R_8$ and $R_9$ are defined above for the Benzoazolylpiperazine Compounds of formula (IIIa) and (IIIb), is used in place of the compound of Formula B.

The Compound of Formula P can be obtained by a method analogous to that used to obtain the compound of Formula B as described above in Scheme B except that a compound of Formula Q, shown below,

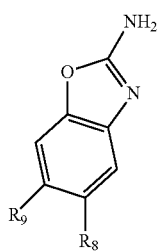

Q wherein $R_8$ and $R_9$ are defined above for the Benzoazolylpiperazine Compounds of formula (IIIa) and (IIIb), is used in place of the compound of Formula C. The compounds of Formula Q are commercially available or can be prepared by procedures well known to those skilled in the art. The compounds of Formula Q can be obtained by a method analogous to that used to obtain the compound of Formula BB, as described in Scheme H, except that a compound of Formula HH, shown below,

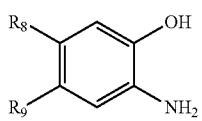

HH is used in place of a compound of Formula Z.

An illustrative procedure for obtaining a compound of Formula HH is shown below in Scheme O:

Scheme O

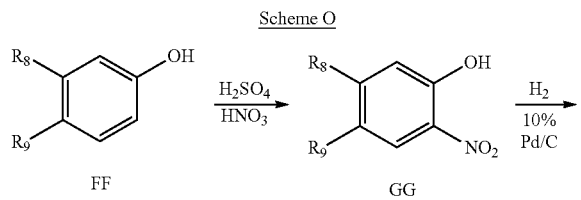

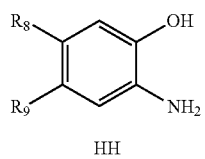

HH wherein $R_8$ and $R_9$ are defined above for the Benzoazolylpiperazine Compounds of formula (IIIa) and (IIIb).

Phenol FF (about 12 mmol) is dissolved in concentrated sulfuric acid (about 10 mL) at 0° C. and the resulting solution cooled to a temperature of about −13° C. to about −15° C. About 1 mL of 70% nitric acid is added to the resulting solution over a time period of about 30 min. and the resulting reaction mixture allowed to stir for about 2 h at a temperature of between about −13° C. to about −15° C. The reaction mixture is then poured into ice water (about 100 mL), neutralized with 5% to 10% aqueous sodium hydroxide, and extracted with about 50 mL of chloroform. The chloroform is separated from the aqueous layer and removed under reduced pressure to provide a residue that is purified using flash chromatography (silica column and chloroform eluant) to provide a compound of Formula GG The compound of Formula GG is dissolved in ethanol (about 50 mL) and hydrogenated for about 12 h at room temperature using 10% palladium on carbon as a catalyst. The catalyst is removed by filtration and the ethanol is removed under reduced pressure to provide a residue that is purified using flash chromatography (silica gel eluted with 20:1 dichloromethane:methanol) to provide the compound of Formula HH The compounds of Formula FF are commercially available or can be prepared by procedures well known to those skilled in the art.

The Benzoazolylpiperazine Compounds of formula (IIIa) and (IIIb) wherein x is 1, A is —C(O)—NR$_4$—, and R$_4$ is —(C$_1$-C$_6$)alkyl can be obtained by a method analogous to the method used to obtain the Benzoazolylpiperazine Compounds of formula (Ia) and (Ib) wherein x is 1, A is —C(O)—NR$_4$—, and R$_4$ is —(C$_1$-C$_6$)alkyl as shown above in Scheme E except that the Benzoazolylpiperazine Compounds of formula (Ia) and (Ib) wherein x is 1, A is —C(O)—NR$_4$—, and R$_4$ is —H is replaced with a Benzoazolylpiperazine Compounds of formula (IIIa) and (IIIb) wherein x is 1, A is —C(O)—NR$_4$—, and R$_4$ is —H, obtained as described above.

4.2.8 Methods for Making the Benzoazolylpiperazine Compounds of Formula (IIIa) and (IIIb) wherein x is 1 and A is —C(S)NR$_4$ The Benzoazolylpiperazine Compounds of formula (IIIa) and (IIIb) wherein x is 1, A is —C(S)—NR$_4$—, and R$_4$ is —H can be obtained by a method analogous to that used to obtain the Benzoazolylpiperazine Compounds of formula (Ia) and (Ib) wherein x is 1 and A is —C(S)—NR$_4$—, and R$_4$ is —H as described above in Scheme F except that a compound of Formula Q is used in place of the compound of Formula C. The compound of Formula Q can be obtained as described above.

The Benzoazolylpiperazine Compounds of formula (IIIa) and (IIIb) wherein x is 1, A is —C(S)—NR$_4$—, and R$_4$ is —(C$_1$-C$_6$)alkyl can be obtained by a method analogous to the method used to obtain the Benzoazolylpiperazine Compounds of formula (Ia) and (Ib) wherein x is 1, A is —C(O)—NR$_4$—, and R$_4$ is —(C$_1$-C$_6$)alkyl as described in Scheme E except that a Benzoazolylpiperazine Compound of formula (IIIa) and (IIIb) wherein x is 1, A is —C(S)—NR$_4$—, and R$_4$ is —H, obtained as described above, is used in place of the Benzoazolylpiperazine Compounds of formula (Ia) and (Ib) wherein x is 1, A is —C(O)—NR₄—, and R₄ is —H.

4.2.9 Methods for Making the Benzoazolylpiperazine Compounds of Formula (IIIa) and (IIIb) wherein x is 0

The Benzoazolylpiperazine Compounds of formula (IIIa) and (IIIb) wherein x is 0 can be obtained by the following illustrative method shown in Scheme P.

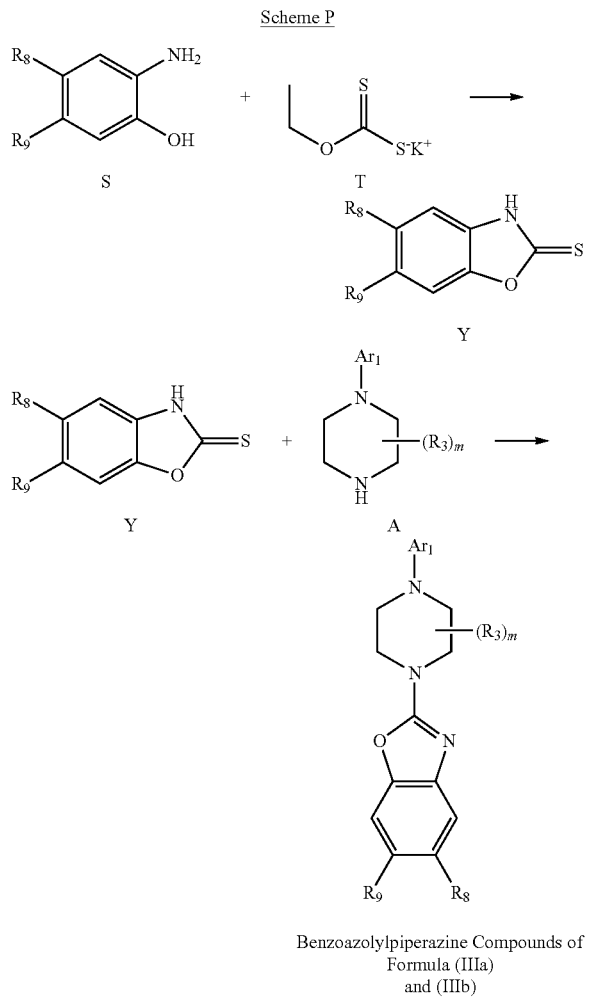

wherein $Ar_1$, $R_3$, $R_8$, $R_9$, and m are above for the Benzoazolylpiperazine Compounds of formula (IIIa) and (IIIb)

A compound of Formula S (about 15 to about 20 mmol) and a compound of Formula T (about 1 eq.) are dissolved in ethanol (about 30 to about 40 mL) and the resulting reaction mixture heated at reflux temperature for about 5 h. The reaction mixture is concentrated under reduced pressure to provide a residue that is diluted with water (about 30 mL) and acidified with acetic acid to a pH value of about 6. The aqueous mixture is then extracted with ethyl acetate, the ethyl acetate dried ($Na_2SO_4$), and the solvent removed under reduced pressure to provide a compound of Formula Y which is used without further purification. The compound of Formula Y (about 1 mmol) and a compound of Formula A (about 1 eq.) are dissolved in toluene or p-xylene (about 0.5 mL to about 1 mL) and the reaction mixture heated in a sealed tube at a temperature of about 150° C. for about 24 h. The reaction mixture is concentrated under reduced pressure to provide a residue. The resulting residue can be purified using flash chromatography (silica gel, 5:95 methanol:DCM) to provide the Benzoazolylpiperazine Compounds of formula (IIIa) and (IIIb) wherein x is 0.

The compounds of Formula S are commercially available or can be prepared by procedures well known to those skilled in the art. An illustrative procedure for obtaining a compound of Formula S is shown below in Scheme Q:

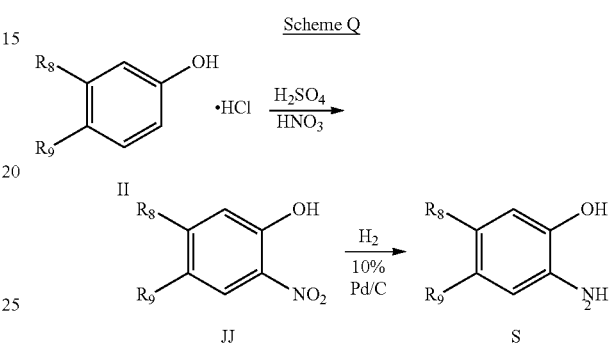

wherein $R_8$ and $R_9$ are defined above for the Benzoazolylpiperazine Compounds of formula (IIIa) and (IIIb).

Phenol II (about 12 mmol) is dissolved in concentrated sulfuric acid (about 10 mL) at 0° C. and the resulting solution cooled to a temperature of about −13° C. to about −15° C. About 1 ml, of 70% nitric acid is added to the resulting solution over a time period of about 30 min. and the resulting reaction mixture allowed to stir for about 2 h at a temperature of between about −13° C. to about −15° C. The reaction mixture is then poured into ice water (about 100 mL), neutralized with 5% to 10% aqueous sodium hydroxide and extracted with about 50 mL of chloroform. The chloroform is separated from the aqueous layer and removed under reduced pressure to provide a residue that is purified using flash chromatography (silica column and chloroform eluant) to provide a compound of Formula JJ. The compound of Formula JJ is dissolved in ethanol (about 50 mL) and hydrogenated for about 12 h at room temperature using 10% palladium on carbon as a catalyst. The catalyst is removed by filtration and the ethanol is removed under reduced pressure to provide a residue that is purified using flash chromatography (silica gel eluted with 20:1 dichloromethane:methanol) to provide the compound of Formula S. The compounds of Formula S are commercially available or can be prepared by procedures well known to those skilled in the art.

The compound of Formula T is commercially available from Sigma-Aldrich, St. Louis, Mo. (www.sigma-aldrich.com).

The compounds of Formula A can be obtained as described above.

Suitable aprotic organic solvents for use in the illustrative methods include, but are not limited to, DCM, DMSO, chloroform, toluene, benzene, acetonitrile, carbon tetrachloride, pentane, hexane, ligroin, and diethylether. In one embodiment, the aprotic organic solvent is DCM.

Certain Benzoazolylpiperazine Compounds can have one or more asymmetric centers and therefore exist in different enantiomeric and diastereomeric forms. A Benzoazolylpiperazine Compound can be in the form of an optical isomer or a diastereomer. Accordingly, the invention encompasses Benzoazolylpiperazine Compounds and their uses as described herein in the form of their optical isomers, diasteriomers, and mixtures thereof, including a racemic mixture.

In addition, one or more hydrogen, carbon or other atoms of a Benzoazolylpiperazine Compound can be replaced by an isotope of the hydrogen, carbon or other atoms. Such compounds, which are encompassed by the present invention, are useful as research and diagnostic tools in metabolism pharmacokinetic studies and in binding assays.

4.3 Therapeutic Uses of the Benzoazolylpiperazine Compounds

In accordance with the invention, the Benzoazolylpiperazine Compounds are administered to an animal in need of treatment or prevention of pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression.

In one embodiment, an effective amount of a Benzoazolylpiperazine Compound can be used to treat or prevent any condition treatable or preventable by inhibiting VR1. Examples of conditions that are treatable or preventable by inhibiting VR1 include, but are not limited to, pain, UI, an ulcer, IBD, and IBS.

In another embodiment, an effective amount of a Benzoazolylpiperazine Compound can be used to treat or prevent any condition treatable or preventable by inhibiting mGluR5. Examples of conditions that are treatable or preventable by inhibiting mGluR5 include, but are not limited to, pain, an addictive disorder, Parkinson's disease, parkinsonism, anxiety, a pruritic condition, and psychosis.

In another embodiment, an effective amount of a Benzoazolylpiperazine Compound can be used to treat or prevent any condition treatable or preventable by inhibiting mGluR1. Examples of conditions that are treatable or preventable by inhibiting mGluR1 include, but are not limited to, pain, UI, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, and depression.

The Benzoazolylpiperazine Compounds can be used to treat or prevent acute or chronic pain. Examples of pain treatable or preventable using the Benzoazolylpiperazine Compounds include, but are not limited to, cancer pain, central pain, labor pain, myocardial infarction pain, pancreatic pain, colic pain, post-operative pain, headache pain, muscle pain, pain associated with intensive care, arthritic pain, and pain associated with a periodontal disease, including gingivitis and periodontitis.

The pain to be treated or prevented can be associated with inflammation associated with an inflammatory disease, which can arise where there is an inflammation of the body tissue, and which can be a local inflammatory response and/or a systemic inflammation. For example, the Benzoazolylpiperazine Compounds can be used to treat, or prevent pain associated with inflammatory disease including, but not limited to: organ transplant rejection; reoxygenation injury resulting from organ transplantation (see Grupp et al., J. Mol, Cell Cardiol. 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory disease of the gum, including gingivitis and periodontitis; tuberculosis; leprosy; inflammatory diseases of the kidney, including uremic complications, glomerulonephritis and nephrosis; inflammatory disease of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microaluminuria and progressive diabetic nephropathy), polyneuropathy, mononeuropathies, autonomic neuropathy, gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum); immune-complex vasculitis, and systemic lupus erythematosus (SLE); inflammatory disease of the heart, such as cardiomyopathy, ischemic heart disease hypercholesterolemia, and artherosclerosis; as well as various other diseases that can have significant inflammatory components, including preeclampsia, chronic liver failure, brain and spinal cord trauma, and cancer. The Benzoazolylpiperazine Compounds can also be used for inhibiting, treating, or preventing pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

The Benzoazolylpiperazine Compounds can be used to treat or prevent UI. Examples of UI treatable or preventable using the Benzoazolylpiperazine Compounds include, but are not limited to, urge incontinence, stress incontinence, overflow incontinence, neurogenic incontinence, and total incontinence.

The Benzoazolylpiperazine Compounds can be used to treat or prevent an ulcer. Examples of ulcers treatable or preventable using the Benzoazolylpiperazine Compounds include, but are not limited to, a duodenal ulcer, a gastric ulcer, a marginal ulcer, an esophageal ulcer, or a stress ulcer.

The Benzoazolylpiperazine Compounds can be used to treat or prevent IBD, including Crohn's disease and ulcerative colitis.

The Benzoazolylpiperazine Compounds can be used to treat or prevent IBS. Examples of IBS treatable or preventable using the Benzoazolylpiperazine Compounds include, but are not limited to, spastic-colon-type IBS and constipation-predominant IBS.

The Benzoazolylpiperazine Compounds can be used to treat or prevent an addictive disorder, including but not limited to, an eating disorder, an impulse-control disorder, an alcohol-related disorder, a nicotine-related disorder, an amphetamine-related disorder, a *cannabis*-related disorder, a cocaine-related disorder, an hallucinogen-related disorder, an inhalant-related disorders, and an opioid-related disorder, all of which are further sub-classified as listed below.

Eating disorders include, but are not limited to, Bulimia Nervosa, Nonpurging Type; Bulimia Nervosa, Purging Type; Anorexia; and Eating Disorder not otherwise specified (NOS).

Impulse control disorders include, but are not limited to, Intermittent Explosive Disorder, Kleptomania, Pyromania, Pathological Gambling, Trichotillomania, and Impulse Control Disorder not otherwise specified (NOS).

Alcohol-related disorders include, but are not limited to, Alcohol-Induced Psychotic Disorder with delusions, Alcohol Abuse, Alcohol Intoxication, Alcohol Withdrawal, Alcohol Intoxication Delirium, Alcohol Withdrawal Delirium, Alcohol-Induced Persisting. Dementia, Alcohol-Induced Persisting Amnestic Disorder, Alcohol Dependence, Alcohol-Induced Psychotic Disorder with hallucinations, Alcohol-Induced Mood Disorder, Alcohol-Induced Anxiety Disorder, Alcohol-Induced Sexual Dysfunction, Alcohol-Induced Sleep Disorder, Alcohol-Related Disorder not otherwise specified (NOS), Alcohol Intoxication, and Alcohol Withdrawal.

Nicotine-related disorders include, but are not limited to, Nicotine Dependence, Nicotine Withdrawal, and Nicotine-Related Disorder not otherwise specified (NOS).

Amphetamine-related disorders include, but are not limited to, Amphetamine Dependence, Amphetamine Abuse, Amphetamine Intoxication, Amphetamine Withdrawal, Amphetamine Intoxication Delirium, Amphetamine-Induced Psychotic Disorder with delusions, Amphetamine-Induced Psychotic Disorders with hallucinations, Amphetamine-Induced Mood Disorder, Amphetamine-Induced Anxiety Disorder, Amphetamine-Induced Sexual Dysfunction, Amphetamine-Induced Sleep Disorder, Amphetamine Related Disorder not otherwise specified (NOS), Amphetamine Intoxication, and Amphetamine Withdrawal.

*Cannabis*-related disorders include, but are not limited to, *Cannabis* Dependence, *Cannabis* Abuse, *Cannabis* Intoxication, *Cannabis* Intoxication Delirium, *Cannabis*-Induced Psychotic Disorder with delusions, *Cannabis*-Induced Psychotic Disorder with hallucinations, *Cannabis*-Induced Anxiety Disorder, *Cannabis* Related Disorder not otherwise specified (NOS), and *Cannabis* Intoxication.

Cocaine-related disorders include, but are not limited to, Cocaine Dependence, Cocaine Abuse, Cocaine Intoxication, Cocaine Withdrawal, Cocaine Intoxication Delirium, Cocaine-Induced Psychotic Disorder with delusions, Cocaine-Induced Psychotic Disorders with hallucinations, Cocaine-Induced Mood Disorder, Cocaine-Induced Anxiety Disorder, Cocaine-Induced Sexual Dysfunction, Cocaine-Induced Sleep Disorder, Cocaine Related Disorder not otherwise specified (NOS), Cocaine Intoxication, and Cocaine Withdrawal.

Hallucinogen-related disorders include, but are not limited to, Hallucinogen Dependence, Hallucinogen Abuse, Hallucinogen Intoxication, Hallucinogen Withdrawal, Hallucinogen Intoxication Delirium, Hallucinogen-Induced Psychotic Disorder with delusions, Hallucinogen-Induced Psychotic Disorders with hallucinations, Hallucinogen-Induced Mood Disorder, Hallucinogen-Induced Anxiety Disorder, Hallucinogen-Induced Sexual Dysfunction, Hallucinogen-Induced Sleep Disorder, Hallucinogen Related Disorder not otherwise specified (NOS), Hallucinogen Intoxication, and Hallucinogen Persisting Perception Disorder (Flashbacks).

Inhalant-related disorders include, but are not limited to, Inhalant Dependence, Inhalant Abuse, Inhalant Intoxication, Inhalant Intoxication Delirium, Inhalant-Induced Psychotic Disorder with delusions, Inhalant-Induced Psychotic Disorder with hallucinations, Inhalant-Induced Anxiety Disorder, Inhalant Related Disorder not otherwise specified (NOS), and Inhalant Intoxication.

Opioid-related disorders include, but are not limited to, Opioid Dependence, Opioid Abuse, Opioid Intoxication, Opioid Intoxication Delirium, Opioid-Induced Psychotic Disorder with delusions, Opioid-Induced Psychotic Disorder with hallucinations, Opioid-Induced Anxiety Disorder, Opioid Related Disorder not otherwise specified (NOS), Opioid Intoxication, and Opioid Withdrawal.

The Benzoazolylpiperazine Compounds can be used to treat or prevent Parkinson's disease and parkinsonism and the symptoms associated with Parkinson's disease and parkinsonism, including but not limited to, bradykinesia, muscular rigidity, resting tremor, and impairment of postural balance.

The Benzoazolylpiperazine Compounds can be used to treat or prevent generalized anxiety or severe anxiety and the symptoms associated with anxiety, including but not limited to, restlessness; tension; tachycardia; dyspnea; depression, including chronic "neurotic" depression; panic disorder; agoraphobia and other specific phobias; eating disorders; and personality disorders.

The Benzoazolylpiperazine Compounds can be used to treat or prevent epilepsy, including but not limited to, partial epilepsy, generalized epilepsy, and the symptoms associated with epilepsy, including but not limited to, simple partial seizures, jacksonian seizures, complex partial (psychomotor) seizures, convulsive seizures (grand mal or tonic-clonic seizures), petit mal (absence) seizures, and status epilepticus.

The Benzoazolylpiperazine Compounds can be used to treat or prevent strokes, including but not limited to, ischemic strokes and hemorrhagic strokes.

The Benzoazolylpiperazine Compounds can be used to treat or prevent a seizure, including but not limited to, infantile spasms, febrile seizures, and epileptic seizures.

The Benzoazolylpiperazine Compounds can be used to treat or prevent a pruritic condition, including but not limited to, pruritus caused by dry skin, scabies, dermatitis, herpetiformis, atopic dermatitis, pruritus vulvae et ani, miliaria, insect bites, pediculosis, contact dermatitis, drug reactions, urticaria, urticarial eruptions of pregnancy, psoriasis, lichen planus, lichen simplex chronicus, exfoliative dermatitis, folliculitis, bullous pemphigoid, or fiberglass dermatitis.

The Benzoazolylpiperazine Compounds can be used to treat or prevent psychosis, including but not limited to, schizophrenia, including paranoid schizophrenia, hebephrenic or disorganized schizophrenia, catatonic schizophrenia, undifferentiated schizophrenia, negative or deficit subtype schizophrenia, and non-deficit schizophrenia; a delusional disorder, including erotomanic subtype delusional disorder, grandiose subtype delusional disorder, jealous subtype delusional disorder, persecutory subtype delusional disorder, and somatic subtype delusional disorder; and brief psychosis.

The Benzoazolylpiperazine Compounds can be used to treat or prevent a cognitive disorder, including but not limited to, delirium and dementia such as multi-infarct dementia, dementia pugilistica, dimentia caused by AIDS, and dementia caused by Alzheimer's disease.

The Benzoazolylpiperazine Compounds can be used to treat or prevent a memory deficiency, including but not limited to, dissociative amnesia and dissociative fugue.

The Benzoazolylpiperazine Compounds can be used to treat or prevent restricted brain function, including but not limited to, that caused by surgery or an organ transplant, restricted blood supply to the brain, a spinal cord injury, a head injury, hypoxia, cardiac arrest, or hypoglycemia.

The Benzoazolylpiperazine Compounds can be used to treat or prevent Huntington's chorea.

The Benzoazolylpiperazine Compounds can be used to treat or prevent ALS.

The Benzoazolylpiperazine Compounds can be used to treat or prevent retinopathy, including but not limited to, arteriosclerotic retinopathy, diabetic arteriosclerotic retinopathy, hypertensive retinopathy, non-proliferative retinopathy, and proliferative retinopathy.

The Benzoazolylpiperazine Compounds can be used to treat or prevent a muscle spasm.

The Benzoazolylpiperazine Compounds can be used to treat or prevent a migraine including, but not limited to, migraine without aura ("common migraine"), migraine with aura ("classic migraine"), migraine without headache, basilar migraine, familial hemiplegic migraine, migrainous infarction, and migraine with prolonged aura.

The Benzoazolylpiperazine Compounds can be used to treat or prevent vomiting, including but not limited to, nausea vomiting, dry vomiting (retching), and regurgitation.

The Benzoazolylpiperazine Compounds can be used to treat or prevent dyskinesia, including but not limited to, tardive dyskinesia and biliary dyskinesia.

The Benzoazolylpiperazine Compounds can be used to treat or prevent depression, including but not limited to, major depression and bipolar disorder.

Applicants believe that the Benzoazolylpiperazine Compounds are antagonists for VR1.

The invention also relates to methods for inhibiting VR1 function in a cell comprising contacting a cell capable of expressing VR1 with an effective amount of a Benzoazolylpiperazine Compound. This method can be used in vitro, for example, as an assay to select cells that express VR1 and, accordingly, are useful as part of an assay to select compounds useful for treating or preventing pain, UI, an ulcer, IBD, or IBS. The method is also useful for inhibiting VR1 function in a cell in vivo, in an animal, a human in one embodiment, by contacting a cell, in an animal, with an effective amount of a Benzoazolylpiperazine Compound. In one embodiment, the method is useful for treating or preventing pain in an animal. In another embodiment, the method is useful for treating or preventing UI in an animal. In another embodiment, the method is useful for treating or preventing an ulcer in an animal. In another embodiment, the method is useful for treating or preventing IBD in an animal. In another embodiment, the method is useful for treating or preventing IBS in an animal.

Examples of tissue comprising cells capable of expressing VR1 include, but are not limited to, neuronal, brain, kidney, urothelium, and bladder tissue. Methods for assaying cells that express VR1 are well known in the art.

Applicants believe that the Benzoazolylpiperazine Compounds are antagonists for mGluR5.

The invention also relates to methods for inhibiting mGluR5 function in a cell comprising contacting a cell capable of expressing mGluR5 with an amount of a Benzoazolylpiperazine Compound effective to inhibit mGluR5 function in the cell. This method can be used in vitro, for example, as an assay to select cells that express mGluR5 and, accordingly, are useful as part of an assay to select compounds useful for treating or preventing pain, an addictive disorder, Parkinson's disease, parkinsonism, anxiety, a pruritic condition, or psychosis. The method is also useful for inhibiting mGluR5 function in a cell in vivo, in an animal, a human in one embodiment, by contacting a cell, in an animal, with an amount of a Benzoazolylpiperazine Compound effective to inhibit mGluR5 function in the cell. In one embodiment, the method is useful for treating or preventing pain in an animal in need thereof. In another embodiment, the method is useful for treating or preventing an addictive disorder in an animal in need thereof. In another embodiment, the method is useful for treating or preventing Parkinson's disease in an animal in need thereof. In another embodiment, the method is useful for treating or preventing parkinsonism in an animal in need thereof. In another embodiment, the method is useful for treating or preventing anxiety in an animal in need thereof. In another embodiment, the method is useful for treating or preventing a pruritic condition in an animal in need thereof. In another embodiment, the method is useful for treating or preventing psychosis in an animal in need thereof.

Examples of cells capable of expressing mGluR5 are neuronal and glial cells of the central nervous system, particularly the brain, especially in the nucleus accumbens. Methods for assaying cells that express mGluR5 are well known in the art.

Applicants believe that the Benzoazolylpiperazine Compounds are antagonists for mGluR1.

The invention also relates to methods for inhibiting mGluR1 function in a cell comprising contacting a cell capable of expressing mGluR1 with an amount of a Benzoazolylpiperazine Compound effective to inhibit mGluR1 function in the cell. This method can be used in vitro, for example, as an assay to select cells that express mGluR1 and, accordingly, are useful as part of an assay to select compounds useful for treating or preventing pain, UI, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression. The method is also useful for inhibiting mGluR1 function in a cell in vivo, in an animal, a human in one embodiment, by contacting a cell, in an animal, with an amount of a Benzoazolylpiperazine Compound effective to inhibit mGluR1 function in the cell. In one embodiment, the method is useful for treating or preventing pain in an animal in need thereof. In another embodiment, the method is useful for treating or preventing UI in an animal in need thereof. In another embodiment, the method is useful for treating or preventing an addictive disorder in an animal in need thereof. In another embodiment, the method is useful for treating or preventing Parkinson's disease in an animal in need thereof. In another embodiment, the method is useful for treating or preventing parkinsonism in an animal in need thereof. In another embodiment, the method is useful for treating or preventing anxiety in an animal in need thereof. In another embodiment, the method is useful for treating or preventing epilepsy in an animal in need thereof. In another embodiment, the method is useful for treating or preventing stroke in an animal in need thereof. In another embodiment, the method is useful for treating or preventing a seizure in an animal in need thereof. In another embodiment, the method is useful for treating or preventing a pruritic condition in an animal in need thereof. In another embodiment, the method is useful for treating or preventing psychosis in an animal in need thereof. In another embodiment, the method is useful for treating or preventing a cognitive disorder in an animal in need thereof. In another embodiment, the method is useful for treating or preventing a memory deficit in an animal in need thereof. In another embodiment, the method is useful for treating or preventing restricted brain function in an animal in need thereof. In another embodiment, the method is useful for treating or preventing Huntington's chorea in an animal in need thereof. In another embodiment, the method is useful for treating or preventing ALS in an animal in need thereof. In another embodiment, the method is useful for treating or preventing dementia in an animal in need thereof. In another embodiment, the method is useful for treating or preventing retinopathy in an animal in need thereof. In another embodiment, the method is useful for treating or preventing a muscle spasm in an animal in need thereof. In another embodiment, the method is useful for treating or preventing a migraine in an animal in need thereof. In another embodiment, the method is useful for treating or preventing vomiting in an animal in need thereof. In another embodiment, the method is useful for treating or preventing dyskinesia in an animal in need thereof. In another embodiment, the method is useful for treating or preventing depression in an animal in need thereof.

Examples of cells capable of expressing mGluR1 include, but are not limited to, cerebellar Purkinje neuron cells, Purkinje cell bodies (punctate), cells of spine(s) of the cerebellum; neurons and neurophil cells of olfactory-bulb glomeruli; cells of the superficial layer of the cerebral cortex; hippocampus cells; thalamus cells; superior colliculus cells; and spinal trigeminal nucleus cells. Methods for assaying cells that express mGluR1 are well known in the art.

4.3.1 Therapeutic/Prophylactic Administration and Compositions of the Invention Due to their activity, the Benzoazolylpiperazine Compounds are advantageously useful in veterinary and human medicine. As described above, the Benzoazolylpiperazine Compounds are useful for treating or preventing pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression in an animal in need thereof.

When administered to an animal, the Benzoazolylpiperazine Compounds can be administered as a component of a composition that comprises a pharmaceutically acceptable vehicle. The present compositions, which comprise a Benzoazolylpiperazine Compound, can be administered orally. The Benzoazolylpiperazine Compounds of the invention can also be administered by any other convenient route, for example, by infusion or bolus injection, by absorption through epithelial or mucocutaneous linings (e.g., oral, rectal, and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer the Benzoazolylpiperazine Compound.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration can be left to the discretion of the practitioner. In most instances, administration will result in the release of the Benzoazolylpiperazine Compounds into the bloodstream.

In specific embodiments, it can be desirable to administer the Benzoazolylpiperazine Compounds locally. This can be achieved, for example, and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce the Benzoazolylpiperazine Compounds into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the Benzoazolylpiperazine Compounds can be formulated as a suppository, with traditional binders and excipients such as triglycerides.

In another embodiment, the Benzoazolylpiperazine Compounds can be delivered in a vesicle, in particular a liposome (see Langer, *Science* 249:1527-1533 (1990) and Treat et al., *Liposomes in the Therapy of Infectious Disease and Cancer* 317-327 and 353-365 (1989)).

In yet another embodiment, the Benzoazolylpiperazine Compounds can be delivered in a controlled-release system or sustained-release system (see, e.g., Goodson, in Medical Applications of Controlled Release, supra, vol. 2, pp. 115-138 (1984)). Other controlled- or sustained-release systems discussed in the review by Langer, *Science* 249:1527-1533 (1990) can be used. In one embodiment, a pump can be used (Langer, *Science* 249:1527-1533 (1990); Sefton, *CRC Crit. Ref Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled- or sustained-release system can be placed in proximity of a target of the Benzoazolylpiperazine Compounds, e.g., the spinal column, brain, or gastrointestinal tract, thus requiring only a fraction of the systemic dose.

In one embodiment, the pharmaceutically acceptable vehicle is an excipient Such a pharmaceutical excipient can be a liquid, such as water or an oil, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to an animal. Water is a particularly useful excipient when the Benzoazolylpiperazine Compound is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see e.g., U.S. Pat. No. 5,698,155). Other examples of suitable pharmaceutical excipients are described in *Remington's Pharmaceutical Sciences* 1447-1676 (Alfonso R. Gennaro ed., 19th ed. 1995), incorporated herein by reference.

In one embodiment, the Benzoazolylpiperazine Compounds are formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs, for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the Benzoazolylpiperazine Compounds can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the Benzoazolylpiperazine Compounds are to be administered by infusion, they can be dispensed, for example, with an infusion bottle containing sterile pharmaceutical grade water or saline. Where the Benzoazolylpiperazine Compounds are administered by injection, an ampule of sterile water for injection or saline can be provided so that the ingredients can be mixed prior to administration.

The Benzoazolylpiperazine Compounds can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained counterparts. In one embodiment, a controlled- or sustained-release composition comprises a minimal amount of a Benzoazolylpiperazine Compound to cure or control the condition in a minimum amount of time. Advantages of controlled- or sustained-release compositions include extended activity of the drug, reduced dosage frequency, and increased patient compliance. In addition, controlled- or sustained-release compositions can favorably affect the time of onset of action or other characteristics, such as blood levels of the Benzoazolylpiperazine Compound, and can thus reduce the occurrence of adverse side effects.

Controlled- or sustained-release compositions can initially release an amount of a Benzoazolylpiperazine Compound that promptly produces the desired therapeutic or prophylactic effect, and gradually and continually release other amounts of the Benzoazolylpiperazine Compound to maintain this level of therapeutic or prophylactic effect over an extended period of time. To maintain a constant level of the Benzoazolylpiperazine Compound in the body, the Benzoazolylpiperazine Compound can be released from the dosage form at a rate that will replace the amount of Benzoazolylpiperazine Compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the Benzoazolylpiperazine Compound that is effective in the treatment or prevention of pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression and can be determined by standard clinical techniques. In addition, in vitro or in vivo assays can optionally be employed to help identify optimal dosage ranges. The precise dose to be employed will also depend on the route of administration, and the seriousness of the condition being treated and should be decided according to the judgment of the practitioner and each patient's circumstances in view of, e.g., published clinical studies. Suitable effective dosage amounts, however, range from about 10 micrograms to about 2500 milligrams about every 4 h, although they are typically about 100 mg or less. In one embodiment, the effective dosage amount ranges from about 0.01 milligrams to about 100 milligrams of a Benzoazolylpiperazine Compound about every 4 h, in another embodiment, about 0.020 milligrams to about 50 milligrams about every 4 h, and in another embodiment, about 0.025 milligrams to about 20 milligrams about every 4 h. The effective dosage amounts described herein refer to total amounts administered; that is, if more than one Benzoazolylpiperazine Compound is administered, the effective dosage amounts correspond to the total amount administered.

Where a cell capable of expressing VR1, mGluR5, or mGluR1 is contacted with a Benzoazolylpiperazine Compound in vitro, the amount effective for inhibiting the receptor function in a cell will typically range from about 0.01 µg/L to about 5 mg/L, in one embodiment, from about 0.01 µg/L to about 2.5 mg/L, in another embodiment, from about 0.01 µg/L to about 0.5 mg/L, and in another embodiment, from about 0.01 µg/L to about 0.25 mg/L of a solution or suspension of a pharmaceutically acceptable carrier or excipient. In one embodiment, the volume of solution or suspension is from about 1 µL to about 1 mL. In another embodiment, the volume of solution or suspension is about 200 µL.

Where a cell capable of expressing VR1, mGluR5, or mGluR1 is contacted with a Benzoazolylpiperazine Compound in vivo, the amount effective for inhibiting the receptor function in a cell will typically range from about 0.01 mg to about 100 mg/kg of body weight per day, in one embodiment, from about 0.1 mg to about 50 mg/kg body weight per day, and in another embodiment, from about 1 mg to about 20 mg/kg of body weight per day.

The Benzoazolylpiperazine Compounds can be assayed in vitro or in vivo for the desired therapeutic or prophylactic activity prior to use in humans. Animal model systems can be used to demonstrate safety and efficacy.

The present methods for treating or preventing pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression in an animal in need thereof can further comprise administering to the animal being administered a Benzoazolylpiperazine Compound another therapeutic agent.

In one embodiment, the other therapeutic agent is administered in an effective amount.

The present methods for inhibiting VR1 function in a cell capable of expressing VR1 can further comprise contacting the cell with an effective amount of another therapeutic agent.

The present methods for inhibiting mGluR5 function in a cell capable of expressing mGluR5 can further comprise contacting the cell with an effective amount of another therapeutic agent.

The present methods for inhibiting mGluR1 function in a cell capable of expressing mGluR1 can further comprise contacting the cell with an effective amount of another therapeutic agent.

The other therapeutic agent includes, but is not limited to, an opioid agonist, a non-opioid analgesic, a non-steroid anti-inflammatory agent, an antimigraine agent, a Cox-II inhibitor, an antiemetic, a β-adrenergic blocker, an anticonvulsant, an antidepressant, a Ca2+-channel blocker, an anticancer agent, an agent for treating or preventing UI, an agent for treating or preventing an ulcer, an agent for treating or preventing IBD, an agent for treating or preventing IBS, an agent for treating addictive disorder, an agent for treating Parkinson's disease and parkinsonism, an agent for treating anxiety, an agent for treating epilepsy, an agent for treating a stroke, an agent for treating a seizure, an agent for treating a pruritic condition, an agent for treating psychosis, an agent for treating Huntington's chorea, an agent for treating ALS, an agent for treating a cognitive disorder, an agent for treating a migraine, an agent for treating vomiting, an agent for treating dyskinesia, or an agent for treating depression, and mixtures thereof.

Effective amounts of the other therapeutic agents are well known to those skilled in the art. However, it is well within the skilled artisan's purview to determine the other therapeutic agent's optimal effective-amount range. In one embodiment of the invention, where another therapeutic agent is administered to an animal, the effective amount of the Benzoazolylpiperazine Compound is less than its effective amount would be where the other therapeutic agent is not administered. In this case, without being bound by theory, it is believed that the Benzoazolylpiperazine Compounds and the other therapeutic agent act synergistically to treat or prevent pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include nonsteroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxipinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Other suitable non-opioid analgesics include the following, non-limiting, chemical classes of analgesic, antipyretic, nonsteroidal anti-inflammatory drugs: salkylic acid derivatives, including aspirin, sodium salkylate, choline magnesium trisalkylate, salsalate, diflunisal, salkylsalkylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic-Antipyretic and Anti-inflammatory Agents and Drugs Employed in the Treatment of Gout*, in Goodman & Gilman's The Pharmacological Basis of Therapeutics 617-57 (Perry B. Molinhoff and Raymond W. Ruddon eds., 9$^{th}$ ed 1996) and Glen R. Hanson, *Analgesic, Antipyretic and Anti-Inflammatory Drugs in Remington: The Science and Practice of Pharmacy Vol II* 1196-1221 (A. R. Gennaro ed. 19th ed. 1995) which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, rofecoxib and celecoxib.

Examples of useful antimigraine agents include, but are not limited to, alpiropride, dihydroergotamine, dolasetron, ergocornine, ergocorninine, ergocryptine, ergot, ergotamine, flumedroxone acetate, fonazine, lisuride, lomerizine, methysergide oxetorone, pizotyline, and mixtures thereof.

The other therapeutic agent can also be an agent useful for reducing any potential side effects of a Benzoazolylpiperazine Compounds. For example, the other therapeutic agent can be an antiemetic agent. Examples of useful antiemetic agents include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, dimethazan, fencamine, indalpine, indeloxazine hydrocholride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful Ca2+-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, and perhexyline.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, fluorocitabine, fosquidone, fostriecin sodium, gemcitabine, gemcitabine hydrochloride, hydroxyurea, idarubicin hydrochloride, ifosfamide, ilmofosine, interleukin II (including recombinant interleukin II or rIL2), interferon alfa-2a, interferon alfa-2b, interferon alfa-n1, interferon alfa-n3, interferon beta-I a, interferon gamma-I b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride.

Examples of other anti-cancer drugs include, but are not limited to, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide;

stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Examples of useful therapeutic agents for treating or preventing UI include, but are not limited to, propantheline, imipramine, hyoscyamine, oxybutynin, and dicyclomine.

Examples of useful therapeutic agents for treating or preventing an ulcer include, antacids such as aluminum hydroxide, magnesium hydroxide, sodium bicarbonate, and calcium bicarbonate; sucraflate; bismuth compounds such as bismuth subsalkylate and bismuth subcitrate; $H_2$ antagonists such as cimetidine, ranitidine, famotidine, and nizatidine; $H^+$, $K^+$-ATPase inhibitors such as omeprazole, iansoprazole, and lansoprazole; carbenoxolone; misprostol; and antibiotics such as tetracycline, metronidazole, timidazole, clarithromycin, and amoxicillin.

Examples of useful therapeutic agents for treating or preventing IBD include, but are not limited to, anticholinergic drugs; diphenoxylate; loperamide; deodorized opium tincture; codeine; broad-spectrum antibiotics such as metronidazole; sulfasalazine; olsalazie; mesalamine; prednisone; azathioprine; mercaptopurine; and methotrexate.

Examples of useful therapeutic agents for treating or preventing IBS include, but are not limited to, propantheline; muscarine receptor antagonists such as pirenzapine, methoctramine, ipratropium, tiotropium, scopolamine, methscopolamine, homatropine, homatropine methylbromide, and methantheline; and antidiarrheal drugs such as diphenoxylate and loperamide.

Examples of useful therapeutic agents for treating or preventing an addictive disorder include, but are not limited to, methadone, desipramine, amantadine, fluoxetine, buprenorphine, an opiate agonist, 3-phenoxypyridine, levomethadyl acetate hydrochloride, and serotonin antagonists.

Examples of useful therapeutic agents for treating or preventing Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsaprione, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating or preventing epilepsy include, but are not limited to, carbamazepine, ethosuximide, gabapentin, lamotrignine, phenobarbital, phenyloin, primidone, valproic acid, trimethadione, bemzodiaepines, gabapentin, lamotrigine, γ-vinyl GABA, acetazolamide, and felbamate.

Examples of useful therapeutic agents for treating or preventing stroke include, but are not limited to, anticoagulants such as heparin, agents that break up clots such as streptokinase or tissue plasminogen activator, agents that reduce swelling such as mannitol or corticosteroids, and acetylsalkylic acid.

Examples of useful therapeutic agents for treating or preventing a seizure include, but are not limited to, carbamazepine, ethosuximide, gabapentin, lamotrignine, phenobarbital, phenyloin, primidone, valproic acid, trimethadione, bemzodiaepines, gabapentin, lamotrigine, γ-vinyl GABA, acetazolamide, and felbamate.

Examples of useful therapeutic agents for treating or preventing a pruritic condition include, but are not limited to, naltrexone; nalmefene; danazol; tricyclics such as amitriptyline, imipramine, and doxepin; antidepressants such as those given below, menthol; camphor; phenol; pramoxine; capsaicin; tar; steroids; and antihistamines.

Examples of useful therapeutic agents for treating or preventing psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating or preventing Huntington's chorea include, but are not limited to, haloperidol and pimozide.

Examples of useful therapeutic agents for treating or preventing ALS include, but are not limited to, baclofen, neurotrophic factors, riluzole, tizanidine, benzodiazepines such as clonazepan and dantrolene.

Examples of useful therapeutic agents for treating or preventing cognitive disorders include, but are not limited to, agents for treating or preventing dementia such as tacrine; donepezil; ibuprofen; antipsychotic drugs such as thioridazine and haloperidol; and antidepressant drugs such as those given below.

Examples of useful therapeutic agents for treating or preventing a migraine include, but are not limited to, sumatriptan; methysergide; ergotamine; caffeine; and beta-blockers such as propranolol, verapamil, and divalproex.

Examples of useful therapeutic agents for treating or preventing vomiting include, but are not limited to, 5-$HT_3$ receptor antagonists such as ondansetron, dolasetron, granisetron, and tropisetron; dopamine receptor antagonists such as prochlorperazine, thiethylperazine, chlorpromazin, metoclopramide, and domperidone; glucocorticoids such as dexamethasone; and benzodiazepines such as lorazepam and alprazolam.

Examples of useful therapeutic agents for treating or preventing dyskinesia include, but are not limited to, reserpine and tetrabenazine.

Examples of useful therapeutic agents for treating or preventing depression include, but are not limited to, tricyclic antidepressants such as amitryptyline, amoxapine, bupropion, clomipramine, desipramine, doxepin, imipramine, maprotilinr, nefazodone, nortriptyline, protriptyline, trazodone, trimipramine, and venlaflaxine; selective serotonin reuptake inhibitors such as fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A Benzoazolylpiperazine Compound and the other therapeutic agent can act additively or, in one embodiment, synergistically. In one embodiment, a Benzoazolylpiperazine Compound is administered concurrently with another therapeutic agent. In one embodiment, a composition comprising an effective amount of a Benzoazolylpiperazine Compound and an effective amount of another therapeutic agent can be administered. Alternatively, a composition comprising an effective amount of a Benzoazolylpiperazine Compound and a different composition comprising an effective amount of another therapeutic agent can be concurrently administered. In another embodiment, an effective amount of a Benzoazolylpiperazine Compound is administered prior or subsequent to administration of an effective amount of another therapeutic agent. In this embodiment, the Benzoazolylpiperazine Compound is administered while the other therapeutic agent exerts its therapeutic effect, or the other therapeutic agent is administered while the Benzoazolylpiperazine Compound exerts its preventative or therapeutic effect for treating or preventing a Condition in an animal.

A composition of the invention is prepared by a method comprising admixing a Benzoazolylpiperazine Compound and a pharmaceutically acceptable carrier or excipient. Admixing can be accomplished using methods well known for admixing a compound (or salt) and a pharmaceutically acceptable vehicle. In one embodiment, the Benzoazolylpiperazine Compound is present in the composition in an effective amount.

4.3.2 Kits

The invention encompasses kits that can simplify the administration of a Benzoazolylpiperazine Compound to an animal.

A typical kit of the invention comprises a unit dosage form of a Benzoazolylpiperazine Compound. In one embodiment, the unit dosage form is a container, which can be sterile, containing an effective amount of a Benzoazolylpiperazine Compound and a pharmaceutically acceptable vehicle. The kit can further comprise a label or printed instructions instructing the use of the Benzoazolylpiperazine Compound to treat pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression. The kit can also further comprise a unit dosage form of another therapeutic agent, for example, a container containing an effective amount of the other therapeutic agent. In one embodiment, the kit comprises a container containing an effective amount of a Benzoazolylpiperazine Compound and an effective amount of another therapeutic agent. Examples of other therapeutic agents include, but are not limited to, those listed above.

Kits of the invention can further comprise a device that is useful for administering the unit dosage forms. Examples of such a device includes, but are not limited to, a syringe, a drip bag, a patch, an inhaler, and an enema bag.

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

5. EXAMPLES

5.1. Example 1

Synthesis of Benzoazolylpiperazine Compounds of Formula (Ia) AAM, AAS, AAQ, AAP, AYF, AYD, AZW, AZZ, AYH, AYE, AYI, AYK, AYG, AYC, AZA, AZD, AYN, and AYM

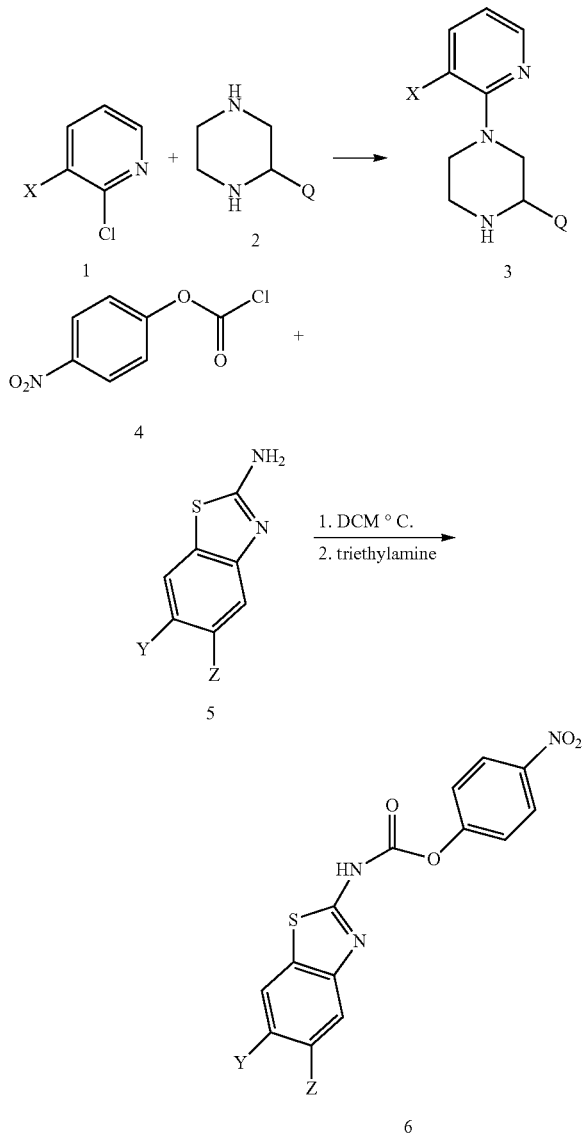

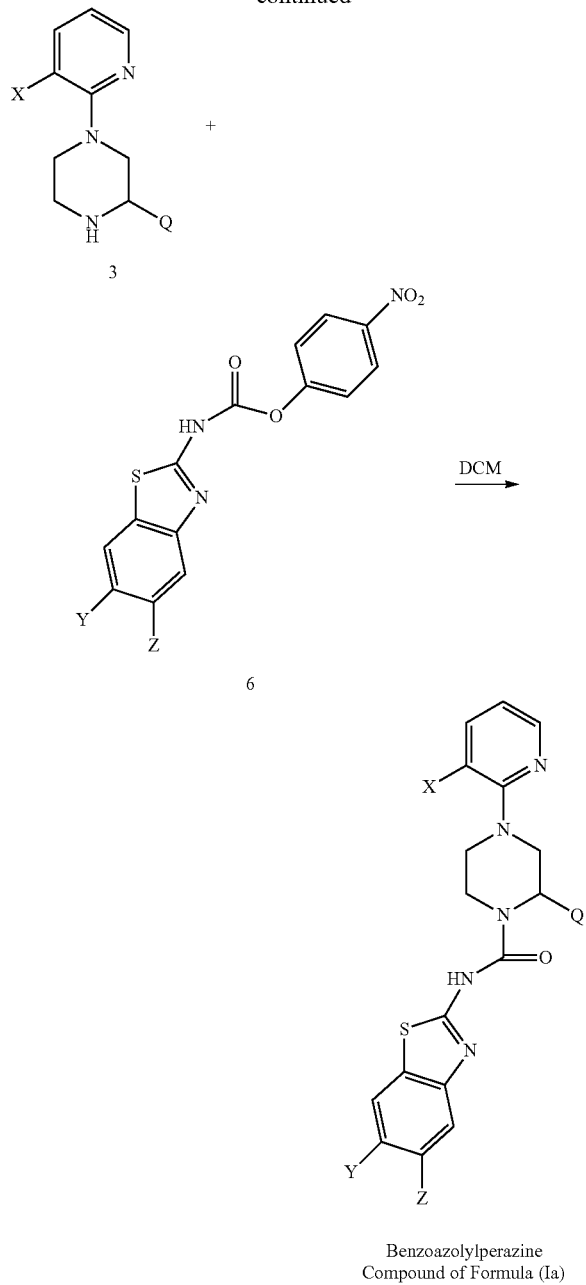

compound 6 at room temperature and the resulting reaction mixture was allowed to stir for about 10 min. The reaction mixture was then concentrated under reduced pressure at 40° C. to provide the Benzoazolylpiperazine Compound of formula (Ia). The Benzoazolylpiperazine Compound of formula (Ia) was purified using a silica gel column eluted with 5:95 ethyl acetate/hexane.

Table XXIII lists the Benzoazolylpiperazine Compounds that were prepared according to the method of Example 1.

TABLE XXIII

| Benzoazolylpiperazine Compound | X | Q | Y | Z |
|---|---|---|---|---|
| AAM | —Cl | —H | —Cl | —H |
| AAS | —Cl | —H | —OCH$_2$CH$_3$ | —H |
| AAQ | —Cl | —H | —CF$_3$ | —H |
| AAP | —Cl | —H | —CH$_3$ | —H |
| AYF | —Cl | (R)—CH$_3$ | —Br | —H |
| AYD | —Cl | (R)—CH$_3$ | —H | —H |
| AZW | —CF$_3$ | (R)—CH$_3$ | —Cl | —H |
| AZZ | —CF$_3$ | (R)—CH$_3$ | —CH$_3$ | —H |
| AYH | —Cl | (R)—CH$_3$ | —CH$_3$ | —H |
| AYE | —Cl | (R)—CH$_3$ | —Cl | —H |
| AYI | —Cl | (R)—CH$_3$ | —CF$_3$ | —H |
| AYK | —Cl | (R)—CH$_3$ | —OCH$_2$CH$_3$ | —H |
| AYG | —Cl | (R)—CH$_3$ | —F | —H |
| AYC | —Cl | (R)—CH$_3$ | —CH$_3$ | —CH$_3$ |
| AZA | —CH$_3$ | (R)—CH$_3$ | —Cl | —H |
| AZD | —CH$_3$ | (R)—CH$_3$ | —CH$_3$ | —H |
| AYN | —Cl | (R)—CH$_3$ | —CH(CH$_3$)$_2$ | —H |
| AYM | —Cl | (R)—CH$_3$ | —C(CH$_3$)$_3$ | —H |

(R)—CH$_3$ means that the carbon atom to which the methyl group is attached is in the (R) configuration.

The identity of Compound AAM was confirmed using H$^1$ NMR.

Compound AAM: $^1$H NMR (400 MHz, CDCl$_3$), δ8.24-8.19 (m, 1H), 7.77-7.76 (m, 1H), 7.67-7.64 (m, 1H), 7.57-7.54 (m, 1H), 7.38-7.36 (m, 1H), 6.95-6.90 (m, 1H), 3.77-3.75 (m, 4H), 3.45-3.42 (m, 4H).

The identity of Compound AAS was confirmed using H$^1$ NMR.

Compound AAS: $^1$H NMR (400 MHz, CDCl$_3$), δ10.17 (s, 1H), 8.19-8.15 (m, 1H), 7.61-7.58 (m, 1H), 7.51-7.46 (m, 1H), 7.28-7.22 (m, 1H), 6.98-6.95 (m, 1H), 6.89-6.86 (m, 1H), 4.11-4.04 (m, 2H), 3.77-3.71 (m, 4H), 3.37-3.34 (m, 4H), 1.43 (t, 3H).

The identity of Compound AAQ was confirmed using H$^1$ NMR.

Compound AAQ: $^1$H NMR (400 MHz, CDCl$_3$): δ8.22-8.19 (m, 1H), 8.09-8.05 (m, 1H), 7.76-7.71 (m, 1H), 7.66-7.64 (m, 2H), 6.94-6.91 (m, 1H), 3.80-3.75 (m, 4H), 3.47-3.45 (m, 4H).

The identity of Compound AAP was confirmed using H$^1$ NMR.

Compound AAP: $^1$H NMR (CDCl$_3$), δ8.22-8.20 (m, 1H), 7.65-7.63 (m, 1H), 7.57-7.55 (m, 1H), 7.52-7.48 (m, 1H), 7.22-7.18 (m, 1H), 6.92-6.87 (m, 1H), 3.78-3.76 (m, 4H), 3.45-3.42 (m, 4H), 2.46 (s, 3H).

The identity of Compound AYF was confirmed using H$^1$ NMR.

Compound AYF: $^1$H NMR (CDCl$_3$), δ 8.23-8.20 (m, 1H), 7.93-7.90 (m, 1H), 7.67-7.62 (m, 1H), 7.54-7.50 (m, 2H), 6.95-6.91 (m, 1H), 4.45 (bs, 1H), 4.11-4.05 (m, 1H), 3.86-3.76 (m, 2H), 3.57-3.46 (m, 1H), 3.12-3.06 (m, 1H), 3.02-2.94 (m, 1H), 1.50 (d, 3H, J=6.8).

The identity of Compound AYD was confirmed using H$^1$ NMR and mass spectrometry.

A solution of 2-chloro-3-X-pyridine 1 (about 0.5M-about 1 M) and 1 eq. of 2-Q-piperazine 2 in DMSO was heated to about 140° C. with stirring for about 2 to 4 h. The resulting reaction mixture was then cooled to room temperature and the DMSO was removed under reduced pressure to provide compound 3.

In a separate flask a solution of 0.75 eq. of chloroformate 4 in dichloromethane (DCM) (0.04M) was cooled to 0° C. and 0.75 eq. of 5-Z-6-Y-benzothiazol-2-ylamine 5 was slowly added to the cooled solution of chloroformate 4. The resulting reaction mixture was stirred at 0° C. for 5 min. and then 5 eq. of triethylamine was added to the reaction mixture. The reaction mixture was then warmed to room temperature and concentrated under reduced pressure at 40° C. to provide compound 6.

Compound 6 was dissolved in DCM (0.1M) and 1 eq. of 3 as a 1 M solution in DCM was added to the solution of Compound AYD: $^1$H NMR (CDCl$_3$), δ 8.83 (br, 1H), 8.24-8.20 (m, 1H), 7.81-7.74 (m, 1H), 7.68-759 (m, 2H), 7.48-7.38 (m, 1H), 7.33-7.24 (m, 2H+CHCl$_3$), 6.96-6.87 (m, 1H), 4.55-4.43 (m, 1H), 4.17-4.06 (m, 1H), 3.89-3.75 (m, 2H), 3.58-3.42 (m, 1H), 3.16-2.89 (m, 1H), 1.45 (d, 3H, J=6.8 Hz).

(M+1) m/z: 388.0.

The identity of Compound AZW was confirmed using H$^1$ NMR.

Compound AZW: $^1$H NMR (CDCl$_3$), δ8.49-8.45 (m, 1H), 7.94-7.90 (m, 1H), 7.57-7.54 (m, 1H), 7.52-7.46 (m, 1H), 7.22-7.18 (m, 1H), 7.11-7.06 (m, 1H), 4.46 (bs, 1H), 4.09-4.00 (m, 1H), 3.52-3.42 (m, 2H), 3.38-3.33 (m, 1H), 3.25-3.19 (m, 1H), 3.04-2.96 (m, 1H), 1.39 (d, 3H, J=6.8).

The identity of Compound AZZ was confirmed using H$^1$ NMR.

Compound AZZ: $^1$H NMR (CDCl$_3$), δ8.50-8.46 (m, 1H), 7.94-7.91 (m, 1H), 7.55 (bs, 1H), 7.51-7.47 (m, 1H), 7.21-7.17 (m, 1H), 7.11-7.06 (m, 1H), 4.45 (bs, 1H), 4.09-4.01 (m, 1H), 3.53-3.45 (m, 2H), 3.41-3.34 (m, 1H), 3.26-3.20 (m, 1H), 3.07-2.95 (m, 1H), 2.46 (s, 3H), 1.38 (d, 3H, J=6.7).

The identity of Compound AYH was confirmed using H$^1$ NMR.

Compound AYH: $^1$H NMR (CDCl$_3$), δ8.71 (bs, 1H), 8.24-8.20 (m, 1H), 7.67-762 (m, 1H), 7.58 (bs, 1H), 7.55-7.49 (m, 1H), 7.25-7.19 (m, 1H), 6.94-6.89 (m, 1H), 4.46 (bs, 1H), 4.14-4.06 (m, 1H), 3.86-3.74 (M, 2H), 3.56-3.43 (m, 1H), 3.13-3.05 (m, 1H), 3.03-2.95 (m, 1H), 2.47 (s, 3H), 1.64 (s, 3H), 1.47 (d, 3H, J=7.0).

The identity of Compound AYE was confirmed using H$^1$ NMR.

Compound AYE: $^1$H NMR (CDCl$_3$), δ8.37 (bs, 1H), 8.24-8.21 (m, 1H), 7.77-7.75 (m, 1H), 7.67-7.64 (m, 1H), 7.61-7.57 (m, 1H), 7.39-7.35 (m, 1H), 6.95-6.90 (m, 1H), 4.40 (bs, 1H), 4.15-4.01 (m, 1H), 3.90-3.77 (m, 1H), 3.58-3.47 (m, 1H), 3.14-3.07 (m, 1H), 3.05-2.96 (m, 1H), 1.51 (d, 3H, J=6.8).

The identity of Compound AYI was confirmed using H$^1$ NMR.

Compound AYI: $^1$H NMR (CDCl$_3$), δ9.31 (bs, 1H), 8.22-8.19 (m, 1H), 8.08 (bs, 1H), 7.76-7.70 (m, 1H), 7.68-7.61 (m, 2H), 6.94-6.89 (m, 1H), 4.46 (bs, 1H), 4.11-4.02 (m, 1H), 3.85-3.74 (m, 2H), 3.59-3.48 (m, 1H), 3.12-3.05 (m, 1H), 3.02-2.92 (m, 1H), 1.49 (d, 3H, J=6.8).

The identity of Compound AYK was confirmed using H$^1$ NMR.

Compound AYK: $^1$H NMR (CDCl$_3$), δ9.40 (bs, 1H), 8.22-8.18 (m, 1H), 7.64-7.60 (m, 1H), 7.57-7.51 (m, 1H), 7.30-7.25 (m, 1H+CHCl$_3$), 7.03-6.97 (m, 1H), 6.93-6.88 (m, 1H), 4.45 (bs, 1H), 4.14-4.00 (m, 3H), 3.81-3.69 (m, 2H), 3.53-3.43 (m, 1H), 3.09-3.02 (m, 1H), 3.00-2.91 (m, 1H), 1.48-1.43 (m, 6H).

The identity of Compound AYG was confirmed using H$^1$ NMR.

Compound AYG: NMR (CDCl$_3$), δ8.41 (bs, 1H), 8.24-8.20 (m, 1H), 7.68-7.56 (m, 2H), 7.52-7.46 (m, 1H), 7.18-7.11 (m, 1H), 6.95-6.90 (m, 1H), 4.41 (bs, 1H), 4.09-4.02 (m, 1H), 3.89-3.77 (m, 2H), 3.58-3.49 (m, 1H), 3.14-307 (m, 1H), 3.05-2.96 (m, 1H), 1.5 (d, 3H, J=6.8).

The identity of Compound AYC was confirmed using H$^1$ NMR.

Compound AYC: $^1$H NMR (CDCl$_3$), δ8.23-8.19 (m, 1H), 765-7.61 (m, 1H), 7.52 (bs, 1H), 7.40 (bs, 1H), 6.93-6.88 (m, 1H), 4.50 (bs, 1H), 4.17-4.06 (m, 1H), 3.84-3.73 (m, 2H), 3.56-3.44 (m, 1H), 3.11-3.03 (m, 1H), 3.01-2.92 (m, 1H), 2.36 (s, 6H), 1.48 (d, 3H, J=6.8).

The identity of Compound AZA was confirmed using H$^1$ NMR.

Compound AZA: $^1$H NMR (CDCl$_3$), δ8.93 (bs, 1H), 8.17-8.14 (m, 1H), 8.00-7.96 (m, 1H), 7.77 (bs, 1H), 7.60-7.53 (m, 1H), 7.41-7.33 (m, 1H), 4.49 (bs, 1H), 4.16-4.06 (m, 1H), 4.00-3.94 (m, 2H), 3.57-3.46 (m, 1H), 3.19-3.11 (m, 1H), 3.07-2.98 (m, 1H), 1.70 (s, 3H), 1.47 (d, 3H, J=6.8).

The identity of Compound AZD was confirmed using H$^1$ NMR.

Compound AZD: $^1$H NMR (CDCl$_3$), δ8.68 (bs, 1H), 8.21-8.18 (m, 1H), 7.61-7.43 (m, 3H), 7.24-7.19 (m, 1H), 6.94-6.90 (m, 1H), 4.45 (bs, 1H), 4.13-4.04 (m, 1H), 3.54-3.41 (m, 2H), 3.37-3.32 (m, 1H), 3.12-3.04 (m, 1H), 3.64-2.90 (m 1H), 2.46 (s, 3H), 2.35 (s, 3H), 1.48 (d, 3H, J=6.8).

The identity of Compound AYN was confirmed using H$^1$ NMR.

Compound AYN: $^1$H NMR (CDCl$_3$), δ8.20-8.18 (m, 1H), 7.64-7.59 (m, 1H), 7.58-7.50 (m, 1H), 7.29-7.25 (m, 1H+CHCl$_3$), 6.91-6.87 (m, 1H), 4.49 (bs, 1H), 4.14-4.05 (m, 1H), 3.79-3.68 (m, 2H), 3.07-2.89 (m, 3H), 1.44 (d, 3H, J=6.8), 1.31 (d, 3H, =7.0).

The identity of Compound AYM was confirmed using H$^1$ NMR.

Compound AYM: $^1$H NMR (CDCl$_3$), δ8.24-8.20 (m, 1H), 7.76 (bs, 1H), 7.66-7.62 (m, 1H), 7.55-7.52 (m, 1H), 7.49-7.43 (m, 1H), 6.94-6.89 (m, 1H), 4.46 (bs, 1H), 4.16-4.07 (m, 1H), 3.87-3.73 (m, 2H), 3.56-3.45 (m, 1H), 3.14-3.05 (m, 1H), 3.04-2.91 (m, 1H), 1.49 (d, 3H, J=6.8), 1.40 (s, 9H).:

5.2. Example 2

Synthesis of Benzoazolylpiperazine Compounds of Formula (Ib) BDJ and BDG

Compounds BDJ and BDG were prepared by a method analogous to that used in Example 1 except that 2,3-dichloropyrazine was used in place of 2-chloro-3-X-pyridine 1. In the preparation of Compound BDJ, the 2-Q-piperazine 2 was (R)-2-methylpiperidine and the 5-Z-6-Y-benzothiazol-2-ylamine 5 was 6-methyl benzothiazol-2-ylamine. In the preparation of Compound BDG, the 2-Q-piperazine 2 was (R)-2-methylpiperidine and the 5-Z-6-Y-benzothiazol-2-ylamine 5 was 6-chloro benzothiazol-2-ylamine.

The identity of Compound BDJ was confirmed using H$^1$ NMR.

Compound BDJ: $^1$H NMR (CDCl$_3$), δ8.16-8.13 (m, 1H), 7.96-7.93 (m, 1H), 7.56 (bs, 1H), 7.47 (bs, 1H), 7.22-7.18 (m, 1H), 4.56 (bs, 1H), 4.19-4.13 (m, 1H), 3.94-3.85 (m, 2H), 3.49-3.41 (m, 1H), 3.13-3.06 (m, 1H), 3.01-2.94 (m, 1H), 2.45 (s, 3H), 1.41 (d, 3H, J=6.9).

The identity of Compound BDG was confirmed using H$^1$ NMR.

Compound BDG: $^1$H NMR (CDCl$_3$), δ8.66 (bs, 1H), 8.17-8.15 (m, 1H), 8.00-7.97 (m, 1H), 7.76 (bs, 1H), 7.59-7.54 (m, 1H), 7.40-7.35 (m, 1H), 4.47 (bs, 1H), 4.16-4.07 (m, 1H), 4.02-3.92 (m, 2H), 3.57-3.48 (m, 1H), 3.20-3.13 (m, 1H), 3.09-2.98 (m, 1H), 1.48 (d, 3H, J=6.8).

5.3. Example 3

Synthesis of Benzoazolylpiperazine Compounds of Formula (Ib) BIL, BII, and BJE

Compounds BIL BII, and BJE were prepared by a method analogous to that used in Example 1 except that 4,5-dichlorothiadiazole was used in place of 2-chloro-3-X-pyridine 1 to make Compounds BIL and BII and 4-methyl-5-chlorothiadiazole was used to make Compound BJE. In the preparation of Compound BIL, the 2-Q-piperazine 2 was (R)-2-methylpiperidine and the 5-Z-6-Y-benzothiazol-2-ylamine 5 was 6-methyl benzothiazol-2-ylamine. In the preparation of Compounds BII, and BJE the 2-Q-piperazine 2 was (R)-2-methylpiperidine and the 5-Z-6-Y-benzothiazol-2-ylamine 5 was 6-chloro benzothiazol-2-ylamine.

The identity of Compound BIL was confirmed using $H^1$ NMR.

Compound BIL: $^1$H NMR (CDCl$_3$), δ7.54 (bs, 1H), 7.49-7.42 (m, 1H), 7.24-7.17 (m, 1H), 4.55 (bs, 1H), 4.24-4.15 (m, 1H), 4.02-3.89 (m, 2H), 3.54-3.39 (m, 1H), 3.21-3.12 (m, 1H), 3.11-3.02 (m, 1H), 2.46 (s, 3H), 1.46 (d, 3H, J=6.8).

The identity of Compound BII was confirmed using $H^1$ NMR.

Compound BII: $^1$H NMR (CDCl$_3$), δ8.64 (bs, 1H), 7.75 (bs, 1H), 7.58-7.51 (m, 1H), 7.41-7.34 (m, 1H), 4.50 (bs, 1H), 4.18-4.06 (m, 1H), 4.01-3.92 (m, 2H), 3.56-3.44 (m, 1H), 3.21-3.13 (m, 1H), 3.12-3.04 (m, 1H), 1.48 (d, 3H, J=6.8).

The identity of Compound BJE was confirmed using $H^1$ NMR.

Compound BJE: $^1$H NMR (CDCl$_3$), δ8.59 (bs, 1H), 7.73 (bs, 1H), 7.53-7.47 (m, 1H), 7.41-7.34 (m, 1H), 4.55 (bs, 1H), 4.23-4.14 (m, 1H), 3.59-3.46 (m, 1H), 3.43-3.38 (m, 1H), 3.37-3.28 (m, 1H), 3.11-3.02 (m, 1H), 3.00-2.90 (m, 1H), 2.65 (s, 3H), 1.61 (d, 3H, J=6.8).

5.4. Example 4

Synthesis of Benzoazolylpiperazine Compound of Formula (IIa) and (IIb) CBG, CAW, CRU, CSE, DIS, DJC, DIQ, CSE, EAA, DZU, CTA, CTW, CRW, and CSB

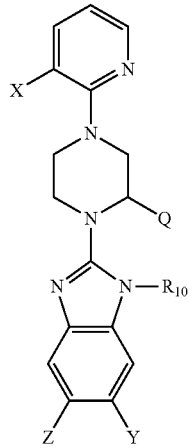

Benzoazolylperazine Compound of Formula (IIa) and (IIb)

A solution of 2-chloro-3-X-pyridine 1 (about 0.5 M to about 1M) and 1 eq. of 2-Q-piperazine 2 in DMSO was heated to about 140° C. with stirring for about 2 to 4 h. The resulting reaction mixture was then cooled to room temperature and the DMSO was removed under reduced pressure to provide compound 3.

A solution of compound 3 (about 0.25 mmol-about 1 mmol) and 1 eq. of compound 7 in about 3 mL of toluene or xylene was heated at a temperature of between about 140° C. and 150° C. for about 3 days. The resulting reaction mixture was then concentrated under reduced pressure to provide a residue that was purified using flash chromatography (silica gel, gradient elution 2% methanol:DCM to 6% methanol:DCM).

Compound 7, wherein $R_{10}$ is —H was either commercially available or obtained from commercially available compounds 8 as illustrated below

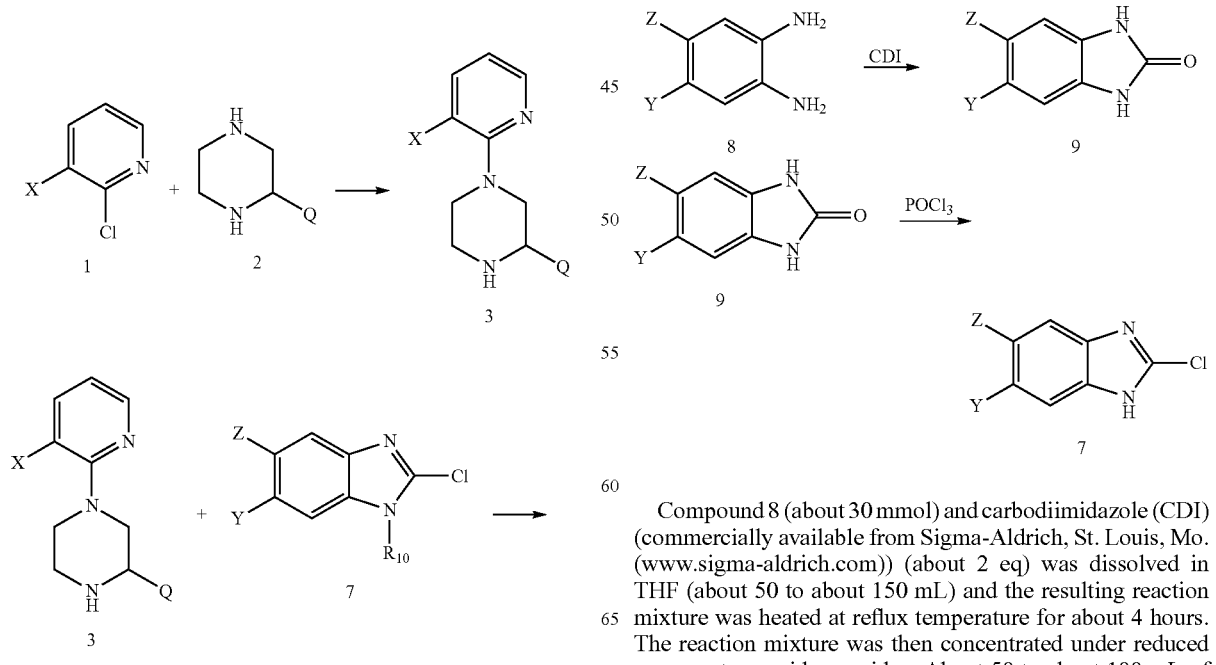

Compound 8 (about 30 mmol) and carbodiimidazole (CDI) (commercially available from Sigma-Aldrich, St. Louis, Mo. (www.sigma-aldrich.com)) (about 2 eq) was dissolved in THF (about 50 to about 150 mL) and the resulting reaction mixture was heated at reflux temperature for about 4 hours. The reaction mixture was then concentrated under reduced pressure to provide a residue. About 50 to about 100 mL of ethyl acetate or ethyl acetate/hexane (20:80 to about 40:60) was added to the residue and the resulting insoluble material was collected by filtration and washed with ethyl acetate or ethyl acetate/hexane (20:80 to about 40:60) to provide compound 9. Compound 9 was then reacted with POCl₃ according to the procedure described in *J. Med. Chem.* 40:586-593 (1997) to provide compound 7.

Compound 7, wherein $R_{10}$ is —$CH_3$ was obtained from compound 7 wherein $R_{10}$ is —H as illustrated below

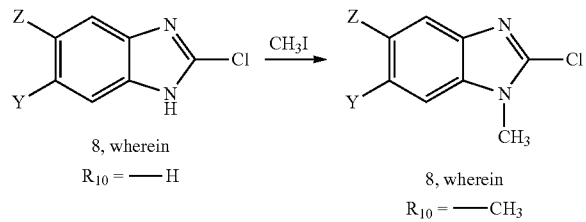

NaH (about 2 eq) was added to a solution of a compound of Formula 8 wherein $R_{10}$ is —H in DMF at 0° C. and the resulting mixture was allowed to stir and to warm to room temperature over a period of about one hour. Methyl iodide (about 1.2 eq) was then added to the solution and the resulting reaction mixture was allowed to stir for several minutes. Water was then added to the reaction mixture to produce a precipitate of compound 8 wherein $R_{10}$ is —$CH_3$ which was filtered, collected, and dried.

Table XXIV lists the Benzoazolylpiperazine Compounds that were prepared according to the method of Example 4.

TABLE XXIV

| Benzoazolyl-piperazine Compound | $R_{10}$ | Y | Z | X | Q |
|---|---|---|---|---|---|
| CBG | —H | -tert-butyl | —H | —Cl | —H |
| CAW | —H | —$CH_3$ | —$CH_3$ | —Cl | —H |
| CRU | —H | —$CH_3$ | —$CH_3$ | —Cl | (R)—$CH_3$ |
| CRU | —H | —$CH_3$ | —$CH_3$ | —Cl | (S)—$CH_3$ |
| CSE | —H | -tert-butyl | —H | —Cl | (R)—$CH_3$ |
| DIS | —$CH_3$ | —$CH_3$ | —$CH_3$ | —Cl | —H |
| DJC | —$CH_3$ | -tert-butyl | —H | —Cl | —H |
| DIQ | —$CH_3$ | —H | -tert-butyl | —Cl | —H |
| CSE | —H | -tert-butyl | —H | —Cl | (S)—$CH_3$ |
| EAA | —$CH_3$ | -tert-butyl | —H | —Cl | (R)—$CH_3$ |
| DZO | —$CH_3$ | —H | -tert-butyl | —Cl | (R)—$CH_3$ |
| CTA | —H | -tert-butyl | —H | —$CH_3$ | (R)—$CH_3$ |
| CTW | —H | -tert-butyl | —H | —$CF_3$ | (R)—$CH_3$ |
| CRW | —H | —Cl | —H | —Cl | (R)—$CH_3$ |
| CSB | —H | —$OCH_3$ | —H | —Cl | (R)—$CH_3$ |

(R)—$CH_3$ means that the carbon atom to which the methyl group is attached is in the (R) configuration. (S)—$CH_3$ means that the carbon atom to which the methyl group is attached is in the (S) configuration.

The identity of Compound CBG was confirmed using $H^1$ NMR and mass spectrometry.

Compound CBG: $^1H$ NMR (CD₃OD), δ 8.21(dd, 1H, J1=1.6 Hz, J2=4.8 Hz); 7.77(dd, 1H, J1=1.6 Hz, J2=7.6 Hz); 7.34(d, 1H, J=2 Hz); 7.21(d, 1H, J1=0.4 Hz, J2=8.4 Hz); 7.14(dd, 1H, J1=2 Hz, J2=8.4 Hz); 7.01(dd, 1H, J1=4.8 Hz, J2=7.6 Hz); 3.70(m, 4H); 3.49(m, 4H); 1.37(s, 9H).

MS: 370.2 (M+1).

The identity of Compound CAW was confirmed using $H^1$ NMR and mass spectrometry.

Compound CAW: $^1H$ NMR (CD₃OD), δ 8.25(dd, 1H, J1=1.6 Hz, J2=4.8 Hz); 7.82(dd, 1H, J1=1.6 Hz, J2=8 Hz); 7.06(dd, 1H, J1=4.8 Hz, J2=7.6 Hz); 3.82(m, 4H); 3.58(m, 4H); 2.38(s, 6H).

MS: 342.1(M+1).

The identity of Compound CRU wherein Q is (R)-$CH_3$ was confirmed using $H^1$ NMR and mass spectrometry.

Compound CRU wherein Q is (R)-$CH_3$: $^1H$ NMR (CD₃OD), δ 8.25(dd, 1H, J1=1.6 Hz, J2=4.8 Hz); 7.82(dd, 1H, J1=2 Hz, J2=8 Hz); 7.07(dd, 1H, J1=4.4 Hz, J2=8 Hz); 4.30(m 1H); 3.90(m, 4H); 3.26(dd, 1H, J1=13 Hz, J2=1.6 Hz); 3.17(m, 1H); 2.38(s, 6H); 1.59(d, 3H, J=6.8 Hz).

MS: 356.1(M+1).

The identity of Compound CRU wherein Q is (S)-$CH_3$ was confirmed using $H^1$ NMR and mass spectrometry.

Compound CRU wherein Q is (S)-$CH_3$: $^1H$ NMR (CD₃OD), δ 8.25(dd, 1H, J1=1.2 Hz, J2=4.4 Hz); 7.81(dd, 1H, J1=1.6 Hz, J2=7.6 Hz); 7.07(dd, 1H, J1=4.8 Hz, J2=7.6 Hz); 4.31(m, 1H); 3.88(m, 4H); 3.26(dd, 1H, J1=3.6 Hz, J2=13 Hz); 3.16(m, 1H); 2.38(s, 6H); 1.59(d, 3H, J=6.4 Hz).

MS: 356.1(M+1).

The identity of Compound CSE wherein Q is (R)-$CH_3$ was confirmed using $H^1$ NMR and mass spectrometry.

Compound CSE wherein Q is (R)-$CH_3$: $^1H$ NMR (CD₃OD), δ 8.22(dd, 1H, J1=1.6 Hz, J2=4.8 Hz0; 7.78(dd, 1H, J1=1.6 Hz, J2=7.6 Hz0; 7.33(dd, 1H, J1=0.8 Hz, J2=2 Hz); 7.19(dd, 1H, J1=0.8 Hz, J2=8.4 Hz0; 7.12(dd, 1H, J1=1.6 Hz, J2=8.4 Hz); 7.02(dd, 1H, J1=4.8 Hz, J2=8 Hz); 4.37(m, 1H); 3.84(m, 3H): 3.58(m, 1H); 3.20(dd, 1H, J1=4 Hz, J2=12 Hz); 3.08(dt, 1H, J1=3.2 Hz, J2=12 Hz); 1.45(d, 3H, J=6.4 Hz); 1.37(s, 9H).

MS: 420(M+36).

The identity of Compound DIS was confirmed using $H^1$ NMR and mass spectrometry.

Compound DIS: $^1H$ NMR (CD₃OD), δ 8.23(dd, 1H, J1=1.6 Hz, J2=4.8 Hz); 7.78(dd, 1 h, J1=2 Hz, J2=8 Hz); 727(bs, 1H); 7.14(bs, 1H); 7.02(dd, 1H, J1=4.8 Hz, J2=7.6 Hz); 3.69(s, 3H); 3.56(m, 4H); 3.45(m, 4H); 2.39(s, 3H); 2.35(s, 3H).

MS: 356.1(M+1).

The identity of Compound DJC was confirmed using $H^1$ NMR and mass spectrometry.

Compound DJC: $^1H$ NMR (CD₃OD), δ 8.23(dd, 1H, J1=1.6 Hz, J2=4.8 Hz); 7.78(dd, 1H, J1=2 Hz, J2=8 Hz); 7.53(dd, 1H, J1=0.8 Hz, J2=2 Hz); 7.31(dd, 1H, J1=1.6 Hz, J2=8.4 Hz); 7.26(dd, 1H, J1=0.4 Hz, J2=8.4 Hz); 7.02(dd, 1H, J1=4.8 Hz, J2=8 Hz); 3.70(s, 3H); 3.57(m, 4H); 3.47(m, 4H); 1.39(s, 9H).

MS: 384.1(M+1).

The identity of Compound DIQ was confirmed using $H^1$ NMR and mass spectrometry.

Compound DIQ: $^1H$ NMR (CD₃OD), δ 8.23(dd, 1H, J1=1.6 Hz, J2=4.8 Hz); 7.78(dd, 1H, J1=2 Hz, J2=8 Hz); 7.41(dd, 1H, J1=0.4 Hz, J2=8.4 Hz); 7.36(d, 1H, J=1.2 Hz); 7.29(dd, 1H, J1=1.6 Hz, J2=8.4 Hz); 7.02(dd, 1H, J1=4.8 Hz, J2=7.6 Hz); 3.70(s, 3H); 3.57(m, 4H); 3.47(m, 4H); 1.41(s, 9H).

MS: 384.1(M+1).

The identity of Compound CSE wherein Q is (S)-$CH_3$ was confirmed using $H^1$ NMR and mass spectrometry.

Compound CSE wherein Q is (S)-$CH_3$: $^1H$ NMR (CD₃OD), δ 8.22(dd, 1H, J1=1.6 Hz, J2=4.8 Hz); 7.78(dd, 1H, J1=1.6 Hz, J2=7.6 Hz); 7.34(d, 1H, J=1.6 Hz); 7.20(d, 1H, J=8.4 Hz); 7.13(dd, 1H, J1=2 Hz, J2=8.4 Hz); 7.02(dd, 1H, J1=4.8 Hz, J2=8 Hz); 4.36(m, 1H); 3.85(m, 3H); 3.60(dt, 1H, J1=2.8 Hz, J2=12 Hz); 3.20(dd, 1H, J1=4 Hz, J2=12 Hz); 3.08(dt, 1H, J1=3.2 Hz, J2=13 Hz); 1.45(d, 3H, J=6.4 Hz); 1.37(s, 9H).

MS: 420(M+36).

The identity of Compound EAA wherein Q is (R)-$CH_3$ was confirmed using $H^1$ NMR and mass spectrometry.

Compound EAA wherein Q is (R)-CH$_3$: $^1$H NMR (DMSO d$_6$), δ 8.23(dd, 1H, J1=1.6 Hz, J2=2.8 Hz); 7.63(dd, 1H, J1=1.6 Hz, J2=7.6 Hz); 7.61(d, 1H, J1=8.4 Hz); 7.32(dd, 1H, J=2 Hz, J2=8 Hz); 7.26(dd, 1H, J1=1.6 Hz, J2=8 Hz); 6.90 (dd, 1H, J1=4.8 Hz, J2=8 Hz); 3.80(m, 1H); 3.70(s, 3H); 3.69(dd, 1H, J1=2.8 Hz, J2=12 Hz); 3.63(m, 1H); 3.45(m, 2H); 3.35(m, 1H); 3.24(dd, 1H, J1=7.6 Hz, J2=12 Hz); 1.43(s, 9H); 1.20(d, 3H, J=6.4 Hz).

MS: 398.1(M+1).

The identity of Compound DZO wherein Q is (R)-CH$_3$ was confirmed using H$^1$ NMR and mass spectrometry.

Compound DZO wherein Q is (R)-CH$_3$: $^1$H NMR (DMSO d$_6$), δ 8.23(dd, 1H, J1=2 Hz, J2=4.8 Hz); 7.75(d); 7.63(dd, 1H, J1=2 Hz, J2=7.6 Hz); 7.32(dd, 1H, J1=2 Hz, J2=8.4 Hz); 7.20(d, 1H, J=8.4 Hz); 6.89(dd, 1H, J1=4.8 Hz, J2=7.6 Hz); 3.82(m, 1H); 3.68(s, 3H); 3.68(m, 1H); 3.61(m, 1H); 3.48(m, 2H); 3.37(m, 1H); 3.28(dd, 1H, J1=8 Hz, J2=12 Hz); 1.41(s, 9H); 1.22(d, 3H, J=6.4 Hz).

MS: 398.3(M+1).

The identity of Compound CTA wherein Q is (R)-CH$_3$ was confirmed using H$^1$ NMR and mass spectrometry.

Compound CTA wherein Q is (R)-CH$_3$: $^1$H NMR (CDCl$_3$), δ 8.17(d, 1H, J=4.8 Hz); 7.44(d, 1H, J=7.6 Hz); 7.42(s, 1H); 7.27(d, 1H, J=8.4 Hz); 7.13(d, 1H, J=8.4 Hz); 6.91(dd, 1H, J1=4.8 Hz, J2=7.2 Hz); 4.42(m, 1H); 3.97(d, 1H, J=12 Hz); 3.62(dt, 1H, J1=3.2 Hz, J2=12 Hz); 3.47(d, 1H, J=12 Hz); 3.33(d, 1H, J=13 Hz); 3.18(dd, 1H, J1=3.2 Hz, J2=12 Hz); 3.06(dt, 1H, J1=2.8 Hz, J2=˜12 Hz); 2.32(s, 3H); 1.45(d, 3H, J=6.8 Hz); 1.33(s, 9H).

MS: 364.2(M+1).

The identity of Compound CTW wherein Q is (R)-CH$_3$ was confirmed using H$^1$ NMR and mass spectrometry.

Compound CTW wherein Q is (R)-CH$_3$: $^1$H NMR (CDCl$_3$), δ 8.49(d, 1H, J=4.8 Hz); 7.93(dd, 1H, J1=1.6 Hz, J2=8.0 Hz); 7.42(s, 1H); 7.26(d, 1H, J=8.4 Hz); 7.14(dd, 1H, J1=1.6 Hz, J2=8.4 Hz); 7.08(dd, 1H, J1=4.8 Hz, J2=8.0 Hz); 4.37(m, 1H); 3.89(d, 1H, J=12 Hz); 3.64(dt, 1H, J1=3.2 Hz, J2=12 Hz); 3.56(d, 1H, J=13 Hz); 3.45(d, 1H, J=13 Hz); 3.37(dd, 1H, J1=3.6 Hz, J2=12 Hz); 3.17(dt, 1H, J1=3.2 Hz, J2=12 Hz); 1.39(d, 3H, J=6.8 Hz); 1.35(s, 9H).

MS: 418.2(M+1).

The identity of Compound CRW wherein Q is (R)-CH$_3$ was confirmed using H$^1$ NMR and mass spectrometry.

Compound CRW wherein Q is (R)-CH$_3$: $^1$H NMR (CD$_3$OD), δ 8.21(dd, 1H, J1=1.6 Hz, J2=4.8 Hz); 7.78(dd, 1H, J1=1.6 Hz, J2=7.6 Hz); 7.24(s, 1H); 7.20(d, 1H, J=8 Hz); 7.02(dd, 1H, J1=4.8 Hz, J2=8 Hz); 7.01(d, 1H, J=8 Hz); 4.36(m, 1H); 3.86(m, 3H); 3.62(dt, 1H, J1=3.2 Hz, J2=12 Hz); 3.18(dd, 1H, J1=2.8 Hz, J2=13 Hz); 3.07(dt, 1H, J1=3.2 Hz, J2=13 Hz); 1.46(d, 3H, J=6.8 Hz).

MS: 362.1(M+1).

The identity of Compound CSB wherein Q is (R)-CH$_3$ was confirmed using H$^1$ NMR and mass spectrometry.

Compound CSB wherein Q is (R)-CH$_3$: $^1$H NMR (CD$_3$OD), δ 8.24(dd, 1H, J1=1.8 Hz, J2=4.8 Hz); 7.80(dd, 1H, J1=1.8 Hz, J2=7.9 Hz); 4.31(m, 1H); 3.91(m, 2H); 3.80 (dt, 1H, J1=3.5 Hz, J2=12 Hz); 3.25(dd, 1H, J1=3.2 Hz, J2=12 Hz); 3.15(dt, 1H, J1=4.0 Hz, J2=12 Hz); 1.56(d, 3H, J=6.6 Hz).

MS: 358.1(M+1).

5.5. Example 5

Synthesis of Benzoazolylpiperazine Compound of Formula (IIb) DCI(b)

Compound DCI(b) wherein R$_3$ is (R)-CH$_3$ was prepared by a method analogous to that used in Example 4 except that 4,5-dichlorothiadiazole was used in place of 2-chloro-3-X-pyridine 1 and the 2-Q-piperazine 2 was 2-(R)-methylpiperazine and the 5-Z-6-Y-2-chloro-1-H-benzoimidazole 7 was 6-tent-butyl-2-chloro-1-H-benzo-imidazole.

The identity of Compound DCI(b) wherein Q is (R)-CH$_3$ was confirmed using H$^1$ NMR and mass spectrometry.

Compound DCI(b) wherein Q is (R)-CH$_3$: $^1$H NMR (CD$_3$OD), δ 7.34(s, 1H); 7.20(d, 1H, J=8.4 Hz); 7.13(dd, 1H, J1=1.6 Hz, J2=8.4 Hz); 4.38(m, 1H); 4.05(bd, 2H, J=12 Hz); 3.90(bd, 1H, J=13 Hz); 3.58(dt, 1H, J1=3.6 Hz, J2=12 Hz); 3.27(dd, 1H, J1=3.6 Hz, J2=12 Hz); 3.20(dt, 1H, J1=3.6 Hz, J2=12 Hz); 1.43(d, 3H, J=6.4 Hz); 1.37(s, 9H).

MS: 391.1(M+1).

5.6. Example 6

Synthesis of Benzoazolylpiperazine Compound of Formula 10

Benzoazolylpiperazine compound of Formula 10

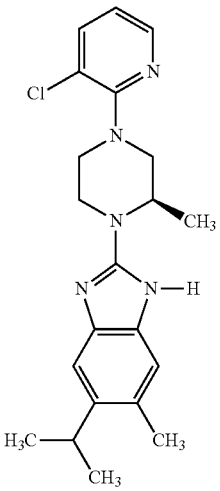

was prepared by a method analogous to that used in Example 4 using compound 7 wherein Y is —CH$_3$ and Z is —CH(CH$_3$)$_2$ and 2-(R)-methylpiperazine for the 2-Q-piperazine 2.

The identity of Compound 10 wherein Q is (R)-CH$_3$ was confirmed using H$^1$ NMR and mass spectrometry.

Compound 10 wherein Q is (R)-CH$_3$: $^1$H NMR (CD$_3$OD), δ 8.22(dd, 1H, J1=1.8 Hz, J2=4.9 Hz); 7.78(dd, 1H, J1=1.6 Hz, J2=8.0z); 7.20(s, 1H); 7.04(dd, 1H, J1=4.9 Hz, J2=7.7 Hz); 4.35(m, 1H); 3.85(m, 3H); 3.62(dt, 1H, J1=3.3 Hz, J2=12 Hz); 3.21(m, 2H); 3.06(dt, 1H, J1=4.0 Hz, J2=13 Hz); 2.40(s, 3H); 1.47(d, 3H, J=6.8 Hz); 1.27(d, 6H, J=6.8 Hz).

MS: 384.1(M+1).

5.7. Example 7

Synthesis of Benzoazolylpiperazine Compound of Formula (IIIa) FUY, and EXG

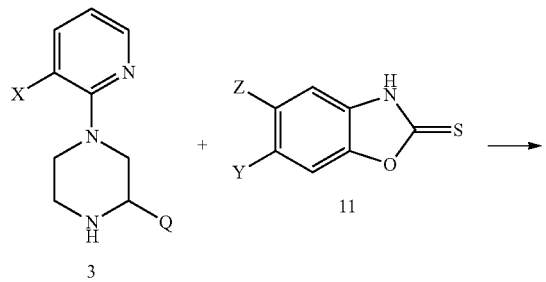

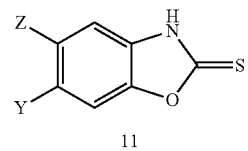

Benzoazolylperazine Compound of Formula (IIIa)

Compound 3 (about 1 mmol), prepared as described above in Example 5.1 and 1 eq. of compound II were dissolved in toluene or p-xylene (about 0.5 to about 1 mL) and the resulting reaction mixture was heated in a sealed tube at a temperature of about 150° C. for about 24 h. The reaction mixture was then concentrated under reduced pressure to provide a residue. The resulting residue was purified using flash chromatography (silica gel, 5% methanol:DCM) to provide the Benzoazolylpiperazine Compounds of formula (IIIa).

Compound 11 was obtained as described below

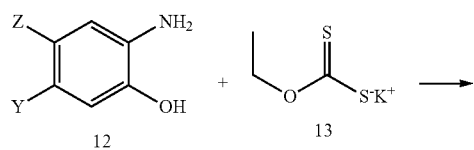

Compound 12 (about 15 to about 20 mmol) and 1 eq. of compound 13, were dissolved in ethanol (about 30 to about 40 mL) and the resulting reaction mixture heated at reflux temperature for about 5 h. The reaction mixture was then concentrated under reduced pressure to provide a residue that was diluted with water (about 30 mL) and acidified with acetic acid to a pH value of about 6. The aqueous mixture was extracted with ethyl acetate, the ethyl acetate dried ($Na_2SO_4$), and the solvent removed under reduced pressure to provide compound 7 that was used without further purification.

Table XXV lists the Benzoazolylpiperazine Compounds that were prepared according to the method of Example 7.

TABLE XXV

| Benzoazolylpiperazine Compound | Y | Z | X | Q |
| --- | --- | --- | --- | --- |
| FUY | —H | tert-butyl | —Cl | (R)—$CH_3$ |
| EXG | —H | tert-butyl | —Cl | —H |

(R)—$CH_3$ means that the carbon atom to which the methyl group is attached is in the (R) configuration.

The identity of Compound FUY was confirmed using $H^1$ NMR and mass spectrometry.

Compound FUY: $^1$H NMR ($CDCl_3$), δ 8.23(dd, 1H, J1=1.6 Hz, J2=4.8 Hz); 7.65(dd, 1H, J1=2 Hz, J2=7.6 Hz); 7.47(d, 1H, J=2 Hz); 7.20(d, 1H, J=8.4 Hz); 7.10(dd, 1H, J1=2 Hz, J2=8.4 Hz); 6.91(dd, 1H, J1=4.8 Hz, J2=8 Hz); 4.60(m, 1H); 4.60(d, 1H, J=13 Hz); 3.84(m, 2H); 3.67(dt, 1H, J1=3.6 Hz, J2=13 Hz); 3.17(dd, 1H, J1=4 Hz, J2=12 Hz); 3.08(dt(1H, J1=3.2 Hz, J2=12 Hz); 1.52(d, 3H, J=6.8 Hz); 1.37(s, 9H).

MS: 385.2(M+1).

The identity of Compound EXG wherein Q is (R)-$CH_3$ was confirmed using $H^1$ NMR and mass spectrometry.

Compound EXG: $^1$H NMR ($CDCl_3$), δ 8.23(dd, 1H, J1=1.6 Hz, J2=4.8 Hz); 7.65(dd, 1H, J1=2 Hz, J2=7.6 Hz); 7.46(d, 1H, J=1.6 Hz); 7.20(dd, 1H, J1=0.4 Hz, J2=8.4 Hz); 7.10(dd, 1H, J1=2 Hz, J2=8.4 Hz);6.91(dd, 1H, J1=5.2 Hz, J2=7.6 Hz); 3.88(m, 4H); 3.50(m, 4H); 1.37(s, 9H).

MS: 371.1(M+1).

5.8. Example 8

Synthesis of Benzoazolylpiperazine Compound of Formula (IIIa) FIU

Compound FIU was prepared by a method analogous to that used in Example 1 except that 5-chloro-benzooxoazol-2-ylamine was used in place of the 5-Z-6-Y-benzothiazol-2-ylamine.

The identity of Compound FIU was confirmed using $H^1$ NMR.

Compound FIU: $^1$H NMR ($CDCl_3$), δ11.45 (bs, 1H), 8.23-8.18 (m, 1H), 7.66-7.61 (m, 1H), 7.25-7.21 (m, 1H), 7.18-7.12 (m, 1H), 6.92-6.86 (m, 1H), 5.06-4.71 (m, 1H), 4.67-4.32 (m, 1H), 3.87-3.72 (m, 2H), 3.56-3.29 (m, 1H), 3.07-2.86 (m, 2H), 1.45 (d, 3H, J=6.8).

5.9. Example 9

Synthesis of Benzoazolylpiperazine Compound of Formula 14

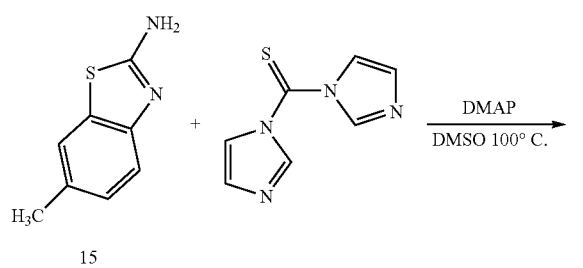

15

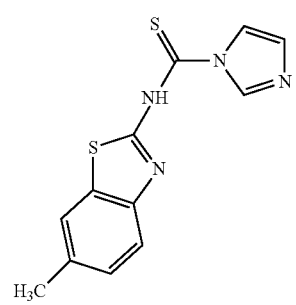

14

2-Amino-6-methyl-benzothiazole 15 (2.0 mmol, 328 mg) (commercially available from Sigma-Aldrich, St. Louis, Mo. (www.sigma-aldrich.com)) and 1,1'-thiocarbonyldiimidazole (2.0 mmol, 356 mg) (commercially available from Sigma-Aldrich, St. Louis, Mo. (www.sigma-aldrich.com)) were suspended in DMSO (3 mL). 4-Dimethyl-aminopyridine (30 mg) (commercially available from Sigma-Aldrich, St. Louis, Mo. (www.sigma-aldrich.com)) was then added to the suspension and the resulting reaction mixture heated to 100° C. and stirred at 100° C. for about 6 hours. The reaction mixture was then cooled to room temperature and (R)-4-(3-chloro-2-pyridinyl)-2-methylpiperazine (2.0 mmol, 422 mg) (commercially available from Sigma-Aldrich, St. Louis, Mo. (www.sigma-aldrich.com)) was added to the reaction mixture. The reaction mixture was heated to 100° C. and stirred at 100° C. for 16 hours. The solvent was then removed under reduced pressure to provide a residue that was purified using flash chromatography on a silica column eluted with ethyl acetate/hexane (gradient elution from 20:80 ethyl acetate/hexane to 10:90 ethyl acetate/hexane) to provide compound 14 as a yellow solid.

The identity of Compound 14 was confirmed using $H^1$ NMR.

Compound 14: $^1$H NMR (CDCl$_3$), 8.21 (1H, dd, J=1.6, 4.7 Hz), 7.63 (1H, dd, J=1.6, 7.8 Hz), 7.40 (1H, d, J=0.5 Hz), 7.18 (2H, d, J=0.5 Hz), 6.89 (1H, dd, J=4.7, 7.8 Hz), 5.62 (1H, br), 5.27 (m, 1H), 3.84 (2H, t, J=10.6 Hz), 3.50 (1H, dt, J=2.9, 15.3 Hz), 3.08 (1H, dd, J=3.6, 12.6 Hz), 3.00 (1H, dt, J=3.3, 15.3 Hz), 2.44 (3H, s), 1.48 (3H, d, J=7.2 Hz) ppm.

(M+1) m/z: 418.0.

5.10. Example 10

Synthesis of Benzoazolylpiperazine Compound GIO

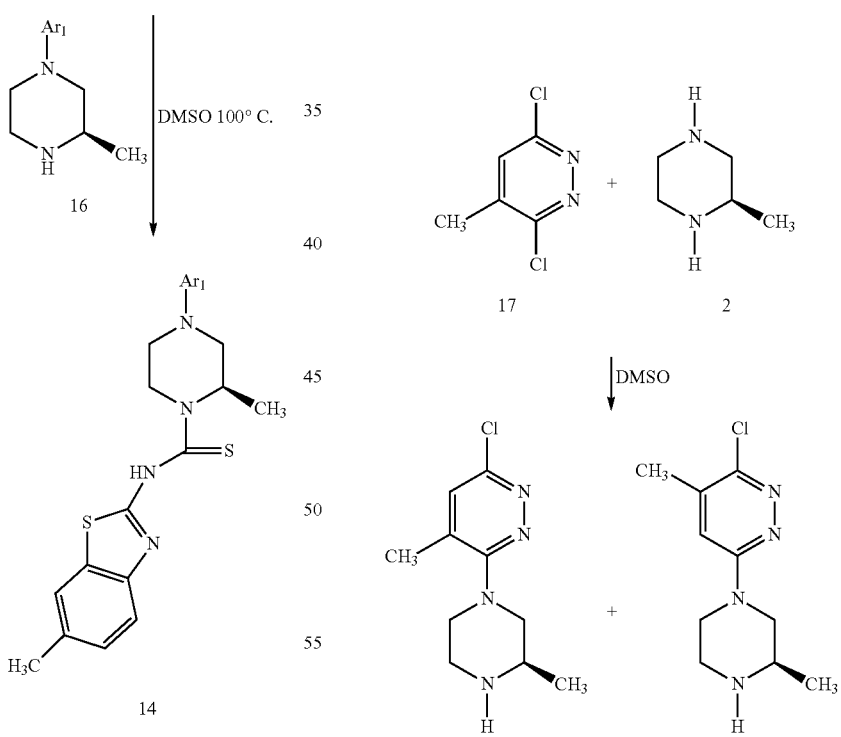

Compound 17 (5 g, 30.7 mmol) and piperazine 2 (3.1 g, 30.7 mmol) were dissolved in 18 mL of DMSO and stirred at 100° C. for about 3 h. The reaction mixture was then cooled to room temperature and the solvent removed under reduced pressure to provide a mixture of compounds 18 and 19.

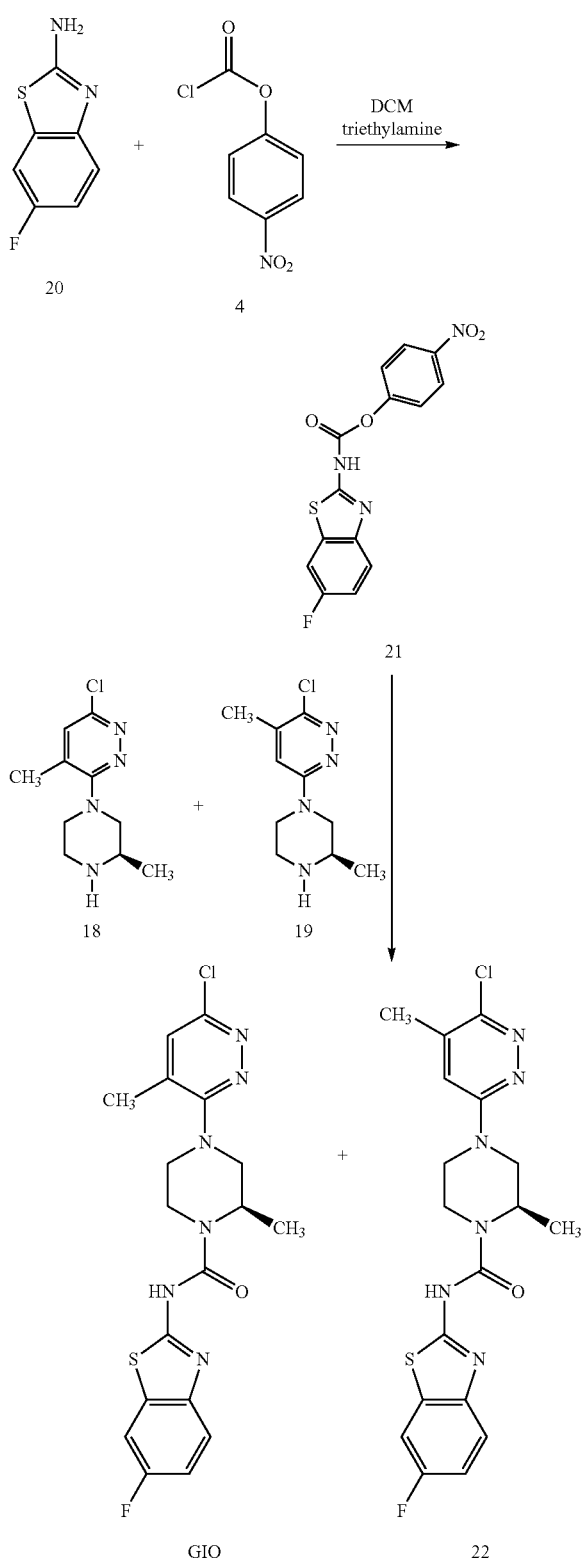

A solution of 6-fluoro-benzothiazol-2-ylamine 20 (3.7 g, 23.0 mmol) in DCM (15 mL) was added portionwise to a cooled solution of chloroformate 4. The resulting reaction mixture was stirred for 5 min. and 10 mL of triethylamine was added to the solution. The reaction mixture was then allowed to warm to room temperature and concentrated under reduced pressure at about 40° C. to provide the compound of formula 21. The compound of formula 21 was redissolved in DCM (30 mL) and to the resulting solution was added the mixture of compounds 18 and 19, prepared as described above, in DCM (10 mL). The resulting reaction mixture was allowed to stir for 5 min. and the solvent was removed under reduced pressure to provide a residue comprising Compound GIO and a Benzoazolylpiperazine Compound of Formula 22. The residue was purified using a silica gel column eluted with 5:95 ethyl acetate:hexane to provide 0.69 g of Compound GIO.

5.11. Example 11

Binding of Benzoazolylpiperazine Compounds to mGluR5

The following assay can be used to demonstrates Benzoazolylpiperazine Compounds that bind to and modulate the activity of mGluR5.

Cell cultures: Primary glial cultures are prepared from cortices of Sprague-Dawley 18 days old embryos. The cortices are dissected and then dissociated by trituration. The resulting cell homogenate is plated onto poly-D-lysine precoated T175 flasks (BIOCOAT, commercially available from Becton Dickinson and Company Inc. of Franklin Lakes, N.J.) in Dulbelcco's Modified Eagle's Medium ("DMEM," pH 7.4), buffered with 25 mM HEPES, and supplemented with 15% fetal calf serum ("FCS," commercially available from Hyclone Laboratories Inc. of Omaha, Nebr.), and incubated at 37° C. and 5% $CO_2$. After 24 hours, FCS supplementation is reduced to 10%. On day six, oligodendrocytes and microglia are removed by strongly tapping the sides of the flasks. One day following this purification step, secondary astrocyte cultures are established by subplating onto 96 poly-D-lysine precoated T175 flasks (BIOCOAT) at a density of 65,000 cells/well in DMEM and 10% FCS. After 24 hours, the astrocytes are washed with serum free medium and then cultured in DMEM, without glutamate, supplemented with 0.5% FCS, 20 mM HEPES, 10 ng/mL epidermal growth factor ("EGF"), 1 mM sodium pyruvate, and 1× penicillin/streptomycin at pH 7.5 for 3 to 5 days at 37° C. and 5% $CO_2$. The procedure allows the expression of the mGluR5 receptor by astrocytes, as demonstrated by S. Miller et al., *J. Neuroscience* 15(9): 6103-6109 (1995).

Assay Protocol: After 3-5 days incubation with EGF, the astrocytes are washed with 127 mM NaCl, 5 mM KCl, 2 mM $MgCl_2$, 700 mM $NaH_2PO_4$, 2 mM $CaCl_2$, 5 mM $NaHCO_3$, 8 mM HEPES, 10 mM Glucose at pH 7.4 ("Assay Buffer") and loaded with the dye Fluo-4 (commercially available from Molecular Probes Inc. of Eugene, Oreg.) using 0.1 mL of Assay Buffer containing Fluo-4 (3 mM final). After 90 minutes of dye loading, the cells are then washed twice with 0.2 mL Assay Buffer and resuspended in 0.1 mL of Assay Buffer. The plates containing the astrocytes are then transferred to a Fluorometric Imaging Plate reader (commercially available from Molecular Devices Corporation of Sunnyvale, Calif.) for the assessment of calcium mobilization flux in the presence of glutamate and in the presence or absence of antagonist. After monitoring fluorescence for 15 seconds to establish a base line, DMSO solutions containing various concentrations of a Benzoazolylpiperazine Compound diluted in Assay Buffer (0.05 mL of 4× dilutions for competition curves) are added to the cell plate and fluorescence is monitored for 2 minutes. 0.05 mL of a 4× glutamate solution (agonist) is then added to each well to provide a final glutamate concentration in each well of 10 mM. Plate fluorescence is then monitored for an additional 60 seconds after agonist addition. The final DMSO concentration in the assay is 1.0%. In each experiment, fluorescence is monitored as a function of time and the data analyzed using Microsoft Excel and GraphPad Prism. Dose-response curves are fit using a non-linear regression to determine $IC_{50}$ value. In each experiment, each data point is determined two times. The assay results will demonstrate Benzoazolylpiperazine Compounds that bind to and modulate the activity of mGluR5.

5.12. Example 12

In Vivo Assays for Prevention or Treatment of Pain

Test Animals: Each experiment uses rats weighing between 200-260 g at the start of the experiment. The rats are group-housed and have free access to food and water at all times, except prior to oral administration of a Benzoazolylpiperazine Compound when food is removed for 16 hours before dosing. A control group acts as a comparison to rats treated with a Benzoazolylpiperazine Compound. The control group is administered the carrier for the Benzoazolylpiperazine Compound. The volume of carrier administered to the control group is the same as the volume of carrier and Benzoazolylpiperazine Compound administered to the test group.

Acute Pain: To assess the actions of the Benzoazolylpiperazine Compounds for the treatment or prevention of acute pain the rat tail flick test can be used. Rats are placed inside a cotton pouch and the tail exposed to a focused beam of radiant heat at a point 3 cm from the tip using a tail flick unit (Model 7360, commercially available from Ugo Basile of Italy). Tail flick latencies are defined as the interval between the onset of the thermal stimulus and the flick of the tail. Animals not responding within 15 seconds are removed from the tail flick unit and assigned a withdrawal latency of 15 seconds. Tail flick latencies are measured immediately before (pre-treatment) and 1, 3, and 6 hours following administration of a Benzoazolylpiperazine Compound. Data are expressed as tail flick latency(s) and the percentage of the maximal possible effect (% MPE), i.e., 15 seconds, is calculated as follows:

$$\% \ MPE = \frac{[(\text{post administration latency}) - (\text{pre-administration latency})]}{(15 \ s \ \text{pre-administration latency})} \times 100$$

The rat tail flick test is described in F. E. D'Amour et al., "A Method for Determining Loss of Pain Sensation," *J. Pharmacol. Exp. Ther.* 72:74-79 (1941). The results will demonstrate Benzoazolylpiperazine Compounds that are useful for treating or preventing acute pain.

Acute pain can also be assessed by measuring the animal's response to noxious mechanical stimuli by determining the paw withdrawal threshold (PWT), as described below.

Inflammatory Pain: To assess the actions of the Benzoazolylpiperazine Compounds for the treatment or prevention of inflammatory pain the Freund's complete adjuvant (FCA) model of inflammatory pain is used. FCA-induced inflammation of the rat hind paw is associated with the development of persistent inflammatory mechanical hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-Schmiedeberg's Archives of Pharmacology* 342:666-670 (1990)). The left hind paw of each animal is administered a 50 μL intraplantar injection of 100% FCA. 24 hour post injection, the animal is assessed for response to noxious mechanical stimuli by determining the PWT, as described below. Rats are then administered a single injection of 1, 3, 10 or 30 mg/Kg of either a Benzoazolylpiperazine Compound, 30 mg/Kg indomethacin or carrier. Responses to noxious mechanical stimuli are then determined 2, 4, 6, and 24 hours post administration. Percentage reversal of hyperalgesia for each animal is defined as:

$$\% \ Reversal = \frac{[(\text{post administration } PWT) - (\text{pre-administration } PWT)]}{(\text{Baseline pre-administration } PWT)} \times 100$$

The results will demonstrate Benzoazolylpiperazine Compounds that are useful for treating or preventing inflammatory pain.

Neuropathic Pain: To assess the actions of the Benzoazolylpiperazine Compounds for the treatment or prevention of neuropathic pain either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under enflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (7-0 silk) and a Michelle clip. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, immediately prior to and 1, 3, and 6 hours after drug administration for both the left rear paw and right rear paw of the animal. Percentage reversal of neuropathic hyperalgesia is defined as:

% reversal=100−[(right pre-administration PWT−left post-administration PWT)/(right pre-administration PWT−left pre-administration PWT)]×100.

In the Chung model, the spinal nerve ligation model of neuropathic pain is used to produce mechanical hyperalgesia, themal hyperalgesia and tactile allodynia in rats. Surgery is performed under isoflurane/$O_2$ inhalation anaesthesia. Following induction of anaesthesia a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then be returned to their home cages until behavioral testing begins. The animals are assessed for response to noxious mechanical stimuli by determining PWT, as described below, immediately prior to and 1, 3, and 5 hours after being administered a Benzoazolylpiperazine Compound for both the left rear paw and right rear paw of the animal. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," *Pain* 50(3):355-363 (1992). The results show demonstrate Benzoazolylpiperazine Compounds that are useful for treating or preventing neuropathic pain.

Response to Mechanical Stimuli as an Assessment of Mechanical Hyperalgesia: The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," *Pharmacology Biochemistry and Behavior* 31:451-455 (1988). The maximum weight that can be applied to the hind paw is set at 250 g and the end point is taken as complete withdrawal of the paw. PWT is determined once for each rat at each time point and only the affected (ipsilateral) paw is tested.

Response to Thermal Stimuli as an Assessment of Thermal Hyperalgesia: The plantar test can be used to assess thermal hyperalgesia. For this test, hind paw withdrawal latencies to a noxious thermal stimulus are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Only the affected (ipsilateral) paw is tested.

Assessment of Tactile Allodynia: To assess tactile allodynia, rats are placed in clear, plexiglass compartments with a wire mesh floor and allowed to habituate for a period of at least 15 minutes. After habituation, a series of von Frey monofilaments are presented to the plantar surface of the left (operated) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

5.13 Example 13

In Vivo Assays for Prevention or Treatment of Anxiety

The elevated plus maze test or the shock-probe burying test can be used to assess the anxiolytic activity of Benzoazolylpiperazine Compounds in rats or mice.

The Elevated Plus Maze Test: The elevated plus maze consists of a platform with 4 arms, two open and two closed (50×10×50 cm enclosed with an open roof). Rats (or mice) are placed in the center of the platform, at the crossroad of the 4 arms, facing one of the closed arms. Time spent in the open arms vs the closed arms and number of open arm entries during the testing period are recorded. This test is conducted prior to drug administration and again after drug administration. Test results are expressed as the mean time spent in open arms and the mean number of entries into open arms. Known anxiolytic drugs increase both the time spent in open arms and number of open arm entries. The elevated plus maze test is described in D. Treit, "Animal Models for the Study of Antianxiety Agents: A Review," *Neuroscience & Biobehavioral Reviews* 9(2):203-222 (1985).

The Shock-Probe Burying Test: For the shock-probe burying test the testing apparatus consists of a plexiglass box measuring 40×30×40 cm, evenly covered with approximately 5 cm of bedding material (odor absorbent kitty litter) with a small hole in one end through which a shock probe (6.5 cm long and 0.5 cm in diameter) is inserted. The plexiglass shock probe is helically wrapped with two copper wires through which an electric current is administered. The current is set at 2 mA. Rats are habituated to the testing apparatus for 30 min on 4 consecutive days without the shock probe in the box. On test day, rats are placed in one corner of the test chamber following drug administration. The probe is not electrified until the rat touches it with its snout or fore paws, at which point the rat receives a brief 2 mA shock. The 15 min testing period begins once the rat receives its first shock and the probe remains electrified for the remainder of the testing period. The shock elicits burying behavior by the rat. Following the first shock, the duration of time the rat spends spraying bedding material toward or over the probe with its snout or fore paws (burying behavior) is measured as well as the number of contact-induced shocks the rat receives from the probe. Known anxiolytic drugs reduce the amount of burying behavior. In addition, an index of the rat's reactivity to each shock is scored on a 4 point scale. The total time spent immobile during the 15 min testing period is used as an index of general activity. The shock-probe burying test is described in D. Treit, 1985, supra. The results of this test will demonstrate Benzoazolylpiperazine Compounds that are useful for treating or preventing anxiety.

5.14. Example 14

In Vivo Assays for Prevention or Treatment of an Addictive Disorder

The condition place preference test or drug self-administration test can be used to assess the ability of Benzoazolylpiperazine Compounds to attenuate the rewarding properties of known drugs of abuse.

The Condition Place Preference Test: The apparatus for the conditioned place preference test consists of two large compartments (45×45×30 cm) made of wood with a plexiglass front wall. These two large compartments are distinctly different. Doors at the back of each large compartment lead to a smaller box (36×18×20 cm) box made of wood, painted grey, with a ceiling of wire mesh. The two large compartments differ in terms of shading (white vs black), level of illumination (the plexiglass door of the white compartment is covered with aluminum foil except for a window of 7×7 cm), texture (the white compartment has a 3 cm thick floor board (40×40 cm) with nine equally spaced 5 cm diameter holes and the black has a wire mesh floor), and olfactory cues (saline in the white compartment and 1 mL of 10% acetic acid in the black compartment). On habituation and testing days, the doors to the small box remain open, giving the rat free access to both large compartments.

The first session that a rat is placed in the apparatus is a habituation session and entrances to the smaller grey compartment remain open giving the rat free access to both large compartments. During habituation, rats generally show no preference for either compartment. Following habituation, rats are given 6 conditioning sessions. Rats are divided into 4 groups: carrier pre-treatment+carrier (control group), 2-Pyrimidinylpiperazine Compound pre-treatment+carrier, carrier pre-treatment+morphine, 2-Pyrimidinylpiperazine Compound pre-treatment+morphine. During each conditioning session the rat is injected with one of the drug combinations and confined to one compartment for 30 min. On the following day, the rat receives a carrier+carrier treatment and is confined to the other large compartment. Each rat receives three conditioning sessions consisting of 3 drug combination-compartment and 3 carrier-compartment pairings. The order of injections and the drug/compartment pairings are counterbalanced within groups. On the test day, rats are injected prior to testing (30 min to 1 hour) with either morphine or carrier and the rat is placed in the apparatus, the doors to the grey compartment remain open and the rat is allowed to explore the entire apparatus for 20 min. The time spent in each compartment is recorded. Known drugs of abuse increase the time spent in the drug-paired compartment during the testing session. If the Benzoazolylpiperazine Compound blocks the acquisition of morphine conditioned place preference (reward), there will be no difference in time spent in each side in rats pre-treated with a Benzoazolylpiperazine Compound and the group will not be different from the group of rats that was given carrier+carrier in both compartments. Data will be analyzed as time spent in each compartment (drug combination-paired vs carrier-paired). Generally, the experiment is repeated with a minimum of 3 doses of a Benzoazolylpiperazine Compound.

The Drug Self-Administration Test: The apparatus for the drug self-administration test is a standard commercially available operant conditioning chamber. Before drug trials begin rats are trained to press a lever for a food reward. After stable lever pressing behavior is acquired, rats are tested for acquisition of lever pressing for drug reward. Rats are implanted with chronically indwelling jugular catheters for i.v. administration of compounds and are allowed to recover for 7 days before training begins. Experimental sessions are conducted daily for 5 days in 3 hour sessions. Rats are trained to self-administer a known drug of abuse, such as morphine. Rats are then presented with two levers, an "active" lever and an "inactive" lever. Pressing of the active lever results in drug infusion on a fixed ratio 1 (FR1) schedule (i.e., one lever press gives an infusion) followed by a 20 second time out period (signaled by illumination of a light above the levers). Pressing of the inactive lever results in infusion of excipient. Training continues until the total number of morphine infusions stabilizes to within ±10% per session. Trained rats are then used to evaluate the effect of Benzoazolylpiperazine Compounds pre-treatment on drug self-administration. On test day, rats are pre-treated with a Benzoazolylpiperazine Compound or excipient and then are allowed to self-administer drug as usual. If the Benzoazolylpiperazine Compound blocks the rewarding effects of morphine, rats pre-treated with the Benzoazolylpiperazine Compound will show a lower rate of responding compared to their previous rate of responding and compared to excipient pre-treated rats. Data is analyzed as the change in number of drug infusions per testing session (number of infusions during test session–number of infusions during training session). The results will demonstrate Benzoazolylpiperazine Compounds are useful for treating or preventing an addictive disorder.

5.15. Example 15

Functional Assay for Characterizing mGluR 1 Antagonistic Properties

Functional assays for the characterization of mGluR 1 antagonistic properties are well known in the art. For example, the following procedure can be used.

A CHO-rat mGluR1 cell line is generated using cDNA encoding rat mGluR1 receptor (M. Masu and S, Nakanishi, *Nature* 349: 760-765 (1991)). The cDNA encoding rat mGluR1 receptor can be obtained from, e.g., Prof. S, Nakanishi (Kyoto, Japan).

40,000 CHO-rat mGluR1 cells/well are plated into a Costar 3409, black, clear bottom, 96 well, tissue culture treated plate (commercially available from Fisher Scientific of Chicago, Ill.) and are incubated in Dulbecco's Modified Eagle's Medium (DMEM, pH 7.4) supplemented with glutamine, 10% FBS, 1% Pen/Strep, and 500 µg/mL Geneticin for about 12 h. The CHO-rat mGluR1 cells are then washed and treated with Optimem medium (commercially available from Invitrogen, Carlsbad, Calif.) and incubated for a time period ranging from 1 to 4 hours prior to loading the cells with the dye Fluo-4 (commercially available from Molecular Probes Inc., Eugene Oreg.). After incubation, the cell plates are washed with loading buffer (127 mM NaCl, 5 mM KCl, 2 mM $MgCl_2$, 700 $NaH_2PO_4$, 2 mM $CaCl_2$, 5 mM $NaHCO_3$, 8 mM HEPES, and 10 mM glucose, pH 7.4) and incubated with 3 µM Fluo-4 in 0.1 ml, loading buffer for 90 min. The cells are then washed twice with 0.2 mL loading buffer, resuspended in 0.1 mL of loading buffer, and transferred to a Fluorometric Imaging Plate Reader (FLIPR) (commercially available from Molecular Devices Corp., Sunnyvale, Calif.) for measurement of calcium mobilization flux in the presence of glutamate and in the presence or absence of a Benzoazolylpiperazine Compound.

To measure calcium mobilization flux, fluoresence is monitored for about 15 s to establish a baseline and DMSO solutions containing various concentrations of a Benzoazolylpiperazine Compound ranging from about 50 µM to about 0.8 nM diluted in loading buffer (0.05 mL of a 4× dilution) are added to the cell plate and fluoresence is monitored for about 2 min. 0.05 mL of a 4× Glutamate solution (agonist) is then added to each well to provide a final glutamate concentration in each well of 10 µM and fluoresence is monitored for about 1 additional min. The final DMSO concentration in the assay is 1%. In each experiment fluoresence is monitored as a function of time and the data is analyzed using a non-linear regression to determine the $IC_{50}$ value. In each expereiment each data point is determined twice.

5.16 Example 16

Binding of Benzoazolylpiperazine Compounds to VR1

Methods for demonstrating a compound's ability to inhibit VR1 are well known to those skilled in the art, for example, those methods disclosed in U.S. Pat. No. 6,239,267 to Duckworth et al.; U.S. Pat. No. 6,406,908 to McIntyre et al.; or U.S. Pat. No. 6,335,180 to Julius et al. The results of this assay will demonstrate Benzoazolylpiperazine Compounds that bind to and modulate the activity of VR1.

Binding of Compound AAQ to VR1: Assay Protocol

Human VR1 cloning. Human spinal cord RNA (commercially available from Clontech, Palo Alto, Calif.) was used. Reverse transcription was conducted on 1.0 μg total RNA using Thermoscript Reverse Transcriptase (commercially available from Invitrogen, Carlsbad, Calif.) and oligo dT primers as detailed in its product description. Reverse transcription reactions were incubated at 55° C. for 1 h, heat-inactivated at 85° C. for 5 min, and RNase H-treated at 37° C. for 20 min.

Human VR1 cDNA sequence was obtained by comparison of the human genomic sequence, prior to annotation, to the published rat sequence. Intron sequences were removed and flanking exonic sequences were joined to generate the hypothetical human cDNA. Primers flanking the coding region of human VR1 were designed as follows: forward primer, AAGATCTTCGCTGGTTGCACACTGGGCCACA; and reverse primer, GAAGATCTTCGGGGACAGTGACGGTTGGATGT.

PCR of VR1 was performed on one tenth of the reverse transcription reaction mixture using Expand Long Template Polymerase and Expand Buffer 2 in a final volume of 50 μL according to the manufacturer's instructions (Roche Applied Sciences, Indianapolis, Ind.). After denaturation at 94° C. for 2 min PCR amplification was performed for 25 cycles at 94° C. for 15 sec, 58° C. for 30 sec, and 68° C. for 3 min followed by a final incubation at 72° C. for 7 min to complete the amplification. A PCR product of ~2.8 kb was gel-isolated using a 1.0% agarose, Tris-Acetate gel containing 1.6 μg/mL of crystal violet and purified with a S.N.A.P. UV-Free Gel Purification Kit (commercially available from Invitrogen). The VR1 PCR product was cloned into the pIND/V5-His-TOPO vector (commercially available from Invitrogen) according to the manufacturer's instructions. DNA preparations, restriction enzyme digestions, and preliminary DNA sequencing were performed according to standard protocols. Full-length sequencing confirmed the identity of the human VR1.

Generation of inducible cell lines. Unless noted otherwise, cell culture reagents were purchased from Life Technologies of Rockville, Md. HEK293-EcR cells expressing the ecdysone receptor (commercially available from Invitrogen) were cultured in Growth Medium (Dulbecco's Modified Eagles Medium containing 10% fetal bovine serum (commercially available from HYCLONE, Logan, Utah), 1× penicillin/streptomycin, 1× glutamine, 1 mM sodium pyruvate and 400 μg/mL Zeocin (commercially available from Invitrogen)). The VR1-pIND constructs were transfected into the HEK293-EcR cell line using Fugene transfection reagent (commercially available from Roche Applied Sciences, Basel, Switzerland). After 48 h, cells were transferred to Selection Medium (Growth Medium containing 300 μg/mL G418 (commercially available from Invitrogen)). Approximately 3 weeks later individual Zeocin/G418 resistant colonies were isolated and expanded. To identify functional clones, multiple colonies were plated into 96-well plates and expression was induced for 48 h using Selection Medium supplemented with 5 μM ponasterone A ("PonA") (commercially available from Invitrogen). On the day of assay, cells were loaded with Fluo-4 (a calcium-sensitive dye that is commercially available from Molecular Probes, Eugene, Oreg.) and CAP-mediated calcium influx was measured using a Fluorometric Imaging Plate Reader ("FLIPR") (commercially available from Molecular Devices Corp., Sunnyvale, Calif.) as described below. Functional clones were re-assayed, expanded, and cryopreserved.

pH-Based Assay. Two days prior to performing this assay, cells were seeded on poly-D-lysine-coated 96-well clear-bottom black plates (commercially available from Becton-Dickinson) at 75,000 cells/well in growth media containing 5 μM PonA (commercially available from Invitrogen) to induce expression. On the day of the assay, the plates were washed with 0.2 mL 1× Hank's Balanced Salt Solution (commercially available from Life Technologies) containing 1.6 mM CaCl$_2$ and 20 mM HEPES, pH 7.4 ("wash buffer"), and loaded using 0.1 mL of wash buffer containing Fluo-4 (3 μM final concentration, commercially available from Molecular Probes). After 1 h, the cells were washed twice with 0.2 mL wash buffer and resuspended in 0.05 mL 1× Hank's Balanced Salt Solution (commercially available from Life Technologies) containing 3.5 mM CaCl$_2$ and 10 mM Citrate, pH 7.4 ("assay buffer"). Plates were then transferred to a FLIPR (commercially available from Molecular Devices) for assay. Compound AAQ was diluted in assay buffer, and 50 mL of the resultant solution were added to the cell plates and the solution monitored for two minutes. The final concentration of Compound AAQ ranged from about 50 pM to about 3 μM. Agonist buffer (wash buffer titrated with 1N HCl to provide a solution having a pH of 5.5 when mixed 1:1 with assay buffer) (0.1 mL) was then added to each well, and the plates were incubated for 1 additional min. Data were collected over the entire time course and analyzed using Excel and Graph Pad Prism. Compound AAQ when assayed according to this protocol had an IC$_{50}$ of 261.8±75.1 (n=6).

Capsaicin-based Assay. Two days prior to performing this assay, cells were seeded in poly-D-lysine-coated 96-well clear-bottom black plates (50,000 cells/well) in growth media containing 5 μM PonA (commercially available from Invitrogen) to induce expression. On the day of the assay, the plates were washed with 0.2 mL 1× Hank's Balanced Salt Solution (commercially available from Life Technologies) containing 1 mM CaCl$_2$ and 20 mM HEPES, pH 7.4, and cells were loaded using 0.1 mL of wash buffer containing Fluo-4 (3 μM final). After one h, the cells were washed twice with 0.2 mL of wash buffer and resuspended in 0.1 mL of wash buffer. The plates were transferred to a FLIPR (commercially available from Molecular Devices) for assay. 50 μL of Compound AAQ diluted with assay buffer were added to the cell plates and incubated for 2 min. The final concentration of Compound AAQ ranged from about 50 pM to about 3 μM. Human VR1 was activated by the addition of 50 μL of capsaicin (400 nM), and the plates were incubated for an additional 3 min. Data were collected over the entire time course and analyzed using Excel and GraphPad Prism. Compound AAQ when assayed according to this protocol had an IC$_{50}$ of 50.7±14.7 (n=3).

The results of the pH-based assay and the capsaicin-based assay demonstrate that Compound AAQ, an illustrative Benzoazolylpiperazine Compound, binds to and modulates the activity of human VR1 and, accordingly, is useful for treating or preventing pain, UI, an ulcer, IBD, or IBS.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

What is claimed is:

1. A compound of formula:

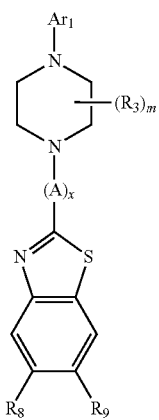

(Ib)

or a pharmaceutically acceptable salt thereof, wherein:

$Ar_1$ is:

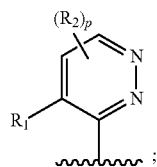

A is:

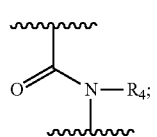

$R_1$ is —H, -halo, —$(C_1-C_6)$alkyl, —$NO_2$, —CN, —OH, —$OCH_3$, —$NH_2$, —C(halo)$_3$, —CH(halo)$_2$, or —$CH_2$(halo);

each $R_2$ is independently:

(a) -halo, —CN, —OH, —$O(C_1-C_6)$alkyl, —$NO_2$, or —$NH_2$; or (b) —$(C_1-C_{10})$alkyl, —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, —$(C_8-C_{14})$bicycloalkenyl, —$(C_8-C_{14})$tricycloalkenyl, -(3- to 7-membered)heterocycle, or -(7- to 10-membered)bicycloheterocycle, each of which is unsubstituted or substituted with one or more $R_5$ groups; or (c) -phenyl, -naphthyl, —$(C_{14})$aryl, or -(5- to 10-membered)heteroaryl, each of which is unsubstituted or substituted with one or more $R_6$ groups;

each $R_3$ is independently:

(a) -halo, —CN, —OH, —$O(C_1-C_6)$alkyl, —$NO_2$, or —$NH_2$; or (b) —$(C_1-C_{10})$alkyl, —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, —$(C_8-C_{14})$bicycloalkenyl, —$(C_8-C_{14})$tricycloalkenyl, -(3- to 7-membered)heterocycle, or -(7- to 10-membered)bicycloheterocycle, each of which is unsubstituted or substituted with one or more $R_5$ groups; or (c) -phenyl, -naphthyl, —$(C_{14})$aryl, or -(5- to 10-membered)heteroaryl, each of which is unsubstituted or substituted with one or more $R_6$ groups;

$R_4$ is —H;

each $R_5$ is independently —CN, —OH, -halo, —$N_3$, —$NO_2$, —$N(R_7)_2$, —CH=$NR_7$, —$NR_7$OH, —$OR_7$, —C(O)$R_7$, —C(O)$OR_7$, —OC(O)$R_7$, —OC(O)$OR_7$, —$SR_7$, —S(O)$R_7$, or —S(O)$_2R_7$;

each $R_6$ is independently —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, —$(C_3-C_5)$heterocycle, —C(halo)₃, —CH(halo)₂, —CH₂(halo), —CN, —OH, -halo, —N₃, —NO₂, —N(R₇)₂, —CH=NR₇, —NR₇OH, —OR₇, —C(O)R₇, —C(O)OR₇, —OC(O)R₇, —OC(O)OR₇, —SR₇, —S(O)R₂, or —S(O)₂R₇;

each R₇ is independently —H, —(C₁-C₆)alkyl, —(C₂-C₆)alkenyl, —(C₂-C₆)alkynyl, —(C₃-C₈)cycloalkyl, —(C₅-C₈)cycloalkenyl, -phenyl, —(C₃-C₅)heterocycle, —C(halo)₃, —CH₂(halo), or —CH(halo)₂;

R₈ and R₉ are each independently —H, —(C₁-C₆)alkyl, —(C₂-C₆)alkenyl, —(C₂-C₆)alkynyl, —(C₃-C₈)cycloalkyl, —(C₅-C₈)cycloalkenyl, -phenyl, —C(halo)₃, —CH(halo)₂, —CH₂(halo), —CN, —OH, -halo, —N₃, —N(R₇)₂, —CH=NR₇, —NR₇OH, —OR₇, —C(O)R₇, —C(O)OR₇, —OC(O)R₇, —OC(O)OR₇, —SR₇, —S(O)R₇, or —S(O)₂R₇;

each -halo is —F, —Cl, —Br, or —I;
p is an integer ranging from 1 to 2;
m is 0 or 1; and
x is 0 or 1.

2. The compound of claim 1, wherein x is 0.
3. The compound of claim 1, wherein x is 1
4. The compound of claim 1, wherein p is 1.
5. The compound of claim 4, wherein R₂ is —(C₁-C₁₀)alkyl, —(C₂-C₁₀)alkenyl, —(C₂-C₁₀)alkynyl, —(C₃-C₁₀)cycloalkyl, —(C₈-C₁₄)bicycloalkyl, —(C₈-C₁₄)tricycloalkyl, —(C₅-C₁₀)cycloalkenyl, —(C₈-C₁₄)bicycloalkenyl, —(C₈-C₁₄)tricycloalkenyl, -(3- to 7-membered)heterocycle, or -(7- to 10-membered)bicycloheterocycle, each of which is unsubstituted or substituted with one or more R₅ groups.
6. The compound of claim 5, wherein R₂ is —(C₁-C₁₀) alkyl substituted with two R₅ groups.
7. The compound of claim 1, wherein R₃ is attached to a carbon atom adjacent to a nitrogen atom attached to the -(A)ₓ- group.
8. The compound of claim 7, wherein the carbon to which R₃ is attached is in the (R) configuration.
9. The compound of claim 8, wherein R₃ is —CH₃.
10. The compound of claim 1, wherein:
R₁ is —CH₃, —CF₃, —Cl, —Br, or —I;
m is 0;
p is 1;
x is 1;
R₈ is —H; and
R₉ is —CH₃, —CF₃, —OCH₂CH₃, tert-butyl, —Cl, —Br, or —F.
11. The compound of claim 10, wherein R₁ is —CH₃ or —Cl and R₉ is —Cl, —Br, or —F.
12. The compound of claim 1, wherein:
R₁ is —CH₃, —CF₃, —Cl, —Br, or —I;
m is 1;
R₃ is —(C₁-C₁₀)alkyl;
p is 1;
x is 1;
R₈ is —H; and
R₉ is —CH₃, —CF₃, —OCH₂CH₃, tert-butyl, —Cl, —Br, or —F.
13. The compound of claim 12, wherein R₃ is attached to a carbon atom adjacent to a nitrogen atom attached to the -(A)ₓ- group.
14. The compound of claim 13, wherein the carbon to which R₃ is attached is in the (R) configuration.
15. The compound of claim 14, wherein R₃ is —CH₃.
16. The compound of claim 15, wherein R₁ is —CH₃ or —Cl and R₉ is —Cl, —Br, or —F.
17. The compound of claim 1, wherein the compound is selected from:

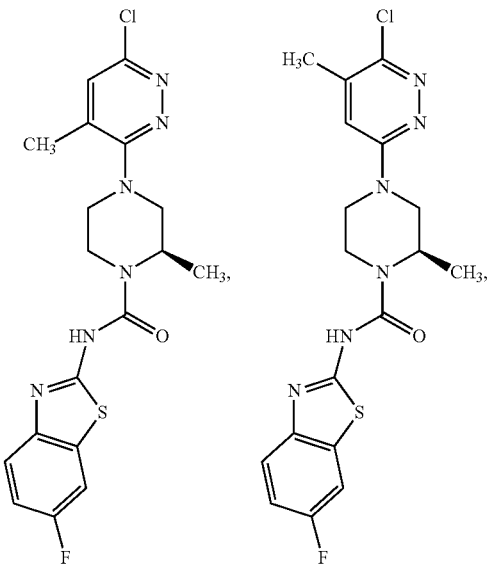 [SMILES: Cc1cc(Cl)nnc1N1CCN(C(=O)Nc2nc3ccc(F)cc3s2)[C@H](C)C1 ; Cc1cc(N2CCN(C(=O)Nc3nc4ccc(F)cc4s3)[C@H](C)C2)nnc1Cl]

and pharmaceutically acceptable salts thereof.

18. A compound of formula:

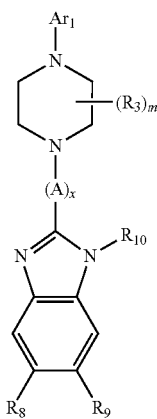

(IIb)

or a pharmaceutically acceptable salt thereof, wherein:
Ar₁ is:

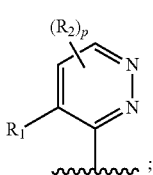

A is:

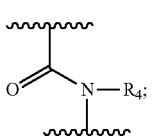

$R_1$ is —H, -halo, —$(C_1$-$C_6)$alkyl, —$NO_2$, —CN, —OH, —$OCH_3$, —$NH_2$, —C(halo)$_3$, —CH(halo)$_2$, or —$CH_2$(halo);

each $R_2$ is independently:
(a) -halo, —CN, —OH, —O($C_1$-$C_6$)alkyl, —$NO_2$, or —$NH_2$; or
(b) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups; or
(c) -phenyl, -naphthyl, —($C_{14}$)aryl, or -(5- to 10-membered)heteroaryl, each of which is unsubstituted or substituted with one or more $R_6$ groups;

each $R_3$ is independently:
(a) -halo, —CN, —OH, —O($C_1$-$C_6$)alkyl, —$NO_2$, or —$NH_2$; or
(b) —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups; or
(c) -phenyl, -naphthyl, —($C_{14}$)aryl, or -(5- to 10-membered)heteroaryl, each of which is unsubstituted or substituted with one or more $R_6$ groups;

$R_4$ is —H;

each $R_5$ is independently —CN, —OH, -halo, —$N_3$, —$NO_2$, —N($R_7$)$_2$, —CH=$NR_7$, —$NR_7$OH, —$OR_7$, —C(O)$R_7$, —C(O)O$R_7$, —OC(O)$R_7$, —OC(O)O$R_7$, —$SR_7$, —S(O)$R_7$, or —S(O)$_2R_7$;

each $R_6$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —($C_3$-$C_5$)heterocycle, —C(halo)$_3$, —CH(halo)$_2$, —$CH_2$(halo), —CN, —OH, -halo, —$N_3$, —$NO_2$, —N($R_7$)$_2$, —CH=$NR_7$, —$NR_7$OH, —$OR_7$, —C(O)$R_7$, —C(O)O$R_7$, —OC(O)$R_7$, —OC(O)O$R_7$, —$SR_7$, —S(O)$R_7$, or —S(O)$_2R_7$;

each $R_7$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —($C_3$-$C_5$)heterocycle, —C(halo)$_3$, —$CH_2$(halo), or —CH(halo)$_2$;

$R_8$ and $R_9$ are each independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —C(halo)$_3$, —CH(halo)$_2$, —$CH_2$(halo), —CN, —OH, -halo, —$N_3$, —N($R_7$)$_2$, —CH=$NR_7$, —$NR_7$OH, —$OR_7$, —C(O)$R_7$, —C(O)O$R_7$, —OC(O)$R_7$, —OC(O)O$R_7$, —$SR_7$, —S(O)$R_7$, or —S(O)$_2R_7$;

$R_{10}$ is —H or —($C_1$-$C_4$)alkyl;

each -halo is —F, —Cl, —Br, or —I;

p is an integer ranging from 1 to 2;

m is 0 or 1; and x is 0 or 1.

19. The compound of claim 18, wherein x is 0.
20. The compound of claim 18, wherein x is 1.
21. The compound of claim 18, wherein p is 1.
22. The compound of claim 21, wherein $R_2$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups.

23. The compound of claim 22, wherein $R_2$ is —($C_1$-$C_{10}$)alkyl substituted with two $R_5$ groups.

24. The compound of claim 18, wherein $R_3$ is attached to a carbon atom adjacent to a nitrogen atom attached to the -(A)$_x$- group.

25. The compound of claim 24, wherein the carbon to which $R_3$ is attached is in the (R) configuration.

26. The compound of claim 25, wherein $R_3$ is —$CH_3$.

27. The compound of claim 18, wherein $R_{10}$ is —H.

28. The compound of claim 18, wherein $R_{10}$ is —$CH_3$.

29. The compound of claim 18, wherein:

$R_1$ is —$CH_3$, —$CF_3$, —Cl, —Br, or —I;

m is 0;

p is 1;

x is 1;

$R_8$ is —H; and $R_9$ is —$CH_3$, —$CF_3$, —$OCH_2CH_3$, tert-butyl, —Cl, —Br, or —F.

30. The compound of claim 29, wherein $R_1$ is —$CH_3$ or —Cl and $R_9$ is —Cl, —Br, or —F.

31. The compound of claim 18, wherein:

$R_1$ is —$CH_3$, —$CF_3$, —Cl, —Br, or —I;

m is 1;

$R_3$ is —($C_1$-$C_{10}$)alkyl;

p is 1;

x is 1;

$R_8$ is —H; and $R_9$ is —$CH_3$, —$CF_3$, —$OCH_2CH_3$, tert-butyl, —Cl, —Br, or —F.

32. The compound of claim 31, wherein $R_3$ is attached to a carbon atom adjacent to a nitrogen atom attached to the -(A)$_x$- group.

33. The compound of claim 32, wherein the carbon to which $R_3$ is attached is in the (R) configuration.

34. The compound of claim 33, wherein $R_3$ is —$CH_3$.

35. The compound of claim 34, wherein $R_1$ is —$CH_3$ or —Cl and $R_9$ is —Cl, —Br, or —F.

36. A compound of formula:

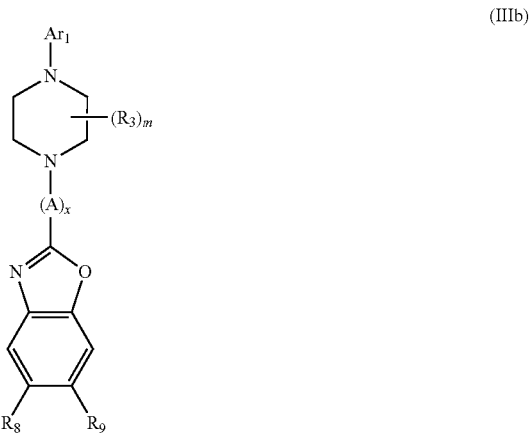

(IIIb)

or a pharmaceutically acceptable salt thereof, wherein:
Ar$_1$ is:

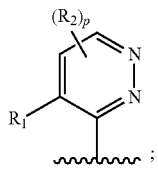

;

A is:

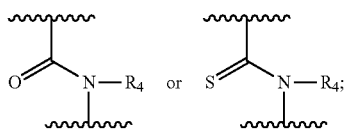

;

R$_1$ is —H, -halo, —(C$_1$-C$_6$)alkyl, —NO$_2$, —CN, —OH, —OCH$_3$, —NH$_2$, —C(halo)$_3$, —CH(halo)$_2$, or —CH$_2$(halo);

each R$_2$ is independently:
 (a) -halo, —CN, —OH, —O(C$_1$-C$_6$)alkyl, —NO$_2$, or —NH$_2$; or
 (b) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, or -(7- to 10-membered) bicycloheterocycle, each of which is unsubstituted or substituted with one or more R$_5$ groups; or
 (c) -phenyl, -naphthyl, or —(C$_{14}$)aryl, each of which is unsubstituted or substituted with one or more R$_6$ groups;

each R$_3$ is independently:
 (a) -halo, —CN, —OH, —(C$_1$-C$_6$)alkyl, —NO$_2$, or —NH$_2$; or
 (b) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more R$_5$ groups; or
 (c) -phenyl, -naphthyl, —(C$_{14}$)aryl, or -(5- to 10-membered)heteroaryl, each of which is unsubstituted or substituted with one or more R$_6$ groups;

R$_4$ is —H;

each R$_5$ is independently —CN, —OH, -halo, —N$_3$, —NO$_2$, —N(R$_7$)$_2$, —CH═NR$_7$, —NR$_7$OH, —OR$_7$, —C(O)R$_7$, —C(O)OR$_7$, —OC(O)R$_7$, —OC(O)OR$_7$, —SR$_7$, —S(O)R$_7$, or —S(O)$_2$R$_7$;

each R$_6$ is independently —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —(C$_3$-C$_5$)heterocycle, —C(halo)$_3$, —CH(halo)$_2$, —CH$_2$(halo), —CN, —OH, -halo, —N$_3$, —NO$_2$, —N(R$_7$)$_2$, —CH═NR$_7$, —NR$_7$OH, —OR$_7$, —C(O)R$_7$, —C(O)OR$_7$, —OC(O)R$_7$, —OC(O)OR$_7$, —SR$_7$, —S(O)R$_7$, or —S(O)$_2$R$_7$;

each R$_7$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —(C$_3$-C$_5$)heterocycle, —C(halo)$_3$, —CH$_2$(halo), or —CH(halo)$_2$;

R$_8$ and R$_9$ are each independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —C(halo)$_3$, —CH(halo)$_2$, —CH$_2$(halo), —CN, —OH, -halo, —N$_3$, —N(R$_7$)$_2$, —CH═NR$_7$, —NR$_7$OH, —OR$_7$, —C(O)R$_7$, —C(O)OR$_7$, —OC(O)R$_7$, —OC(O)OR$_7$, —SR$_7$, —S(O)R$_7$, or —S(O)$_2$R$_7$;

each -halo is —F, —Cl, —Br, or —I;
p is an integer ranging from 1 to 2;
m is 0 or 1; and
x is 0 or 1.

37. The compound of claim 36, wherein x is 0.
38. The compound of claim 36, wherein x is 1.
39. The compound of claim 36, wherein p is 1.
40. The compound of claim 39, wherein R$_2$ is —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, or -(7- to 10-membered)bicycloheterocycle, each of which is unsubstituted or substituted with one or more R$_5$ groups.
41. The compound of claim 40, wherein R$_2$ is —(C$_1$-C$_{10}$) alkyl substituted with two R$_5$ groups.
42. The compound of claim 36, wherein R$_3$ is attached to a carbon atom adjacent to a nitrogen atom attached to the -(A)$_x$- group.
43. The compound of claim 42, wherein the carbon to which R$_3$ is attached is in the (R) configuration.
44. The compound of claim 43, wherein R$_3$ is —CH$_3$.
45. The compound of claim 36, wherein:
R$_1$ is —CH$_3$, —CF$_3$, —Cl, —Br, or —I;
m is 0;
p is 1;
x is 1;
R$_8$ is —H; and
R$_9$ is —CH$_3$, —CF$_3$, —OCH$_2$CH$_3$, tert-butyl, —Cl, —Br, or —F.
46. The compound of claim 45, wherein R$_1$ is —CH$_3$ or —Cl and R$_9$ is —Cl, —Br, or —F.
47. The compound of claim 36, wherein:
R$_1$ is —CH$_3$, —CF$_3$, —Cl, —Br, or —I;
m is 1;
R$_3$ is —(C$_1$-C$_{10}$)alkyl;
p is 1;
x is 1;
R$_8$ is —H; and
R$_9$ is —CH$_3$, —CF$_3$, —OCH$_2$CH$_3$, tert-butyl, —Cl, —Br, or —F.
48. The compound of claim 47, wherein R$_3$ is attached to a carbon atom adjacent to a nitrogen atom attached to the -(A)$_x$- group.
49. The compound of claim 48, wherein the carbon to which R$_3$ is attached is in the (R) configuration.
50. The compound of claim 49, wherein R$_3$ is —H$_3$.
51. The compound of claim 50, wherein R$_1$ is —CH$_3$ or —Cl and R$_9$ is —Cl, —Br, or —F.
52. A composition comprising the compound or a pharmaceutically acceptable salt of the compound of claim 1 and a pharmaceutically acceptable carrier or excipient.
53. A composition comprising the compound or a pharmaceutically acceptable salt of the compound of claim 18 and a pharmaceutically acceptable carrier or excipient.
54. A composition comprising the compound or a pharmaceutically acceptable salt of the compound of claim 36 and a pharmaceutically acceptable carrier or excipient.
55. A method for preparing a composition comprising the step of admixing a compound or a pharmaceutically acceptable salt of the compound of claim 1 and a pharmaceutically acceptable carrier or excipient.

56. A method for preparing a composition comprising the step of admixing a compound or a pharmaceutically acceptable salt of the compound of claim 18 and a pharmaceutically acceptable carrier or excipient.

57. A method for preparing a composition comprising the step of admixing a compound or a pharmaceutically acceptable, salt of the compound of claim 36 and a pharmaceutically acceptable carrier or excipient.

* * * * *